US007501251B2

(12) United States Patent
Köster et al.

(10) Patent No.: US 7,501,251 B2
(45) Date of Patent: *Mar. 10, 2009

(54) DNA DIAGNOSTICS BASED ON MASS SPECTROMETRY

(75) Inventors: Hubert Köster, Figino (CH); Andreas Braun, San Diego, CA (US); Dirk van den Boom, La Jolla, CA (US); Christian Jurinke, La Jolla, CA (US); Andreas Ruppert, Hamburg (DE); Franz Hillenkamp, Munster (DE)

(73) Assignee: Sequenom, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/541,871

(22) Filed: Oct. 2, 2006

(65) Prior Publication Data

US 2007/0202514 A1 Aug. 30, 2007

Related U.S. Application Data

(60) Continuation of application No. 09/686,148, filed on Oct. 10, 2000, now Pat. No. 7,198,893, which is a division of application No. 09/297,676, filed on May 6, 1999, now Pat. No. 6,187,842, and a continuation-in-part of application No. 08/947,801, filed on Oct. 8, 1997, now abandoned, and a continuation-in-part of application No. 08/933,792, filed on Sep. 19, 1997, now Pat. No. 6,133,436, and a continuation-in-part of application No. 08/787,639, filed on Jan. 23, 1997, now Pat. No. 6,024,925, and a continuation-in-part of application No. 08/786,988, filed on Jan. 23, 1997, now Pat. No. 7,285,422, and a continuation-in-part of application No. 08/746,055, filed on Nov. 6, 1996, now abandoned, and a continuation-in-part of application No. 08/746,036, filed on Nov. 6, 1996, now Pat. No. 5,900,481, and a continuation-in-part of application No. 08/744,590, filed on Nov. 6, 1996, now Pat. No. 6,074,823, and a continuation-in-part of application No. 08/744,481, filed on Nov. 6, 1996, now Pat. No. 6,428,955, said application No. 08/947,801 is a continuation-in-part of application No. 08/786,988, and a continuation-in-part of application No. 08/787,639, and a continuation-in-part of application No. 08/746, 055.

(51) Int. Cl.
*C12Q 1/68* (2006.01)
*C12P 19/34* (2006.01)

(52) U.S. Cl. .......................................... 435/6; 435/91.2

(58) Field of Classification Search ..................... 435/6, 435/91.2

See application file for complete search history.

(56) References Cited

U.S. PATENT DOCUMENTS

| | | | |
|---|---|---|---|
| 3,553,452 | A | 1/1971 | Tiernan et al. |
| 3,568,735 | A | 3/1971 | Lancaster |
| 3,776,700 | A | 12/1973 | Gallant |
| 3,807,235 | A | 4/1974 | Lefkovitz |
| 3,931,516 | A | 1/1976 | Fletcher et al. |
| 3,999,689 | A | 12/1976 | Ciantro et al. |
| 4,047,030 | A | 9/1977 | Lobach |
| 4,076,982 | A | 2/1978 | Ritter et al. |
| 4,139,346 | A | 2/1979 | Rabbani |
| 4,214,159 | A | 7/1980 | Hillenkamp et al. |
| 4,418,576 | A | 12/1983 | White |
| 4,442,354 | A | 4/1984 | Hurst et al. |
| 4,461,328 | A | 7/1984 | Kenney |
| 4,515,781 | A | 5/1985 | Torrence et al. |
| 4,548,245 | A | 10/1985 | Crandell et al. |
| 4,554,839 | A | 11/1985 | Hewett et al. |
| 4,582,789 | A | 4/1986 | Sheldon, III et al. |
| 4,604,363 | A | 8/1986 | Newhouse et al. |
| 4,625,112 | A | 11/1986 | Yoshida |
| 4,663,944 | A | 5/1987 | Bernius et al. |
| 4,683,194 | A | 7/1987 | Saiki et al. |
| 4,683,195 | A | 7/1987 | Mullis et al. |

(Continued)

FOREIGN PATENT DOCUMENTS

| | | |
|---|---|---|
| DE | 3221681 | 12/1983 |

(Continued)

OTHER PUBLICATIONS

Aberth, "Secondary ion mass spectrometry with cesium ion primary beam and liquid target matrix for analysis of bioorganic compounds", Anal. Chem., 54:2029-2034 (1982).

Adler et al. "Cell Membrane Coating with Glutaraldehyde: Application to a Versatile Solid-Phase Assay for Throid Membrane Proteins and Molecules Interacting with Thyroid Membranes," Analytical Chemistry 148: 320-327 (1985).

Alderton et al., Magnetic bead purification of M13 DNA sequencing templates, Anal. Biochem. 201:166-169 (1992).

Allin, S.M. and Shuttleworth, S.J., "The Preparation and First Application of a Polymer-Supported "Evans" Oxazolidinone", Tetrahedron Lett., 37(44):8023-8026 (1996).

(Continued)

*Primary Examiner*—Kenneth R. Horlick
(74) *Attorney, Agent, or Firm*—Grant Anderson LLP

(57) ABSTRACT

Provided are methods for detecting a target nucleic acid in a biological sample using RNA amplification. In an embodiment, provided is a method that comprises (a) amplifying a target nucleic acid, or portion thereof, using a primer comprising a sequence that is complementary to a polynucleotide sequence in the target nucleic acid, or a complement thereof, and a sequence that encodes an RNA polymerase promoter; (b) synthesizing RNA using an RNA polymerase that recognizes the promoter; and (c) detecting the presence or absence of the resulting RNA using mass spectrometry thereby detecting the presence or absence of the target nucleic acid in the biological sample.

10 Claims, 123 Drawing Sheets

U.S. PATENT DOCUMENTS

| | | | | |
|---|---|---|---|---|
| 4,689,405 | A | 8/1987 | Frank et al. | |
| 4,711,955 | A | 12/1987 | Ward et al. | |
| 4,725,677 | A | 2/1988 | Koster et al. | |
| 4,729,947 | A | 3/1988 | Middendorf et al. | |
| 4,731,335 | A | 3/1988 | Brigati | |
| 4,733,073 | A | 3/1988 | Becker et al. | |
| 4,740,692 | A | 4/1988 | Yamamoto et al. | |
| 4,749,742 | A | 6/1988 | Elmore | |
| 4,757,141 | A | 7/1988 | Fung et al. | |
| 4,775,619 | A | 10/1988 | Urdea | |
| 4,778,993 | A | 10/1988 | Waugh | |
| 4,779,467 | A | 10/1988 | Rainin et al. | |
| 4,794,150 | A | 12/1988 | Steel | |
| 4,797,355 | A | 1/1989 | Stabinsky | |
| 4,798,706 | A | 1/1989 | Brigati | |
| 4,806,546 | A | 2/1989 | Carrico et al. | |
| 4,808,520 | A | 2/1989 | Dattagupta et al. | |
| 4,826,360 | A | 5/1989 | Iwasawa et al. | |
| 4,844,298 | A | 7/1989 | Ohoka et al. | |
| 4,855,225 | A | 8/1989 | Fung et al. | |
| 4,877,745 | A | 10/1989 | Hayes et al. | |
| 4,882,127 | A | 11/1989 | Rosenthal et al. | |
| 4,902,481 | A | 2/1990 | Clark et al. | |
| 4,920,264 | A | 4/1990 | Becker | |
| 4,925,629 | A | 5/1990 | Schramm | |
| 4,931,400 | A | 6/1990 | Jitsukawa | |
| 4,935,357 | A | 6/1990 | Szybalski | |
| 4,948,442 | A | 8/1990 | Manns | |
| 4,948,882 | A | 8/1990 | Ruth | |
| 4,952,518 | A | 8/1990 | Johnson et al. | |
| 4,983,521 | A | 1/1991 | Lingappa et al. | |
| 4,988,617 | A | 1/1991 | Landegren et al. | |
| 4,988,879 | A | 1/1991 | Zare et al. | |
| 4,994,373 | A | 2/1991 | Stavrianopoulos et al. | |
| 5,000,921 | A | 3/1991 | Hanaway et al. | |
| 5,002,867 | A | 3/1991 | Macevicz | |
| 5,003,059 | A | 3/1991 | Brennan | |
| 5,013,830 | A | 5/1991 | Ohtsuka et al. | |
| 5,023,187 | A | 6/1991 | Koebler et al. | |
| 5,037,882 | A | 8/1991 | Steel | |
| 5,045,694 | A | 9/1991 | Beavis et al. | |
| 5,047,215 | A | 9/1991 | Manns | |
| 5,059,654 | A | 10/1991 | Hou et al. | |
| 5,062,935 | A | 11/1991 | Schlag et al. | |
| 5,064,754 | A | 11/1991 | Mills | |
| 5,077,210 | A | 12/1991 | Eigler et al. | |
| 5,082,935 | A | 1/1992 | Cruickshank | |
| 5,108,703 | A | 4/1992 | Pfost et al. | |
| 5,114,839 | A | 5/1992 | Blocker | |
| 5,118,605 | A | 6/1992 | Urdea | |
| 5,118,937 | A | 6/1992 | Hillenkamp et al. | |
| 5,122,342 | A | 6/1992 | McCulloch et al. | |
| 5,135,870 | A | 8/1992 | Williams et al. | |
| 5,143,451 | A | 9/1992 | Millgard | |
| 5,143,854 | A | 9/1992 | Pirrung et al. | |
| 5,149,625 | A | 9/1992 | Church et al. | |
| 5,164,594 | A | 11/1992 | Thompson et al. | |
| 5,171,989 | A | 12/1992 | Williams et al. | |
| 5,174,962 | A | 12/1992 | Brennan | |
| 5,175,209 | A | 12/1992 | Beattie et al. | |
| 5,175,430 | A | 12/1992 | Enke et al. | |
| 5,185,243 | A | 2/1993 | Ullman et al. | |
| 5,195,657 | A | 3/1993 | Wells | |
| 5,198,531 | A | 3/1993 | Webber et al. | |
| 5,198,540 | A | 3/1993 | Koster | |
| 5,202,231 | A | 4/1993 | Drmanac et al. | |
| 5,202,561 | A | 4/1993 | Giessmann et al. | |
| 5,210,412 | A | 5/1993 | Levis et al. | |
| 5,221,518 | A | 6/1993 | Mills | |
| 5,234,824 | A | 8/1993 | Mullis | |
| 5,237,016 | A | 8/1993 | Ghosh et al. | |
| 5,242,974 | A | 9/1993 | Holmes | |
| 5,247,175 | A | 9/1993 | Schoen et al. | |
| 5,262,128 | A | 11/1993 | Leighton et al. | |
| 5,273,718 | A | 12/1993 | Skold et al. | |
| 5,283,342 | A | 2/1994 | Gustavson et al. | |
| 5,288,644 | A | 2/1994 | Beavis et al. | |
| 5,300,774 | A | 4/1994 | Buttrill | |
| 5,312,233 | A | 5/1994 | Tanny et al. | |
| 5,325,021 | A | 6/1994 | Duckworth et al. | |
| 5,338,688 | A | 8/1994 | Deeg et al. | |
| 5,350,676 | A | 9/1994 | Oberhardt et al. | |
| 5,363,883 | A | 11/1994 | Weidmann | |
| 5,363,885 | A | 11/1994 | McConnell et al. | |
| 5,364,760 | A | 11/1994 | Chu et al. | |
| 5,365,063 | A | 11/1994 | Kaesdorf et al. | |
| 5,373,156 | A | 12/1994 | Franzen | |
| 5,376,788 | A | 12/1994 | Standing et al. | |
| 5,380,833 | A | 1/1995 | Urdea | |
| 5,381,008 | A | 1/1995 | Tanner et al. | |
| 5,382,793 | A | 1/1995 | Weinberger et al. | |
| 5,399,501 | A | 3/1995 | Pope et al. | |
| 5,399,857 | A | 3/1995 | Doroshenko et al. | |
| 5,403,711 | A | 4/1995 | Walder et al. | |
| 5,410,068 | A | 4/1995 | Coull et al. | |
| 5,412,083 | A | 5/1995 | Giese et al. | |
| 5,427,929 | A | 6/1995 | Richards et al. | |
| 5,430,136 | A | 7/1995 | Urdea et al. | |
| 5,436,143 | A | 7/1995 | Hyman | |
| 5,436,327 | A | 7/1995 | Southern et al. | |
| 5,439,649 | A | 8/1995 | Tseung et al. | |
| 5,440,119 | A | 8/1995 | Labowsky | |
| 5,453,613 | A | 9/1995 | Gray et al. | |
| 5,457,041 | A | 10/1995 | Ginaven et al. | |
| 5,459,039 | A | 10/1995 | Modrich et al. | |
| 5,474,895 | A | 12/1995 | Ishii et al. | |
| 5,478,893 | A | 12/1995 | Ghosh et al. | |
| 5,480,784 | A * | 1/1996 | Kacian et al. | 435/91.21 |
| 5,482,836 | A | 1/1996 | Cantor et al. | |
| 5,484,701 | A | 1/1996 | Cocuzza et al. | |
| 5,492,817 | A | 2/1996 | Thompson et al. | |
| 5,492,821 | A | 2/1996 | Callstrom et al. | |
| 5,498,545 | A | 3/1996 | Vestal | |
| 5,503,980 | A | 4/1996 | Cantor | |
| 5,506,348 | A | 4/1996 | Pieles | |
| 5,508,169 | A | 4/1996 | Deugau et al. | |
| 5,510,270 | A | 4/1996 | Fodor et al. | |
| 5,510,613 | A | 4/1996 | Reilly et al. | |
| 5,512,295 | A | 4/1996 | Kornberg et al. | |
| 5,512,439 | A | 4/1996 | Hornes et al. | |
| 5,514,548 | A | 5/1996 | Krebber et al. | |
| 5,527,675 | A | 6/1996 | Coull et al. | |
| 5,532,227 | A | 7/1996 | Golub et al. | |
| 5,538,897 | A | 7/1996 | Yates et al. | |
| 5,541,313 | A | 7/1996 | Ruth | |
| 5,545,539 | A | 8/1996 | Miller | |
| 5,547,835 | A | 8/1996 | Koster | |
| 5,552,535 | A | 9/1996 | McLean et al. | |
| 5,563,410 | A | 10/1996 | Mullock | |
| 5,571,669 | A | 11/1996 | Lu et al. | |
| 5,571,902 | A | 11/1996 | Ravikumar et al. | |
| 5,580,434 | A | 12/1996 | Robotti et al. | |
| 5,580,733 | A | 12/1996 | Levis et al. | |
| 5,583,042 | A | 12/1996 | Roth | |
| 5,589,136 | A | 12/1996 | Northrup et al. | |
| 5,599,500 | A | 2/1997 | Jones | |
| 5,601,982 | A | 2/1997 | Sargent et al. | |
| 5,604,099 | A | 2/1997 | Erlich et al. | |
| 5,605,662 | A | 2/1997 | Heller et al. | |
| 5,605,798 | A * | 2/1997 | Koster | 435/6 |
| 5,607,912 | A | 3/1997 | Samejima et al. | |
| 5,609,907 | A | 3/1997 | Natan | |
| 5,612,474 | A | 3/1997 | Patel | |
| 5,616,698 | A | 4/1997 | Krepinsky et al. | |

5,616,700 A 4/1997 Reddy et al.
5,622,821 A 4/1997 Selvin et al.
5,622,824 A 4/1997 Koster et al.
5,622,829 A 4/1997 King et al.
5,624,711 A 4/1997 Sundberg et al.
5,625,184 A 4/1997 Vestal et al.
5,627,369 A 5/1997 Vestal et al.
5,631,134 A 5/1997 Cantor
5,633,496 A 5/1997 Sakairi et al.
5,635,598 A 6/1997 Lebl et al.
5,635,713 A 6/1997 Labowsky
5,639,633 A 6/1997 Callstrom et al.
5,641,862 A 6/1997 Rutter et al.
5,641,959 A 6/1997 Holle et al.
5,643,722 A 7/1997 Rothschild et al.
5,643,798 A 7/1997 Beavis et al.
5,643,800 A 7/1997 Tarantino et al.
5,648,462 A 7/1997 Funakoshi et al.
5,648,480 A 7/1997 Letsinger et al.
5,650,274 A 7/1997 Kambara et al.
5,650,277 A 7/1997 Navot et al.
5,650,489 A 7/1997 Lam et al.
5,652,358 A 7/1997 Pfleiderer et al.
5,654,150 A 8/1997 King et al.
5,654,545 A 8/1997 Holle et al.
5,663,242 A 9/1997 Ghosh et al.
5,665,967 A 9/1997 Coxon et al.
5,668,266 A 9/1997 Ruth
5,670,322 A 9/1997 Eggers et al.
5,670,381 A 9/1997 Jou et al.
5,677,195 A 10/1997 Winkler et al.
5,679,773 A 10/1997 Holmes
5,686,656 A 11/1997 Amirav et al.
5,688,642 A 11/1997 Chrisey et al.
5,691,141 A 11/1997 Koster et al.
5,700,642 A 12/1997 Monforte et al.
5,710,028 A 1/1998 Eyal et al.
5,716,825 A 2/1998 Hancock et al.
5,726,243 A 3/1998 Fields
5,736,625 A 4/1998 Callstrom et al.
5,736,626 A 4/1998 Mullah et al.
5,742,049 A 4/1998 Holle et al.
5,743,960 A 4/1998 Tisone
5,746,373 A 5/1998 Sanada
5,756,050 A 5/1998 Ershow et al.
5,757,392 A 5/1998 Zhang
5,760,393 A 6/1998 Vestal et al.
5,770,272 A 6/1998 Biemann et al.
5,770,367 A 6/1998 Southern et al.
5,770,860 A 6/1998 Franzen
5,777,324 A 7/1998 Hillenkamp
5,777,325 A 7/1998 Weinberger et al.
5,789,395 A 8/1998 Amin et al.
5,795,714 A 8/1998 Cantor et al.
5,798,210 A 8/1998 Canard et al.
5,807,522 A 9/1998 Brown et al.
5,812,272 A 9/1998 King et al.
5,821,063 A 10/1998 Patterson et al.
5,828,063 A 10/1998 Koster et al.
5,830,655 A 11/1998 Monforte et al.
5,846,710 A 12/1998 Bajaj
5,846,717 A 12/1998 Brow et al.
5,851,765 A 12/1998 Koster
5,853,979 A 12/1998 Green et al.
5,853,989 A 12/1998 Jeffreys et al.
5,854,486 A 12/1998 Dreyfus
5,856,092 A 1/1999 Dale et al.
5,864,137 A 1/1999 Becker et al.
5,869,240 A 2/1999 Patterson
5,869,242 A 2/1999 Kamb
5,872,003 A 2/1999 Koster
5,872,010 A 2/1999 Karger et al.
5,885,775 A 3/1999 Haff et al.
5,885,841 A 3/1999 Higgs, Jr. et al.
5,888,778 A 3/1999 Shuber
5,888,819 A 3/1999 Goelet et al.
5,894,063 A 4/1999 Hutchens et al.
5,900,481 A 5/1999 Lough et al.
5,925,520 A 7/1999 Tully et al.
5,927,547 A 7/1999 Papen et al.
5,928,906 A 7/1999 Koster et al.
5,928,952 A 7/1999 Hutchins et al.
5,948,624 A 9/1999 Rothschild et al.
5,955,729 A 9/1999 Nelson et al.
5,965,363 A 10/1999 Monforte et al.
5,969,350 A 10/1999 Kerley et al.
5,975,492 A 11/1999 Brenes
5,976,798 A 11/1999 Parker et al.
5,981,185 A 11/1999 Matson et al.
5,985,356 A 11/1999 Schultz et al.
5,989,871 A 11/1999 Grossman et al.
6,001,567 A 12/1999 Brow et al.
6,004,744 A 12/1999 Goelett et al.
6,006,171 A 12/1999 Vines et al.
6,007,987 A 12/1999 Cantor et al.
6,017,693 A 1/2000 Yates, III et al.
6,022,688 A 2/2000 Jurinke et al.
6,024,925 A 2/2000 Little et al.
6,025,193 A 2/2000 Weiss
6,027,890 A 2/2000 Ness et al.
6,040,193 A 3/2000 Winkler et al.
6,043,031 A * 3/2000 Koster et al. .................. 435/6
6,045,997 A 4/2000 Futreal et al.
6,051,378 A 4/2000 Monforte et al.
6,060,022 A 5/2000 Pang et al.
6,074,823 A 6/2000 Koster
6,083,762 A 7/2000 Shalon et al.
6,090,558 A 7/2000 Butler et al.
6,104,028 A 8/2000 Hunter et al.
6,110,426 A 8/2000 Shalon et al.
6,111,251 A 8/2000 Hillenkamp
6,121,048 A 9/2000 Zaffaroni et al.
6,132,685 A 10/2000 Kercso et al.
6,132,724 A 10/2000 Blum
6,133,436 A 10/2000 Koster et al.
6,136,269 A 10/2000 Winkler et al.
6,140,045 A 10/2000 Wohlstadter et al.
6,140,053 A 10/2000 Koster
6,146,854 A 11/2000 Koster et al.
6,147,344 A 11/2000 Annis et al.
6,156,512 A 12/2000 Schumm et al.
6,188,064 B1 2/2001 Koster
6,194,144 B1 2/2001 Koster
6,197,498 B1 * 3/2001 Koster .......................... 435/5
6,207,370 B1 3/2001 Little et al.
6,214,551 B1 4/2001 Saghvi et al.
6,221,601 B1 * 4/2001 Koster et al. .................. 435/6
6,221,605 B1 * 4/2001 Koster .......................... 435/6
6,225,061 B1 5/2001 Becker et al.
6,225,450 B1 5/2001 Koster
6,232,076 B1 5/2001 Schulz
6,235,478 B1 * 5/2001 Koster .......................... 435/6
6,238,871 B1 5/2001 Koster
6,258,538 B1 * 7/2001 Koster et al. .................. 435/6
6,265,716 B1 7/2001 Hunter et al.
6,268,131 B1 7/2001 Kang et al.
6,268,144 B1 * 7/2001 Koster .......................... 435/6
6,270,835 B1 8/2001 Hunt et al.
6,277,573 B1 * 8/2001 Koster .......................... 435/6
6,300,076 B1 * 10/2001 Koster .......................... 435/6
6,303,309 B1 10/2001 Jurinke et al.
6,322,970 B1 11/2001 Little et al.
6,342,396 B1 1/2002 Perrin et al.
6,387,628 B1 5/2002 Little et al.
6,423,966 B2 7/2002 Hillenkamp et al.
6,428,955 B1 8/2002 Koster et al.

| | | | | |
|---|---|---|---|---|
| 6,468,748 | B1 | 10/2002 | Monforte et al. | |
| 6,475,766 | B1 | 11/2002 | Hastings et al. | |
| 6,485,913 | B1 | 11/2002 | Becker et al. | |
| 6,500,621 | B2 * | 12/2002 | Koster | 435/6 |
| 6,602,662 | B1 * | 8/2003 | Koster et al. | 435/6 |
| 7,074,563 | B2 * | 7/2006 | Koster | 435/6 |
| 2002/0005478 | A1 | 1/2002 | Hillenkamp et al. | |
| 2002/0040130 | A1 | 4/2002 | Braun | |
| 2002/0042112 | A1 | 4/2002 | Koster et al. | |
| 2002/0045178 | A1 | 4/2002 | Cantor | |
| 2002/0109085 | A1 | 8/2002 | Hillenkamp et al. | |
| 2002/0137046 | A1 | 9/2002 | Koster | |
| 2002/0142483 | A1 | 10/2002 | Yao et al. | |
| 2002/0150903 | A1 | 10/2002 | Koster | |
| 2002/0155587 | A1 | 10/2002 | Opalsky et al. | |

FOREIGN PATENT DOCUMENTS

| | | |
|---|---|---|
| DE | 3930312 | 4/1990 |
| DE | 4011991 | 10/1990 |
| DE | 4431174 | 3/1996 |
| DE | 19617011 | 4/1996 |
| DE | 4438630 | 5/1996 |
| DE | 19618032 | 5/1996 |
| DE | 19628178 | 7/1996 |
| DE | 19731479 | 7/1997 |
| DE | 19754978 | 12/1997 |
| EP | 175467 | 3/1986 |
| EP | 268237 | 5/1988 |
| EP | 269520 | 6/1988 |
| EP | 339781 | 11/1989 |
| EP | 360676 | 3/1990 |
| EP | 360677 | 3/1990 |
| EP | 396116 | 11/1990 |
| EP | 412883 | 2/1991 |
| EP | 455905 | 11/1991 |
| EP | 456304 | 11/1991 |
| EP | 500506 | 8/1992 |
| EP | 543550 | 5/1993 |
| EP | 593789 | 4/1994 |
| EP | 630972 | 12/1994 |
| EP | 655501 | 5/1995 |
| EP | 683234 | 11/1995 |
| EP | 684315 | 11/1995 |
| EP | 701001 | 3/1996 |
| EP | 771019 | 5/1997 |
| EP | 785278 | 7/1997 |
| EP | 648280 | 5/1999 |
| FR | 2597260 | 10/1987 |
| FR | 2749662 | 10/1987 |
| GB | 2017105 | 3/1979 |
| GB | 2233654 | 1/1991 |
| GB | 2260811 | 4/1993 |
| GB | 2168478 | 11/1997 |
| GB | 2312782 | 11/1997 |
| GB | 2332273 | 6/1999 |
| JP | 63230086 | 9/1988 |
| JP | 2215399 | 8/1990 |
| JP | 4178359 | 6/1992 |
| JP | 6294796 | 10/1994 |
| JP | 8509857 | 10/1996 |
| JP | 8290377 | 11/1996 |
| WO | WO 8402579 | 7/1984 |
| WO | WO 8502907 | 7/1985 |
| WO | WO 8805074 | 7/1988 |
| WO | WO 8903432 | 4/1989 |
| WO | WO 8906700 | 7/1989 |
| WO | WO 8907149 | 8/1989 |
| WO | WO 89/09282 | 10/1989 |
| WO | WO 8909282 | 10/1989 |
| WO | WO 8909406 | 10/1989 |
| WO | WO 8910786 | 11/1989 |
| WO | WO 8911270 | 11/1989 |
| WO | WO 8912624 | 12/1989 |
| WO | WO 8912694 | 12/1989 |
| WO | WO 9001564 | 2/1990 |
| WO | WO 9003382 | 4/1990 |
| WO | WO 9007582 | 7/1990 |
| WO | WO 9014148 | 11/1990 |
| WO | WO 9015883 | 12/1990 |
| WO | WO 9106678 | 5/1991 |
| WO | WO 9111533 | 8/1991 |
| WO | WO 9113075 | 9/1991 |
| WO | WO 9115600 | 10/1991 |
| WO | WO 9203575 | 3/1992 |
| WO | WO 9205287 | 4/1992 |
| WO | WO 9207879 | 5/1992 |
| WO | WO 9210092 | 6/1992 |
| WO | WO 9210588 | 6/1992 |
| WO | WO 9213629 | 8/1992 |
| WO | WO 9215712 | 9/1992 |
| WO | WO 9306925 | 4/1993 |
| WO | WO 9308305 | 4/1993 |
| WO | WO 9309668 | 5/1993 |
| WO | WO 9314108 | 7/1993 |
| WO | WO 9315407 | 8/1993 |
| WO | WO 9320236 | 10/1993 |
| WO | WO 9323563 | 11/1993 |
| WO | WO 9324834 | 12/1993 |
| WO | WO 9400562 | 1/1994 |
| WO | WO 9403774 | 2/1994 |
| WO | WO 9411529 | 5/1994 |
| WO | WO 9411530 | 5/1994 |
| WO | WO 9411735 | 5/1994 |
| WO | WO 9416090 | 7/1994 |
| WO | WO 9416101 | 7/1994 |
| WO | WO 9420978 | 9/1994 |
| WO | WO 9421811 | 9/1994 |
| WO | WO 9421822 | 9/1994 |
| WO | WO 9427719 | 12/1994 |
| WO | WO 9428418 | 12/1994 |
| WO | WO 9504524 | 2/1995 |
| WO | WO 9507361 | 3/1995 |
| WO | WO 9511755 | 5/1995 |
| WO | WO 9513381 | 5/1995 |
| WO | WO 9513538 | 5/1995 |
| WO | WO 9515400 | 6/1995 |
| WO | WO 9504160 | 9/1995 |
| WO | WO 9525116 | 9/1995 |
| WO | WO 9525737 | 9/1995 |
| WO | WO 9530773 | 11/1995 |
| WO | WO 9531429 | 11/1995 |
| WO | WO 9535505 | 12/1995 |
| WO | WO 9602836 | 2/1996 |
| WO | WO 9605323 | 2/1996 |
| WO | WO 9610648 | 4/1996 |
| WO | WO 9614406 | 5/1996 |
| WO | WO 9615262 | 5/1996 |
| WO | WO 9617080 | 6/1996 |
| WO | WO 9619587 | 6/1996 |
| WO | WO 9621042 | 7/1996 |
| WO | WO 9629431 | 9/1996 |
| WO | WO 9630545 | 10/1996 |
| WO | WO 9632504 | 10/1996 |
| WO | WO 9636731 | 11/1996 |
| WO | WO 9636732 | 11/1996 |
| WO | WO 9636736 | 11/1996 |
| WO | WO 9636986 | 11/1996 |
| WO | WO 9636987 | 11/1996 |
| WO | WO 9637630 | 11/1996 |
| WO | WO 9627681 | 12/1996 |
| WO | WO 9639437 | 12/1996 |
| WO | WO 9708306 | 3/1997 |
| WO | WO 9716699 | 5/1997 |
| WO | WO 9719110 | 5/1997 |
| WO | WO 9733000 | 9/1997 |

| | | |
|---|---|---|
| WO | WO 9737041 | 10/1997 |
| WO | WO 9740462 | 10/1997 |
| WO | WO 9742348 | 11/1997 |
| WO | WO 9743617 | 11/1997 |
| WO | WO 9803257 | 1/1998 |
| WO | WO 9805965 | 2/1998 |
| WO | WO 9811249 | 3/1998 |
| WO | WO 9812355 | 3/1998 |
| WO | WO 9812734 | 3/1998 |
| WO | WO 9814982 | 4/1998 |
| WO | WO 9820019 | 5/1998 |
| WO | WO 9820020 | 5/1998 |
| WO | WO 9820166 | 5/1998 |
| WO | WO 9822541 | 5/1998 |
| WO | WO 9826095 | 5/1998 |
| WO | WO 9823284 | 6/1998 |
| WO | WO 9826095 | 6/1998 |
| WO | WO 9826179 | 6/1998 |
| WO | WO 9833052 | 7/1998 |
| WO | WO 9833808 | 8/1998 |
| WO | WO 9834116 | 8/1998 |
| WO | WO 9835609 | 8/1998 |
| WO | WO 9819578 | 9/1998 |
| WO | WO 9839481 | 9/1998 |
| WO | WO 9824935 | 11/1998 |
| WO | WO 9854571 | 12/1998 |
| WO | WO 9854751 | 12/1998 |
| WO | WO 9905323 | 2/1999 |
| WO | WO 9912040 | 3/1999 |
| WO | WO 9914362 | 3/1999 |
| WO | WO 9925724 | 5/1999 |
| WO | WO 9931278 | 6/1999 |
| WO | WO 9955718 | 11/1999 |
| WO | WO 9957318 | 11/1999 |
| WO | WO 0051053 | 8/2000 |
| WO | WO 0056446 | 9/2000 |
| WO | WO 0060361 | 10/2000 |
| WO | PCT/US01/06728 | 3/2001 |
| WO | PCT/US01/12903 | 4/2001 |
| WO | WO 0127857 | 4/2001 |
| WO | PCT/US01/29290 | 9/2001 |
| WO | PCT/US01/45123 | 10/2001 |
| WO | WO 0196607 | 12/2001 |
| WO | WO 0204489 | 1/2002 |
| WO | WO 0225567 | 3/2002 |
| WO | PCT/US02/34447 | 10/2002 |
| WO | PCT/US02/34490 | 10/2002 |
| WO | PCT/US02/34640 | 10/2002 |

OTHER PUBLICATIONS

Andersen, et al., Electrospray ionization and matrix assisted laser desorption/ionization mass spectrometry: Powerful analytical tools in recombinant protein chemistry. Nature Biotech. 14:449-457 (1996).

Arlinghaus et al., "Applications of resonance ionization spectroscopy for semiconductor, environmental and biomedical analysis, and for DNA sequencing", SPIE, vol. 1435, Opt. Methods Ultrasensitive Detect. Anal. Tech. Appl. pp. 26-35 (1991).

Arshady, Reza, Beaded polymer supports and gels: I. Manufacturing techniques, Journal of Chromatography, 586:181-197 (1991).

Arshady, Reza, Beaded polymer supports and gels: II. Physico-chemical criteria and functionalization, Journal of Chromatography, 586:199-219 (1991).

Asseline et al., "New Solid-Phase for Automated Synthesis of Oligonucleotides Containing an Amino-Alkyl Linker at thier 3'-End", Tetrahedron Lett., 31:81-84 (1990).

Axelrod et al. "Transcription from Bacteriophage T7 and SP6 RNA Polymerase Promoters in the Presence of 3'-Deoxyribonucleoside 5'-Triphosphate Chain Terminators", Biochemistry, 24:5716-5723 (1985).

Backes, B.J. et al., "Activation Method to Prepare a Highly Reactive Acylsulfonamide "Safety Catch" Linker for Solid-Phase Synthesis. sup.1", J. Am. Chem. Soc., 118:3055-3056 (1996).

Bai et al., "Matrix-Assisted Laser Desprption/Ionization Mass Spectrometry of Restriction Enzyme-Digested Plasmid DNA Using an Active Nafion Substrate", Rapid Comm. Mass Spec. 8:687-691 (1994).

Baines, W., "DNA sequencing by mass spectrometry. Outline of a potential future application", Chimicaoggi pp. 13-16 (1991).

Bains, DNA sequencing by mass spectrometry: Outline of a potential future application, Chimicaoggi 9:13-16 (1991).

Bains, Setting a sequence to sequence a sequence, Biotechnology 10:757-758 (1992).

Bains, W., "Setting a sequence to sequence a sequence", Bio/Tech 10:757-758 (1992).

Bannwarth, Solid-phase synthesis of oligodeoxynucleotides containing phosphoramidate internucleotide linkages and their specific chemical cleavage, Helvetica Chimica Acta 71:1517-1527 (1988).

Barany F., Genetic disease detection and DNA amplification using cloned thermostable ligase, Proc. Natl. Acad. Sci. 88:189-193 (1991).

Barrell B., "DNA sequencing: present limitations and prospects for the future", FASEB Journal 5:40-45 (1991).

Batista-Viera et al., A new method for reversible immobilization of thiol biomolecules bsed on solid-phase bound thiolsulfonate groups, App. Biochem and Biotech,31:175-195 (1991).

Beattie et al., "Synthesis and Use of Oligonucleotide Libraries", Chem. Abstr. 123:112588 (1995).

Beaucage et al., The synthesis of modified oligonucleotides by the phosphoramidite approach and their applications, Tetrahedron 49:6123-6194 (1993).

Beck and Koster, Applications of dioxetane chemiluminescent probes to molecular biology, Anal. Chem. 62:2258-2270 (1990).

Beck et al., Chemiluminescent detection of DNA: application of DNA sequencing and hybridization, Nucleic Acids Res. 17(13):5115-5123 (1989).

Belanger et al., "Molecular mass and carbohydrate structure of prostate specific antigen: studies for establishment of an international PA standard", Prostate 27(4):187-197 (1995).

Benner et al., "DNA Base-Pair Substitutions Detected in Double-Stranded DNA With Matrix-Assisted Laser Desorption/Ionization Time-of-Flight Mass Spectrometry", Eur. Mass Spectrum., 1:479-485 (1995).

Bentzley et al., "Oligonucleotide Sequence and Composition Determined by Matrix-Assisted Laser Desorption/Ionization," Analytical Chemistry 68: 2141-6 (1996).

Berenkamp et al., "Performance of Infrared Matrix-assisted Laser Desorption/Ionization Mass Spectrometry with Lasers Emitting in the 3 um Wavelength Range", Rapid Comm. Mass Spec., 11:1399-1406 (1997).

Bonfils et al., "Solid Phase Synthesis of 5', 3'-Bifunctional Oligodeoxribonucleotides Bearing a Masked Thiol Group at the 3'End", Tetrahedron lett., 32:3053-56 (1991).

Bornsen et al., "Influence of Solvents and Detergents on Matrix-assisted Laser Desorption/Ionization Mass Spectrometry Measurements of Proteins and Oligonucleotides", Rapid Comm. Mass Spec., 11:603-609 (1997).

Braun et al., "Improved Analysis of Microsatellites Using Mass Spectrometry", Genomics 46:18-23 (1997).

Braun et al., Detecting CFTR gene mutations by using primer oligo base extension and mass spectrometry, Clinical Chemistry 43:1151-1158 (1997).

Braun, A., et al., Molecular analysis of the gene for the human vitamin-D-binding protein (group-specific component): allelic differences of the common genetic GC types, Hum. Genet.89:401-406 (1992).

Brennan et al., New methods to sequence DNA by mass spectrometry, SPIE, vol. 1206, New Technol. Cytom. Mol. Biol. pp. 60-77 (1990).

Broccoli et al., "Telomerase activity in normal and malignant hematopoietic cells", Proc. Nat'l. Acad. Sci. U.S.A., 92:9082-9086 (1995).

Broude, Natalia E. et al., “Enhanced DNA sequencing by hybridization (streptavidin/biotin/stacking interaction/T4 DNA ligase/DNA polymerase)”, Proc. Natl. Acad. Sci., 91:3072-3076 (1994).
Brown et al., “Mass Resolution Improvement by Incorporation of Pulsed Ion Extraction in a Matrix-Assisted Laser Desorption/Ionization Linear Time-of-Flight Mass Spectrometer”, Anal. Chem., 67:1998-2003 (1995).
Brown et al., A single-bead decode strategy using electrospray ionization mass spectrometry and a new photolabile linker: 3-Amino-3-(2-nitrophenyl)propionic acid, Molec. Diversity 1:4-12 (1995).
Brummel et al., “Evaluation of mass spectrometric methods applicable to the direct analysis of non-peptide bead-bound combinatorial libraries”, Anal. Chem., 68:237-242 (1996).
Burgess, K. et al., “An Approach to Photolabile, Fluorescent Protecting Groups”, J. Org. Chem., 62:5165-6168 (1997).
Burlingame et al. “Mass Spectrometry,” Analytical Chemistry 70: 647R-716R (1998).
Busch et al. “Mass spectrometry of large, fragile, and involatile molecules” Science 218:247-254 (1982).
Cai et al., “Different discrete wavelet transforms applied to denoising analytical data”, J. Chem. Inf. Comput. Sci., 3B(6):1161-1170 (1998).
Cantor C.R. et al., Instrumentation in molecular biomedical diagnostics: an overview, Genet Anal. 14(2):31-6 (1997).
Cantor CR and Fields CA, “Meeting report: Genome Sequencing Conference III: Evolution and Progress”, Genomics 12:419-420 (1992).
Cantor et al., “DNA sequencing after human genome project”, Nucleosides and Nucleotides 16:591-598 (1997).
Cantor et al., “Lighting up hybridization”, Nature Biotech. 14:264, (1992).
Cantor et al., “Meeting Report: Report on the Sequencing by Hybridization Workshop”, Genomics 13: 1378-1383 (1992).
Cantor et al., “Parallel processing in DNA analysis”, In Proceedings of 2nd International Workshop on Parallel Algorithms for Irregularly Structured Problems, Lyon, France: Lecture Notes in Computer Science 980, eds. A. Ferreira, J. Rolim, Springer Verag, Berlin, New York 171-185 (1995).
Cantor et al., “The future of DNA sequencing: methods and applications”, In Mass Spectrometry in the Biological Sciences, A.L. Burlingame and S.A. Carr eds., Totawa, NJ: Humana Press, 529-533 (1996).
Caruthers C.H., “Gene synthesis machines: DNA chemistry and its uses”, Science, 230:281-285 (1985).
Caruthers et al., “Chemical synthesis of deoxyoligonucleotides by the phosphoramidite method”, in Methods in Enzymology 154:287-313 (1987).
Chait et al., “Weighing naked proteins: practical, high-accuracy mass measurement of peptides and proteins”, Science, 257:1885-1894 (1992).
Chan et al., “Matrix-assisted Laser Desorption/Ionization Using a Liquid Matrix: Formation of High-Mass Cluster Ions from Proteins”, Org. Mass Spec., 27:53-56 (1992).
Chang et al., “Detection of .DELTA.F508 Mutation of the cystic Fibrosis Gene by Matrix-Assisted Laser Desorption/Ionization Mass Spectrometry”, Rapid Comm. in Mass Spectrom., 9:772-774, (1995).
Chee, Enzymatic multiples DNA sequencing, Nucleic Acids Res. 19(12):3301-3305 (1991).
Chen and Seeburg, Supercoil sequencing: A fast and simple method for sequencing plasmid DNA, DNA 4(2):165-170 (1985).
Chrisey et al., Covalent attachment of synthetic DNA to self-assembled monlayer films, Nucl. Acids Res. 24:3031-3039 (1996).
Chrisey et al., Fabrication of patterned DNA surfaces, Nucl. Acids. Res. 24:3040-3047 (1996).
Church et al., “Multiplex DNA Sequencing”, Science 240:185-188 (1988).
Cohen et al. “Emerging Technologies for Sequencing Antisense Oligonucleotides: Capillary Electrophoresis and Mass Spectrometry,” Advanced Chromatography 36: 127-62 (1996).
Collins et al., “A DNA Polymorphism Discovery Resource on Human Genetic Variation”, Genome Res., 8:1229-1231 (1998).
Connolly, B. A., “Oligonucleotides containing modified bases”, Oligonucleotides and Analogues, A Practical Approach, Edited by F. Eckstein, Oxford University Press, Ch. 7, pp. 40-45 (1991).
Cook et al., “Synthesis and hybridization of a series of biotinylated oligonucleotides”, Nucleic Acids Research 16:4077-4095 (1988).
Cornett et al., “Liquid Mixtures for Matrix-Assisted Laser Desorption”, Anal. Chem., 65:2608-2613 (1993).
Cosstick et al., “Synthesis and Poperties of dithymidine phosphate analogues containing 3'-thiothimidine”, Nucl. Acid Res., 18:829-835 (1990).
Crain et al. “Applications of mass spectrometry to the characterization of oligonucleotides and nucleic acids,” Current Opinion in Biotechnology 9: 25-34 (1998).
Crain et al., “Mass spectrometric techniques in nucleic acid research”, Mass Spectrometry Reviews 9: 505-554 (1990).
Crain, “Mass spectrometric techniques in nucleic acid research”, Mass Spectr. Rev. 9:505-554 (1990).
Dale et al., “Graphite/Liquid Mixed Matrices for Laser Desorption/Ionization Mass Spectrometry”, Anal. Chem., 68:3321-3329 (1996).
Damha, Masad J. et al.; An improved procedure for derivatization of controlled-pore glass beads for solid-phase oligonucleotide synthesis; Nucleic Acids Research 18(13):3813-3821 (1990).
Dass et al., “Particle Beam Induced Reactions Between Peptides and Liquid Matrices”, Anal. Chem., 60:2723-2729 (1988).
Database WPI, Derwent Publication #198822, citing European Patent No. 269520 A, New HIV-2 retrovirus causing AIDS—and new antigenic proteins, antibodies and complementary nucleic acid sequences, (1990).
Database WPI, Derwent Publications #198942, citing International PCT Application No. WO 89/09406 published Oct. 5, 1989.
Database WPI, Derwent Publications #199015, citing European Patent No. EP 0360677 published Mar. 28, 1990.
Database WPI, Derwent Publications #199516, citing Wo 9507361 A, (1989).
Database WPI, Derwent Publications #199830, citing International PCT Application No. WO 98/26179 published Jun. 18, 1998.
Day et al., “Immobilization of Polynucleotides on Magnetic Particles”, Biochem J. 278:735-740 (1991).
Debitsudo et al., “Organic Super-Thin Film of Oligonucleotide Derivative and Method for its Preparation”, Chem Abstr. 122:291447q (1995).
Debitsudo et al., “Preparation of Nucleotide Thioalkyl Esters and Monomolecular Membrane”, Chem Abstr. 121:83891g (1994).
Derwent# 008221915, WPI Acc. No. 90-108916/199015 for European Patent Application No. EP 0360676, “Size analysis of biological mol. fragments—by mass spectrometry, esp. in nucleic acid sequencing,” (1993).
Derwent# 009135586, WPI Acc. No. 1992-263024/199232 for Japanese Patent Application No. JP 4178359, “new antiinflammatory tetracycline derivs.—for treting articular rheumatism, osteoarthritis, Reiter’s syndrome, Lyme disease, etc,” (1990).
Derwent# 010634381, WPI Acc. No. 1996-131334/199614 for PCT Patent Application No. WO 96/05323, “Nucleic acid amplification and opt. detection—using construct comprising complementary strand linked to RNA polymerase promoter,” (1989).
Derwent# 011635345, WPI Acc. No. 1998-052473/199805 for French Patent Application No. FR 2749662, “Automatic laboratory for analysing samples—has robot and analysers in one chamber connected by sample transfer conveyors to second chamber with human operator access,” (1989).
Derwent# 011716230, WPI Acc. No. 1998-133140/199813 for PCT Patent Application No. WO 98/05965, “Identification of characteristics of eukaryotic cells—after covalent immobilisation on solid support,” (1991).
Drmanac et al., “An Algorithm for the DNA Sequence Generationfrom k-Tuple Word Contents of the Minimal Number of Random Fragments”, J. Biomol. Struct. Dynamics 5(5): 1085-1102 (1991).
Drmanac et al., “Reliable Hybridization of Oligonucleotides as Short as Six Nucleotides”,DNA and Cell Biology 9:527-534 (1998).
Drmanac, et al., “Sequencing of megabase plus DNA by hybridization: theory of the method”, Genomics 4:114-128 (1989).

Duchateau et al., "Selection of buffers and of an ion-pairing agent for thermospray liquid chromatography-mass spectrometric analysis of ionic compounds," J. Chromatogr, 552:605-612 (1991).
Eckstein, F., (Ed.) Oligonucleotides and Analogues: A Practical Approach Oxford:Oxford University Press, 56-57, 137-139, 256-259, (1991).
Fabris et al., "Massive Cluster Impact Ionization on a Four Sector Tandem Mass Spectrometer", J. Mass Spec.30:140-143 (1995).
Ferrie et al., Development, multiplexing, and application of ARMS tests for common mutations in the CFTR gene, Am. J. Hum. Genet. 51:251-262 (1992).
Fitzgrald et al., "Basic Matrices for the Matrix-Assisted Laser Desorption/Ionization Mass Spectrometry of Proteins and Oligonucleotides", Anal. Chem., 65:3204-3211 (1993).
Foster, M.W. and Freeman, W.L., "Naming Names in Human Genetic Variation Research", Genome Res., 8:755-757, (1998).
Frank and Koster, DNA chain length and the influence of base composition on electrophoretic mobility of oligodeoxyribonucleotides in polyacrylamide-gels, Nucl. Acids Res. 6:2069-2087 (1979).
Frohman, "Cloning PCR Products" Chapter 2 in The Polymerase Chain Reaction, Mullis et al., (Eds.), Birkhauser, Boston, pp. 14-37, (1994).
Fu et al., A DNA sequencing strategy which requires only five bases of known terminal sequence for priming, Paper presented, Genome Mapping and Sequencing, Cold Spring Harbor Laboratory, (1991).
Fu et al., Efficient preparation of short DNA sequence ladders potentially suitable for MALDI-TOF DNA sequencing, Genetic Analysis 12:137-142 (1996).
Fu et al., Sequencing double-stranded DNA by strand displacement, Nucl Acids Res 25:677-679 (1997).
Fu et al., Sequencing exons 5 to 8 of the p53 gene by MALDI-TOF mass spectrometry, Nat Biotechnol 16:381-4 (1998).
Fu, et al., "A DNA sequencing strategy that requires only five bases of known terminal sequence for priming (primer extention/stacking interaction/fluorescein/solid state/duplex probe)", Proc. Natl. Acad. Sci. USA 92:10162-10166 (1995).
Ganem et al., Detection of oligonucleotide duplex forms by ion-spray mass spectrometry, Tetrahedron Letters 34(9):1445-1448, (1993).
George et al., "Current Methods in Sequence Comparison and Analysis," Chapter 12 of: Macromolecule Sequencing and Synthesis, Selected Methods and Applications, Schlesinger (Ed.), 127-139, (1988).
Ghosh, et al., "Covalent attachment of oligonucleotides to solid supports", Nuc. Acids. Res. 15)13):5353-5372 (1987).
Gildea et al., A versatile acid-labile linker for modification of synthetic biomolecules, Tetrahedron Letters 31:7095-7398 (1990).
Gross et al., "Matrix-assisted laser desorption/ionisation-mass spectrometry applied to biological macromolecules", Trends in Analytical Chemistry 17(8-9): 470-484 (1998).
Grotjahn, L., "Oligonucleotide Sputtering from Liquid Matrices", Springer Proc. Phys., 9:118-125 (1986).
Grotjahn, L., "Sequencing of Oligodeoxyribonucleotides by Negative FAB-MS", Int. J. Mass Spec. Ion Phys., 46:439-442 (1983).
Grui-Sovulj I. et al., Matrix-assisted laser desorption/ionisation mass spectrometry of transfer ribonucleic acids isolated from yeast, Nucleic Acids Res. 25(9):1859-61 (1997).
Gust et al., Taxomonic classification of Hepatitis A virus Intervirology 20:1-7 (1983).
Guyader, et al., "Genome organization and transactivation of the human immunodeficiency virus type 2", Nature 326:662-669 (1987).
Haag et al., "Rapid identification and speciation of Haemophilus bacteria by matrix-assisted laser desorption/ionization time-of-flight mass spectrometry", J. Mass Spec., 33(8):750-756 (1998).
Harada et al., "Diethanolamine Assisted Secondary Ion Mass Spectrometry of Naturally Occurring Complex Oligosaccharides", Org. Mass Spec., 17:386-391 (1982).
Hayashi, et al., "Immobilization of Thiol Proteases onto porous poly-(vinyl alcohol) beads", Polymer Journal, 25(5):489-497 (1993).
Heermann, et al., "Liquid-phase hybridization and capture of hepatitis B virus DNA with magnetic beads and fluorescence detection of PCR product", J. of Virol. Methods 50:43-58 (1994).
Herpich, Burkhard and Kreuss, "HPLC of nucleic acid components with volatile mobile phases 1. Fast nucleotide separators using ammonium carbonate and ammonium bicarbonate gradients," J. High Resolut Chromatogr, 15:41-42 (1992).
Higuchi, et al., A general method of in vitro preparation and mutagenesis of DNA fragments: Study of protein and DNA interactions, Nucleic Acids Res. 16:7351-7367 (1988).
Hillenkamp and Ehring, Laser desorption mass spectrometry Part 1: Basic mechanisms and techniques, Mass Spectrometry in the Biological Sciences: A tutorial, pp. 165-179 (1992).
Hillenkamp et al., "Matrix Assisted UV-Laser Desorption/ionization: A New Approach to Mass Spectrometry of Large Biomolecules", Bio Mass Spectr., Burlingame and McCloskey (eds.), pp. 49-61, Elsevier Science Publishers B.V., Amsterdman (1989).
Hinton et al., "The Application of Robotics to Fluorometric and Isotopic Analyses of Uranium", Laboratory Automation & Information Management, NL, Elsevier Science Publishers BV, Amsterdam, 21:223-227 (1993).
Horie, Y., et al., The functional characteristics of a human apolipoprotein E variant (cysteine at residue 142) may explain its association with dominant expression of type III hyperlipoproteinemia, J. Biol. Chem., 267:1962-1968 (1992).
Hornes and Korsnes, Magnetic DNA hybridization of oligonucleotide probes attached to superparamagnetic beads and their use in the isolation of Poly(A) mRNA from eukaryotic cells, GATA 7:145-150, (1990).
Hsiung et al., A new simpler photoaffinity analogue of peptidyl rRNA, Nucl Acids Res 1:1753-1762 (1974).
Hu, G., et al., DNA polymerase-catalyzed addition of nontemplated extra nucleotides to the 3' end of a DNA fragment, DNA and Cell Biol., 12:763-770 (1993).
Hultman et al., Direct solid phase sequencing of genomic and plasmid DNA using magnetic beads as solid support, Nucl. Acids Res. 17:4937-4946 (1989).
Hunter, et al., "Frozen-solution MALDI mass spectrometry studies of DNA" Proc SPIE-Int Soc. Opt. Eng., 2680:384-389 (1996).
Huth-Fehre et al., Matrix-assisted laser desorption mass spectrometry of oligodeoxythymidulic acids, Rapid Communications in Mass Spectrometry 6(3):209-213 (1992).
Hyman, A new method of sequencing DNA, Anal. Biochem. 174:423-436 (1988).
Ikehara, M., et al., Mechanism of hydrolysis of phosphodiesters with ribonuclease T1, Pure Appl. Chem., 59:965-968 (1987).
Innis et al., DNA sequencing with Thermus aquaticus DNA polymerase and direct sequencing of polymerase chain reaction-amplified DNA, Proc. Natl. Acad. Sci. USA 85:9436-9440 (1988).
Jacobson, et al., "Applications of mass spectrometry to DNA fingerprinting and DNA sequencing", International Symposium on the Forensic Aspects of DNA Analysis, pp. 1-18, Mar. 29-Apr. 2, 1993.
Jacobson, et al., "Applications of mass spectrometry to DNA sequencing", GATA 8(8):223-229 (1991).
Jacutin et al., Nucleic Acid Research 25(24): 5072-5076 (1997).
Jensen et al., "Mass Spectrometric Identification and Microcharacterization of Protein From Electrophoretic Gels: Strategies and Applications", Proteins: Structure, Function, and Genetics Suppl., 2:74-89 (1998).
Jespersen et al. "Attomole Detection of Proteins by Matrix-assisted Laser Desorption/Ionization Mass Spectrometry with the Use of Picolitre Vials," Rapid Communications in Mass Spectrometry 8(8): 581-584 (1994).
Jett et al., "High-Speed DNA Sequencing: An Approach Based Upon fluorescence Detection of Single Molecules", J. Bio Strut & Dynam. 7(2):301-09 (1989).
Jiang et al., "The Liquid Matrix Effects For Determinationof Oligosaccharides by LSIMS", Chin Sci. Bull, 37:1431-1435 (1992).
Jonkman et al., "Low-temperature Positive Secondary Ion Mass Spectrometry of Neat and Argon-Diluted Organic Solids", Anal. Chem., 50:2078-2082 (1978).
Kambara, H., "Characteristics of Molecular Secondary Ion Mass Spectrometry", Springer Ser. Chem. Phys., 36:357-362 (1984).
Khrapko et al., "A method for DNA sequencing by hybridization with oligonucleotide matrix", J. DNA Sequencing and Mapping 1:375-388 (1991).
Khrapko et al., An oligonucleotide hybridization approach to DNA sequencing, FEB 256(1,2):118-122 (1989).

Kim et al., "Investigation of Porphyrins and Metalloporphyrins by Liquid Matrix-Assisted Laser Desorption Mass Spectrometry", Mikrochim Acta, 113:101-111 (1994).
Kim, N.W., et al., Specific association of human telomerase activity with immortal cells and cancer, Science, 266:2011-2015 (1994).
Kirpekar et al., "7-deaza purine bases offer a higher ion stability in the analysis of DNA by matrix-assisted laser desorption/ionization mass spectrometry" Rapid Commun. Mass Spectrom. 9:525-531 (1995).
Kirpekar et al., DNA sequence analysis by MALDI mass spectrometry, Nucleic Acid Research, 26(11): 2554-2559 (1998).
Kirpekar, F., et al., Matrix assisted laser desorption/ionization mass spectrometry of enzymatically synthesized RNA up to 150 kDa, Nucleic Acid Res., 22:3866-3870 (1994).
Kolli et al., "A New Matrix for Matrix-Assisted Laser Desorption/Ionization on Magnetic Sector Instruments with Point Detectors", Rapid Comm. Mass Spec., 10:923-926 (1996).
Koster et al. Oligonucleotide synthesis and multiplex DNA sequencing using chemiluminescent detection, Nucl. Acids Res., Symposium Series No. 24:318-321, (1991).
Koster et al., N-acyl protecting groups for deoxynucleotides: A quantitative and comparative study, Tetrahedron 37:363-369 (1981).
Koster et al., Polymer support oligonucleotide synthesis—XV.sup. 1,2, Tetrahedron 40:102-112 (1984).
Koster et al., Some improvements in the synthesis of DNA of biological interest, Nucl Acids Res 7:39-59 (1980).
Koster et al., Well-Defined Insoluble Primers for the Enzymatic Synthesis of Oligo- and Polynucleotides, Hoppe-Seyler's Z. Physiol. Chem. 359:1579-1589 (1978).
Koster et al.,A strategy for rapid and efficient DNA sequencing by mass spectrometry, Nature Bio 14:1123-1128 (1996).
Kovacik, "Liquid secondary ion mass spectrometry of methyl glycosides of oligosaccharides using matrices containing carboxamides", Rapid Comm. Mass Spec., 10:1661-1667 (1996).
Kozal et al., "Extensive polymorphisms observed in HIV-1 clade B protease gene using high-density oligonucleotide arrays", Nature Medicine 2(7):753-759 (1996).
Krishnamurthy and Ross, "Rapid identification of bacteria by direct matrix assisted laser desorption/ionization mass spectrometric analysis of whole cells", Rapid Comm. Mass Spec., 10(15):1992-1996 (1996).
Krishnamurthy et al., "Biomolecules and mass spectroscopy", J. of Natural Toxins 6(2):121-162 (1997).
Kuppuswamy, et al., "Single nucleotide primer extension to detect gentic diseases: experimental application to hemophilia B (factor IX) and cystic fibrosis genes", Proc. Natl. Acad. Sci. USA 88:1143-1147 (1991).
Lagerstrom et al, "Capture PCR: Efficient amplification of DNA fragments adjacent to a known sequence in human YAC DNA," PCR Methods and Applications, 1:111-119 (1991).
Lamture et al., Direct detection of nucleic acid hybridization on the surface of a charge coupled device, Nucl. Acids Res. 22:2121-2125 (1994).
Landegren et al., "DNA Diagnostics—Molecular techniques and automation", Science 242:229-237 (1988).
Laramee et al., "Evidence for radical anion formation during liquid secondary ion mass spectrometry analysis of oligonucleotides and synthetic oligomeric analogues: a deconvolution algorithm for molecular ion region clusters", Anal. Chem., 61:2154-2160 (1989).
Lee et al., "Direct Measurement of the Forces Between Complementary Strands of DNA", Science, 266:771-773 (1994).
Lemmo et al., "Characterization of an inkjet chemical microdispenser for combinatorial library synthesis", Analytical Chem, 69(4):543-551 (1997).
Li et al. "Pulsed Laser Desorption Method for Volatilizing Thermally Labile Molecules for Suprsonic Jet Spectroscopy", Rev. Sci. Instrum., 59(4):557-561 (1988).
Li et al., "Analysis of single mammalian cell lysates by mass spectrometry", J. Am. Chem. Soc. 118:11662-11663 (1996).
Li et al., "High-Resolution MALDI Fourier Transform Mass Spectrometry of Oligonucleotides", Anal Chem 68(13):2090-2096 (1996).
Li, et al., Boron-containing oligodeoxyribonucleotide 14mer duplexes: enzymatic synthesis and melting studies, Nucl. Acids Res., 23:4495-4501 (1995).
Litborn et al., "Parallel reactions in open chip-based nanovials with continuous compensation for solvent evaporation", Electrophoresis, 21:91-99 (2000).
Little et al., "MALDI on a Chip: Analysis of Arrays of Low-Femtomole to Subfemtomole Quantities of Synthetic Oligonucleotides and DNA Diagnostic Products Dispensed by a Piezoelectric Pipet", Anal chem 69:4540-4546 (1997).
Little et al., "Mass spectrometry from miniaturized arrays for full comparative DNA analysis", Nature Med 3(12):1413-1416 (1997).
Little et al., Detection of RET proto-oncogene codon 634 mutations using mass spectrometry, J. Mol Med. 75:745-750 (1997).
Little et al., Identification of apolipoprotein E polymorphisms using temperature cycled primer oligo base extension and mass spectrometry, Short Communication, Eur J Clin Chem Clin Biochem 35(7):545-8 (1997).
Little et al., Verification of 50- to 100-mer DNA and RNA sequences with high-resolution mass spectrometry, Proc. Natl. Acad. Sci. USA 92:2318-2322 (1995).
Loboda et al., "Extraction pulse generator for time-of-flight mass spectrometry", Rev. Sci. Instrum. 66:4740-4741 (1995).
Lopez-Galindez, et al., "Characterization of genetic variation and 3'-azido-3'-deoxythymidine-resistance mutations of human immunodeficiency virus by the RNase A mismatch cleavage method", Proc. Natl. Acad. Sci, USA 88:4280-4284 (1991).
Lubman et al., "Linear Mass Reflectron with a Laser Photoionization Source for Time-of-Flight Mass Spectrometry", Anal. Chem., 55:1437-1440 (1983).
Lund et al., Assessment of methods for covalent binding of nucleic acids to magnetic beads, Dynabeads.TM. and the characteristics of the bound nucleic acids in hybridization reactions, Nucl. Acids Res. 16(22):10861-10880 (1988).
Lysov et al., "DNA sequencing by hybridisation to oligonucleotide matrix. Calculation of continuous stacking hybridisation efficiency", J Biomolec Struct Dynam., 11(4):797-812 (1994).
Lyttle et al., "Versatile Linker Chemistry for Synthesis of 3'Modified DNA", Chem Abstr. 126(18):235533k (1997).
Manoharan et al., A 2'-O-thiol tether in the ribose moiety of nucleic acids for conjugation chemistry, Gene, 149:147-156 (1994).
Martin, "New technologies for large-genome sequencing", Genome 31:1073-1080 (1989).
Maskos et al., "Oligonucleotide Hybridisations on Glass Supports: A Novel Linker for Oligonucleotide Synthesis and Hybridisation Properties to Oligonucleotides Synthesised in situ", Nucleic Acids Research 20(7): 1679-1684 (1992).
Matthews et al., "Analytical Strategies for the Use of DNA Probes", Analytical Chemistry 169: 1-25 (1988).
Matthews, et al., "Analytical strategies for the use of DNA probes", Analytical Biochemistry 169:1-25 (1988).
McCray and Trentham, "Properties and uses of photoreactive caged compounds", Annu. Rev. Biophys. Biophys. Chem. 18:239-270 (1989).
Missing author—"Mass Spectrometry used to find mass of large intact nucleic acids", Chem. Eng. News, p. 55 (1998).
Mizusawa, et al., "Improvement of the dideoxy chain termination method of DNA sequencing by use of deoxy-7-deazaguanosine triphosphate in place of dGTP", Nucleic Acids Res. 14(3):1319-1325 (1986).
Moalem et al., "Cluster formationin the vapor produced by laser pulsing of the Y1Ba2Cu307 superconducting solid", J. of Vacuum Sci. Tech., 10:3292-3299 (1992).
Moini et al., "A Moving Belt Device to Couple High-Performance Liquid Chromatography and Chemical Reaction Interface Mass Spectrometry", Bio Mass Spect 20:308-312 (1991).
Molecular Cloning: A laboratory manual, 2nd, ed., Ch. 11: Synthetic oligonucleotide probes, Sambrook, Cold Spring Harbor Laboratory Press New York, pp. 11.1-11.61 (1989).
Monforte and Becker, High-throughput DNA analysis by time-of-flight mass spectrometry, Nature Medicine 3:360-362 (1997).
Morphy, J.R. et al., "A Novel Linker Strategy for Solid-Phase Synthesis", Tetrahedron Lett., 37(18):3209-3212 (1996).

Morrison et al. (Eds.), in Organic Chemistry, published by Allyn and Bacon, Inc., Boston, Massachusetts, USA, pp. 406-409 (1973).
Mosca et al., Mass spectrometry and DNA analysis, Hemoglobin 17(3):261-268 (1993).
Murray, "DNA sequencing by mass spectrometry", J. Mass. Spect. 31:1203-1215 (1996).
Naito, H., et al., Detection of tyrosine hydroxylase mRNA and minimal neuroblastoma cells by reverse transcription-polymerase chain reaction, Eur. J. Cancer, 27:762-765 (1991).
Nakamaya et al., "Direct sequencing of polymerase chain reaction amplified DNA fragments through the incorporation of deoxymucleoside .alpha.-thiotriphosphates", Nucleic Acids Res. 16(21):9947-9959 (1988).
Nelson et al., "Accuracy of Quantification from 1D NMR Spectra Using the PIQABLE Algorithm", J. Mag. Reg., 84:95-109 (1989).
Nelson et al, Time-of-flight mass spectrometry of nucleic acids by laser ablation and ionization from a frozen aqueous matrix, Rapid Communications in Mass Spectrometry 4:348-351 (1990).
Nelson et al., Volatilization of High Molecular Weight DNA by Pulsed Laser Ablation of Frozen Aqueous Solutions, Science, 246:1585-1587 (1989).
Newton et al., "The production of PCR products with 5' single-stranded tails using primers that incorporate novel phospohoramidite intermediates", Nucl. Acids. Res. 21:1155-1162 (1993).
Nikiforov and Rogers, The use of 96-well polystyrene plates for DNA hybridization-based assays: An evaluation of different approaches to oligonucleotide immobilization, Anal. Biochem. 227:201-209 (1995).
Nikiforov et al., Genetic bit analysis: a solid phase method for typing single nucleotide polymorphisms, Nucleic Acids Res 22(20):4167-4175 (1994).
Nordhoff et al., "Comparison of IR- and UV Matrix-Assisted Laser Desorption/Ionization Mass Spectrometry of Oligodeoxynucleotides", Nuc. Acids Res., 22:2460-2465 (1994).
Nordhoff et al., "Ion stability of nucleic acids in infrared matrix-assisted laser desorption/ionization of mass spectrometry", Nuc Acids Res. 21(15):3347-3357 (1993).
Nordhoff et al., "Matrix-assisted laser desorption/ionization mass spectrometry of nucleic acids with wavelength in the ultraviolet and infrared", Rapid Comm. Mass Spectrom. 6:771-776 (1992).
Norton, J.C. et al, "Targeting Peptide Nucleic Acid-Protein Conjugates to Structural Features within Duplex DNA", Bioorg. Med. Chem., 3(4):437-445 (1995).
O'Connor PB et al., Isotopic assignment in large-molecule mass spectra by fragmentation of a selected isotopic peak, Anal Chem. 68(3):542-5 (1996).
O'Donnell et al., "High-Density, Covalent Attachment of DNA to Silicon Wafers for Analysis by MALDI-TOF Mass Spectrometry", Analytical Chemistry 69(13):2438-2443 (1997).
O'Donnell et al., "MassArray as an Enabling Technology for the Industrial-Scale Analysis of DNA", Genetic Engineering News 17(21) (1997).
O'Donnell-Maloney et al., "Microfabrication and array technologies for DNA sequencing and diagnostics", Genetic Analysis: Biomolecular Engineering 13:151-157 (1996).
O'Donnell-Maloney et al., "The development of microfabricated arrays for DNA sequencing and analysis" TIBTECH 14:401-407 (1996).
Olejnik, J. et al., Photocleavable biotin phosphoramidite for 5'-end labeling, affinity purification and phosphorylation of synthetic oligonucleotides, Nucleic Acids Res. 24:361-66 (1996).
Olsson, "Isolation and Characterization of a Tumor Necrosis Factor Binding Protein from Urine", Eur. J. Haematol., 42:270-275 (1989).
Orita et al., "Detection of Polymorphisms of Human DNA by Gel Electrophoresis as Single-Strand Conformation Polymorphisms", Proc. Natl. Acad. Sci. USA, 86:2760-2770, (1989).
Overberg et al., "Laser Desorption Mass Spectrometry. Part II Performance and Applications of Matrix-Assisted Laser Desorption/Ionization of Large Biomolecules", Mass Spect in the Biolog Science: A Tutorial 181-197 (1992).
Overberg et al., "Matrix-assisted laser desorption of large biomolecules with a TEA-CO.sub.2-laser", Rapid Comm in Mass Spectro 5(3):128-131 (1991).
Overberg, et al., "Matrix-assisted infrared-laser (2.94 um) Desorption/Ionization Mass Spectrometry of Large Biomolecules", Rapid Comm. Mass. Spectro., 4:293-296 (1990).
Pevzner et al., "1-Tuple DNA Sequencing: Computer Analysis", J.Biomol. Struct Dynamics, 7(1): 63-69 (1989).
Pevzner et al., "Improved Chips for Sequencing by Hybridization", J. Biomolec. Struct. Dynam., 9(2):399-410, (1991).
Pieles et al., Matrix-assisted laser desorption ionization time-of-flight mass spectrometry: a powerful tool for the mass and sequence analysis of natural and modified oligonucleotides, Nucleic Acids Res. 21(14):3191-3196 (1993).
Pierce Catalog, pp. T123-T154 (1994).
Pierce ImmunoTechnology Catalog, p. 57 (1993).
Plunkett, M.J. and Ellman, J.A., "A Silicon-Based Linker for Traceless Solid-Phase Synthesis", J. Org. Chem., 60:6006-6007 (1995).
Polettini et al., "Fully-automated systematic toxicological analysis of drugs, poisons, and metobolites in whole blood, urine, and plasma by gas chromatograph-full scan mass spectrometry", J. Chromatography B, 713(1):265-279 (1998).
Pomerantz et al., Determination of oligonucleotide composition from mass spectrometrically measured molecular weight, Am. Soc. Mass Spectrom. 4:204-09 (1993).
Pon et al., "Derivatization of Controlled Pore Glass Beads for Solid Phase Oligonucleotide Synthesis", Biotechniques, 6:768-770, 773-775 (1988).
Pon, et al., Derivation of controlled pore glass beads fo rsolid phase oligonucleotide synthesis, BioTechniques, 6:8, 770-775 (1988).
Porter, et al., N.sup.7-cyanoborane—2'-deoxyguanosine 5'-triphosphate is a good substrate for DNA polymerase, Biochemistry, 34:11963-11969 (1995).
Prome et al., Use of combined mass spectrometry methods for the characterization of a new variant of human hemoglobin: The double mutant hemoglobin villeparisis beta 77(EF1), J. American Society for Mass Spect 7(2):163-167 (1996).
Raftery, et al., Characterization of a mutant recombinant S100 protein usng electrospray ionization mass spectrometry. Rapid Comm. Mass Spec. 11:405-409 (1997).
Rall, S.C., Jr., et al., Structural basis for receptor binding heterogeneity of apolipoprotein E from type III hyperlipoproteinemic subjects, Proc. Natl. Acad. Sci. U.S.A., 79:4696-4700 (1982).
Rasmussen et al., Covalent immobilization of DNA onto polystyrene microwells: The molecules are only bound at the 5'end, Anal. Biochem. 198:138-142 (1991).
Ratner et al., Complete nucleotide sequence of the AIDS virus, HTLV-III, Nature 313:227-284 (1985).
Richterich et al., "Cytosine Specific DNA Sequencing with Hydrogen Peroxide", Nucl. Acids Res., 23(23):4922-4923 (1995).
Ruckman and Clarke, "Laser-induced ion mass analysis: a novel technique for solid-state examination", Vacuum, 34:911-924 (1984).
Running and Urdea, A procedure for productive coupling of synthetic oligonucleotides to polystyrene microtiter wells for hybridization capture, Biotechniques 8:276-277 (1990).
Ruppert et al., "A filtration method for plasmid isolation using microtiter filter plates", Anal. Biochem. 230:130-134 (1995).
Ruppert et al., "A rapid and high throughput method for plasmid isolations", Presented: Automation in Mapping and DNA Sequencing Conference, Aug. 31-Sep. 2, 1994.
Ruppert et al., "Preparation of plasmid DNA as Sequencing Templates in a Microtiter Plate Format", Paper presented, Cold Spring Harbor Laboratory, (1989).
Sadeghi et al., "Compact Tunable Cr:LiSAF Laser for Infrared Matrix-assisted Laser Desorption/Ionization", Rapid Comm. Mass Spec., 11:393-397 (1997).
Saiki et al., Genetic analysis of amplified DNA with immobilized sequence-specific oligonucleotide probes, Proc. Natl. Acad. Sci. 86:6230-6234 (1989).
Sarkar et al., "Human Genetic Bi-allelic Sequences (HGBASE), a Database of Intra-genic Polymorphisms", 93(5):693-694, (1998).
Schneider and Chait, Increased stability of nucleic acids containing 7-deaza-guanosine and 7-deaza-adenosine may enable rapid DNA sequencing by matrix-assisted laser desorption mass spectrometry, Nucleic Acids Res. 23(9):1570-1575 (1995).

Schoeber et al., "Accurate High-Speed Liquid Handling of Very Small Biological Samples", Biotechniques, pp. 324-329 (1993).
Schram, Karl H., "Mass Spectrometry of Nucleic Acid Components", Bio Appl of Mass Spect. 34:203-287 (1990).
Schueete et al., "Sequence Analysis of phosphorothioate oligonucleotides via matrix-assisted laser desorption ionization time-of-flight mass spectrometry," J. of Pharm. & Biomedical Analysis 13:1195-1203 (1995).
Seckinger et al., "Purfication and Biologic Characterization of a Specific Tumor Necrosis Factor Alpha Inhibitor", J. Biochem., 264/20:11966-11973 (1989).
Seela and Kehne, Palinddromic octa- and dodecanucleotides containing 2'-deoxytubercidin: Synthesis, hairpin formation, and recognition by the endodeoxyribonuclease EcoRI, Biochemistry 26:2232-2238 (1987).
Seela, F., et al., 7-deazapurine containing DNA: efficiency of c.sup.7G.sub.dTP, c.sup.7A.sub.dTP and c.sup.7I.sub.dTP incorporation during PCR-amplification and protection from endodeoxyribonuclease hydrolysis, Nucleic Acids Res., 20:55-61 (1992).
Senko et al., "Automated Assignment of Charge States From Resolved Isotopic Peaks For Multiply Charged Ions", J. Am. Soc. Mass Spec., 6:52-56 (1995).
Sequenom Advances the Industrial Genomics Revolution with the Launch of Its DNA MassArray.TM. Automated Process Line, Press Release: Sep. 28, 1998, http://www.sequenom.com/pressrelease.htm.
Sequenom Obtains Important New Patent for DNA MassArray Technology, , Press Release: May 24, 1999, http://www.sequenom.com/pr/pressreleases/52499.html.
Sequenom Obtains Patents for DNA MassArraym.sup.SM Technology, Press Release: Apr. 27, 1999, http://www.sequenom.com/pressrelease/42799.htm.
Sequenom Reports DNA MassArray.TM. Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.
Sequenom Reports On Use of Its DNA MassArray.TM. Technology to Analyze Genes Associated with Alzheimer's Disease adn Arteriosclerosis: Technology Has Applications in Drug Development, Press Release: Sep. 22, 1997, http://www.sequenom.com/pressrelease.htm.
Sequenom Signs Agreement With Bruker-Franzen Analytik to Develop Mass Spectrometer for DNA Massarray Analysis, Press Release: Jan. 12, 1998, http://www.sequenom.com/pressrelease.htm, (1998).
Sequenom Uses DNA MassArray.TM. to Sequence Section of Human Cancer-Related p53 Gene, Press Release: Mar. 27, 1998, http://www.sequenom.com/pressrelease.htm.
Shaler et al., "Effect of Impurities on the matrix-Assisted Laser Desorption Mass Spectra of Single-Stranded Oligodeoxynucleotides", Anal. Chem. 68:576-579 (1996).
Siegel et al., "Calicheamicin Derivatives Conjugated to Monolonal Antibodies: Determination of Loading Values and Distributions by Infrared and UV Matrix-Assisted Laser Desorption/Ionization Mass Spectrometry and Electrosprary Ionization Mass Spectrometry", Anal. Chem., 69:2716-2726 (1997).
Siuzdak, Gary, "The emergence of mass spectrometry in biochemical research", Proc. natl. Acad. Sci. USa 91:11290-11297 (1994).
Smith et al., Capillary zone electrophoresis-mass spectrometry using an electrospray ionization interface, Anal. Chem. 60:436-441 (1988).
Smith et al., Fluorescence detection in automated DNA sequence analysis, Nature 321:674-679 (1986).
Smith R. D., "New Developments in Biochemical mass Spectrometry: Electrospray Ionization", Anal. Chem. 62:882-899 (1990).
Solouki et al., "Attomole Biomolecule Mass Analysis by Matrix-Assisted Laser Desorption/Ionization Fourier Transform Ion Cyclotron Resonance", Anal. Chem., 11662 (1995).
Stratagene Cloning Systems, Product Catalog, p. 106 (1992).
Stratagene Product Catalog, p. 39 (1988).
Strezoska et al., DNA sequencing by hybridization: 100 bases read by a non-gel-based method, Proc. Natl. Acad. Sci. 88:10089-10093 (1991).
Szybalski et al., "Universal restriction endonucleases: designing novel cleavage specificities by combining adapter olideoxinucleotide and enzyme moieties", Gene, 40:169-173 (1985).
Tabor and Richardson, DNA sequence analysis with a modified bacteriophage T7 DNA polymerase, Proc. Natl. Acad. Sci. 84:4767-4771 (1987).
Takayama et al., "Pentanediol as a Matrix for Negative-ion Fast Atom Bombardmetn Mass Spectrometry", Org. Mass Spec., 26:1123-1124 (1991).
Tammen et al., "Proteolytic cleavage of glucagon-like peptide-1 by pancreatic B cells and by fetal calf serum analyzed by mass spectrometry", J. Chrom., 852:285-295 (1999).
Tang et al., "Improving mass resolution in MALDI/TOF analysis of DNA", (1992).
Tang et al., "MALDI-MS of restriction enzyme digested DNA," Nucleic Acid Research, 23(16):3126-3131 (1995).
Tang et al., "Matrix-assisted laser desorption/ionization mass spectrometry of immobilized duplex DNA probes", Nucleic Acids Research 23:3126-3131 (1995).
Tang et al., Detection of 500-nucleotide DNA by laser desorption mass spectrometry, Rapid Commun. Mass Spectrom. 8:727-730 (1994).
Tang et al., Matrix-assisted laser desorption/ionization of restriction enzyme-digested DNA, Rapid Commun. Mass Spectrom. 8:183-186 (1994).
Tas et al., "Characterization of virus infected cell cultures by pyrolysis/direct chemical ionization mass spectrometry", Biomed and Environ Mass Spec. 18(9):757-760 (1989).
Thompson, J.N., "Fitting Robots with white coat," Laboratory Automation and Information Management 31:173-193 (1996).
Tomer et al., "Coaxial Continuous Flow Fast Atom Bombardment for Higher-Molecular-Weight Peptides: Comparison with Static Fast Atom Bombardment and electrospray Ionization", Bio Mass Spect 20:783-788 (1991).
Traini et al., "Towards an automated approach for protein identification in proteome projects", Electrophoresis, 19:1941-1949 (1998).
Trainor, "DNA Sequencing, Automation, and the Human Genome", Anal. Chem. 62:418-426 (1990).
U.S. Appl. No. 08/988,024, filed Dec. 10, 1997.
U.S. Appl. No. 09/089,730, filed Jun. 3, 1998.
U.S. Appl. No. 09/139,386, filed Aug. 25, 1998.
U.S. Appl. No. 09/395,409, filed Sep. 14, 1999.
U.S. Appl. No. 09/541,210, filed Apr. 3, 2000.
U.S. Appl. No. 09/604,698, filed Jun. 26, 2000.
U.S. Appl. No. 09/628,478, filed Jul. 31, 2000.
U.S. Appl. No. 09/663,968, filed Sep. 19, 2000.
U.S. Appl. No. 09/678,620, filed Oct. 2, 2000.
U.S. Appl. No. 09/680,581, filed Oct. 5, 2000.
U.S. Appl. No. 09/687,483, filed Oct. 13, 2000.
U.S. Appl. No. 09/802,640, filed Mar. 9, 2001.
U.S. Appl. No. 09/834,700, filed Apr. 12, 2001.
U.S. Appl. No. 09/839,629, filed Aug. 20, 2001.
U.S. Appl. No. 09/879,341, filed Jun. 11, 2001.
U.S. Appl. No. 10/007,557, filed Nov. 6, 2001.
U.S. Appl. No. 10/037,356, filed Oct. 24, 2001.
U.S. Appl. No. 10/117,558, filed Apr. 3, 2002.
U.S. Appl. No. 10/128,680, filed Apr. 22, 2002.
U.S. Appl. No. 10/136,829, filed Apr. 30, 2002.
U.S. Appl. No. 10/145,970, filed May 13, 2002.
U.S. Appl. No. 10/202,189, filed Jul. 22, 2002.
U.S. Appl. No. 10/272,756, filed Oct. 15, 2002.
U.S. Appl. No. 10/273,228, filed Oct. 15, 2002.
U.S. Appl. No. 10/273,321, filed Oct. 15, 2002.
U.S. Appl. No. 10/273,665, filed Oct. 15, 2002.
U.S. Appl. No. 10/281,428, filed Oct. 25, 2002.
U.S. Appl. No. 10/281,464, filed Oct. 25, 2002.
U.S. Appl. No. 10/281,476, filed Oct. 25, 2002.
Valaskovic et al., "Attomole protein characterization by capillary electrophoresis-mass spectrometry", Science 273:1199-1202 (1996).

Valaskovic, et al., Attamole-sensitivity electrospray source for large-molecule mass spectrometry, Anal. Chem. 67:3802-3805 (1995).
Vorm et al., "Improved Mass Accuracy in Matrix-Assisted Laser Desorption/Ionization Time-of-Flight Mass Spectrometry of Peptides", J. Am. Soc. for Mass Spec., 5(N11):955-958 (1994).
Wahlberg et al., "Rapid detection and sequencing of specific in vitro amplified DNA sequences using solid phase methods", Mol. Cell. Probes 4(4): 285-297 (1990).
Wain-Hobson et al., Nucleotide sequence of the AIDS virus, LAV, Cell 40:9-17 (1985).
Walker et al., Multiplex strand displacement amplification (SDA) and detection of DNA sequences from Mycobacterium tuberculosis and other mycobacteria, Nucleic Acids Res. 22(13):2670-2677 (1994).
Wallace, "Ink-jet based fluid microdispensing in biochemical applications", Laboratory Automation News 1(15):6-9 (1996).
Wang, Solid phase synthesis of protected peptides via photolytic cleavage of the .alpha.-methylphenacyl ester anchoring linkage, J. Org. Chem. 41(20):3258-3261 (1976).
Welham et al., "The rapid identification of intact microorganisms by matrix-assisted laser desorption/ionization time-of-flight mass spectrometry", Pharmacy and Pharmacology Comm. 4(2):81-87 (1998).
Wiedmann M. et al., Ligase chain reaction (LCR)—overview and applications, PCR Methods Appl. 3(4):S51-S64 (1994).
Williams et al., "p-Nitroaniline/glycerol: A binary Liquid Matrix for Matrix-assisted Laser Desorption/Ionization Analysis", Eur. Mass Spec., 4:379-383 (1998).
Williams, Time of flight mass spectrometry of DNA laser-ablated from frozen aqueous solutions: applications to the Human Genome Project, Intl. J. Mass Spectrom. and Ion Processes 131:335-344 (1994).
Wolter et al., Negative ion FAB mass spectrometric analysis of non-charged key intermediated in oligonucleotide synthesis: rapid identification of partially protected dinucleoside monophosphates, Biomedical Environmental Mass Spectrometry 14:111-116 (1987).
Wolter, "Influence of the matrix on the analysis of small oligoribonucleotides by fast atom bombardment mass spectrometry,", J. Mass Spec., 30:485-491 (1995).
Wong, Conjugation of proteins to solid matrices, Chemistry of Protein Conjugation and Cross-Linking 12:295-317 (1993).
Wu et al., "Matrix-assisted Laser Desorption Time-of-flight Mass Spectrometry of Oligonucleotides Using 3-Hydroxypicolinic Acid as an Ultraviolet-sensitive Matrix", Rapid Comm Mass Spec 7:142-146 (1993).
Wu et al., "Time-of-Flight Mass Spectrometry of Underivatized Single-Stranded DNA Oligomers by Matrix-Assisted Laser Desorption", Anal. Chem. 66:1637-1645 (1994).
Wu et al., Allele-specific enzymatic amplification of .beta.-globin genomic DNA for diagnosis of sickle cell anemia, Proc. Natl. Acad. Sci. USA 86:2757-2760 (1989).
Wu et al., The ligation amplification reaction (LAR)-amplification of cific DNA sequences using sequential rounds of template-depetion Genomics, 4:560-569, (1989).
Yang, et al., "Detection of hepatitis B virus in plasma using flow cytometric analyses of polymerase chain reaction-amplified DNA incorporating digoxigenin-11-dUTP", Blood 81(4):1083-1088 (1993).
Yau et al., "Threshold fluences for production of positive and negative ions in matrix-assisted laser desorption/ionization using liquid and solid matrices", Chem. Phys. Lett., 202:93-100 (1993).
Yoshida et al., "Detection of High Mass Molecular Ions by Lasr Desorption Time-of-Flight Mass Spectrometry", Shitsuryo Bunscki, 36:59-69 (1988).
Youil et al., "Screening for Mutations by Enzyme Mismatch Cleavage with T4 Endonuclease VII", Proc. Natl. Acad. Sci. USA, 92:87-91, (1995). cited by other.
Zhang et al., Single-base mutational analysis of cancer and genetic diseases using membrane bound modified oligonucleotides, Nucl. Acids Res. 19:3929-3933 (1991).
Zimmermann et al., Automated preparation and purification of M13 templates for DNA sequencing, Meth. Mol. Cell. Biol. 1:29-34 (1989).
Zuckerman et al., Efficient methods for attachment of thiol specific probes to the 3'-ends of synthetic oligodeoxyribonucleotides, Nucleic Acids Research, 15:13, 5305-5321 (1987).
"Time of Flight Mass Spectrometry of DNA for Rapid Sequence Determination. Technical Progress Report, Jul. 31, 1991-Jul. 31, 1992" Arizona State University, Tempe, AZ (1992).
Agrawal et al., Efficient methods for attaching non-radioactive labels to the 5' ends of synthetic oligodeoxyribonucleotides, Nucleic Acids Res. H:6227-6245 (1986).
Ardrey, "Electrospray mass spectrometry", Spectroscopv Europe 4(4):10-18 (1992).
Benner et al., Identification of denatured double-stranded DNA by matrix-assisted laser desorptionlionization time-of-flight mass spectrometry, Rapid Commun. Mass Spectrom., 9:537-540 (1995).
Brekenkamp et al., Infrared MALDI mass spectrometry of large nucleic acids, Science 281 :260-2 (1998).
Boguski, M.S., et al., Identification of a cytidine-specific ribonuclease from chicken liver, J. Biol. Chem., 255:2160-2163 (1980).
Bray, et al., "Direct Cleavage of Peptides from a Solid Support into Aqueous Buffer. Application in Simultaneous Multiple Peptide Synthesis", J. Orn. Chem., 56:6659-6666 (1991).
Breslow, R., et al. , Recognition and catalysis in nucleic acid chemistry, Proc. Natl. Acad. Sci. USA, 90:1201-1207 (1993).
Caldwell et al., Mid-infrared matrix assisted laser desorption ionization with a water/glycerol matrix, Applied Surface Science 127-1 29:242-247 (1998).
Cantor and Schimmel, Biophysical Chemistry Part 1: The conformation of Biomolecules, W.H. Freeman, New York, p. 176, (1980).
Cantor C.R. et al., Massive attack on high-throughput biology, Nat Genet. 20(7):5-6 (1998).
Cantor C.R., How will the Human Genome Project improve our quality of life? Nat Biotechnol. 16(3):212-3 (1998).
Certified English Language translation of the PCT Application filed under No. PCT/EP97/103571, published under No. WO 98/03257, provide by the Australian Patent Office, for application No. AU 3541997, (1990).
Certified English translation of European patent 0412883A1, Fast screening and/or identification of a single base on a nucleic acid sequence, including applications, (1990).
Certified English translation of Japanese patent 6-294796, Nucleic acid analysis method, (1989).
Chakrabarti et al., Sequence of simian immunodeficiency virus from macaque and its relationship to other human and simian retrovirues, Nature 328:543-547 (1987).
Chen, et al., "Laser mass spectrometry for DNA fingerprinting for forensic applications", Annual Meeting of the Societv of Photo Optical Instrumentation Engineers, Jul. 24-29, 1994.
Chorush R.A. etal., Surface-induced dissociation of multiply-protonated proteins, Anal Chem. 67(6):1042-6 (1995).
Cohen. J. et al. . "Exploiting the HIV-chemokine Nexus", Science, 275:1261-64 (1997).
Covey et al., The determination of protein, oligonucleotide and peptide molecular weights by ionspray mass spectrometry, Rapid Communications in Mass Spectrometry 2(11): 249-256 (1988).
Das, H.K., et al., Isolation, characterization, and mapping to chromosome 19 of the human apolipoprotein E gene, J, Biol. Chem., 260:6240-6247 (1985).
Database WPI, Derwent Publication #199615, citing German Patent No. 4431174 A, Detecting tumour specific mRNA by conversion to cDNA and amplification—provides early, sensitive and specific diagnosis and monitoring, partic. by analysis of blood or sputum, (1988).
Database WPI, Derwent Publication #1996623, citing German Patent No. 4438630A, Amplificatiion of non-characterised DNA fragments—using only a single primer, with formation of hairpin loops during second strand synthesis, (1992).
Database WPI, Derwent Publications #198350, citing German Patent No. DE3221681 (1990).
Database WPI, Derwent Publications #198749, citing French Patent No. 2597260 (1992).
Database WPI, Derwent Publications #198844, citing Japanese Patent No. JP63230086 published Sep. 26, 1988.

Database WPI, Derwent Publications #199018, citing German Patent No. DE3930312 published Apr. 26, 1990.
Database WPI, Derwent Publications # 199040, citing Japanese Patent No. JP2215399 published Aug. 28, 1990.
Database WPI, Derwent Publications #199043, citing German Patent No. DE4011991 published Oct. 18, 1990.
Database WPI, Derwent Publications #199703, citing Japanese Patent No. 8290377 published Nov. 5, 1996.
DeGrado, W.F. and Kaiser, E.T., "Polymer-Bound Oxime Esters as Supports for Solid-Phase Peptide Synthesis. Preparation of Protected Peptide Fragments", J. Org. Chem., 45:1295-1300 (1980).
Doktycz, et al., Analysis of polymerase chain reaction-amplified DNA products by mass spectrometry using matrix-assisted laser desorption and electrospray: current status, Anal. Biochem., 230:205-214 (1995).
Donis-Keller, H., et al., Mapping adenines, guanines, and pyrimidines in RNA, Nucleic Acids Res., 4:2547-2537 (1977).
Donis-Keller, H., et at., Phy M: an RNase activity specific for U and A residues useful in RNA sequence analysis, Nucteic Acids Res., 8:3133-3142 (1977).
Eckstein (ed.), Oliqonucleotides and Analoques, IRL Press, Oxford (1991).
Eckstein and Goody, Synthesis and properties of diastereoisomers of adenosine 5'-(O-1-thiotriphosphate) and adenosine 5'-(O-2-thiotriphosphate), Biochemistry—(8):1685-1691 (1976).
Eckstein, F., Phosphorothioate analogues of nucleotides, Accounts Chem. Res. 2:204-210 (1979).
Eckstein, Nucleoside phosphorothioates, Ann. Rev. Biochem. 54:367-402 (1985).
Edmonds et al., Thermospray liquid chromatography-mass spectrometry of nucleosides and of enzymatic hydrolysates of nucleic acids, Nucleic Acids Research 13:8197-8206 (1985).
Eggers et al., "A microchip for quantitative detection of molecules utilizing luminescent and radioisotope reporter groups", Bio Techniques 17:516-524 (1994).
Ehring et al., Photochemical versus thermal mechanisms in matrix-assisted laser desorptionlionization probed by back side desorption, Rapid Comm in Mass Spect 10:821-824 (1996).
Yolov et al., Synthesis of RNA using T7 RNA polymerase and immobilized DNA in a stream type reactor, Biooraanicheskala Khhimia, 17(6) 789-794 (1991 ).
English Language translation of Yolov et al., Biooraanicheskala Khhimia, 17(6) 789-794 (1991).
Eperon, I. C., Rapid preparation of bacteriophage DNA for sequence analysis in sets of 96 clones, using filtration, Anal. Biochem 1 56:406-412 (1986).
Fattom et al. , "Comparative immunogenicity of conjugates composed of the *Staphylococus aureus* type 8 capsular polysaccharide bound to carrier proteins by adipic acid dihydrazide or N-succinimidyl-3-(2-Pyridyldithio)propionate" Infection & Immun. 60: 584-589 (1992).
Feng, J., et al., The RNA component of human telomerase, Science, 269(5228):1236-41 (1995).
Fujita et al., Surprising lability of biotin-streptavidin bond during transcription of biotinylated DNA bound to paramagnetic beads, BioTechniaues 14:608-617 (1993).
Gayo, L.M. and Suto, M.J., "Traceless Linker: Oxidative Activation and Displacement of a Sulfur-Based Linker", Tetrahedron Lett., 38(2):21 1-21 4 (1997).
Goh, et al., p53 mutation and survival in colorectal cancer patients, Cancer Res., 55:5217-5221 (1995).
Goldmacher et al., Photoactivation of toxin conjugates, Bioconiugate Chem. 3:104-107, (1992).
Graber J.H. et al., Advances in DNA diagnostics, Curr Opin Biotechnol. 9(1): 14-8 (1998).
Graber J.H. et al., Differential sequencing with mass spectrometry, Genet Anal. 14(5-6):215-9 (1999).
Greenblatt, et al,, Mutations in the p53 tumor suppressor gene: clues to cancer etiology and molecular pathogenesis, Cancer Res., 54:4855-4878 (1994).
Gross et al., Investigations of the metastable decay of DNA under ultraviolet matrix-assisted laser desorptionlionization conditions with post-source-decay analysis and hydrogenldeuterium exchange, J Amer Soc for Mass Spect 9:866-878 (1998).
Gupta, R.C., et al., Use of specific endonuclease cleavage in RNA sequencing, Nucleic Acids Res., 4:1957-1978 (1977).
Haglund et al., Marix-assisted laser-desorption mass spectrometry of DNA using an infrared freeelectron laser, SPIE 1854: 117-128 (1993).
Hahner, S., et al., "Sequencing of nucleic acids by MALDI-MS," Proceedings ASMS Conference on Mass Spectrometry and Allied Topics, Portland, Oregon, (44th) 1996 p. 983.
Hainaut, et al., Database of p53 gene somatic mutations in human tumors and cell lines: updated compilation and future prospects, Nucleic Acids Res., 25:151-7 (1997).
Harris, C.C., The 1995 Walter Hubert lecture—molecular epidemiology of human cancer: insights from the mutational analysis of the p63 tumour-suppressor gene, British J. Cancer, 73:261-269 (1996).
Han, Y. et al., "Silicon Directed ipso-Substitution of Polymer Bound Arylsilanes: Preparation of Biaryls via the Suzuki Cross-Coupling Reaction", Tetrahedron Lett., 37(16):2703-2706 (1996).
Hasan, et al., Base-boronated dinucleotides: synthesis and effect of N7-cyanoborane substitution on the base protons, Nucleic Acids Res., 24:2150-2157 (1996).
Hazum et al., A photocleavable protecting group for the thiol function of cysteine, Pept., Proc. Eur. Pept. Symp., 16th, Brunfeldt, K (Ed), pp. 105-110 (1981).
Heinemann, U.W., et al., Mechanism of guanosine recognition and RNA hydrolysis by ribonuclease, T, Pure Appl. Chem., 57:417-422 (1985).
Higgins, G.S., et al., Competitive oligonucleotide single-base extension combined with mass spectrometric detection for mutation screening, Biotechniques 23(4):710-4 (1997).
Higuchi, et al., Kinetic PCR analysis: Real-time monitoring of DNA amplification reactions, BiolTechnoloay 11: 1026-1 030 (1993).
Hixson, Restriction isotyping of human apolipoprotein E by gene amplification and cleavage with Hhal, J. Lipid Res., 31 :545-549 (1990).
Hobbs and Eckstein, A general method for the synthesis of 2'-azido-2'deoxy-and 2'-amino-2'-deoxyribofuranoxyl purines, J. Org. Chem. 42:714-719 (1976).
Jain, Delivery of molecular medicine to solid tumors, Science, 277:1079-1080 (1996).
Jennings, et al., Fetal neuroblastoma: prenatal diagnosis and natural history, J. Ped. Surgery, 28:1168-1174 (1993).
Ji et al. , Two-dimensional electrophoretic analysis of proteins expressed by normal and cancerous human crypts: Application of mass spectrometry to peptide-mass fingerprinting, Electrophoresis 15:391-405 (1994).
Juhasz, P., et al., Applications of delayed extraction matrix-assisted laser desorption ionization time-of-flight mass spectrometry to oligonucleotide analysis, Anal. Chem. 68:941-946 (1996).
Jurinke et al., Analysis of lisase chain reaction products via matrix-assisted laser desorption/ionization time-2-flight-mass spectrometry, Anal Biochem 237:174-181 (1996).
Jurinke et al., Application of nested PCR and mass spectrometry for DNA-based virus detection: HBV-DNA detected in the majority of isolated anti-HBc positive sera, Genetic Analysis 14:97-102 (1998).
Jurinke et al., Detection of hepatitis B virus DNA in serum samples via nested PCR and MALDI-TOF mass spectrometry, Genetic Analysis 13:67-71 (1996).
Jurinke et al., Recovery of nucleic acids from immobilized biotin-streptavidin complexes using ammonium hydroxide and applications in MALDI-TOF mass spectrometry, Anal. Chem. 69:904-910 (1997).
Kaldor, S.W. et al., "Use of Solid Supported Nucleophiles and Electrophiles for the Purification of Non-Peptide Small Molecule Libraries", Tetrahedron Lett., 37(40):7193-7196 (1996).
Karas, et al. , UV laser matrix desorptionlionization mass spectrometry of proteins in the 100,000 dalton range, J. Mass Spectrom., Ion Processes, 92:231 (1989).
Kumar, G. and Poonian, M.S., "Improvements in Oligodeoxyribonucleotide Synthesis: Methyl N,N-Dialkylphosphoramidite Dimer Units for Solid Support Phosphite Methodology", J. Orn. Chem., 49:4905-4912 (1984).

Kussmann, et al. , Matrix-assisted laser desorption/ionization mass spectrometry sample preparation techniques designed for various peptide and protein analytes, J. Mass Spec. 32: 593-601 (1997).
Labeit et al., Laboratory methods: A new method of DNA sequencing using deoxynucleoside uthiotriphophates, DNA 5:173-177 (1986).
Lawrance et al., Megabase-scale mapping of the HLA gene complex by pulsed field gel electrophoresis, Science 235:1387-1389 (1987).
Lecchi, et al., "The detection of intact double-stranded DNA by MALDI" J. Am. Soc. Mass Spectrom., 6:972 (1995).
Leonard et al., High-resolution structure of mutagenic lesion in DNA, Proc. Nat. Acad. Sci. Biochemistry, 87:9573-9576, (1990).
Leznoff, C.C. and Wong, J.Y., "The Use of Polymer Supports in Organic Synthesis. The Synthesis of Monotrityl Ethers of Symmetrical Diols", Can. J. Chem., 50:2892-2893 (1972).
Limbach, P.A., et al., Molecular mass measurement of intact ribonucleic acids via electrospray ionization quadrupole mass spectrometry, J. Am. Soc. Mass. Spectrom., 6:27-39 (1995).
Little, D.P., et al., Rapid sequencing of oligonucleotides by high-resolution mass spectrometry, J. Am. Chem. Soc., 7 76:4893-4897 (1994).
Little et al,, "Direct detection of synthetic and biologically generated double-stranded DNA by MALDI-TOF MS", J. Mass Spec 17:1-8 (1997).
Liu, et al., Use of a nitrocellulose film substrate in matrix-assisted laser desorption/ionization mass spectrometry for DNA mapping and screening, Anal. Chem., 67:3482 (1995).
Lloyd-Williams, P. et al., "Convergent Solid-Phase Peptide Synthesis", Tetrahedron, 49(48):11065-11133 (1993).
Lorsbach, B.A. et al., "Reissert-Based "Traceless" Solid-Phase Synthesis: Isoquinoline, and Isoxazoline-Containing Heterocycles", J. Org. Chem., 61 :8716-8717 (1996).
Mann, W.A., et al., Dominant expression of Type III hyperlipoproteinemia, J. Clin. Invest., 96:1100-1107 (1995).
Marshall, A.G., et al., Fourier transform ion cyclotron resonance mass spectrometry: the teenage years, Anal, Chem. 63:215A-229A (1991).
Marshall and Hodgson, "DNA chips: An array of possibilities", Nature Biotechnology 16:27-31 (1998).
Matteucci et al., Synthesis of deoxyoligonucleotides on a polymer support, J. A. Chem. Soc. 103:3185-3191, 1981.
Maxam and Gilbert, Sequencing end-labeled DNA with base-specific chemical cleavages, Methods in Enzvmology 65:499-560 (1980).
McLafferty, et al., Double stranded DNA sequencing by tandem mass spectrometry, Intl. J. Mass Spectrom., Ion Processes 165/166:457-466 (1997).
Methods of Enzymol., vol. 193 Mass Spectrometry (McCloskey, editor), p. 425, Academic Press, New York (1990).
Miyazaki, et al., The first Japanese case of Hb Santa Ana, an unstable abnormal hemoglobin, identified rapidly by electrospray ionization mass spectrometry. Internal Medicine 36:365-370 (1997).
Newlander, K.A. et al., "Simple Silyl Linker for the Solid Phase Organic Synthesis of Aryl-Containing Molecules", J. Org. Chem., 62:6726-6732 (1997).
Nielsen, et al., Sequence-selective recognition of DNA by strand displacement with a thymine-substituted polyamide, Science, 254: 1497 (1991).
Oliqonucleotides and Analogues: A Practical Approach, Eckstein, edr., Oxford University PressCh. 3, pp. 49-59, 137-1 39, 255-259 (1991).
Ordoukhanian, P., et al., Design and synthesis of a versatile photocleavable DNA building block: application to phototriggered hybridation, Journal of the Amerian Chemical Society, 7 7 7:9570-71 (1995).
Ornstein et al., Sequencing DNA using 35S-labeling: A troubleshooting guide, Biotechniques 3:476-483 (1985).
Palejwala et aL., Quantitative Multiplex Sequence Analysis of Mutational Hot Spots. Frequency and Specificity of Mutations Induced by a Site-Specific Ethenocytosine in M13 Viral DNA, Biochemistry 32:4105-4111 (1993).
Pasini B., et al., RET mutations in human disease, Trends in Genetics, 12(14):138-44 (1996).
Patek, M. and Lebl, M., "Safety-Catch Anchoring Linkage for Synthesis of Peptide Amides by Boc/Fmoc Strategy", Tetrahedron Lett., 32(31):3891-3894 (1991).
Qiagen catalog for Plasmid DNA, pp. 6-7, Feb. (1991).
Rink, "Solid-phase synthesis of protected peptide fragments using a trialkoxy-diphenylmethlester resin", Tetrahedron Lett. 28:3787-3790 (1987).
Rojo, M.A., et al., Cusativin, a new cytidine-specific ribonuclease accumulated in seeds of Cucumis sativus L., Planta, 794:328:338 (1994).
Routledge, A. et al., "The Use of a Dithiane Protected Benzoin Photolabile Safety Catch Linker for Solid Phase Synthesis", Tetrahedron Lett., 38(7): 1227-1 230 (1997).
Saha et al,, "Diisopropylsilyl-linked oligonucleotide analogs: Solid-phase synthesis and physicochemcial properties," J. Orn. Chem. 58:7827-7831 (1993).
Salmon, S.E. et al., "Discovery of Biologically Active Peptides in Random Libraries: Solution Phase Testing after Staged Orthogonal Release from Resin Beads", Proc. Natl. Acad. Sci. USA, 90:11708-1 171 2 (1993).
Sanger et al., DNA sequencing with chain-terminating inhibitors, Proc. Natl. Acad. Sci. 74:5463-67 (1977).
Sasaki et al., Introduction of an azide group into some uridine derivatives via 2',3'-benzoxonium and 2',3'-azidonium intermediates, J. Org. Chem. 41:3138-3143 (1976).
Schlesinger, D. H ., Macromolecular Sequencing and Synthesis: Selected Methods and Applications, Alan R. Liss, Inc., New York, pp. 127-149 (1988).
Senter et al., Novel photocleavable protein crosslinking reagents and their use in the preparation of antibody-toxin conjugates, Photochem. Photobiol. 42:231-237, (1985).
Shaler et al., "Analysis of enzymatic DNA sequencing reactions by matrix-assisted laser desorption/ionization time-of-flight mass spectometry", Rapid Commun Mass Spectrom 9(10):942-947 (1995).
Sidransky, D., et al., Clinical implications of the p53 gene, Annu. Res. Med., 47:285-301 (1996).
Siegert et al., "Matrix-assisted laser desorption/ionization time-of-flight mass spectrometry for the detection of polymerase chain reaction products containing 7-deazapurine moieties", Analytical Biochemistry 243:55-65 (1996).
Singh et al., Oligonucleotides, part 5+:synthesis and fluorescence studies of DNA oligomers d(AT)5 containing adenines covalently linked at C-8 with dansyl fluorophore, Nucleic Acids Res. 18(11):3339-3345 (1990).
Sinha et al. , B-cyanoethyl N, N-dialkylamino/N-morpholinomonochloro phosphoamidites, new phosphitylating agents facilitating ease of deprotection and work-up of synthesized oligonucleotides, Tetrahedron Lett. 24:5843 5846 (1983).
Sinha et al., Polymer support oligonucleotide synthesis XVIII: use of B-cyanoethyl-N,N-dialkylamino-/N-morpholino phosphoramidite of deoxynucleosides for the synthesis of DNA fragments simplyfying deprotection and isolation of the final product, Nucleic Acids Res. 12: 4539-4557 (1984).
Slim et al., Configurationally defined phosphorothioate-containing oligoribonucleotides in the study of the mechanism of cleavage of hammerhead ribozymes, Nucleic Acids Res. 19:1183-1188 (1991).
Smit, M., et al. , Genetic heterogeneity in familial dysbetalipoproteinemia. The E2(lysl46) gln) variant results ina dominant mode of inheritance, J. Lipid Res., 31:45-53 (1990).
Sproat et al., The synthesis of protected 5'-amino-2',5'-dideoxyribonucleoside-3'-0-phosphoramidites; applications of 5'-amino-oligodeoxyribonucleotides, Nucleic Acids Res. 15:6181-6196 (1987).
Stahl, et al., "Solid phase DNA sequencing using the biotin-avidin system", Nucleic Acids Res. 16(7):3025-3039 (1988).
Stults and Marsters, Rapid Comm. Mass Spetrom. 5:359-363 (1991).
Swerdlow and Gesteland, Capillary gel electrophoresis for rapid, high resolution DNA sequencing, Nucleic Acids Res. 18(6):1415-1 419 (1990).
Syvanen, A.C., et al., Detection of point mutations by solid-phase methods, Human Mutation, 3(3):172-9 (1994).

Thuong and Asseline, Oligonucleotides attached to intercalators, photoreactive and cleavage agents, Olinonucleotides and Analoques: A Practical Approach, Eckstein, edr., Oxford University Press Ch. 12, pp. 283-308 (1991).

Tong et al., Solid-phase method for the purification of DNA sequencing reactions, Anal. Chem. 64: 2672-2677, (1992).

Uhlmann et al., Antisense Oligonucleotides: A New Therapeutic Principle, Chemical Reviews, 90(4):544-583 (1990).

van den Boom D et al., Combined amplification and sequencing in a single reaction using two DNA polymerases with differential incorporation rates for dideoxynucleotides, J. Biochem Biophys Methods. 35(2):69-79 (1997).

van den Boom D et al., Forward and reverse DNA sequencing in a single reaction, Anal Biochem. 256(1): 127-9 (1998).

van Maarseveen, J.H. et al., "Solid Phase Ring-Closing Metathesis: Cyclization/Cleavage Approach towards a Seven Membered Cycloolefin", Tetrahedron Lett., 37(45):8249-8252 (1996).

Vorm, et al., Improved resolution and very high sensitivity in MALDI TOF of matrix surfaces made by fast evaporation, Anal. Chem. 66:3281-3287 (1994).

Wardell, M.R., et al. , Apolipoprotein E2—Christchurch (136 Arg J Ser) New variat of human apolipoprotein E in a patient with type III hyperlipoproteinemia, J. Clin. Invest., 80:483-490 (1987).

Weisgraber, K.H., et al., A novel electrohoretic variant of human apolipoprotein E, J. Clin. Invest., 73:1024-1033 (1984).

Wellhoner et al., Uptake and concentration of bioactive macromolecules by K562 cells via the transferrin cycle utilizing an acid-labile transferrin conjugate, J. Biol. Chem. 256:4309-4314 (1991).

Wood TD et al., Direct sequence data from heterogeneous creatine kinase (43 kDa) by highresolution tandem mass spectrometry, Biochemistry 34(50): 16251-4 (1995).

Yamashita et al., Electrospray ion source. Another variation on the free-jet theme, J. Phys. Chem. 88:4451-4459, (1984).

Yates, III, Mass spectrometry and the age of the proteome, J. Mass Spec. 33:1-19 (1998).

Yen et al., Synthesis of water-soluble copolymers containing photocleavable bonds, Makromol. Chem. 190:69-82 (1989).

* cited by examiner

MOLECULAR WEIGHT OF THE VARIABLE FRAGMENTS IN Da:

| | | | ε2/ε2 | ε3/ε3 | ε4/ε4 | ε2/ε3 | ε2/ε4 | ε3/ε4 |
|---|---|---|---|---|---|---|---|---|
| 91 bp | SENSE<br>ANTISENSE | 28421<br>27864 | X | X | | X | X | X |
| 83bp | SENSE<br>ANTISENSE | 25747<br>25591 | X | | | X | X | |
| 72bp | SENSE<br>ANTISENSE | 22440<br>21494 | | | X | | X | X |
| 48bp | SENSE<br>ANTISENSE | 14844<br>14857 | | X | X | X | X | X |
| 35bp | SENSE<br>ANTISENSE | 10921<br>10751 | | X | X | X | X | X |

```
                   506507508
                   IleIlePhe
ACCATTAAAGAAAATATCATCTTTGGTGTTTCCTATGATGAATATAGAAGCGTCATC
primer                       ACCACAAAGGATACTACTTATATC  (7289,8)
wildtype                  TAGAAACCACAAAGGATACTACTTATATC  (8846,8)
ΔF508                     TA---ACCACAAAGGATACTACTTATATC  (7891,2)
ΔI507                   TAG---AAACCACAAAGGATACTACTTATATC  (8846,8)
```

FIG. 34A

```
                   506507508
                   IleIlePhe
ACCATTAAAGAAAATATCATCTTTGGTGTTTCCTATGATGAATATAGAAGCGTCATC
primer                       ACCACAAAGGATACTACTTATATC  (7289,8)
wildtype     CTTTTATAGTAGAAACCACAAAGGATACTACTTATATC  (11612,6)
ΔF508        CTTTTATAGTA---ACCACAAAGGATACTACTTATATC  (10657,0)
ΔI507        CTTTTATAG---AAACCACAAAGGATACTACTTATATC  (10666,0)
506Ser                 CGTAGAAACCACAAAGGATACTACTTATATC  (9465,2)
```

FIG. 34B

...AACGTGCTGCCTTCCACCGCGATGTTGATGATTATGTGTCTGAATTTGATGGGGGCAGGCGGCCCCCGGTGTGTTTGTCGCGGGTCTGGTGTTGATGGTGGTT TCCTGCCT
...TTGCACGACGGAAGGTGGCGCTACAACTACTAATACACAGACTTAAACTACCCCCGTCCGCCGGGGGCAGACAAACAGCGCCCAGACCACAACTACCACCAA AGGACGGA

CTTCCACCGCGATGTTGA
18-mer REVERSE PRIMER (200-mer)

19-mer PRIMER
TGACCGGCAGCAAAATGTT

TGTCACCCTCGACCTGCAGCCCAAGCTTGGGATCCACCACCATCACCATCACTAATAATGCATGGGCTGCAGCCAATTGGCACTGGCCGTCGTTTTACAACGTCGTG...
ACAGTGGGAGCTGGACGTCGGGTTCGAACCCTAGGTGGTGGTAGTGGTAGTGATTATTACGTACCCGACGTCGGTTAACCGTGACCGGCAGCAAAATGTTGCAGCAC...

GTCACCCTCGACCTGCAG
18-mer REVERSE PRIMER (99-mer)

FIG. 36

17-mer PRIMER
TGACCGGCAGCAAAATG

...ACACAGGAAACAGCTATGACCATGATTACGAATTCGAGCTCGGTACCCGGGGATCCTCTAGAGTCGACCTGCAGGCATGCAAGCTTGGCACTGGCCGTCGTTTTACAACG...
...TGTGTCCTTTGTCGATACTGGTACTAATGCTTAAGCTCGAGCCATGGGCCCCTAGGAGATCTCAGCTGGACGTCCGTACGTTCGAACCGTGACCGGCAGCAAAATGTTGC...

CAGGAAACAGCTATGAC
17-mer PRIMER

FIG. 37

PARTIAL SEQUENCE OF THE β-GLOBIN TEMPLATE

3'-$(H)_n$-ACCACGTGGACTGAG GACACCTCTT CAGACGGCAA TGACGGGACA CCCCGTTCCA CTTGCACCTA-$(N)_n$-5'

5'-TGCACCTGACTC-3' (PRIME)
5'-TGCACCTGACTC C-3'
5'-TGCACCTGACTC CT-3'
5'-TGCACCTGACTC CTG-3'
5'-TGCACCTGACTC CTGT-3'
5'-TGCACCTGACTC CTGTG-3'
5'-TGCACCTGACTC CTGTGG-3'
5'-TGCACCTGACTC CTGTGGA-3'
5'-TGCACCTGACTC CTGTGGAG-3'
5'-TGCACCTGACTC CTGTGGAGA-3'
5'-TGCACCTGACTC CTGTGGAGAA-3'

5'-TGCACCTGACTC CTGTGGAGAA G-3'
5'-TGCACCTGACTC CTGTGGAGAA GT-3'
5'-TGCACCTGACTC CTGTGGAGAA GTC-3'
5'-TGCACCTGACTC CTGTGGAGAA GTCT-3'
5'-TGCACCTGACTC CTGTGGAGAA GTCTG-3'
5'-TGCACCTGACTC CTGTGGAGAA GTCTGC-3'
5'-TGCACCTGACTC CTGTGGAGAA GTCTGCC-3'
5'-TGCACCTGACTC CTGTGGAGAA GTCTGCCG-3'
5'-TGCACCTGACTC CTGTGGAGAA GTCTGCCGT-3'
5'-TGCACCTGACTC CTGTGGAGAA GTCTGCCGTT-3'

5'-TGCACCTGACTC CTGTGGAGAA GTCTGCCGTT A-3'
5'-TGCACCTGACTC CTGTGGAGAA GTCTGCCGTT AC-3'
5'-TGCACCTGACTC CTGTGGAGAA GTCTGCCGTT ACT-3'
5'-TGCACCTGACTC CTGTGGAGAA GTCTGCCGTT ACTG-3'
5'-TGCACCTGACTC CTGTGGAGAA GTCTGCCGTT ACTGC-3'
5'-TGCACCTGACTC CTGTGGAGAA GTCTGCCGTT ACTGCC-3'
5'-TGCACCTGACTC CTGTGGAGAA GTCTGCCGTT ACTGCCC-3'
5'-TGCACCTGACTC CTGTGGAGAA GTCTGCCGTT ACTGCCCT-3'
5'-TGCACCTGACTC CTGTGGAGAA GTCTGCCGTT ACTGCCCTG-3'
5'-TGCACCTGACTC CTGTGGAGAA GTCTGCCGTT ACTGCCCTGT-3'

5'-TGCACCTGACTC CTGTGGAGAA GTCTGCCGTT ACTGCCCTGT G-3'
5'-TGCACCTGACTC CTGTGGAGAA GTCTGCCGTT ACTGCCCTGT GG-3'
5'-TGCACCTGACTC CTGTGGAGAA GTCTGCCGTT ACTGCCCTGT GGG-3'
5'-TGCACCTGACTC CTGTGGAGAA GTCTGCCGTT ACTGCCCTGT GGGG-3'
5'-TGCACCTGACTC CTGTGGAGAA GTCTGCCGTT ACTGCCCTGT GGGGC-3'
5'-TGCACCTGACTC CTGTGGAGAA GTCTGCCGTT ACTGCCCTGT GGGGCA-3'
5'-TGCACCTGACTC CTGTGGAGAA GTCTGCCGTT ACTGCCCTGT GGGGCAA-3'
5'-TGCACCTGACTC CTGTGGAGAA GTCTGCCGTT ACTGCCCTGT GGGGCAAG-3'
5'-TGCACCTGACTC CTGTGGAGAA GTCTGCCGTT ACTGCCCTGT GGGGCAAGG-3'
5'-TGCACCTGACTC CTGTGGAGAA GTCTGCCGTT ACTGCCCTGT GGGGCAAGGT-3'

12 met PRIMER

*FIG. 50A*

REACTION STOPPED WITH

| ddATP | ddCTP | ddGTP | ddTTP |
|---|---|---|---|
| 3581.4 da | 3581.4 da | 3581.4 da | 3581.4 da |
| | 3854.6 da | | |
| | | | 4158.9 da |
| | | 4488.0 da | |
| | | | 4791.2 da |
| | | 5120.4 da | |
| | | 5448.6 da | |
| 5760.8 da | | | |
| | | 6089.0 da | |
| 6401.2 da | | | |
| 6713.4 da | | | |
| | | 7041.6 da | |
| | | | 7344.8 da |
| | 7634.0 da | | |
| | | | 7938.2 da |
| | | 8267.4 da | |
| | 8555.6 da | | |
| | 8844.8 da | | |
| | | 9174.0 da | |
| | | | 9477.2 da |
| | | | 9781.4 da |
| 10094.6 da | | | |
| | 10382.8 da | | |
| | | | 10687.0 da |
| | | 11016.2 da | |
| | 11304.4 da | | |
| | 11593.6 da | | |
| | 11652.8 da | | |
| | | | 12187.0 da |
| | | 12516.2 da | |
| | | | 12819.4 da |
| | | 13148.6 da | |
| | | 13476.8 da | |
| | | 13805.0 da | |
| | | 14133.2 da | |
| | 14421.4 da | | |
| 14734.6 da | | | |
| 15146.8 da | | | |
| | | 15375.0 da | |
| | | 15703.2 da | |
| | | | 16006.4 da |

FIG. 50B

SEQUENCE OF THE AMPLIFIED 209 bp PCR-PRODUCT OF THE β-GLOBIN GENE

FORWARD PRIMER: β2
CATTTGCTTC TGACACAACT GTGTTCACTA GCAACCTCAA ACAGACACCA
12mer PRIMER
TGGTGCACCT GACTCCTGTG GAGAAGTCTG CCGTTACTGC CCTGTGGGGC

AAGGTGAACG TGGATGAAGT TGGTGGTGAG GCCCTGGGCA GGTTGGTATC

AAGGTTACAA GACAGGTTTA AGGAGACCAA TAGAAACTGG GCATGTGGAG

ACAGAGAAG
REVERSE PRIMER β11

FIG. 51

| | 1 | 2 | 3 | 4 | 5 | 6 | 7 | 8 | 9 | 10 | 11 | 12 | 13 | |
|---|---|---|---|---|---|---|---|---|---|---|---|---|---|---|
| | | | c | | | | | g | | | | | | |
| 5' – gcattctttctttttttactt | attt | attt | attt | attt | attt | attt | attt | attt | attt | attt | attt | attt | attt | ttgagacagagtctca–3' |
| 3' –cgtaagaaagaaaaaatgaa | taaa | taaa | taaa | taaa | taaa | taaa | taaa | taaa | taaa | taaa | taaa | taaa | taaa | aactctgtctcagagt–5' |
| | | | g | | | | | c | | | | | | |

| ALLELE | THEORETICALLY CALCULATED MOLECULAR MASS | | |
|---|---|---|---|
| NUMBER OF REPEATS | ddG | ddC | ddG AND ddC |
| TRUNCATED | 19440.60 | 11643.60 | 11643.60 |
| 8xAAAT | 15718.20 | 21033.60 | 15718.20 |
| 9xAAAT | 16959.00 | 22274.40 | 16959.00 |
| 10xAAAT | 18199.80 | 23515.20 | 18199.80 |
| 11xAAAT | 19440.60 | 24756.00 | 19440.60 |
| 12xAAAT | 20681.40 | 25996.80 | 20681.40 |
| 13xAAAT | 21922.20 | 27237.60 | 21922.20 |

*FIG. 52*

```
5' -GTGTGTGTGTGTGTGTGTTTTT (TT) (TT) AACAGGGATTTGGGGAATTATTTGAGA-3'
    PRIMER                            TTGTCCCTAAACCCCTT (4448.0)
    T5 ALLELE        CAAAAA -- --     TTGTCCCTAAACCCCTT (6890.6)
    T7 ALLELE        CAAAAA AA --     TTGTCCCTAAACCCCTT (7515.0)
    T9 ALLELE        CAAAAA AA AA     TTGTCCCTAAACCCCTT (8139.4)
```

FIG. 55

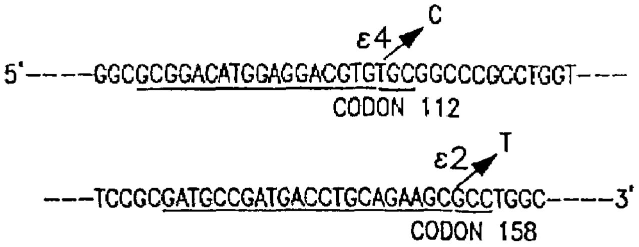
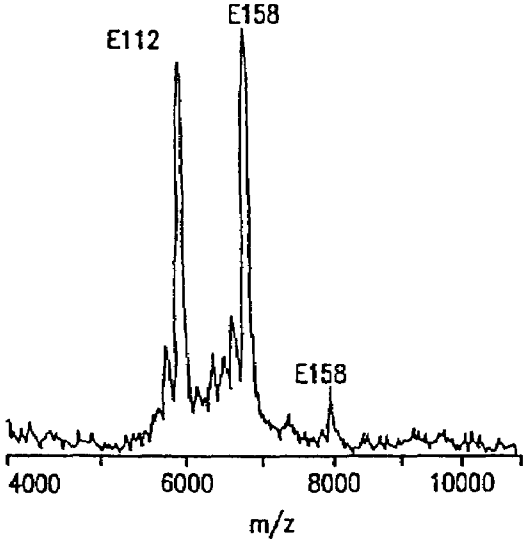
FIG. 61A
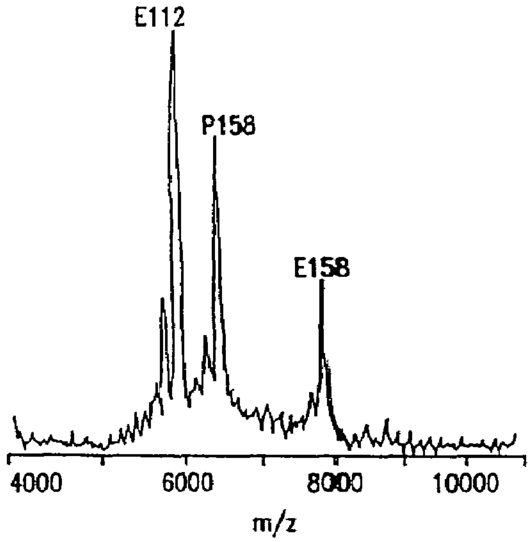
FIG. 61B
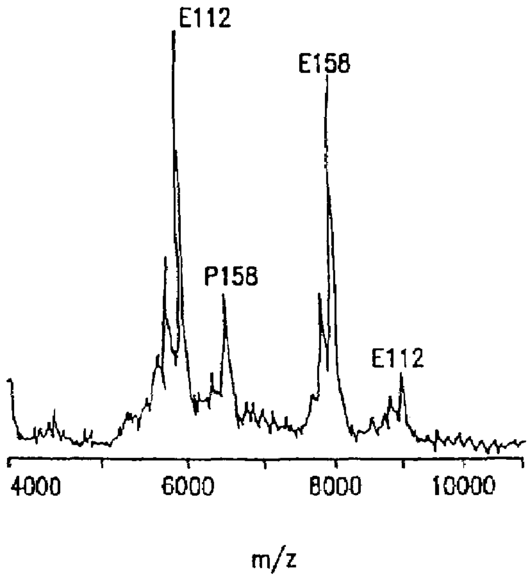
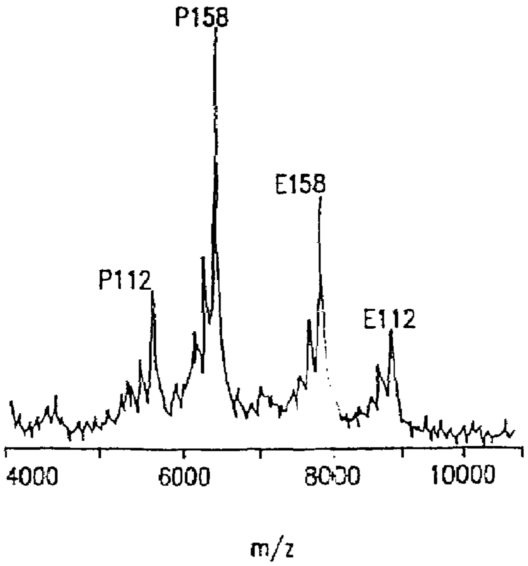

| ddTTP + dNTP (N=A,C,G) | ddATP + dNTP (N=C,T,G) |
|---|---|
| CGG CTG CGA TCA CCG TGC GG C ACA GCT | CGG CTG CGA TCA CCG TGC GG C A |
| WILDTYPE 8246 Da | WILDTYPE 6721 Da |
| CGG CTG CGA TCA CCG TGC GG T | CGG CTG CGA TCA CCG TGC GG T A |
| 6423 Da | 6736 Da |
| CGG CTG CGA TCA CCG TGC GG A ACA GCT | CGG CTG CGA TCA CCG TGC GG A |
| 8270 Da | 6432 Da |

$R^1$=COO;$(CH_2)_n$; (PARA OR META)
$R^2$=MeO;H
$R^3$=MeO;H
$R^4$=Cl;H
$R^5$=$(CH_2)_n$;$(CH_2)_n$CONH$(CH_2)_n$ $R^1$=OMe,H
$R^2$=OMe,H
$R^3$=O,NH

FIG. 72A LOOP-PROBE FOR MUTATION DETECTION IN THE β-GLOBIN GENE AT CODON 5 AND CODON 6
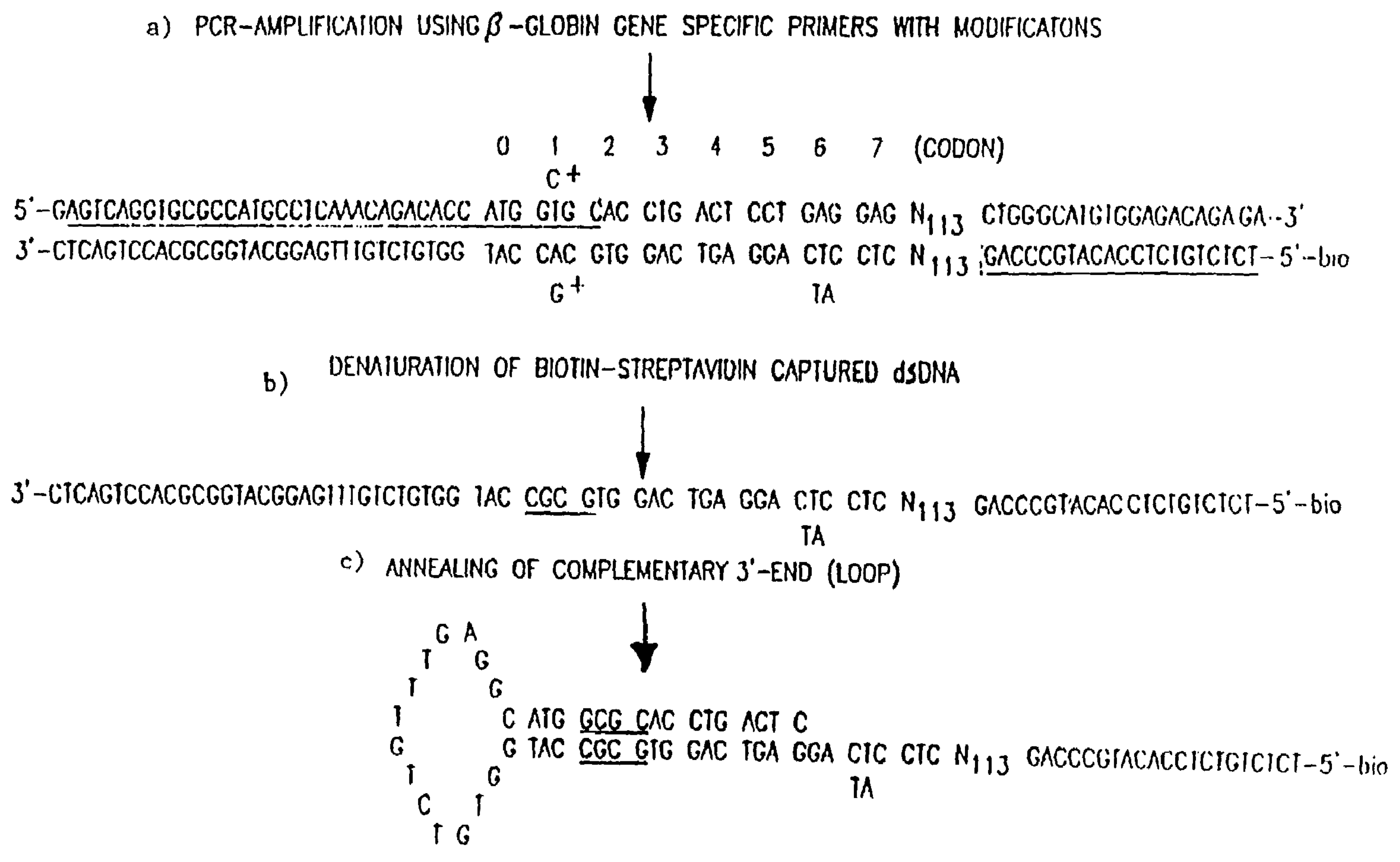

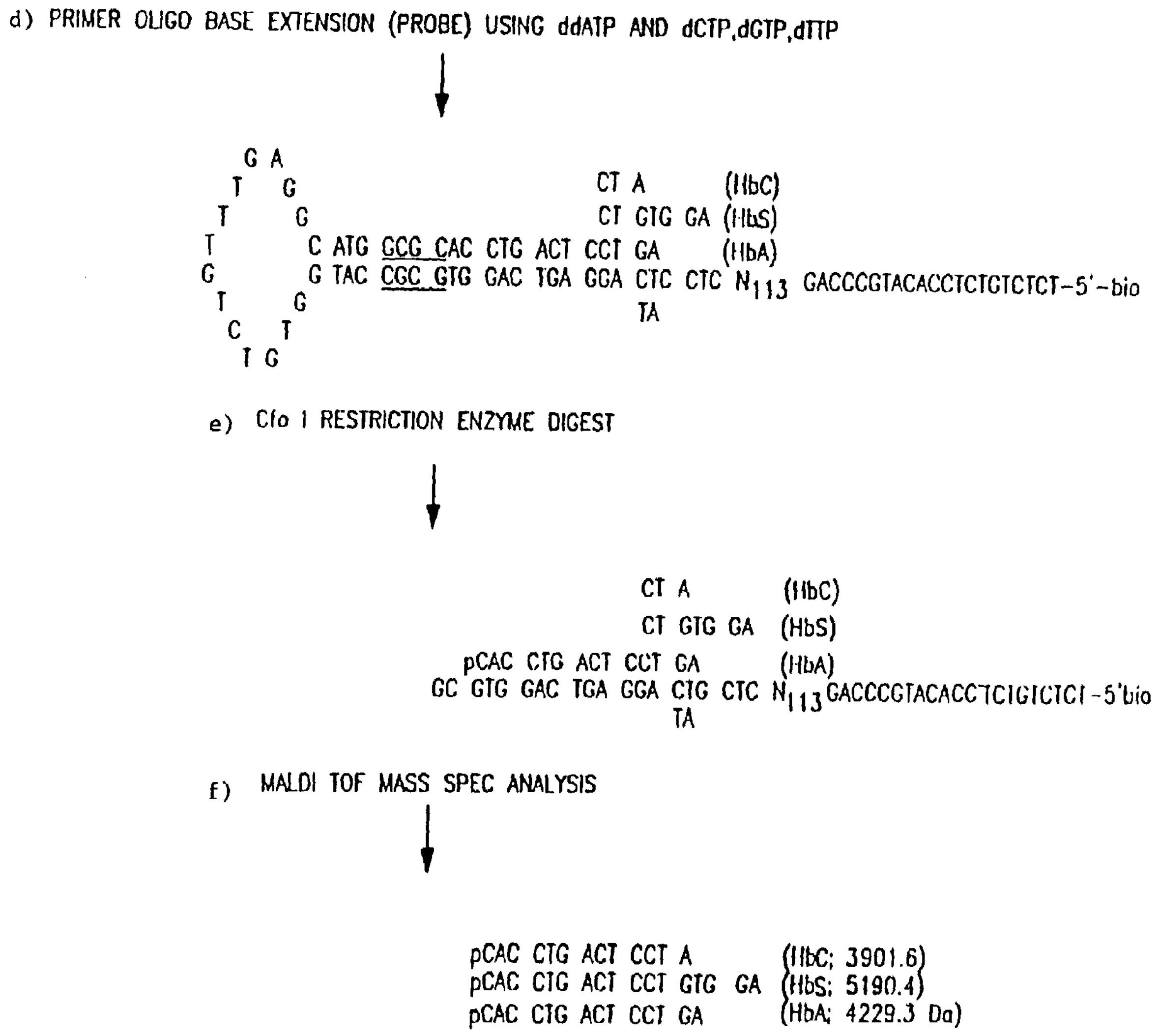

FIG. 72B d) PRIMER OLIGO BASE EXTENSION (PROBE) USING ddATP AND dCTP,dGTP,dTTP

```
              G  A
              T  G
              T     G
              G  T
                 C  T
                    G
         CT A           (HbC)
         CT GTG GA      (HbS)
   C ATG GCG CAC CTG ACT CCT GA    (HbA)
   G TAC CGC GTG GAC TGA GGA CTC CTC N₁₁₃ GACCCGTACACCTCTGTGTCT-5'-bio
                                TA
```

e) Cfo I RESTRICTION ENZYME DIGEST

```
         CT A           (HbC)
         CT GTG GA      (HbS)
   pCAC CTG ACT CCT GA    (HbA)
   GC GTG GAC TGA GGA CTG CTC N₁₁₃ GACCCGTACACCTCTGTGTCT-5'bio
                          TA
```

f) MALDI TOF MASS SPEC ANALYSIS pCAC CTG ACT CCT A          (HbC; 3901.6)
pCAC CTG ACT CCT GTG GA     (HbS: 5190.4)
pCAC CTG ACT CCT GA         (HbA: 4229.3 Da)

5' CAGCTCTCATTTTCCATACAGTCAGTATCAATTCTGGAAGAATTTCCAGACATTAAA
GATAGTCATCTTGGGGCT 3'

*FIG. 74*

5' ACCTAGCGTTCAGTTCGACTGAGATAATACGACTCATATAGCAGCTCTCATTTTCCATAC3'

RANDOM SEQUENCE T7 PROMOTER SEQUENCE CKR-5 HOMOLOGUE

```
                                                 β-TAG1       1   2   3   4   5   6   7   8  (CODON)
                                                 GTCGTCCC ATG GTG CAC CTG ACT C
β-2
CATTTGCTTC TGACACAACT GTGTTCACTA GCAACCTCAA ACAGACACC ATG GTG CAC CTG ACT CCT GAG GAG AAG TCT GCC GTT
                                                                          -CT       THALASSEMIA (COD5 ΔCT)
                                                                               A    HbC  ---
                                                                                T   HbS

                                                 β-TAG2       27  28  29  30   (CODON)
                                                 CGCTGTGGT GAG GCC CTG GGC A
ACT GCC CTG TGG GGC AAG GTG AAC GTG GAT GAA GTT GGT GGT GAG GCC CTG GGC AG GTTGGTATCA AGGTTACAAG
                                                                           A    THALASSEMIA ( IVS -1 nt1 G>A)
                                                                              C THALASSEMIA ( IVS -1 nt5 G>C)
                                                                               CTHALASSEMIA ( IVS -1 nt6 T>C)

ACAGGTTTAA  GGAGACCAAT AGAAACTGGG CATGTGGAGA CAGAGAAG
                                            β -11
```

FIG. 82B (1) SINGLE STRANDED (STV) BIO3' - ACCTCAGTCCATCGTCAGC|AGCAG - 5'

UNIVERSAL SS SEQUENCE | COMPLEMENTARY

E.G. β-TAG1

(2) PARTLY DOUBLE STRANDED

5'-TGGAGTCAGGTAGCAGTC-3'

(STV) BIO 3'-ACCTCAGTCCATCGTCAC|GCGACA - 5'

UNIVERSAL DS SEQUENCE | COMPLEMENTARY

E.G. β-TAG2

FIG. 87A

PCR PRODUCT
$CKR_{\Delta}$-F
CAGCTCTCAT TTTCCATACA GTCAGTATCA ATTCTGGAAG AATTTCCAGACA TTAAAGAT
AGTCATCTTG GGGCT GTCGAGAGTA AAAGGTATGT CAGTCATAGT TAAGACCTTC TTAAAGGTCT $CKR_{\Delta}$-R-BIO
GTAATTTCTA TCAGTAGAAC CCCGA-BIOTIN

FIG. 87B

SIZE ANALYSES: WILDTYPE
SENSE STRAND W/O A:
CAGCTCTCAT TTTCCATACA GTCAGTATCA ATTCTGGAAG AATTTCCAGA CATTAAAGAT
AGTCATCTTG GGGCT 75 bp 23036 Da
SENSE STRAND WITH A:
CAGCTCTCAT TTTCCATACA GTCAGTATCA ATTCTGGAAG AATTTCCAGA CATTAAAGAT
AGTCATCTTG GGGCTA 76 bp 23349 Da

FIG. 87C

SIZE ANALYSES: 32 bp DELETION
SENSE STRAND W/O A:
CAGCTCTCAT TTTCCATACA TTAAAGAT AGTCATCTTG GGGCT 43 bp 13143 Da
SENSE STRAND WITH A:
CAGCTCTCAT TTTCCATACA TTAAAGAT AGTCATCTTG GGGCTA 44 bp 13456 Da

FIG. 87D

PROBE ANALYSES: WILDTYPE (ddTTP TERMINATION): 22 bp 6604 Da
CAGCTCTCAT TTTCCATACA GT

FIG. 87E

PROBE ANALYSES: 32 bp DELETION (ddTTP TERMINATION): 21 bp 6275 Da
CAGCTCTCAT TTTCCATACA T

1. MICROTITER PLATE ISOTHERMAL SEQUENCING
2. 'PIEZOELECTRIC PIPETTE' TRANSFER
3. CORETECH MS

P—ATCCACTACAACTACATGTGTAACAGTTGGwGCwwGddCddC
5 10 15 20 25 30 35 40

1-20: 5'-GUC ACU ACA GGU GAG CUC CA-3'

DNA DIAGNOSTICS BASED ON MASS SPECTROMETRY

RELATED APPLICATIONS

This application is a continuation of U.S. Ser. No. 09/686,148, filed on Oct. 10, 2000 (now U.S. Pat. No. 7,198,893 issued Apr. 3, 2007), which for national stage purposes is a continuation-in-part of U.S. application Ser. No. 08/744,481, filed on Nov. 6, 1996, to Koster, entitled "DNA Diagnostics based on Mass Spectrometry" (now U.S. Pat. No. 6,428,955 issued Aug. 6, 2002). U.S. Ser. No. 09/686,148 is also a division of Ser. No. 09/297,676 filed on May 6, 1999 now U.S. Pat. No. 6,187,842 and a continuation-in-part of U.S. application Ser. No. 08/744,590 filed on Nov. 6, 1996 (now U.S. Pat. No. 6,074,823 issued Jun. 13, 2000), Ser. No. 08/746,036 filed on Nov. 6, 1996 (now U.S. Pat. No. 5,900,481 issued May 4, 1999), Ser. No. 08/746,055 filed on Nov. 6, 1996 (abandoned), Ser. No. 08/786,988 filed on Jan. 23, 1997 (now U.S. Pat. No. 7,285,422 issued Oct. 23, 2007), Ser. No. 08/787,639 filed on Jan. 23, 1997 (now U.S. Pat. No. 6,024,925 issued Feb. 15, 2000), Ser. No. 08/933,792 filed on Sep. 19, 1997 (now U.S. Pat. No. 6,133,436 issued Oct. 17, 2000), and U.S. application Ser. No. 08/947,801 filed Oct. 8, 1997 (abandoned), which is a continuation-in-part of U.S. application Ser. No. 08/746,055 filed on Nov. 6, 1996 (abandoned), Ser. No. 08/786,988 filed Jan. 23, 1997 (now U.S. Pat. No. 7,285,422 issued Oct. 23, 2007), and Ser. No. 08/787,639 filed Jan. 23, 1997 (now U.S. Pat. No. 6,024,925 issued Feb. 15, 2000). For international purposes, benefit of priority is claimed to each of these applications.

Where permitted the subject matter of each of the above-noted patent applications and the patent is herein incorporated in its entirety.

BACKGROUND OF THE INVENTION

Detection of Mutations

The genetic information of all living organisms (e.g., animals, plants and microorganisms) is encoded in deoxyribonucleic acid (DNA). In humans, the complete genome is contains of about 100,000 genes located on 24 chromosomes (The Human Genome, T. Strachan, BIOS Scientific Publishers, 1992). Each gene codes for a specific protein, which after its expression via transcription and translation, fulfills a specific biochemical function within a living cell. Changes in a DNA sequence are known as mutations and can result in proteins with altered or in some cases even lost biochemical activities; this in turn can cause genetic disease. Mutations include nucleotide deletions, insertions or alterations (i.e. point mutations). Point mutations can be either "missense", resulting in a change in the amino acid sequence of a protein or "nonsense" coding for a stop codon and thereby leading to a truncated protein.

More than 3000 genetic diseases are currently known (Human Genome Mutations, D. N. Cooper and M. Krawczak, BIOS Publishers, 1993), including hemophilias, thalassemias, Duchenne Muscular Dystrophy (DMD), Huntington's Disease (HD), Alzheimer's Disease and Cystic Fibrosis (CF). In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klienfelter's Syndrome (XXY). Further, there is growing evidence that certain DNA sequences may predispose an individual to any of a number of diseases such as diabetes, arteriosclerosis, obesity, various autoimmune diseases and cancer (e.g., colorectal, breast, ovarian, lung).

Viruses, bacteria, fungi and other infectious organisms contain distinct nucleic acid sequences, which are different from the sequences contained in the host cell. Therefore, infectious organisms can also be detected and identified based on their specific DNA sequences.

Since the sequence of about 16 nucleotides is specific on statistical grounds even for the size of the human genome, relatively short nucleic acid sequences can be used to detect normal and defective genes in higher organisms and to detect infectious microorganisms (e.g., bacteria, fungi, protists and yeast) and viruses. DNA sequences can even serve as a fingerprint for detection of different individuals within the same species (see, Thompson, J. S. and M. W. Thompson, eds., *Genetics in Medicine*, W. B. Saunders Co., Philadelphia, Pa. (1991)).

Several methods for detecting DNA are currently being used. For example, nucleic acid sequences can be identified by comparing the mobility of an amplified nucleic acid fragment with a known standard by gel electrophoresis, or by hybridization with a probe, which is complementary to the sequence to be identified. Identification, however, can only be accomplished if the nucleic acid fragment is labeled with a sensitive reporter function (e.g., radioactive ($^{32}P$, $^{35}S$), fluorescent or chemiluminescent). Radioactive labels can be hazardous and the signals they produce decay over time. Non-isotopic labels (e.g., fluorescent) suffer from a lack of sensitivity and fading of the signal when high intensity lasers are being used. Additionally, performing labeling, electrophoresis and subsequent detection are laborious, time-consuming and error-prone procedures. Electrophoresis is particularly error-prone, since the size or the molecular weight of the nucleic acid cannot be directly correlated to the mobility in the gel matrix. It is known that sequence specific effects, secondary structure and interactions with the gel matrix are causing artifacts.

Use of Mass Spectrometry for Detection and Identification of Nucleic Acids

Mass spectrometry provides a means of "weighing" individual molecules by ionizing the molecules in vacuo and making them "fly" by volatilization. Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Many applications of mass spectrometric methods are known in the art, particularly in biosciences (see, e.g., *Methods in Enzymol.*, Vol. 193: "Mass Spectrometry" (J. A. McCloskey, editor), 1990, Academic Press, New York).

Because of the apparent analytical advantages of mass spectrometry in providing high detection sensitivity, accuracy of mass measurements, detailed structural information by CID in conjunction with an MS/MS configuration and speed, as well as on-line data transfer to a computer, there has been interest in the use of mass spectrometry for the structural analysis of nucleic acids. Recent reviews summarizing this field include K. H. Schram, "Mass Spectrometry of Nucleic Acid Components," *Biomedical Applications of Mass Spectrometry* 34: 203-287 (1990); and P. F. Crain, "Mass Spectrometric Techniques in Nucleic Acid Research," *Mass Spectrometry Reviews* 9: 505-554 (1990); see, also U.S. Pat. No. 5,547,835 and U.S. Pat. No. 5,622,824).

Nucleic acids, however, are very polar biopolymers that are very difficult to volatilize. Consequently, mass spectrometric detection has been limited to low molecular weight synthetic oligonucleotides for confirming an already known oligonucleotide sequence by determining the mass of the parent molecular ion, or alternatively, confirming a known sequence through the generation of secondary ions (fragment ions) via CID in an MS/MS configuration using, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Köster et al. (1987) *Biomed. Environ. Mass Spectrometry* 14: 111-116).

Other ionization/desorption techniques include electrospray/ion-spray (ES) and matrix-assisted laser desorption/ionization (MALDI). ES mass spectrometry has been introduced by Fenn et al. (*J. Phys. Chem.* 88: 4451-59 (1984); PCT Application No. WO 90/14148) and current applications are summarized in review articles (see, e.g., Smith et al. (1990) *Anal. Chem.* 62: 882-89 and Ardrey (1992), "Electrospray Mass Spectrometry", *Spectroscopy Europe* 4: 10-18). The molecular weights of a tetradecanucleotide (see, Covey et al. (1988) The "Determination of Protein, Oligonucleotide and Peptide Molecular Weights by Ionspray Mass Spectrometry," *Rapid Commun. in Mass Spectrometry* 2:249-256), and of a 21-mer (*Methods in Enzymol.,* 193, "Mass Spectrometry" (McCloskey, editor), p. 425, 1990, Academic Press, New York) have been published. As a mass analyzer, a quadrupole is most frequently used. Because of the presence of multiple ion peaks that all could be used for the mass calculation, the determination of molecular weights in femtomole amounts of sample is very accurate.

MALDI mass spectrometry, in contrast, can be attractive when a time-of-flight (TOF) configuration (see, Hillenkamp et al. (1990) pp 49-60 in "Matrix Assisted UV-Laser Desorption/Ionization: A New Approach to Mass Spectrometry of Large Biomolecules," *Biological Mass Spectrometry*, Burlingame and McCloskey, editors, Elsevier Science Publishers, Amsterdam) is used as a mass analyzer. Since, in most cases, no multiple molecular ion peaks are produced with this technique, the mass spectra, in principle, look simpler compared to ES mass spectrometry.

Although DNA molecules up to a molecular weight of 410,000 daltons have been desorbed and volatilized (Williams et al., "Volatilization of High Molecular Weight DNA by Pulsed Laser Ablation of Frozen Aqueous Solutions," *Science* 246: 1585-87 (1989)), this technique had only shown very low resolution (oligothymidylic acids up to 18 nucleotides, Huth-Fehre et al. *Rapid Commun. in Mass Spectrom.,* 6: 209-13 (1992); DNA fragments up to 500 nucleotides in length K. Tang et al., *Rapid Commun. in Mass Spectrom.,* 8: 727-730 (1994); and a double-stranded DNA of 28 base pairs (Williams et al., "Time-of-Flight Mass Spectrometry of Nucleic Acids by Laser Ablation and Ionization from a Frozen Aqueous Matrix," *Rapid Commun. in Mass Spectrom.,* 4: 348-351 (1990)). Japanese Patent No. 59-131909 describes an instrument, which detects nucleic acid fragments separated either by electrophoresis, liquid chromatography or high speed gel filtration. Mass spectrometric detection is achieved by incorporating into the nucleic acids, atoms, such as S, Br, I or Ag, Au, Pt, Os, Hg, that normally do not occur in DNA.

Co-owned U.S. Pat. No. 5,622,824 describes methods for DNA sequencing based on mass spectrometric detection. To achieve this, the DNA is by means of protection, specificity of enzymatic activity, or immobilization, unilaterally degraded in a stepwise manner via exonuclease digestion and the nucleotides or derivatives detected by mass spectrometry. Prior to the enzymatic degradation, sets of ordered deletions that span a cloned DNA fragment can be created. In this manner, mass-modified nucleotides can be incorporated using a combination of exonuclease and DNA/RNA polymerase. This permits either multiplex mass spectrometric detection, or modulation of the activity of the exonuclease so as to synchronize the degradative process. Co-owned U.S. Pat. Nos. 5,605,798 and 5,547,835 provide methods for detecting a particular nucleic acid sequence in a biological sample. Depending on the sequence to be detected, the processes can be used, for example, in methods of diagnosis. These methods, while broadly useful and applicable to numerous embodiments, represent the first disclosure of such applications and can be improved upon.

Therefore, it is an object herein to provided improved methods for sequencing and detecting DNA molecules in biological samples. It is also an object herein to provided improved methods for diagnosis of genetic diseases, predispositions to certain diseases, cancers, and infections.

SUMMARY OF THE INVENTION

Methods of diagnosis by detecting and/or determining sequences of nucleic acids that are based on mass spectrometry are provided herein. Methods are provided for detecting double-stranded DNA, detecting mutations and other diagnostic markers using MS analysis. In particular, methods for diagnosing neuroblastoma, detecting heredity relationships, HLA compatibility, genetic fingerprinting, detecting telomerase activity for cancer diagnosis are provided.

In certain embodiments the DNA is immobilized on a solid support either directly or via a linker and/or bead. Three permutations of the methods for DNA detection in which immobilized DNA is used are exemplified. These include: (1) immobilization of a template; hybridization of the primer; extension of the primer, or extension of the primer (single ddNTP) for sequencing or diagnostics or extension of the primer and Endonuclease degradation (sequencing); (2) immobilization of a primer; hybridization of a single stranded template; and extension of the primer, or extension of the primer (single ddNTP) for sequencing or diagnostics or extension of the primer and Endonuclease degradation (sequencing); (3) immobilization of the primer; hybridization of a double stranded template; extension of the primer, or extension of the primer (single ddNTP) for sequencing or diagnostics or extension of the primer and Endonuclease degradation (sequencing).

In certain embodiments the DNA is immobilized on the support via a selectively cleavable linker. Selectively cleavable linkers include, buta are not limited to photocleavable linkers, chemically cleavable linkers and an enzymatically (such as a restriction site (nucleic acid linker), a protease site) cleavable linkers. Inclusion of a selectively cleavable linker expands the capabilities of the MALDI-TOF MS analysis because it allows for all of the permutations of immobilization of DNA for MALDI-TOF MS, the DNA linkage to the support through the 3'- or 5'-end of a nucleic acid; allows the amplified DNA or the target primer to be extended by DNA synthesis; and further allows for the mass of the extended product (or degraded product via exonuclease degradation) to be of a size that is appropriate for MALDI-TOF MS analysis (i.e., the isolated or synthesized DNA can be large and a small primer or a large primer sequence can be used and a small restriction fragment of a gene or single strand thereof hybridized thereto).

In a preferred embodiment, the selectively cleavable linker is a chemical or photocleavable linker that is cleaved during the ionizing step of mass spectrometry. Exemplary linkers include linkers containing, a disulfide group, a leuvinyl group, an acid-labile trityl group and a hydrophobic trityl group. In other embodiments, the enzymatically cleavable linker can be a nucleic acid that is an RNA nucleotide or that encodes a restriction endonuclease site. Other enzymatically cleavable linkers include linkers that contain a pyrophosphate group, an arginine-arginine group and a lysine-lysine group. Other linkers are exemplified herein.

Methods for sequencing long fragments of DNA are provided. To perform such sequencing, specific base terminated fragments are generated from a target nucleic acid. The analysis of fragments rather than the full length nucleic acid shifts the mass of the ions to be determined into a lower mass range, which is generally more amenable to mass spectrometric detection. For example, the shift to smaller masses increases mass resolution, mass accuracy and, in particular, the sensitivity for detection. Hybridization events and the actual molecular weights of the fragments as determined by mass spectrometry provide sequence information (e.g., the presence and/or identity of a mutation). In a preferred embodiment, the fragments are captured on a solid support prior to hybridization and/or mass spectrometry detection. In another preferred embodiment, the fragments generated are ordered to provide the sequence of the larger nucleic acid.

One preferred method for generating base specifically terminated fragments from a nucleic acid is effected by contacting an appropriate amount of a target nucleic acid with an appropriate amount of a specific endonuclease, thereby resulting in partial or complete digestion of the target nucleic acid. Endonucleases will typically degrade a sequence into pieces of no more than about 50-70 nucleotides, even if the reaction is not run to full completion. In a preferred embodiment, the nucleic acid is a ribonucleic acid and the endonuclease is a ribonuclease (RNase) selected from among: the G-specific RNase $T_1$, the A-specific RNase $U_2$, the A/U specific RNase PhyM, U/C specific RNase A, C specific chicken liver RNase (RNase CL3) or crisavitin. In another preferred embodiment, the endonuclease is a restriction enzyme that cleaves at least one site contained within the target nucleic acid. Another preferred method for generating base specifically terminated fragments includes performing a combined amplification and base-specific termination reaction (e.g., using an appropriate amount of a first DNA polymerase, which has a relatively low affinity towards the chain-terminating nucleotides resulting in an exponential amplification of the target; and a polymerase with a relatively high affinity for the chain terminating nucleotide resulting in base-specific termination of the polymerization. Inclusion of a tag at the 5' and/or 3' end of a target nucleic acid can facilitates the ordering of fragments.

Methods for determining the sequence of an unknown nucleic acid in which the 5' and/or 3' end of the target nucleic acid can include a tag are provided. Inclusion of a non-natural tag on the 3' end is also useful for ruling out or compensating for the influence of 3' heterogeneity, premature termination and nonspecific elongation. In a preferred embodiment, the tag is an affinity tag (e.g., biotin or a nucleic acid that hybridizes to a capture nucleic acid). Most preferably the affinity tag facilitates binding of the nucleic acid to a solid support. In another preferred embodiment, the tag is a mass marker (i.e. a marker of a mass that does not correspond to the mass of any of the four nucleotides). In a further embodiment, the tag is a natural tag, such as a polyA tail or the natural 3' heterogeneity that can result, for example, from a transcription reaction.

Methods of sequence analysis in which nucleic acids have been replicated from a nucleic acid molecule obtained from a biological sample are specifically digested using one or more nucleases (deoxyribonucleases for DNA, and ribonucleases for RNA) are provided. The fragments captured on a solid support carrying the corresponding complementary sequences. Hybridization events and the actual molecular weights of the captured target sequences provide information on mutations in the gene. The array can be analyzed spot-by-spot using mass spectrometry. Further, the fragments generated can be ordered to provide the sequence of the larger target fragment.

In another embodiment, at least one primer with a 3'-terminal base is hybridized to the target nucleic acid near a site where possible mutations are to be detected. An appropriate polymerase and a set of three nucleoside triphosphates (NTPs) and the fourth added as a terminator are reacted. The extension reaction products are measured by mass spectrometry and are indicative of the presence and the nature of a mutation. The set of three NTPs and one dd-NTP (or three NTPs and one 3'-deoxy NTP), will be varied to be able to discriminate between several mutations (including compound heterozygotes) in the target nucleic acid sequence.

Methods for detecting and diagnosing neoplasia/malignancies in a tissue or cell sample are provided. The methods rely on a telomeric repeat amplification protocol (TRAP)-MS assay and include the steps of:

a) obtaining a tissue or a cell sample, such as a clinical isolate or culture of suspected cells;
b) isolating/extracting/purifying telomerase from the sample;
c) adding the telomerase extract to a composition containing a synthetic DNA primer, which is optionally immobilized, complementary to the telomeric repeat, and all four dNTPs under conditions that result in telomerase specific extension of the synthetic DNA;
d) amplifying the telomerase extended DNA products, preferably using a primer that contains a “linker moiety”, such as a moiety based on thiol chemistry or streptavidin;
e) isolating linker-amplified primers, such as by using a complementary binding partner immobilized on a solid support;
f) optionally conditioning the DNA for crystal formation; and
g) performing MS by ionizing/volatizing the sample to detect the DNA product.

Telomerase-specific extension is indicative of neoplasia/malignancy. This method can be used to detect specific malignancies. The use of MS to detect the DNA product permits identification the extended product, which is indicative of telomerase activity in the sample. If desired, the synthetic DNA can be in the form an array.

Methods for detecting mutations are provided and the use thereof oncogenes and to thereby screen for transformed cells, which are indicative of neoplasia. Detection of muta tions present in oncogenes are indicative of transformation. This method includes the steps of:

a) obtaining a biological sample;
b) amplifying a portion of the selected proto-oncogene that includes a codon indicative of transformation, where one primer has a linker moiety for immobilization;
c) immobilizing DNA via the linker moiety to a solid support, optionally in the form of an array;
d) hybridizing a primer complementary to the proto oncogene sequence that is upstream from the codon
   e) adding 3dNTPs/1 ddNTP and DNA polymerase and extending the hybridized primer to the next ddNTP location;
f) ionizing/volatizing the sample; and
g) detecting the mass of the extended DNA, whereby mass indicates the presence of wild-type or mutant alleles. The presence of a mutant allele at the codon is diagnostic for neoplasia.

In an exemplary embodiment, extension-MS analysis is used detect the presence of a mutated codon 634 in the retrovirus (RET)-proto oncogene.

In another embodiment, methods for diagnosing diseases using reverse transcription and amplification of a gene expressed in transformed cells. In particular, a method for diagnosis of neuroblastoma using reverse transcriptase (RT)-MS of tyrosine hydroxylase, which is a catecholamine biosynthetic enzyme that expressed in tumor cells, but not in tumor cells but not normal cells, such as normal bone marrow cells is provided. The method includes the steps of:

a) obtaining a tissue sample;
b) isolating polyA RNA from the sample;
c) preparing a cDNA library using reverse transcription;
d) amplifying a cDNA product, or portion thereof, of the selected gene, where one oligo primer has a linker moiety;
e) isolating the amplified product by immobilizing the DNA to solid support via the linker moiety;
f) optionally conditioning the DNA:
g) ionizing/volatizing sample and detecting the presence of a DNA peak that is indicative of expression of the selected gene gene. For example, expression of the tyrosine hydroxylase gene is indicative of neuroblastoma.

Also provided are methods of directly detecting a double-stranded nucleic acid using MALDI-TOF MS. These methods include the steps of:

a) isolating a double stranded DNA of an appropriate size for MS via amplification methods or formed by hybridization of single-stranded DNA fragment;
b) preparing the double-stranded DNA for analysis under conditions that increase the ratio of dsDNA:ssDNA in which the conditions include one or all of the following: preparing samples for analysis at reduced temperatures (i.e. 4° C.), and using of higher DNA concentrations in the matrix to drive duplex formation
c) ionizing/volatizing the sample of step b), where this step uses low acceleration voltage of the ions to assist in maintaining duplex DNA by, for example, adjusting laser power to just above threshold irradiation for ionization, and
d) detecting the presence of the dsDNA of the appropriate mass.

In preferred embodiments, the matrix includes 3-hydroxypicolinic acid. The detected DNA can be indicative of a genetic disorder, genetic disease, genetic predisposition to a disease chromosomal abnormalities. In other embodiments, the mass of the double stranded DNA is indicative of the deletion, insertion, mutation.

A method designated primer oligo base extension (PROBE) is provided. This method uses a single detection primer followed by an oligonucleotide extension step to give products, which can be readily resolved by MALDI-TOF mass spectrometry. The products differ in length by a number of bases specific for a number of repeat units or for second site mutations within the repeated region. The method is exemplified using as a model system the AluVpA polymorphism in intron 5 of the interferon-α receptor gene located on human chromosome 21, and the poly T tract of the splice acceptor site of intron 8 from the CFTR gene located on human chromosome 7. The method is advantageously used for example, for determining identity, identifying mutations, familial relationship, HLA compatibility and other such markers, using PROBE-MS analysis of microsatellite DNA. In a preferred embodiment, the method includes the steps of:

a) obtaining a biological sample from two individuals;
b) amplifying a region of DNA from each individual that contains two or more microsatellite DNA repeat sequences
c) ionizing/volatizing the amplified DNA;
d) detecting the presence of the amplified DNA and comparing the molecular weight of the amplified DNA. Different sizes are indicative of non-identity (i.e. wild-type versus mutation), non-heredity or non-compatibility; similar size fragments indicate the possibility identity, of familial relationship, or HLA compatibility.

More than one marker may be examined simultaneously, primers with different linker moieties are used for immobilization.

Another method loop-primer oligo base extension, designated LOOP-PROBE, for detection of mutations especially predominant disease causing mutations or common polymorphisms is provided. In a particular embodiment, this method for detecting target nucleic acid in a sample, includes the steps of:

a) amplifying a target nucleic acid sequence, such as β-globin, in a sample, using (i) a first primer whose 5'-end shares identity to a portion of the target DNA immediately downstream from the targeted codon followed by a sequence that introduces a unique restriction endonuclease site, such as CfoI in the case of β-globin, into the amplicon and whose 3'-end primer is self-complementary; and (ii) a second downstream primer that contains a tag, such as biotin, for immobilizing the DNA to a solid support, such as streptavidin beads;
c) immobilizing the double-stranded amplified DNA to a solid support via the linker moiety;
d) denaturing the immobilized DNA and isolating the non-immobilized DNA strand;
e) annealing the intracomplementary sequences in the 3'-end of the isolated non-immobilized DNA strand, such that the 3'-end is extendable by a polymerase, which annealing can be performed, for example, by heating then and cooling to about 37° C., or other suitable method;
f) extending the annealed DNA by adding DNA polymerase, 3 dNTPs/1 ddNTP, whereby the 3'-end of the DNA strand is extended by the DNA polymerase to the position of the next ddNTP location (i.e., to the mutation location);
g) cleaving the extended double stranded stem loop DNA with the unique restriction endonuclease and removing the cleaved stem loop DNA i) (optionally adding a matrix) ionizing/volatizing the extended product; and j) detecting the presence of the extended target nucleic acid, whereby the presence of a DNA fragment of a mass different from wild-type is indicative of a mutation at the target codon(s).

This method eliminates one specific reagent for mutation detection compared other methods of MS mutational analyses, thereby simplifying the process and rendering it amenable to automation. Also, the specific extended product that is analyzed is cleaved from the primer and is therefore shorter compared to the other methods. In addition, the annealing efficiency is higher compared to annealing of an added primer and should therefore generate more product. The process is compatible with multiplexing and various detection schemes (e.g., single base extension, oligo base extension and sequencing). For example, the extension of the loop-primer can be used for generation of short diagnostic sequencing ladders within highly polymorphic regions to perform, for example, HLA typing or resistance as well as species typing.

In another embodiment, a methods of detecting a target nucleic acid in a biological sample using RNA amplification is provided. In the method, the target is amplified the target nucleic acid, using a primer that shares a region complementary to the target sequence and upstream encodes a promoter, such as the T7 promoter. A DNA-dependent RNA polymerase and appropriate ribonucleotides are added to synthesize RNA, which is analyzed by MS.

Improved methods of sequencing DNA using MS are provided. In these methods thermocycling for amplification is used prior to MS analysis, thereby increasing the signal.

Also provide are primers for use in MS analyses. In particular, primers, comprising all or, for longer oligonucleotides, at least about 20, preferably about 16, bases of any of the sequence of nucleotides sequences set forth in SEQ ID NOs: 1-22, 24, 27-38, 41-86, 89, 92, 95, 98, 101-110, 112-123, 126, 128, 129, and primers set forth in SEQ ID NOs: 280-287. The primers are unlabeled, and optionally include a mass modifying moiety, which is preferably attached to the 5' end.

Other features and advantages of the methods provided herein will be further described with reference to the following Figures, Detailed Description and Claims.

BRIEF DESCRIPTION OF THE FIGURES

FIG. 34 is a schematic presentation of the oligo base extension of the mutation detection primer as described in Example 7, using ddTTP (A) or ddCTP (B) in the reaction mix, respectively. The theoretical mass calculation is given in parenthesis. The sequence shown is part of the exon 10 of the CFTR gene (SEQ ID NO: 132) that bears the most common cystic fibrosis mutation ΔF508 and more rare mutations A1507 as well as Ile506Ser. The short sequencing products were produced using either ddTTP (FIG. 34A; SEQ ID NOs: 133-135) or ddCTP (FIG. 34B; SEQ ID NOs: 136-139).

FIG. 36 shows the portion of the sequence of pRFc1 DNA, which was used as template for nucleic acid amplification in Example 8 of unmodified and 7-deazapurine containing 99-mer (SEQ ID NO: 141) and 200-mer (SEQ ID NO: 140) nucleic acids as well as the sequences of the 19-mer forward primer (SEQ ID NO: 17) and the two 18-mer reverse primers (SEQ ID NO: 18).

FIG. 37 shows the portion of the nucleotide sequence of M13mp18 RFI DNA, which was used in Example 8 for nucleic acid amplification of unmodified and 7-deazapurine containing 103-mer nucleic acids (SEQ ID NO: 245). Also shown are nucleotide sequences of the 17-mer primers (SEQ ID NOs: 19 and 20) used in the nucleic acid amplification reaction.

FIG. 50 shows a schematic representation of the sequencing ladder generated in FIG. 49 with the corresponding calculated molecular masses up to 40 bases after the primer. For the calculation, the following masses were used: 3581.4Da for the primer, 312.2 Da for 7-deaza-dATP, 304.2 Da for dTTP, 289.2 Da for dCTP and 328.2 Da for 7-deaza-dGTP.

FIG. 51 shows the sequence of the amplified 209 bp amplified product (SEQ ID NO: 261) within the β-globin gene, which was used as a template for sequencing. The sequences of the appropriate amplification primer and the location of the 12mer sequencing primer is also shown. This sequence represents a homozygote mutant at the position 4 bases after the primer. In a wildtype sequence this T would be replaced by an A.

FIG. 52 shows a sequence (SEQ ID NO: 262) which is part of the intron 5 of the interferon-receptor gene that bears the AluVpA polymorphism as further described in Example 11. The scheme presents the primer oligo base extension (PROBE) using ddGTP, ddCTP, or both for termination, respectively. The polymorphism detection primer (IFN) is underlined, the termination nucleotides are marked in bold letters. The theoretical mass values from the alleles found in 28 unrelated individuals and a five member family are given in the table. Both second site mutations found in most 13 units allele, but not all, are indicated.

FIG. 55 shows a schematic presentation of the PROBE method for detection of different alleles in the polyT tract at the 3'-end of intron 8 of the CFTR gene with pppCdd as terminator (Example 11) (SEQ ID NO: 263). The sequence of the T5, T7 and T9 alleles are set forth in SEQ ID NOs: 264-6 respectively.

FIG. 61 shows the multiplex (codons 112 and 158) mass spectrum PROBE results for a) ϵ2/ϵ3, b) ϵ3/ϵ3, c) ϵ3/ϵ4, and d) ϵ4/ϵ4 genotypes. E: extension products; P: unextended primer. Top: codon 112 (SEQ ID NO: 310) and 158 (SEQ ID NO: 311) regions, with polymorphic sites bold and primer sequences underlined.

FIG. 65(*b*) shows the expected PROBE (SEQ ID NO: 53) products for ddT and ddA reactions for wildtype, C→T, and C→A antisense strands.

FIGS. 72A and 72B schematically depicts the steps involved with the Loop-primer oligo base extension (Loop-probe) reaction (SEQ ID NOs: 269 and 273-275).

FIG. 74 shows the nucleic acid sequence (SEQ ID NO: 277) of the amplified region of CKR-5. The underlined sequence corresponds to the region homologous to the amplification primers. The dotted region corresponds to the 32 bp deletion.

FIG. 75 shows the sense primer ckrT7f (SEQ ID NO: 60). Being designed to facilitate binding of T7-RNA polymerase and amplification of the CKR-5 region to be analyzed, it starts with a randomly chosen sequence of 24 bases, the T7 promoter sequence of 18 bases and the sequence homologous to CKR-5 of 19 bases.

FIG. 82 schematically depicts detection of putative mutations in the human β-globin gene at codon 5 and 6 and at codon 30, and the IVS-1 donor site, respectively, done in parallel. FIG. 82A (SEQ ID NOs: 68, 281, 69, 283 and 287)

shows amplification of genomic DNA using the primers β82 and β11. The location of the primers and identification tags as well as an indication of the wild type and mutant sequences are shown. FIG. 82B (SEQ ID NOs: 70, 288 and 289) shows analysis of both sites in a simple Primer Reaction Oligo Base Extension (PROBE) using primers β-TAG1 (which binds upstream of codon 5 and 6) and β-TAG2 (which binds upstream of codon 30 and the IVS-1 donor site). Reaction products are captured using streptavidin-coated paramagnetic particle bound biotinylated capture primers (cap-tag-1 and cap-tag-2, respectively), that have 6 bases at the 5' end that are complementary to the 5' end of β-TAG1 and β-TAG2, respectively, and a portion which binds to a universal primer.

FIG. 87A shows the wildtype sequence of a fragment of the chemokine receptor CKR-5 gene with primers (SEQ ID NO: 73) used for amplification (SEQ ID NOs: 277, 292 and 293). In FIG. 87B, the wildtype strands are depicted with and without an added Adenosine, their length and molecular masses are indicated (SEQ ID NOs: 277, 296 and 297). FIG. 87C indicates the same for the 32 bp deletion (SEQ ID NO: 299). FIG. 87D shows the PROBE products for the wildtype gene (SEQ ID NO: 300) and FIG. 87E shows the mutated allele (SEQ ID NO: 301).

DETAILED DESCRIPTION OF THE INVENTION

Definitions

Figure 1A:
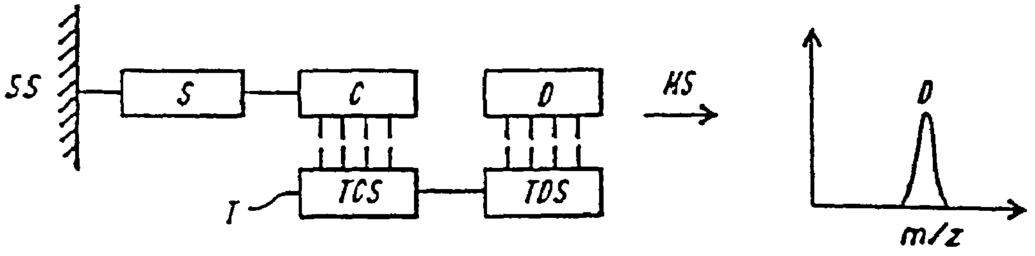
FIG. 1A is a diagram showing a process for performing mass spectrometric analysis on one target detection site (TDS) contained within a target nucleic acid molecule (T), which has been obtained from a biological sample. A specific capture sequence (C) is attached to a solid support (SS) via a spacer (S). The capture sequence is chosen to specifically hybridize with a complementary sequence on the target nucleic acid molecule (T), known as the target capture site (TCS). The spacer (S) facilitates unhindered hybridization. A detector nucleic acid sequence (D), which is complementary to the TDS is then contacted with the TDS. Hybridization between D and the TDS can be detected by mass spectrometry.

Unless defined otherwise, all technical and scientific terms used herein have the same meaning as is commonly understood by one of skill in the art to which this invention belongs. Where permitted the subject matter of each of the co-pending patent applications and the patent is herein incorporated in its entirety.

As used herein, the term "biological sample" refers to any material obtained from any living source (e.g., human, animal, plant, bacteria, fungi, protist, virus). For purposes herein, the biological sample will typically contain a nucleic acid molecule. Examples of appropriate biological samples include, but are not limited to: solid materials (e.g., tissue, cell pellets, biopsies) and biological fluids (e.g., urine, blood, saliva, amniotic fluid, mouth wash, cerebral spinal fluid and other body fluids).

As used herein, the phrases "chain-elongating nucleotides" and "chain-terminating nucleotides" are used in accordance with their art recognized meaning. For example, for DNA, chain-elongating nucleotides include 2' deoxyribonucleotides (e.g., dATP, dCTP, dGTP and dTTP) and chain-terminating nucleotides include 2',3'-dideoxyribonucleotides (e.g., ddATP, ddCTP, ddGTP, ddTTP). For RNA, chain-elongating nucleotides include ribonucleotides (e.g., ATJP, CTP, GTP and UTP) and chain-terminating nucleotides include 3'-deoxyribonucleotides (e.g., 3' dA, 3' dC, 3' dG and 3' dU). A complete set of chain elongating nucleotides refers to dATP, dCTP, dGTP and dTTP. The term "nucleotide" is also well known in the art.

As used herein, nucleotides include nucleoside mono-, di-, and triphosphates. Nucleotides also include modified nucleotides such as phosphorothioate nucleotides and deazapurine nucleotides. A complete set of chain-elongating nucleotides refers to four different nucleotides that can hybridize to each of the four different bases comprising the DNA template.

As used herein, the superscript 0-i designates i+1 mass differentiated nucleotides, primers or tags. In some instances, the superscript 0 can designate an unmodified species of a particular reactant, and the superscript i can designate the i-th mass-modified species of that reactant. If, for example, more than one species of nucleic acids are to be concurrently detected, then i+1 different mass-modified detector oligonucleotides ($D^0$, $D^1$, . . . $D^i$) can be used to distinguish each species of mass modified detector oligonucleotides (D) from the others by mass spectrometry.

As used herein, "multiplexing" refers to the simultaneously detection of more than one analyte, such as more than one (mutated) loci on a particular captured nucleic acid fragment (on one spot of an array).

As used herein, the term "nucleic acid" refers to single-stranded and/or double-stranded polynucleotides such as deoxyribonucleic acid (DNA), and ribonucleic acid (RNA) as well as analogs or derivatives of either RNA or DNA. Also included in the term "nucleic acid" are analogs of nucleic acids such as peptide nucleic acid (PNA), phosphorothioate DNA, and other such analogs and derivatives.

As used herein, the term "conjugated" refers stable attachment, preferably ionic or covalent attachment. Among preferred conjugation means are: streptavidin- or avidin- to biotin interaction; hydrophobic interaction; magnetic interaction (e.g., using functionalized magnetic beads, such as DYNABEADS, which are streptavidin-coated magnetic beads sold by Dynal, Inc. Great Neck, N.Y. and Oslo Norway); polar interactions, such as "wetting" associations between two polar surfaces or between oligo/polyethylene glycol; formation of a covalent bond, such as an amide bond, disulfide bond, thioether bond, or via crosslinking agents; and via an acid-labile or photocleavable linker.

As used herein equivalent, when referring to two sequences of nucleic acids means that the two sequences in question encode the same sequence of amino acids or equivalent proteins. When "equivalent" is used in referring to two proteins or peptides, it means that the two proteins or peptides have substantially the same amino acid sequence with only conservative amino acid substitutions that do not substantially alter the activity or function of the protein or peptide. When "equivalent" refers to a property, the property does not need to be present to the same extent (e.g., two peptides can exhibit different rates of the same type of enzymatic activity), but the activities are preferably substantially the same. "Complementary," when referring to two nucleotide sequences, means that the two sequences of nucleotides are capable of hybridizing, preferably with less than 25%, more preferably with less than 15%, even more preferably with less than 5%, most preferably with no mismatches between opposed nucleotides. Preferably the two molecules will hybridize under conditions of high stringency.

As used herein: stringency of hybridization in determining percentage mismatch are those conditions understood by those of skill in the art and typically are substantially equivalent to the following:

1) high stringency: 0.1×SSPE, 0.1% SDS, 65° C.

2) medium stringency: 0.2×SSPE, 0.1% SDS, 50° C.

3) low stringency: 1.0×SSPE, 0.1% SDS, 50° C.

It is understood that equivalent stringencies may be achieved using alternative buffers, salts and temperatures.

As used herein, a primer when set forth in the claims refers to a primer suitable for mass spectrometric methods requiring immobilizing, hybridizing, strand displacement, sequencing mass spectrometry refers to a nucleic acid must be of low enough mass, typically about 70 nucleotides or less than 70, and of sufficient size to be useful in the mass spectrometric methods described herein that rely on mass spectrometric detection. These methods include primers for detection and sequencing of nucleic acids, which require a sufficient number nucleotides to from a stable duplex, typically about 6-30, preferably about 10-25, more preferably about 12-20. Thus, for purposes herein a primer will be a sequence of nucleotides comprising about 6-70, more preferably a 12-70, more preferably greater than about 14 to an upper limit of 70, depending upon sequence and application of the primer. The primers herein, for example for mutational analyses, are selected to be upstream of loci useful for diagnosis such that when performing using sequencing up to or through the site of interest, the resulting fragment is of a mass that sufficient and not too large to be detected by mass spectrometry. For mass spectrometric methods, mass tags or modifier are preferably included at the 5'-end, and the primer is otherwise unlabeled.

As used herein, "conditioning" of a nucleic acid refers to modification of the phosphodiester backbone of the nucleic acid molecule (e.g., cation exchange) for the purpose of eliminating peak broadening due to a heterogeneity in the cations bound per nucleotide unit. Contacting a nucleic acid molecule with an alkylating agent such as akyliodide, iodoacetamide, β-iodoethanol, or 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides that reduce sensitivity for depurination (fragmentation during MS) e.g., a purine analog such as N7- or N9-deazapurine nucleotides, or RNA building blocks or using oligonucleotide triesters or incorporating phosphorothioate functions that are alkylated or employing oligonucleotide mimetics such as peptide nucleic acid (PNA).

As used herein, substrate refers to an insoluble support onto which a sample is deposited according to the materials described herein. Examples of appropriate substrates include beads (e.g., silica gel, controlled pore glass, magnetic, agarose gel and crosslinked dextroses (i.e. Sepharose and Sephadex, cellulose and other materials known by those of skill in the art to serve as solid support matrices. For example substrates may be formed from any or combinations of: silica gel, glass, magnet, polystyrene/1% divinylbenzene resins, such as Wang resins, which are Fmoc-amino acid-4-(hydroxymethyl)-phenoxymethylcopoly(styrene-1% divinylbenzene (DVD)) resin, chlorotrityl (2-chlorotritylchloride copolystyrene-DVB resin) resin, Merrifield (chloromethylated copolystyrene-DVB) resin metal, plastic, cellulose, cross-linked dextrans, such as those sold under the tradename Sephadex (Pharmacia) and agarose gel, such as gels sold under the tradename Sepharose (Pharmacia), which is a hydrogen bonded polysaccharide-type agarose gel, and other such resins and solid phase supports known to those of skill in the art. The support matrices may be in any shape or form, including, but not limited to: capillaries, flat supports such as glass fiber filters, glass surfaces, metal surfaces (steel, gold, silver, aluminum, copper and silicon), plastic materials including multiwell plates or membranes (e.g., of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without plates, and beads.

As used herein, a selectively cleavable linker is a linker that is cleaved under selected conditions, such as a photocleavable linker, a chemically cleavable linker and an enzymatically cleavable linker (i.e., a restriction endonuclease site or a ribonucleotide/RNase digestion). The linker is interposed between the support and immobilized DNA.

Isolation of Nucleic Acids Molecules

Nucleic acid molecules can be isolated from a particular biological sample using any of a number of procedures, which are well-known in the art, the particular isolation procedure chosen being appropriate for the particular biological sample. For example, freeze-thaw and alkaline lysis procedures can be useful for obtaining nucleic acid molecules from solid materials; heat and alkaline lysis procedures can be useful for obtaining nucleic acid molecules from urine; and proteinase K extraction can be used to obtain nucleic acid from blood (see, e.g., Rolff et al (1994) PCR: Clinical Diagnostics and Research, Springer).

To obtain an appropriate quantity of a nucleic acid molecules on which to perform mass spectrometry, amplification may be necessary. Examples of appropriate amplification procedures for use herein include: cloning (Sambrook et al., *Molecular Cloning: A Laboratory Manual*, Cold Spring Harbor Laboratory Press, 1989), polymerase chain reaction (PCR) (C. R. Newton and A. Graham, PCR, BIOS Publishers, 1994), ligase chain reaction (LCR) (see, e.g., Weidmann et al. (1994) *PCR Methods Appl*. Vol. 3, Pp. 57-64; F. Barany (1991) *Proc. Natl. Acad. Sci. U.S.A.* 88: 189-93), strand displacement amplification (SDA) (see, e.g., Walker et al. (1994) *Nucleic Acids Res.* 22: 2670-77) and variations such as RT-PCR (see, e.g., Higuchi et al. (1993) *Bio/Technology* 11: 1026-1030), allele-specific amplification (ASA) and transcription based processes.

Immobilization of Nucleic Acid Molecules to Solid Supports

To facilitate mass spectrometric analysis, a nucleic acid molecule containing a nucleic acid sequence to be detected can be immobilized to an insoluble (i.e., a solid) support. Examples of appropriate solid supports include beads (e.g., silica gel, controlled pore glass, magnetic, Sephadex/Sepharose, cellulose), capillaries, flat supports such as glass fiber filters, glass surfaces, metal surfaces (steel, gold, silver, aluminum, copper and silicon), plastic materials including multiwell plates or membranes (e.g. it would have been obvious to one of ordinary skill in the art to have, of polyethylene, polypropylene, polyamide, polyvinylidenedifluoride), pins (e.g., arrays of pins suitable for combinatorial synthesis or analysis or beads in pits of flat surfaces such as wafers (e.g., silicon wafers) with or without filter plates.

Samples containing target nucleic acids can be transferred to solid supports by any of a variety of methods known to those of skill in the art. For example, nucleic acid samples can be transferred to individual wells of a substrate, e.g., silicon chip, manually or using a pintool microdispenser apparatus as described herein. Alternatively, a piezoelectric pipette apparatus can be used to transfer small nanoliter samples to a substrate permitting the performance of high throughput miniaturized diagnostics on a chip.

Immobilization can be accomplished, for example, based on hybridization between a capture nucleic acid sequence, which has already been immobilized to the support and a complementary nucleic acid sequence, which is also contained within the nucleic acid molecule containing the nucleic acid sequence to be detected (FIG. 1A). So that hybridization between the complementary nucleic acid molecules is not hindered by the support, the capture nucleic acid can include an e.g., spacer region of at least about five nucleotides in length between the solid support and the capture nucleic acid sequence. The duplex formed will be cleaved under the influence of the laser pulse and desorption can be initiated. The solid support-bound nucleic acid molecule can be presented through natural oligoribo- or oligodeoxyribonucleotide as well as analogs (e.g., thio-modified phosphodiester or phosphotriester backbone) or employing oligonucleotide mimetics such as PNA analogs (see, e.g., Nielsen et al., *Science* 254: 1497 (1991)) which render the base sequence less susceptible to enzymatic degradation and -bound capture base sequence.

Linkers

Figure 1B:
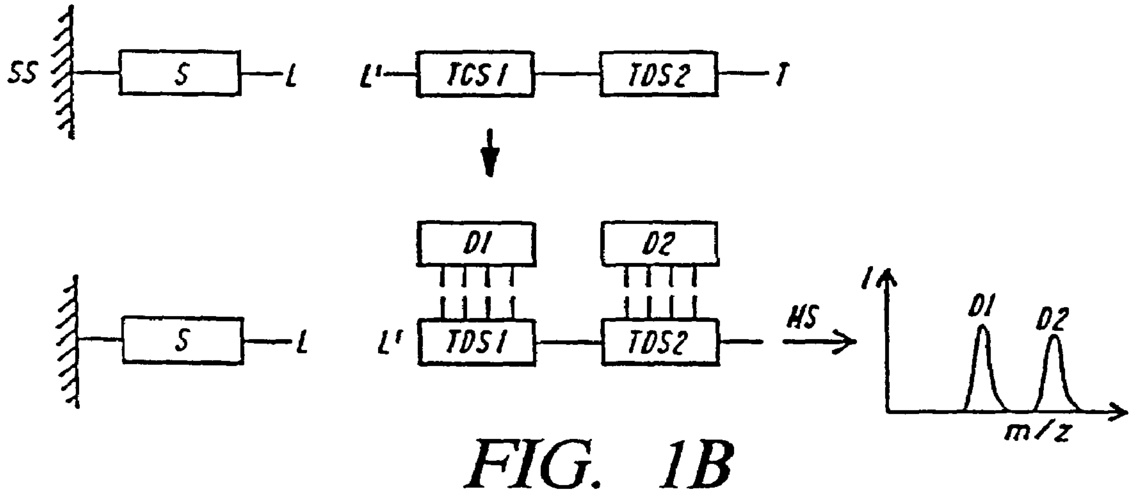
FIG. 1B is a diagram showing a process for performing mass spectrometric analysis on at least one target detection site (here TDS 1 and TDS 2) via direct linkage to a solid support. The target sequence (T) containing the target detection site (TDS 1 and TDS 2) is immobilized to a solid support via the formation of a reversible or irreversible bond formed between an appropriate functionality (L') on the target nucleic acid molecule (T) and an appropriate functionality (L) on the solid support. Detector nucleic acid sequences (here D1 and D2), which are complementary to a target detection site (TDS 1 or TDS 2) are then contacted with the TDS. Hybridization between TDS 1 and D1 and/or TDS 2 and D2 can be detected and distinguished based on molecular weight differences.
Figure 1C:
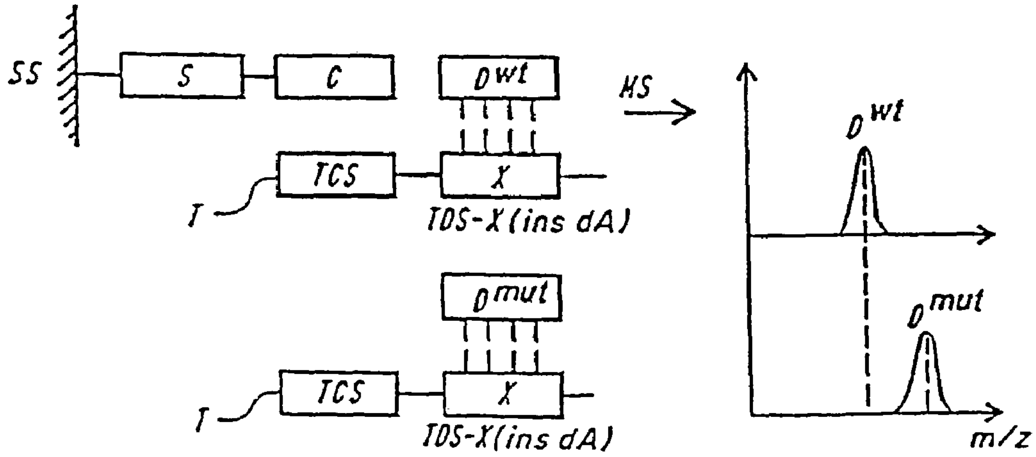
FIG. 1C is a diagram showing a process for detecting a wildtype ($D^{wt}$) and/or a mutant ($D^{mut}$) sequence in a target (T) nucleic acid molecule. As in FIG. 1A, a specific capture sequence (C) is attached to a solid support (SS) via a spacer (S). In addition, the capture sequence is chosen to specifically interact with a complementary sequence on the target sequence (T), the target capture site (TCS) to be detected through hybridization. If the target detection site (TDS) includes a mutation, X, detection sites can be distinguished from wildtype by mass spectrometry. Preferably, the detector nucleic acid molecule (D) is designed so that the mutation is in the middle of the molecule and therefore would not lead to a stable hybrid if the wildtype detector oligonucleotide ($D^{wt}$) is contacted with the target detector sequence, e.g., as a control. The mutation can also be detected if the mutated detector oligonucleotide ($D^{mut}$) with the matching base at the mutated position is used for hybridization. If a nucleic acid molecule obtained from a biological sample is heterozygous for the particular sequence (i.e. contain $D^{wt}$ and $D^{mut}$), $D^{wt}$ and $D^{mut}$ will be bound to the app and $D^{mut}$ to be detected simultaneously.

A target detection site can be directly linked to a solid support via a reversible or irreversible bond between an appropriate functionality (L') on the target nucleic acid molecule (T) and an appropriate functionality (L) on the capture molecule (FIG. 1B). A reversible linkage can be such that it is cleaved under the conditions of mass spectrometry (i.e., a photocleavable bond such as a charge transfer complex or a labile bond being formed between relatively stable organic radicals).

Photocleavable linkers are linkers that are cleaved upon exposure to light (see, e.g., Goldmacher et al. (1992) *Bioconj. Chem.* 3: 104-107), thereby releasing the targeted agent upon exposure to light. Photocleavable linkers that are cleaved upon exposure to light are known (see, e.g., Hazum et al. (1981) in *Pept., Proc. Eur. Pept. Symp.,* 16th, Brunfeldt, K (Ed), pp. 105-110, which describes the use of a nitrobenzyl group as a photocleavable protective group for cysteine; Yen et al. (1989) *Makromol. Chem* 190: 69-82, which describes water soluble photocleavable copolymers, including hydroxypropylmethacrylamide copolymer, glycine copolymer, fluorescein copolymer and methylrhodamine copolymer; Goldmacher et al. (1992) *Bioconj. Chem.* 3: 104-107, which describes a cross-linker and reagent that undergoes photolytic degradation upon exposure to near UV light (350 nm); and Senter et al. (1985) *Photochem. Photobiol* 42: 231-237, which describes nitrobenzyloxycarbonyl chloride cross linking reagents that produce photocleavable linkages), thereby releasing the targeted agent upon exposure to light. In preferred embodiments, the nucleic acid is immobilized using the photocleavable linker moiety that is cleaved during mass spectrometry. Presently preferred photocleavable linkers are set forth in the EXAMPLES.

Furthermore, the linkage can be formed with L' being a quaternary ammonium group, in which case, preferably, the surface of the solid support carries negative charges which repel the negatively charged nucleic acid backbone and thus facilitate the desorption required for analysis by a mass spectrometer. Desorption can occur either by the heat created by the laser pulse and/or, depending on L,' by specific absorption of laser energy which is in resonance with the L' chromophore.

Thus, the L-L' chemistry can be of a type of disulfide bond (chemically cleavable, for example, by mercaptoethanol or dithioerythrol), a biotin/streptavidin system, a heterobifunctional derivative of a trityl ether group (see, e.g., Köster et al. (1990) "A Versatile Acid-Labile Linker for Modification of Synthetic Biomolecules," *Tetrahedron Letters* 31: 7095) that can be cleaved under mildly acidic conditions as well as under conditions of mass spectrometry, a levulinyl group cleavable under almost neutral conditions with a hydrazinium/acetate buffer, an arginine-arginine or lysine-lysine bond cleavable by an endopeptidase enzyme like trypsin or a pyrophosphate bond cleavable by a pyrophosphatase, or a ribonucleotide bond in between the oligodeoxynucleotide sequence, which can be cleaved, for example, by a ribonuclease or alkali.

The functionalities, L and L,' can also form a charge transfer complex and thereby form the temporary L-L' linkage. Since in many cases the "charge-transfer band" can be determined by UV/vis spectrometry (see, e.g., *Organic Charge Transfer Complexes* by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nucleic acid molecule to be detected or vice versa.

In yet another approach, a reversible L-L' linkage can be generated by homolytically forming relatively stable radicals. Under the influence of the laser pulse, desorption (as discussed above) as well as ionization will take place at the radical position. Those skilled in the art will recognize that other organic radicals can be selected and that, in relation to the dissociation energies needed to homolytically cleave the bond between them, a corresponding laser wavelength can be selected (see e.g., *Reactive Molecules* by C. Wentrup, John Wiley & Sons, 1984).

Figure 4:
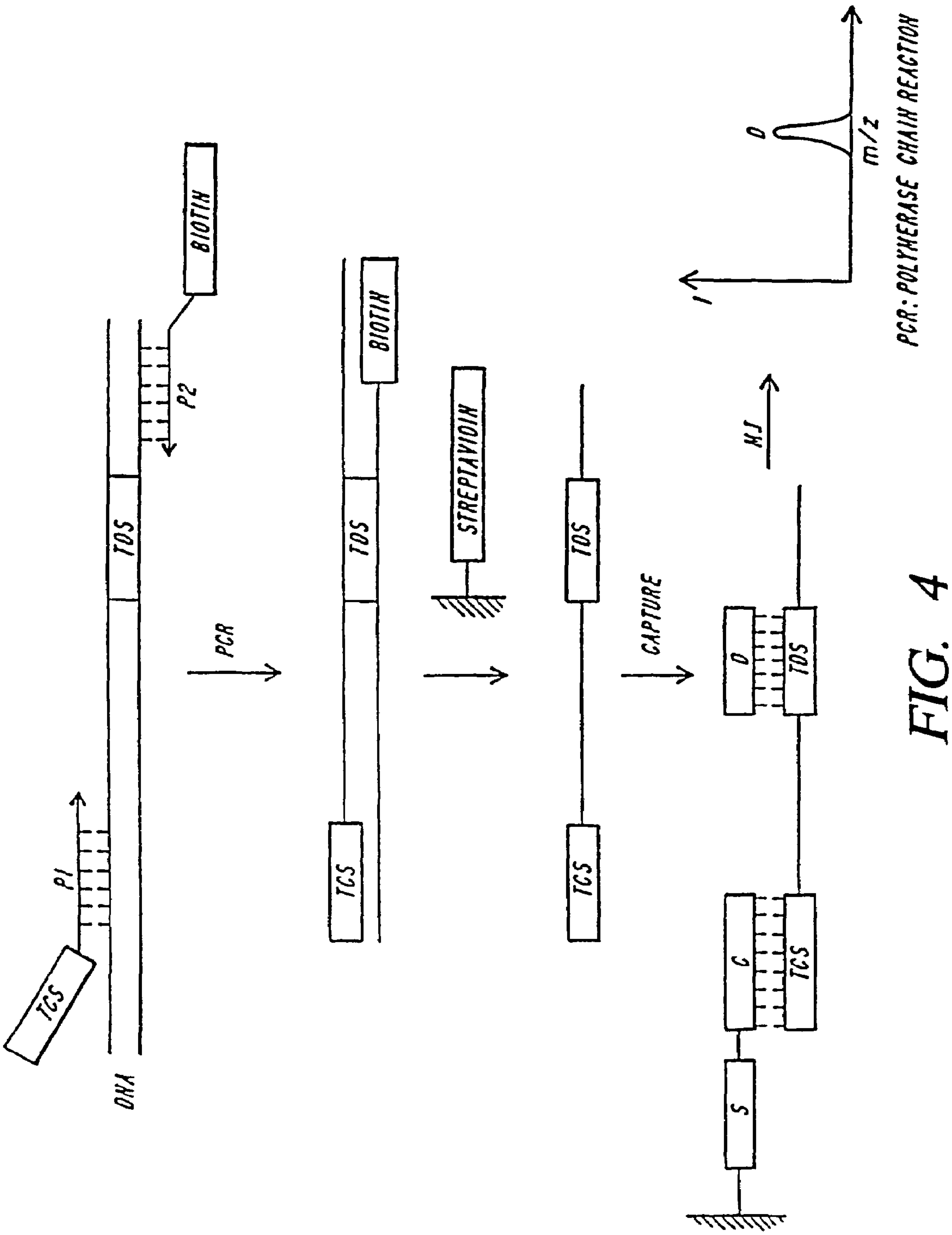
FIG. 4 is a diagram showing a format wherein a predesigned target capture site (TCS) is incorporated into the target sequence using nucleic acid (i.e., PCR) amplification. Only one strand is captured, the other is removed (e.g., based on the interaction between biotin and streptavidin coated magnetic beads). If the biotin is attached to primer 1 the other strand can be appropriately marked by a TCS. Detection is as described above through the interaction of a specific detector oligonucleotide D with the corresponding target detection site TDS via mass spectrometry.
Figure 5:
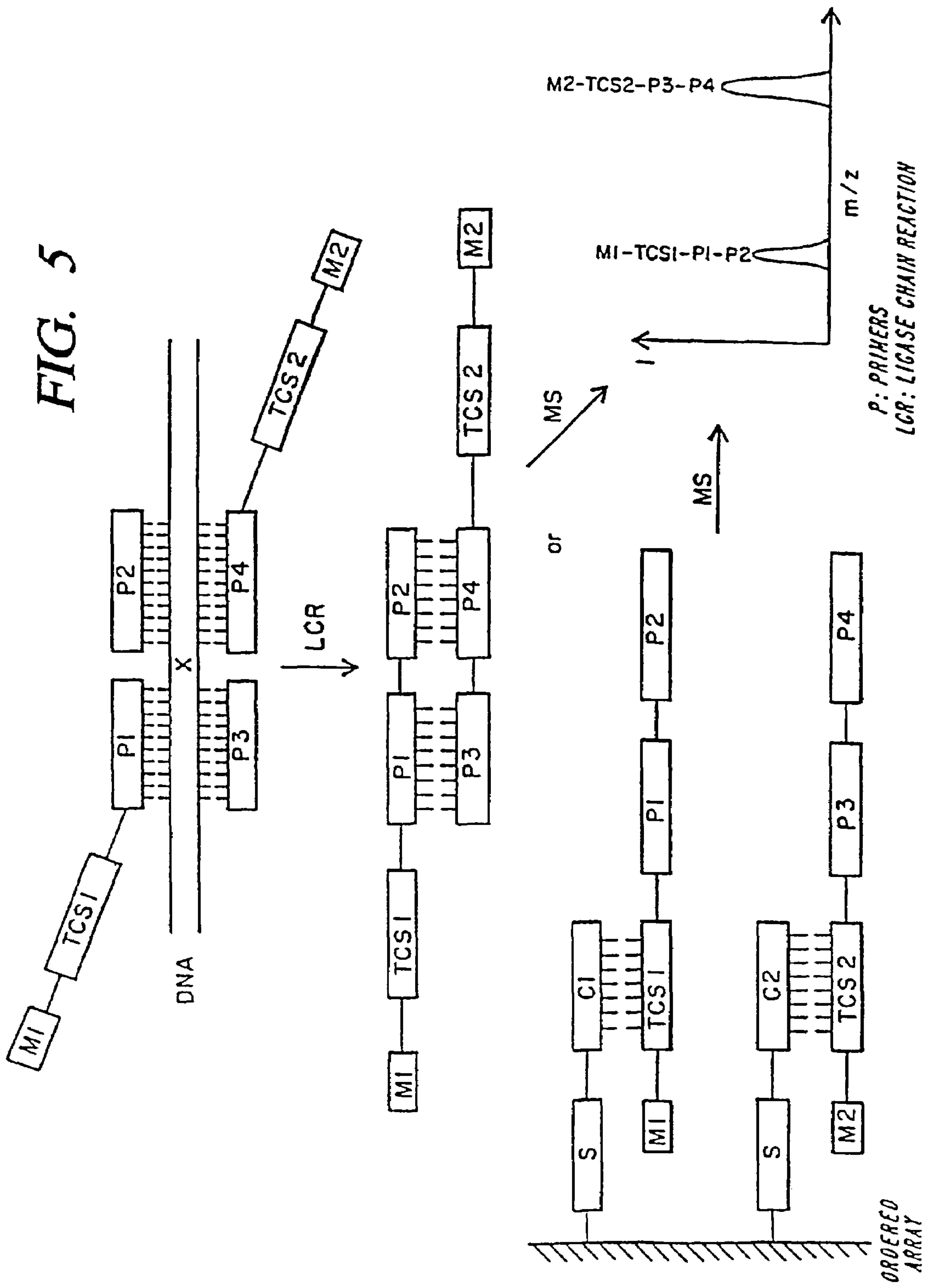
FIG. 5 is a diagram showing how amplification (here ligase chain reaction (LCR)) products can be prepared and detected by mass spectrometry. Mass differentiation can be achieved by the mass modifying functionalities (M1 and M2) attached to primers (P1 and P4 respectively). Detection by mass spectrometry can be accomplished directly (i.e. without employing immobilization and target capturing sites (TCS)). Multiple LCR reactions can be performed in parallel by providing an ordered array of capturing sequences (C). This format allows separation of the ligation products and spot by spot identification via mass spectrometry or multiplexing if mass differentiation is sufficient.
Figure 6A:
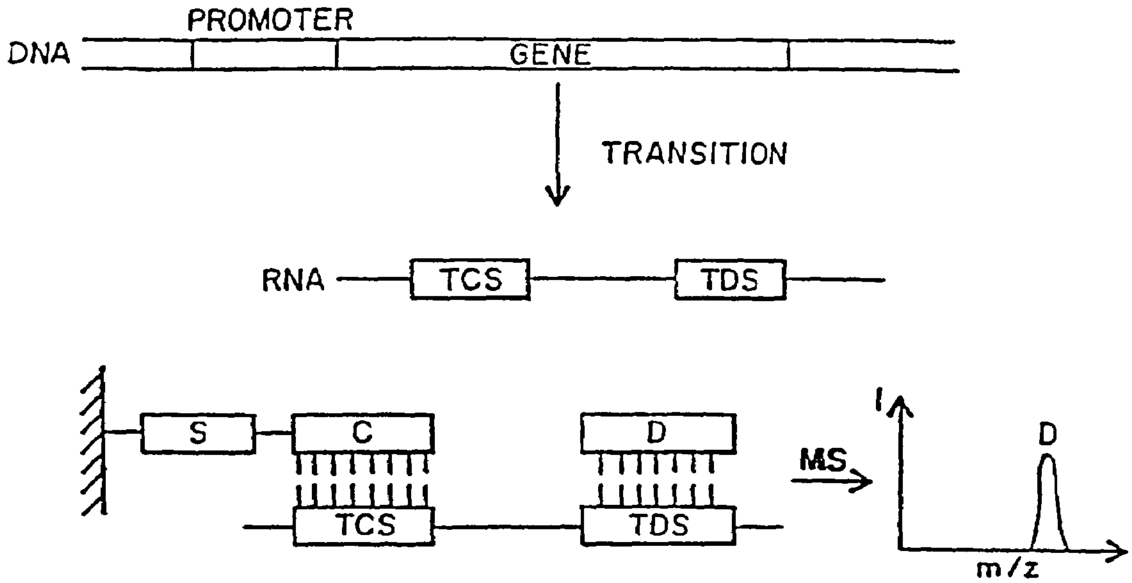
FIG. 6A is a diagram showing mass spectrometric analysis of a nucleic acid molecule, which has been amplified by a transcription amplification procedure. An RNA sequence is captured via its TCS sequence, so that wildtype and mutated target detection sites can be detected as above by employing appropriate detector oligonucleotides (D).

An anchoring function L' can also be incorporated into a target capturing sequence (TCS) by using appropriate primers during an amplification procedure, such as PCR (FIG. 4), LCR (FIG. 5) or transcription amplification (FIG. 6A).

When performing exonuclease sequencing using MALDI-TOF MS, a single stranded DNA molecule immobilized via its 5-end to a solid support is unilaterally degraded with a 3'-processive exonuclease and the molecular weight of the degraded nucleotide is determined sequentially. Reverse Sanger sequencing reveals the nucleotide sequence of the immobilized DNA. By adding a selectively cleavable linker, not only can the mass of the free nucleotides be determined but also, upon removal of the nucleotides by washing, the mass of the remaining fragment can be detected by MALDI-TOF upon cleaving the DNA from the solid support. Using selectively cleavable linkers, such as the photocleavable and chemical cleavable linkers provided herein, this cleavage can be selected to occur during the ionization and volatizing steps of MALDI-TOF. The same rationale applies for a 5' immobilized strand of a double stranded DNA that is degraded while in a duplex. Likewise, this also applies when using a 5'-processive exonuclease and the DNA is immobilized through the 3'-end to the solid support.

As noted, at least three version of immobilization are contemplated herein: 1) the target nucleic acid is amplified or obtained (the target sequence or surrounding DNA sequence must be known to make primers to amplify or isolated); 2) the primer nucleic acid is immobilized to the solid support and the target nucleic acid is hybridized thereto (this is for detecting the presence of or sequencing a target sequence in a sample); or 3) a double stranded DNA (amplified or isolated) is immobilized through linkage to one predetermined strand, the DNA is denatured to eliminate the duplex and then a high concentration of a complementary primer or DNA with identity upstream from the target site is added and a strand displacement occurs and the primer is hybridized to the immobilized strand.

In the embodiments where the primer nucleic acid is immobilized on the solid support and the target nucleic acid is hybridized thereto, the inclusion of the cleavable linker allows the primer DNA to be immobilized at the 5'-end so that free 3'-OH is available for nucleic acid synthesis (extension) and the sequence of the "hybridized" target DNA can be determined because the hybridized template can be removed by denaturation and the extended DNA products cleaved from the solid support for MALDI-TOF MS. Similarly for 3), the immobilized DNA strand can be elongated when hybridized to the template and cleaved from the support. Thus, Sanger sequencing and primer oligo base extension (PROBE), discussed below, extension reactions can be performed using an immobilized primer of a known, upstream DNA sequence complementary to an invariable region of a target sequence. The nucleic acid from the person is obtained and the DNA sequence of a variable region (deletion, insertion, missense mutation that cause genetic predisposition or diseases, or the presence of viral/bacterial or fungal DNA) not only is detected, but the actual sequence and position of the mutation is also determined.

In other cases, the target DNA must be immobilized and the primer annealed. This requires amplifying a larger DNA based on known sequence and then sequencing the immobilized fragments (i.e., the extended fragments are hybridized but not immobilized to the support as described above). In these cases, it is not desirable to include a linker because the MALDI-TOF spectrum is of the hybridized DNA; it is not necessary to cleave the immobilized template.

Any linker known to those of skill in the art for immobilizing nucleic acids to solid supports may be used herein to link the nucleic acid to a solid support. The preferred linkers herein are the selectively cleavable linkers, particularly those exemplified herein. Other linkers include, acid cleavable linkers, such as bismaleimideothoxy propane, acid-labile trityl linkers.

Acid cleavable linkers, photocleavable and heat sensitive linkers may also be used, particularly where it may be necessary to cleave the targeted agent to permit it to be more readily accessible to reaction. Acid cleavable linkers include, but are not limited to, bismaleimideothoxy propane; and adipic acid dihydrazide linkers (see, e.g., Fattom et al. (1992) *Infection & Immun.* 60: 584-589) and acid labile transferrin conjugates that contain a sufficient portion of transferrin to permit entry into the intracellular transferrin cycling pathway (see, e.g., Welhoner et al. (1991) *J. Biol. Chem.* 266: 4309-4314).

Photocleavable Linkers

Photocleavable linkers are provided. In particular, photocleavable linkers as their phosphoramidite derivatives are provided for use in solid phase synthesis of oligonucleotides. The linkers contain o-nitrobenzyl moieties and phosphate linkages which allow for complete photolytic cleavage of the conjugates within minutes upon UV irradiation. The UV wavelengths used are selected so that the irradiation will not damage the oligonucleotides and are preferably about 350-380 nm, more preferably 365 nm. The photocleavable linkers provided herein possess comparable coupling efficiency as compared to commonly used phosphoramidite monomers (see, Sinha et al. (1983) *Tetrahedron Lett.* 24: 5843-5846; Sinha et al. (1984) *Nucleic Acids Res.* 12: 4539-4557; Beaucage et al. (1993) *Tetrahedron* 49: 6123-6194; and Matteucci et al. (1981) *J. Am. Chem. Soc.* 103: 3185-3191).

In one embodiment, the photocleavable linkers have formula I:

(I)

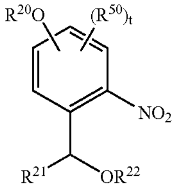

where $R^{20}$ is ω-(4,4'-dimethoxytrityloxy)alkyl or ω-hydroxyalkyl; $R^{21}$ is selected from hydrogen, alkyl, aryl, alkoxycarbonyl, aryloxycarbonyl and carboxy; $R^{22}$ is hydrogen or (dialkylamino)(ω-cyanoalkoxy)P—; t is 0-3; and $R^{50}$ is alkyl, alkoxy, aryl or aryloxy.

In a preferred embodiment, the photocleavable linkers have formula II:

(II)

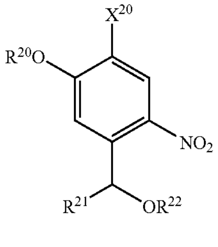

where $R^{20}$ is ω-(4,4'-dimethoxytrityloxy)alkyl, ω-hydroxyalkyl or alkyl; $R^{21}$ is selected from hydrogen, alkyl, aryl, alkoxycarbonyl, aryloxycarbonyl and carboxy; $R^{22}$ is hydrogen or (dialkylamino)(ω-cyanoalkoxy)P—; and $X^{20}$ is hydrogen, alkyl or $OR^{20}$.

In particularly preferred embodiments, $R^{20}$ is 3-(4,4'-dimethoxytrityloxy)propyl, 3-hydroxypropyl or methyl; $R^{21}$ is selected from hydrogen, methyl and carboxy; $R^{22}$ is hydrogen or (diisopropylamino)(2-cyanoethoxy)P—; and $X^{20}$ is hydrogen, methyl or $OR^{20}$. In a more preferred embodiment, $R^{20}$ is 3-(4,4'-dimethoxytrityloxy)propyl; $R^{21}$ is methyl; $R^{22}$ is (diisopropylamino)(2-cyanoethoxy)P—; and $X^{20}$ is hydrogen. In another more preferred embodiment, $R^{20}$ is methyl; $R^{21}$ is methyl; $R^{22}$ is (diisopropylamino)(2-cyanoethoxy)P—; and $X^{20}$ is 3-(4,4'-dimethoxytrityloxy)propoxy.

In another embodiment, the photocleavable linkers have formula III:

(III)

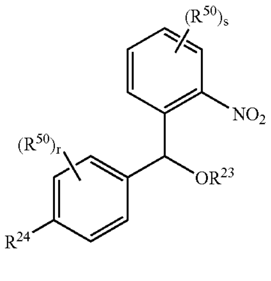

where $R^{23}$ is hydrogen or (dialkylamino)(ω-cyanoalkoxy)P—; and $R^{24}$ is selected from ω-hydroxyalkoxy, ω-(4,4'-dimethoxytrityloxy)alkoxy, ω-hydroxyalkyl and ω-(4,4'-dimethoxytrityloxy)alkyl, and is unsubstituted or substituted on the alkyl or alkoxy chain with one or more alkyl groups; r and s are each independently 0-4; and $R^{50}$ is alkyl, alkoxy, aryl or aryloxy. In certain embodiments, $R^{24}$ is ω-hydroxyalkyl or ω-(4,4'-dimethoxytrityloxy)alkyl, and is substituted on the alkyl chain with a methyl group.

In preferred embodiments, $R^{23}$ is hydrogen or (diisopropylamino)(2-cyanoethoxy)P—; and $R^{24}$ is selected from 3-hydroxypropoxy, 3-(4,4'-dimethoxytrityloxy)propoxy, 4-hydroxybutyl, 3-hydroxy-1-propyl, 1-hydroxy-2-propyl, 3-hydroxy-2-methyl-1-propyl, 2-hydroxyethyl, hydroxymethyl, 4-(4,4'-dimethoxytrityloxy)butyl, 3-(4,4'-dimethoxytrityloxy)-1-propyl, 2-(4,4'-dimethoxytrityloxy)ethyl, 1-(4,4'-dimethoxytrityloxy)-2-propyl, 3-(4,4'-dimethoxytrityloxy)-2-methyl-1-propyl and 4,4'-dimethoxytrityloxymethyl.

In more preferred embodiments, $R^{23}$ is (diisopropylamino)(2-cyanoethoxy)P—; r and s are 0; and $R^{24}$ is selected from 3-(4,4'-dimethoxytrityloxy)propoxy, 4-(4,4'-dimethoxytrityloxy)butyl, 3-(4,4'-dimethoxytrityloxy)propyl, 2-(4,4'-dimethoxytrityloxy)ethyl, 1-(4,4'-dimethoxytrityloxy)-2-propyl, 3-(4,4'-dimethoxytrityloxy)-2-methyl-1-propyl and 4,4'-dimethyoxytrityloxymethyl. $R^{24}$ is most preferably 3-(4,4'-dimethoxytrityloxy)propoxy.

Preparation of the Photocleavable Linkers

A. Preparation of Photocleavable Linkers of Formulae I or II

Photocleavable linkers of formulae I or II may be prepared by the methods described below, by minor modification of the methods by choosing the appropriate starting materials or by any other methods known to those of skill in the art. Detailed procedures for the synthesis of photocleavable linkers of formula II are provided in the Examples.

In the photocleavable linkers of formula II where $X^{20}$ is hydrogen, the linkers may be prepared in the following manner. Alkylation of 5-hydroxy-2-nitrobenzaldehyde with an ω-hydroxyalkyl halide, e.g., 3-hydroxypropyl bromide, followed by protection of the resulting alcohol as, e.g., a silyl ether, provides a 5-(ω-silyloxyalkoxy)-2-nitrobenzaldehyde. Addition of an organometallic to the aldehyde affords a benzylic alcohol. Organometallics which may be used include trialkylaluminums (for linkers where $R^{21}$ is alkyl), such as trimethylaluminum, borohydrides (for linkers where $R^{21}$ is hydrogen), such as sodium borohydride, or metal cyanides (for linkers where $R^{21}$ is carboxy or alkoxycarbonyl), such as potassium cyanide. In the case of the metal cyanides, the product of the reaction, a cyanohydrin, would then be hydrolyzed under either acidic or basic conditions in the presence of either water or an alcohol to afford the compounds of interest.

The silyl group of the side chain of the resulting benzylic alcohols may then be exchanged for a 4,4'-dimethoxytrityl group by desilylation with, e.g., tetrabutylammonium fluoride, to give the corresponding alcohol, followed by reaction with 4,4'-dimethoxytrityl chloride. Reaction with, e.g., 2-cyanoethyl diisopropylchlorophosphoramidite affords the linkers where $R^{22}$ is (dialkylamino)(ω-cyanoalkoxy)P—.

A specific example of a synthesis of a photocleavable linker of formula II is shown in the following scheme, which also demonstrates use of the linker in oligonucleotide synthesis. This scheme is intended to be illustrative only and in no way limits the scope of the invention. Experimental details of these synthetic transformations are provided in the Examples.

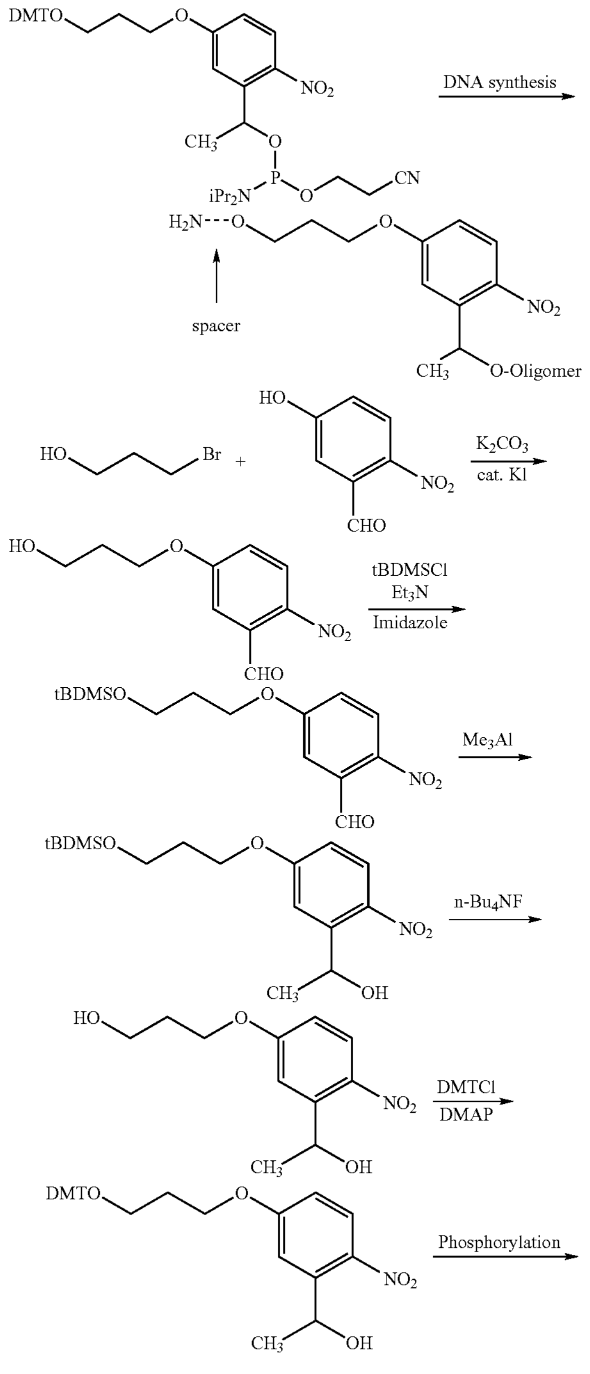

Synthesis of the linkers of formula II where $X^{20}$ is $OR^{20}$, 3,4-dihydroxyacetophenone is protected selectively at the 4-hydroxyl by reaction with, e.g., potassium carbonate and a silyl chloride. Benzoate esters, propiophenones, butyrophenones, etc. may be used in place of the acetophenone. The resulting 4-silyloxy-3-hydroxyacetophenone is then alkylated at the with an alkyl halide (for linkers where $R^{20}$ is alkyl) at the 3-hydroxyl and desilylated with, e.g., tetrabutylammonium fluoride to afford a 3-alkoxy-4-hydroxyacetophenone. This compound is then alkylated at the 4-hydroxyl by reaction with an ω-hydroxyalkyl halide, e.g., 3-hydroxypropyl bromide, to give a 4-(ω-hydroxyalkoxy)-3-alkoxyacetophenone. The side chain alcohol is then protected as an ester, e.g., an acetate. This compound is then nitrated at the 5-position with, e.g., concentrated nitric acid to provide the corresponding 2-nitroacetophenones. Saponification of the side chain ester with, e.g., potassium carbonate, and reduction of the ketone with, e.g., sodium borohydride, in either order gives a 2-nitro-4-(ω-hydroxyalkoxy)-5-alkoxybenzylic alcohol.

Selective protection of the side chain alcohol as the corresponding 4,4'-dimethoxytrityl ether is then accomplished by reaction with 4,4'-dimethoxytrityl chloride. Further reaction with, e.g., 2-cyanoethyl diisopropylchlorophosphoramidite affords the linkers where $R^{22}$ is (dialkylamino)(ω-cyanoalkoxy)P—.

A specific example of the synthesis of a photocleavable linker of formula II is shown the following scheme. This scheme is intended to be illustrative only and in no way limit the scope of the invention. Detailed experimental procedures for the transformations shown are found in the Examples.

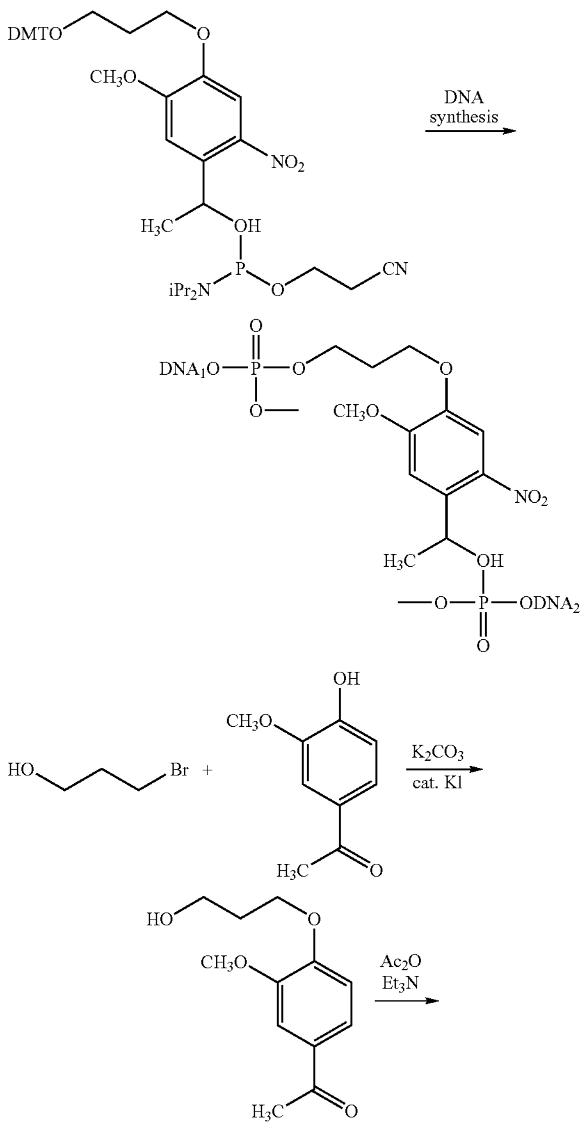

-continued

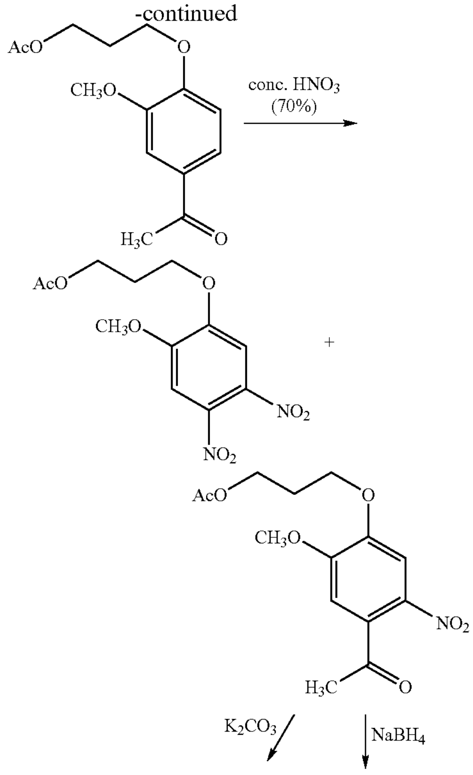

A. Preparation of Photocleavable Linkers of Formulae III

Photocleavable linkers of formula III may be prepared by the methods described below, by minor modification of the methods by choosing appropriate starting materials, or by other methods known to those of skill in the art.

In general, photocleavable linkers of formula III are prepared from ω-hydroxyalkyl- or alkoxyaryl compounds, in particular ω-hydroxy-alkyl or alkoxy-benzenes. These compounds are commercially available, or may be prepared from an ω-hydroxyalkyl halide (e.g., 3-hydroxypropyl bromide) and either phenyllithium (for the ω-hydroxyalkylbenzenes) or

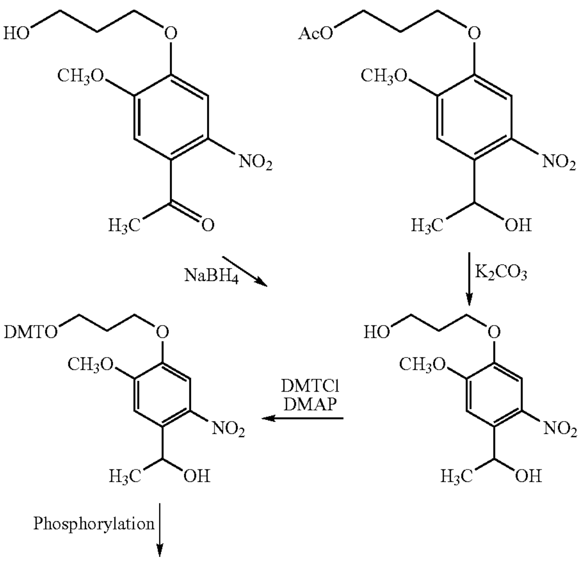

phenol (for the ω-hydroxyalkoxybenzenes). Acylation of the ω-hydroxyl group (e.g., as an acetate ester) followed by Friedel-Crafts acylation of the aromatic ring with 2-nitrobenzoyl chloride provides a 4-(ω-acetoxy-alkyl or alkoxy)-2-nitrobenzophenone. Reduction of the ketone with, e.g., sodium borohydride, and saponification of the side chain ester are performed in either order to afford a 2-nitrophenyl-4-(hydroxy-alkyl or alkoxy)phenylmethanol. Protection of the terminal hydroxyl group as the corresponding 4,4'-dimethoxytrityl ether is achieved by reaction with 4,4'-dimethoxytrityl chloride. The benzylic hydroxyl group is then reacted with, e.g., 2-cyanoethyl diisopropylchlorophosphoramidite to afford linkers of formula II where $R^{23}$ is (dialkylamino)(ω-cyanoalkoxy)P—.

Other photocleavable linkers of formula III may be prepared by substituting 2-phenyl-1-propanol or 2-phenylmethyl-1-propanol for the ω-hydroxy-alkyl or alkoxy-benzenes in the above synthesis. These compounds are commercially available, but may also be prepared by reaction of, e.g., phenylmagnesium bromide or benzylmagnesium bromide, with the requisite oxirane (i.e., propylene oxide) in the presence of catalytic cuprous ion.

Chemically Cleavable Linkers

Figure 68:
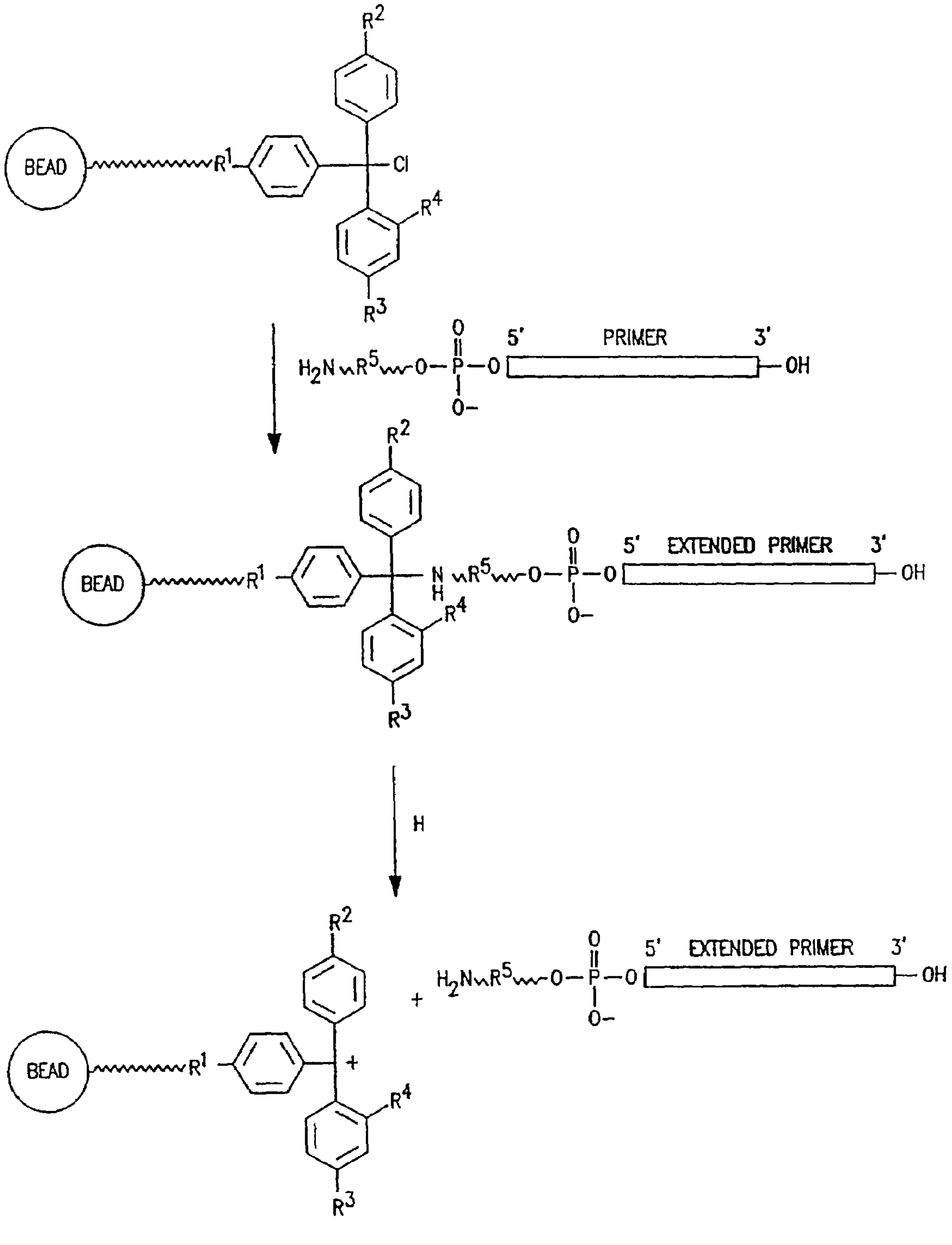
FIG. 68 is a schematic representation of nucleic acid immobilization via covalent bifunctional trityl linkers.

A variety of chemically cleavable linkers may be used to introduce a cleavable bond between the immobilized nucleic acid and the solid support. Acid-labile linkers are presently preferred chemically cleavable linkers for mass spectrometry, especially MALDI-TOF MS, because the acid labile bond is cleaved during conditioning of the nucleic acid upon addition of the 3-HPA matrix solution. The acid labile bond can be introduced as a separate linker group, e.g., the acid labile trityl groups (see FIG. 68; Example 16) or may be incorporated in a synthetic nucleic acid linker by introducing one or more silyl internucleoside bridges using diisopropylsilyl, thereby forming diisopropylsilyl-linked oligonucleotide analogs. The diisopropylsilyl bridge replaces the phoshodiester bond in the DNA backbone and under mildly acidic conditions, such as 1.5% trifluoroacetic acid (TFA) or 3-HPA/1% TFA MALDI-TOF matrix solution, results in the introduction of one or more intra-strand breaks in the DNA molecule. Methods for the preparation of diisopropylsilyl-linked oligonucleotide precursors and analogs are known to those of skill in the art (see e.g., Saha et al. (1993) *J. Org. Chem.* 58: 7827-7831). These oligonucleotide analogs may be readily prepared using solid state oligonucleotide synthesis methods using diisopropylsilyl derivatized deoxyribonucleosides.

Nucleic Acid Conditioning

Prior to mass spectrometric analysis, it may be useful to "condition" nucleic acid molecules, for example to decrease the laser energy required for volatilization and/or to minimize fragmentation. Conditioning is preferably performed while a target detection site is immobilized. An example of conditioning is modification of the phosphodiester backbone of the nucleic acid molecule (e.g., cation exchange), which can be useful for eliminating peak broadening due to a heterogeneity in the cations bound per nucleotide unit. Contacting a nucleic acid molecule with an alkylating agent such as alkyliodide, iodoacetamide, β-iodoethanol, or 2,3-epoxy-1-propanol, the monothio phosphodiester bonds of a nucleic acid molecule can be transformed into a phosphotriester bond. Likewise, phosphodiester bonds may be transformed to uncharged derivatives employing trialkylsilyl chlorides. Further conditioning involves incorporating nucleotides that reduce sensitivity for depurination (fragmentation during MS) e.g., a purine analog such as N7- or N9-deazapurine nucleotides, or RNA building blocks or using oligonucleotide triesters or incorporating phosphorothioate functions which are alkylated or employing oligonucleotide mimetics such as PNA.

Multiplex Reactions

Figure 2:
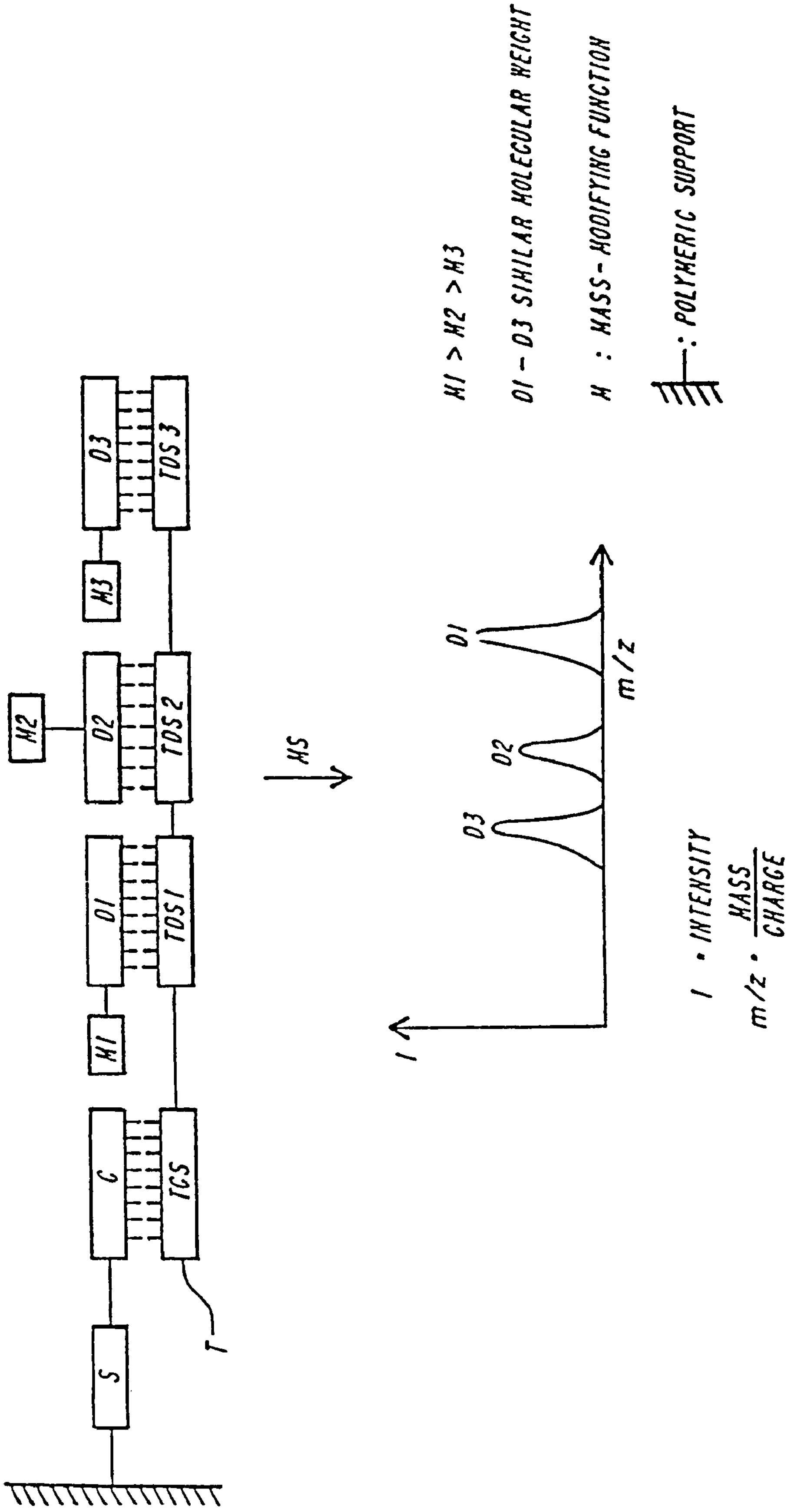
FIG. 2 is a diagram showing a process in which several mutations are simultaneously detected on one target sequence molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1-M3 into the detector oligonucleotide.

For certain applications, it may be useful to simultaneously detect more than one (mutated) loci on a particular captured nucleic acid fragment (on one spot of an array) or it may be useful to perform parallel processing by using oligonucleotide or oligonucleotide mimetic arrays on various solid supports. "Multiplexing" can be achieved by several different methodologies. For example, several mutations can be simultaneously detected on one target sequence by employing corresponding detector (probe) molecules (e.g., oligonucleotides or oligonucleotide mimetics). The molecular weight differences between the detector oligonucleotides D1, D2 and D3 must be large enough so that simultaneous detection (multiplexing) is possible. This can be achieved either by the sequence itself (composition or length) or by the introduction of mass-modifying functionalities M1-M3 into the detector oligonucleotide (see FIG. 2).

Mass Modification of Nucleic Acids

Mass modifying moieties can be attached, for instance, to either the 5'-end of the oligonucleotide ($M^1$), to the nucleobase (or bases) ($M^2$, $M^7$), to the phosphate backbone ($M^3$), and to the 2'-position of the nucleoside (nucleosides) ($M^4$, $M^6$) and/or to the terminal 3'-position ($M^5$). Examples of mass modifying moieties include, for example, a halogen, an azido, or of the type, XR, wherein X is a linking group and R is a mass-modifying functionality. The mass-modifying functionality can thus be used to introduce defined mass increments into the oligonucleotide molecule.

The mass-modifying functionality can be located at different positions within the nucleotide moiety (see, e.g., U.S. Pat. No. 5,547,835 and International PCT application No. WO 94/21822). For example, the mass-modifying moiety, M, can be attached either to the nucleobase, $M^2$ (in case of the $c^7$-deazanucleosides also to C-7, $M^7$), to the triphosphate group at the alpha phosphate, $M^3$, or to the 2'-position of the sugar ring of the nucleoside triphosphate, $M^4$ and $M^6$. Modifications introduced at the phosphodiester bond (M4), such as with alpha-thio nucleoside triphosphates, have the advantage that these modifications do not interfere with accurate Watson-Crick base-pairing and additionally allow for the one-step post-synthetic site-specific modification of the complete nucleic acid molecule e.g., via alkylation reactions (see, e.g., Nakamaye et al. (1988) *Nucl Acids Res.* 16: 9947-59). Particularly preferred mass-modifying functionalities are boron-modified nucleic acids since they are better incorporated into nucleic acids by polymerases (see, e.g., Porter et al. (1995) *Biochemistry* 34: 11963-11969; Hasan et al. (1996) *Nucleic Acids Res.* 24: 2150-2157; Li et al. (1995) *Nucl. Acids Res.* 23: 4495-4501).

Furthermore, the mass-modifying functionality can be added so as to affect chain termination, such as by attaching it to the 3'-position of the sugar ring in the nucleoside triphosphate, $M^5$. For those skilled in the art, it is clear that many combinations can be used in the methods provided herein. In the same way, those skilled in the art will recognize that chain-elongating nucleoside triphosphates can also be mass-modified in a similar fashion with numerous variations and combinations in functionality and attachment positions.

Without being bound to any particular theory, the mass-modification, M, can be introduced for X in XR as well as using oligo-/polyethylene glycol derivatives for R. The mass-modifying increment in this case is 44, i.e. five different mass-modified species can be generated by just changing m from 0 to 4 thus adding mass units of 45 (m=0), 89 (m=1), 133 (m=2), 177 (m=3) and 221 (m=4) to the nucleic acid molecule (e.g., detector oligonucleotide (D) or the nucleoside triphosphates (FIG. 6(C)), respectively). The oligo/polyethylene glycols can also be monoalkylated by a lower alkyl such as methyl, ethyl, propyl, isopropyl, t-butyl and the like. A selection of linking functionalities, X, are also illustrated. Other chemistries can be used in the mass-modified compounds (see, e.g., those described in *Oligonucleotides and Analogues, A Practical Approach*, F. Eckstein, editor, IRL Press, Oxford, 1991).

In yet another embodiment, various mass-modifying functionalities, R, other than oligo/polyethylene glycols, can be selected and attached via appropriate linking chemistries, X. A simple mass-modification can be achieved by substituting H for halogens like F, Cl, Br and/or I, or pseudohalogens such as CN, SCN, NCS, or by using different alkyl, aryl or aralkyl moieties such as methyl, ethyl, propyl, isopropyl, t-butyl, hexyl, phenyl, substituted phenyl, benzyl, or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another mass-modification can be obtained by attaching homo- or heteropeptides through the nucleic acid molecule (e.g., detector (D)) or nucleoside triphosphates. One example. useful in generating mass-modified species with a mass increment of 57. is the attachment of oligoglycines, e.g., mass-modifications of 74 (r=1, m=1), 131 (r=1, m=1), 188 (r=1, m=2), 245 (r=1, m=3) are achieved. Simple oligoamides also can be used, e.g., mass-modifications of 74 (r=1, m=0), 88 (r=2, m=0), 102 (r=3, m=0), 116(r=4, m=0), etc. are obtainable. Variations in additions to those set forth herein will be apparent to the skilled artisan.

Figure 6B:
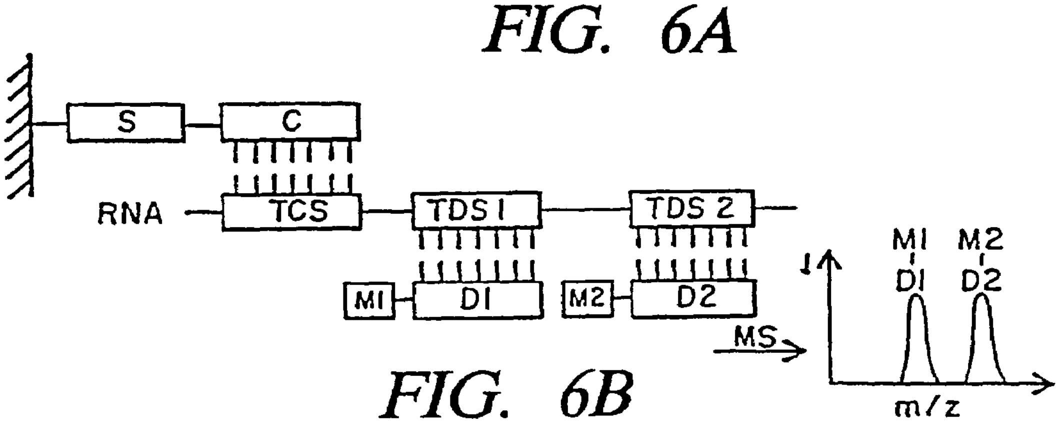
FIG. 6B is a diagram showing multiplexing to detect two different (mutated) sites on the same RNA in a simultaneous fashion using mass-modified detector oligonucleotides M1-D1 and M2-D2.
Figure 6C:
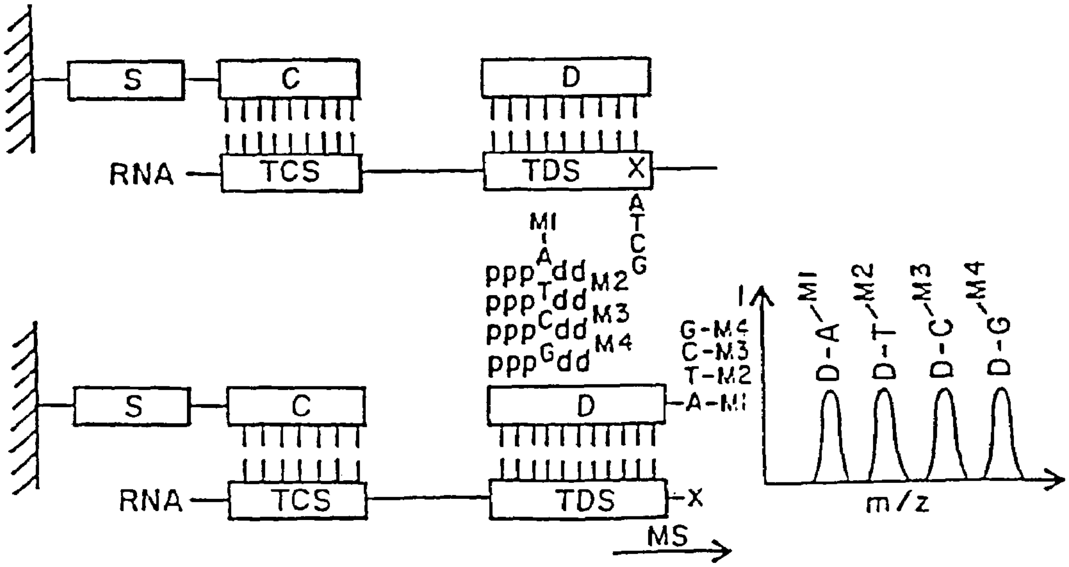
FIG. 6C is a diagram of a different multiplexing procedure for detection of specific mutations by employing mass modified dideoxynucleoside or 3'-deoxynucleoside triphosphates and an RNA dependent DNA polymerase. Alternatively, DNA dependent RNA polymerase and ribonucleotide phosphates can be employed. This format allows for simultaneous detection of all four base possibilities at the site of a mutation (X).
Figure 7A:
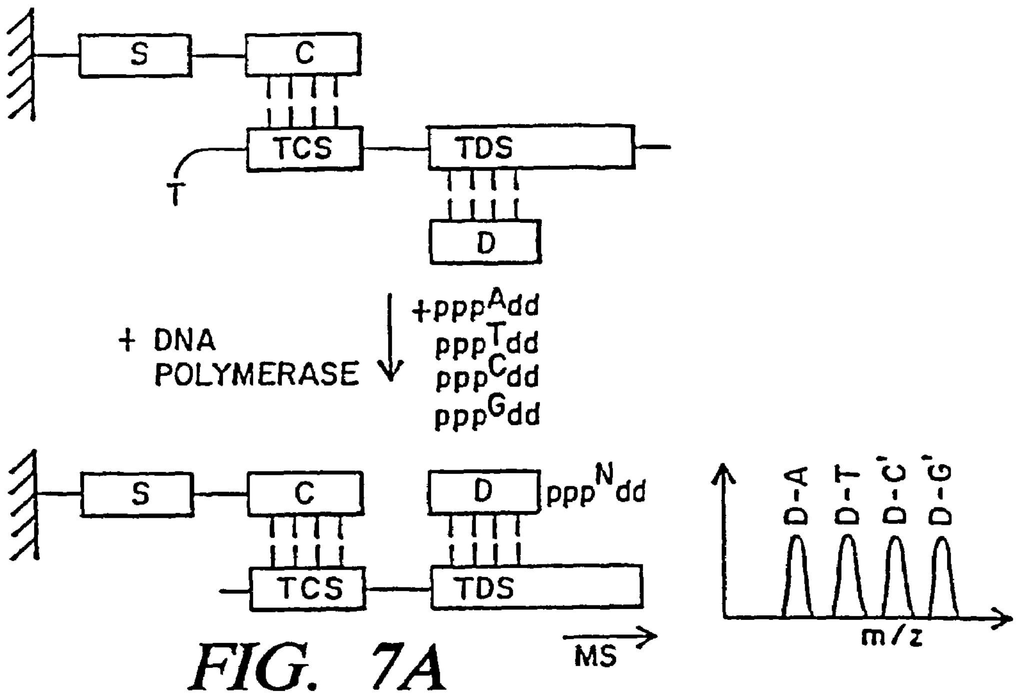
FIG. 7A is a diagram showing a process for performing mass spectrometric analysis on one target detection site (TDS) contained within a target nucleic acid molecule (T), which has been obtained from a biological sample. A specific capture sequence (C) is attached to a solid support (SS) via a spacer (S). The capture sequence is chosen to specifically hybridize with a complementary sequence on T known as the target capture site (TCS). A nucleic acid molecule that is complementary to a portion of the TDS is hybridized to the TDS 5' of the site of a mutation (X) within the TDS. The addition of a complete set of dideoxynucleosides or 3'-deoxynucleoside triphosphates (e.g., pppAdd, pppTdd, pppCdd and pppGdd) and a DNA dependent DNA or RNA polymerase allows for the addition only of the one dideoxynucleoside or 3'-deoxynucleoside triphosphate that is complementary to X.
Figure 7B:
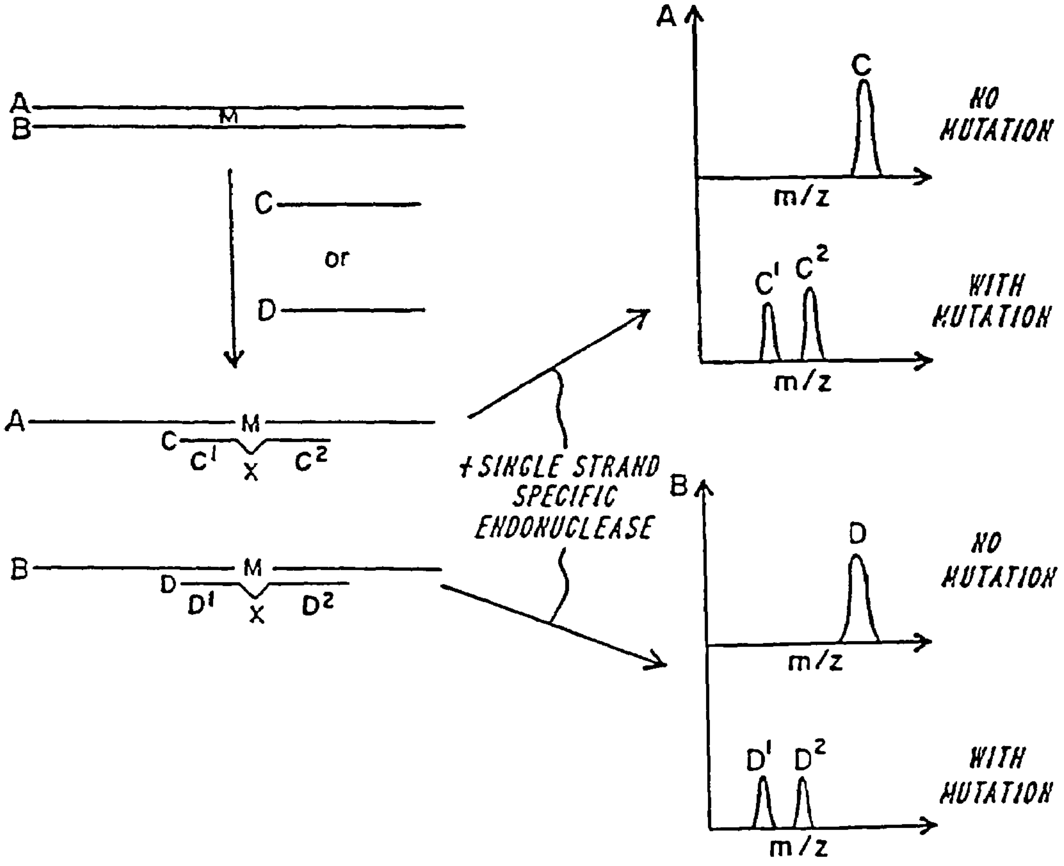
FIG. 7B is a diagram showing a process for performing mass spectrometric analysis to determine the presence of a mutation at a potential mutation site (M) within a nucleic acid molecule. This format allows for simultaneous analysis of alleles (A) and (B) of a double stranded target nucleic acid molecule, so that a diagnosis of homozygous normal, homozygous mutant or heterozygous can be provided. Allele A and B are each hybridized with complementary oligonucleotides ((C) and (D) respectively), that hybridize to A and B within a region that includes M. Each heteroduplex is then contacted with a single strand specific endonuclease, so that a mismatch at M, indicating the presence of a mutation, results in the cleavage of (C) and/or (D), which can then be detected by mass spectrometry.

Different mass-modified detector oligonucleotides can be used to simultaneously detect all possible variants/mutants simultaneously (FIG. 6B). Alternatively, all four base permutations at the site of a mutation can be detected by designing and positioning a detector oligonucleotide, so that it serves as a primer for a DNA/RNA polymerase with varying combinations of elongating and terminating nucleoside triphosphates (FIG. 6C). For example, mass modifications also can be incorporated during the amplification process.

Figure 3:
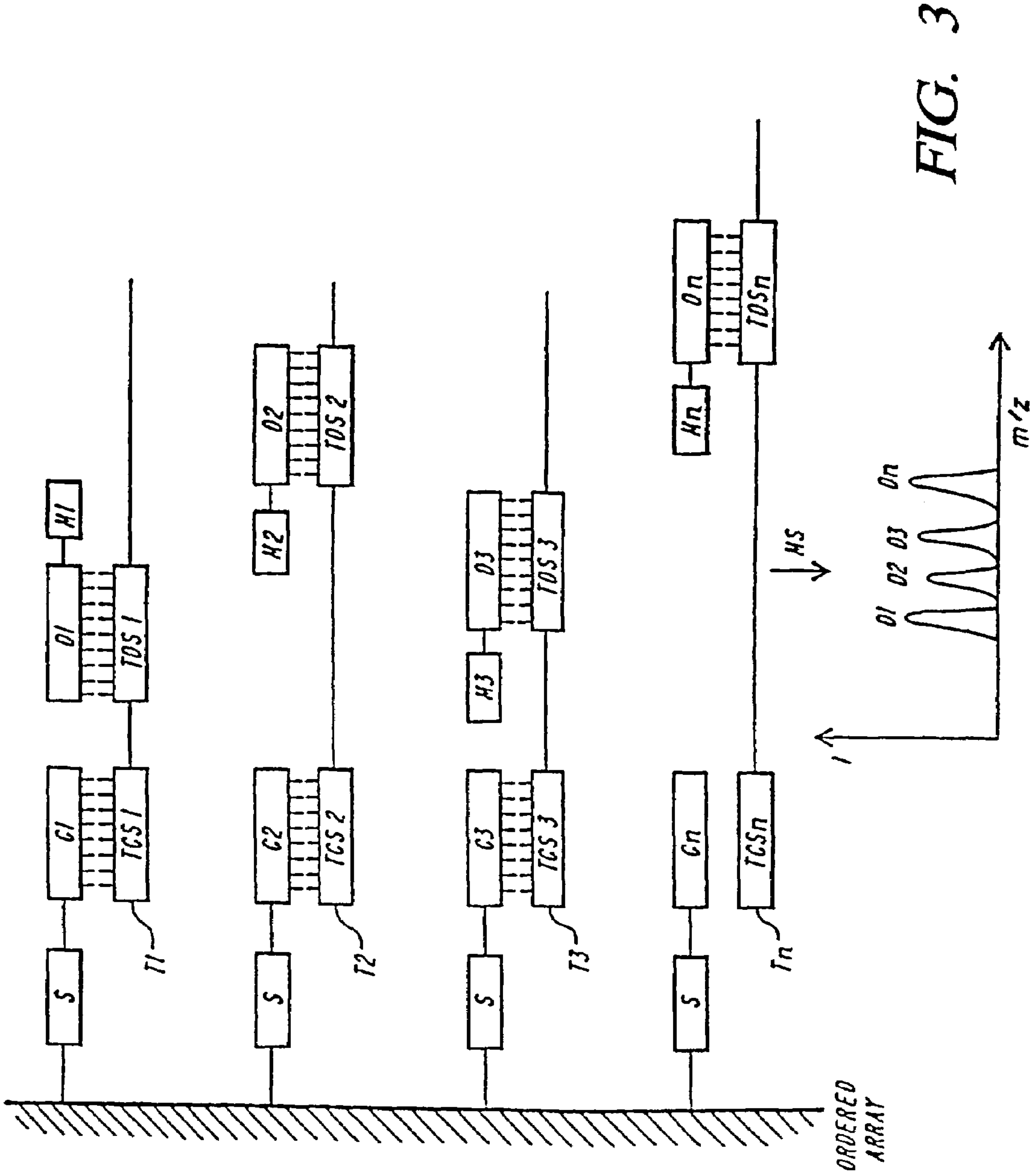
FIG. 3 is a diagram showing still another multiplex detection format. In this embodiment, differentiation is accomplished by employing different specific capture sequences which are position-specifically immobilized on a flat surface (e.g., a 'chip array'). If different target sequences T1-Tn are present, their target capture sites TCS1-TCSn will interact with complementary immobilized capture sequences C1-Cn. Detection is achieved by employing appropriately mass differentiated detector oligonucleotides D1-Dn, which are mass differentiated either by their sequences or by mass modifying functionalities M1-Mn.

FIG. 3 shows a different multiplex detection format, in which differentiation is accomplished by employing different specific capture sequences which are position-specifically immobilized on a flat surface (e.g., a 'chip array'). If different target sequences T1-Tn are present, their target capture sites TCS1-TCSn will specifically interact with complementary immobilized capture sequences C1-Cn. Detection is achieved by employing appropriately mass differentiated detector oligonucleotides D1-Dn, which are mass modifying functionalities M1-Mn.

Mass Spectrometric Methods for Sequencing DNA

Amenable mass spectrometric formats for use herein include the ionization (I) techniques, such as matrix assisted laser desorption ionization (MALDI), electrospray (ESI) (e.g., continuous or pulsed); and related methods (e.g., Ionspray, Thermospray, Fast Atomic Bombardment), and massive cluster impact (MCI); these ion sources can be matched with detection formats including lin-linear fields) time-of-flight (TOF), single or multiple quadrupole, single or multiple magnetic sector, Fourier transform ion cyclotron resonance (FTICR), ion trap, or combinations of these to give a hybrid detector (e.g., ion trap—time of flight). For ionization, numerous matrix/wavelength combinations including frozen analyte preparation (MALDI) or solvent combinations (ESI) can be employed.

Since a normal DNA molecule includes four nucleotide units (A, T, C, G), and the mass of each of these is unique (monoisotopic masses 313.06, 304.05, 289.05, 329.05 Da, respectively), an accurate mass determination can define or constrain the possible base compositions of that DNA. Only above 4900 Da does each unit molecular weight have at least one allowable composition; among all 5-mers there is only one non-unique nominal molecular weight, among 8-mers, 20. For these and larger oligonucleotides, such mass overlaps can be resolved with the ~1/$10^5$ (~10 part per million, ppm) mass accuracy available with high resolution FTICR MS. For the 25-mer $A_5T_{20}$, the 20 composition degeneracies when measured at ±0.5 Da is reduced to three ($A_5T_{20}$, $T_4C_{12}G_9$, $AT_3C_4G_{16}$) when measured with 2 ppm accuracy. Given composition constraints (e.g., the presence or absence of one of the four bases in the strand) can reduce this further (see below).

Medium resolution instrumentation, including but not exclusively curved field reflectron or delayed extraction time-of-flight MS instruments, can also result in improved DNA detection for sequencing or diagnostics. Either of these are capable of detecting a 9 Da (Δm (A-T)) shift in ≧30-mer strands generated from, for example primer oligo base extension (PROBE), or competitive oligonucleotide single base extension (COSBE), sequencing, or direct detection of small amplified products.

BiomassScan

In this embodiment, exemplified in Example 33, two single stranded nucleic acids are individually immobilized to solid supports. One support contains a nucleic acid encoding the wild type sequence whereas the other support contains a nucleic acid encoding a mutant target sequence. Total human genomic DNA is digested with one or more restriction endonuclease enzyme resulting in the production of small fragments of double stranded genomic DNA (10-1,000 bp). The digested DNA is incubated with the immobilized single stranded nucleic acids and the sample is heated to denature the DNA duplex. The immobilized nucleic acid competes with the other genomic DNA strand for the complementary DNA strand and under the appropriate conditions, a portion of the complementary DNA strand hybridizes to the immobilized nucleic acid resulting in a strand displacement. By using high stringency washing conditions, the two nucleic acids will remain as a DNA duplex only if there is exact identity between the immobilized nucleic acid and the genomic DNA strand. The DNA that remains hybridized to the immobilized nucleic acid is analyzed by mass spectrometry and detection of a signal in the mass spectrum of the appropriate mass is diagnostic for the wild type or mutant allele. In this manner, total genomic DNA can be isolated from a biological sample and screened for the presence or absence of certain mutations. By immobilizing a variety of single stranded nucleic acids in an array format, a panel of mutations may be simultaneously screened for a number of genetic loci (i.e., multiplexing).

In addition, using less stringent washing conditions the hybridized DNA strand may be analyzed by mass spectrometry for changes in the mass resulting from a deletion or insertion within the targeted restriction endonuclease fragment.

Primer Oligonucleotide Base Extension

As described in detail in the following Example 11, the primer oligo base extension (PROBE) method combined with mass spectrometry identifies the exact number of repeat units (i.e. the number of nucleotides in homogenous stretches) as well as second site mutations within a polymorphic region, which are otherwise only detectable by sequencing. Thus, the PROBE technique increases the total number of detectable alleles at a distinct genomic site, leading to a higher polymorphism information content (PIC) and yielding a far more definitive identification in for instance statistics-based analyses in paternity or forensics applications.

The method is based on the extension of a detection primer that anneals adjacent to a variable nucleotide tandem repeat (VNTR) or a polymorphic mononucleotide stretch using a DNA polymerase in the presence of a mixture of deoxyNTPs and those dideoxyNTPs that are not present in the deoxy form. The resulting products are evaluated and resolved by MALDI-TOF mass spectrometry without further labeling of the DNA. In a simulated routine application with 28 unrelated individuals, the mass error of this procedure using external calibration was in the worst case 0.38% (56-mer), which is comparable to approximately 0.1 base accuracy; routine standard mass deviations are in the range of 0.1% (0.03 bases). Such accuracy with conventional electrophoretic methods is not realistic, underscoring the value of PROBE and mass spectrometry in forensic medicine and paternity testing.

The ultra-high resolution of Fourier Transform mass spectrometry makes possible the simultaneous measurement of all reactions of a Sanger or Maxam Gilbert sequencing experiment, since the sequence may be read from mass differences instead of base counting from 4 tubes.

Additionally, the mass differences between adjacent bases generated from unilateral degradation in a stepwise manner by an exonuclease can be used to read the entire sequence of fragments generated. Whereas UV or fluorescent measurements will not discriminate mixtures of the nucleoside/nucleotide which are generated when the exonuclease enzyme gets out of phase, this is no problem with mass spectrometry since the resolving power in differentiating between the molecular mass of dA, dT, dG and dC is more than significant. The mass of the adjacent bases (i.e., nucleotides) can be determined, for example, using Fast Atomic Bombardment (FAB) or Electronspray Ionization (ESI) mass spectrometry.

New mutation screening over an entire amplified product can be achieved by searching for mass shifted fragments generated in an endonuclease digestion as described in detail in the following Examples 4 and 12.

Partial sequence information obtained from tandem mass spectrometry ($MS^n$) can place composition constraints as described in the preceding paragraph. For the 25-mer above, generation of two fragment ions formed by collisionally activated dissociation (CAD) which differ by 313 Da discounts $T_4C_{12}G_9$, which contains no A nucleotides; confirming more than a single A eliminates $AT_3C_4G_{16}$ as a possible composition.

$MS^n$ can also be used to determined full or partial sequences of larger DNAs; this can be used to detect, locate, and identify new mutations in a given gene region. Enzymatic digest products whose masses are correct need not be further analyzed; those with mass shifts could be isolated in real time from the complex mixture in the mass spectrometer and partially sequenced to locate the new mutation.

Table I describes the mutation/polymorphism detection tests that have been developed.

TABLE I

Mutation/Polymorphism Detection Tests

| Clinical Association | Gene | Mutation/Polymorphism |
|---|---|---|
| Cystic Fibrosis | CFTR | 38 disease causing mutations in 14 exons/introns |
| Heart Disease (Cholesterol Metabolism) | Apo E | 112R, 112C, 158R, 158C |
| | Apo A-IV | 347S, 347T, 360H, 360Q |
| | Apo B-100 | 3500Q, 3500R |
| Thyroid Cancer | RET proto-oncogene | C634W, C634T, C634R, C634S, C634F |

TABLE I-continued

Mutation/Polymorphism Detection Tests

| Clinical Association | Gene | Mutation/Polymorphism |
|---|---|---|
| Sickle Cell Anemia/ Thalassemia | beta-globin | Sickle cell anemia S and C 45 thalassemia alleles |
| HIV Susceptibility | CKR-5 | 32 bp deletion |
| Breast Cancer Susceptibility | BRCA-2 | 2 bp (AG) deletion in exon 2 |
| Thrombosis | Factor V | R506Q |
| Arteriosclerosis | GpIIIa | L33P |
|  | E-selectin | S128R |
| Hypertension | ACE | I/D polymorphism |

Detection of Mutations

Diagnosis of Genetic Diseases

The mass spectrometric processes described above can be used, for example, to diagnose any of the more than 3000 genetic diseases currently known (e.g., hemophilias, thalassemias, Duchenne Muscular Dystrophy (DMD), Huntington's Disease (HD), Alzheimer's Disease and Cystic Fibrosis (CF)) or to be identified.

The following Example 3 provides a mass spectrometric method for detecting a mutation (ΔF508) of the cystic fibrosis transmembrane conductance regulator gene (CFTR), which differs by only three base pairs (900 daltons) from the wild type of CFTR gene. As described further in Example 3, the detection is based on a single-tube, competitive oligonucleotide single base extension (COSBE) reaction using a pair of primers with the 3'-terminal base complementary to either the normal or mutant allele. Upon hybridization and addition of a polymerase and the nucleoside triphosphate one base downstream, only those primers properly annealed (i.e, no 3'-terminal mismatch) are extended; products are resolved by molecular weight shifts as determined by matrix assisted laser desorption ionization time-of-flight mass spectrometry. For the cystic fibrosis ΔF508 polymorphism, 28-mer 'normal' (N) and 30-mer 'mutant' (M) primers generate 29- and 31-mers for N and M homozygotes, respectively, and both for heterozygotes. Since primer and product molecular weights are relatively low (<10 kDa) and the mass difference between these are at least that of a single ~300 Da nucleotide unit, low resolution instrumentation is suitable for such measurements.

Thermosequence cycle sequencing, as further described in Example 11, is also useful for detecting a genetic disease.

In addition to mutated genes, which result in genetic disease, certain birth defects are the result of chromosomal abnormalities such as Trisomy 21 (Down's Syndrome), Trisomy 13 (Patau Syndrome), Trisomy 18 (Edward's Syndrome), Monosomy X (Turner's Syndrome) and other sex chromosome aneuploidies such as Klienfelter's Syndrome (XXY). Here, "house-keeping" genes encoded by the chromosome in question are present in different quantity and the different amount of an amplified fragment compared to the amount in a normal chromosomal configuration can be determined by mass spectrometry.

Further, there is growing evidence that certain DNA sequences may predispose an individual to any of a number of diseases such as diabetes, arteriosclerosis, obesity, various autoimmune diseases and cancer (e.g., colorectal, breast, ovarian, lung). Also, the detection of "DNA fingerprints", e.g., polymorphisms, such as "mini- and micro-satellite sequences", are useful for determining identity or heredity (e.g., paternity or maternity).

The following Examples 4 and 12 provide mass spectrometer based methods for identifying any of the three different isoforms of human apolipoprotein E, which are coded by the E2, E3 and E4 alleles. For example, the molecular weights of DNA fragments obtained after restriction with appropriate restriction endonucleases can be used to detect the presence of a mutation and/or a specific allele.

Depending on the biological sample, the diagnosis for a genetic disease, chromosomal aneuploidy or genetic predisposition can be preformed either pre- or post-natally.

Diagnosis of Cancer

Preferred mass spectrometer-based methods for providing an early indication of the existence of a tumor or a cancer are provide herein. For example, as described in Example 13, the telomeric repeat amplification protocol (TRAP) in conjunction with telomerase specific extension of a substrate primer and a subsequent amplification of the telomerase specific extension products by an amplification step using a second primer complementary to the repeat structure was used to obtain extension ladders, that were easily detected by MALDI-TOF mass spectrometry as an indication of telomerase activity and therefor tumorigenesis.

Alternatively, as described in Example 14, expression of a tumor or cancer associated gene (e.g., human tyrosine 5-hydroxylase) via RT-PCR and analysis of the amplified products by mass spectrometry can be used to detect the tumor or cancer (e.g., biosynthesis of catecholamine via tyrosine 5-hydroxylase is a characteristic of neuroblastoma).

Further, a primer oligo base extension reaction and detection of products by mass spectrometry provides a rapid means for detecting the presence of oncogenes, such as the RET proto oncogene codon 634, which is related to causing multiple endocrine neoplasia, type II (MEN II), as described in Example 15.

Diagnosis of Infection

Viruses, bacteria, fungi and other infectious organisms contain distinct nucleic acid sequences, which are different from the sequences contained in the host cell. Detecting or quantitating nucleic acid sequences that are specific to the infectious organism is important for diagnosing or monitoring infection. Examples of disease causing viruses that infect humans and animals and which may be detected by the disclosed processes include: Retroviridae (e.g., human immunodeficiency viruses, such as HIV-1 (also referred to as HTLV-III, LAV or HTLV-III/LAV, see, e.g., Ratner et al. (1985) Nature 313: 227-284; Wain-Hobson et al. (1985) Cell 40: 9-17); HIV-2 (see, Guyader et al. (1987) Nature 328: 662-669 European Patent Publication No. 0 269 520; Chakrabarti et al. (1987) Nature 328: 543-547; and European Patent Application No. 0 655 501); and other isolates, such as HIV-LP (International PCT application No. WO 94/00562 entitled "A Novel Human Immunodeficiency Virus"; Picornaviridae (e.g., polio viruses, hepatitis A virus, (see, e.g., Gust et al. (1983) Intervirology 20: 1-7); entero viruses, human coxsackie viruses, rhinoviruses, echoviruses); Calciviridae (e.g., strains that cause gastroenteritis); Togaviridae (e.g., equine encephalitis viruses, rubella viruses); Flaviridae (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ebola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegaovirus (CMV), herpes viruses'); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include, but are not limited to: *Helicobacter pyloris, Borelia burgdorferi, Legionella pneumophilia*, Mycobacteria sps (e.g., *M. tuberculosis, M. avium, M. intracellulare, M. kansaii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (viridans group), *Streptococcus faecalis, Streptococcus bovis, Streptococcus* (anaerobic sps.), *Streptococcus phhenumoniae*, pathogenic *Campylobacter* sp., *Enterococcus* sp., *Haemophilus influenzae, Bacillus antracis, corynebacterium diphtheriae, corynebacterium* sp., *Erysipelothrix rhusiopathiae, Clostridium perfringers, Clostridium tetani, Enterobacter aerogenes, Klebsiella pneumoniae, Pasturella multocida, Bacteroides* sp., *Fusobacterium nuclea tum, Strep tobacillus moniliformis, Treponema palladium, Treponema pertenue, Leptospira*, and *Actinomyces israelli.*

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii.*

Figure 8:
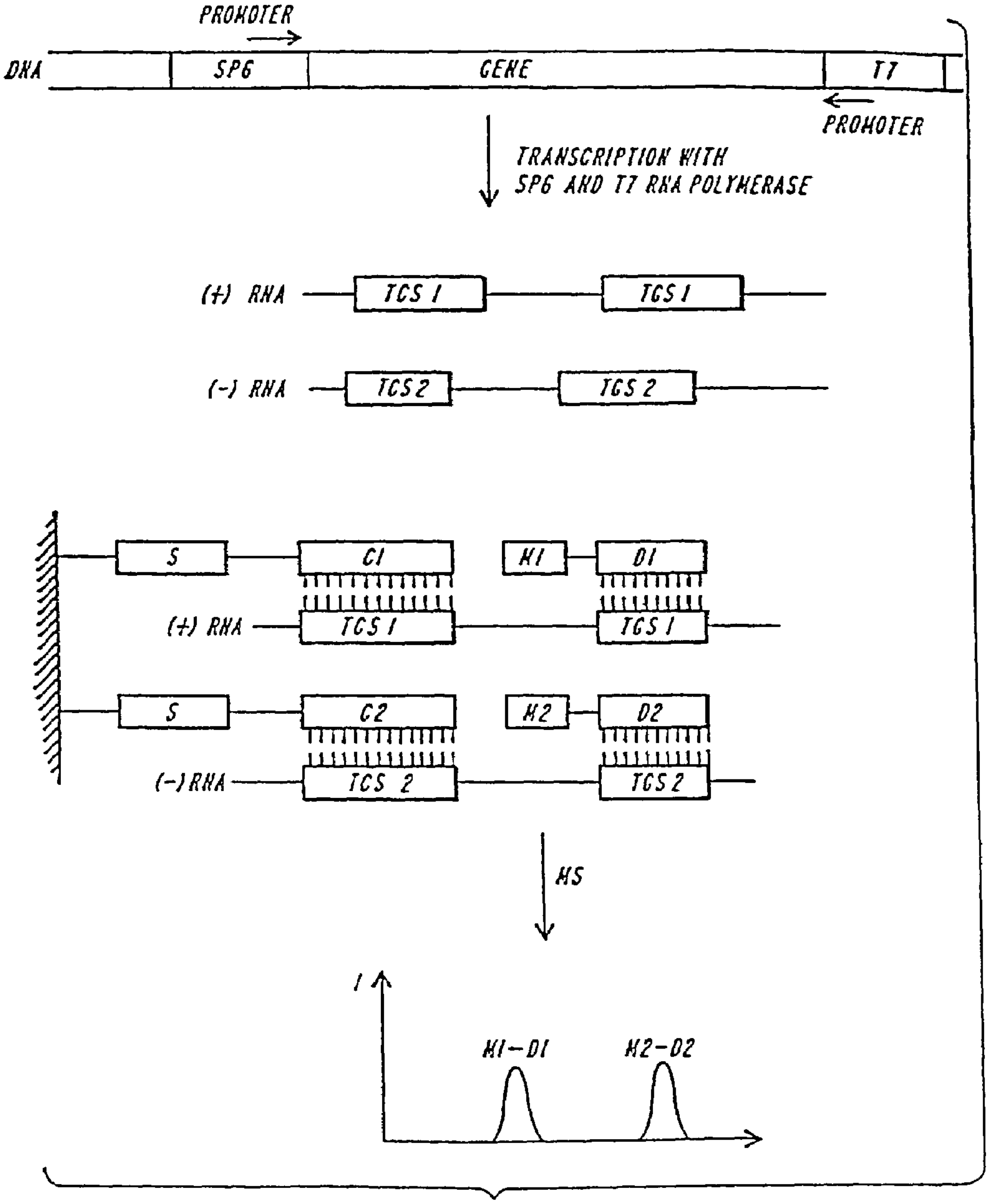
FIG. 8 is a diagram showing how both strands of a target DNA can be prepared for detection using transcription vectors having two different promoters at opposite locations (e.g., the SP6 and T7 promoter). This format is particularly useful for detecting heterozygous target detections sites (TDS). Employing the SP6 or the T7 RNA polymerase both strands could be transcribed separately or simultaneously. The transcribed RNA molecules can be specifically captured and simultaneously detected using appropriately mass-differentiated detector oligonucleotides. This can be accomplished either directly in solution or by parallel processing of many target sequences on an ordered array of specifically immobilized capturing sequences.
Figure 9:
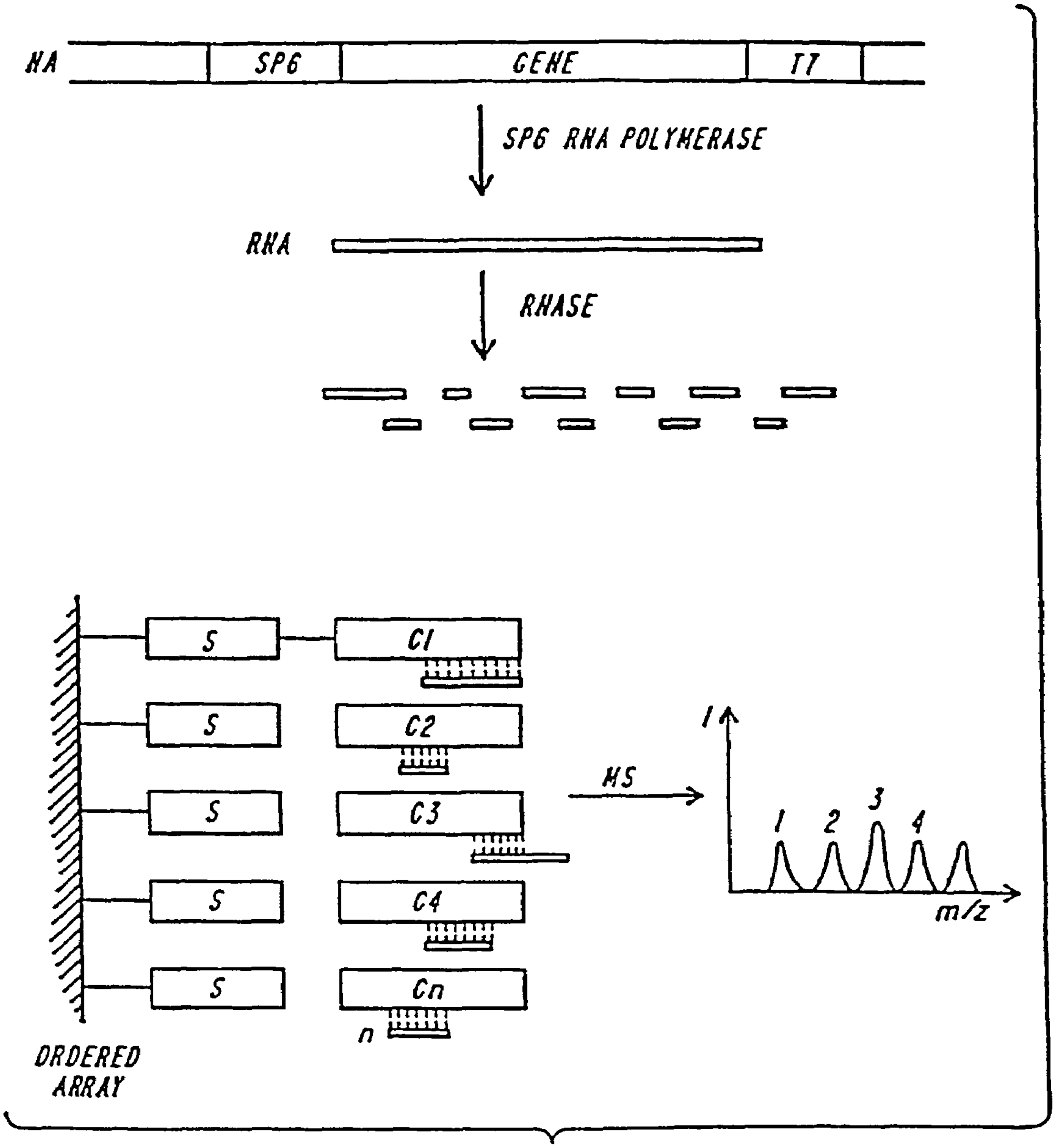
FIG. 9 is a diagram showing how RNA prepared as described in FIGS. 6, 7 and 8 can be specifically digested using one or more ribonucleases and the fragments captured on a solid support carrying the corresponding complementary sequences. Hybridization events and the actual molecular weights of the captured target sequences provide information on whether and where mutations in the gene are present. The array can be analyzed spot by spot using mass spectrometry. DNA can be similarly digested using a cocktail of nucleases including restriction endonucleases. Mutations can be detected by different molecular weights of specific, individual fragments compared to the molecular weights of the wildtype fragments.
Figures 2, 10A:
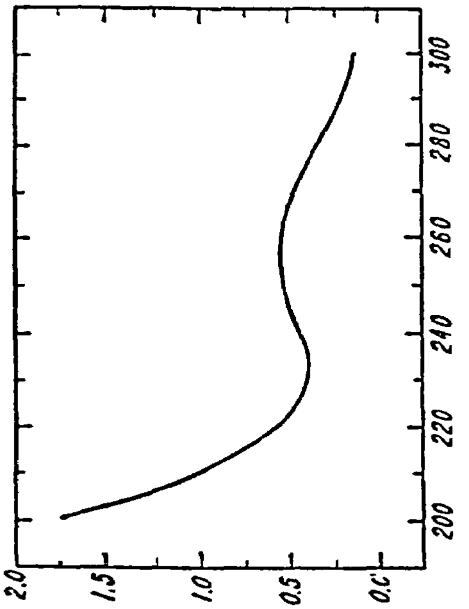
FIG. 10A shows UV spectra resulting from the experiment described in the following Example 1. Panel i) shows the absorbance of the 26-mer before hybridization. Panel ii) shows the filtrate of the centrifugation after hybridization. Panel iii) shows the results after the first wash with 50 mM ammonium citrate. Panel iv) shows the results after the second wash with 50 mM ammonium citrate.
Figures 4, 10A:
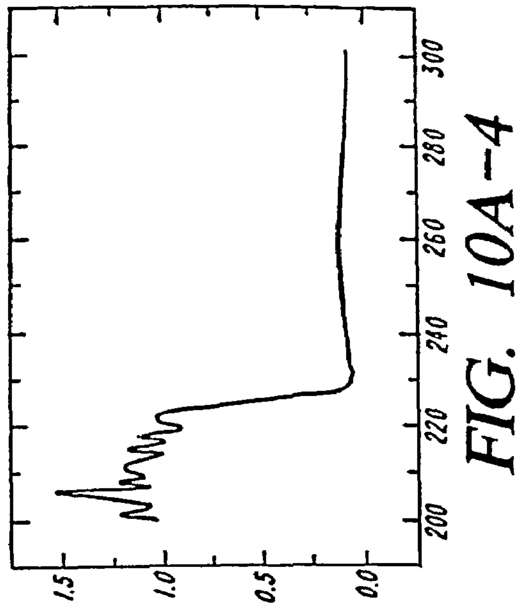
Figures 1, 10A:
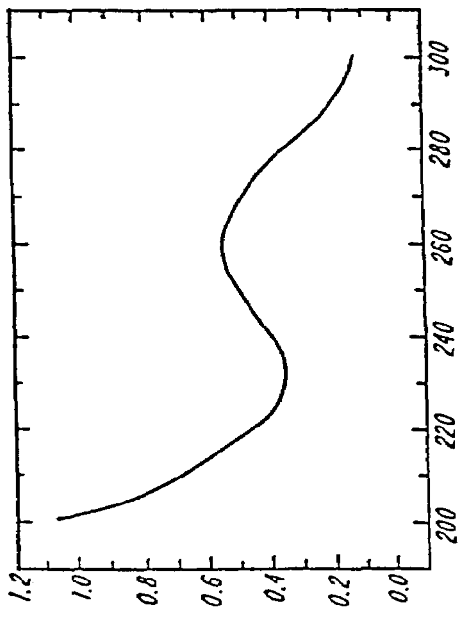
Figures 3, 10A:
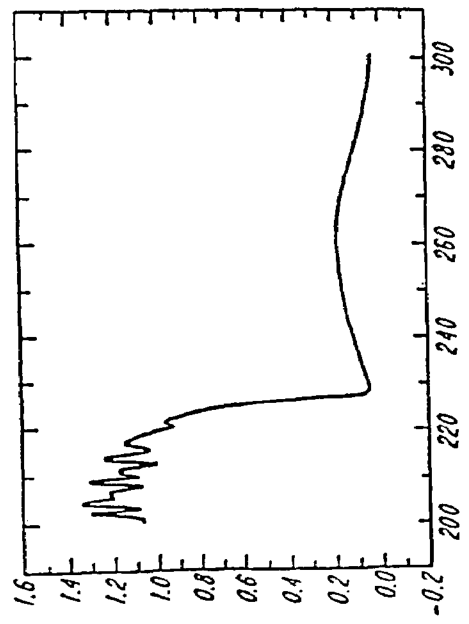
Figure 10B:
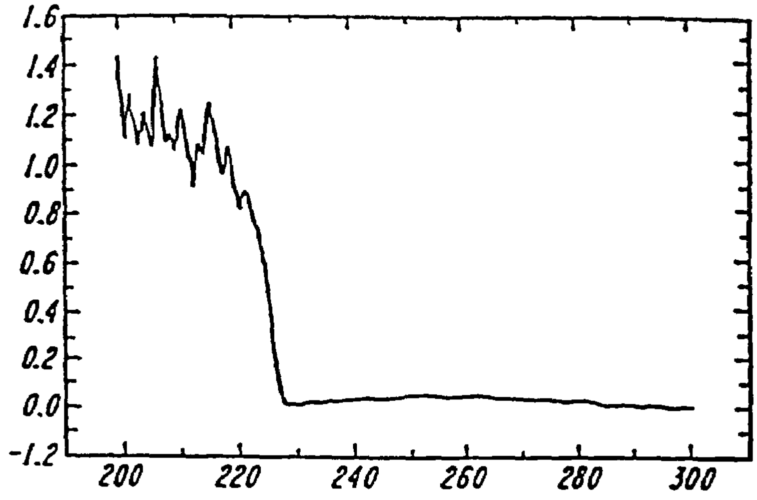
FIG. 10B shows a mass spectrum resulting from the experiment described in the following Example 1 after three washing/centrifugation steps.

The processes provided herein makes use of the known sequence information of the target sequence and known mutation sites. Although new mutations can also be detected. For example, as shown in FIG. 8, transcription of a nucleic acid molecule obtained from a biological sample can be specifically digested using one or more nucleases and the fragments captured on a solid support carrying the corresponding complementary nucleic acid sequences. Detection of hybridization and the molecular weights of the captured target sequences provide information on whether and where in a gene a mutation is present. Alternatively, DNA can be cleaved by one or more specific endonucleases to form a mixture of fragments. Comparison of the molecular weights between wildtype and mutant fragment mixtures results in mutation detection.

Sequencing by Generation of Specifically Terminated Fragments

In another embodiment, an accurate sequence determination of a relatively large target nucleic acid, can be obtained by generating specifically terminated fragments from the target nucleic acid, determining the mass of each fragment by mass spectrometry and ordering the fragments to determine the sequence of the larger target nucleic acid. In a preferred embodiment, the specifically terminated fragments are partial or complete base-specifically terminated fragments.

One method for generating base specifically terminated fragments involves using a base-specific ribonuclease after e.g., a transcription reaction. Preferred base-specific ribonucleases are selected from among: $T_1$-ribonuclease (G-specific), $U_2$-ribonuclease (A-specific), PhyM-ribonuclease U specific and ribonuclease A (U/C specific). Other efficient and base-specific ribonucleases can be identified using the assay described in Example 16. Preferably modified nucleotides are included in the transcription reaction with unmodified nucleotides. Most preferably, the modified nucleotides and unmodified nucleotides are added to the transcription reaction at appropriate concentrations, so that both moieties are incorporated at a preferential rate of about 1:1. Alternatively, two separate transcriptions of the target DNA sequence one with the modified and one with the unmodified nucleotides can be performed and the results compared. Preferred modified nucleotides include: boron or bromine modified nucleotides (Porter et al. (1995) *Biochemistry* 34:11963-11969; Hasan et al. (1996) *Nucl. Acids Res.* 24: 2150-2157; Li et al. (1995) *Nucleic Acids Res.* 23: 4495-4501), α-thio-modified nucleotides, as well as mass-modified nucleotides as described above.

Another method for generating base specifically terminated fragments involves performing a combined amplification and base-specific termination reaction. For example, a combined amplification and termination reaction can be performed using at least two different polymerase enzymes, each having a different affinity for the chain terminating nucleotide, so that polymerization by an enzyme with relatively low affinity for the chain terminating nucleotide leads to exponential amplification whereas an enzyme with relatively high affinity for the chain terminating nucleotide terminates the polymerization and yields sequencing products.

The combined amplification and sequencing can be based on any amplification procedure that employs an enzyme with polynucleotide synthetic ability (e.g., polymerase). One preferred process, based on the polymerase chain reaction (PCR), includes the following three thermal steps: 1) denaturing a double stranded (ds) DNA molecule at an appropriate temperature and for an appropriate period of time to obtain the two single stranded (ss) DNA molecules (the template: sense and antisense strand); 2) contacting the template with at least one primer that hybridizes to at least one ss DNA template at an appropriate temperature and for an appropriate period of time to obtain a primer containing ss DNA template; 3) contacting the primer containing template at an appropriate temperature and for an appropriate period of time with: (i) a complete set of chain elongating nucleotides, (ii) at least one chain terminating nucleotide, (iii) a first DNA polymerase, which has a relatively low affinity towards the chain terminating nucleotide; and (iv) a second DNA polymerase, which has a relatively high affinity towards the chain terminating nucleotide.

Steps 1)-3) can be sequentially performed for an appropriate number of times (cycles) to obtain the desired amount of amplified sequencing ladders. The quantity of the base specifically terminated fragment desired dictates how many cycles are performed. Although an increased number of cycles results in an increased level of amplification, it may also detract from the sensitivity of a subsequent detection. It is therefore generally undesirable to perform more than about 50 cycles, and is more preferable to perform less than about 40 cycles (e.g., about 20-30 cycles).

Another preferred process for simultaneously amplifying and chain terminating a nucleic acid sequence is based on strand displacement amplification (SDA) (see, e.g., Walker et al. (1994) *Nucl. Acids Res.* 22: 2670-77; European Patent Publication Number 0 684 315 entitled "Strand Displacement Amplification Using Thermophilic Enzymes"). In essence, this process involves the following three steps, which altogether constitute a cycle: 1) denaturing a double stranded (ds) DNA molecule containing the sequence to be amplified at an appropriate temperature and for an appropriate period of time to obtain the two single stranded (ss) DNA molecules (the template: sense and antisense strand); 2) contacting the template with at least one primer (P), that contains a recognition/cleavage site for a restriction endonuclease (RE) and that hybridizes to at least one ss DNA template at an appropriate temperature and for an appropriate period of time to obtain a primer containing ss DNA template; 3) contacting the primer containing template at an appropriate temperature and for an appropriate period of time with (i) a complete set of chain elongating nucleotides; (ii) at least one chain terminating nucleotide; (iii) a first DNA polymerase, which has a relatively low affinity towards the chain terminating nucleotide; (iv) a second DNA polymerase, which has a relatively high affinity towards the chain terminating nucleotide; and (v) an RE that nicks the primer recognition/cleavage site.

Steps 1)-3) can be sequentially performed for an appropriate number of times (cycles) to obtain the desired amount of amplified sequencing ladders. As with the PCR based process, the quantity of the base specifically terminated fragment desired dictates how many cycles are performed. Preferably, less than 50 cycles, more preferably less than about 40 cycles and most preferably about 20 to 30 cycles are performed.

Preferably about 0.5 to about 3 units of polymerase is used in the combined amplification and chain termination reaction. Most preferably about 1 to 2 units is used. Particularly preferred polymerases for use in conjunction with PCR or other thermal amplification process are thermostable polymerases, such as Taq DNA polymerase (Boehringer Mannheim), AmpliTaq FS DNA polymerase (Perkin-Elmer), Deep Vent (exo-), Vent, Vent (exo-) and Deep Vent DNA polymerases (New England Biolabs), Thermo Sequenase (Amersham) or exo(−) *Pseudococcus furiosus* (Pfu) DNA polymerase (Stratagene, Heidelberg, Germany). AmpliTaq, Ultman, 9 degree Nm, Tth, Hot Tub, and *Pyrococcus furiosus*. In addition, preferably the polymerase does not have 5'-3' exonuclease activity.

In addition to polymerases, which have a relatively high and a relatively low affinity to the chain terminating nucleotide, a third polymerase, which has proofreading capacity (e.g., *Pyrococcus woesei* (Pwo)) DNA polymerase may also be added to the amplification mixture to enhance the fidelity of amplification.

Yet another method for generating base specifically terminated fragments involves contacting an appropriate amount of the target nucleic acid with a specific endonuclease or exonuclease. Preferably, the original 5' and/or 3' end of the nucleic acid is tagged to facilitate the ordering of fragments. Tagging of the 3' end is particularly preferred when in vitro nucleic acid transcripts are being analyzed, so that the influence of 3' heterogeneity, premature termination and nonspecific elongation can be minimized. 5' and 3' tags can be natural (e.g., a 3' poly A tail or 5' or 3' heterogeneity) or artificial. Preferred 5' and/or 3' tags are selected from among the molecules described for mass-modification above.

The methods provided herein are further illustrated by the following examples, which should not be construed as limiting in any way.

EXAMPLE 1

Figure 11:
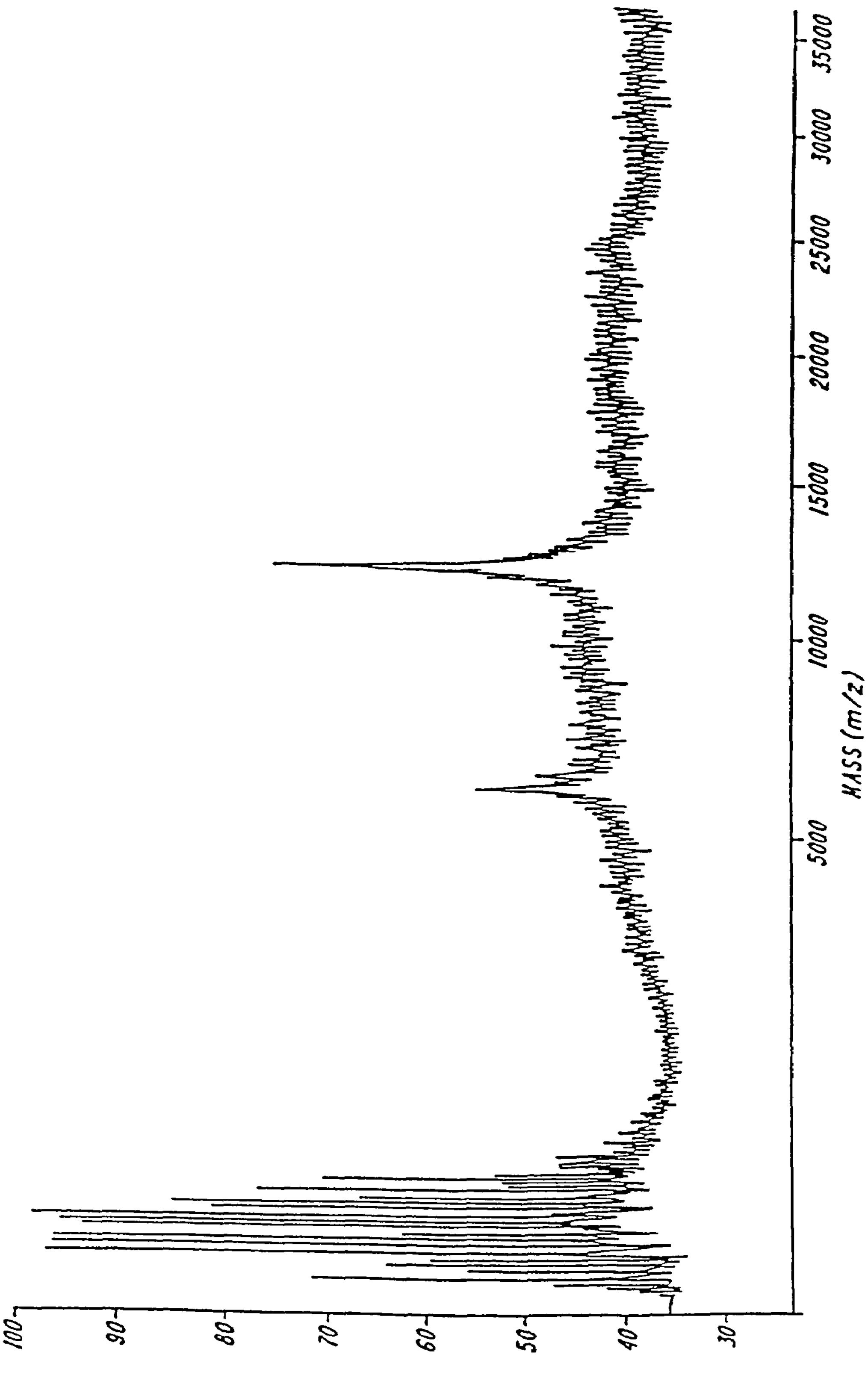
FIG. 11 shows a mass spectrum resulting from the experiment described in the following Example 1 showing the giving proof of an experiment as schematically depicted in FIG. 1B successful desorption of the hybridized 40-mer. The efficiency of detection suggests that fragments much longer than 40-mers can also be desorbed

MALDI-TOF Desorption of Oligonucleotides Directly on Solid Supports 1 g CPG (Controlled Pore Glass) was functionalized with 3-(triethoxysilyl)-epoxypropan to form OH-groups on the polymer surface. A standard oligonucleotide synthesis with 13 mg of the OH-CPG on a DNA synthesizer (Milligen, Model 7500) employing β-cyanoethyl-phosphoamidites (Köster et al. (1994) *Nucleic Acids Res.* 12: 4539) and TAC N-protecting groups (Köster et al. (1981) *Tetrahedron* 37: 362) was performed to synthesize a 3'-$T_5$-50 mer oligonucleotide sequence in which 50 nucleotides are complementary to a “hypothetical” 50mer sequence. $T_5$ serves as a spacer. Deprotection with saturated ammonia in methanol at room temperature for 2 hours furnished according to the determination of the DMT group CPG which contained about 10 umol 55mer/g CPG. This 55mer served as a template for hybridizations with a 26-mer (with 5'-DMT group) and a 40-mer (without DMT group). The reaction volume is 100 μl and contains about 1 nmol CPG bound 55mer as template, an equimolar amount of oligonucleotide in solution (26-mer or 40-mer) in 20 mM Tris-HCl, pH 7.5, 10 mM $MgCl_2$ and 25 mM NaCl. The mixture was heated for 10 min at 65° C. and cooled to 37° C. during 30' (annealing). The oligonucleotide which has not been hybridized to the polymer-bound template were removed by centrifugation and three subsequent washing/centrifugation steps with 100 ul each of ice-cold 50 mM ammoniumcitrate. The beads were air-dried and mixed with matrix solution (3-hydroxypicolinic acid/10 mM ammonium citrate in acetonitrile/water, 1:1), and analyzed by MALDI-TOF mass spectrometry. The results are presented in FIGS. 10 and 11.

EXAMPLE 2

Electrospray (ES) Desorption and Differentiation of an 18-Mer and 19-Mer

DNA fragments at a concentration of 50 pmole/ul in 2-propanol/10 mM ammoniumcarbonate (1/9, v/v) were analyzed simultaneously by an electrospray mass spectrometer.

Figure 12A:
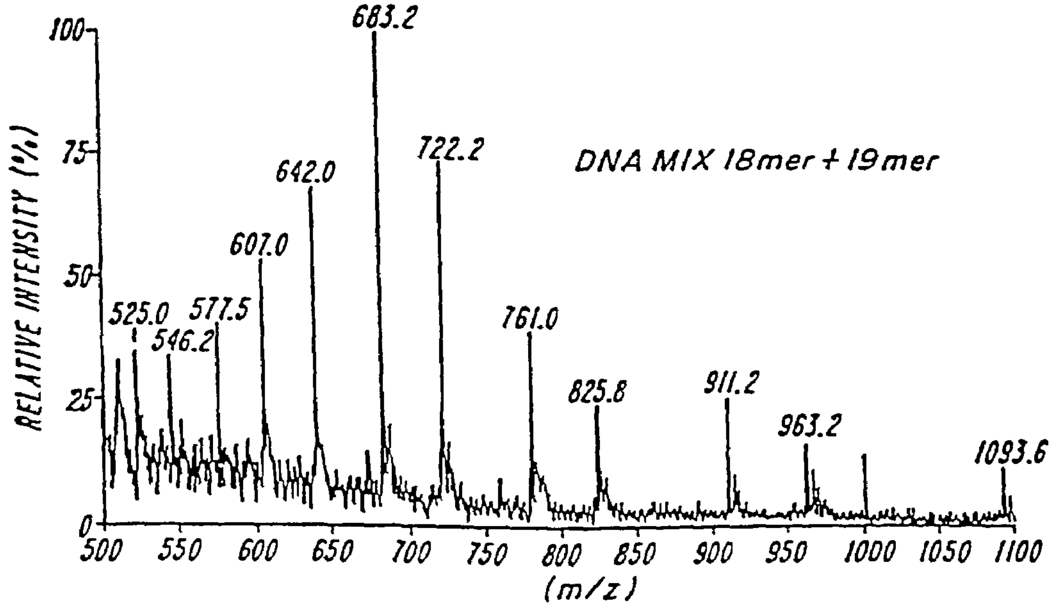
FIG. 12 shows a mass spectrum resulting from the experiment described in the following Example 2 showing the successful desorption and differentiation of an 18-mer and 19-mer by electrospray mass spectrometry, the mixture (top), peaks resulting from 18-mer emphasized (middle) and peaks resulting from 19-mer emphasized (bottom)
Figure 10C:
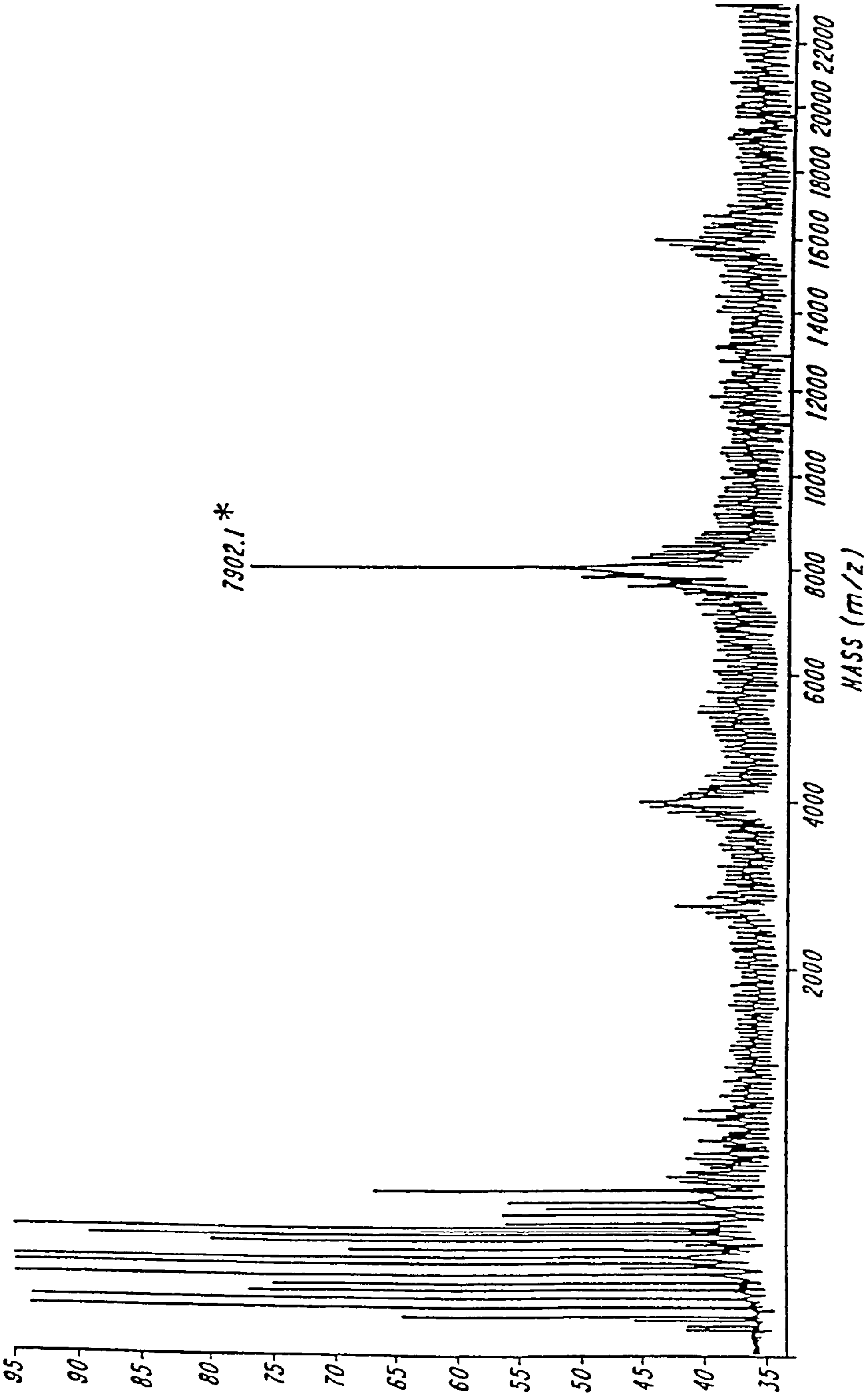
FIG. 10C shows a mass spectrum resulting from the experiment described in the following Example 1 showing the successful desorption of the hybridized 26-mer off of beads in accordance with the format depicted schematically in FIG. 1B.
Figure 12B:
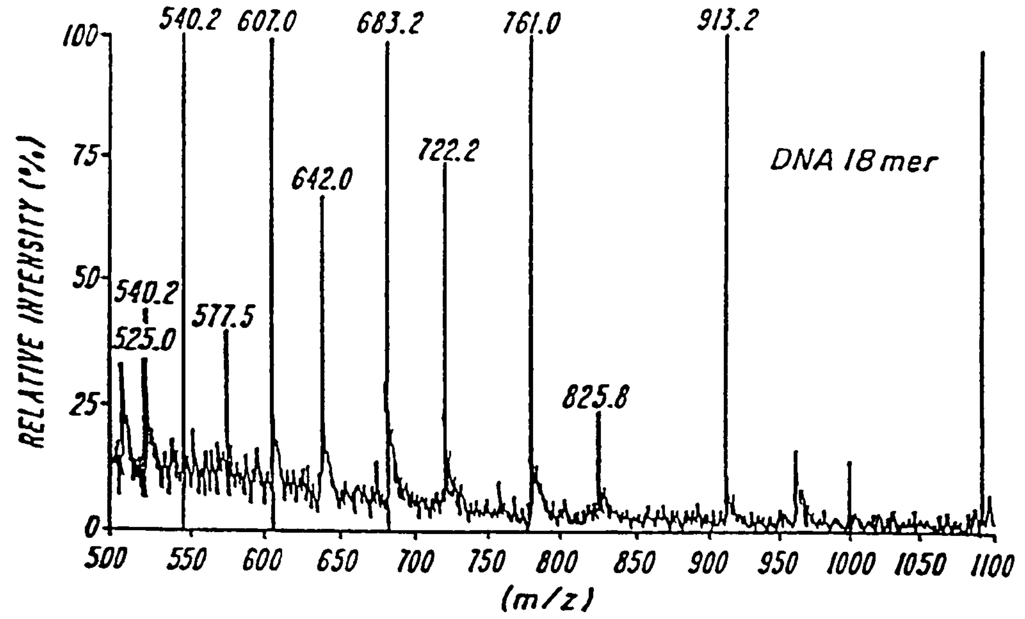
Figure 12C:
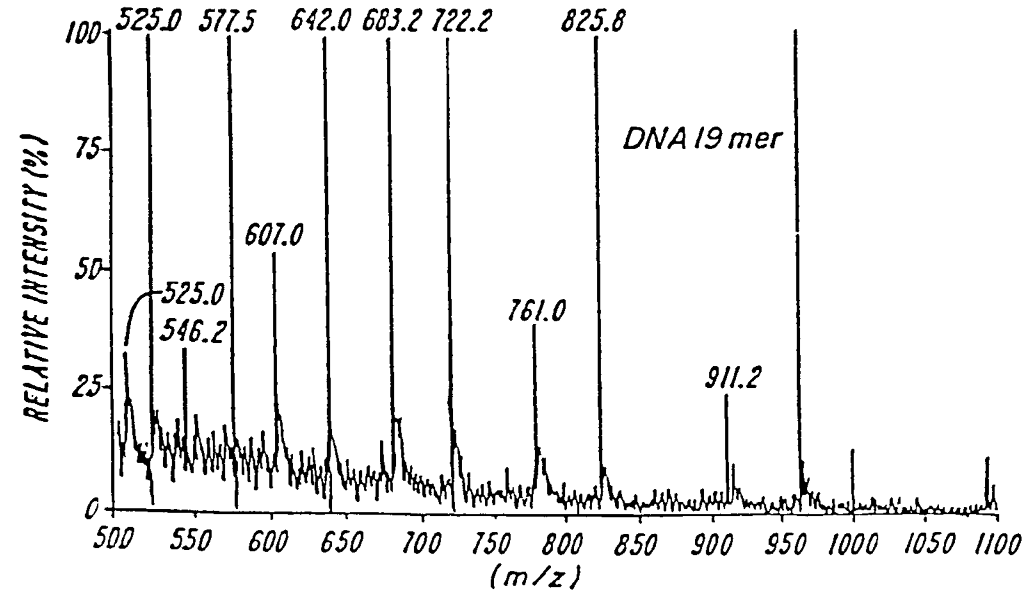

The successful desorption and differentiation of an 18-mer and 19-mer by electrospray mass spectrometry is shown in FIG. 12.

EXAMPLE 3

Detection of the Cystic Fibrosis Mutation ΔF508, by Single Step Dideoxy Extension and Analysis by MALDI-TOF Mass Spectrometry (Competitive Oligonucleotide Simple Base Extension=COSBE)

Figure 13:
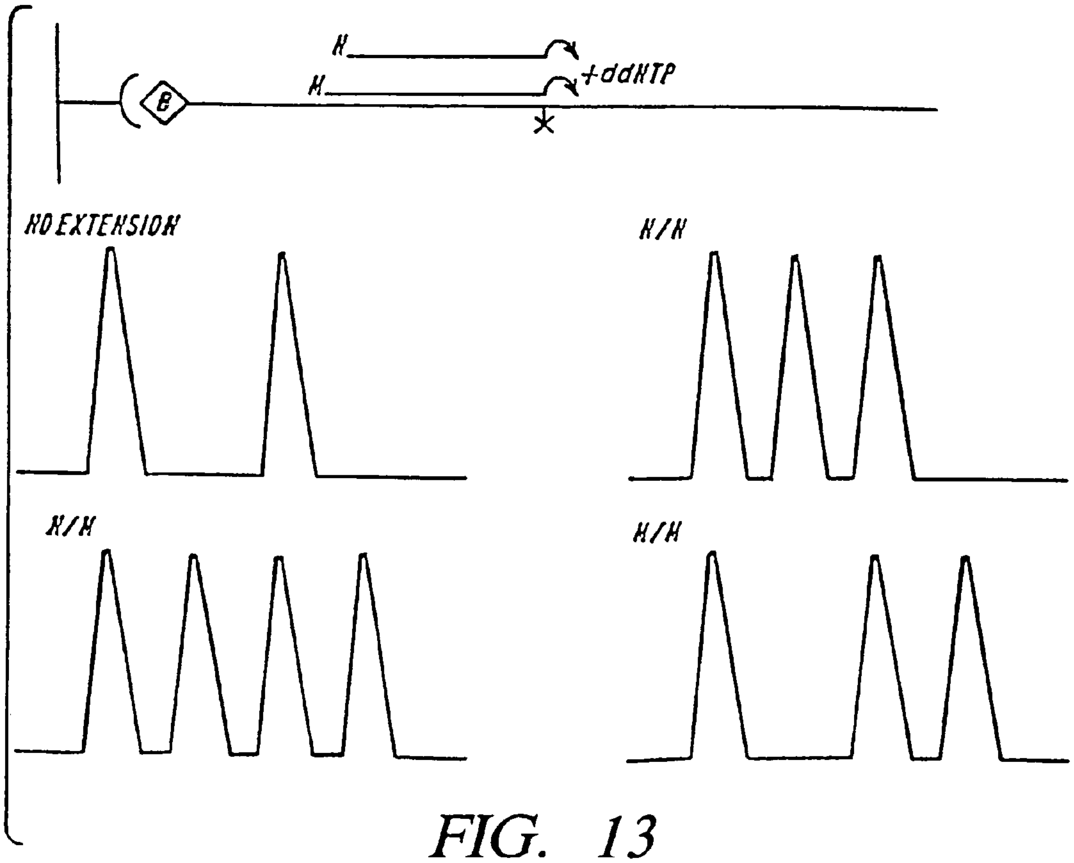
FIG. 13 is a graphic representation of the process for detecting the Cystic Fibrosis mutation AF508 as described in Example 3.
Figure 14:
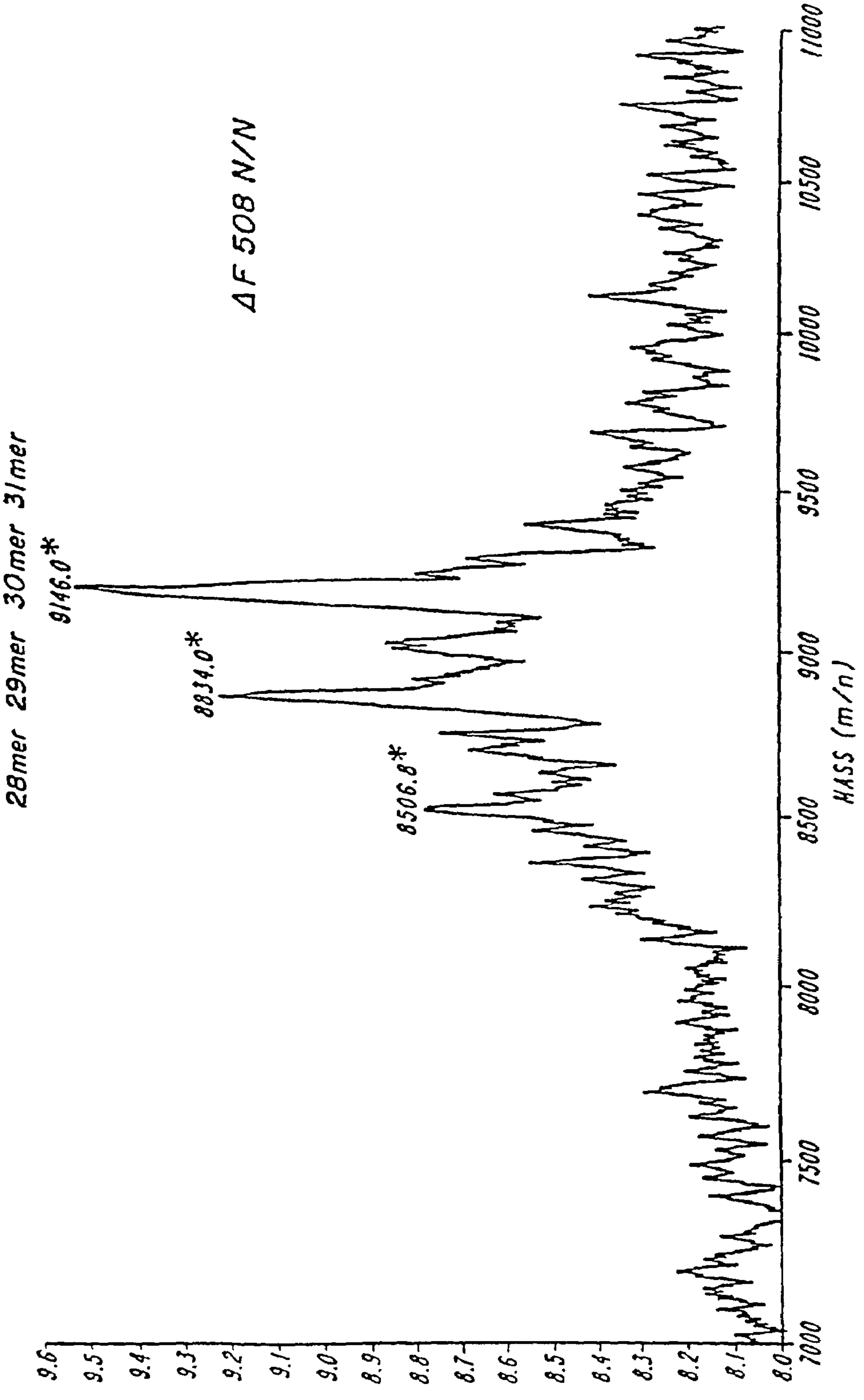
FIG. 14 is a mass spectrum of the DNA extension product of a ΔF508 homozygous normal of Example 3.
Figure 15:
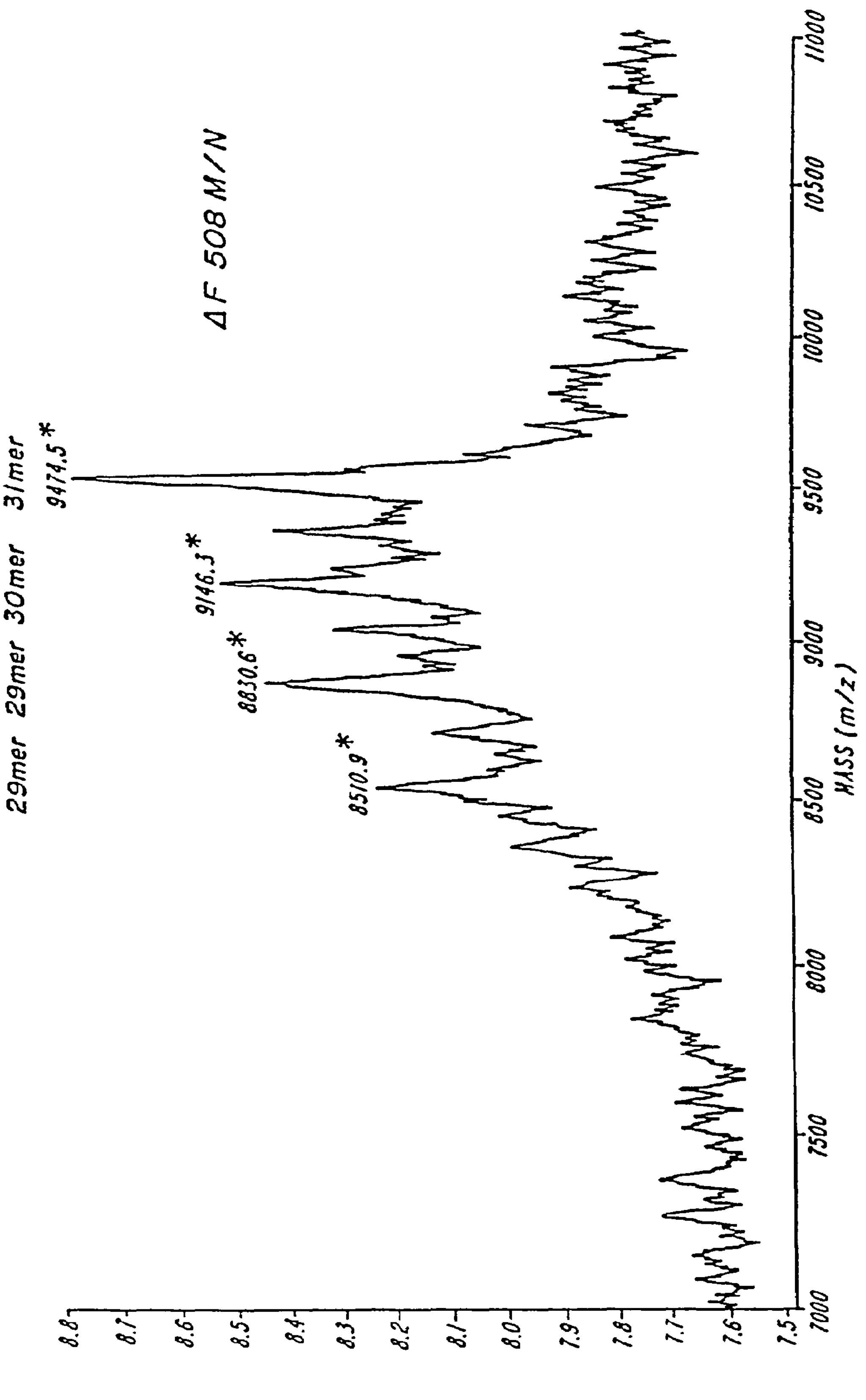
FIG. 15 is a mass spectrum of the DNA extension product of a ΔF508 heterozygous mutant of Example 3.
Figure 16:
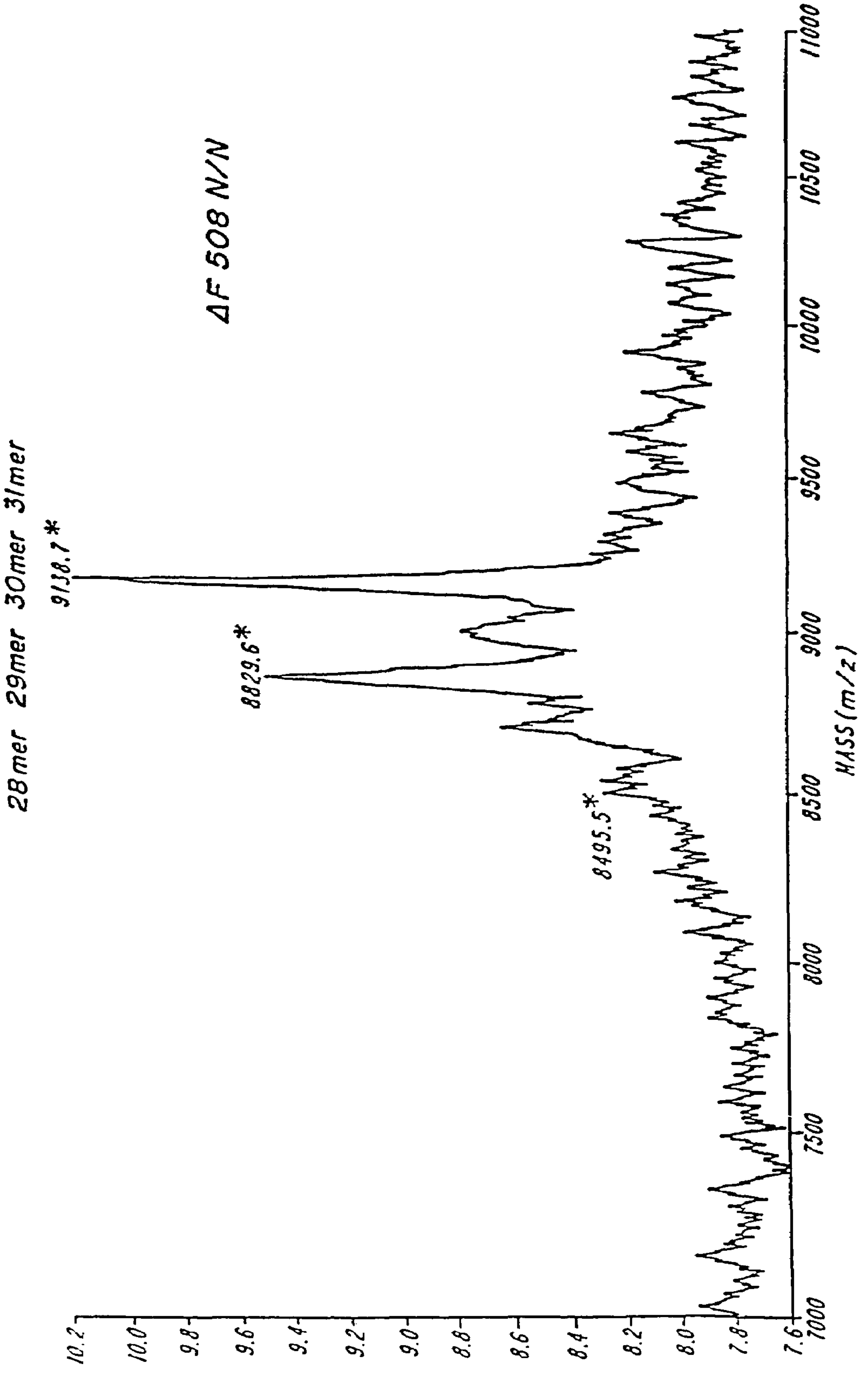
FIG. 16 is a mass spectrum of the DNA extension product of a ΔF508 homozygous normal of Example 3.
Figure 17:
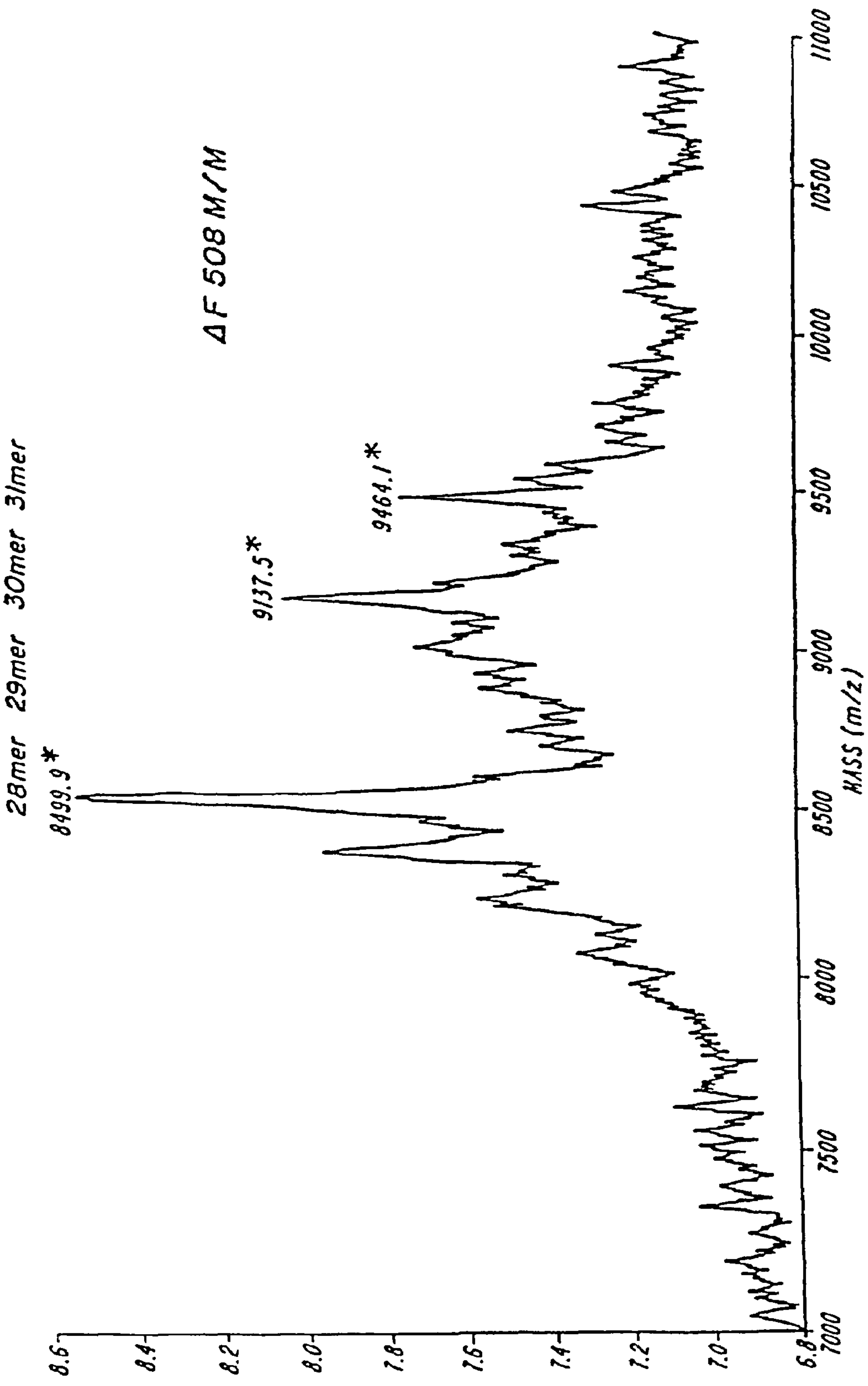
FIG. 17 is a mass spectrum of the DNA extension product of a ΔF508 homozygous mutant of Example 3.
Figure 18:
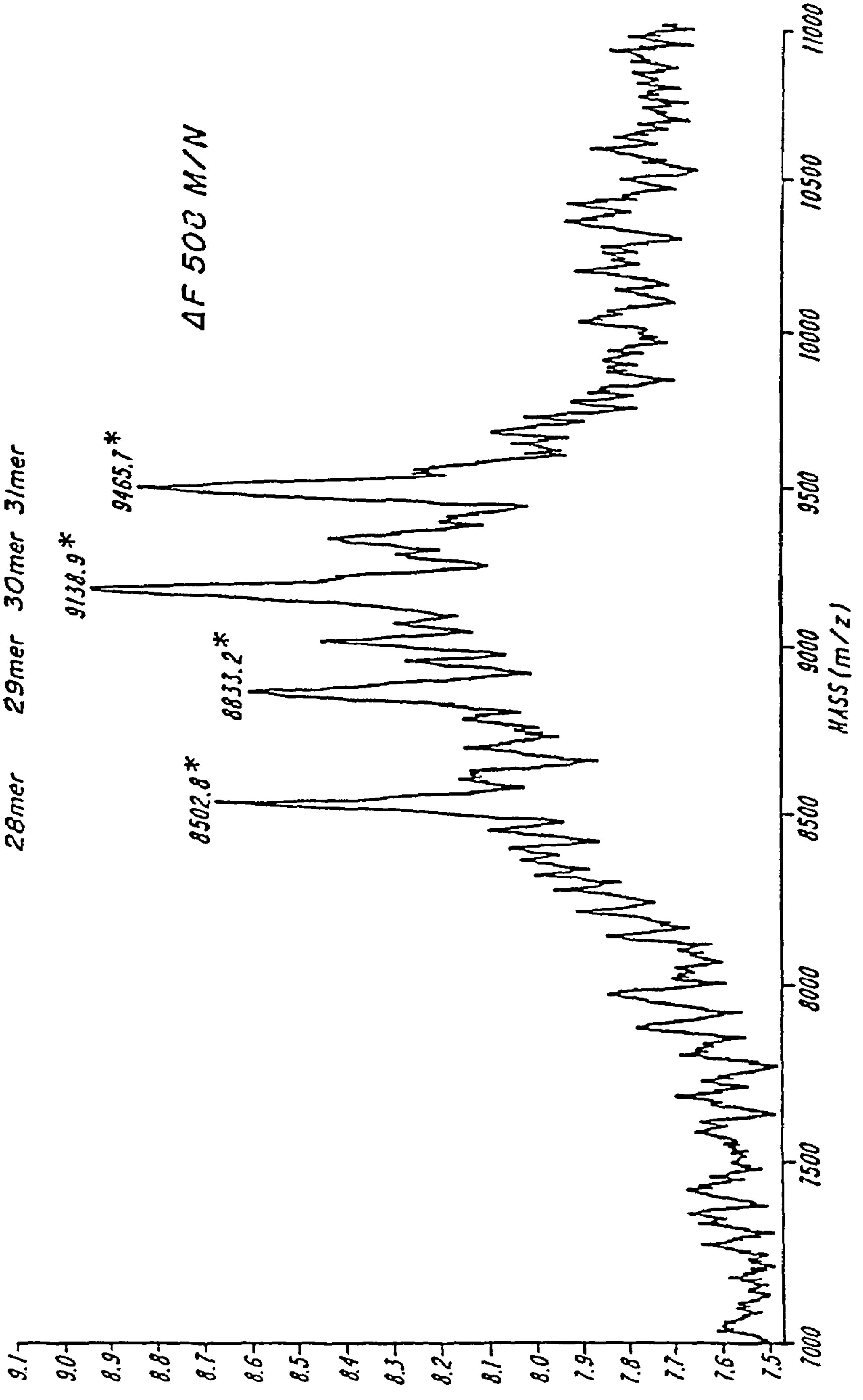
FIG. 18 is a mass spectrum of the DNA extension product of a ΔF508 heterozygous mutant of Example 3.

The principle of the COSBE method is shown in FIG. 13, N being the normal and M the mutation detection primer, respectively.

Materials and Methods

PCR Amplification and Strand Immobilization. Amplification was carried out with exon 10 specific primers using standard PCR conditions (30 cycles: 1'@95° C., 1'@55° C., 2'@72° C.); the reverse primer was 5' labelled with biotin and column purified (Oligopurification Cartridge, Cruachem). After amplification the amplified products were purified by column separation (Qiagen Quickspin) and immobilized on streptavidin coated magnetic beads (Dynabeads, Dynal, Norway) according to their standard protocol; DNA was denatured using 0.1 M NaOH and washed with 0.1 M NaOH, 1×B+W buffer and TE buffer to remove the non-biotinylated sense strand.

COSBE Conditions. The beads containing ligated antisense strand were resuspended in 18 μl of Reaction mix 1 (2 μl 10×Taq buffer, 1 μL (1 unit) Taq Polymerase, 2 μL of 2 mM dGTP, and 13 μL $H_2O$) and incubated at 80° C. for 5' before the addition of Reaction mix 2 (100 ng each of COSBE primers). The temperature was reduced to 60° C. and the mixtures incubated for a 5' annealing/extension period; the beads were then washed in 25 mM triethylammonium acetate (TEAA) followed by 50 mM ammonium citrate.

Primer Sequences. All primers were synthesized on a Perseptive Biosystems Expedite 8900 DNA Synthesizer using conventional phosphoramidite chemistry (Sinha et al. (1984) *Nucleic Acids Res.* 12: 4539). COSBE primers (each containing an intentional mismatch one base before the 3'-terminus) were those used in a previous ARMS study (Ferrie et al. (1992) *Am J Hum Genet* 51: 251-262) with the exception that two bases were removed from the 5'-end of the normal:

```
Ex10 PCR (Forward):
                                        (SEQ ID NO:1)
5'-BIO-GCA AGT GAA TCC TGA GCG TG-3'

Ex10 PCR (Reverse):
                                        (SEQ ID NO:2)
5'-GTG TGA AGG GTT CAT ATG C-3'

COSBE ΔF508-N
                                        (SEQ ID NO:3)
5'-ATC TAT ATT CAT CAT AGG AAA CAC CAC A-3'
(28-mer)

COSBE ΔF508-N
                                        (SEQ ID NO:4)
5'-GTA TCT ATA TTC ATC ATA GGA AAC ACC ATT-3'
(30-mer)
```

Mass Spectrometry. After washing, beads were resuspended in 1 μL 18 Mohm/cm $H_2O$. 300 nL each of matrix (Wu et al. (1993) *Rapid Commun. Mass Spectrom.* 7: 142-146) solution (0.7 M 3-hydroxypicolinic acid, 0.7 M dibasic ammonium citrate in 1:1 $H_2O$:$CH_3CN$) and resuspended beads (Tang et al. (1995) *Rapid Commun Mass Spectrom* 8: 727-730) were mixed on a sample target and allowed to air dry. Up to 20 samples were spotted on a probe target disk for introduction into the source region of an unmodified Thermo Bioanalysis (formerly Finnigan) Visions 2000 MALDI-TOF operated in reflectron mode with 5 and 20 kV on the target and conversion dynode, respectively. Theoretical average molecular weights ($M_r$(calc)) were calculated from atomic compositions. Vendor provided software was used to determine peak centroids using external calibration; 1.08 Da has been subtracted from these to correct for the charge carrying proton mass to yield the text $M_r$(exp) values.

Scheme. Upon annealing to the bound template, the N and M primers (8508.6 and 9148.0 Da, respectively) are presented with dGTP; only primers with proper Watson-Crick base paring at the variable (V) position are extended by the polymerase. Thus if V pairs with the 3'-terminal base of N, N is extended to a 8837.9 Da product (N+1). Likewise, if V is properly matched to the M terminus, M is extended to a 9477.3 Da M+1 product.

Results

FIGS. 14-18 show the representative mass spectra of COSBE reaction products. Better results were obtained when amplified products were purified before the biotinylated antisense strand was bound.

EXAMPLE 4

Differentiation of Human Apolipoprotein E Isoforms by Mass Spectrometry

Apolipoprotein E (Apo E), a protein component of lipoproteins, plays an essential role in lipid metabolism. For example, it is involved with cholesterol transport, metabolism of lipoprotein particles, immunoregulation and activation of a number of lipolytic enzymes.

There are three common isoforms of human Apo E (coded by E2, E3 and E4 alleles). The most common is the E3 allele. The E2 allele has been shown to decrease the cholesterol level in plasma and therefore may have a protective effect against the development of atherosclerosis. The DNA encoding a portion of the E2 allele is set forth in SEQ ID NO: 130. Finally, the E4 isoform has been correlated with increased levels of cholesterol, conferring predisposition to atherosclerosis. Therefore, the identity of the apo E allele of a particular individual is an important determinant of risk for the development of cardiovascular disease.

Figure 19:
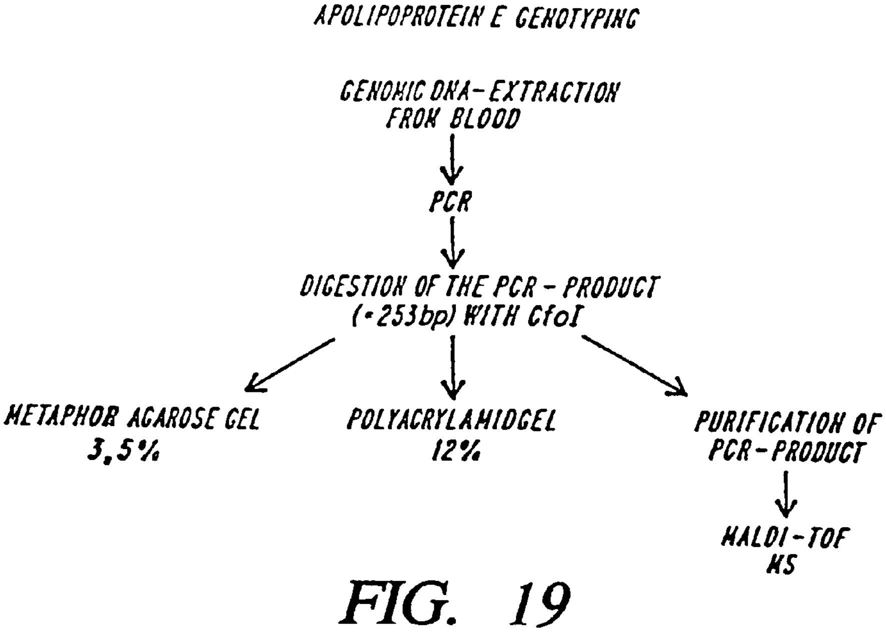
FIG. 19 is a graphic representation of various processes for performing apolipoprotein E genotyping of Example 4.
Figure 20A:
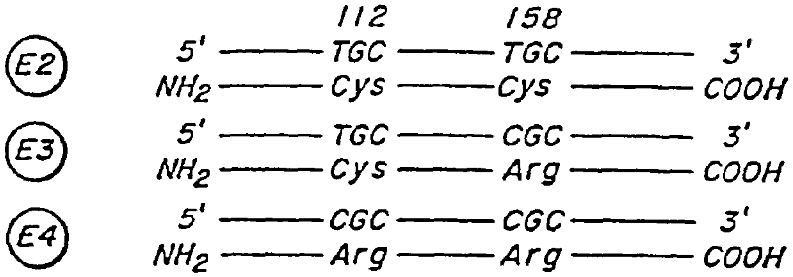
FIG. 20 shows the nucleic acid sequence of normal apolipoprotein E (encoded by the E3 allele, FIG. 20B, SEQ ID NO: 130,) and other isotypes encoded by the E2 and E4 alleles (FIG. 20A).
Figure 20B:
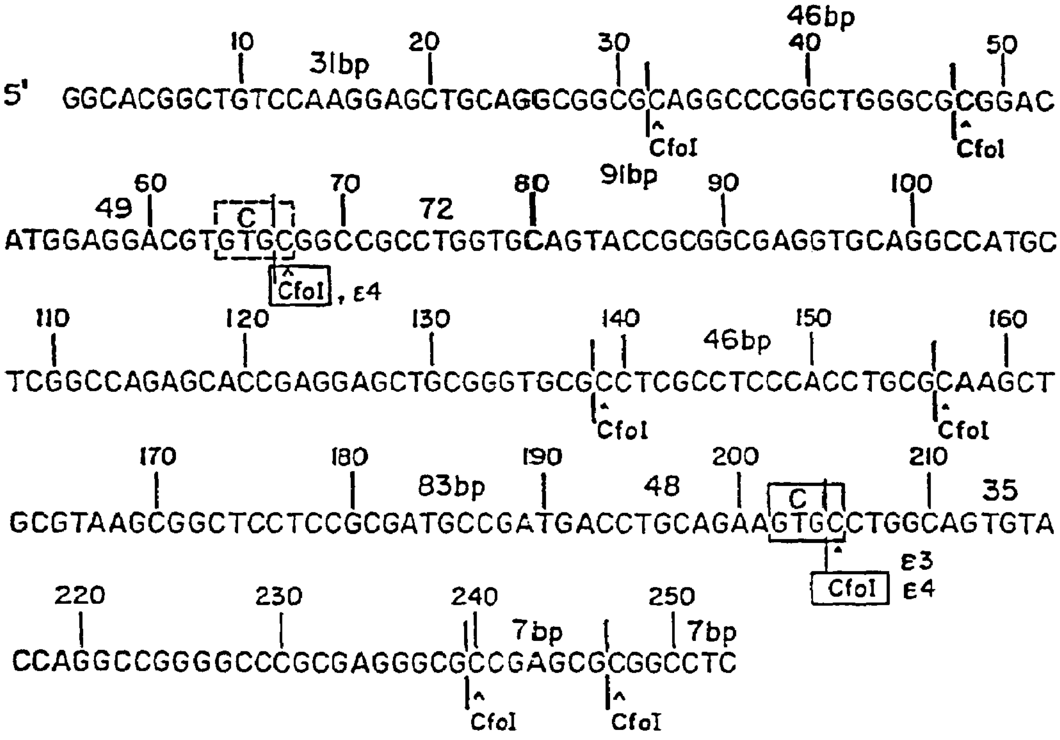

As shown in FIG. 19, a sample of DNA encoding apolipoprotein E can be obtained from a subject, amplified (e.g., via PCR); and the amplified product can be digested using an appropriate enzyme (e.g., CfoI). The restriction digest obtained can then be analyzed by a variety of means. As shown in FIG. 20, the three isotypes of apolipoprotein E (E2, E3 and E4 have different nucleic acid sequences and therefore also have distinguishable molecular weight values.

Figure 21A:
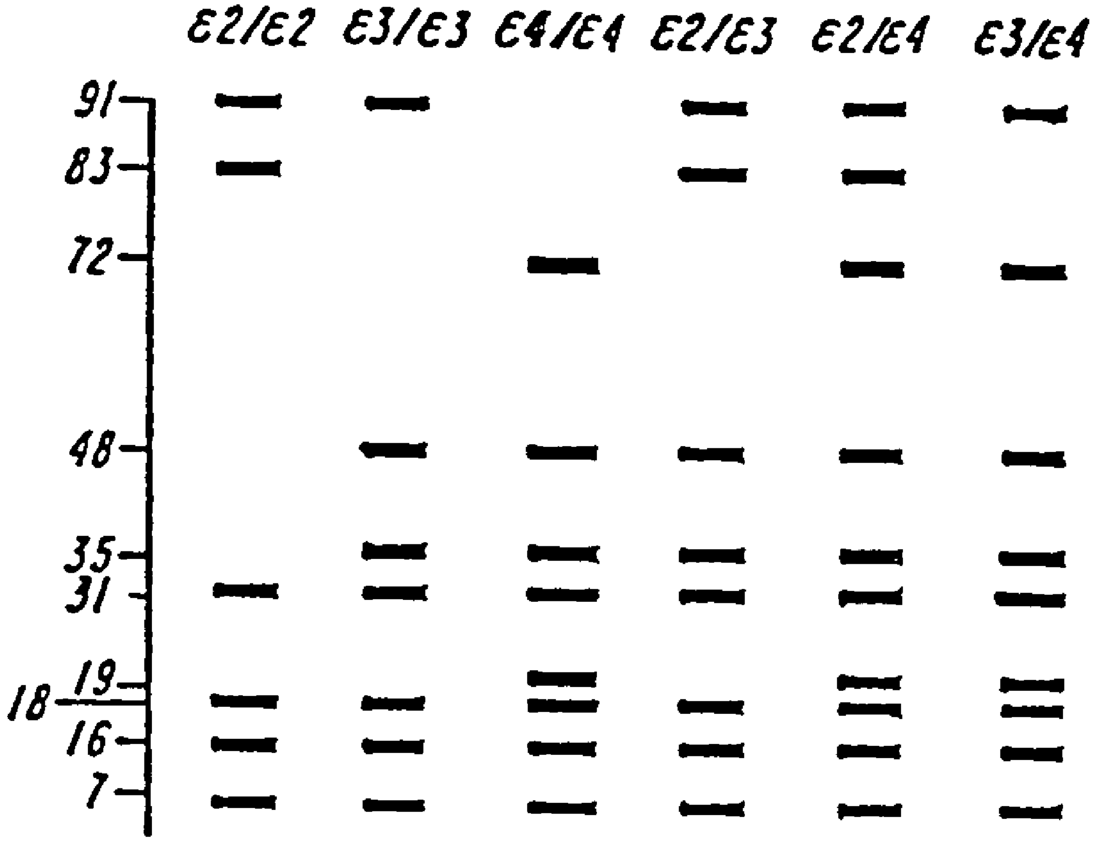
FIG. 21A shows a composite restriction pattern for various genotypes of apolipoprotein E using the CfoI restriction endonuclease.
Figure 21B:
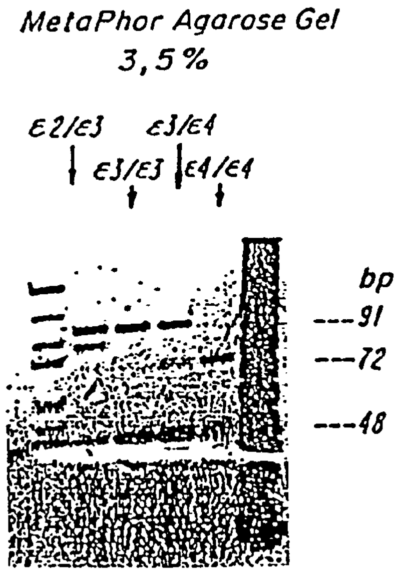
FIG. 21B shows the restriction pattern obtained in a 3.5% MetPhor Agarose Gel for various genotypes of apolipoprotein E.
Figure 21C:
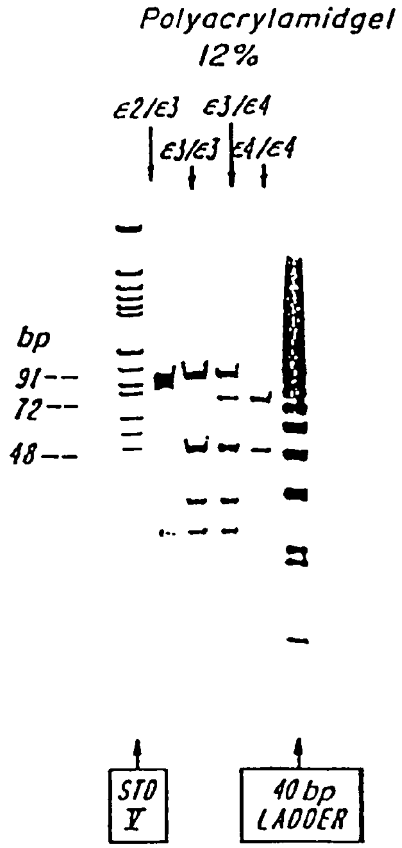
FIG. 21C shows the restriction pattern obtained in a 12% polyacrylamide gel for various genotypes of apolipoprotein E.
Figures 22A, 22B:
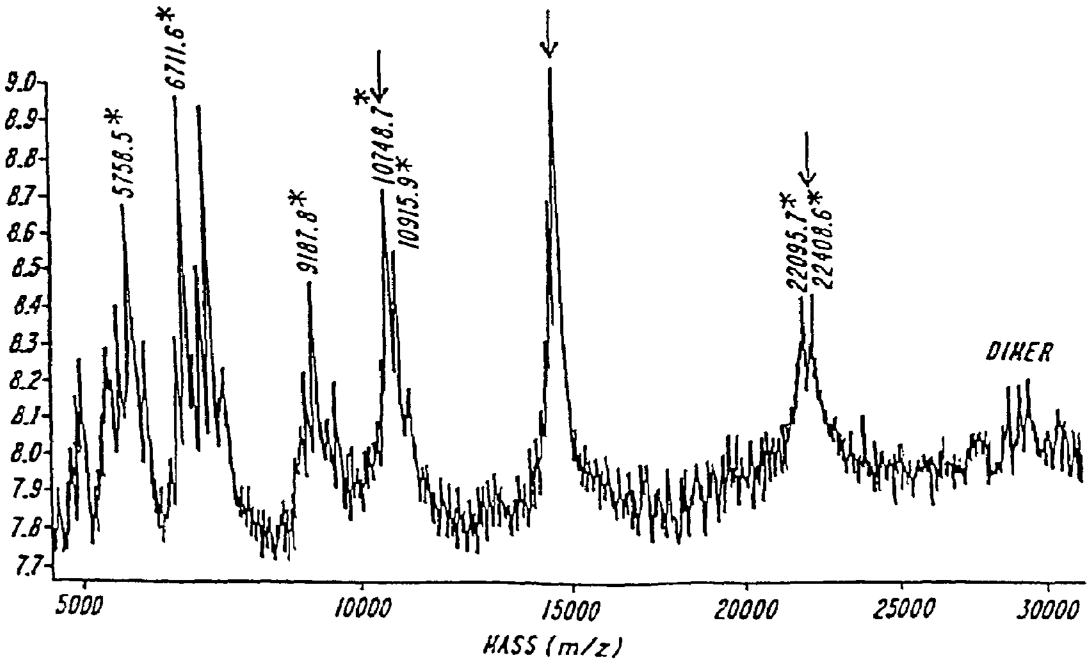
FIG. 22A is a chart showing the molecular weights of the 91, 83, 72, 48 and 35 base pair fragments obtained by restriction enzyme cleavage of the E2, E3 and E4 alleles of apolipoprotein E.
FIG. 22B is the mass spectrum of the restriction product of a homozygous E4 apolipoprotein E genotype.
Figure 23A:
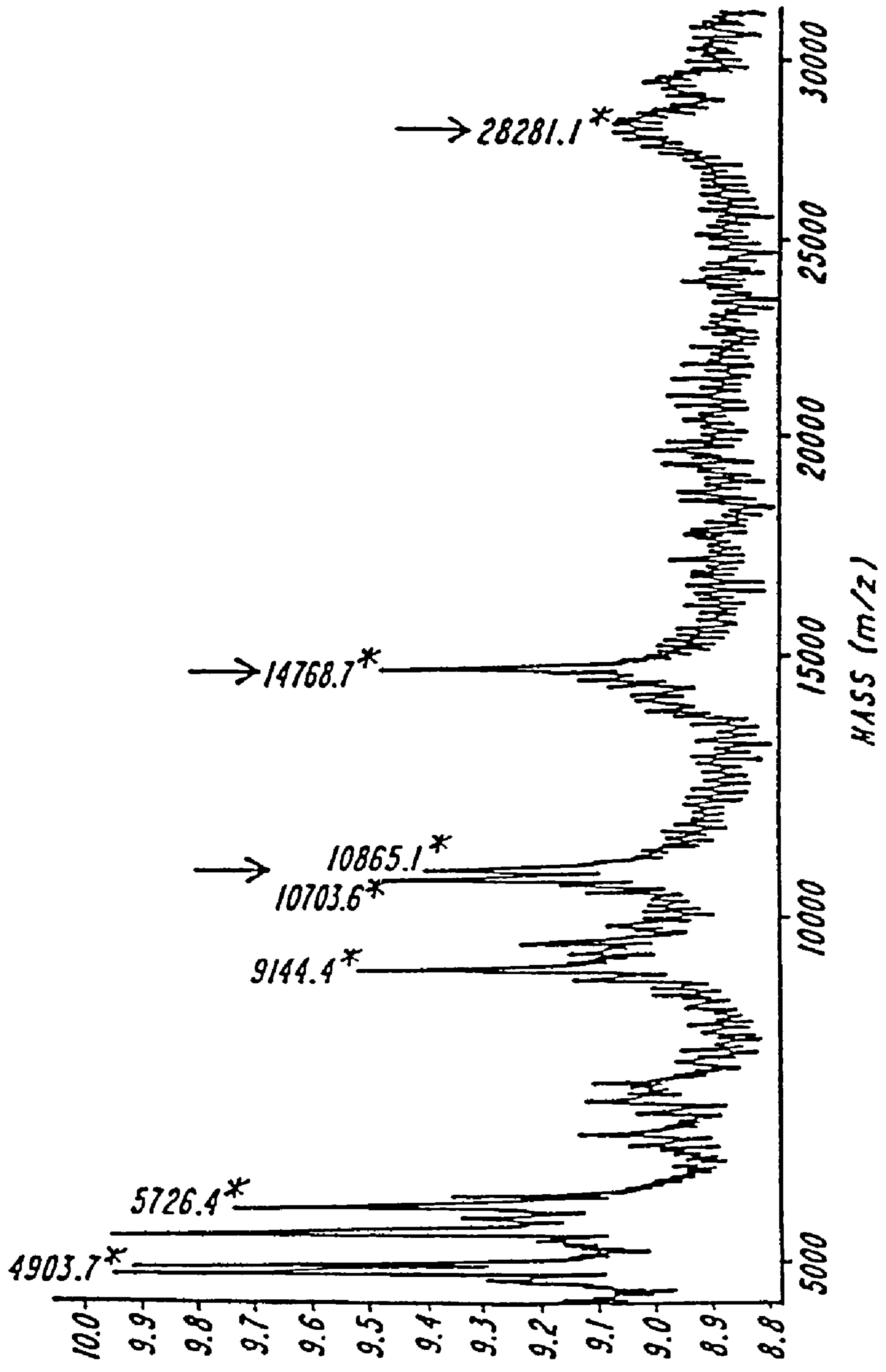
FIG. 23A is the mass spectrum of the restriction product of a homozygous E3 apolipoprotein E genotype.
Figure 23B:
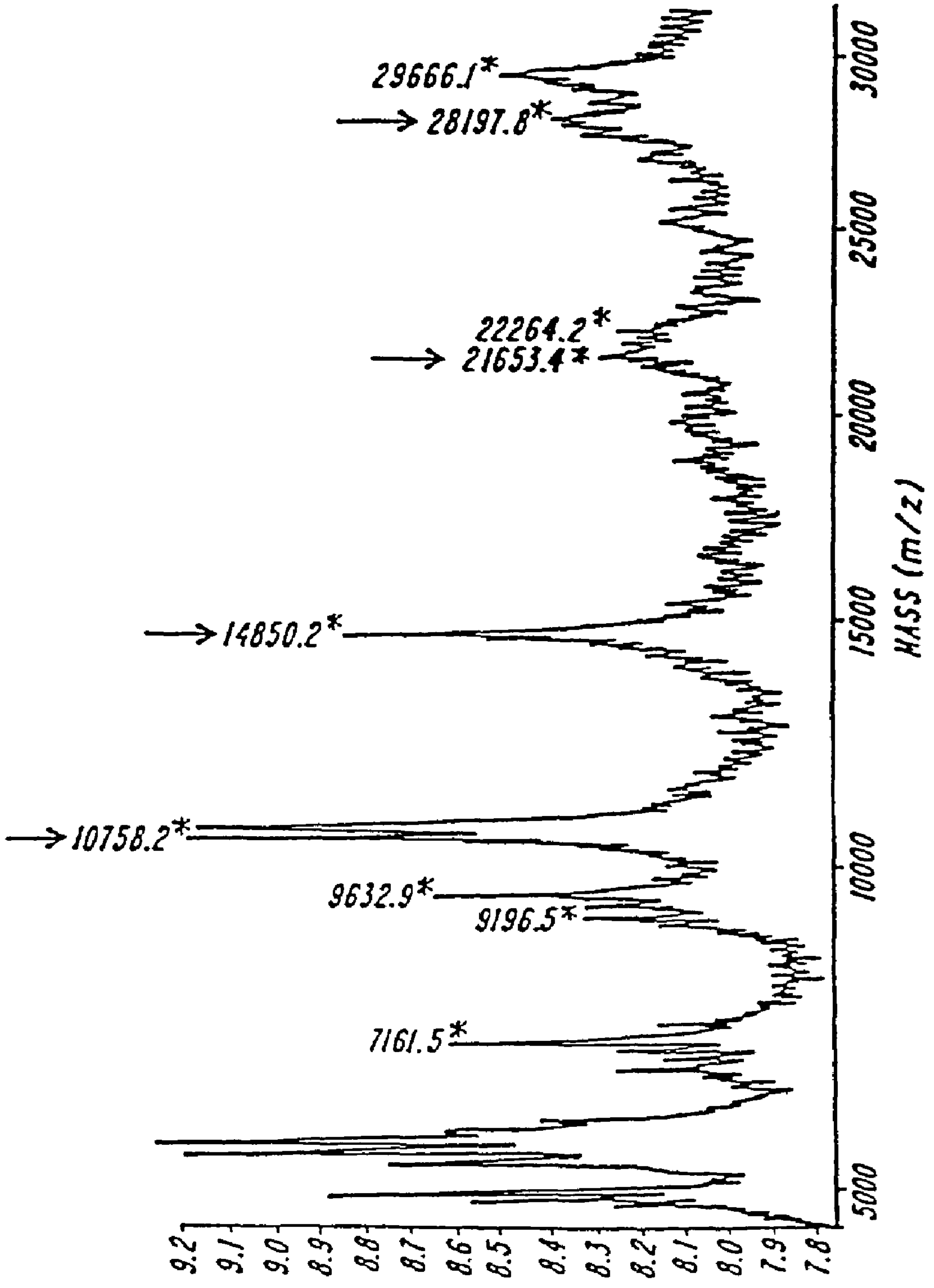
FIG. 23B is the mass spectrum of the restriction product of a E3/E4 apolipoprotein E genotype.

As shown in FIG. 21A-C, different Apolipoprotein E genotypes exhibit different restriction patterns in a 3.5% MetPhor Agarose Gel or 12% polyacrylamide gel. As shown in FIGS. 22 and 23, the various apolipoprotein E genotypes can also be accurately and rapidly determined by mass spectrometry.

EXAMPLE 5

Detection of Hepatitis B Virus in Serum Samples.

Materials and Methods

Sample Preparation

Phenol/chloroform extraction of viral DNA and the final ethanol precipitation was done according to standard protocols.

First PCR

Each reaction was performed with 5 μl of the DNA preparation from serum. 15 pmol of each primer and 2 units Taq DNA polymerase (Perkin Elmer, Weiterstadt, Germany) were used. The final concentration of each dNTP was 200 μMM, the final volume of the reaction was 50 μl. 10×PCR buffer (Perkin Elmer, Weiterstadt, Germany) contained 100 mM Tris-HCl, pH 8.3, 500 mM KCl, 15 mM $MgCl_2$, 0.01% gelatine (w/v).

| Primer | SEQUENCE | SEQ ID NO: |
|---|---|---|
| 1 | 5'-GCTTTGGGGCATGGACATTGACCCGTATAA-3' | 5 |
| 2 | 5'-CTGACTACTAATTCCCTGGATGCTGGGTCT-3' | 6 |

Nested PCR:

Each reaction was performed either with 1 μl of the first reaction or with a 1:10 dilution of the first PCR as template, respectively. 100 pmol of each primer, 2.5 u Pfu(exo-) DNA polymerase (Stratagene, Heidelberg, Germany), a final concentration of 200 μM of each dNTPs and 5 μl 10×Pfu buffer (200 mM Tris-HCl, pH 8.75, 100 mM KCl, 100 mM $(NH_4)_2SO_4$, 1% Triton X-100, 1 mg/ml BSA, (Stratagene, Heidelberg, Germany) were used in a final volume 50 μl. The reactions were performed in a thermocycler (OmniGene, MWG-Biotech, Ebersberg, Germany) using the following program: 92° C. for 1 minute, 60° C. for 1 minute and 72° C. for 1 minute with 20 cycles. Sequence of oligodeoxynucleotides (purchased HPLC-purified from MWG-Biotech, Ebersberg, Germany):

```
                                        (SEQ ID NO:7)
HBV13: 5'-TTGCCTGAGTGCAGTATGGT-3'

                                        (SEQ ID NO:8)
HBV15bio: Biotin-5'-AGCTCTATATCGGGAAGCCT-3'
```

Purification of Amplified Products:

For the recording of each spectrum, one PCR, 50 μl, (performed as described above) was used. Purification was done according to the following procedure: Ultrafiltration was done using Ultrafree-MC filtration units (Millipore, Eschborn, Germany) according to the protocol of the provider with centrifugation at 8000 rpm for 20 minutes. 25μl (10 μg/μl) streptavidin Dynabeads (Dynal, Hamburg, Germany) were prepared according to the instructions of the manufacturer and resuspended in 25 μl of B/W buffer (10 mM Tris-HCl, pH 7.5, 1 mM EDTA, 2 M NaCl). This suspension was added to the PCR samples still in the filtration unit and the mixture was incubated with gentle shaking for 15 minutes at ambient temperature. The suspension was transferred in a 1.5 ml Eppendorf tube and the supernatant was removed with the aid of a Magnetic Particle Collector, MPC, (Dynal, Hamburg, Germany). The beads were washed twice with 50 μl of 0.7 M ammonium citrate solution, pH 8.0 (the supernatant was removed each time using the MPC). Cleavage from the beads can be accomplished by using formamide at 90° C. The supernatant was dried in a speedvac for about an hour and resuspended in 4 μl of ultrapure water (MilliQ UF plus Millipore, Eschborn, Germany). This preparation was used for MALDI-TOF MS analysis.

MALDI-TOF MS:

Half a microliter of the sample was pipetted onto the sample holder, then immediately mixed with 0.5 μl matrix solution (0.7 M3-hydroxypicolinic acid 50% acetonitrile, 70 mM ammonium citrate). This mixture was dried at ambient temperature and introduced into the mass spectrometer. All spectra were taken in positive ion mode using a Finnigan MAT Vision 2000 (Finnigan MAT, Bremen, Germany), equipped with a reflectron (5 keV ion source, 20 keV postacceleration) and a 337 nm nitrogen laser. Calibration was done with a mixture of a 40-mer and a 100-mer. Each sample was measured with different laser energies. In the negative samples, the amplified product was detected neither with less nor with higher laser energies. In the positive samples the amplified product was detected at different places of the sample spot and also with varying laser energies.

Results

A nested PCR system was used for the detection of HBV DNA in blood samples employing oligonucleotides complementary to the c region of the HBV genome (primer 1: beginning at map position 1763, primer 2 beginning at map position 2032 of the complementary strand) encoding the HBV core antigen (HBVcAg). DNA was isolated from patients serum according to standard protocols. A first PCR was performed with the DNA from these preparations using a first set of primers. If HBV DNA was present in the sample a DNA fragment of 269 bp was generated.

In the second reaction, primers which were complementary to a region within the PCR fragment generated in the first PCR were used. If HBV related amplified products were present in the first PCR a DNA fragment of 67 bp was generated (see FIG. 25A) in this nested PCR. The usage of a nested PCR system for detection provides a high sensitivity and also serves as a specificity control for the external PCR (Rolfs et al. (1992) PCR: Clinical Diagnostics and Research, Springer, Heidelberg). A further advantage is that the amount of fragments generated in the second PCR is high enough to ensure an unproblematic detection although purification losses can not be avoided.

The samples were purified using ultrafiltration to restreptavidin Dynabeads. This purification was done because the shorter primer fragments were immobilized in higher yield on the beads due to stearic reasons. The immobilization was done directly on the ultrafiltration membrane to avoid substance losses due to unspecific absorption on the membrane. Following immobilization, the beads were washed with ammonium citrate to perform cation exchange (Pieles et al. (1993) *Nucl. Acids Res.* 21: 3191-3196). The immobilized DNA was cleaved from the beads using 25% ammonia which allows cleavage of DNA from the beads in a very short time, but does not result in an introduction of sodium or other cations.

The nested PCRs and the MALDI TOF analysis were performed without knowing the results of serological analysis. Due to the unknown virus titer, each sample of the first PCR was used undiluted as template and in a 1:10 dilution, respectively.

Sample 1 was collected from a patient with chronic active HBV infection who was positive in Hbs- and Hbe-antigen tests but negative in a dot blot analysis. Sample 2 was a serum sample from a patient with an active HBV infection and a massive viremia who was HBV positive in a dot blot analysis. Sample 3 was a denatured serum sample therefore no serological analysis could be performed by an increased level of transaminases indicating liver disease was detected. In autoradiograph analysis (FIG. 24), the first PCR of this sample was negative. Nevertheless, there was some evidence of HBV infection. This sample is of interest for MALDI-TOF analysis, because it demonstrates that even low-level amounts of amplified products can be detected after the purification procedure. Sample 4 was from a patient who was cured of HBV infection. Samples 5 and 6 were collected from patients with a chronic active HBV infection.

Figure 24:
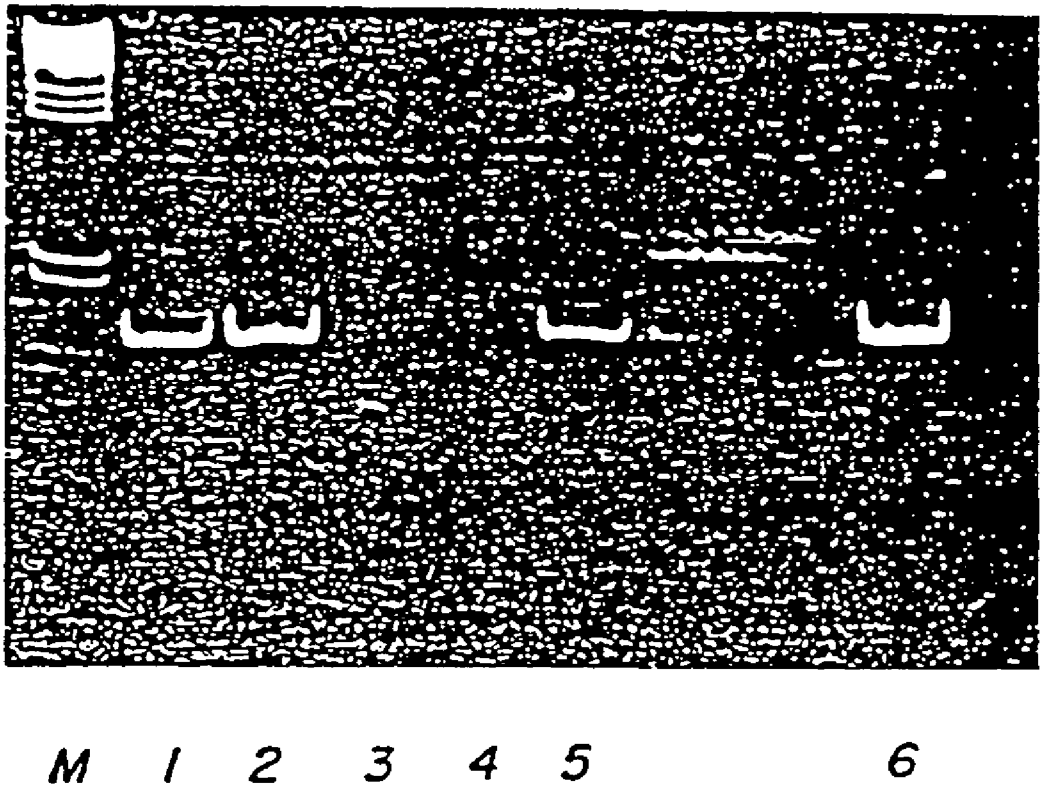
FIG. 24 is an autoradiograph of Example 5 of a 7.5% polyacrylamide gel in which 10% (5 μl) of each amplified sample was loaded: sample M: pBR322 AluI digested; sample 1: HBV positive in serological analysis; sample 2: also HBV positive; sample 3: without serological analysis but with an increased level of transaminases, indicating liver disease; sample 4: HBV negative containing HCV; sample 5: HBV posit-) negative control; (+) positive control). Staining was done with ethidium bromide.

FIG. 24 shows the results of a PAGE analysis of the nested PCR reaction. A amplified product is clearly revealed in samples 1, 2, 3, 5 and 6. In sample 4 no amplified product was generated, it is indeed HBV negative, according to the serological analysis. Negative and positive controls are indicated by + and –, respectively. Amplification artifacts are visible in lanes 2, 5, 6 and + if non-diluted template was used. These artifacts were not generated if the template was used in a 1:10 dilution. In sample 3, amplified product was merely detectable if the template was not diluted. The results of PAGE analysis are in agreement with the data obtained by serological analysis except for sample 3 as discussed above.

Figure 25A:
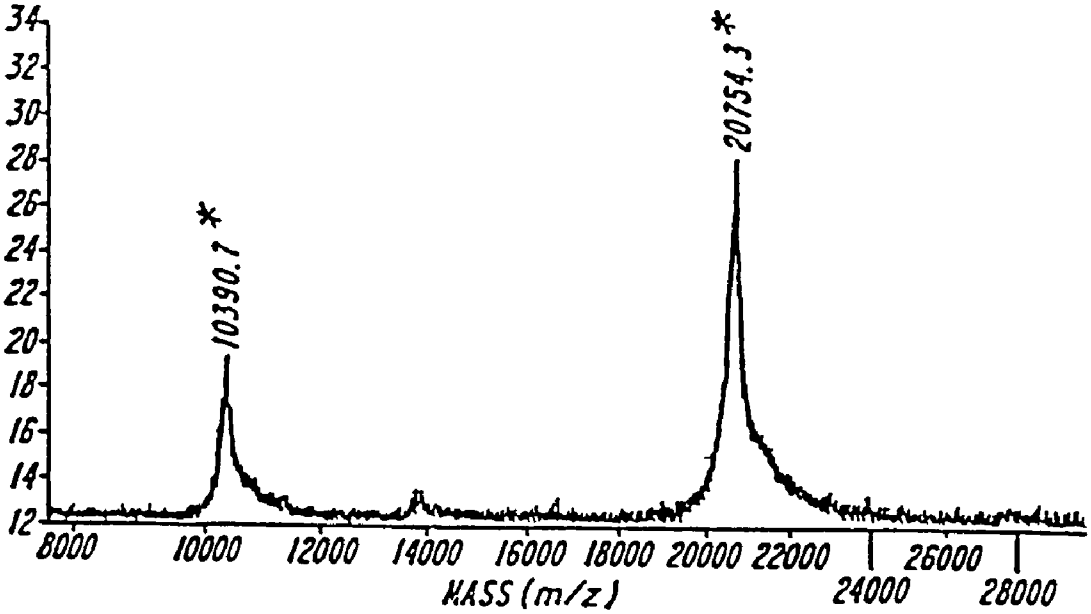
FIG. 25A is a mass spectrum of sample 1, which is HBV positive. The signal at 20754 Da represents the HBV related amplification product (67 nucleotides, calculated mass: 20735 Da). The mass signal at 10390 Da represents the $[M+2H]^{2+}$ molecule ion (calculated: 10378 Da).

FIG. 25A shows a mass spectrum of a nested amplified product from sample number 1 generated and purified as described above. The signal at 20754 Da represents the single stranded amplified product (calculated: 20735 Da, as the average mass of both strands of the amplified product cleaved from the beads). The mass difference of calculated and obtained mass is 19 Da (0.09%). As shown in FIG. 25A, sample number 1 generated a high amount of amplified product, resulting in an unambiguous detection.

Figure 25B:
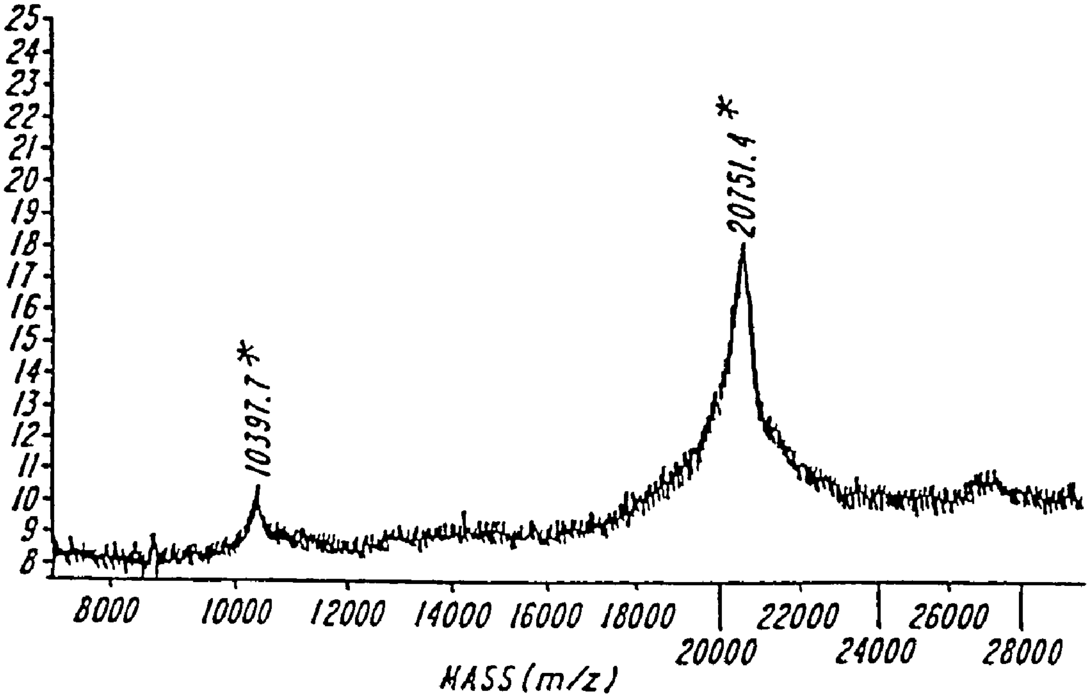
FIG. 25B is a mass spectrum of sample 3, which is HBV negative corresponding to nucleic acid (i.e., PCR), serological and dot blot based assays. The amplified product is generated only in trace amounts. Nevertheless it is unambiguously detected at 20751 Da (calculated mass: 20735 Da). The mass signal at 10397 Da represents the $[M+2H]^{2+}$ molecule ion (calculated: 10376 Da).
Figure 25C:
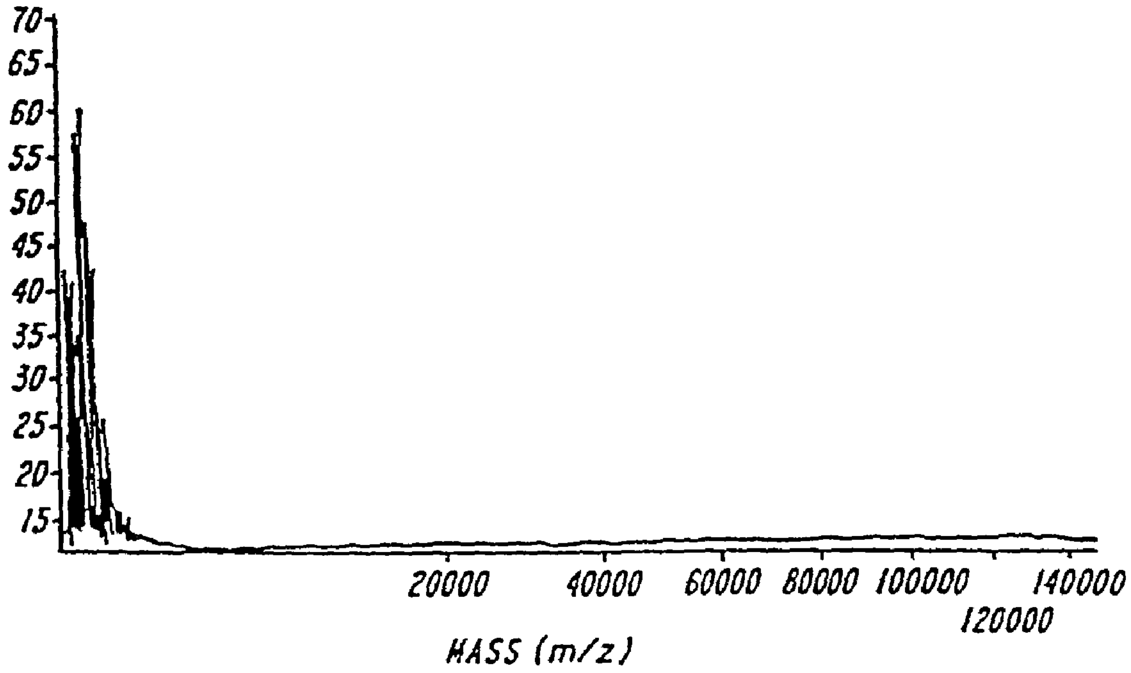
FIG. 25C is a mass spectrum of sample 4, which is HBV negative, but HCV positive. No HBV specific signals were observed.

FIG. 25B shows a spectrum obtained from sample number 3. As depicted in FIG. 24, the amount of amplified product generated in this section is significantly lower than that from sample number 1. Nevertheless, the amplified product is clearly revealed with a mass of 20751 Da (calculated 20735). The mass difference is 16 Da (0.08%). The spectrum depicted in FIG. 25C was obtained from sample number 4 which is HBV negative (as is also shown in FIG. 24). As expected no signals corresponding to the amplified product could be detected. All samples shown in FIG. 25 were analyzed with MALDI-TOF MS, whereby amplified product was detected in all HBV positive samples, but not in the HBV negative samples. These results were reproduced in several independent experiments.

EXAMPLE 6

Analysis of Ligase Chain Reaction Products Via MALDI-TOF Mass Spectrometry

Materials and Methods

Oligodeoxynucleotides

Except the biotinylated one and all other oligonucleotides were synthesized in a 0.2 μmol scale on a MilliGen 7500 DNA Synthesizer (Millipore, Bedford, Mass., USA) using the β-cyanoethylphosphoamidite method (Sinha, N. D. et al. (1984) *Nucleic Acids Res.* 12: 4539-4577). The oligodeoxynucleotides were RP-HPLC-purified and deprotected according to standard protocols. The biotinylated oligodeoxynucleotide was purchased (HPLC-purified) from Biometra, Gottingen, Germany). Sequences and calculated masses of the oligonucleotides used:

| Oligodeoxy-nucleotide | SEQUENCE | SEQ ID NO: |
|---|---|---|
| A | 5'-p-TTGTGCCACGCGGTTGGGAATGTA (7521 Da) | 9 |
| B | 5'-p-AGCAACGACTGTTTGCCCGCCAGTTG (7948 Da) | 10 |
| C | 5'-bio-TACATTCCCAACCGCGTGGCACAAC (7960 Da) | 11 |
| D | 5'-p-AACTGGCGGGCAAACAGTCGTTGCT (7708 Da) | 12 |

5-Phosphorylation of Oligonucleotides A and D

This was performed with polynucleotide kinase (Boehringer, Mannheim, Germany) according to published procedures, the 5'-phosphorylated oligonucleotides were used unpurified for LCR.

Ligase Chain Reaction

The LCR was performed with Pfu DNA ligase and a ligase chain reaction kit (Stratagene, Heidelberg, Germany) containing two different pBluescript KII phagemids. One carrying the wildtype form of the *E. coli* lacI gene and the other one a mutant of this gene with a single point mutation at bp 191 of the lacI gene.

The following LCR conditions were used for each reaction: 100 pg template DNA (0.74 fmol) with 500 pg sonified salmon sperm DNA as carrier, 25 ng (3.3 pmol) of each 5'-phosphorylated oligonucleotide, 20 ng (2.5 pmol) of each non-phosphorylated oligonucleotide, 4 U Pfu DNA ligase in a final volume of 20 μl buffered ss 50-mer was used (I fmol) as template, in this case oligo C was also biotinylated. All reactions were performed in a thermocycler (OmniGene, MWG-Biotech, Ebersberg, Germany) with the following program: 4 minutes 92° C., 2 minutes 60° C. and 25 cycles of 20 seconds 92° C., 40 seconds 60° C. Except for HPLC analysis the biotinylated ligation educt C was used. In a control experiment the biotinylated and non-biotinylated oligonucleotides revealed the same gel electrophoretic results. The reactions were analyzed on 7.5% polyacrylamide gels. Ligation product 1 (oligo A and B) calculated mass: 15450 Da, ligation product 2 (oligo C and D) calculated mass: 15387 Da.

SMART-HPLC

Ion exchange HPLC (IE HPLC) was performed on the SMART-system (Pharmacia, Freiburg, Germany) using a Pharmacia Mono Q, PC 1.6/5 column. Eluents were buffer A (25 mM Tris-HCl, 1 mM EDTA and 0.3 M NaCl at pH 8.0) and buffer B (same as A, but 1 M NaCl). Starting with 100% A for 5 minutes at a flow rate of 50 μl/min. a gradient was applied from 0 to 70% B in 30 minutes, then increased to 100% B in 2 minutes and held at 100% B for 5 minutes. Two pooled LCR volumes (40 μl) performed with either wildtype or mutant template were injected.

Sample Preparation for MALDI-TOF-MS

Preparation of immobilized DNA: For the recording of each spectrum two LCRs (performed as described above) were pooled and diluted 1:1 with 2×B/W buffer (10 mM Tris-HCl, pH 7.5, 1 mM EDTA, 2 M NaCl). To the samples 5 μl streptavidin DynaBeads (Dynal, Hamburg, Germany) were added, the mixture was allowed to bind with gentle shaking for 15 minutes at ambient temperature. The supernatant was removed using a Magnetic Particle Collector, MPC, (Dynal, Hamburg, Germany) and the beads were washed twice with 50 μl of 0.7 M ammonium citrate solution (pH 8.0) (the supernatant was removed each time using the MPC). The beads were resuspended in 1 μl of ultrapure water (MilliQ, Millipore, Bedford, Mabelow).

Combination of ultrafiltration and streptavidin DynaBeads: For the recording of spectrum two LCRs (performed as described above) were pooled, diluted 1:1 with 2×B/W buffer and concentrated with a 5000 NMWL Ultrafree-MC filter unit (Millipore, Eschborn, Germany) according to the instructions of the manufacturer. After concentration the samples were washed with 300 μl 1×B/W buffer to streptavidin DynaBeads were added. The beads were washed once on the Ultrafree-MC filtration unit with 300 μl of 1×B/W buffer and processed as described above. The beads were resuspended in 30 to 50 μl of 1×B/W buffer and transferred in a 1.5 ml Eppendorf tube. The supernatant was removed and the beads were washed twice with 50 μl of 0.7 M ammonium citrate (pH 8.0). Finally, the beads were washed once with 30 μl of acetone and resuspended in 1 μl of ultrapure water. The ligation mixture after immobilization on the beads was used for MALDS-TOF-MS analysis as described below.

MALDI-TOF-MS

A suspension of streptavidin-coated magnetic beads with the immobilized DNA was pipetted onto the sample holder, then immediately mixed with 0.5 μl matrix solution (0.7 M 3-hydroxypicolinic acid in 50% acetonitrile, 70 mM ammonium citrate). This mixture was dried at ambient temperature and introduced into the mass spectrometer. All spectra were taken in positive ion mode using a Finnigan MAT Vision 2000 (Finnigan MAT, Bremen, Germany), equipped with a reflectron (5 keV ion source, 20 keV postacceleration) and a nitrogen laser (337 nm). For the analysis of Pfu DNA ligase 0.5 μl of the solution was mixed on the sample holder with 1 μl of matrix solution and prepared as described above. For the analysis of unpurified LCRs 1 μl of an LCR was mixed with 1 μl matrix solution.

Results

Figure 26:
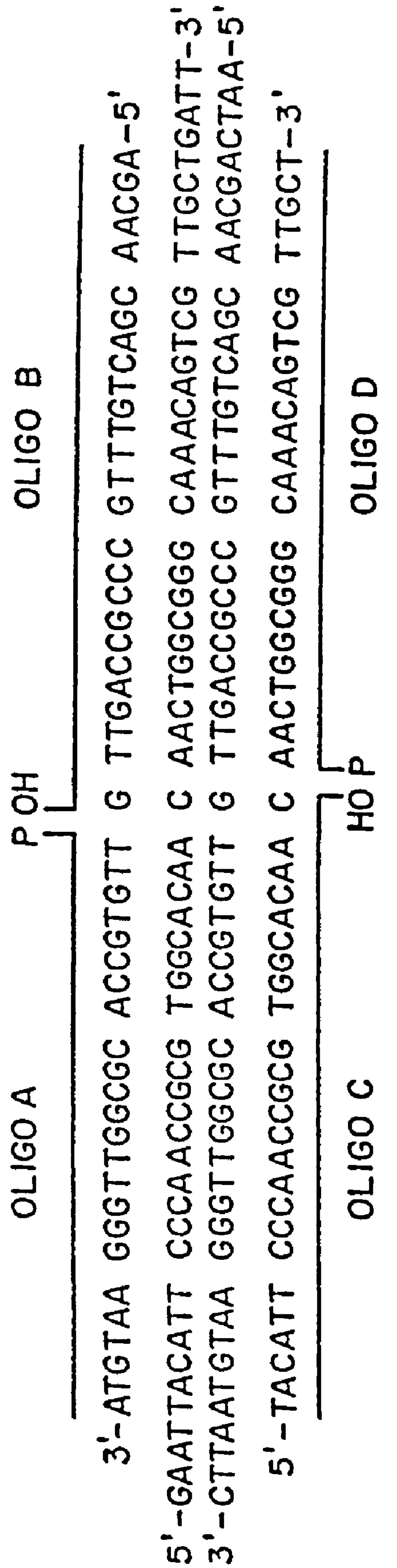
FIG. 26 shows a part of the *E. coli* lacI gene with binding sites of the complementary oligonucleotides used in the ligase chain reaction (LCR) of Example 6. Here the wildtype sequence is displayed. The mutant contains a point mutation at bp 191 which is also the site of ligation (bold). The mutation is a C to T transition (G to A, respectively). This leads to a T-G mismatch with oligo B (and A-C mismatch with oligo C, respectively). Oligo A, B, C, and D sequences are set forth in SEQ ID NO: 9, 10, 11 and 12 respectively.

The *E. coli* lacI gene served as a simple model system to investigate the suitability of MALDI-TOF-MS as detection method for products generated in ligase chain reactions. This template system contains of an *E. coli* lacI wildtype gene in a pBluescript KII phagemid and an *E. coli* lacI gene carrying a single point mutation at bp 191 (C to T transition; SEQ ID NO: 131) in the same phagemid. Four different oligonucleotides were used, which were ligated only if the *E. coli* lacI wildtype gene was present (FIG. 26).

Figure 27:
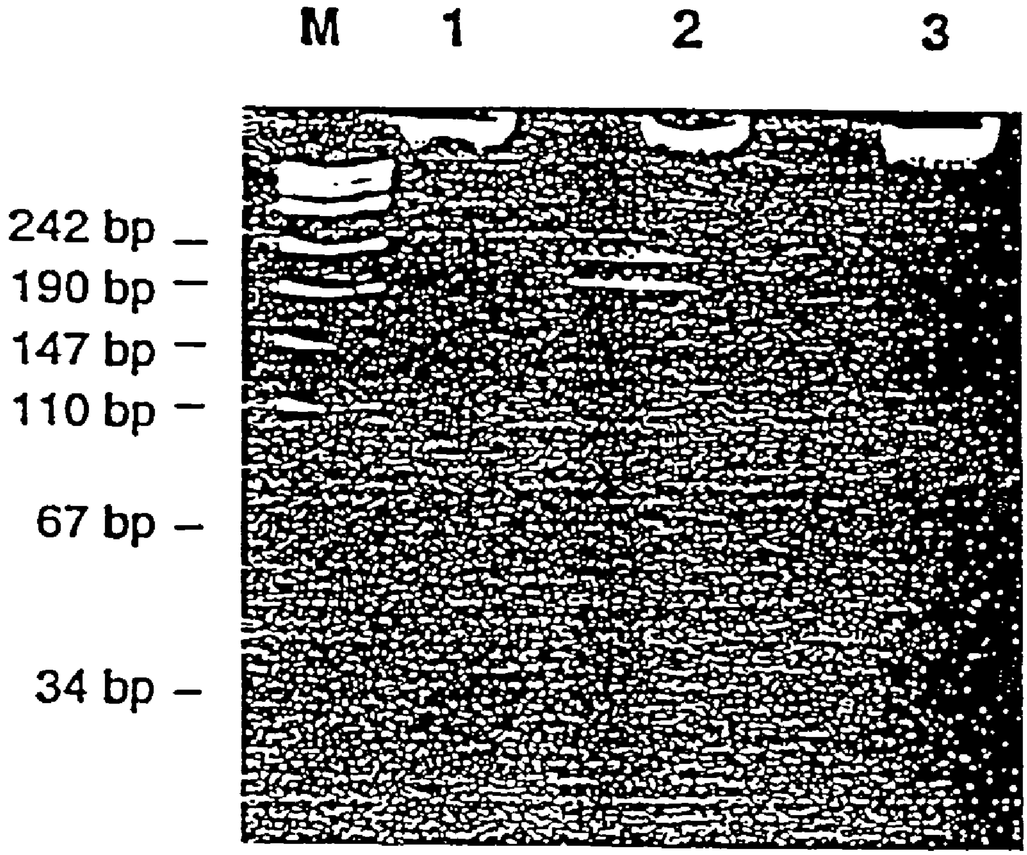
FIG. 27 is a 7.15% polyacrylamide gel of Example 6 stained with ethidium bromide. M: chain length standard (pUC19DNA, MspI digested). Lane 1: LCR with wildtype template. Lane 2: LCR with mutant template. Lane 3: (control) LCR without template. The ligation product (50 bp) was only generated in the positive reaction containing wildtype template.
Figure 28:
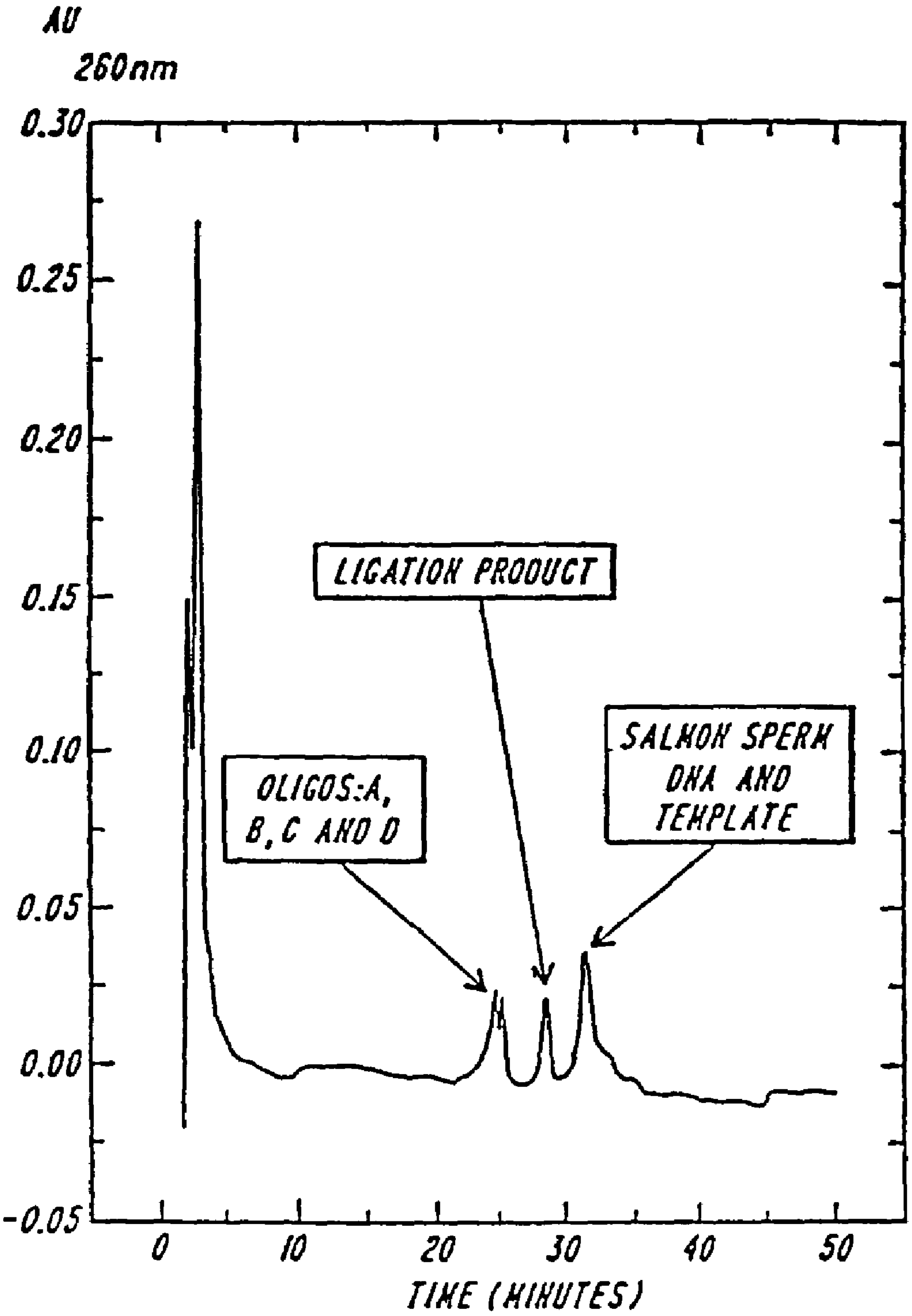
FIG. 28 is an HPLC chromatogram of two pooled positive LCRs.
Figure 29:
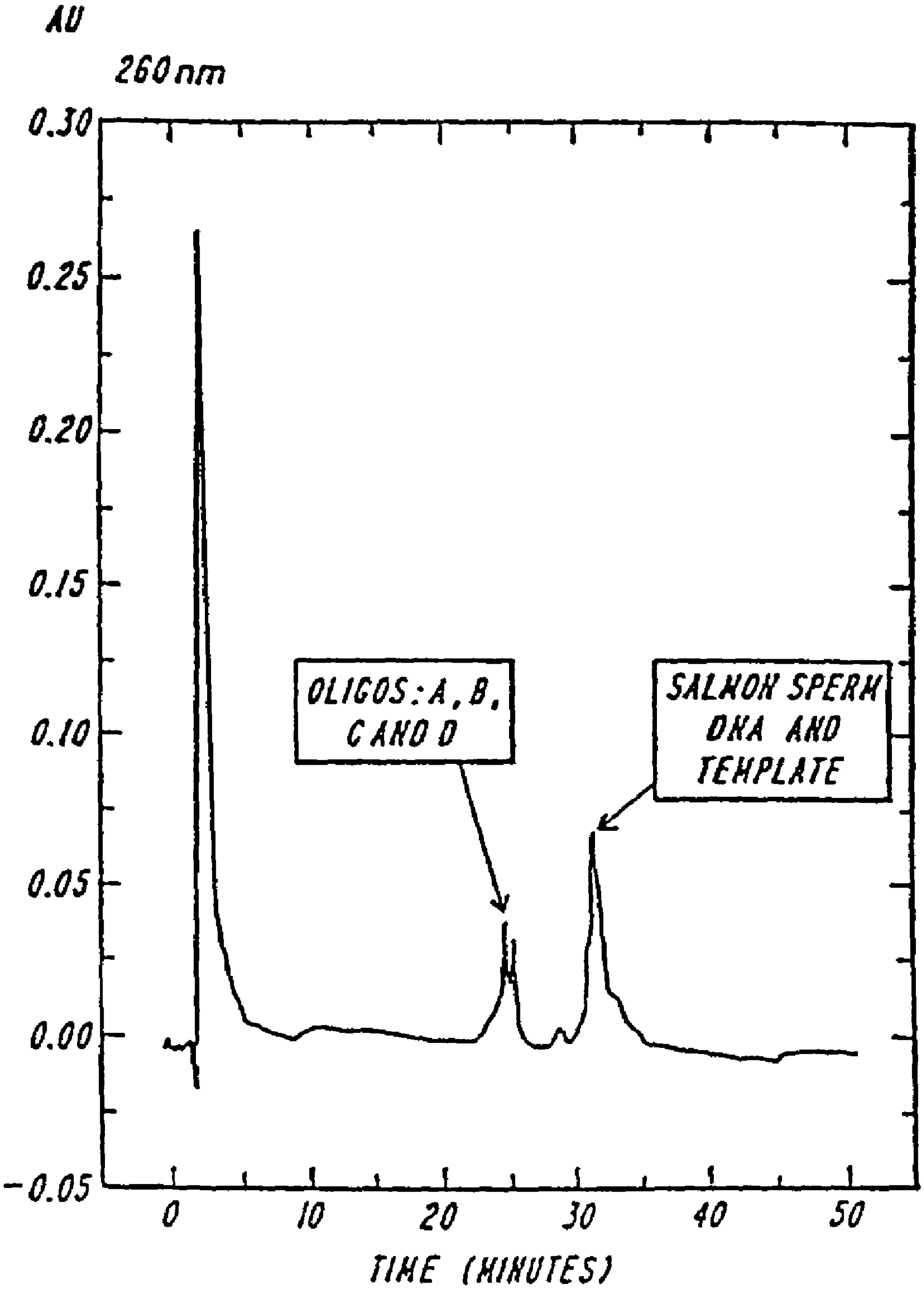
FIG. 29 shows an HPLC chromatogram the same conditions but mutant template were used. The small signal of the ligation product is due to either template-free ligation of the educts or to a ligation at a (G-T, A-C) mismatch. The 'false positive' signal is significantly lower than the signal of ligation product with wildtype template depicted in FIG. 28. The analysis of ligation educts leads to 'double-peaks' because two of the oligonucleotides are 5'-phosphorylated.

LCR conditions were optimized using Pfu DNA ligase to obtain at least 1 pmol ligation product in each positive reaction. The ligation reactions were analyzed by polyacrylamide gel electrophoresis (PAGE) and HPLC on the SMART system (FIGS. 27, 28 and 29). FIG. 27 shows a PAGE of a positive LCR with wildtype template (lane 1), a negative LCR with mutant template (1 and 2) and a negative control which contains enzyme, oligonucleotides and no template but salmon sperm DNA. The gel electrophoresis clearly shows that the ligation product (50 bp) was produced only in the reaction with wildtype template; whereas neither the template carrying the point mutation nor the control reaction with salmon sperm DNA generated amplification products. In FIG. 28, HPLC was used to analyze two pooled LCRs with wildtype template performed under the same conditions. The ligation product was clearly revealed. FIG. 29 shows the results of a HPLC in which two pooled negative LCRs with mutant template were analyzed. These chromatograms confirm the data shown in FIG. 27 and the results taken together clearly demonstrate, that the system generates ligation products in a significant amount only if the wildtype template is provided.

Appropriate control runs were performed to determine retention times of the different compounds involved in the L CR experiments. These include the four oligonucleotides (A, B, C, and D), a synthetic ds 50-mer (with the same sequence as the ligation product), the wildtype template DNA, sonicated salmon sperm DNA and the Pfu DNA ligase in ligation buffer.

Figure 30A:
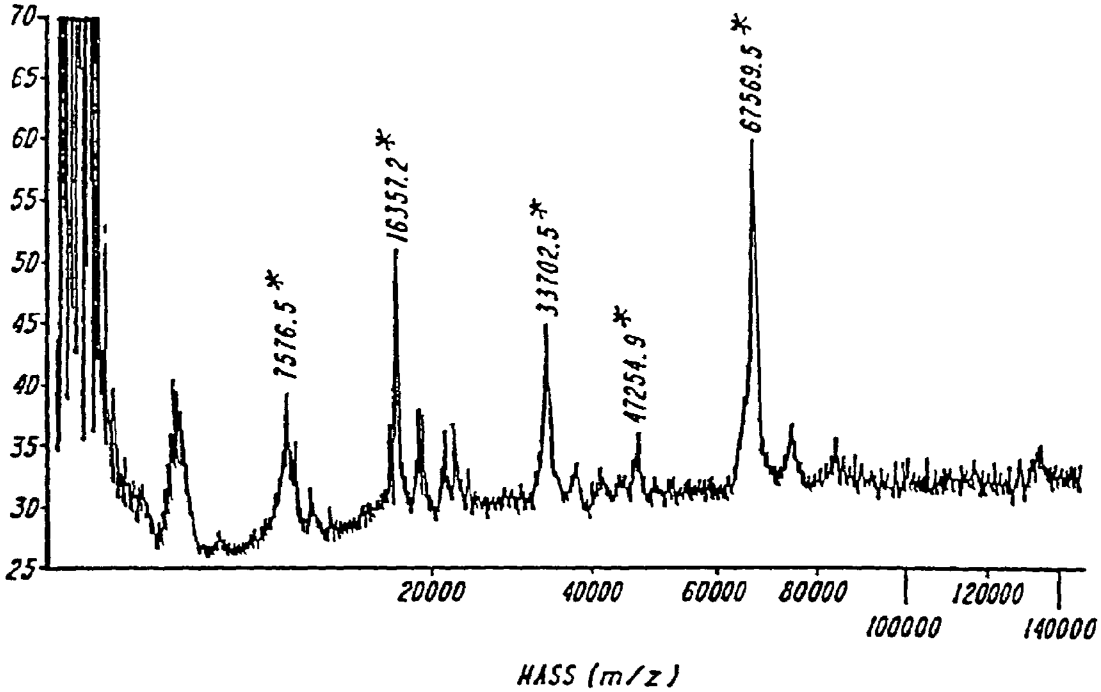
FIG. 30 In (b) the complex signal pattern obtained by MALDI-TOF-MS analysis of Pfu DNA-ligase solution of Example 6 is depicted. In (a) a MALDI-TOF-spectrum of an unpurified LCR is shown. The mass signal 67569 Da probably represents the Pfu DNA ligase.
Figure 30B:
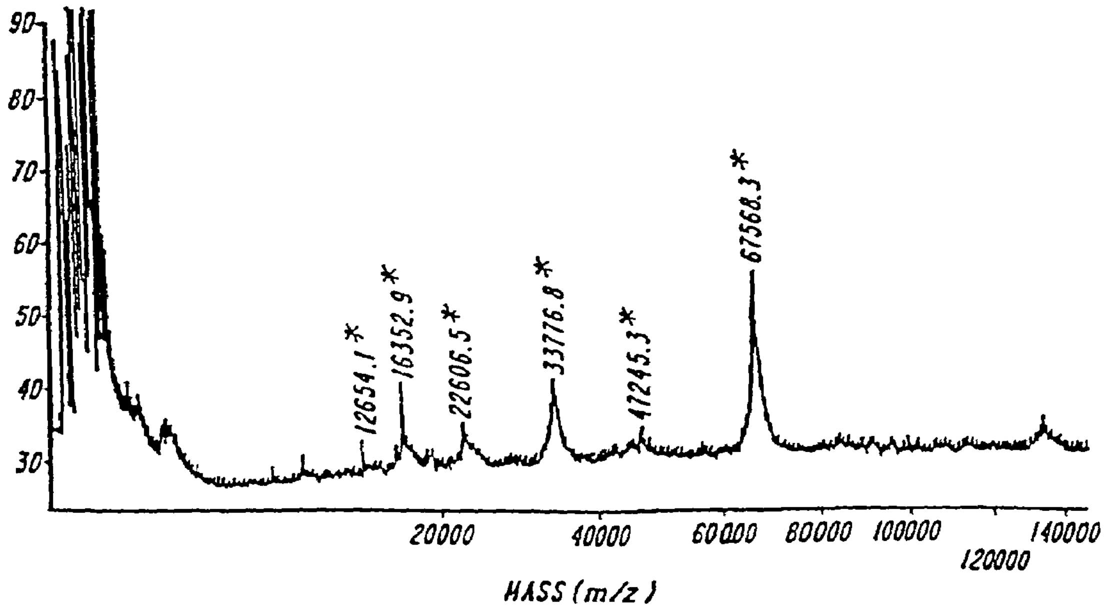

In order to test which purification procedure should be used before a LCR reaction can be analyzed by MALDI-TOF-MS, aliquots of an unpurified LCR (FIG. 30A) and aliquots of the enzyme stock solution (FIG. 30B) were analyzed with MALDI-TOF-MS. It turned out that appropriate sample preparation is absolutely necessary since all signals in the unpurified LCR correspond to signals obtained in the MALDI-TOF-MS analysis of the Pfu DNA ligase. The calculated mass values of oligo A and the ligation product are 7521 Da and 15450 Da, respectively. The data in FIG. 30 show that the enzyme solution leads to mass signals which do interfere with the expected signals of the ligation educts and products and therefore makes an unambiguous signal assignment impossible. Furthermore, the spectra showed signals of the detergent Tween20 being part of the enzyme storage buffer which influences the crystallization behavior of the analyte/matrix mixture in an unfavorable way.

In one purification format streptavidin-coated magnetic beads were used. As was shown in a recent paper, the direct desorption of DNA immobilized by Watson-Crick base pairing to a complementary DNA fragment covalently bound to the beads is possible and the non-biotinylated strand will be desorbed exclusively (Tang et al. (1995) *Nucleic Acids Res.* 23: 3126-3131). This approach in using immobilized ds DNA ensures that only the non-biotinylated strand will be desorbed. If non-immobilized ds DNA is analyzed both strands are desorbed (Tang et al. (1994) *Rapid Comm. Mass Spectrom.* 7: 183-186) leading to broad signals depending on the mass difference of the two single strands. Therefore, employing this system for LCR only the non-ligated oligonucleotide A, with a calculated mass of 7521 Da, and the ligation product from oligo A and oligo B (calculated mass: 15450 Da) will be desorbed if oligo C is biotinylated at the 5'-end and immobilized on steptavidin-coated beads. This results in a simple and unambiguous identification of the LCR educts and products.

Figure 31A:
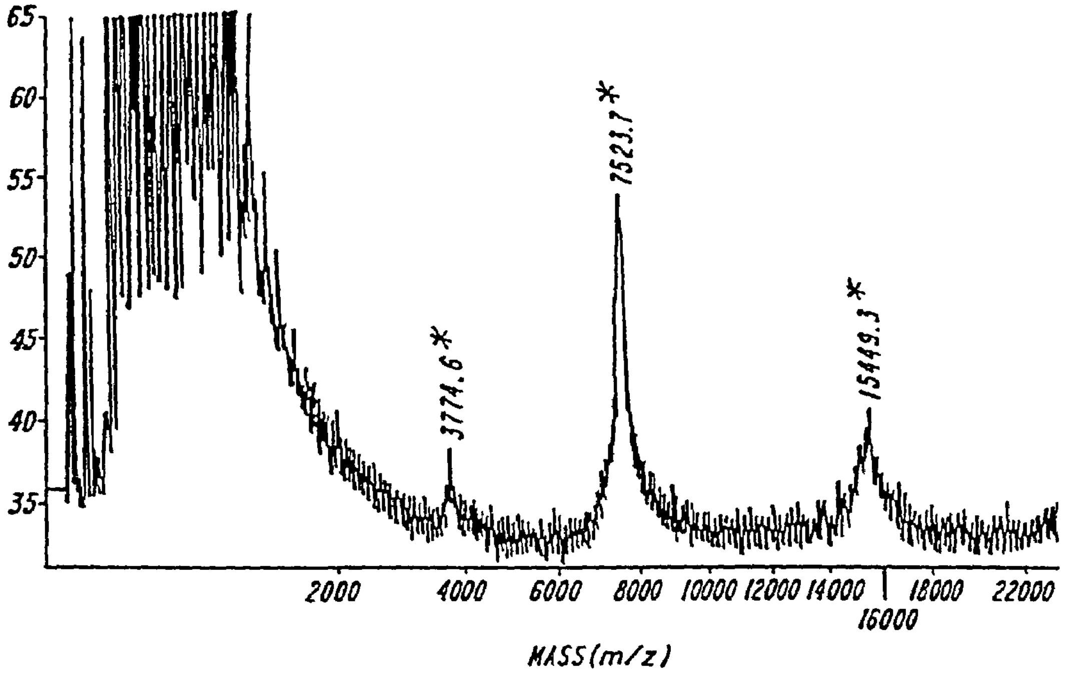
FIG. 31 shows a MALDI-TOF spectrum of two pooled positive LCRs (a). The signal at 7523 Da represents unligated oligo A (calculated: 7521 Da) whereas the signal at 15449 Da represents the ligation product (calculated: 15450 Da). The signal at 3774 Da is the $[M+2H]^{2+}$ signal of oligo A. The signals in the mass range lower than 2000 Da are due to the matrix ions. The spectrum corresponds to lane 1 in FIG. 27 and the chromatogram in FIG. 28. In (b) a spectrum of two pooled negative LCRs (mutant template) is shown. The signal at 7517 Da represents oligo A (calculated: 7521 Da).
Figure 31B:
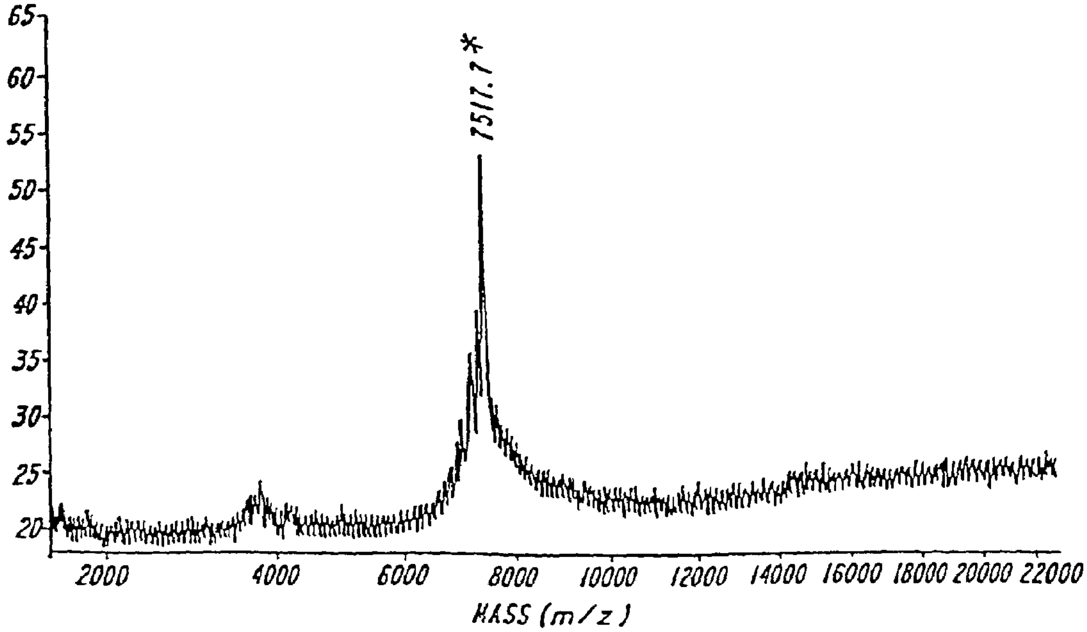
Figure 32:
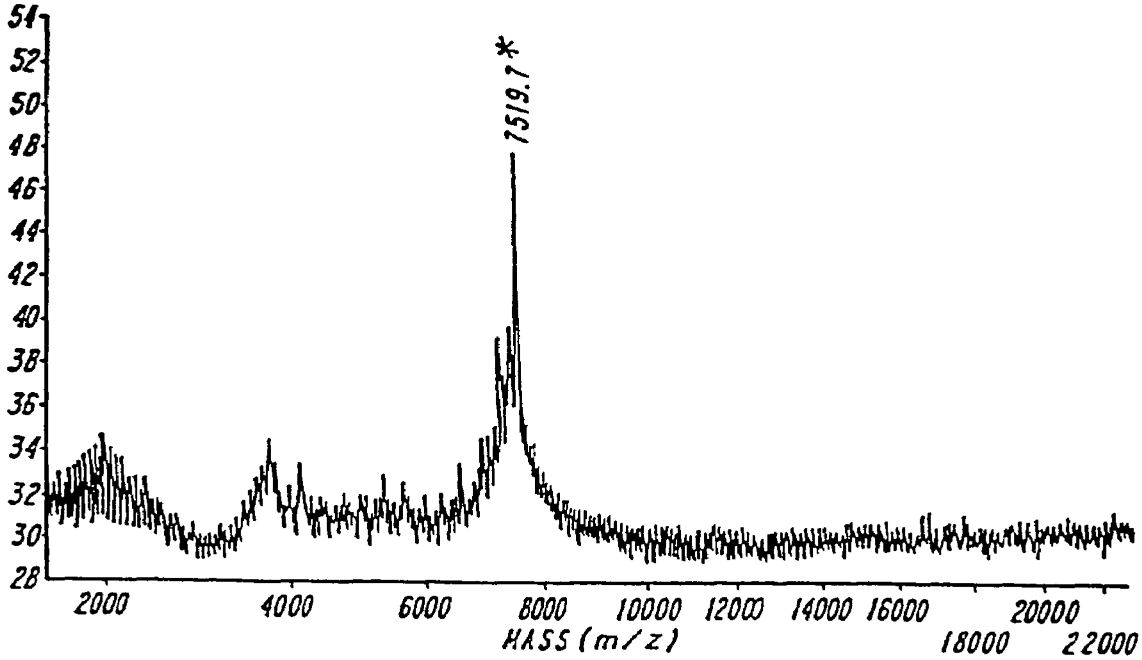
FIG. 32 shows a spectrum of two pooled control reactions (with salmon sperm DNA as template). The signals in the mass range around 2000 Da are due to Tween20, only oligo A could be detected, as expected.

FIG. 31A shows a MALDI-TOF mass spectrum obtained from two pooled LCRs (performed as described above) purified on streptavidin DynaBeads and desorbed directly from the beads showed that the purification method used was efficient (compared with FIG. 30). A signal which represents the unligated oligo A and a signal which corresponds to the ligation product could be detected. The agreement between the calculated and the experimentally found mass values is remarkable and allows an unambiguous peak assignment and accurate detection of the ligation product. In contrast, no ligation product but only oligo A could be detected in the spectrum obtained from two pooled LCRs with mutated template (FIG. 31B). The specificity and selectivity of the LCR conditions and the sensitivity of the MALDI-TOF detection is further demonstrated when performing the ligation reaction in the absence of a specific template. FIG. 32 shows a spectrum obtained from two pooled LCRs in which only salmon sperm DNA was used as a negative control, only oligo A could be detected, as expected.

While the results shown in FIG. 31A can be correlated to lane 1 of the gel in FIG. 27, the spectrum shown in FIG. 31B is equivalent to lane 2 in FIG. 27, and finally also the spectrum in FIG. 32 corresponds to lane 3 in FIG. 27. The results are in congruence with the HPLC analysis presented in FIGS. 28 and 29. While gel electrophoresis (FIG. 27) and HPLC (FIGS. 28 and 29) reveal either an excess or almost equal amounts of ligation product over ligation educts, the analysis by MALDI-TOF mass spectrometry produces a smaller signal for the ligation product (FIG. 31A).

The lower intensity of the ligation product signal could be due to different desorption/ionization efficiencies between 24- and a 50-mer. Since the $T_m$ value of a duplex with 50 compared to 24 base pairs is significantly higher, more 24-mer could be desorbed. A reduction in signal intensity can also result from a higher degree of fragmentation in case of the longer oligonucleotides.

Regardless of the purification with streptavidin DynaBeads, FIG. 32 reveals traces of Tween20 in the region around 2000 Da. Substances with a viscous consistence, negatively influence the process of crystallization and therefore can be detrimental to mass spectrometer analysis. Tween20 and also glycerol which are part of enzyme storage buffers therefore should be removed entirely prior to mass spectrometer analysis. For this reason an improved purification procedure which includes an additional ultrafiltration step prior to treatment with DynaBeads was investigated. Indeed, this sample purification resulted in a significant improvement of MALDI-TOF mass spectrometric performance.

Figure 33A:
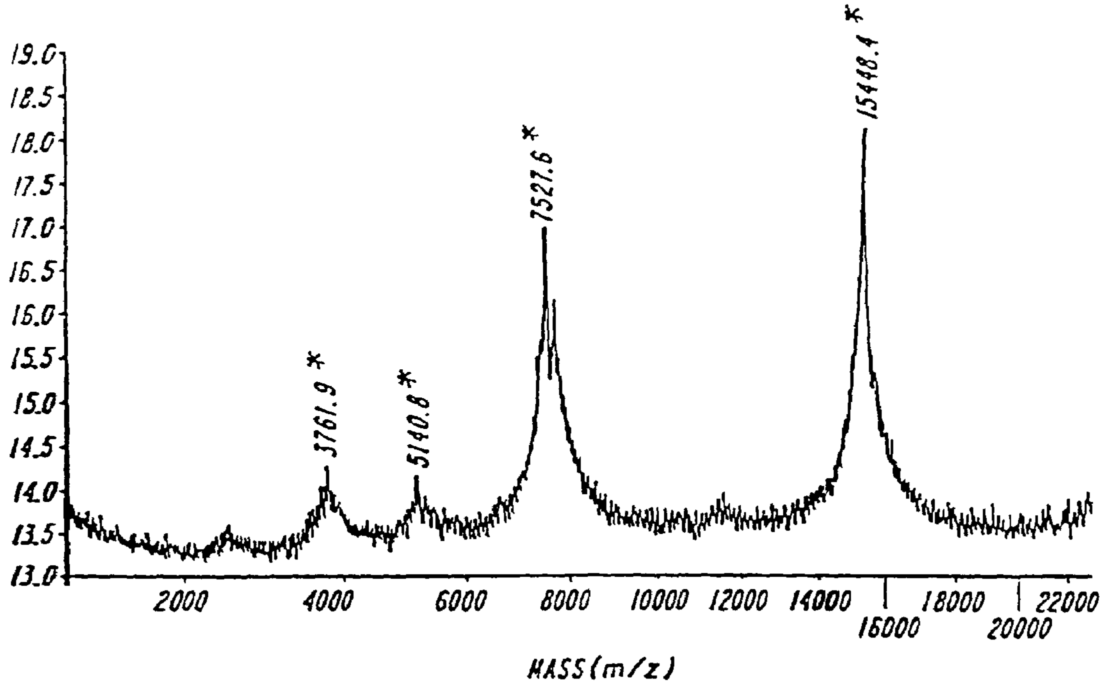
FIG. 33 shows a spectrum of two pooled positive LCRs (a). The purification was done with a combination of ultrafiltration and streptavidin DynaBeads as described in the text. The signal at 15448 Da represents the ligation product (calculated: 15450 Da). The signal at 7527 represents oligo A (calculated: 7521 Da). The signals at 3761 Da is the $[M+2H]^{2+}$ signal of oligo A, whereas the signal at 5140 Da is the $[M+3H]^{2+}$ signal of the ligation product. In (b) a spectrum of two pooled negative LCRs (without template) is shown. The signal at 7514 Da represents oligo A (calculated: 7521 Da).
Figure 33B:
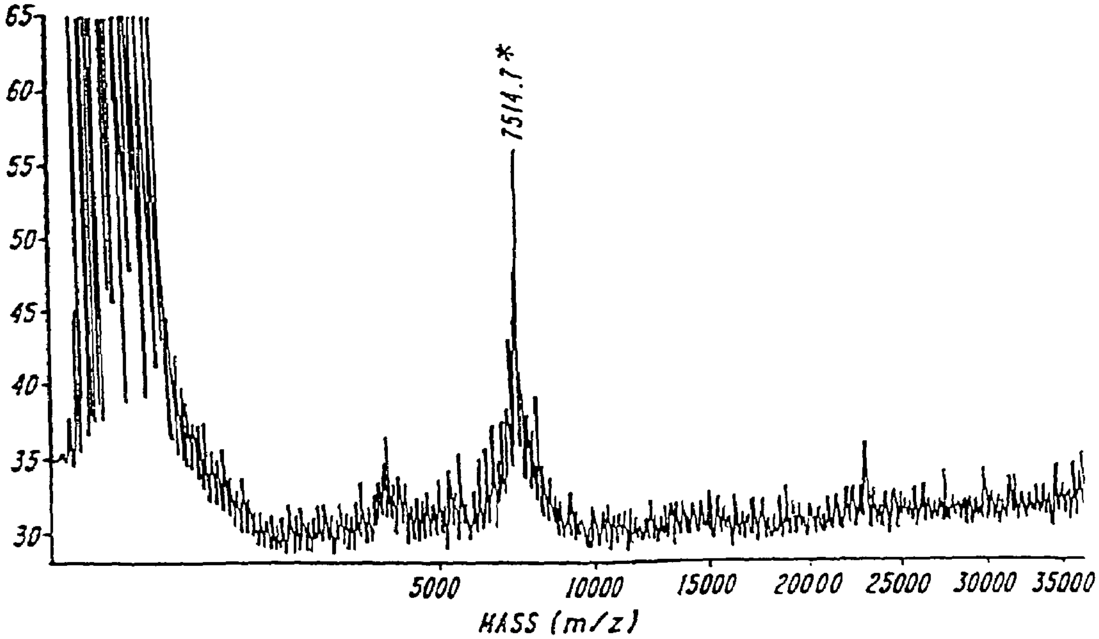
Figure 35A:
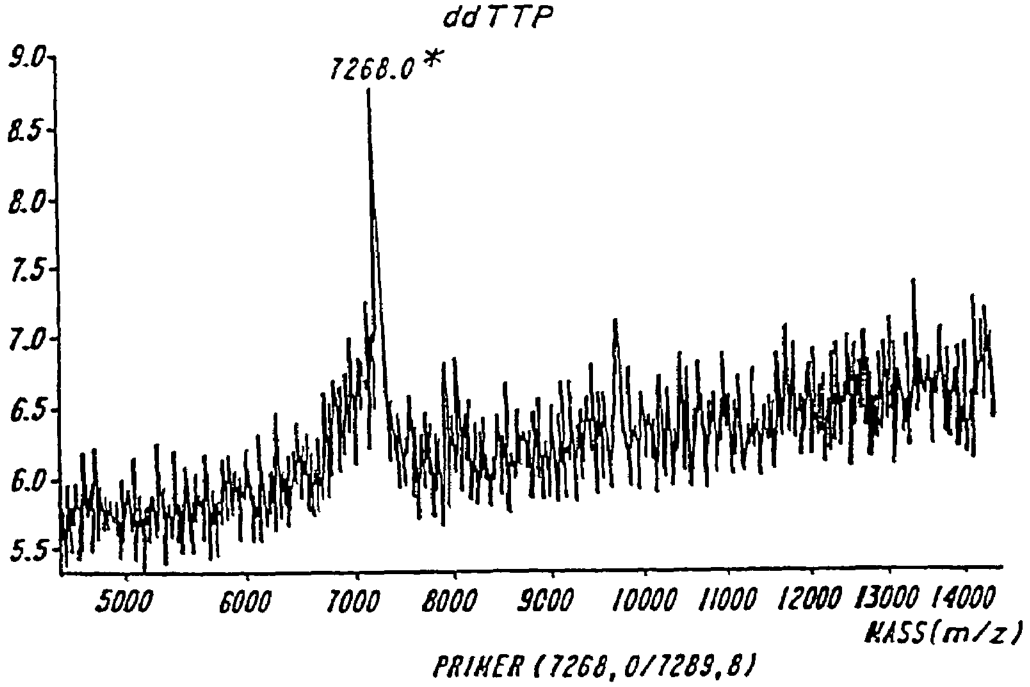
FIG. 35 is a MALDI-TOF-MS spectrum recorded directly from precipitated oligo base extended primers for mutation detection. The spectrum in (A) and (B), respectively show the annealed primer (CF508) without further extension reaction. Panel C displays the MALDI-TOF spectrum of the wild type by using pppTdd in the extension reaction and D a heterozygotic extension products carrying the 506S mutation when using pppCdd as terminator. Panels E and F show a heterozygote with ΔF508 mutation with pppTdd and pppCdd as terminators in the extension reaction. Panels G and H represent a homozygous ΔF508 mutation with either pppTdd or pppCdd as terminators. The template of diagnosis is pointed out below each spectrum and the observed/expected molecular mass are written in parenthesis.
Figure 35B:
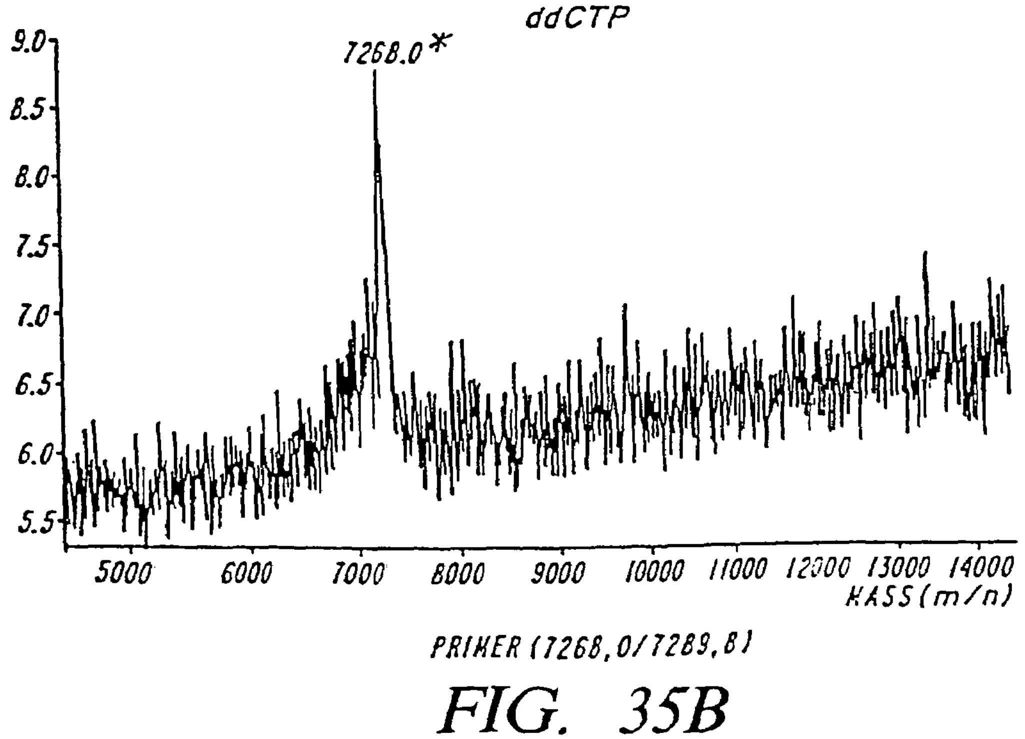
Figure 35C:
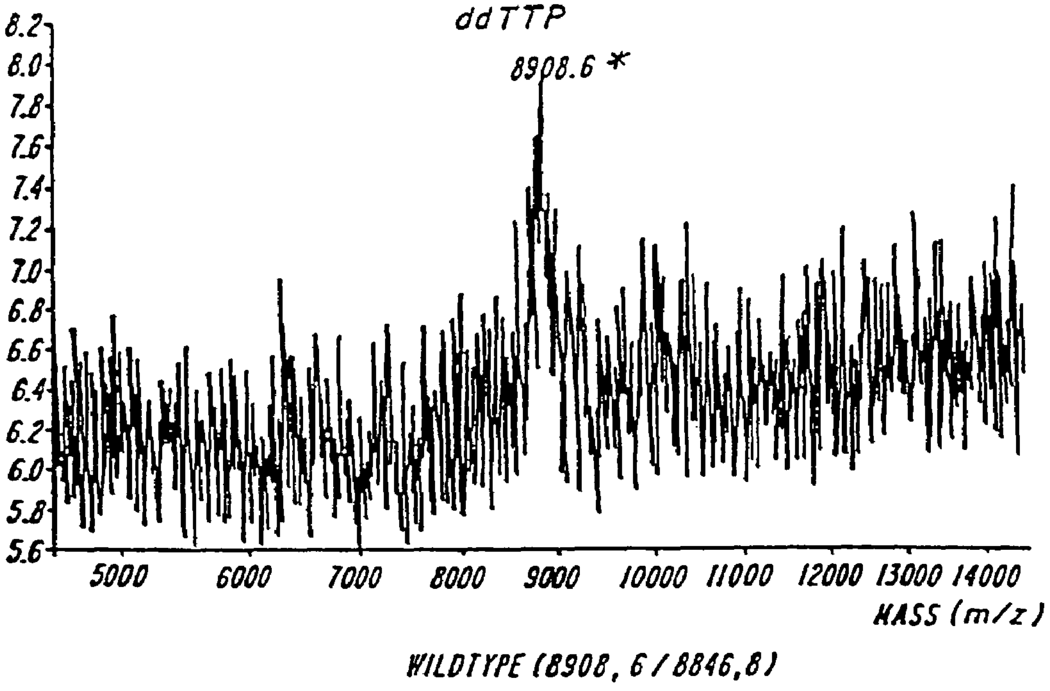
Figure 35D:
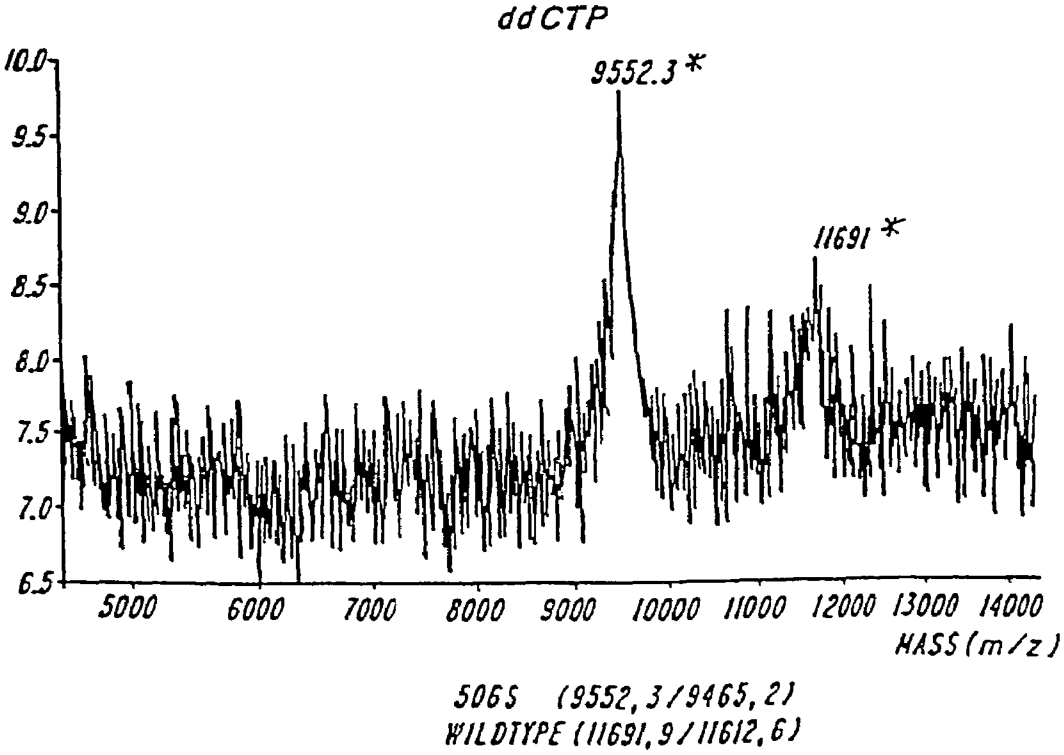
Figure 35E:
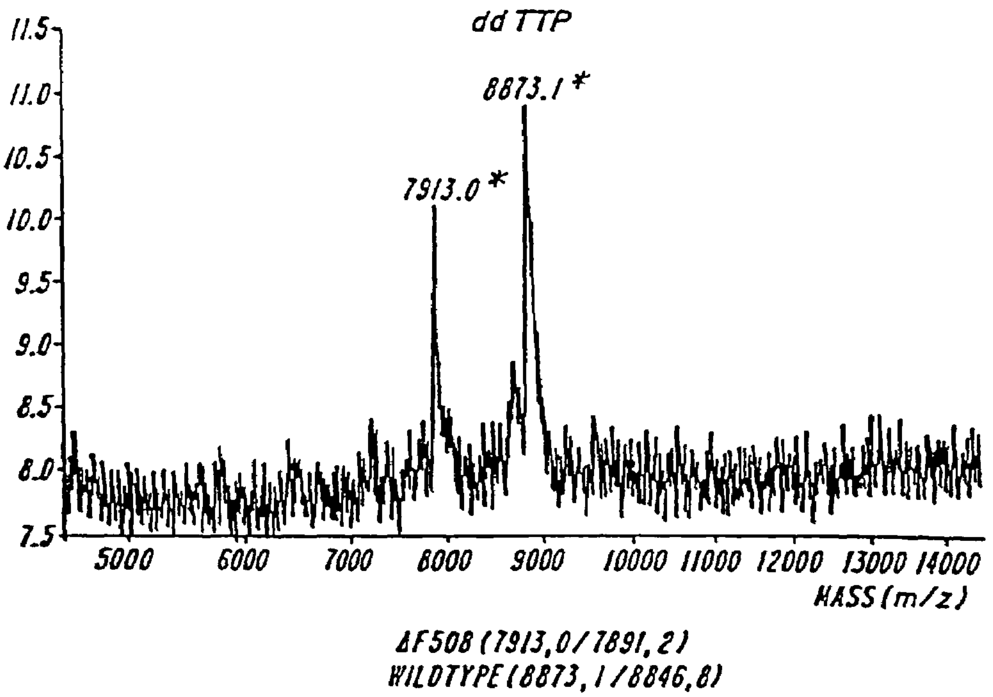
Figure 35F:
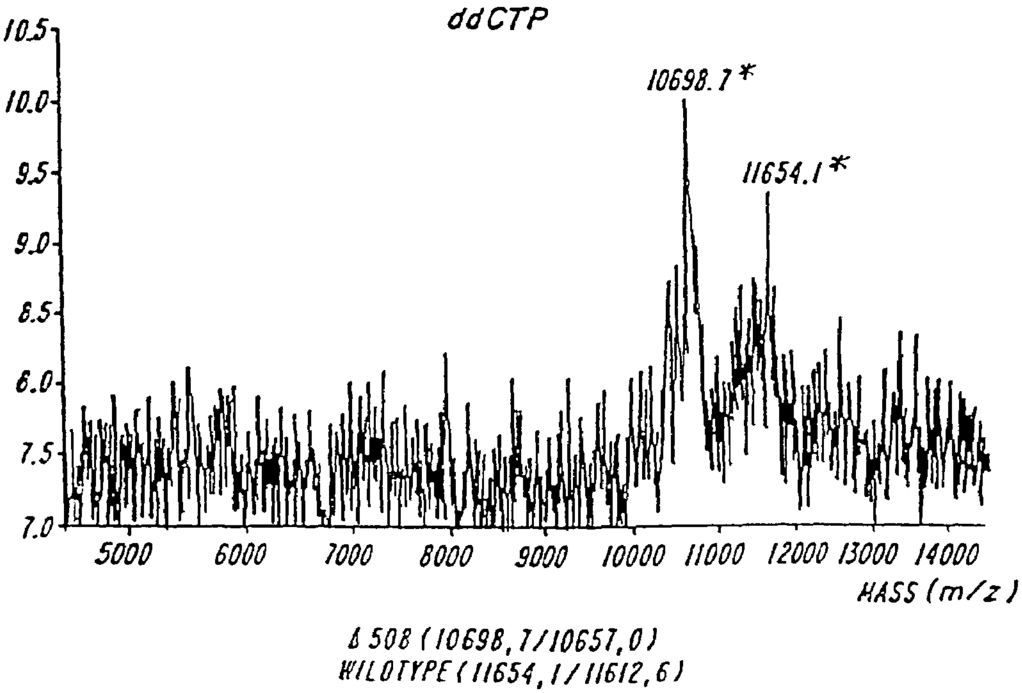
Figure 35G:
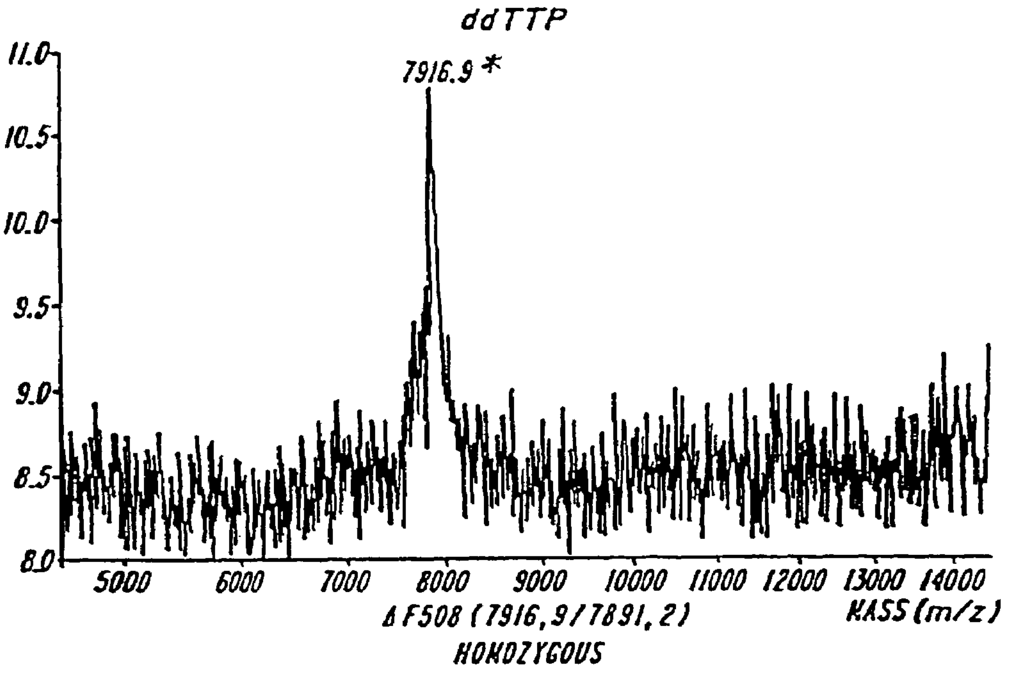
Figure 35H:
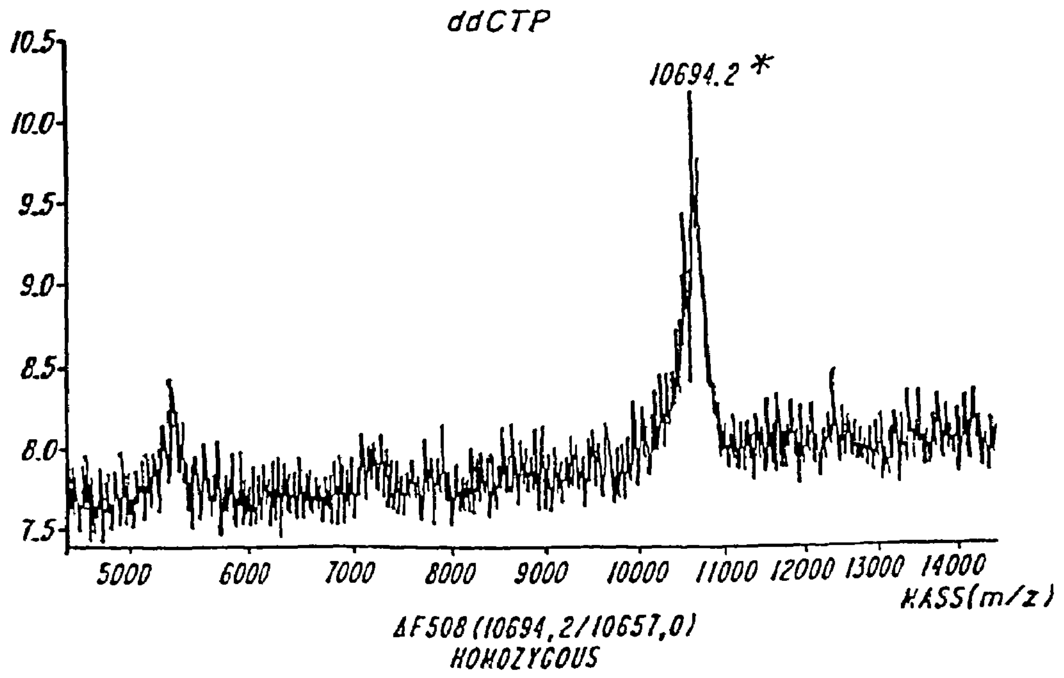

FIG. 33 shows spectra obtained from two pooled positive (FIG. 33A) and negative (FIG. 33B) LCRs, respectively. The positive reaction was performed with a chemically synthesized, single strand 50mer as template with a sequence equivalent to the ligation product of oligo C and D. Oligo C was 5'-biotinylated. Therefore the template was not detected. As expected, only the ligation product of Oligo A and B (calculated mass 15450 Da) could be desorbed from the immobilized and ligated oligo C and D. This newly generated DNA fragment is represented by the mass signal of 15448 Da in FIG. 33A. Compared to FIG. 32A, this spectrum clearly shows that this method of sample preparation produces signals with improved resolution and intensity.

EXAMPLE 7

Mutation Detection by Solid Phase Oligo Base Extension of a Primer and Analysis by MALDI-TOF Mass Spectrometry (Primer Oligo Base Extension=Probe)

Summary

The solid-phase oligo base extension method detects point mutations and small deletions as well as small insertions in amplified DNA. The method is based on the extension of a detection primer that anneals adjacent to a variable nucleotide position on an affinity-captured amplified template, using a DNA polymerase, a mixture of three dNTPs, and the missing one dideoxy nucleotide. The resulting products are evaluated and resolved by MALDI-TOF mass spectrometry without further labeling procedures. The aim of the following experiment was to determine mutant and wildtype alleles in a fast and reliable manner.

Description of the Experiment

The method used a single detection primer followed by a oligonucleotide extension step to give products differing in length by some bases specific for mutant or wildtype alleles which can be easily resolved by MALDI-TOF mass spectrometry. The method is described by using as example the exon 10 of the CFTR-gene. Exon 10 of this gene bears the most common mutation in many ethnic groups (ΔF508) that leads in the homozygous state to the clinical phenotype of cystic fibrosis.

Materials and Methods

Genomic DNA

Genomic DNA were obtained from healthy individuals, individuals homozygous or heterozygous for the ΔF508 mutation, and one individual heterozygous for the 1506S mutation. The wildtype and mutant alleles were confirmed by standard Sanger sequencing.

PCR Amplification of Exon 10 of the CFTR Gene

The primers for PCR amplification were CFEx10-F (5-GCAAGTGAATCCTGAGCGTG-3' (SEQ ID NO: 13) located in intron 9 and biotinylated) and CFEx10-R (5'-GTGTGAAGGGCGTG-3' SEQ ID NO: 14) located in intron 10). Primers were used in a concentration of 8 pmol. Taq-polymerase including 10× buffer were purchased from Boehringer-Mannheim and dTNPs were obtained from Pharmacia. The total reaction volume was 50 μl. Cycling conditions for PCR were initially 5 min. at 95° C., followed by 1 min. at 94° C., 45 sec at 53° C., and 30 sec at 72° C. for 40 cycles with a final extension time of 5 min at 72° C.

Purification of the Amplified Products

Amplification products were purified by using Qiagen's PCR purification kit (No. 28106) according to manufacturer's instructions. The elution of the purified products from the column was done in 50 μl TE-buffer (10 mM Tris, 1 mM EDTA, pH 7.5).

Affinity-Capture and Denaturation of the Double stranded DNA

10 μL aliquots of the purified amplified product were transferred to one well of a streptavidin-coated microtiter plate (No. 1645684 Boehringer-Mannheim or No. 95029262 Labsystems). Subsequently, 10 μl incubation buffer (80 mM sodium phosphate, 400 mM NaCl, 0.4% Tween20, pH 7.5) and 30 μl water were added. After incubation for 1 hour at room temperature the wells were washed three times with 200 μl washing buffer (40 mM Tris, 1 mM EDTA, 50 mM NaCl, 0.1% Tween 20, pH 8.8). To denature the double stranded DNA the wells were treated with 100 μl of a 50 mM NaOH solution for 3 min and the wells washed three times with 200 μl washing buffer.

Oligo Base Extension Reaction

The annealing of 25 pmol detection primer (CF508: 5'-CTATATTCATCATAGGAAACACCA-3' (SEQ ID NO: 15) was performed in 50 μl annealing buffer (20 mM Tris, 10 mM KCl, 10 mM $(NH_4)_2SO_4$, 2 mM MgSO2, 1% Triton X-100, pH 8) at 50° C. for 10 min. The wells were washed three times with 200 μl washing buffer and once in 200 μl TE buffer. The extension reaction was performed by using some components of the DNA sequencing kit from USB (No. 70770) and dNTPs or ddNTPs from Pharmacia. The total reaction volume was 45 μl, containing of 21 μl water, 6 μl Sequenase-buffer, 3μl 10 mM DTT solution, 4.5 μl, 0.5 mM of three dNTPs, 4.5 μl, 2 mM the missing one ddNTP, 5.5 μl glycerol enzyme dilution buffer, 0.25 μl Sequenase 2.0, and 0.25 pyrophosphatase. The reaction was pipetted on ice and then incubated for 15 min at room temperature and for 5 min at 37° C. Hence, the wells were washed three times with 200 μl washing buffer and once with 60 μl of a 70 mM $NH_4$-Citrate solution.

Denaturation and Precipitation of the Extended Primer

The extended primer was denatured in 50 μl 10%-DMSO (dimethylsulfoxide) in water at 80° C. for 10 min. For precipitation, 10 μl $NH_4$-Acetate (pH 6.5), 0.5 μl glycogen (10 mg/ml water, Sigma No. G1765), and 100 μl absolute ethanol were added to the supernatant and incubated for 1 hour at room temperature. After centrifugation at 13.000 g for 10 min the pellet was washed in 70% ethanol and resuspended in 1 μl 18 Mohm/cm $H_2O$ water.

Sample Preparation and Analysis on MALDI-TOF Mass Spectrometry

Sample preparation was performed by mixing 0.3 μl of each of matrix solution (0.7 M 3-hydroxypicolinic acid, 0.07 M dibasic ammonium citrate in 1:1 $H_2O$:$CH_3CN$) and of resuspended DNA/glycogen pellet on a sample target and allowed to air dry. Up to 20 samples were spotted on a probe target disk for introduction into the source region of an unmodified Thermo Bioanalysis (formerly Finnigan) Visions 2000 MALDI-TOF operated in reflectron mode with 5 and 20 kV on the target and conversion dynode, respectively. Theoretical average molecular mass ($M_r$(calc)) were calculated from atomic compositions; reported experimental Mr ($M_r$(exp)) values are those of the singly-protonated form, determined using external calibration.

Results

The aim of the experiment was to develop a fast and reliable method independent of exact stringencies for mutation detection that leads to high quality and high throughput in the diagnosis of genetic diseases. Therefore a special kind of DNA sequencing (oligo base extension of one mutation detection primer) was combined with the evaluation of the resulting mini-sequencing products by matrix-assisted laser desorption ionization (MALDI) mass spectrometry (MS). The time-of-flight (TOF) reflectron arrangement was chosen as a possible mass measurement system. To prove this hypothesis, the examination was performed with exon 10 of the CFTR-gene, in which some mutations could lead to the clinical phenotype of cystic fibrosis, the most common monogenetic disease in the Caucasian population.

The schematic presentation as given in FIG. 34 shows the expected short sequencing products with the theoretically calculated molecular mass of the wildtype and various mutations of exon 10 of the CFTR-gene (SEQ ID NO: 132). The short sequencing products were produced using either ddTTP (FIG. 34A; SEQ ID NOs: 133-135) or ddCTP (FIG. 34B; SEQ ID NOs: 136-139) to introduce a definitive sequence related stop in the nascent DNA strand. The MALDI-TOF-MS spectra of healthy, mutation heterozygous, and mutation homozygous individuals are presented in FIG. 35. All samples were confirmed by standard Sanger sequencing which showed no discrepancy in comparison to the mass spec analysis. The accuracy of the experimental measurements of the various molecular masses was within a range of minus 21.8 and plus 87.1 dalton (Da) to the range expected. This allows a definitive interpretation of the results in each case. A further advantage of this procedure is the unambiguous detection of the A1507 mutation. In the ddTTP reaction, the wild-type allele would be detected, whereas in the ddCTP reaction the three base pair deletion would be disclosed.

The method described is highly suitable for the detection of single point mutations or microlesions of DNA. Careful choice of the mutation detection primers will open the window of multiplexing and lead to a high throughput including high quality in genetic diagnosis without any need for exact stringencies necessary in comparable allele-specific procedures. Because of the uniqueness of the genetic information, the oligo base extension of mutation detection primer is applicable in each disease gene or polymorphic region in the genome like variable number of tandem repeats (VNTR) or other single nucleotide polymorphisms (e.g., apolipoprotein E gene), as also described here.

EXAMPLE 8

Detection of Polymerase Chain Reaction Products Containing 7-Deazapurine Moieties with Matrix-Assisted Laser Desorption/Ionization Time-of-Flight (MALDI-TOF) Mass Spectrometry

Materials and Methods

Nucleic Acid Amplifications

The following oligodeoxynucleotide primers were either synthesized according to standard phosphoamidite chemistry (Sinha, N. D, et al., (1983) *Tetrahedron Let*. Vol. 24, Pp. 5843-5846; Sinha, N. D., et al., (1984) *Nucleic Acids Res*., Vol. 12, Pp. 4539-4557) on a MilliGen 7500 DNA synthesizer (Millipore, Bedford, Mass., USA) in 200 nmol scales or purchased from MWG-Biotech (Ebersberg, Germany, primer 3) and Biometra (Goettingen, Germany, primers 6-7).

```
                                       (SEQ ID NO:16)
primer 1: 5'-GTCACCCTCGACCTGCAG;

                                       (SEQ ID NO:17)
primer 2: 5'-TTGTAAAACGACGGCCAGT;

                                       (SEQ ID NO:18)
primer 3: 5'-CTTCCACCGCGATGTTGA;

                                       (SEQ ID NO:19)
primer 4: 5'-CAGGAAACAGCTATGAC;

                                       (SEQ ID NO:20)
primer 5: 5'-GTAAAACGACGGCCAGT;

                                       (SEQ ID NO:21)
primer 6: 5'-GTCACCCTCGACCTGCAgC (g: RiboG);

                                       (SEQ ID NO:22)
primer 7: 5'-GTTGTAAAACGAGGGCCAgT (g: RiboG);
```

The 99-mer (SEQ ID NO: 141) and 200-mer DNA strands (SEQ ID NO: 140; modified and unmodified) as well as the ribo- and 7-deaza-modified 100-mer were amplified from pRFc1 DNA (10 ng, generously supplied by S. Feyerabend, University of Hamburg) in 100 μL reaction volume containing 10 mmol/L KCl, 10 mmol/L $(NH_4)_2SO_4$, 20 mmol/L Tris HCl (pH 8.8), 2 mmol/L $MgSO_{41}$ (exo(−) *Pseudococcus furiosus* (Pfu)-Buffer, Pharmacia, Freiburg, Germany), 0.2 mmol/L each dNTP (Pharmacia, Freiburg, Germany), 1 μmol/L of each primer and 1 unit of exo(−)Pfu DNA polymerase (Stratagene, Heidelberg, Germany). For the 99-mer primers 1 and 2, for the 200-mer primers 1 and 3 and for the 100-mer primers 6 and 7 were used. To obtain 7-deazapurine modified nucleic acids, during PCR-amplification dATP and dGTP were replaced with 7-deaza-dATP and 7-deaza-dGTP. The reaction was performed in a thermal cycler (OmniGene, MWG-Biotech, Ebersberg, Germany) using the cycle: denaturation at 95° C. for 1 min., annealing at 51° C. for 1 min. and extension at 72° C. for 1 min. For all PCRs the number of reaction cycles was 30. The reaction was allowed to extend for additional 10 min. at 72° C. after the last cycle.

The 103-mer DNA strands (modified and unmodified; SEQ ID NO: 245) were amplified from M13mp18 RFI DNA (100 ng, Pharmacia, Freiburg, Germany) in 100 μL reaction volume. using primers 4 and 5 all other concentrations were unchanged. The reaction was performed using the cycle: denaturation at 95° C. for 1 min., annealing at 40° C. for 1 min. and extension at 72° C. for 1 min. After 30 cycles for the unmodified and 40 cycles for the modified 103-mer respectively, the samples were incubated for additional 10 min. at 72° C.

Synthesis of 5'-[$^{32}$-P]-Labeled PCR-Primers

Primers 1 and 4 were 5'-[$^{32}$-P]-labeled employing T4-polynucleotidekinase (Epicentre Technologies) and (γ-$^{32}$P)-ATP. (BLU/NGG/502A, Dupont, Germany) according to the protocols of the manufacturer. The reactions were performed substituting 10% of primer 1 and 4 in PCR with the labeled primers under otherwise unchanged reaction-conditions. The amplified DNAs were separated by gel electrophoresis on a 10% polyacrylamide gel. The appropriate bands were excised and counted on a Packard TRI-CARB 460C liquid scintillation system (Packard, Conn., USA).

Primer-Cleavage from Ribo-Modified PCR-Product

The amplified DNA was purified using Ultrafree-MC filter units (30,000 NMWL), it was then redissolved in 100 μl of 0.2 mol/L NaOH and heated at 95° C. for 25 minutes. The solution was then acidified with HCl (1 mol/L) and further purified for MALDI-TOF analysis employing Ultrafree-MC filter units (10,000 NMWL) as described below.

Purification of Amplified Products

All samples were purified and concentrated using Ultrafree-MC units 30000 NMWL (Millipore, Eschborn, Germany) according to the manufacturer's description. After lyophilization, amplified products were redissolved in 5 μL (3 μL for the 200-mer) of ultrapure water. This analyte solution was directly used for MALDI-TOF measurements.

MALDI-TOF MS

Aliquots of 0.5 μL of analyte solution and 0.5 μL of matrix solution (0.7 mol/L 3-HPA and 0.07 mol/L ammonium citrate in acetonitrile/water (1:1, v/v)) were mixed on a flat metallic sample support. After drying at ambient temperature the sample was introduced into the mass spectrometer for analysis. The MALDI-TOF mass spectrometer used was a Finnigan MAT Vision 2000 (Finnigan MAT, Bremen, Germany). Spectra were recorded in the positive ion reflector mode with a 5 keV ion source and 20 keV postacceleration. The instrument was equipped with a nitrogen laser (337 nm wavelength). The vacuum of the system was $3\text{-}4\cdot10^{-8}$ hPa in the analyzer region and $1\text{-}4\cdot10^{-7}$ hPa in the source region. Spectra of modified and unmodified DNA samples were obtained with the same relative laser power; external calibration was performed with a mixture of synthetic oligodeoxynucleotides (7-to 5O-mer).

Results and Discussion

Enzymatic Synthesis of 7-deazapurine Nucleotide Containing Nucleic Acids by PCR

In order to demonstrate the feasibility of MALDI-TOF MS for the rapid, gel-free analysis of short amplified products and to investigate the effect of 7-deazapurine modification of nucleic acids under MALDI-TOF conditions, two different primer-template systems were used to synthesize DNA fragments. Sequences are displayed in FIGS. 36 and 37. While the two single strands of the 103-mer amplified product had nearly equal masses (Δm=8 u), the two single strands of the 99-mer differed by 526 u. Considering that 7-deaza purine nucleotide building blocks for chemical DNA synthesis are approximately 160 times more expensive than regular ones (Product Information, Glen Research Corporation, Sterling, Va.) and their applification in standard β-cyano-phosphoamidite chemistry is not trivial (Product Information, Glen Research Corporation, Sterling, Va.; Schneider et al. (1995) *Nuc. Acids Res.* 23: 1570) the cost of 7-deaza purine modified primers would be very high. Therefore, to increase the applicability and scope of the method, all PCRs were performed using unmodified oligonucleotide primers which are routinely available. Substituting dATP and dGTP by $c^7$-dATP and $c^7$-dGTP in polymerase chain reaction led to products containing approximately 80% 7-deaza-purine modified nucleosides for the 99-mer and 103-mer; and about 90% for the 200-mer, respectively. Table II shows the base composition of all PCR products.

TABLE II

Base composition of the 99-mer, 103-mer and 200-mer PCR amplification products (unmodified and 7-deaza purine modified)

| DNA-fragments[1] | C | T | A | G | $c^7$-deaza-A | $c^7$-deaza-6 | rel. mod.[2] |
|---|---|---|---|---|---|---|---|
| 200-mers | 54 | 34 | 56 | 56 | — | — | — |
| modified 200-mer s | 54 | 34 | 6 | 5 | 50 | 51 | 90% |
| 200-mer a | 56 | 56 | 34 | 54 | — | — | — |
| modified 200-mer a | 56 | 56 | 3 | 4 | 31 | 50 | 92% |
| 103-mer s | 28 | 23 | 24 | 28 | — | — | — |
| modified 103-mer s | 28 | 23 | 6 | 5 | 18 | 23 | 79% |
| 103-mer a | 28 | 24 | 23 | 28 | — | — | — |
| modified 103-mer a | 28 | 24 | 7 | 4 | 16 | 24 | 78% |
| 99-mer s | 34 | 21 | 24 | 20 | — | — | — |
| modified 99-mer s | 34 | 21 | 6 | 5 | 18 | 15 | 75% |
| 99-mer a | 20 | 24 | 21 | 34 | — | — | — |
| modified 99-mer a | 20 | 24 | 3 | 4 | 18 | 30 | 87% |

[1]"s" and "a" describe "sense" and "antisense" strands of the double-stranded amplified product.
[2]indicates relative modification as percentage of 7-deaza purine modified nucleotides of total amount of purine nucleotides.

Figure 38:
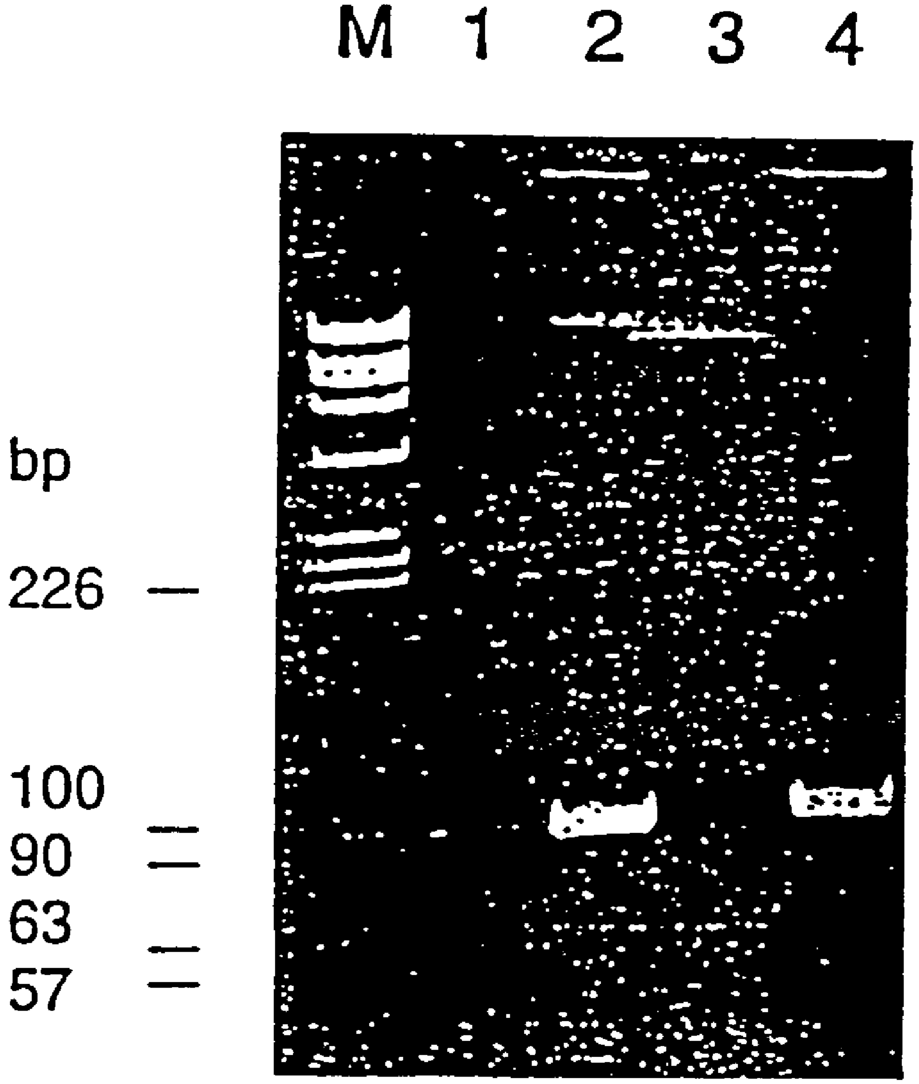
FIG. 38 shows the result of a polyacrylamide gel electrophoresis of amplified products described in Example 8 purified and concentrated for MALDI-TOF MS analysis. M: chain length marker, lane 1: 7-deazapurine containing 99-mer amplified product, lane 2: unmodified 99-mer, lane 3: 7-deazapurine containing 103-mer and lane 4: unmodified 103-mer amplified product.

It remained to be determined whether 80-90% 7-deazapurine modification is sufficient for accurate mass spectrometer detection. It was therefore important to determine whether all purine nucleotides could be substituted during the enzymatic amplification step. This was not trivial since it had been shown that $c^7$-dATP cannot fully replace dATP in PCR if Taq DNA polymerase is employed (Seela, F. and A. Roelling (1992) Nucleic Acids Res., 20, 55-61). Fortunately it was found that exo(−)Pfu DNA polymerase indeed could accept $c^7$-dATP and $c^7$-dGTP in the absence of unmodified purine nucleoside triphosphates. The incorporation was less efficient leading to a lower yield of amplified product (FIG. 38).

Figure 39:
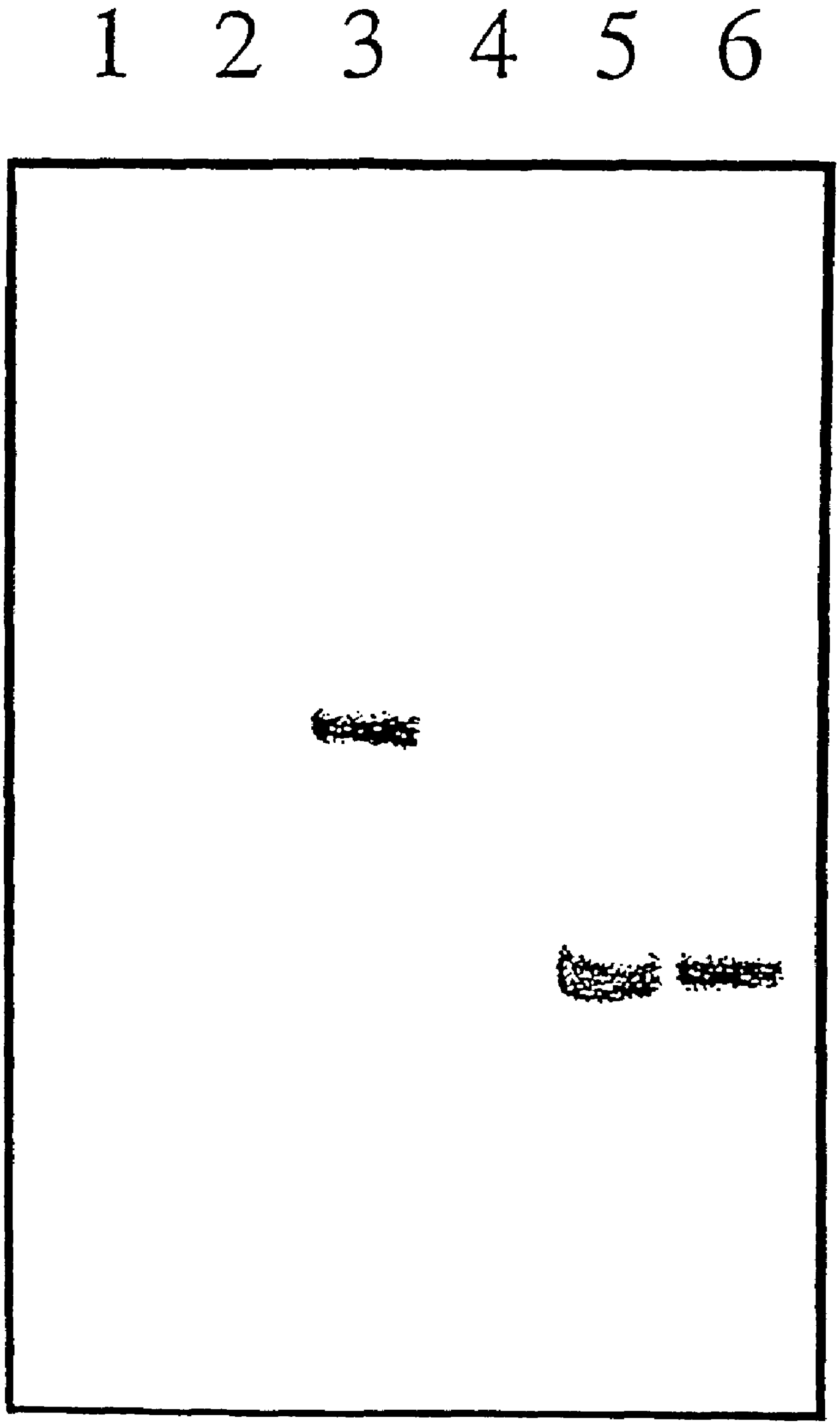
FIG. 39: an autoradiogram of polyacrylamide gel electrophoresis of nucleic acid (i.e., PCR) reactions carried out with 5'-[$^{32}$P]-labeled primers 1 and 4. Lanes 1 and 2: unmodified and 7-deazapurine modified 103-mer amplified product (53321 and 23520 counts), lanes 3 and 4: unmodified and 7-deazapurine modified 200-mer (71123 and 39582 counts) and lanes 5 and 6: unmodified and 7-deazapurine modified 99-mer (173216 and 94400 counts).

To verify these results, the amplications with [$^{32}$P]-labeled primers were repeated. The autoradiogram (FIG. 39) clearly shows lower yields for the modified PCR-products. The bands were excised from the gel and counted. For all amplified products the yield of the modified nucleic acids was about 50%, referring to the corresponding unmodified amplification product. Further experiments showed that exo(−)DeepVent and Vent DNA polymerase were able to incorporate $c^7$-dATP and $c^7$-dGTP during PCR as well. The overall performance, however, turned out to be best for the exo(−)Pfu DNA polymerase giving least side products during amplification. Using all three polymerases, it was found that such PCRs employing $c^7$-dATP and $c^7$-dGTP instead of their isosteres showed less side-reactions giving a cleaner PCR-product. Decreased occurrence of amplification side products may be explained by a reduction of primer mismatches due to a ling template which is synthesized during PCR. Decreased melting point for DNA duplexes containing 7-deaza-purine have been described (Mizusawa, S. et al., (1986) *Nucleic Acids Res.,* 14, 1319-1324). In addition to the three polymerases specified above (exo(−) Deep Vent DNA polymerase, 5Vent DNA polymerase and exo(−) (Pfu) DNA polymerase), it is anticipated that other polymerases, such as the Large Klenow fragment of *E. coli* DNA polymerase, Sequenase, Taq DNA polymerase and U AmpliTaq DNA polymerase can be used. In addition, where RNA is the template, RNA polymerases, such as the SP6 or the T7 RNA polymerase, must be used.

MALDI-TOF Mass Spectrometry of Modified and Unmodified Amplified Products.

The 99-mer, 103-mer and 200-mer amplified products were analyzed by MALDI-TOF MS. Based on past experience, it was known that the degree of depurination depends on the laser energy used for desorption and ionization of the analyte. Since the influence of 7-deazapurine modification on fragmentation due to depurination was to be investigated, all spectra were measured at the same relative laser energy.

Figure 40A:
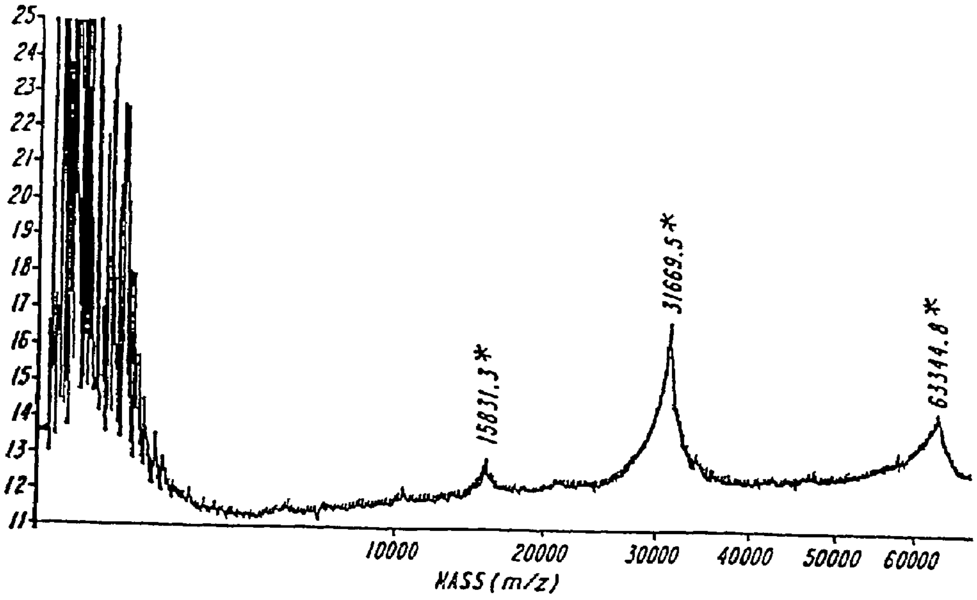
FIG. 40 a) MALDI-TOF mass spectrum of the unmodified 103-mer amplified products (sum of twelve single shot spectra). The mean value of the masses calculated for the two single strands (31768 u and 31759 u) is 31763 u. Mass resolution: 18. b) MALDI-TOF mass spectrum of 7-deazapurine containing 103-mer amplified product (sum of three single shot spectra). The mean value of the masses calculated for the two single strands (31727 u and 31719 u) is 31723 u. Mass resolution: 67.
Figure 40B:
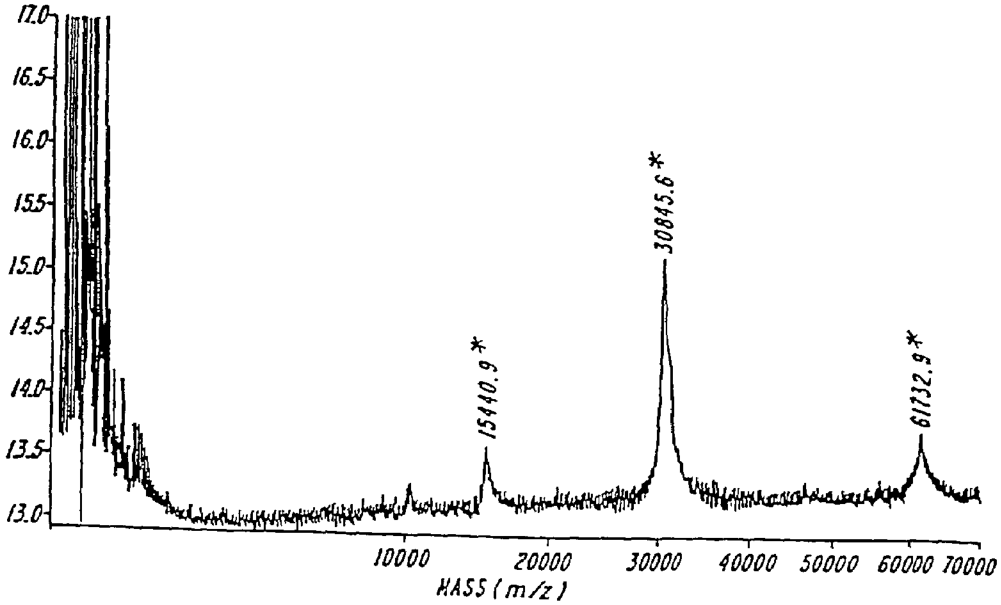

FIGS. 40*a* and 40*b* show the mass spectra of the modified and unmodified 103-mer nucleic acids. In case of the modified 103-mer, fragmentation causes a broad $(M+H)^+$ signal. The maximum of the peak is shifted to lower masses so that the assigned mass represents a mean value of $(M+H)^+$ signal and signals of fragmented ions, rather than the $(M+H)^+$ signal itself. Although the modified 103-mer still contains about 20% A and G from the oligonucleotide primers, it shows less fragmentation which is featured by much more narrow and symmetric signals. Especially peak tailing on the lower mass side due to depurination, is substantially reduced. Hence, the difference between measured and calculated mass is strongly reduced although it is still below the expected mass. For the unmodified sample a $(M+H)^+$ signal of 31670 was observed, which is a 97 u or 0.3% difference to the calculated mass. While, in case of the modified sample this mass difference diminished to 10 u or 0.03% (31713 u found, 31723 u calculated). These observations are verified by a significant increase in mass resolution of the $(M+H)^+$ signal of the two signal strands (n/Am=67 as opposed to 18 for the unmodified sample with Δm=full width at half maximum, fwhm). Because of the low mass difference between the two single strands (8 u) their individual signals were not resolved.

Figure 41A:
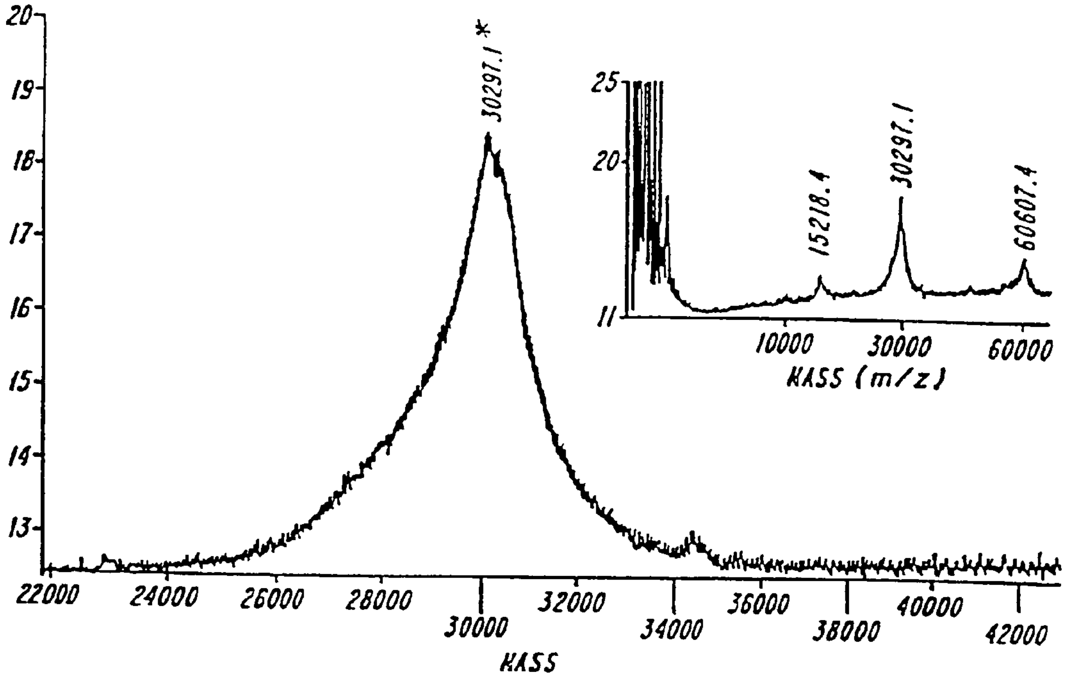
FIG. 41: a) MALDI-TOF mass spectrum of the unmodified 99-mer amplified product (sum of twenty single shot spectra). Values of the masses calculated for the two single strands: 30261 u and 30794 u. b) MALDI-TOF mass spectrum of 7-deazapurine containing 99-mer amplified product (sum of twelve single shot spectra). Values of the masses calculated for the two single strands: 30224 u and 30750 u.
Figure 41B:
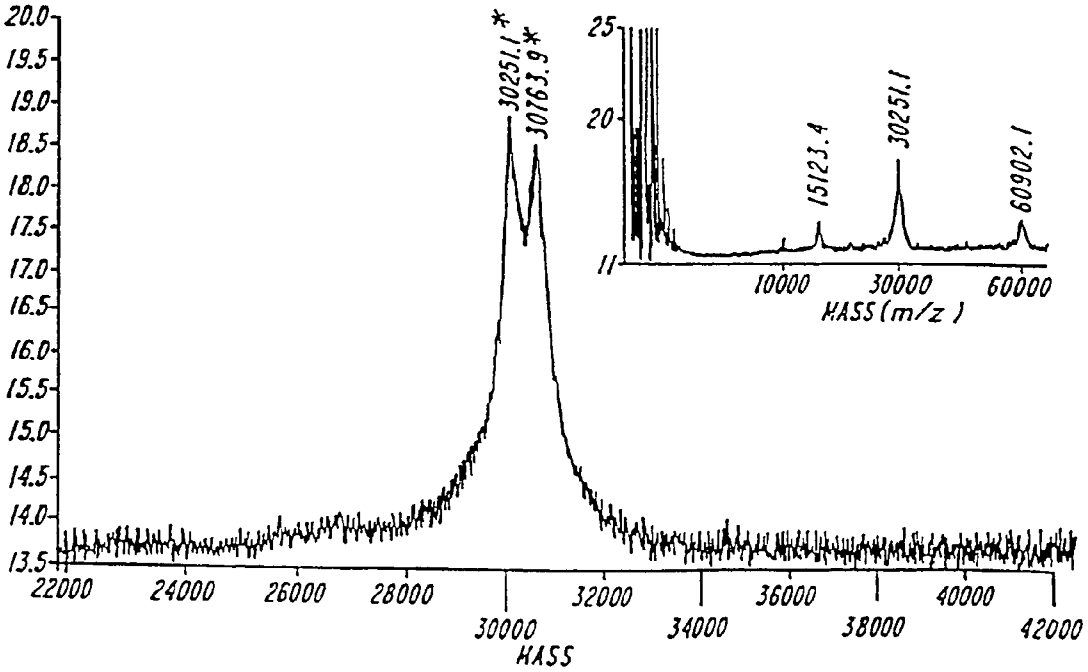

With the results of the 99 base pair DNA fragments the effects of increased mass resolution for 7-deazapurine containing DNA becomes even more evident. The two single strands in the unmodified sample were not resolved even though the mass difference between the two strands of the amplified product was very high with 526 u due to unequal distribution of purines and pyrimidines (FIG. 41*a*). In contrast to this, the modified DNA showed distinct peaks for the two single strands (FIG. 41*b*) which demonstrates the superiority of this approach for the determination of molecular weights to gel electrophoretic methods even more profound. Although base line resolution was not obtained the individual masses were able to be assigned with an accuracy of 0.1%: Δm=27 u for the lighter (calc. mass=30224 u) and Δm=14 u for the heavier strand (calc. mass=30750 u). Again, it was found that the full width at half maximum was substantially decreased for the 7-deazapurine containing sample.

In case the 99-mer and 103-mer, the 7-deazapurine containing nucleic acids seem to give higher sensitivity despite the fact that they still contain about 20% unmodified purine nucleotides. To get comparable signal-to-noise ratio at similar intensities for the $(M+H)^+$ signals, the unmodified 99-mer required 20 laser shots in contrast to 12 for the modified one and the 103-mer required 12 shots for the unmodified sample as opposed to three for the 7-deazapurine nucleoside-containing amplified product.

Figure 42A:
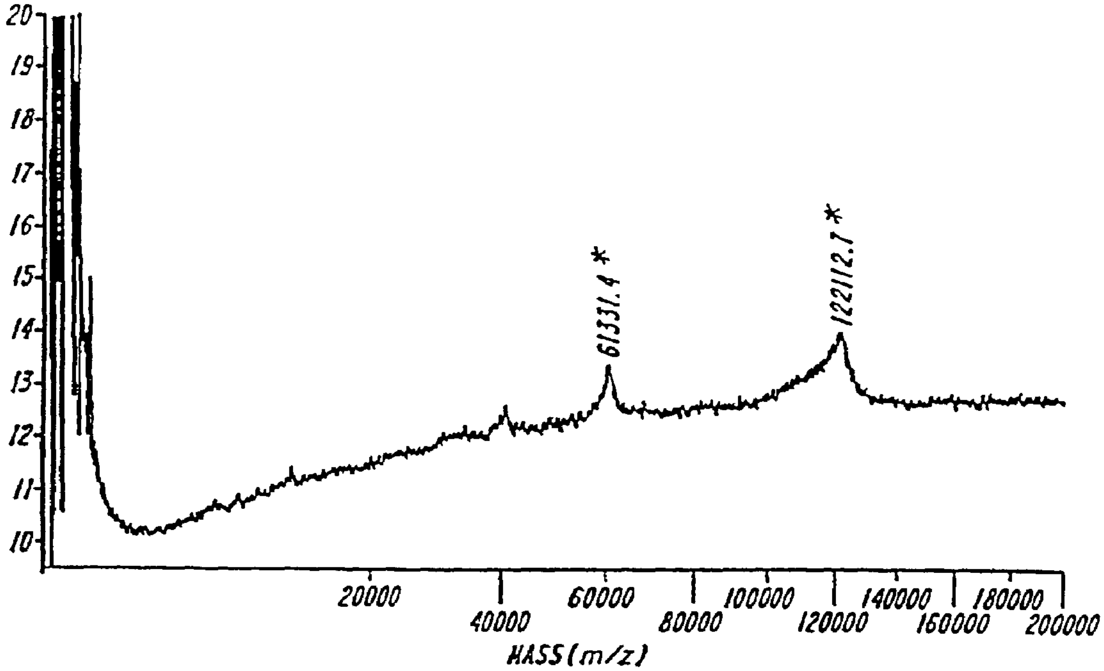
FIG. 42: a) MALDI-TOF mass spectrum of the unmodified 200-mer amplified product (sum of 30 single shot spectra). The mean value of the masses calculated for the two single strands (61873 u and 61595 u) is 61734 u. Mass resolution: 28. b) MALDI-TOF mass spectrum of 7-deazapurine containing 200-mer amplified product (sum of 30 single shot spectra). The mean value of the masses calculated for the two single strands (61772 u and 61714 u) is 61643 u. Mass resolution: 39.
Figure 42B:
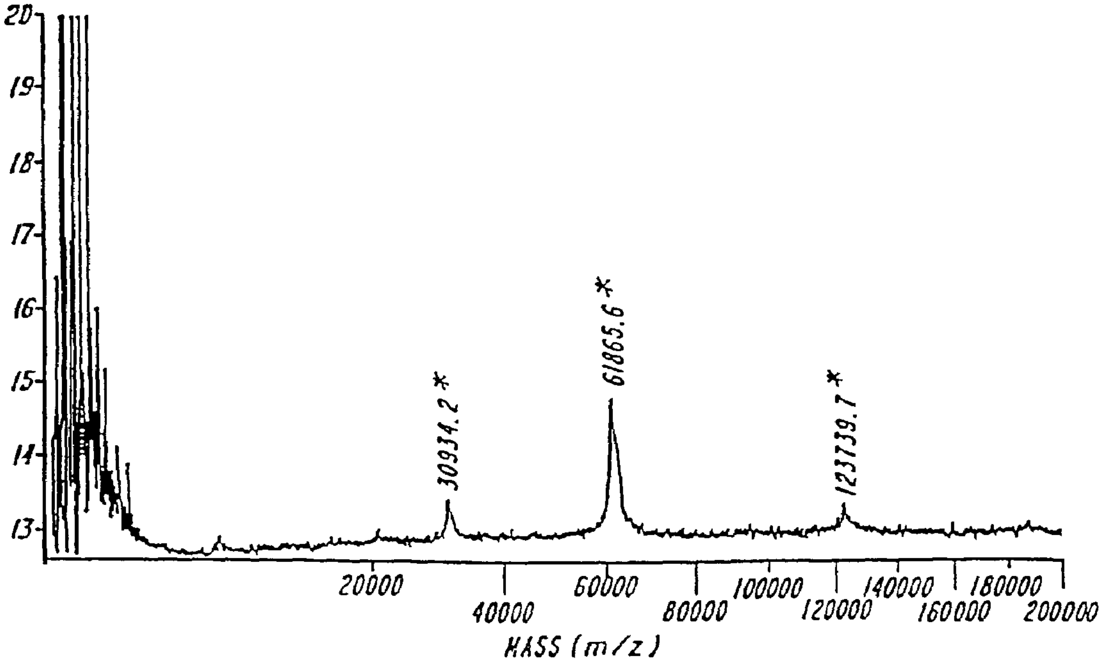

Comparing the spectra of the modified and unmodified 200-mer amplicons, improved mass resolution was again found for the 7-deazapurine containing sample as well as increased signal intensities (FIGS. 42A and 42B). While the signal of the single strands predominates in the spectrum of the modified sample the DNA-duplex and dimers of the single strands gave the strongest signal for the unmodified sample.

Figure 43A:
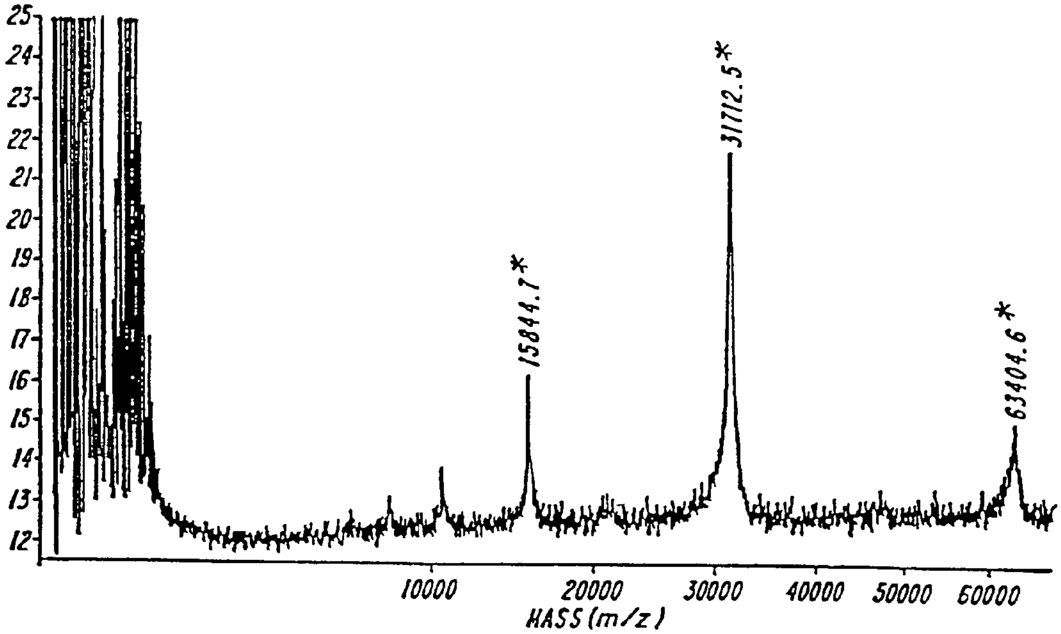
FIG. 43: a) MALDI-TOF mass spectrum of 7-deazapurine containing 100-mer amplified product with ribomodified primers. The mean value of the masses calculated for the two single strands (30529 u and 31095 u) is 30812 u. b) MALDI-TOF mass spectrum of the amplified product after hydrolytic primer-cleavage. The mean value of the masses calculated for the two single strands (25104 u and 25229 u) is 25167 u. The mean value of the cleaved primers (5437 u and 5918 u) is 5677 u.
Figure 43B:
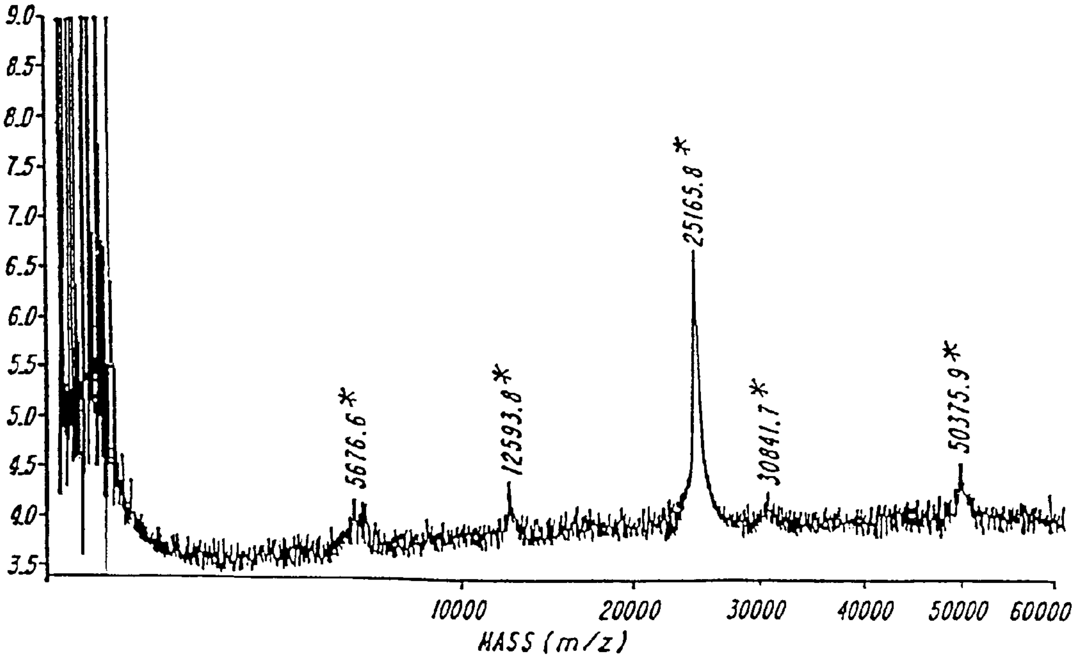
Figure 44A:
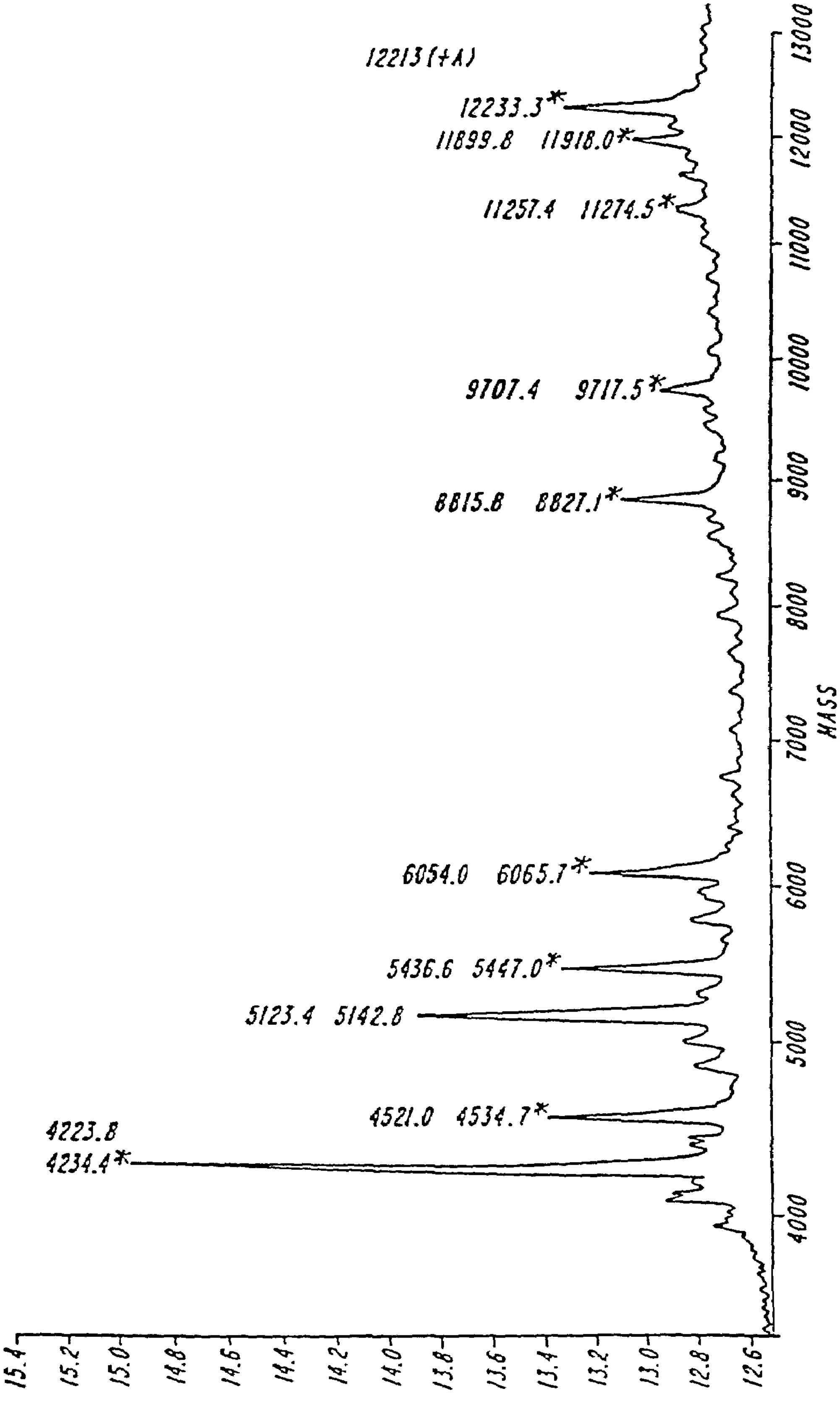
FIG. 44A-D shows the MALDI-TOF mass spectrum of the four sequencing ladders obtained from a 39-mer template (SEQ ID NO: 23), which was immobilized to streptavidin beads via a 3' biotinylation. A 14-mer primer (SEQ ID NO: 24) was used in the sequencing according to Example 9.
Figure 44B:
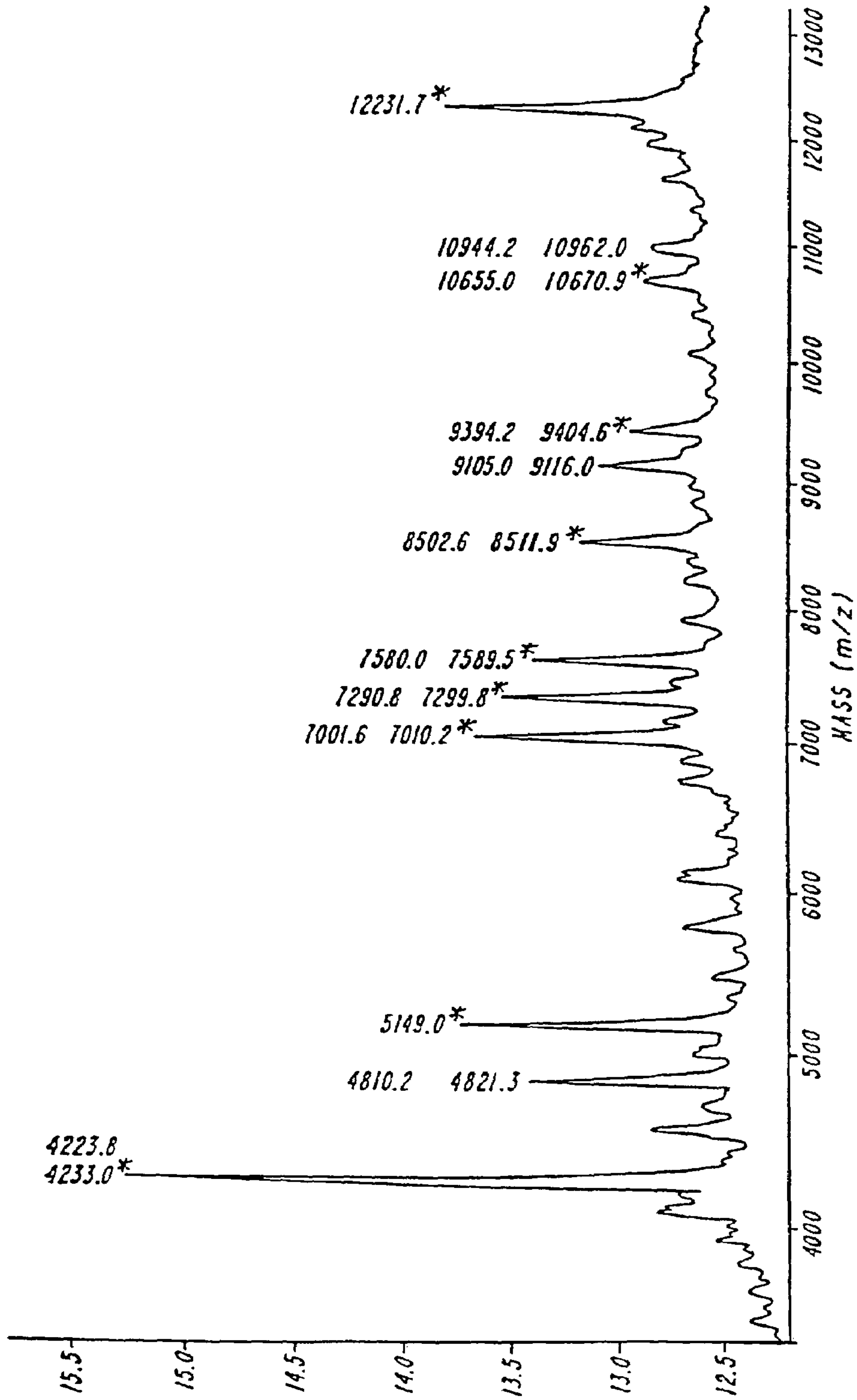
Figure 44C:
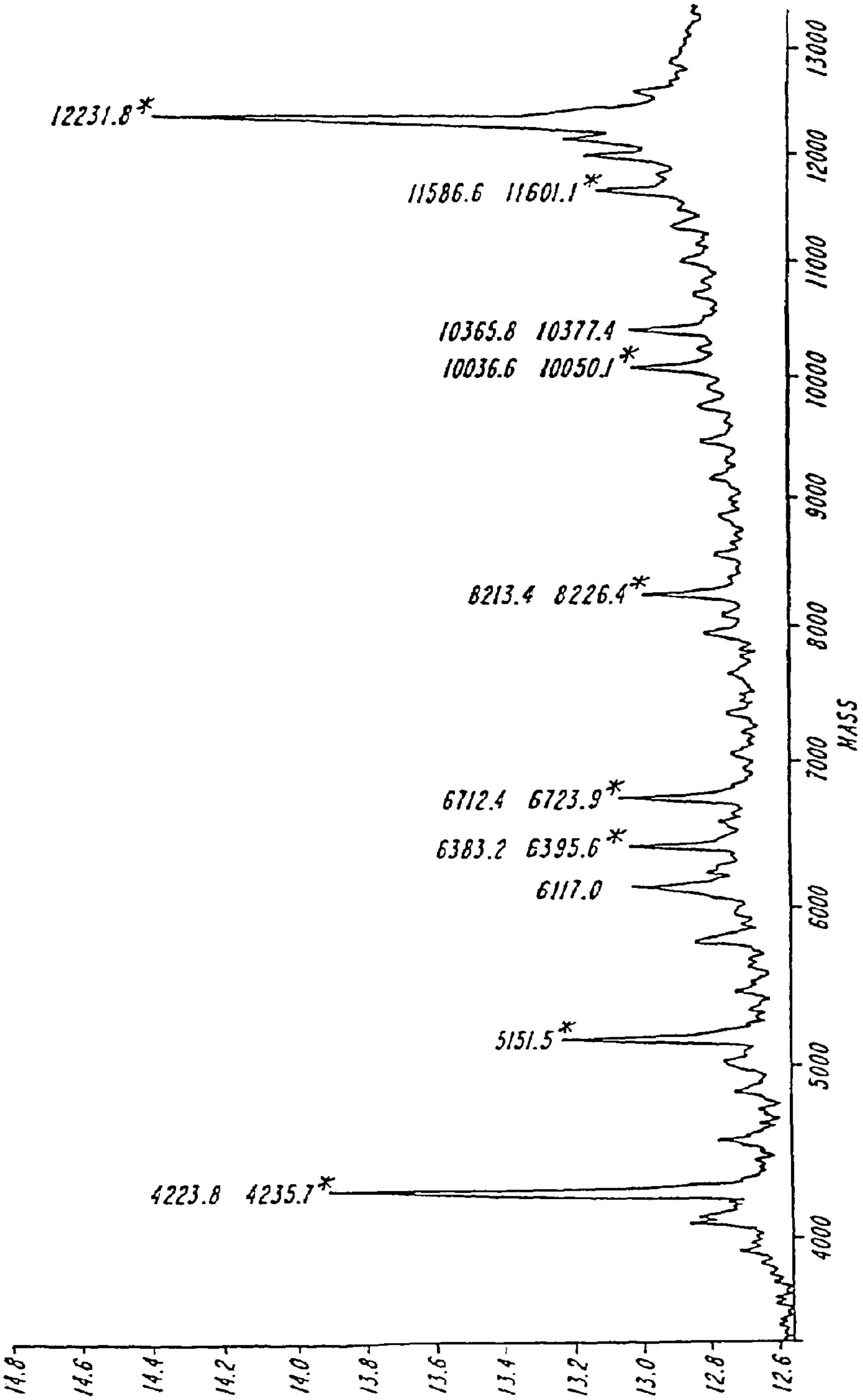
Figure 44D:
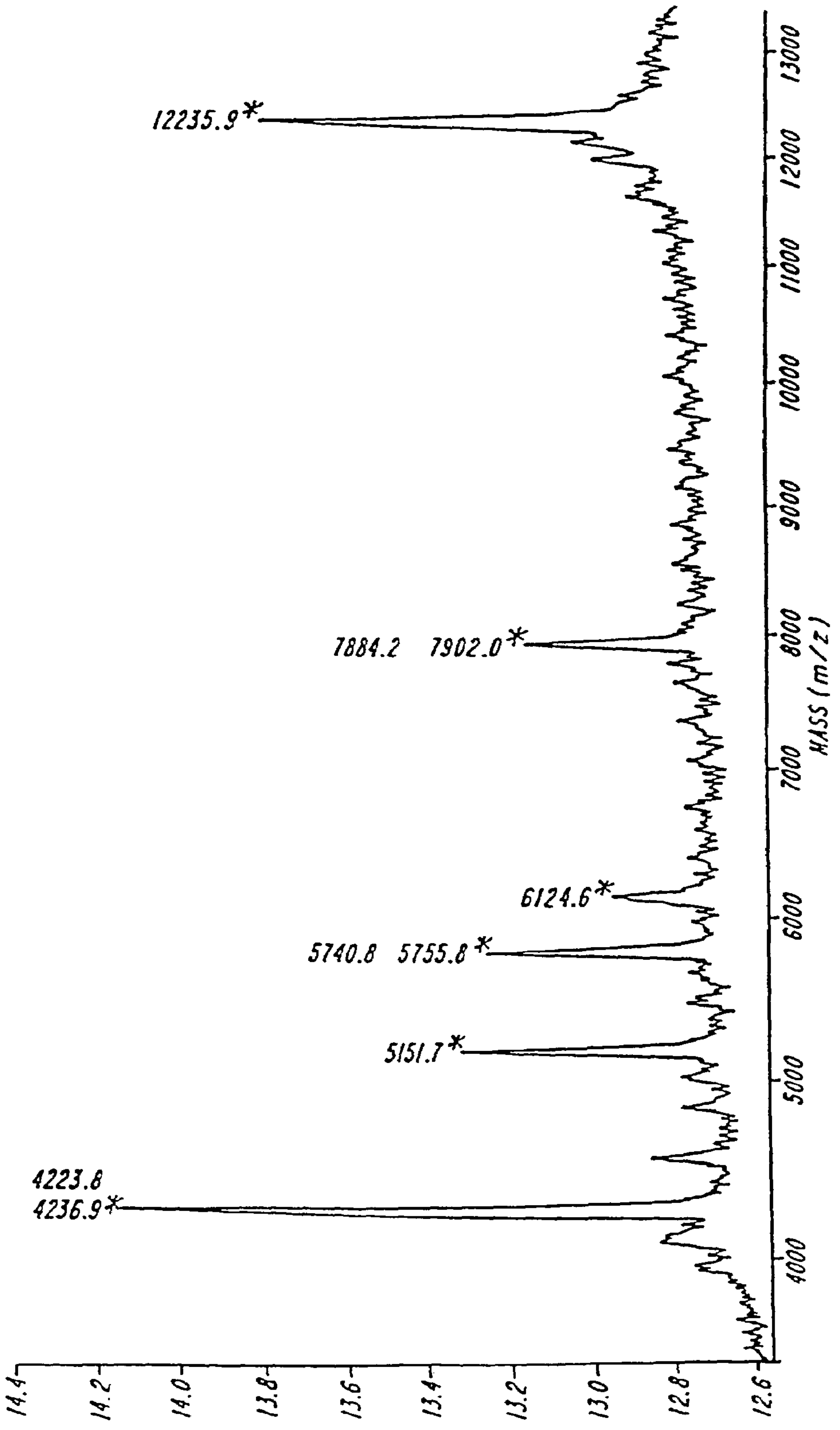

A complete 7-deaza purine modification of nucleic acids may be achieved either using modified primers in PCR or cleaving the unmodified primers from the partially modified amplified product. Since disadvantages are associated with modified primers, as described above, a 100-mer was synthesized using primers with a ribo-modification. The primers were cleaved hydrolytically with NaOH according to a method developed earlier in our laboratory (Koester, H. et al., *Z Physiol. Chem.,* 359, 1570-1589). FIGS. 43A and 43B display the spectra of the amplified product before and after primer cleavage. FIG. 43*b* shows that the hydrolysis was successful: The hydrolyzed amplified product as well as the two released primers could be detected together with a small signal from residual uncleaved 100-mer. This procedure is especially useful for the MALDI-TOF analysis of very short PCR-products since the share of unmodified purines originating from the primer increases with decreasing length of the amplified sequence.

The remarkable properties of 7-deazapurine modified nucleic acids can be explained by either more effective desorption and/or ionization, increased ion stability and/or a lower denaturation energy of the double stranded purine modified nucleic acid. The exchange of the N-7 for a methyl group results in the loss of one acceptor for a hydrogen bond which influences the ability of the nucleic acid to form secondary structures due to non-Watson-Crick base pairing (Seela, F. and A. Kehne (1987) *Biochemistry,* 26, 2232-2238.). In addition to this the aromatic system of 7-deazapurine has a lower electron density that weakens Watson-Crick base pairing resulting in a decreased melting point (Mizusawa, S. et al., (1986) *Nucleic Acids Res.,* 14, 1319-1324) of the double-strand. This effect may decrease the energy needed for denaturation of the duplex in the MALDI process. These aspects as well as the loss of a site which probably will carry a positive charge on the N-7 nitrogen renders the 7-deazapurine modified nucleic acid less polar and may promote the effectiveness of desorption.

Because of the absence of N-7 as proton acceptor and the decreased polarization of the C—N bond in 7-deazapurine nucleosides depurination following the mechanisms established for hydrolysis in solution is prevented. Although a direct correlation of reactions in solution and in the gas phase is problematic, less fragmentation due to depurination of the modified nucleic acids can be expected in the MALDI process. Depurination may either be accompanied by loss of charge which decreases the total yield of charged species or it may produce charged fragmentation products which decreases the intensity of the non fragmented molecular ion signal.

The observation of increased sensitivity and decreased peak tailing of the $(M+H)^+$ signals on the lower mass side due to decreased fragmentation of the 7-deazapurine containing samples indicate that the N-7 atom indeed is essential for the mechanism of depurination in the MALDI-TOF process. In conclusion, 7-deazapurine containing nucleic acids show distinctly increased ion-stability and sensitivity under MALDI-TOF conditions and therefore provide for higher mass accuracy and mass resolution.

EXAMPLE 9

Solid Phase Sequencing and Mass Spectrometer Detection

Materials and Methods

Oligonucleotides were purchased from Operon Technologies (Alameda, Calif.) in an unpurified form. Sequencing reactions were performed on a solid surface using reagents from the sequencing kit for Sequenase Version 2.0 (Amersham, Arlington Heights, Ill.).

Sequencing a 39-Mer Target

Sequencing Complex:

| SEQUENCE | SEQ ID NO: |
|---|---|
| 5'-TCTGGCCTGGTGCAGGGCCTATTGTAGTTGTGACGTACA-($A^b$)$_a$-3' | 23 |
| 5'-TGTACGTCACAACT-3' (PNA 16/DNA) | 24 |

In order to perform solid-phase DNA sequencing, template strand DNA11683 was 3'-biotinylated by terminal deoxynucleotidyl transferase. A 30 μl reaction, containing 60 pmol of DNA11683, 1.3 nmol of biotin 14-dATP (GIBCO BRL, Grand Island, N.Y.), 30 units of terminal transferase (Amersham, Arlington Heights, Ill.), and 1× reaction buffer (supplied with enzyme), was incubated at 37° C. for 1 hour. The reaction was stopped by heat inactivation of the terminal transferase at 70° C. for 10 min. The resulting product was desalted by passing through a TE-10 spin column (Clontech). More than one molecules of biotin-14-dATP could be added to the 3'-end of DNA11683. The biotinylated DNA11683 was incubated with 0.3 mg of Dynal streptavidin beads in 30 μl 1× binding and washing buffer at ambient temperature for 30 min. The beads were washed twice with TE and redissolved in 30 μl TE, 10 μl aliquot (containing 0.1 mg of beads) was used for sequencing reactions.

The 0.1 mg beads from previous step were resuspended in a 10 μl volume containing 2 μl of 5× Sequenase buffer (200 mM Tris-HCl, pH 7.5, 100 mM $MgCl_2$, and 250 mM NaCl) from the Sequenase kit and 5 pmol of corresponding primer PNA 16/DNA. The annealing mixture was heated to 70° C. and allowed to cool slowly to room temperature over a 20-30 min time period. Then 1 μl 0.1 M dithiothreitol solution, 1 μl Mn buffer (0.15 M sodium isocitrate and 0.1 M $MgCl_2$), and 2 μl of diluted Sequenase (3.25 units) were added. The reaction mixture was divided into four aliquots of 3 μl each and mixed with termination mixes (each contains of 3 μl of the appropriate termination mix: 32 μM c7dATP, 32 μM dCTP, 32 μM c7dGTP, 32 μM dTTP and 3.2 μM of one of the four ddTNPs, in 50 mM NaCl). The reaction mixtures were incubated at 37° C. for 2 min. After the completion of extension, the beads were precipitated and the supernatant was removed. The beads were washed twice and resuspended in TE and kept at 4° C.

Sequencing a 78-Mer Target

Sequencing Complex:

```
                                          (SEQ ID NO:25)
5'-AAGATCTGACCAGGGATTCGGTTAGCGTGACTGCTGCTGCTGCTGCT

GCTGCTGGATGATCCGACGCATCAGATCTGG-(A^b)_n-3'

(TNR.PLASM 2)

                                          (SEQ ID NO:26)
5'-CTGATGCGTCGGATCATC-3'

(CM1)
```

The target TNR.PLASM2 was biotinylated and sequenced using procedures similar to those described in previous section (sequencing a 39-mer target).

Sequencing a 15-Mer Target With Partially Duplex Probe Sequencing Complex:

```
                                          (SEQ ID NO:27)
   5'-F-GATGATCCGACGCATCACAGCTC3'

                                          (SEQ ID NO:28)
   5'-TCGGTTCCAAGAGCTGTGATGCGTCGGATCATC-b-3'
```

CM1B3B was immobilized on Dynabeads M280 with streptavidin (Dynal, Norway) by incubating 60 pmol of CM1B3B with 0.3 magnetic beads in 30 μl M NaCl and TE (1× binding and washing buffer) at room temperature for 30 min. The beads were washed twice with TE and redissolved in 30 μl TE, 10 or 20 μl aliquot (containing 0.1 or 0.2 mg of beads respectively) was used for sequencing reactions.

The duplex was formed by annealing corresponding aliquot of beads from previous step with 10 pmol of DF11a5F (or 20 pmol of DF11a5F for 0.2 mg of beads) in a 9 μl volume containing 2 μl of 5× Sequenase buffer (200 mM Tris-HCl, pH 7.5, 100 mM $MgCl_2$, and 250 mM NaCl) from the Sequenase kit. The annealing mixture was heated to 65° C. and allowed to cool slowly to 37° C. over a 20-30 min time period. The duplex primer was then mixed with 10 pmol of TS10 (20 pmol of TS10 for 0.2 mg of beads) in 1 μl volume, and the resulting mixture was further incubated at 37° C. for 5 min, room temperature for 5-10 min. Then 1 μl 0.1 M dithiothreitol solution, 1 μl Mn buffer (0.15 M sodium isocitrate and 0.1 M $MnCl_2$), and 2 μl of diluted Sequenase (3.25 units) were added. The reaction mixture was divided into four aliquots of 3 μl each and mixed with termination mixes (each contains of 4 μl of the appropriate termination mix: 16 μM dATP, 16 μM dCTP, 16 μl pM dGTP, 16 μM dTTP and 1.6 μM of one of the four ddNTPs, in 50 mM NaCl). The reaction mixtures were incubated at room temperature for 5 min, and 37° C. for 5 min. After the completion of extension, the beads were precipitated and the supernatant was removed. The beads were resuspended in 20 μl TE and kept at 4° C. An aliquot of 2 μl (out of 20 μl) from each tube was taken and mixed with 8 μl of formamide, the resulting samples were denatured at 90-95° C. for 5 min and 2 μl (out of 10 μl total) was applied to an ALF DNA sequencer (Pharmacia, Piscataway, N.J.) using a 10% polyacrylamide gel containing 7 M urea and 0.6×TBE. The remaining aliquot was used for MALDI-TOF MS analysis.

MALDI Sample Preparation and Instrumentation

Before MALDI analysis, the sequencing ladder loaded magnetic beads were washed twice using 50 mM ammonium citrate and resuspended in 0.5 μl pure water. The suspension was then loaded onto the sample target of the mass spectrometer and 0.5 μl of saturated matrix solution (3-hydroxypicolinic acid (HPA): ammonium citrate=10:1 mole ratio in 50% acetonitrile) was added. The mixture was allowed to dry prior to mass spectrometer analysis.

The reflectron TOFMS mass spectrometer (Vision 2000, Finnigan MAT, Bremen, Germany) was used for analysis. 5 kV was applied in the ion source and 20 kV was applied for postacceleration. All spectra were taken in the positive ion mode and a nitrogen laser was used. Normally, each spectrum was averaged for more than 100 shots and a standard 25-point smoothing was applied.

Results and Discussion

Conventional Solid-Phase Sequencing

In conventional sequencing methods, a primer is directly annealed to the template and then extended and terminated in a Sanger dideoxy sequencing. Normally, a biotinylated primer is used and the sequencing ladders are captured by streptavidin-coated magnetic beads. After washing, the products are eluted from the beads using EDTA and formamide. Previous findings indicated that only the annealed strand of a duplex is desorbed and the immobilized strand remains on the beads. Therefore, it is advantageous to immobilize the template and anneal the primer. After the sequencing reaction and washing, the beads with the immobilized template and annealed sequencing ladder can be loaded directly onto the mass spectrometer target and mix with matrix. In MALDI, only the annealed sequencing ladder will be desorbed and ionized, and the immobilized template will remain on the target.

A 39-mer template (SEQ ID NO: 23) was first biotinylated at the 3'-end by adding biotin-14-dATP with terminal transferase. More than one biotin-14-dATP molecule could be added by the enzyme. Since the template was immobilized and remained on the beads during MALDI, the number of biotin-14-dATP would not affect the mass spectra. A 14-mer primer (SEQ ID NO: 24) was used for the solid-state sequencing to generate DNA fragments 3-27 below (SEQ ID NOs: 142-166). MALDI-TOF mass spectra of the four sequencing ladders are shown in FIG. 44 and the expected theoretical values are shown in Table III.

TABLE III

| | |
|---|---|
| 1 | 5'-TCTGGCCTGGTGCAGGGCCTATTGTAGTTGTGACGTACA-$(A^B)_n$-3' |
| 2 | 3'-TCAACACTGCATGT-5- |
| 3 | 3'-ATCAACACTGCATGT-5' |

TABLE III-continued

| | |
|---|---|
| 4 | 3'-CATCAACACTGCATGT-5' |
| 5 | 3'-ACATCAAGACTGCATGT-5' |
| 6 | 3'-AACATCAACACTGCATGT-5' |
| 7 | 3'-TAACATCAACACTGCATGT-5' |
| 8 | 3'-ATAACATCAACACTGCATGT-5' |
| 9 | 3'-GATAACATGAACACTGCATGT-5' |
| 10 | 3'-GGATAACATCAACACTGCATGT-5' |
| 11 | 3'-CGGATAACATCAACACTGCATGT-5' |
| 12 | 3'-CCGGATAACATCAACACTGCATGT-5' |
| 13 | 3'-CCCGGATAACATCAACACTGCATGT-5' |
| 14 | 3'-TCCCGGATAACATCAACACTGCATGT-5' |
| 15 | 3'-GTCCCGGATAACATCAACACTGCATGT-5' |
| 16 | 3'-CGTCCCGGATAACATCAACACTGCATGT-5' |
| 17 | 3'-ACGTCCCGGATAACATCAACACTGCATGT-5' |
| 18 | 3'-CACGTCCCGGATAACATCAACACTGCATGT-5' |
| 19 | 3'-CCACGTCCCGGATAACATCAACACTGCATGT-5' |
| 20 | 3'-ACCACGTCCCGGATAACATCAACACTGCATGT-5' |
| 21 | 3'-GACCACGTCCCGGATAACATCAACACTGCATGT-5' |
| 22 | 3'-GGACCACGTCCCGGATAACATCAACACTGCATGT-5' |
| 23 | 3'-CGGACCACGTCCCGGATAACATCAACACTGCATGT-5' |
| 24 | 3'-CCGGACCACGTCCCGGATAACATCAACACTGCATGT-5' |
| 25 | 3'-ACCGGACCACGTCCCGGATAACATCAACACTGCATGT-5' |
| 26 | 3'-GACCGGACCACGTCCCGGATAACATCAACACTGCATGT-5' |
| 27 | 3'-AGACCGGACCACGTCCCGGATAACATCAACACTGCATGT-5' |

| | A-reaction | C-reaction | G-reaction | T-reaction |
|---|---|---|---|---|
| 1. | | | | |
| 2. | 4223.8 | 4223.8 | 4223.8 | 4223.8 |
| 3. | 4521.1 | | | |
| 4. | | 4809.2 | | |
| 5. | 5133.4 | | | |
| 6. | 5434.6 | | | |
| 7. | | | | 5737.8 |
| 8. | 6051.1 | | | |
| 9. | | | 6379.2 | |
| 10. | | | 6704.4 | |
| 11. | | 6995.6 | | |
| 12. | | 7284.8 | | |
| 13. | | 7574.0 | | |
| 14. | | | | 7878.2 |
| 15. | | | 8207.4 | |
| 16. | | 8495.6 | | |
| 17. | 8808.8 | | | |
| 18. | | 9097.0 | | |
| 19. | | 9386.2 | | |
| 20. | 9699.4 | | | |
| 21. | | | 10027.6 | |
| 22. | | | 10355.8 | |
| 23. | | 10644.0 | | |
| 24. | | 10933.2 | | |
| 25. | 11246.4 | | | |
| 26. | | | 11574.6 | |
| 27. | 11886.8 | | | |

The sequencing reaction produced a relatively homogenous ladder, and the full-length sequence was determined easily. One peak around 5150 appeared in all reactions are not identified. A possible explanation is that a small portion of the template formed some kind of secondary structure, such as a loop, which hindered sequenase extension. Mis-incorporation is of minor importance, since the intensity of these peaks were much lower than that of the sequencing ladders. Although 7-deaza purines were used in the sequencing reaction, which could stabilize the N-glycosidic bond and prevent depurination, minor base losses were still observed since the primer was not substituted by 7-deazapurines. The full length ladder, with a ddA at the 3' end, appeared in the A reaction with an apparent mass of 11899.8. A more intense peak of 12333 appeared in all four reactions and is likely due to an addition of an extra nucleotide by the Sequenase enzyme.

Figure 45:
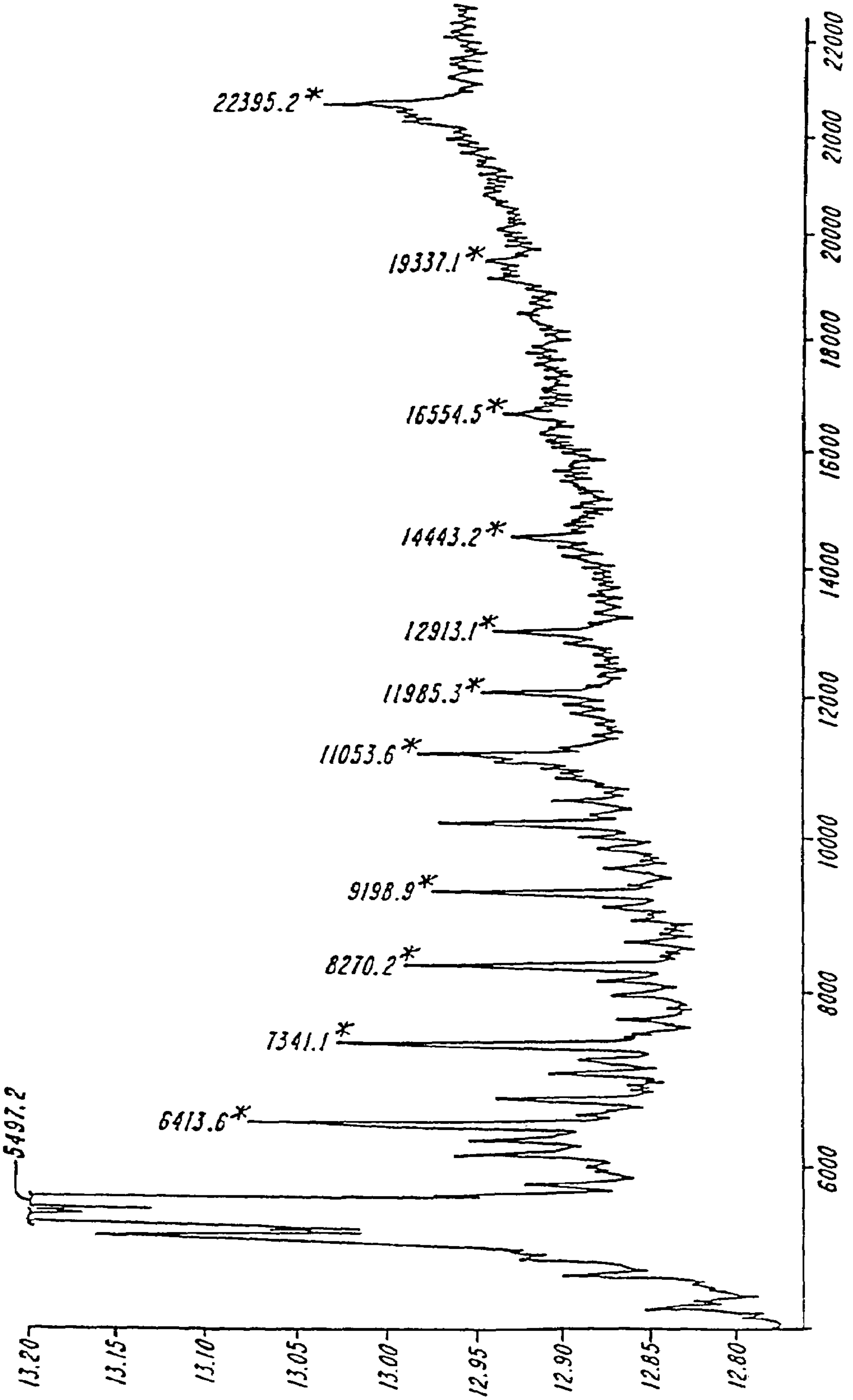
FIG. 45 shows a MALDI-TOF mass spectrum of a solid phase sequencing of a 78-mer template (SEQ ID NO: 25), which was immobilized to streptavidin beads via a 3' biotinylation. A 18-mer primer (SEQ ID NO: 26) and ddGTP were used in the sequencing.

The same technique could be used to sequence longer DNA fragments. A 78-mer template containing a CTG repeat (SEQ ID NO: 25) was 3'-biotinylated by adding biotin-14-dATP with terminal transferase. An 18-mer primer (SEQ ID NO: 26) was annealed right outside the CTG repeat so that the repeat could be sequenced immediately after primer extension. The four reactions were washed and analyzed by MALDI-TOFMS as usual. An example of the G-reaction is shown in FIG. 45 (SEQ ID NOs: 167-220) and the expected sequencing ladder is shown in Table IV with theoretical mass values for each ladder component. All sequencing peaks were well resolved except the last component (theoretical value 20577.4) was indistinguishable from the background. Two neighboring sequencing peaks (a 62-mer and a 63-mer) were also separated indicating that such sequencing analysis could be applicable to longer templates. Again, an addition of an extra nucleotide by the Sequenase enzyme was observed in this spectrum. This addition is not template specific and appeared in all four reactions which makes it easy to be identified. Compared to the primer peak, the sequencing peaks were at much lower intensity in the long template case.

TABLE IV

| | AAGATCTGACCAGGGATTCGGTTAGCGTGACTGCTGCTGCTGCTGCTGGATGATCCGACGCATCAGATCTGG-$(A^B)_n$-3' |
|---|---|
| 1 | 3'-CTACTAGGCTGCGTAGTC-5' |
| 2 | 3'-CCTACTAGGCTGCGTAGTC-5' |
| 3 | 3'-ACCTACTAGGCTGCGTAGTC-5' |
| 4 | 3'-GACCTACTAGGCTGCGTAGTC-5' |
| 5 | 3'-CGACCTACTAGGCTGCGTAGTC-5' |
| 6 | 3'-ACGACCTACTAGGCTGCGTAGTC-5' |
| 7 | 3'-GACGACCTACTAGGCTGCGTAGTC-5' |
| 8 | 3'-CGACGACCTACTAGGCTGCGTAGTC-5' |
| 9 | 3'-ACGACGACCTACTAGGCTGCGTAGTC-5' |
| 10 | 3'-GACGACGACCTACTAGGCTGCGTAGTC-5' |
| 11 | 3'-CGACGACGACCTACTAGGCTGCGTAGTC-5' |
| 12 | 3'-ACGACGACGACCTACTAGGCTGCGTAGTC-5' |
| 13 | 3'-GACGACGACGACCTACTAGGCTGCGTAGTC-5' |
| 14 | 3'-CGACGACGACGACCTACTAGGCTGCGTAGTC-5' |
| 15 | 3'-ACGACGACGACGACCTACTAGGCTGCGTAGTC-5' |
| 16 | 3'-GACGACGACGACGACCTACTAGGCTGCGTAGTC-5' |
| 17 | 3'-CGACGACGACGACGACCTACTAGGCTGCGTAGTC-5' |
| 18 | 3'-ACGACGACGACGACGACCTACTAGGCTGCGTAGTC-5' |
| 19 | 3'-GACGACGACGACGACGACCTACTAGGCTGCGTAGTC-5' |
| 20 | 3'-CGACGACGACGACGACGACCTACTAGGCTGCGTAGTC-5' |
| 21 | 3'-ACGACGACGACGACGACGACCTACTAGGCTGCGTAGTC-5' |
| 22 | 3'-GACGACGACGACGACGACGACCTACTAGGCTGCGTAGTC-5' |
| 23 | 3'-CGACGACGACGACGACGACGACCTACTAGGCTGCGTAGTC-5' |
| 24 | 3'-ACGACGACGACGACGACGACGACCTACTAGGCTGCGTAGTC-5' |
| 25 | 3'-GACGACGACGACGACGACGACGACCTACTAGGCTGCGTAGTC-5' |
| 26 | 3'-TGACGACGACGACGACGACGACGACCTACTAGGCTGCGTAGTC-5' |

TABLE IV-continued

| | |
|---|---|
| 27 | 3'-CTGACGACGACGACGACGACGACCTACTAGGCTGCGTAGTC-5' |
| 28 | 3'-ACTGACGACGACGACGACGACGACCTACTAGGCTGCGTAGTC-5' |
| 29 | 3'-CACTGACGACGACGACGACGACGACCTACTAGGCTGCGTAGTC-5' |
| 30 | 3'-GCACTGACGACGACGACGACGACGACCTACTAGGCTGCGTAGTC-5' |
| 31 | 3'-CGCACTGACGACGACGACGACGACGACCTACTAGGCTGCGTAGTC-5' |
| 32 | 3'-TCGCACTGACGACGACGACGACGACGACCTACTAGGCTGCGTAGTC-5' |
| 33 | 3'-ATCGCACTGACGACGACGACGACGACGACCTACTAGGCTGCGTAGTC-5' |
| 34 | 3'-AATCGCACTGACGACGACGACGACGACGACCTACTAGGCTGCGTAGTC-5' |
| 35 | 3'-CAATCGCACTGACGACGACGACGACGACGACCTACTAGGCTGCGTAGTC-5' |
| 36 | 3'-CCAATCGCACTGACGACGACGACGACGACGACCTACTAGGCTGCGTAGTC-5' |
| 37 | 3'-GCCAATCGCACTGACGACGACGACGACGACGACCTACTAGGCTGCGTAGTC-5' |
| 38 | 3'-AGCCAATCGCACTGACGACGACGACGACGACGACCTACTAGGCTGCGTAGTC-5' |
| 39 | 3'-AAGCCAATCGCACTGACGACGACGACGACGACGACCTACTAGGCTGCGTAGTC-5' |
| 40 | 3'-TAAGCCAATCGCACTGACGACGACGACGACGACGACCTACTAGGCTGCGTAGTC-5' |
| 41 | 3'-CTAAGCCAATCGCACTGACGACGACGACGACGACGACCTACTAGGCTGCGTAGTC-5' |
| 42 | 3'-CCTAAGCCAATCGCACTGACGACGACGACGACGACGACCTACTAGGCTGCGTAGTC-5' |
| 43 | 3'-CCCTAAGCCAATCGCACTGACGACGACGACGACGACGACCTACTAGGCTGCGTAGTC-5' |
| 44 | 3'-TCCCTAAGCCAATCGCACTGACGACGACGACGACGACGACCTACTAGGCTGCGTAGTC-5' |
| 45 | 3'-GTCCCTAAGCCAATCGCACTGACGACGACGACGACGACGACCTACTAGGCTGCGTAGTC-5' |
| 46 | 3'-GGTCCCTAAGCCAATCGCACTGACGACGACGACGACGACGACCTACTAGGCTGCGTAGTC-5' |
| 47 | 3'-TGGTCCCTAAGCCAATCGCACTGACGACGACGACGACGACGACCTACTAGGCTGCGTAGTC-5' |
| 48 | 3'-CTGGTCCCTAAGCCAATCGCACTGACGACGACGACGACGACGACCTACTAGGCTGCGTAGTC-5' |
| 49 | 3'-ACTGGTCCCTAAGCCAATCGCACTGACGACGACGACGACGACGACCTACTAGGCTGCGTAGTC-5' |
| 50 | 3'-GACTGGTCCCTAAGCCAATCGCACTGACGACGACGACGACGACGACCTACTAGGCTGCGTAGTC-5' |
| 51 | 3'-AGACTGGTCCCTAAGCCAATCGCACTGACGACGACGACGACGACGACCTACTAGGCTGCGTAGTC-5' |
| 52 | 3'-TAGACTGGTCCCTAAGCCAATCGCACTGACGACGACGACGACGACGACCTACTAGGCTGCGTAGTC-5' |
| 53 | 3'-CTAGACTGGTCCCTAAGCCAATCGCACTGACGACGACGACGACGACGACCTACTAGGCTGCGTAGTC-5' |
| 54 | 3'-TCTAGACTGGTCCCTAAGCCAATCGCACTGACGACGACGACGACGACGACCTACTAGGCTGCGTAGTC-5' |
| 55 | 3'-TTCTAGACTGGTCCCTAAGCCAATCGCACTGACGACGACGACGACGACGACCTACTAGGCTGCGTAGTC-5' |

| | ddATP | ddCTP | ddGTP | ddTTP |
|---|---|---|---|---|
| 1. | 5491.6 | 5491.6 | 5491.6 | 5491.6 |
| 2. | | 5764.8 | | |
| 3. | 6078.0 | | | |
| 4. | | | 6407.2 | |
| 5. | | 6696.4 | | |
| 6. | 7009.6 | | | |
| 7. | | | 7338.8 | |
| 8. | | 7628.0 | | |
| 9. | 7941.2 | | | |
| 10. | | | 8270.4 | |
| 11. | | 8559.6 | | |
| 12. | 8872.8 | | | |
| 13. | | | 9202.0 | |
| 14. | | 9491.2 | | |
| 15. | 9804.4 | | | |
| 16. | | | 10133.6 | |
| 17. | | 10422.88 | | |
| 18. | 10736.0 | | | |
| 19. | | | 11065.2 | |

TABLE IV-continued

| | | | | |
|---|---|---|---|---|
| 20. | | 11354.4 | | |
| 21. | 11667.6 | | | |
| 22. | | | 11996.8 | |
| 23. | | 12286.0 | | |
| 24. | 12599.2 | | | |
| 25. | | | 12928.4 | |
| 26. | | | | 13232.6 |
| 27. | | 13521.8 | | |
| 28. | 13835.0 | | | |
| 29. | | 14124.2 | | |
| 30. | | | 14453.4 | |
| 31. | | 14742.6 | | |
| 32. | | | | 15046.8 |
| 33. | 15360.0 | | | |
| 34. | 15673.2 | | | |
| 35. | | 15962.4 | | |
| 36. | | 16251.6 | | |
| 37. | | | 16580.8 | |
| 38. | 16894.0 | | | |
| 39. | 17207.2 | | | |
| 40. | | | | 17511.4 |
| 41. | | 17800.6 | | |
| 42. | | 18189.8 | | |
| 43. | | 18379.0 | | |
| 44. | | | | 18683.2 |
| 45. | | | 19012.4 | |
| 46. | | | 19341.6 | |
| 47. | | | | 19645.8 |
| 48. | | 19935.0 | | |
| 49. | 20248.2 | | | |
| 50. | | | 20577.4 | |
| 51. | 20890.6 | | | |
| 52. | | | | 21194.4 |
| 53. | | 21484.0 | | |
| 54. | | | | 21788.2 |
| 55. | | | | 22092.4 |

Sequencing Using Duplex DNA Probes for Capturing and Priming

Figure 46:
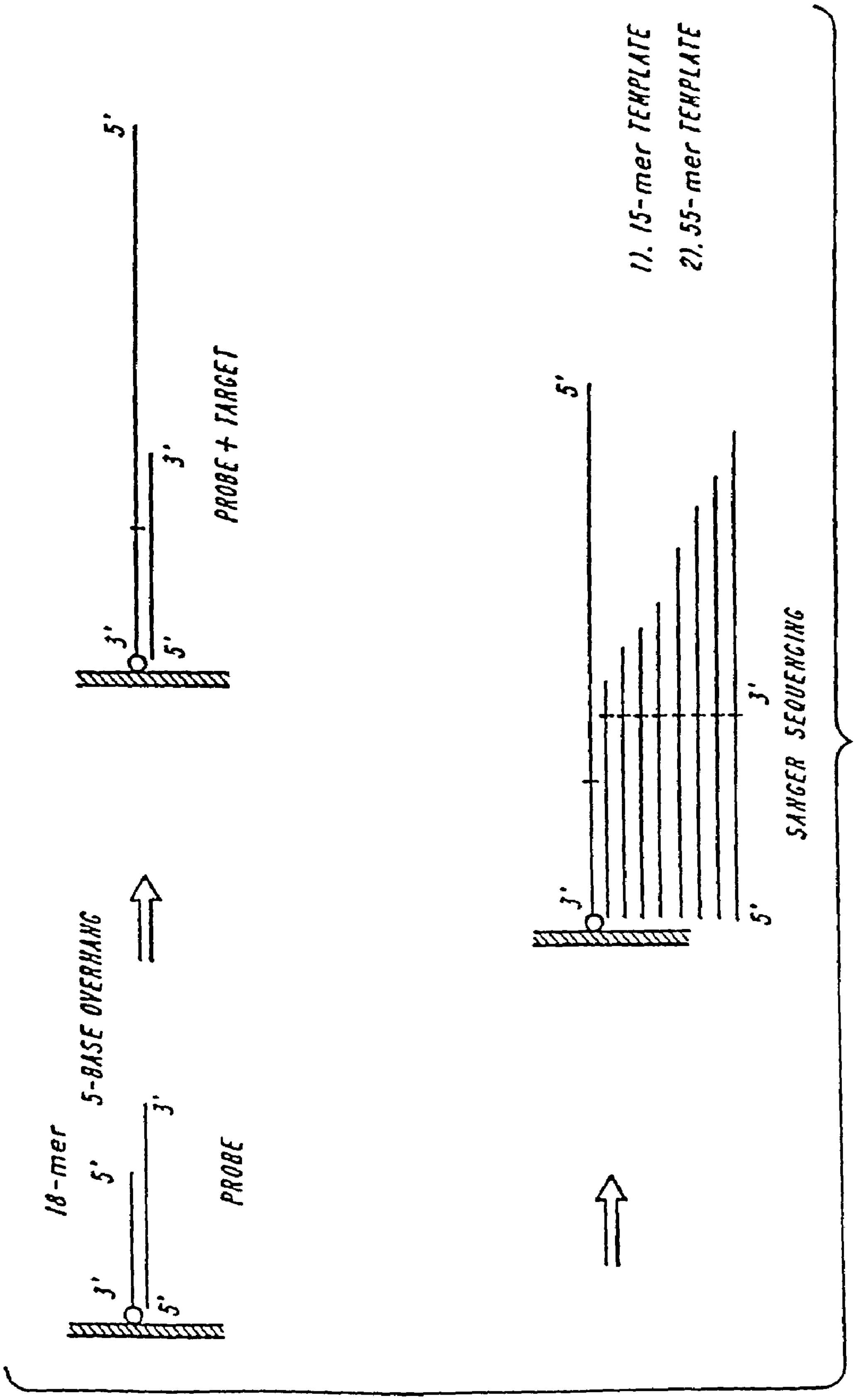
FIG. 46 shows a scheme in which duplex DNA probes with single-stranded overhang capture specific DNA templates and also serve as primers for solid phase sequencing.
Figure 47A:
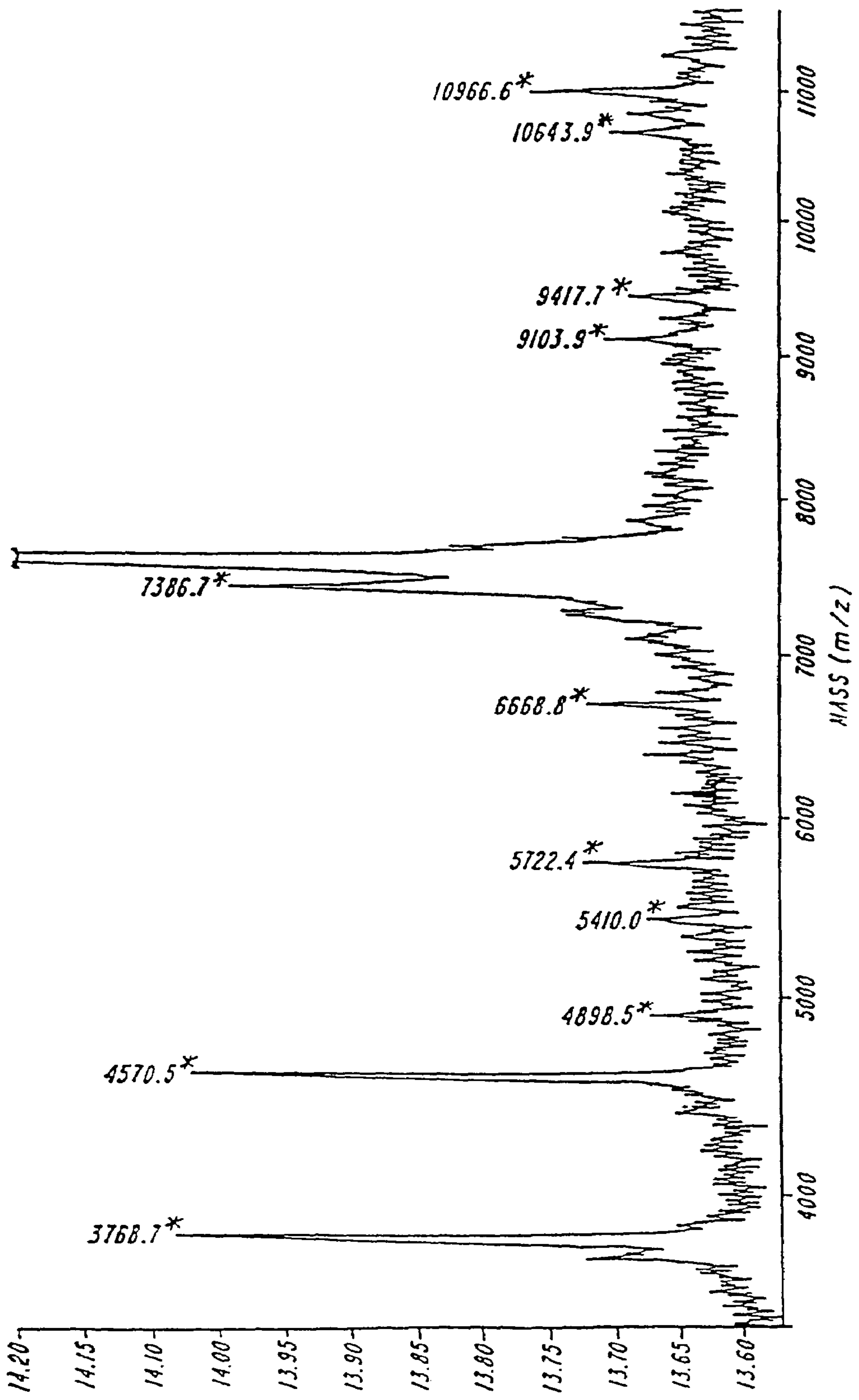
FIG. 47A-D shows MALDI-TOF mass spectra obtained from a sequencing reaction using 5' fluorescent labeled 23-mer (SEQ ID NO: 29) annealed to a 3' biotinylated 18-mer (SEQ ID NO: 30), leaving a 5-base overhang, which captured a 15-mer template (SEQ ID NO: 31) as described in Example 9.
Figure 47B:
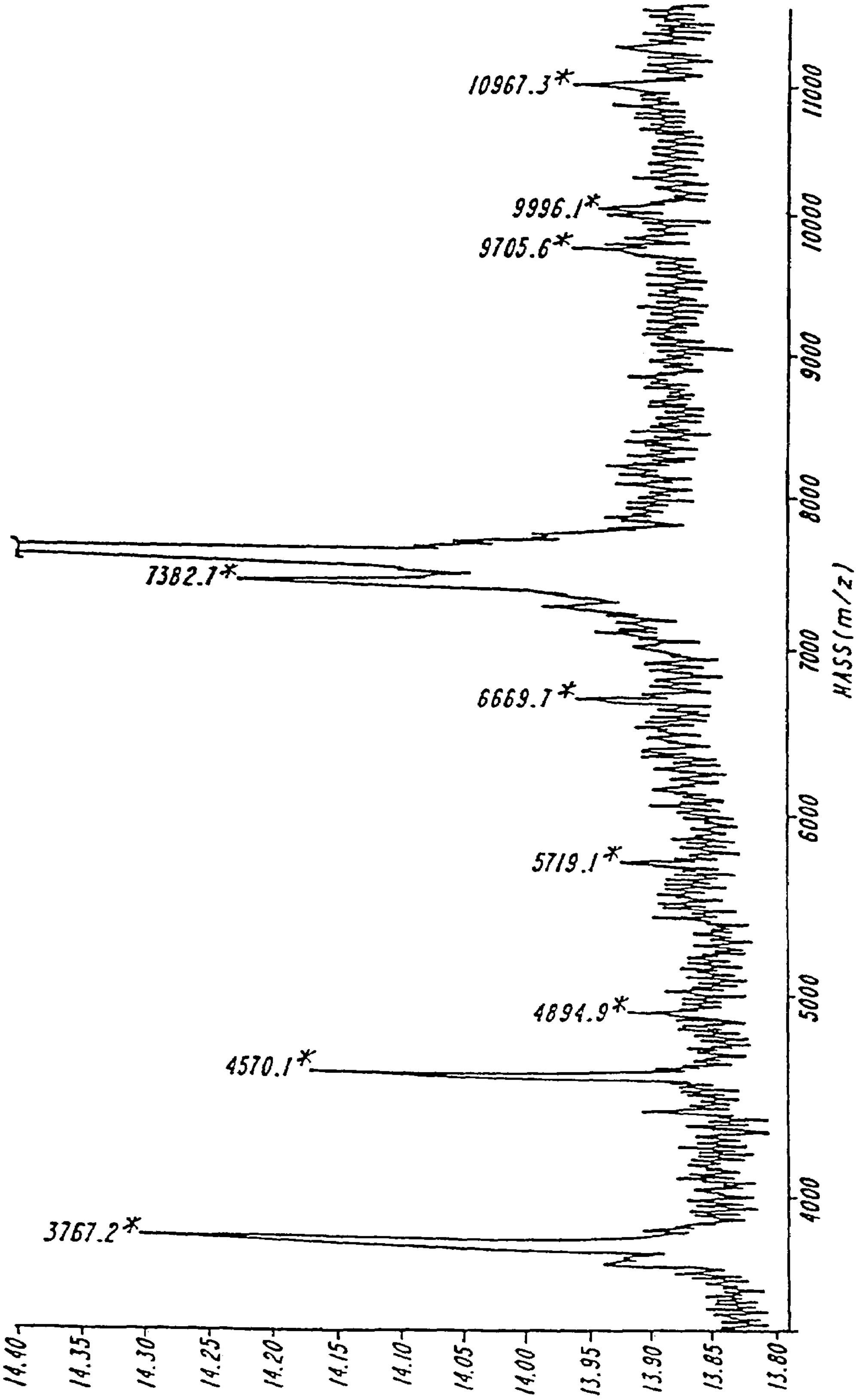
Figure 47C:
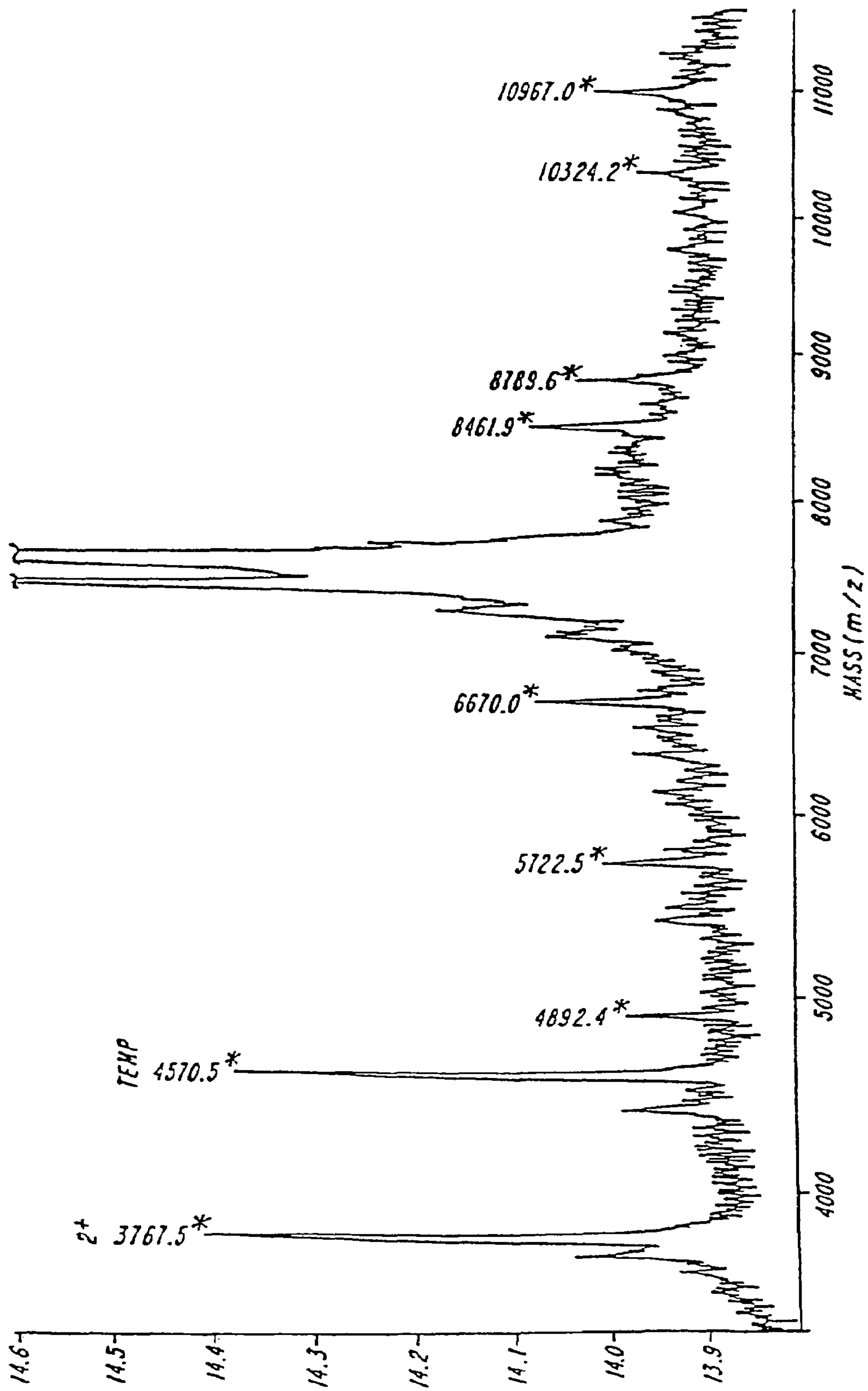
Figure 47D:
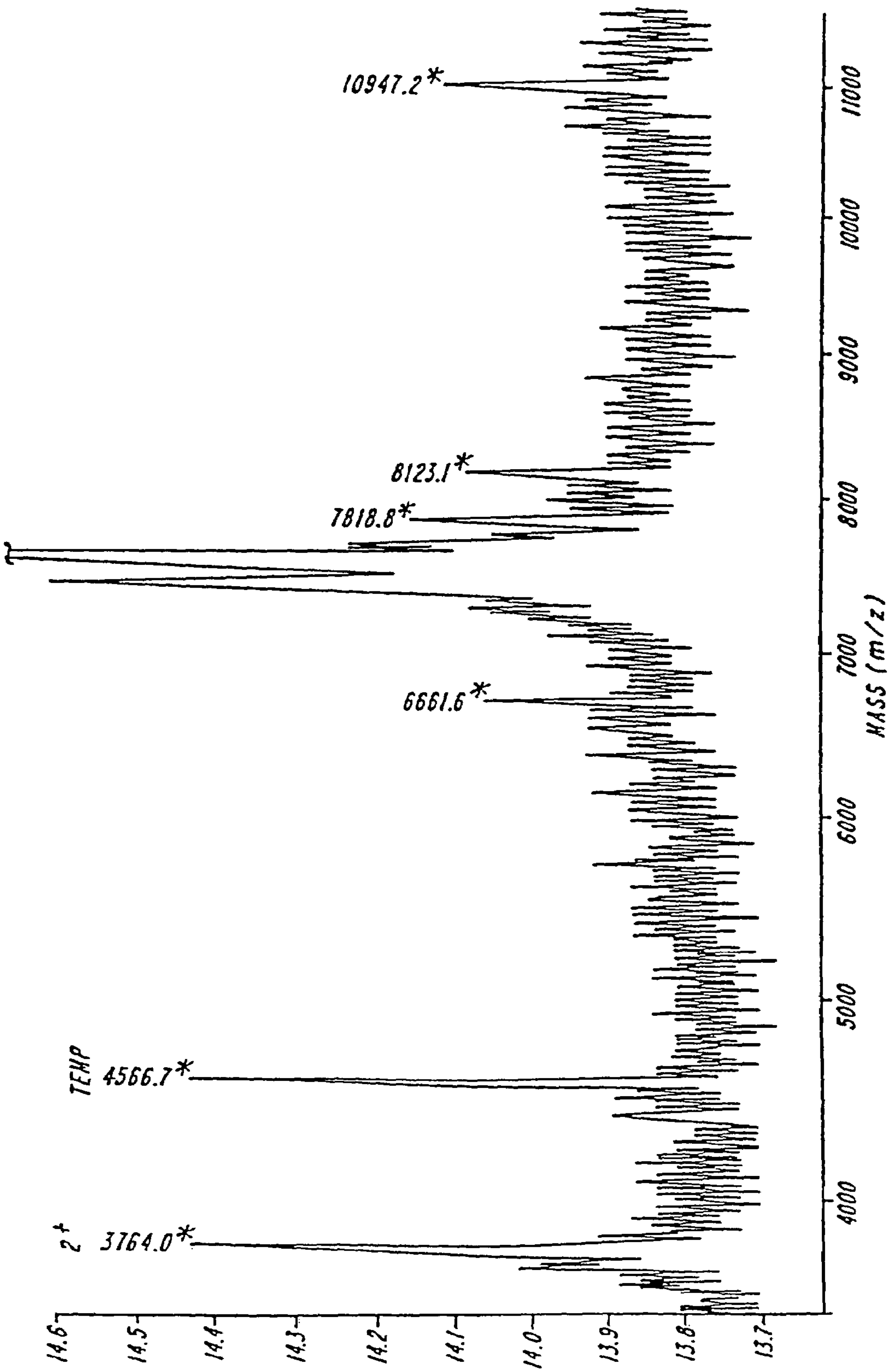
Figure 48A:
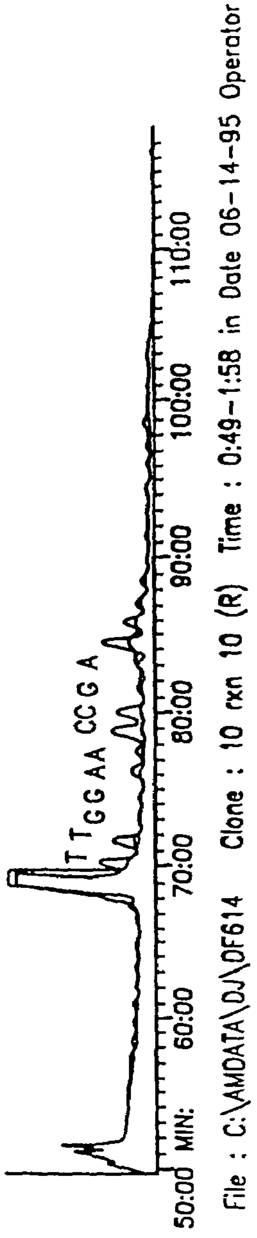
FIG. 48 shows a stacking fluorogram of the same products obtained from the reaction described in FIG. 47, but run on a conventional DNA sequencer.
Figure 48B:
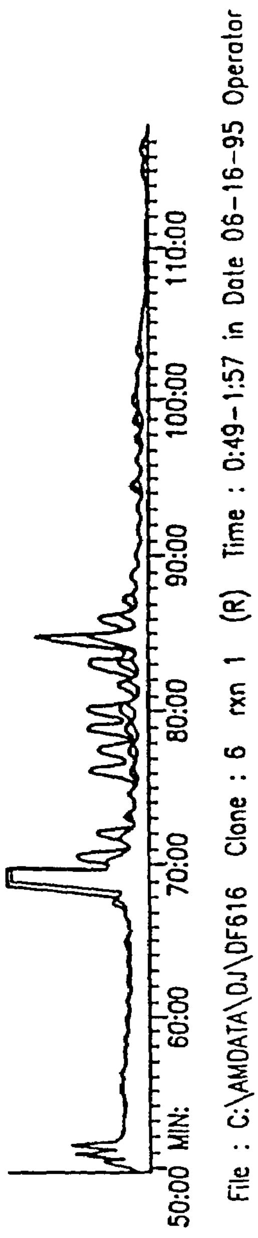
Figure 48C:
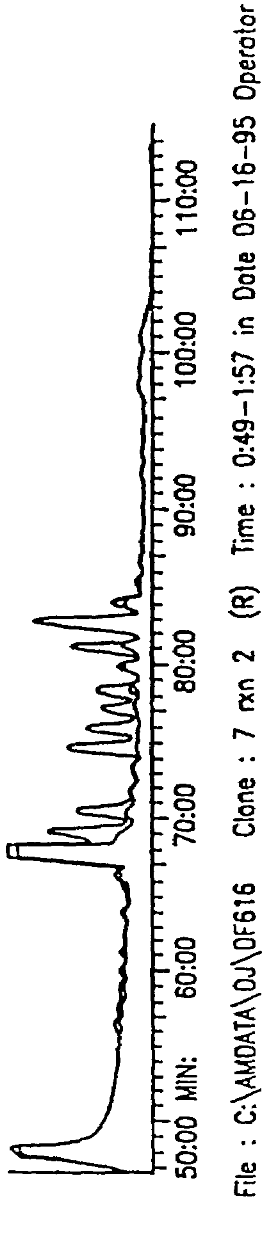
Figure 48D:
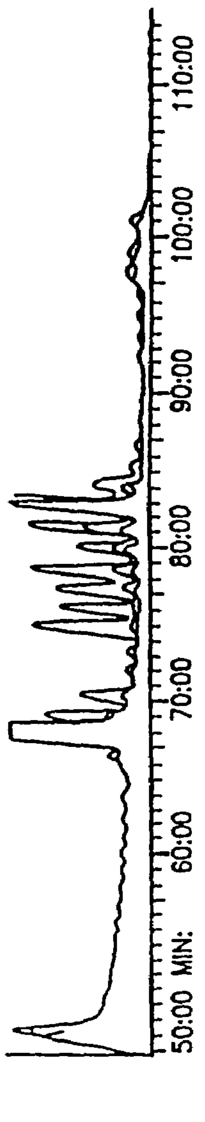
Figure 49A:
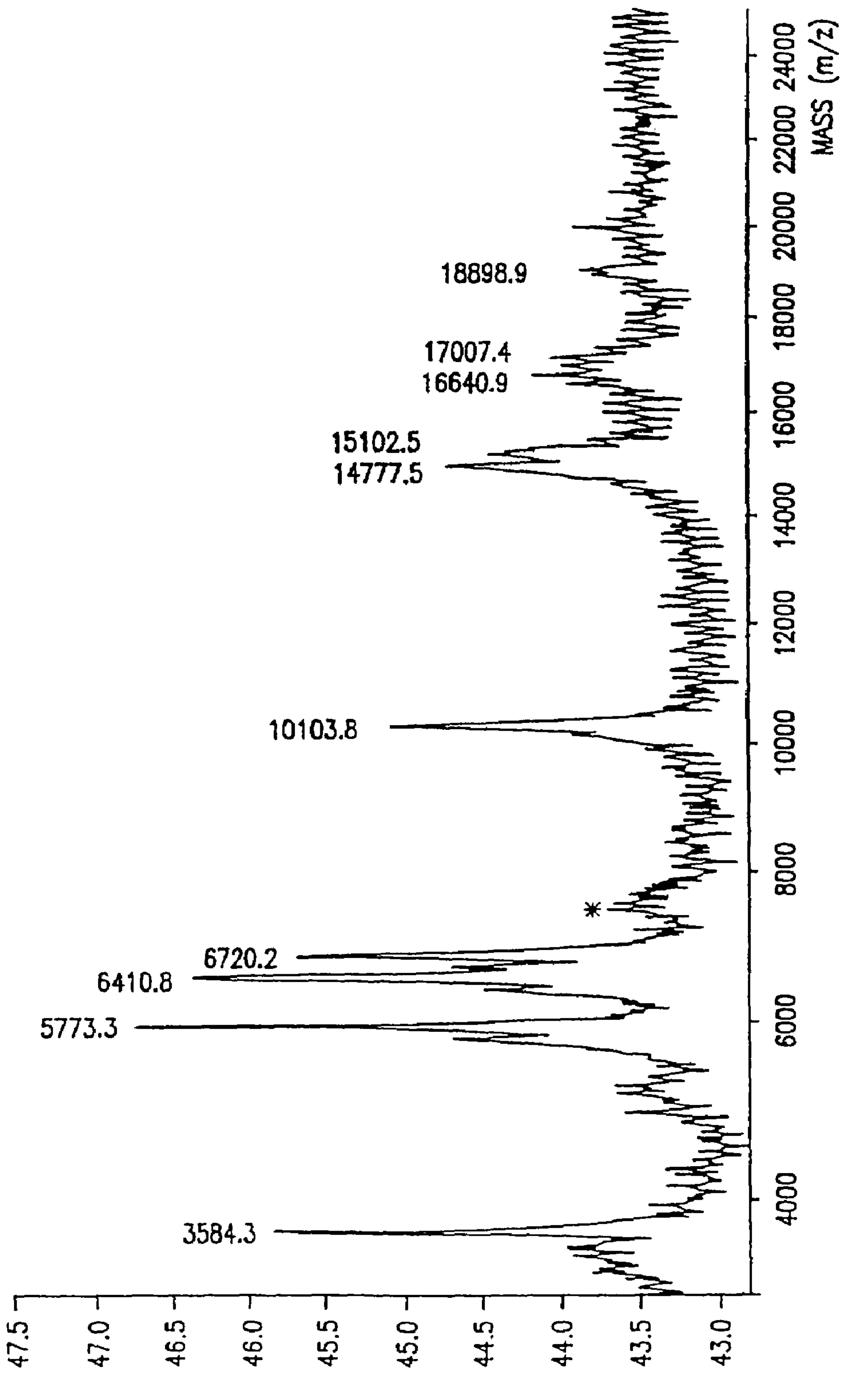
FIG. 49 shows a MALDI-TOF mass spectrum of the sequencing ladder using cycle sequencing as described in Example 1 generated from a biological amplified product as template and a 12mer (5'-TGC ACC TGA CTC-3' (SEQ ID NO: 34)) sequencing primer. The peaks resulting from depurinations and peaks which are not related to the sequence are marked by an asterisk. MALDI-TOF MS measurements were taken on a reflectron TOF MS. A.) Sequencing ladder stopped with ddATP; B.) Sequencing ladder stopped with ddCTP; C.) Sequencing ladder stopped with ddGTP; D.) Sequencing ladder stopped with ddTTP.
Figure 49B:
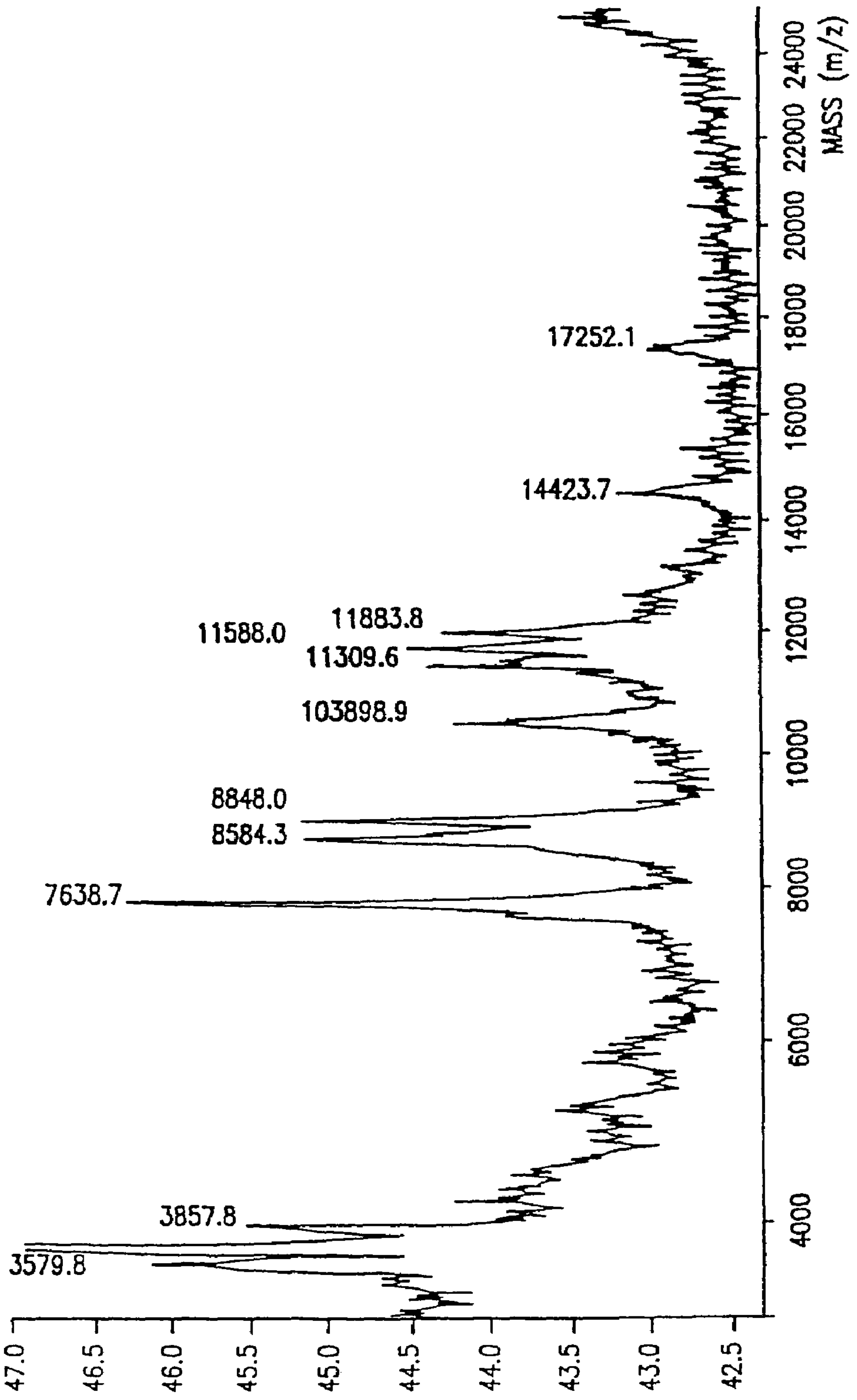
Figure 49C:
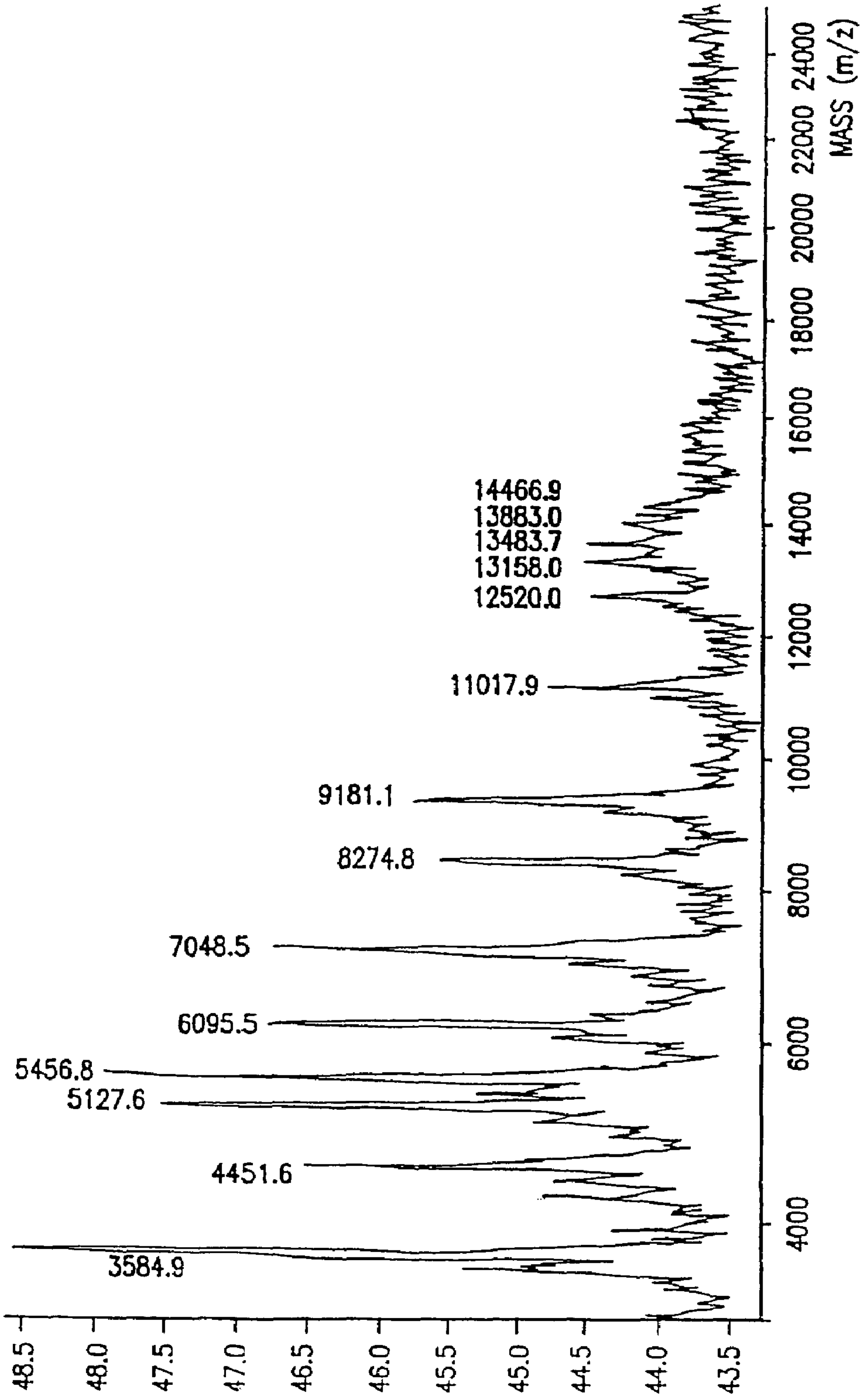
Figure 49D:
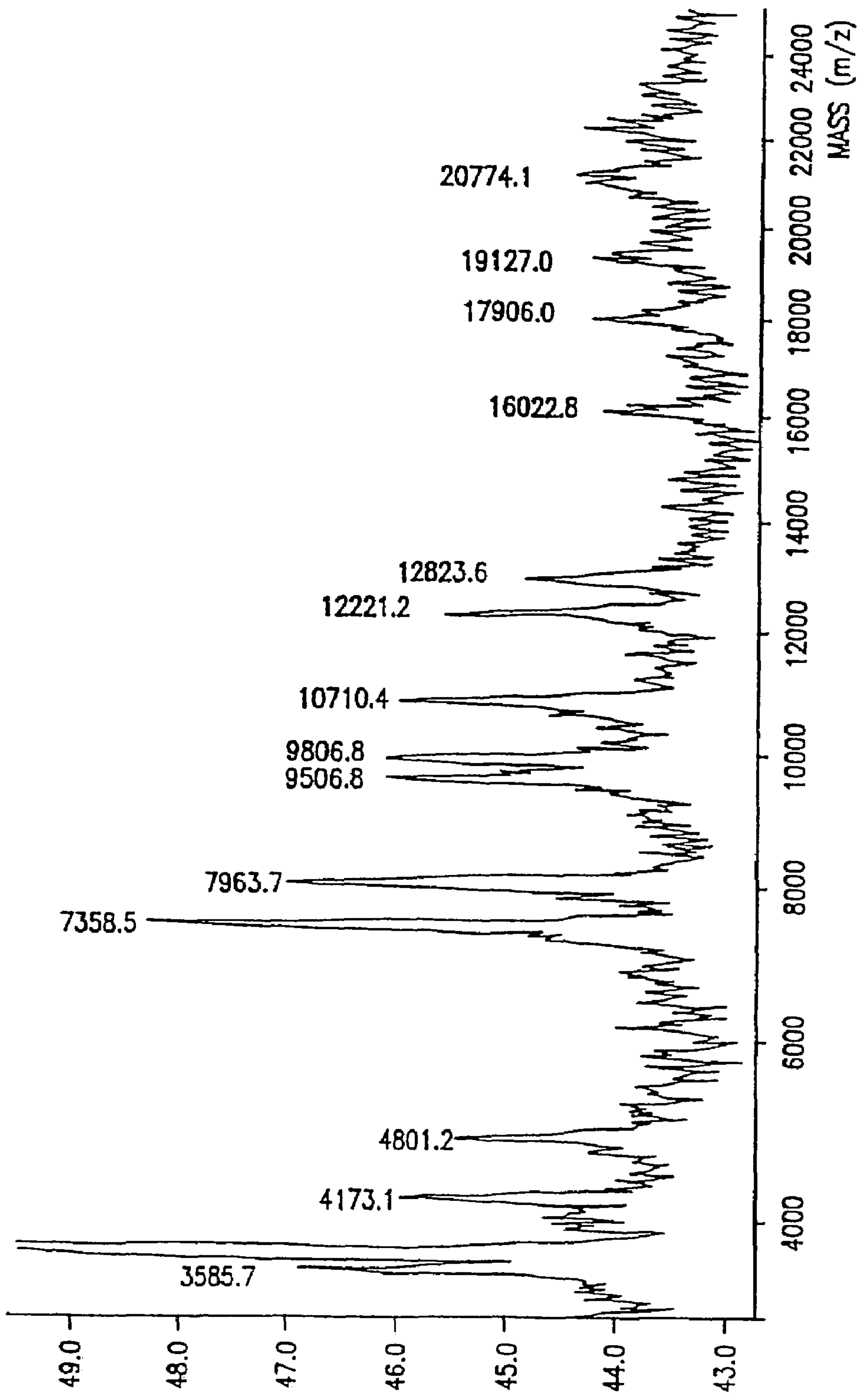
Figure 53A:
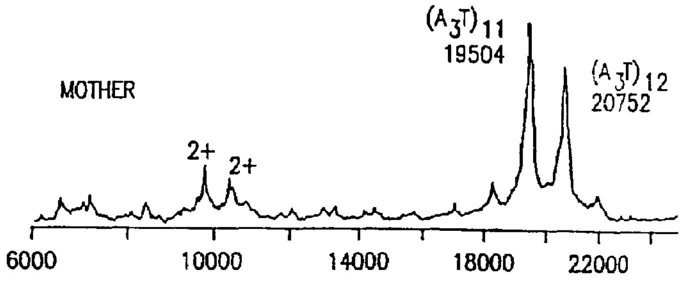
FIG. 53 shows the MALDI-TOF-MS spectra recorded directly form precipitated extended cyclePROBE reaction products. Family study using AluVpA polymorphism in intron 5 of the interferon-a receptor gene (Example 11).
Figure 53B:
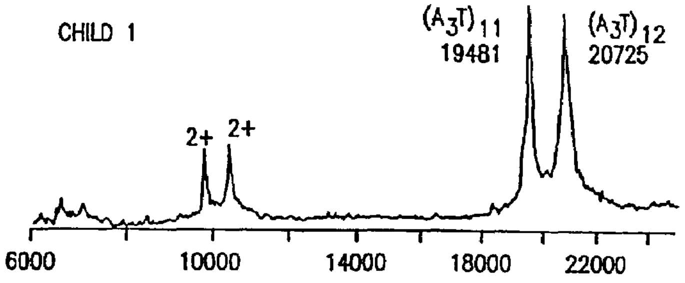
Figure 53C:
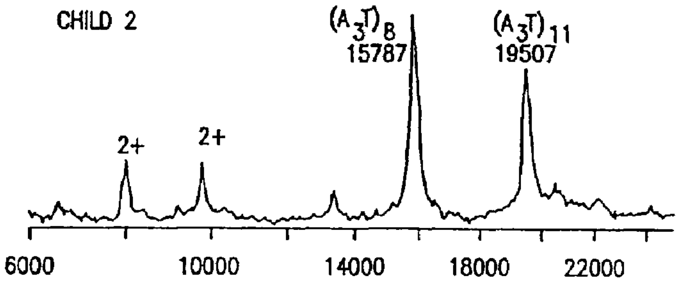
Figure 53D:
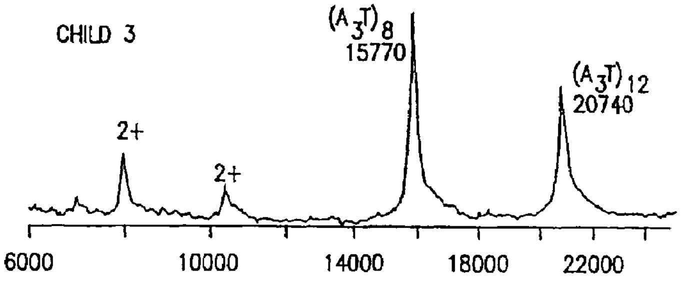
Figure 53E:
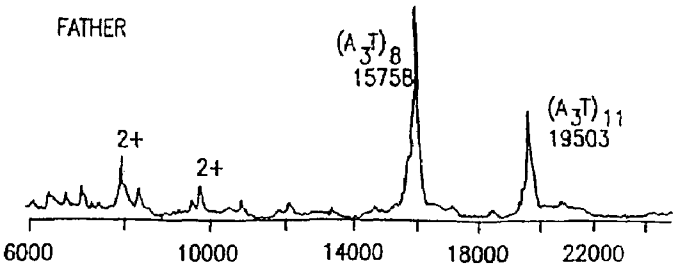

Duplex DNA probes with single-stranded overhang have been demonstrated to be able to capture specific DNA templates and also serve as primers for solid-state sequencing. The scheme is shown in FIG. 46. Stacking interactions between a duplex probe and a single-stranded template allow only a 5-base overhang to be sufficient for capturing. Based on this format, a 5' fluorescent-labeled 23-mer (5'-GAT GAT CCG ACG CAT CAC AGC TC-3') (SEQ ID NO: 29) was annealed to a 3'-biotinylated 18-mer (5'-GTG ATG CGT CGG ATC ATC-3') (SEQ ID NO: 30), leaving a 5-base overhang. A 15-mer template (5'-TCG GTT CCA AGA GCT-3') (SEQ ID NO: 31) was captured by the duplex and sequencing reactions were performed by extension of the 5-base overhang. MALDI-TOF mass spectra of the reactions are shown in FIG. 47A-D. All sequencing peaks were resolved although at relatively low intensities. The last peak in each reaction is due to unspecific addition of one nucleotide to the full length extension product by the Sequenase enzyme. For comparison, the same products were run on a conventional DNA sequencer and a stacking fluorogram of the results is shown in FIG. 48. As can be seen from the Figure, the mass spectra had the same pattern as the fluorogram with sequencing peaks at much lower intensity compared to the 23-mer primer.

EXAMPLE 10

Thermo Sequenase Cycle Sequencing

Materials and Methods

PCR amplification. Human leukocytic genomic DNA was used for PCR amplification. PCR primers to amplify a 209 bp fragment of the β-globin gene were the β2 forward primer (5'-CAT TTG CTT CTG ACA CAA CTG-3' SEQ ID NO: 32) and the β11 reverse primer (5'-CTT CTC TGT CTC CAC ATG C-3' SEQ ID NO: 33). Taq polymerase and 10× buffer were purchased from Boehringer-Mannheim (Germany) and dNTPs from Pharmacia (Freiburg, Germany). The total reaction volume was 50 μl including 8 pmol of each primer with approximately 200 ng of genomic DNA used as template and a final dNTP concentration of 200 μM. PCR conditions were: 5 min at 94° C., followed by 40 cycles of 30 sec at 94° C., 45 sec at 53° C., 30 sec at 72° C., and a final extension time of 2 min at 72° C. The generated amplified product was purified and concentrated (2×) with the Qiagen 'Qiaquick' PCR purification kit (#28106) and stored in $H_2O$.

Cycle Sequencing. Sequencing ladders were generated by primer extension with Thermo Sequenase™-DNA Polymerase (Amersham LIFE Science, #E79000Y) under the following conditions: 7 pmol of HPLC purified primer (Cod5 12mer: 5'-TGC ACC TGA CTC-3' SEQ ID NO: 34) were added to 6 μl purified and concentrated amplified product (i.e. 12 μl of the original amplified product), 2.5 units Thermo Sequenase and 2.5 ml Thermo Sequenase reaction buffer in a total volume of 25 μl. The final nucleotide concentrations were 30 μM of the appropriate ddNTP (ddATP, ddCTP, ddGTP or ddTTP; Pharmacia Biotech, #27-2045-01) and 210 μM of each dNTP (7-deaza-dATP, DCTP, 7-deaza-GTP, dTTP; Pharmacia Biotech).

Cycling conditions were: denaturation for 4 min at 94° C., followed by 35 cycles of 30 sec at 94° C., 30 sec at 38° C., 30 sec at 55° C., and a final extension of 2 min at 72° C.

Sample preparation and analysis by MALDI-TOF MS. After completion of the cycling program, the reaction volume was increased to 50 μl by addition of 25 μl $H_2O$. Desalting was achieved by shaking 30 μl of ammonium saturated DOWEX (Fluka #44485) cation exchange beads with 50 μl of the analyte for 2 min at room temperature. The Dowex beads, purchased in the protonated form, were pre-treated with 2M $NH_4OH$ to convert them to the ammonium form, then washed with $H_2O$ until the supernatant was neutral, and finally put in 10 mM ammonium citrate for usage. After the cation exchange, DNA was purified and concentrated by ethanol precipitation by adding 5 μl 3 M ammonium acetate (pH 6.5), 0.5 μl glycogen (10 mg/ml, Sigma), and 110 μl absolute ethanol to the analyte and incubated at room temperature for 1 hour. After 12 min centrifugation at 20,000× g the pellet was washed in 70% ethanol and resuspended in 1 μl 18 Mohm/cm $H_2O$ water.

For MALDI-TOF MS analysis 0.35 μl of resuspended DNA was mixed with 0.35-1.3 μl matrix solution (0.7 M 3-hydroxypicolinic acid (3-HPA), 0.07 M ammonium citrate in 1:1 $H_2O$:$CH_3CN$) on a stainless steel sample target disk and allowed to air dry preceding spectrum acquisition using a Thermo Bioanalysis Vision 2000 MALDI-TOF operated in reflectron mode with 5 and 20 kV on the target and conversion dynode, respectively. External calibration generated from eight peaks (3000-18000 Da) was used for all spectra.

Results

FIG. 49 shows a MALDI-TOF mass spectrum of the sequencing ladder generated from a biological amplified product as template and a 12 mer (5'-TGC ACC TGA CTC-3' (SEQ ID NO: 34)) sequencing primer. The peaks resulting from depurinations and peaks which are not related to the sequence are marked by an asterisk. MALDI-TOF MS measurements were taken on a reflectron TOF MS. A.) Sequencing ladder stopped with ddATP; B.) Sequencing ladder stopped with ddCTP; C.) Sequencing ladder stopped with ddGTP; D.) Sequencing ladder stopped with ddTTP.

FIG. 50 shows a schematic representation of the sequencing ladder generated in FIG. 49 with the corresponding calculated molecular masses up to 40 bases after the primer (SEQ ID NOs: 221-260). For the calculation the following masses were used: 3581.4 Da for the primer, 312.2 Da for 7-deaza-dATP, 304.2 Da for dTTP, 289.2 Da for dCTP and 328.2 Da for 7-deaza-dGTP.

FIG. 51 shows the sequence of the amplified 209 bp amplified product within the β-globin gene (SEQ ID NO: 261), which was used as a template for sequencing. The sequences of the appropriate PCR primer and the location of the 12 mer sequencing primer is also shown. This sequence represents a homozygote mutant at the position 4 after the primer. In a wildtype sequence this T would be replaced by an A.

EXAMPLE 11

Microsatellite Analysis Using Primer Oligo Base Extension (PROBE) and MALDI-TOF Mass Spectrometry Summary The method uses a single detection primer followed by an oligonucleotide extension step to give products differing in length by a number of bases specific for the number of repeat units or for second site mutations within the repeated region, which can be easily resolved by MALDI-TOF mass spectrometry. The method is demonstrated using as a model system the AluVpA polymorphism in intron 5 of the interferon-a receptor gene located on human chromosome 21, and the poly T tract of the splice acceptor site of intron 8 from the CFTR gene located on human chromosome 7.

Materials and Methods

Genomic DNA was obtained from 18 unrelated individuals and one family including of a mother, father, and three children. The repeated region was evaluated conventionally by denaturing gel electrophoresis and results obtained were confirmed by standard Sanger sequencing.

The primers for PCR amplification (8 pmol each) were IFNAR-IVS5-5': (5'-TGC TTA CTT AAC CCA GTG TG-3' SEQ ID NO: 35) and IFNAR-IVS5-3'.2: (5'-CAC ACT ATG TAA TAC TAT GC-3' SEQ ID NO: 36) for a part of the intron 5 of the interferon-α receptor gene, and CFEx9-F:(5'-GAA AAT ATC TGA CAA ACT CAT C-3' SEQ ID NO: 37) (5'-biotinylated) and CFEx9-R:(5'-CAT GGA CAC CAA ATT AAG TTC-3' SEQ ID NO: 38) for CFTR exon 9 with flanking intron sequences of the CFTR gene. Taq-polymerase including 10× buffer were purchased from Boehringer-Mannheim and dNTPs were obtained from Pharmacia. The total reaction volume was 50 μl. PCR conditions were 5 min at 94° C. followed by 40 cycles of: 1 min at 94° C., 45 sec at 53° C., and 30 sec at 72° C., and a final extension time of 5 min at 72° C.

Amplification products were purified using Qiagen's PCR purification kit (No.28106) according to manufacturer's instructions. Purified products were eluted from the column in 50 μl TE-buffer (10 mM Tris-HCl, 1 mM EDTA, pH 7.5).

A) Primer Oligo Base Extension Reaction (Thermo Cycling Method

CyclePROBE was performed with 5 pmol appropriate detection primer (IFN:5'-TGA GAC TCT GTC TC-3' SEQ ID NO: 39) in a total volume of 25 μl including 1 pmol purified template, 2 units Thermosequenase (Amersham Life Science, Cat. #E79000Y) 2.5 μl Thermosequenase buffer, 25 μmol of each deoxynucleotide (7-deaza-dATP, dTTP, and in some experiments extra dCTP) and 100 μmol of dideoxyguanine and in some experiments additional ddCTP. Cycling conditions: initial denaturation 94° C. for 5 min followed by 30 cycles with 44° C. annealing temperature for 30 sec and 55° C. extension temperature for 1 min.

Primer Oligo Base Extension Reaction (Isothermal Method)

10 μl aliquots of the purified double-stranded amplified product (~3 pmol) were transferred to a streptavidin-coated microliter plate well (~16 pmol capacity per 50 μl volume; No. 1645684 Boehringer-Mannheim), followed by addition of 10 μl incubation buffer (80 mM sodium phosphate, 400 mM NaCl, 0.4% Tween 20, pH 7.5) and 30 μl water. After incubation for 1 hour at room temperature, the wells were washed three times with 200 μl washing buffer A (40 mM Tris, 1 mM EDTA, 50 mM NaCl, 0.1% Tween 20, pH 8.8) and incubated with 100 μl of 50 mM NaOH for 3 min to denature the double-stranded DNA. Finally, the wells were washed three times with 200 μl 70 mM ammonium citrate solution.

The annealing of 100 pmol detection primer (CFpT: 5'-TTC CCC AAA TCC CTG-3' SEQ ID NO: 40) was performed in 50 μl annealing buffer (50 mM ammonium phosphate buffer, pH 7.0 and 100 mM ammonium chloride) at 65° C. for 2 min, at 37° C. for 10 min, and at room temperature for 10 min. The wells were washed three times with 200 μl washing buffer B (40 mM Tris, 1 mM EDTA, 50 mM $NH_4Cl$, 0.1% Tween 20, pH 8.8) and once in 200 μl TE buffer. The extension reaction was performed using some components of the DNA sequencing kit from USB (No. 70770) and dNTPs or ddNTPs from Pharmacia. Total reaction volume was 45 μl, containing of 21 μl water, 6 μl Sequenase-buffer, 3 μl 100 mM DTT solution, 50 μmol of 7-deaza-dATP, 20 μmol ddCTP, 5.5 μl glycerol enzyme dilution buffer, 0.25 μl Sequenase 2.0, and 0.25 μl pyrophosphatase. The reaction was pipetted on ice and incubated for 1 5 min at room temperature and for 5 min at 37° C. Finally,the wells were washed three times with 200 μl washing buffer B.

The extended primer was denatured from the template strand by heating at 80° C. for 10 min in 50 μl of a 50 mM ammonium hydroxide solution.

For precipitation, 10 μl 3 M NH4-acetate (pH 6.5), 0.5 μl glycogen (10 mg/ml water, Sigma, Cat. #G1765), and 110 μl absolute ethanol were added to the supernatant and incubated for 1 hour at room temperature. After centrifugation at 13.000 g for 10 min the pellet was washed in 70% ethanol and resuspended in 1 μl 18 Mohm/cm $H_2O$ water.

Sample preparation was performed by mixing 0.6 μl of matrix solution (0.7 M 3-hydroxypicolinic acid, 0.07 M dibasic ammonium citrate in 1:1 $H_2O$:$CH_3CN$) with 0.3 μl of resuspended DNA/glycogen pellet on a sample target and allowed to air dry. Up to 20 samples were spotted on a probe target disk for introduction into the source region of a Thermo Bioanalysis (formerly Finnigan) Visions 2000 MALDI-TOF operated in reflectron mode with 5 and 20 kV on the target and conversion dynode, respectively. Theoretical average molecular mass ($M_r$(calc)) were calculated from atomic compositions; reported experimental $M_r$ ($M_r$(exp)) values are those of the singly-protonated form, determined using external calibration.

Results

The aim of the experiments was to develop a fast and reliable method for the exact determination of the number of repeat units in microsatellites or the length of a mononucleotide stretch including the potential to detect second site mutations within the polymorphic region. Therefore, a special kind of DNA sequencing (primer oligo base extension, PROBE) was combined with the evaluation of the resulting products by matrix-assisted laser desorption ionization (MALDI) mass spectrometry (MS). The time-of-flight (TOF) reflectron arrangement was chosen-as a possible mass measurement system. As an initial feasibility study, an examination was performed first on an AluVpA repeat polymorphism located in intron 5 of the human interferon-α receptor gene (cyclePROBE reaction) and second on the poly T tract located in intron 8 of the human CFTR gene (isothermal PROBE reaction).

Figure 54A:
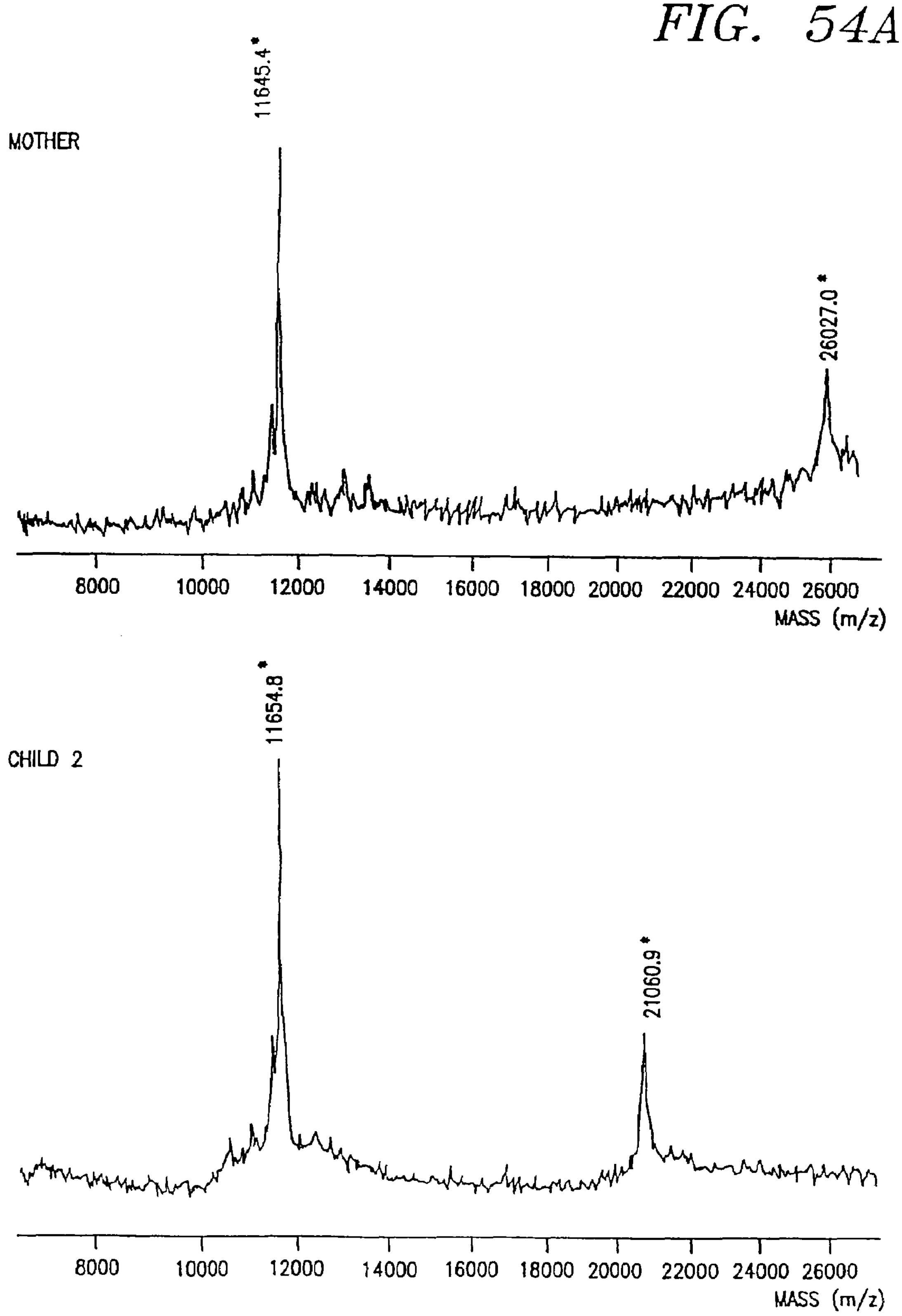
FIG. 54 shows the mass spectra from PROBE products using ddC as termination nucleotide in the reaction mix. The allele with the molecular mass of approximately 11650 da from the DNA of the mother and child 2 is a hint to a second site mutation within one of the repeat units.

A schematic presentation of the cyclePROBE experiment for the AluVpA repeat polymorphism is given in FIG. 52. The extension of the antisense strand (SEQ ID NO: 262) was performed with the sense strand serving as the template. The detection primer is underlined. In a family study co-dominant segregation of the various alleles could be demonstrated by the electrophoretic procedure as well as by the cyclePROBE method followed by mass spec analysis (FIG. 53). Those alleles of the mother and child 2, for which direct electrophoresis of the amplified product indicated one of the two copies to have 13 repeat units,were measured using cyclePROBE to have instead only 11 units using ddG as terminator. The replacement of ddG by ddC resulted in a further unexpected short allele with a molecular mass of approximately 11650 in the DNA of the mother and child 2 (FIG. 54). Sequence analysis verified this presence of two second site mutations in the allele with 13 repeat units. The first is a C to T transition in the third repeat unit and the second mutation is a T to G transversion in the ninth repeat unit. Examination of 28 unrelated individuals shows that the 13 unit allele is spliced into a normal allele and a truncated allele using cyclePROBE. Statistical evaluation shows that the polymorphism is in Hardy-Weinberg equilibrium for both methods, however, using cyclePROBE as detection method the polymorphism information content is increased to 0.734.

PROBE was also used as an isothermic method for the detection of the three common alleles at the intron 8 splice acceptor site of the CFTR gene (SEQ ID NO: 263). FIG. 55 shows a schematic presentation of the expected diagnostic products (SEQ ID NOs: 264-266) with the theoretical mass values. The reaction was also performed in the antisense direction.

Figure 56A:
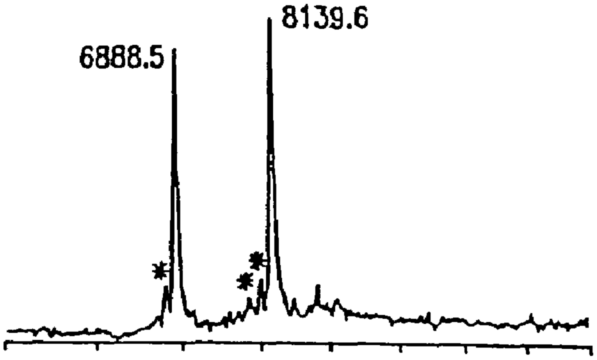
FIG. 56 shows the MALDI-TOF-MS spectra recorded directly from the precipitated extended PROBE reaction products. Detection of all three common alleles of the polyT tract at the 3' end of Intron 8 of the CFTR gene. (a) T5/T9 heterozygous, (b) T7/T9 heterozygous (Example 11).
Figure 56B:
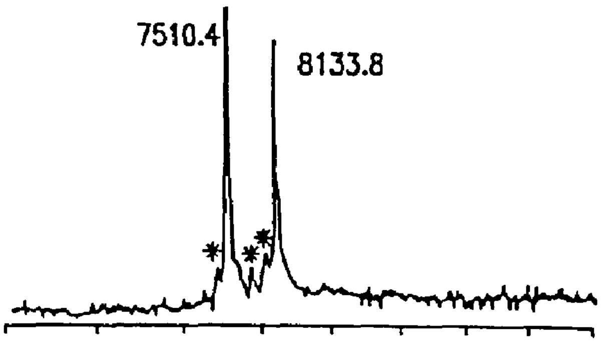

FIG. 56 demonstrates that all three common alleles (T5, T7, and T9, respectively) at this locus could be reliably disclosed by this method. Reference to FIG. 56 indicates that mass accuracy and precision with the reflectron time of flight used in this study ranged from 0-0.4%, with a relative standard deviation of 0.13%. This corresponds to far better than single base accuracy for the up to <90-mer diagnostic products generated in the IFNAR system. Such high analytical sensitivity is sufficient to detect single or multiple insertion/deletion mutations within the repeat unit or its flanking regions, which would induce >1% mass shifts in a 90-mer. This is analogous to the FIG. 56 polyT tract analysis. Other mutations (i.e. an A to T or a T to A mutation within the IFNAR gene A3T repeat) which do not cause premature product termination are not detectable using any dNTP/ddNTP combination with PROBE and low performance MS instrumentation; a 9 Da shift in a 90-mer corresponds to a 0.03% mass shift. Achieving the accuracy and precision required to detect such minor mass shifts has been demonstrated with higher performance instrumentation such as Fourier transform (FT)MS, for which single Da accuracy is obtained up to 100-mers. Further, tandem FTMS, in which a mass shifted fragment can be isolated within the instrument and dissociated to generate sequence specific fragments, has been demonstrated to locate point mutations to the base in comparably sized products. Thus the combination of PROBE with higher performance instrumentation will have an analytical sensitivity which can be matched only by cumbersome full sequencing of the repeat region.

EXAMPLE 12

Improved Apolipoprotein E Genotyping Using Primer Oligo Base Extension (PROBE) and MALDI-TOF Mass Spectrometry Materials and Methods PCR Amplification.

Human leukocytic genomic DNA from 100 anonymous individuals from a previously published study (Braun, A et al., (1992) *Human Genet.* 89: 401-406) were screened for apolipoprotein E genotypes using conventional methods. PCR primers to amplify a portion of exon 4 of the apo E gene were delineated according to the published sequence (Das, H K et al, (1985) *J. Biol. Chem.* 260: 6240-6247) (forward primer, apoE-F: 5'-GGC ACG GCT GTC CAA GGA G-3' SEQ ID NO: 41; reverse, apoE-R: 5'-AGG CCG CGC TCG GCG CCC TC-3' SEQ ID NO: 42). Taq polymerase and 10× buffer were purchased from Boehringer-Mannheim (Germany) and dNTPs from Pharmacia (Freiburg, Germany). The total reaction volume was 50 μL including 8 pmol of each primer and 10% DMSO (dimethylsulfoxide, Sigma) with approximately 200 ng of genomic DNA used as template. Solutions were heated to 80° C. before the addition of 1 U polymerase; PCR conditions were: 2 min at 94° C., followed by 40 cycles of 30 sec at 94° C., 45 sec at 63° C., 30 sec at 72° C., and a final extension time of 2 min at 72° C.

Restriction Enzyme Digestion and Polyacrylamide Electrophoresis.

CfoI and RsaI and reaction buffer L were purchased from Boehringer-Mannheim, and HhaI from Pharmacia (Freiburg, Germany). For CfoI alone and simultaneous CfoI/RsaI digestion, 20 pL of amplified products were diluted with 15 μl water and 4 pL Boehringer-Mannheim buffer L; after addition of 10 units of appropriate restriction enzyme(s) the samples were incubated for 60 min at 37° C. The procedure for simultaneous HhaI/RsaI digestion required first digestion by RsaI in buffer L for one hour followed by addition of NaCl (50 mM end concentration) and HhaI, and additional incubation for one hour. 20 pL of the restriction digest were analyzed on a 12% polyacrylamide gel as described elsewhere (Hixson (1990) *J. Lipid Res.* 31: 545-548). Recognition sequences of RsaI and CfoI (HhaI) are GT/AC and GCG/C, respectively; masses of expected digestion fragments from the 252-mer amplified product with CfoI alone and the simultaneous double digest with CfoI (or HhaI) and RsaI are given in Table V.

Thermo-PROBE.

PCR amplification was performed as described above, but with products purified with the Qiagen' Qiaquick' kit to remove unincorporated primers. Multiplex Thermo-PROBE was performed with 35 μl amplified product and 8 pmol each of the codon 112 (5'-GCG GAC ATG GAG GAC GTG-3' SEQ ID NO: 43) and 158 (5'-GAT GCC GAT GAC CTG CAG AAG-3' SEQ ID NO: 44) detection primers in 20 μl including ~1 pmol purified biotinylated antisense template immobilized on streptavidin coated magnetic beads, 2.5 units Thermosequenase, 2 μl Thermosequenase buffer, 50 μM of each dNTP and 200 μM of ddXTP, with the base identity of N and X as described in the text. Cycling conditions were: denaturation (94° C., 30 sec) followed by 30 cycles at 94° C. (10 min) and 60° C. (45 sec).

Sample Preparation and Analysis by MALDI-TOF MS.

For precipitation (Stults et al., (1991) *Rapid Commun. Mass Spectrom.* 5: 359-363) of both digests and PROBE products, 5 μl 3M ammonium acetate (pH 6.5), 0.5 μl glycogen (10 mg/ml, Sigma), and 110 μl absolute ethanol were added to 50 μl of the analyte solutions and stored for 1 hour at room temperature. After 10 min centrifugation at 13,000× g the pellet was washed in 70% ethanol and resuspended in 1 μl 18 Mohm/cm $H_2O$ water. Where noted in the text, additional desalting was achieved by shaking 10-20 μL of ammonium saturated DOWEX (Fluka #44485) cation exchange beads in 40μL of analyte. The beads, purchased in the protonated form, were pre-treated with three 5 min spin-decant steps in 2M $NH_4OH$, followed with $H_2O$ and 10 mM ammonium citrate.

0.35 μL of resuspended DNA was mixed with 0.35-1.3 μL matrix solutions (Wu et al. (1993) *Rapid Commun. Mass Spectrom.* 7: 142-146) 0.7 M 3-hydroxypicolinic acid (3-HPA), 0.07 M ammonium citrate in 1:1 $H_2O:CH_3CN$) on a stainless steel sample target disk and allowed to air dry preceding spectrum acquisition using a Thermo Bioanalysis Vision 2000 MALDI-TOF operated in reflectron mode with 5 and 20 kV on the target and conversion dynode, respectively. Theoretical average molecular masses ($M_r$(calc)) of the fragments were calculated from atomic compositions; the mass of a proton (1.08 Da) is subtracted from raw data values in reporting experimental molecular masses ($M_r$(exp)) as neutral basis. An external calibration generated from eight peaks (3000-18000 Da) was applied to all spectra.

Results

Digestion with CfoI Alone.

Figure 57A:
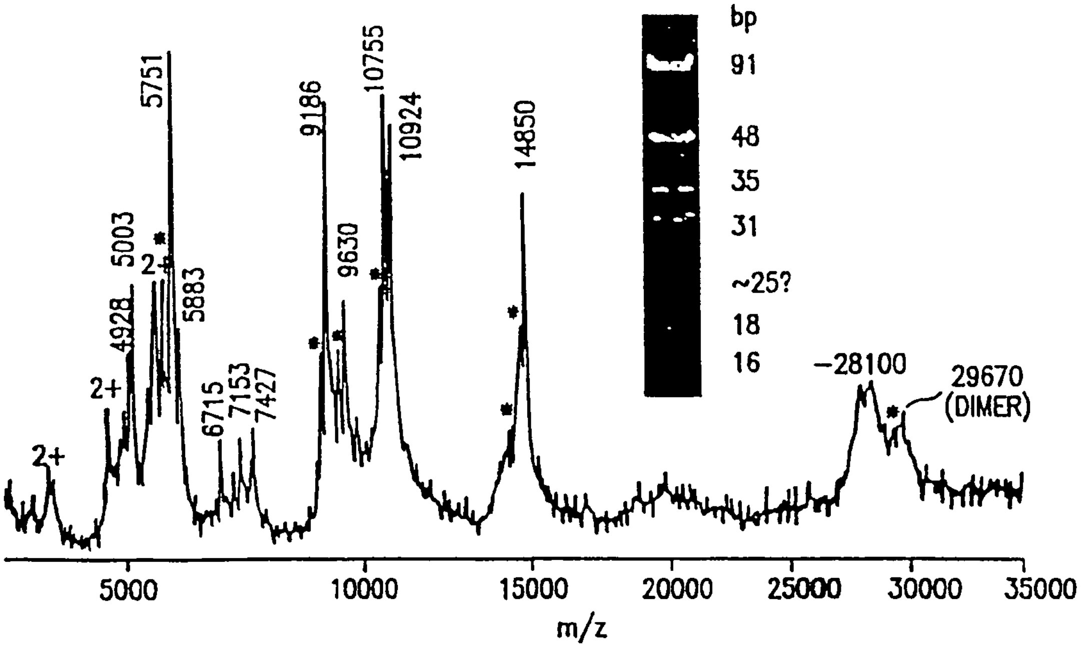
FIG. 57 shows a mass spectrum of the digestion of a 252-mer ApoE gene amplified product (ϵ3/ϵ3 genotype) as described in Example 12 using a) CfoI alone and b) CfoI plus RsaI. Asterisks: depurination peaks.

The inset to FIG. 57*a* shows a 12% polyacrylamide gel electrophoretic separation of an ϵ3/ϵ3 genotype after digestion of the 252 bp apo E amplified product with CfoI. Comparison of the electrophoretic bands with a molecular weight ladder shows the cutting pattern to be as mostly as expected (Table V) for the ϵ3/ϵ3 genotype. Differences are that the faint band at approximately 25 bp is not expected, and the smallest fragments are not observed. The accompanying mass spectrum of precipitated digest products shows a similar pattern, albeit at higher resolution. Comparison with Table V shows that the observed masses are consistent with those of single-stranded DNA; the combination of an acidic matrix environment (3-HPA, $pK_a$ 3) and the absorption of thermal energy via interactions with the 337 nm absorbing 3-HPA upon ionization is known to denature short stretches of dsDNA under normal MALDI conditions (Tang, K et al., (1994) Rapid Commun Mass Spectrom 8:183-186).

The approximately 25-mers, unresolved with electrophoresis, are resolved by MS as three single stranded fragments; while the largest (7427 Da) of these may represent a doubly charged ion from the 14.8 kDa fragments (m=14850, z=2; m/z=7425), the 6715 and 7153 Da fragments could result from PCR artifacts or primer impurities; all three peaks are not observed when amplified products are purified with Qiagen purification kits prior to digestion. The Table V 8871 Da 29-mer sense strand 3'-terminal fragment is not observed; the species detected at 9186 Da is consistent with the addition of an extra base (9187-8871=316, consistent with A) by the Taq-polymerase during PCR amplification (Hu, G et al., (1993) DNA and Cell Biol 12:763-770). The individual single strands of each double strand with <35 bases (11 kDa) are resolved as single peaks; the 48-base single strands ($M_r$(calc) 14845 and 14858), however, are observed as an unresolved single peak at 14850 Da. Separating these into single peaks would require a mass resolution (m/Δm, the ratio of the mass to the peak width at half height) of 14850/13=1140, nearly an order of magnitude greater than what is routine with the standard reflectron time-of-flight instrumentation used in this study; resolving such small mass differences with high performance instrumentation such as Fourier transform MS, which provides up to three orders of magnitude higher resolution in this mass range, has been demonstrated. The 91-mer single strands ($M_r$(calc)27849 and 28436) are also not resolved, even though this requires a resolution of only <50. The dramatic decrease in peak quality at higher masses is due to metastable fragmentation (i.e. depurination) resulting from excess internal energy absorbed during and subsequent to laser irradiation.

Simultaneous Digestion with CfoI and RsaI.

Figure 57B:
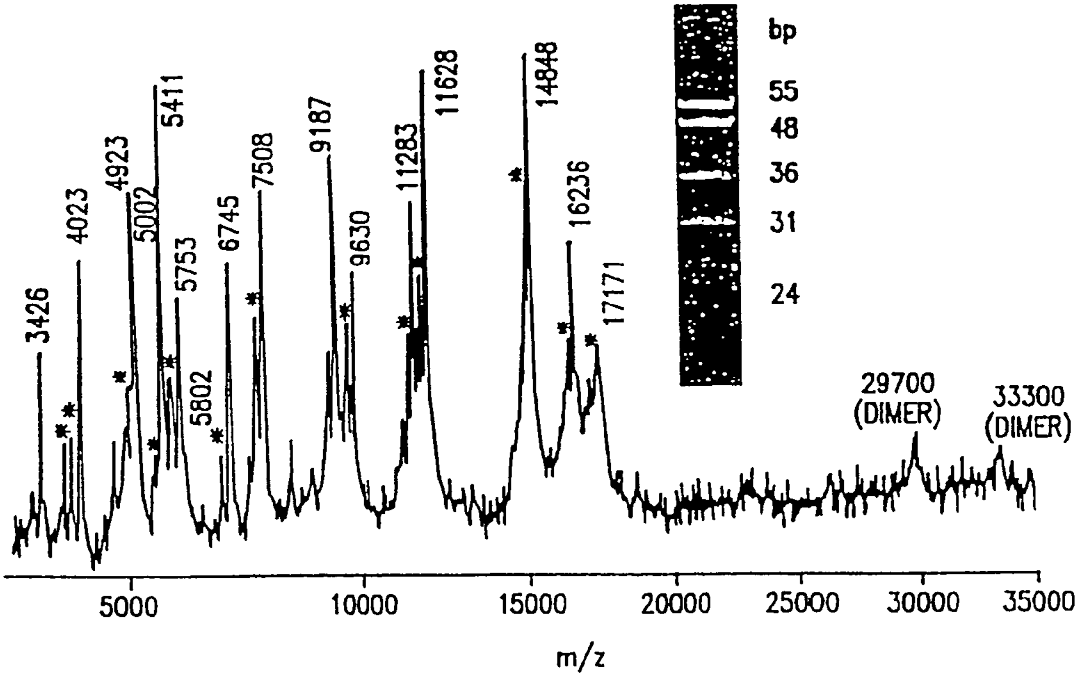

FIG. 57*b* (inset) shows a 12% polyacrylamide gel electrophoresis separation of ϵ3/ϵ3 double digest products, with bands consistent with dsDNA with 24, 31, 36, 48, and 55 base pairs, but not for the smaller fragments. Although more peaks are generated (Table V) than with CfoI alone, the corresponding mass spectrum is more easily interpreted and reproducible since all fragments contain <60 bases, a size range far more appropriate for MALDI-MS if reasonably accurate $M_r$ values (e.g., 0.1%) are desired. For fragments in this mass range, the mass measuring accuracy using external calibration is –0.1% (i.e. <+10 Da at 10 kDa). Significant depurination (indicated in Figure by asterisk) is observed for all peaks above 10 kDa, but even the largest peak at 17171 Da is clearly resolved from its depurination peak so that an accurate $M_r$ can be measured. Although molar concentrations of digest products should be identical, some discrimination against those fragments with <11 bases is observed, probably due to their loss in the ethanol/glycogen precipitation step. The quality of MS results from simultaneous digestion with CfoI (or HhaI) and RsaI is superior to those with CfoI (or HhaI) alone, since the smaller fragments generated are good for higher mass accuracy measurements, and with all genotypes there is no possibility for dimer peaks overlapping with high mass diagnostic peaks. Since digestion by RsaI/CfoI and RsaI/HhaI produce the same restriction fragments but the former may be performed as a simultaneous digest since their buffer requirements are the same, this enzyme mixture was used for all subsequent genotyping by restriction digest protocols.

TABLE V

Mass and Copy Number of Expected Restriction Digest Products

| Table Va CfoI Digestion[a] | | | | | | |
|---|---|---|---|---|---|---|
| (+) (−) | e2/e2 | e2/e2 | e2/e2 | e2/e2 | e2/e2 | e2/e2 |
| 5781, 5999 | — | — | 1 | — | 1 | 2 |
| 10752, 10921 | — | 1 | 1 | 2 | 2 | 2 |
| 14845, 14858 | — | 1 | 1 | 2 | 2 | 2 |
| 22102, 22440 | — | — | 1 | — | 1 | 2 |
| 25575, 25763 | 2 | 1 | 1 | — | — | — |
| 27849, 28436 | 2 | 2 | 1 | 2 | 1 | — |

| Table Vb. CfoI/RsaI Digestion[b] | | | | | | |
|---|---|---|---|---|---|---|
| (+) (−) | e2/e2 | e2/e3 | e2/e4 | e3/e3 | e3/e4 | e4/e4 |
| 3428, 4025 | — | 1 | 1 | 2 | 2 | 2 |
| 5283, 5880 | — | — | 1 | — | 1 | 2 |
| 5781, 5999 | — | — | 1 | — | 1 | 2 |
| 11279, 11627 | 2 | 2 | 1 | 2 | 1 | — |
| 14845, 14858 | — | 1 | 1 | 2 | 2 | 2 |
| 18269, 18848 | 2 | 2 | 1 | — | — | — |

[a]CfoI Invariant fragment masses: 1848, 2177, 2186, 2435, 4924, 5004, 5412, 5750, 8871, 9628 Da.
[b]CfoI/RsaI Invariant fragment masses: 1848, 2177, 2186, 2436, 4924, 5004, 5412, 5750, 6745, 7510, 8871, 9628, 16240, 17175 Da.

TABLE VI

| | ddT $M_r$ (Calc) | ddT $M_r$ (Exp) | ddC $M_5$ (Calc) | ddC $M_r$ (Exp) |
|---|---|---|---|---|
| e2/e2 | [a]5918, [b]6768 | — | [a]6536, [b]7387 | — |
| e2/e3 | [a]5918, [b]6768, [b]7965 | 5919, 6769, 7967 | [a]6536, [b]6753, [b]7387 | 6542, 6752, 7393 |
| e2/e4 | [a]5918, [b]6768, [b]7965, [a]8970 | — | [a]5903, [b]6536, [b]6753, [a]7387 | — |
| e3/e3 | [a]5918, [b]7965 | 5918, 7966 | [a]6536, [b]6753 | 6542, 6756 |
| e3/e4 | [a]5918, [b]7965, [a]8970 | 5914, 7959, 8965 | [a]5903, [b]6536, [b]6753 | 5898, 6533, 6747 |
| e4/e4 | [b]7965, [a]8970 | 7966, 8969 | [a]5903, [b]6753 | 5900, 6752 |

[a]From codon 112 detection primer (unextended 5629.7 Da).
[b]From codon 158 detection primer (unextended 6480.3 Da).
Dashed lines: this genotype not available from the analyzed pool of 100 patients.

Figure 58A:
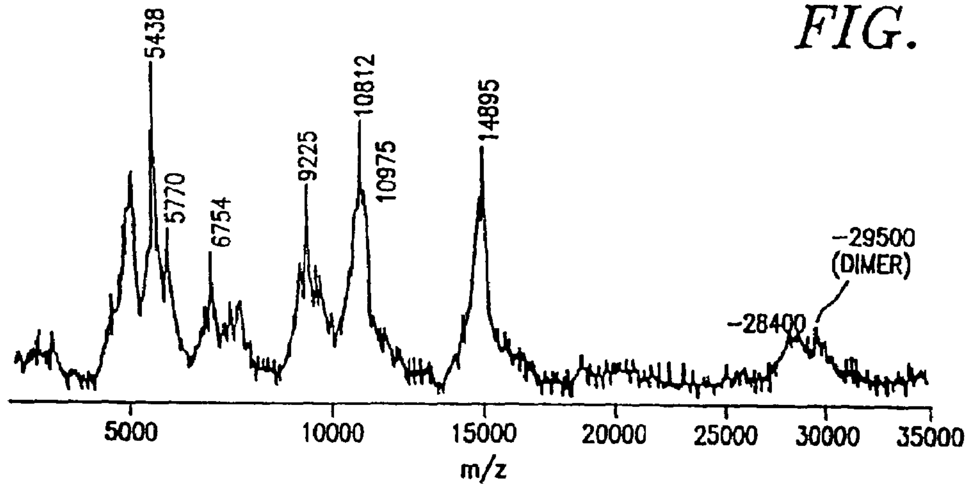
FIG. 58 shows a mass spectrum of the ApoE gene amplified product (ϵ3/ϵ3 genotype) digested by CfoI and purified by a) single and b) double ethanol/glycogen and c) double isopropyl alcohol/glycogen precipitations.
Figure 58B:
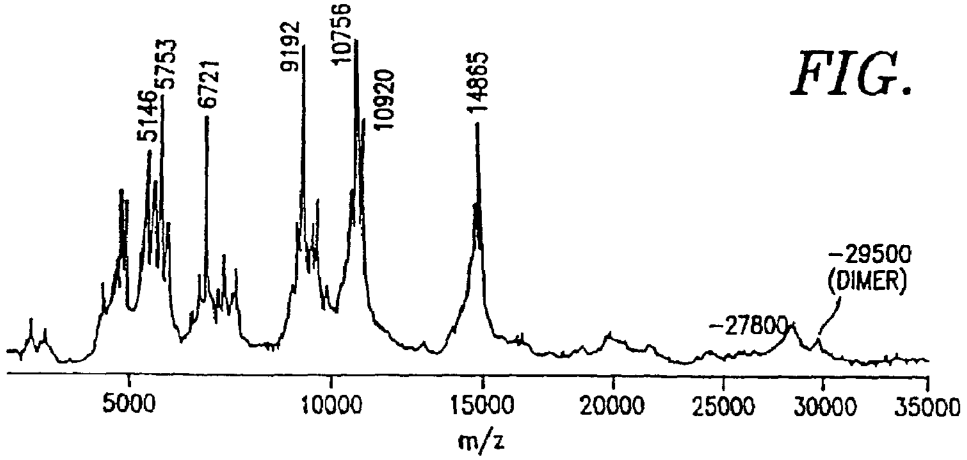
Figure 58C:
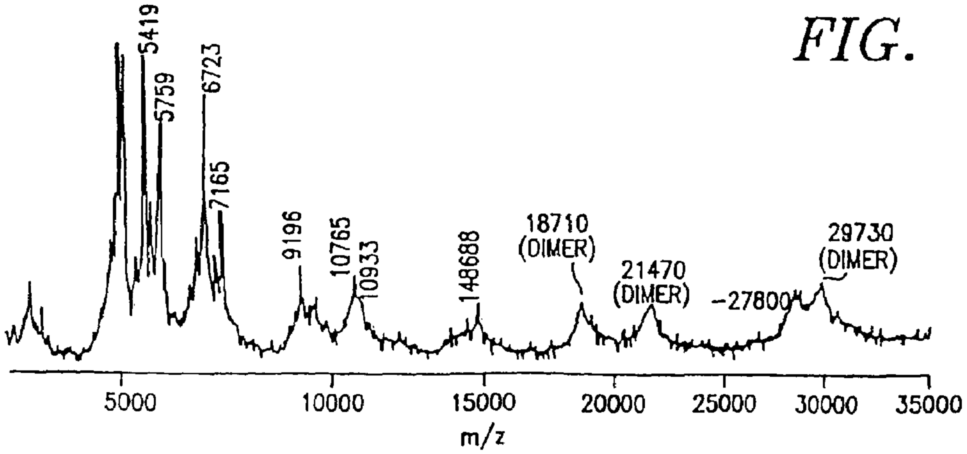

FIG. 58*a-c* shows the ApoE ∈3/∈3 genotype after digestion with CfoI and a variety of precipitation schemes; equal volume aliquots of the same amplified product were used for each. The sample treated with a single precipitation (FIG. 58*a*) from an ammonium acetate/ethanol/glycogen solution results in a mass spectrum characterized by broad peaks, especially at high mass. The masses for intense peaks at 5.4, 10.7, and 14.9 kDa are 26 Da (0.5%), 61 Da (0.6%), and 45 Da (0.3%) Da higher, respectively, than the expected values; the resolution (the ratio of a peak width at half its total intensity to the measured mass of the peak) for each of these is −50, and decreases with increasing mass. Such observations are consistent with a high level of nonvolatile cation adduction; for the 10.8 kDa fragment, the observed mass shift is consistent with a greater than unit ratio of adducted:nonadducted molecular ions.

MS peaks from a sample redissolved and precipitated a second time are far sharper (FIG. 58*b*), with resolution values nearly double those of the corresponding FIG. 58*a* peaks. Mass accuracy values are also considerably improved; each is within 0.07% of its respective calculated values, close to the independently determined instrumental limits for DNA measurement using 3-HPA as a matrix. Single (not shown) and double (FIG. 58C) precipitations with isopropyl alcohol (IPA) instead of ethanol result in resolution and mass accuracy values comparable to those for corresponding ethanol precipitations, but enhanced levels of dimerization are observed, again potentially confusing measurements when such dimers overlap with higher mass "diagnostics" monomers present in the solution. EtOH/ammonium acetate precipitation with glycogen as a nucleation agent results in nearly quantitative recovery of fragments except for the 7-mers, serving as a simultaneous concentration and desalting step prior to MS detection. Precipitation from the same EtOH/ammonium acetate solutions in the absence of glycogen results in far poorer recovery, especially at low mass.

The results indicate that to obtain accurate ($M_r$(exp) values after either 1PA and EtOH precipitations, a second precipitation is necessary to maintain high mass accuracy and resolution.

The ratio of matrix:digest product also affects spectral quality; severe suppression of higher mass fragments (not shown) observed with 1:1 volume matrix: digest product (redissolved in 1 μL) is alleviated by using a 3-5 fold volume excess of matrix.

Apo E genotyping by enzymatic digestion. Codon 112 and 158 polymorphisms fall within CfoI (but not RsaI) recognition sequences. In the 252 bp amplified product studied here, invariant (i.e. cut in all genotypes) sites cause cuts after bases 31, 47, 138, 156, 239, and 246. The cutting site after base 66 is only present for ∈4, while that after base 204 is present in ∈3 and ∈4; the ∈2 genotype is cut at neither of these sites. These differences in the restriction pattern can be demonstrated as variations in mass spectra. FIG. 59 shows mass spectra from several ApoE genotypes available from a pool of 100 patients (Braun, A et al., (1992) *Hum. Genet.* 89: 401-406). Vertical dashed lines are drawn through those masses corresponding to the expected Table V diagnostic fragments; other labeled fragments are invariant. Referring to Table V, note that a fragment is only considered "invariant" if it is present in duplicate copies for a given allele; to satisfy this requirement, such a fragment must be generated in each of the ∈2m ∈3, and ∈4 alleles.

Figure 59A:
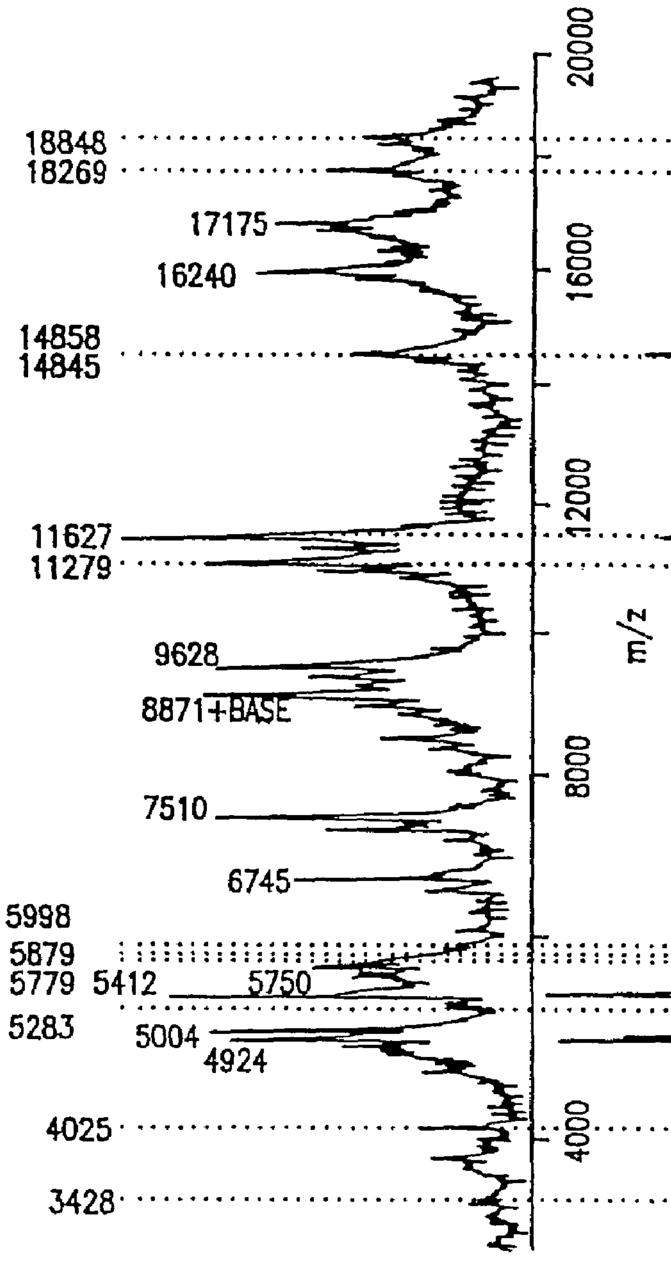
FIG. 59 shows a mass spectrum of the CfoI/RsaI digest products from a) ϵ2/ϵ3, b) ϵ3/ϵ3, c) ϵ3/ϵ4, and d) ϵ4/ϵ4 genotypes. Dashed lines are drawn through diagnostic fragments.
Figure 59B:
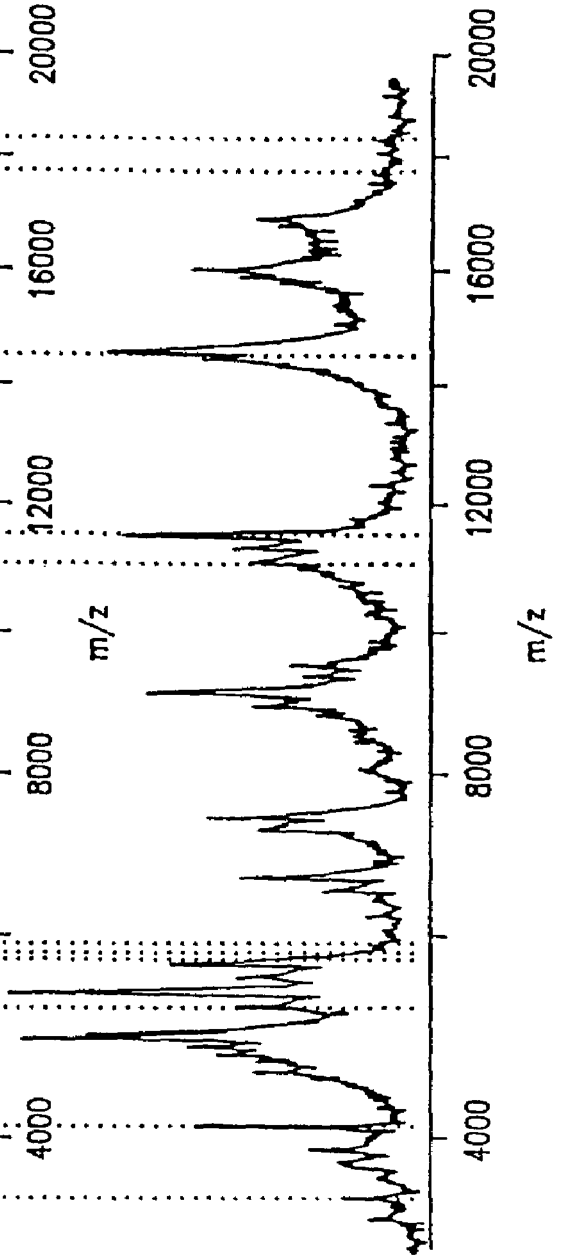
Figure 59C:
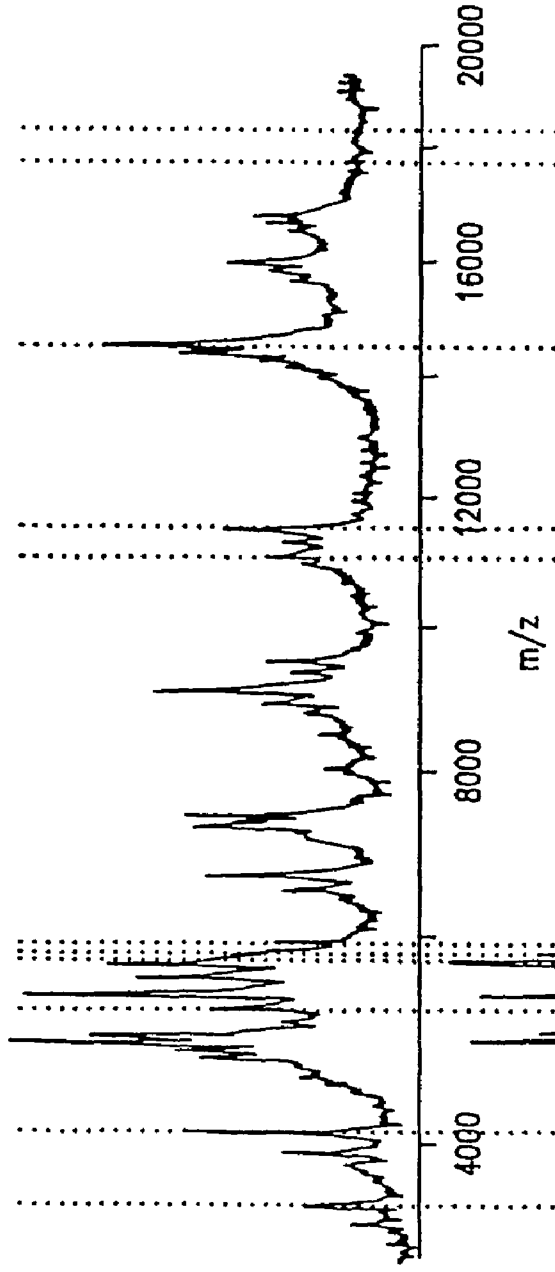
Figure 59D:
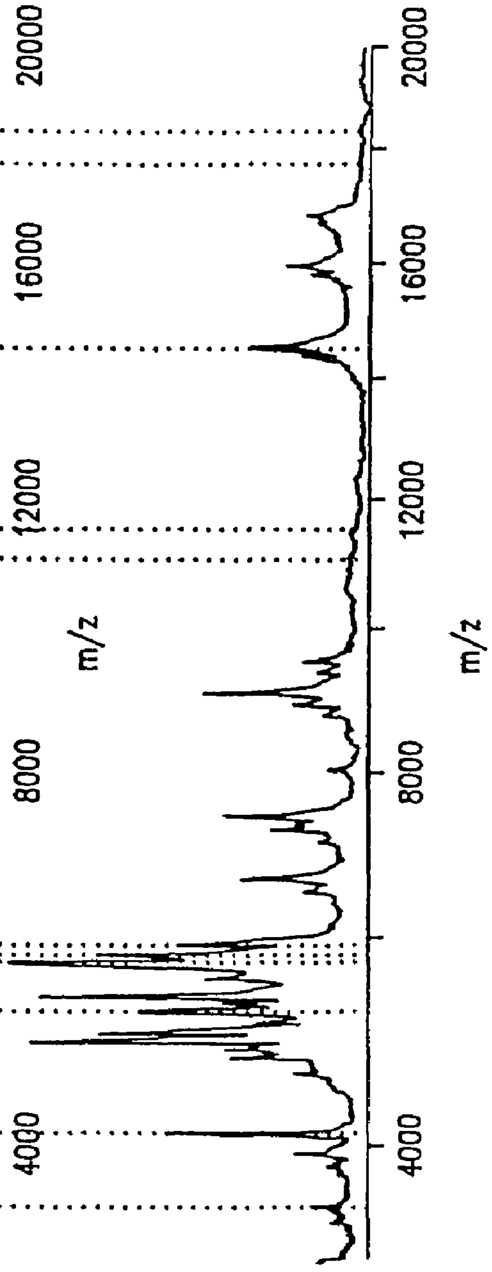

The spectrum in FIG. 59*a* contains all of the expected invariant fragments above 3 kDa, as well as diagnostic peaks at 3428 and 4021 (both weak), 11276 and 11627 (both intense), 14845, 18271, and 18865 Da. The spectrum in FIG. 59*b* is nearly identical except that the pair of peaks at 18 kDa is not detected, and the relative peak intensities, most notably among the 11-18 kDa fragments, are different. The spectrum in FIG. 59*c* also has no 18 kDa fragments, but instead has new low intensity peaks between 5-6 kDa. The intensity ratios for fragments above 9 kDa are similar to those of FIG. 59*b* except for a relatively lower 11 kDa fragment pair. FIG. 59*d*, which again contains the 5-6 kDa cluster of peaks, is the only spectrum with no 11 kDa fragments, and like the previous two also has no 18 kDa fragment.

Despite the myriad of peaks in each spectrum, each genotype can be identified by the presence and absence of only a few of the Table Vb diagnostic peaks. Due to the limited resolution of the MALDI-TOF instrumentation employed, the most difficult genotypes to differentiate are those based upon the presence or absence of the four diagnostic fragments between 5.2 and 6.0 kDa characteristic of the $\epsilon^4$ allele, since these fragments nearly overlap with several invariant peaks. It has been found herein that the 5283 Da diagnostic fragment overlaps with a depurination peak from the 5412 Da invariant fragment, and the 5781 Da diagnostic peak is normally not completely resolved from the 5750 Da invariant fragment. Thus, distinguishing between an ϵ2/ϵ4 and ϵ2/ϵ3, or between an ϵ3/ϵ4 and an ϵ3/ϵ3 allele, relies upon the presence or absence of the 5880 and 5999 Da fragments. Each of these is present in FIGS. 59*c* and 59*d*, but not in 59*a* or 59*b*.

Figure 60:
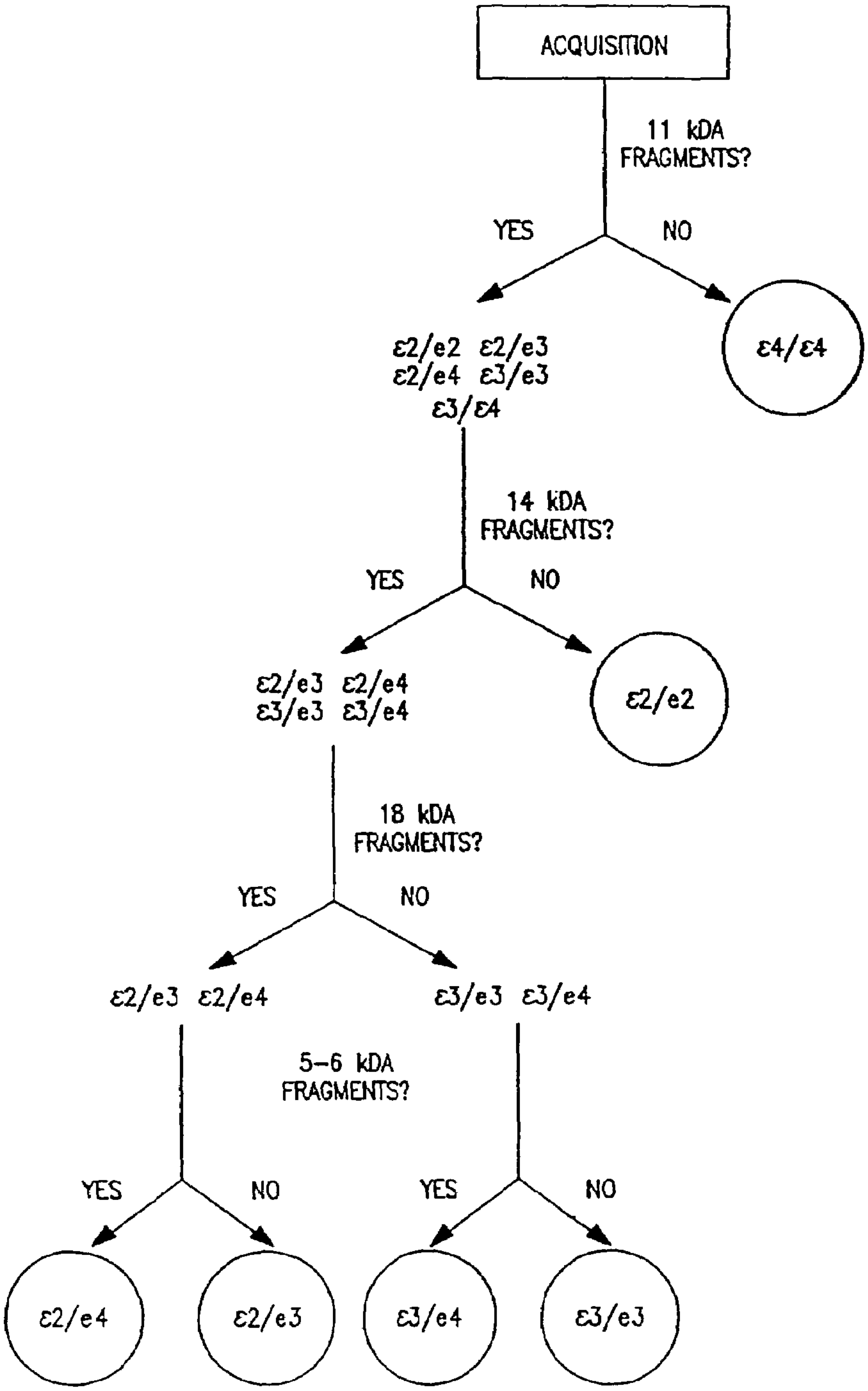
FIG. 60 shows a scheme for rapid identification of unknown ApoE genotypes following simultaneous digestion of a 252-mer apo E gene amplified product by the restriction enzymes CfoI and RsaI.

The genotype of each of the patients in FIG. 59 can be more rapidly identified by reference to the flowchart in FIG. 60. Consider the FIG. 59*a* spectrum. The intense pair of peaks at 11 kDa discounts the possibility of homozygous ϵ4, but does not differentiate between the other five genotypes. Likewise, the presence of the unresolved 14.8 kDa fragments is inconsistent with homozygous ϵ2, but leaves four possibilities (ϵ2/ϵ3, ϵ2/ϵ4, ϵ3/ϵ3, ϵ3/ϵ4). Of these only ϵ2/ϵ3 and ϵ2/ϵ4 are consistent with the 18 kDa peaks; the lack of peaks at 5283, 5879, 5779, and 5998, Da indicate that the FIG. 59*a* sample is ϵ2/ϵ3. Using the same procedure, the FIGS. 59*b-d* genotypes can be identified as ϵ3/ϵ3, ϵ3/ϵ4, and ϵ4/ϵ4, respectively. To date, all allele identifications by this method have been consistent with, and in many cases more easily interpreted than, those attained via conventional methods. The assignment can be further confirmed by assuring that fragment intensity ratios are consistent with the copy numbers of Table V. For instance, the 14.8 kDa fragments are of lower intensity than those at 16-17 kDa in FIG. 59*a*, but the opposite is seen in FIGS. 59*b-d*. This is as expected, since in the latter three genotypes the 14.8 kDa fragments are present in duplicate, but the first is a heterozygote containing ϵ2, so that half of the amplified products do not contribute to the 14.8 kDa signal. Likewise, comparison of the 11 kDa fragment intensify to those at 9.6 and 14.8 kDa indicate that this fragment is double, double, single, and zero copy in FIGS. 59*a, d*, respectively. These data confirm that MALDI can perform in a semi-quantitative way under these conditions.

ApoE genotyping by Primer Oligo Base Extension (PROBE). The PROBE reaction was also tested as a means of simultaneous detection of the codon 112 and 158 polymorphisms. A detection primer is annealed to a single-stranded PCR-amplified template so that its 3' terminus is just downstream of the variable site. Extension of this primer by a DNA polymerase in the presence of three dNTPs and one ddXTP (that is not present as a dNTP) results in products whose length and mass depend upon the identity of the polymorphic base. Unlike standard Sanger type sequencing, in which a particular base-specific tube contains –99% dXTP and –1% ddXTP, the PROBE mixture contains 100% of a particular ddXTP combined with the other three dNTPs. Thus with PROBE a full stop of all detection primers is achieved after the first base complementary to the ddXTP is reached.

For the ϵ2/ϵ3 genotype, the PROBE reaction (mixture of ddTTP, dATP, dCTP, dGTP) causes a $M_r$(exp) shift of the codon 112 primer to 5919 Da, and of the codon 158 primer to 6769 and 7967 Da (Table VI); a pair of extension products results from the single codon 1 58 primer because the ϵ2/ϵ3 genotype is heterozygous at this position. Three extension products (one from codon 158, two from 112) are also observed from the heterozygote ϵ3/ϵ4 (FIG. 61*c* and Table VI), while only two products (one from each primer) are observed from the FIG. 61*b* (ϵ3/ϵ3) and FIG. 59*d* (ϵ4/ϵ4) homozygote alleles. Referring to Table VI, each of the available alleles result in all expected ddT reaction product masses within 0.1% of the theoretical mass, and thus each is unambiguously characterized by this data alone. Further configuration of the allele identities may be obtained by repeating the reaction with ddCTP (plus dATP, dTTP, dGTP); these results, summarized also in Table VI, unambiguously confirm the ddT results.

Appropriateness of the methods. Comparison of FIGS. 59 (restriction digestion) and 61 (PROBE) indicates that the PROBE method provides far more easily interpreted spectra for the multiplex analysis of codon 112 and 158 polymorphisms than does the restriction digest analysis. While the digests generate up to –25 peaks per mass spectrum and in some case diagnostic fragments overlapping with invariant fragments, the PROBE reaction generates a maximum of only two peaks per detection primer (i.e. polymorphism). Automated peak detection, spectrum analysis, and allele identification would clearly be far more straightforward for the latter. Spectra for highly multiplexed PROBE, in which several polymorphic sites from the same or different amplified products are measured from one tube, are also potentially simple to analyze. Underscoring its flexibility, PROBE data analysis can be further simplified by judicious a priori choice of primer lengths, which can be designed so that no primers or products can overlap in mass.

Thus while PROBE is the method of choice for large scale clinical testing of previously well characterized polymorphic sites, the restriction digest analysis as described here is ideally suited to screening for new mutations. The identity of each of the two polymorphisms discussed in this study affects the fragment pattern; if this is the only information used, then the MS detection is a faster alternative to conventional electrophoretic separation of restriction fragment length polymorphism products. The exact measurement of fragment $M_r$ values can also give information on about sites completely remote from the enzyme recognition site since other single point mutations necessarily alter the mass of each of the single strands of the double stranded fragment containing the mutation. The 252 bp amplified product could also contain allelic variants resulting in, for example, previously described Glyl27 Asp (Weisgraber, K H et al., (1984) *J. Clin. Invest.* 73: 1024-1033), Argl36Ser (Wardell, M R et al., (1987) *J. Clin. Invest.* 80: 483-490), Argl42Cys (Horie, Y et al., (1992) *J. Biol. Chem.* 267: 1962-1968), Arg145Cys (Rall S C Jr et al., (1982) *Proc. Natl. Acad. Sci. U.S.A.* 79: 4696-4700), Lysl46Glu (Mann, W A et al., (1995) *J. Clin. Invest.* 96: 1100-1107), or Lysl46Gln (Smit, M et al., (1990) *J. Lipid Res.* 31: 45-53) substitutions. The G→A base substitution which codes for the Gly127 Asp amino acid substitution would result in a –16 Da shift in the sense strand, and in a +15 Da (C→T) shift in the antisense strand, but not in a change in the restriction pattern. Such a minor change would be virtually invisible by electrophoresis; however, with accurate mass determination the substitution could be detected; the invariant 55-mer fragment at 16240 (sense) and 17175 Da would shift to 16224 and 17190 Da, respectively. Obtaining the mass accuracy required to detect such minor mass shifts using current MALDI-TOF instrumentation, even with internal calibration, is not routine since minor unresolved adducts and/or poorly defined peaks limit the ability for accurate mass calling. With high performance electrospray ionization Fourier transform (ESI-FTMS) single Da accuracy has been achieved with synthetic oligonucleotides (Little, D P et al., (1995) *Proc. Natl. Acad. Sci. U.S.A.* 92: 2318-2322) up to 100-mers (Little, D P et al., (1994) *J. Am. Chem. Soc.* 116:

4893-4897), and similar results have recently been achieved with up to 25-mers using MALDI-FTMS (Li, Y et al., (1996) *Anal. Chem.* 68: 2090-2096).

EXAMPLE 13

A Method for Mass Spectrometric Detection of DNA Fragments Associated With Telomerase Activity Introduction One-fourth of all deaths in the United States are due to malignant tumors (R. K. Jain, (1996) *Science* 271:1079-1080). For diagnostic and therapeutic purposes there is a high interest in reliable and sensitive methods of tumor cell detection.

Malignant cells can be distinguished from normal cells by different properties. One of those is the immortalization of malignant cells which enables uncontrolled cell-proliferation. Normal diploid mammalian cells undergo a finite number of population doublings in culture, before they undergo senescence. It is supposed that the number of population doublings in culture, before they undergo senescence. It is supposed that the number of population doublings is related to the shortening of chromosome ends, called telomers, in every cell division. The reason for said shortening is based on the properties of the conventional semiconservative replication machinery. DNA polymerases only work in 5' to 3' direction and need an RNA primer.

Immortalization is thought to be associated with the expression of active telomerase. Said telomerase is a ribonucleoprotein catalyzing repetitive elongation of templates. This activity can be detected in a native protein extract of telomerase containing cells by a special PCR-system (N. W. Kim et al. (1994) *Science* 266: 2011-2015) known as telomeric repeat amplification protocol (TRAP). The assay, as used herein, is based on the telomerase specific extension of a substrate primer (TS) and a subsequent amplification of the telomerase specific extension products by a PCR step using a second primer (bioCX) complementary to the repeat structure. The characteristic ladder fragments of those assays are conventionally detected by the use of gel electrophoretic and labeling or staining systems. These methods can be replaced by MALDI-TOF mass spectrometry leading to faster accurate and automated detection.

Materials and Methods

Preparation of Cells $1\times10^6$ cultured telomerase-positive cells were pelleted, washed once with PBS (137 mM NaCl, 2.7 mM KCl, 4.3 mM $Na_2HPO_4.7H_2O$, 1.4 mM $KH_2PO_4$ in sterile DEPC water). The prepared cells may be stored at −75° C. Tissue samples have to be homogenized, according to procedures well known in the art, before extraction.

Telomerase Extraction

Pellet was resuspended in 200 µl CHAPS lysis buffer (10 mM Tris-HCl pH 7.5, 1 mM $MgCl_2$, 1 mM EGTA, 0.1 mM benzamidine, 5 mM β-mercaptoethanol, 0.5% CHAPS, 10% glycerol) and incubated on ice for 30 min. The sample was centrifuged at 12,000 g for 30 min at 4° C. The supernatant was transferred into a fresh tube and stored at 75° C. until use.

TRAP-assay

2 µl of telomerase extract were added to a mixture of 10×TRAP buffer (200 mM Tris-HCl pH 8.3, 15 mM $MgCl_2$, 630 mM KCl, 0.05% Tween 20, 10 mM EGTA) 50×dNTP-mix (2.5 mM each dATP, dTTP, dGTP, and dCTP), 10 pmol of TS primer and 50 pmol of bio CX primer in a final volume of 50 µl. The mixture was incubated at 30° C. for 10 minutes and 5 min. at 94° C., 2 units of Taq Polymerase were added and a PCR was performed with 30 cycles of 94° C. for 30 seconds, 50° C. for 30 seconds and 72° C. for 45 seconds.

Purification of TRAP-assay Products

For every TRAP-assay to be purified, 50 µl Streptavidin M-280 Dynabeads (10 mg/ml) were washed twice with 1×BW buffer (5 mM Tris-HCl, pH 7.5, 0.5 mM EDTA, 1 M NaCl). 50 µl of 2×BW buffer were added to the PCR mix and the beads were resuspended in this mixture. The beads were incubated under gentle shaking for 15 min. at ambient temperature. The supernatant was removed and the beads were washed twice with 1×BW buffer. To the beads 50 µl 25% ammonium hydroxide were added and incubated at 60° C. for 10 min. The supernatant was saved, the procedure repeated, both supernatants were pooled and 300 µl ethanol (100%) were added. After 30 min. the DNA was pelleted at 13,000 rpm for 12 min., the pellet was air-dried and resuspended in 600 nl ultrapure water.

MALDI-TOF MS of TRAP-assay Products 300 nl sample were mixed with 500 nl of saturated matrix-solution (3-HPA:ammonium citrate=10:1 molar ratio in 50% aqueous acetonitrile), dried at ambient temperature and introduced into the mass spectrometer (Vision 2000, Finigan MAT). All spectra were collected in reflector mode using external calibration.

Sequences and Masses

```
bioCX: d(bio-CCC TTA CCC TTA CCC TTA CCC TAA

SEQ ID NO:45), mass: 7540 Da.

TS: d(AAT CCG TGC AGC AGA GTT SEQ ID NO:46),

mass: 5523 Da.
```

Telomeric-repeat structure: $(TTAGGG)_n$, mass of one repeat: 1909.2

Amplification Products:

TS elongated by three telomeric repeats (first amplification product): 12452 Da. ($N_3$)

TS elongated by four telomeric repeats: 14361 Da. ($N_4$)

TS elongated by seven telomeric repeats: 20088 Da. ($N_7$)

Results

Figure 62:
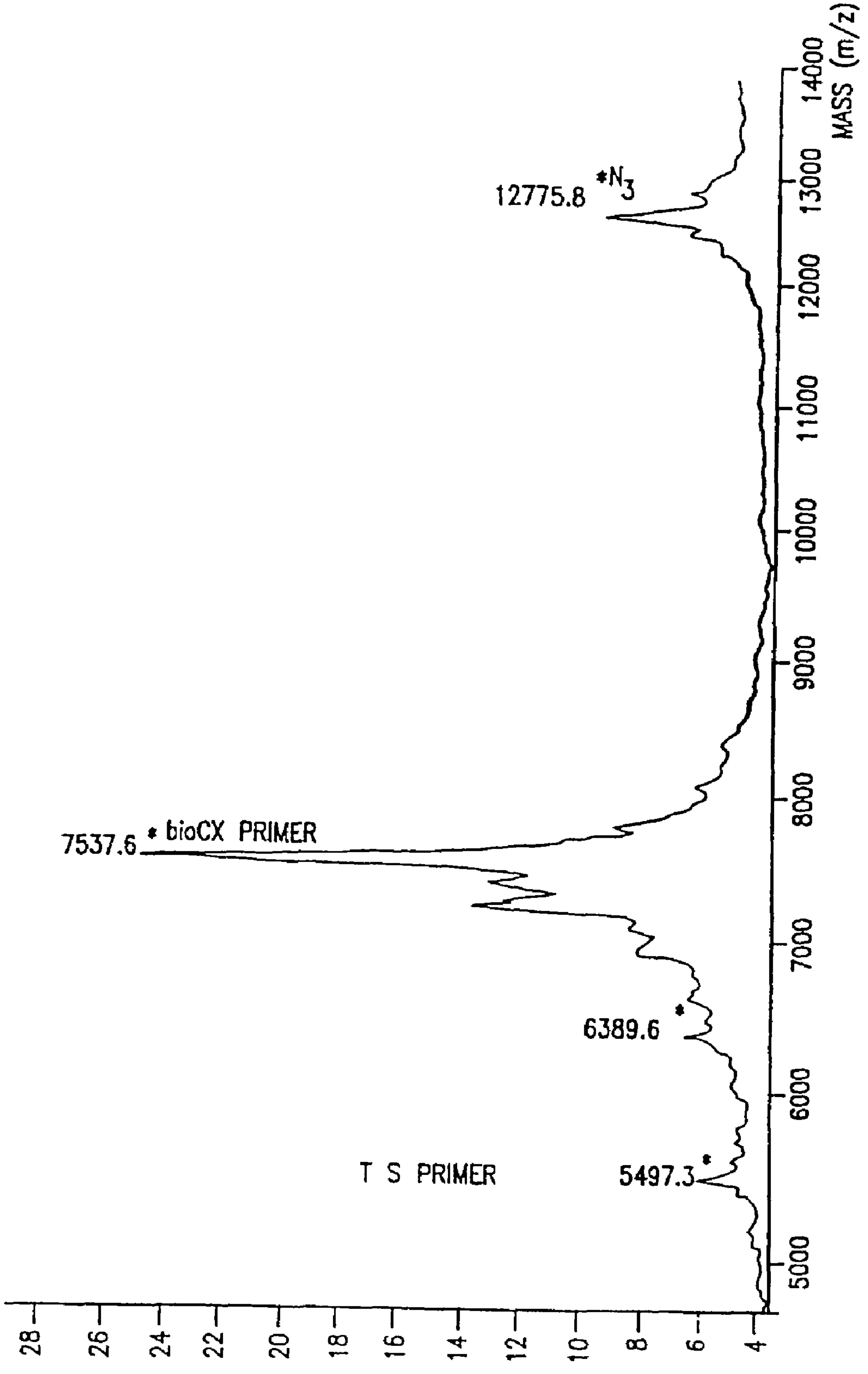
FIG. 62 shows a mass spectrum of a TRAP assay to detect telomerase activity (Example 13). The spectrum shows two of the primer signals of the amplified product TS primer at 5,497.3 Da (calc. 5523 Da) and the biotinylated bioCX primer at 7,537.6 Da (calc. 7,537 Da) and the first telomerase-specific assay product containing three telomeric repeats at 12,775.8 Da (calc. 12,452 Da) its mass is larger by one dA nucleotide (12,765 Da) due to extendase activity of Taq DNA polymerase.
Figure 63:
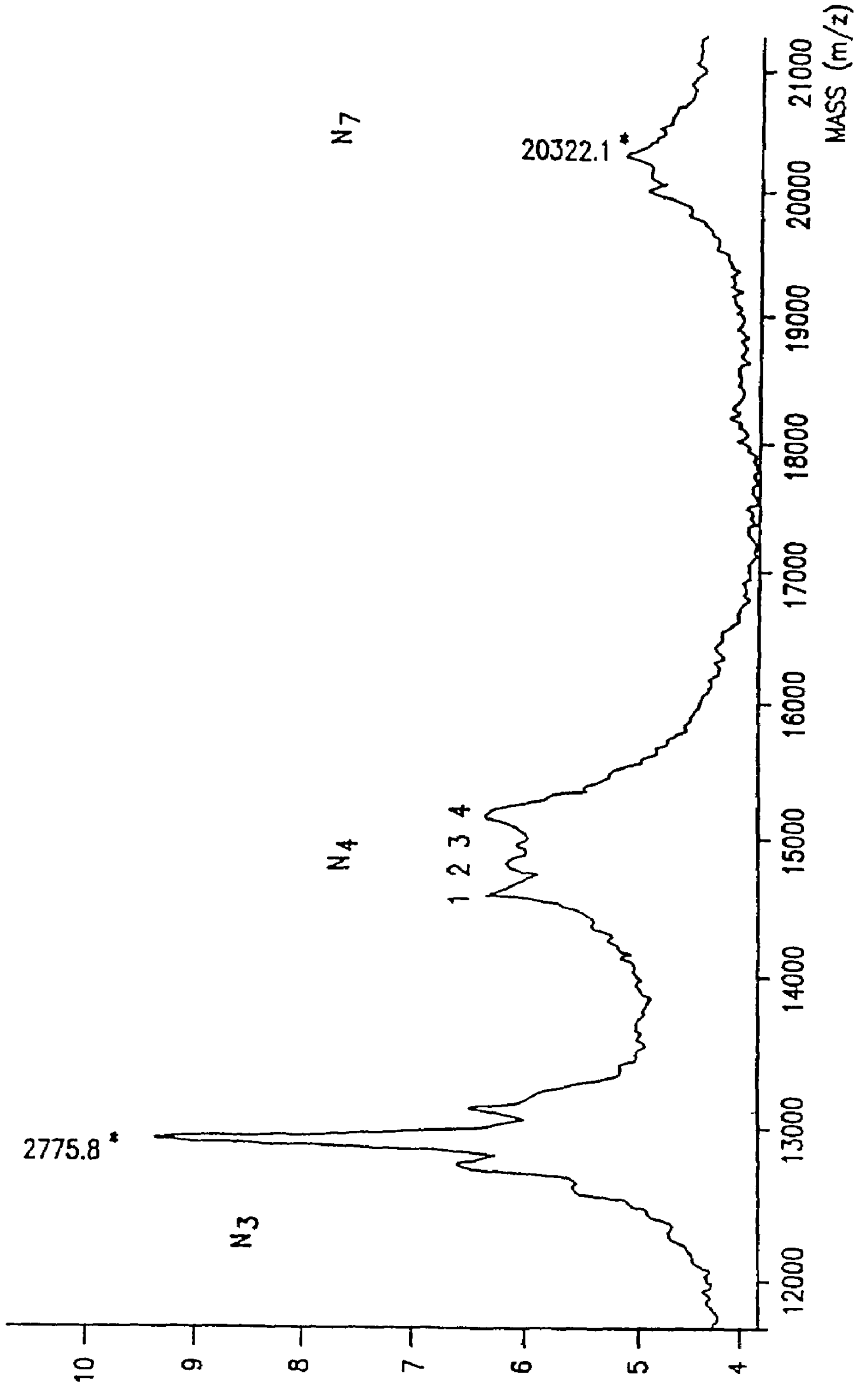
FIG. 63 depicts the higher mass range of FIG. 62, i.e. the peak at 12,775.6 Da represents the products with these telomeric repeats. The peaks at 20,322.1 Da is the result of a telomerase activity to form seven telomeric repeats (calc. 20,395 Da including the extension by one dA nucleotide). The peaks marked 1, 2, 3 and 4 contain a four telomeric repeats at 14,674 Da as well as secondary ion product.

FIG. 62 depicts a section of a TRAP-assay MALDI-TOF mass spectrum. Assigned are the primers TS and bioCX at 5497 and 7537 Da, respectively (calculated 5523 and 7540 Da). The signal marked by an asterisk represents n-1 primer product of chemical DNA synthesis. The first telomerase specific TRAP-assay product is assigned at 12775 Da. This product represents a 40-mer containing three telomeric repeats. Due to primer sequences this is the first expected amplification product of a positive TRAP-assay. The product is elongated by an additional nucleotide due to extendase activity of Taq DNA polymerase (calculated non-extended product: 12452 Da, by A extended product: 12765 Da). The signal at 6389 Da represents the doubly charged ion of this product (calculated: 6387 Da). FIG. 63 shows a section of higher masses of the same spectrum as depicted in FIG. 62, therefore the signal at 12775 Da is identical to that in FIG. 62. The TRAP-assay product containing seven telomeric repeats, representing a 64-mer also elongated by an additional nucleotide, is detected at 20322 Da (calculated: 20395 Da). The signals marked 1, 2, 3 and 4 cannot be base-line resolved. This region includes of: 1. signal of dimeric n-1 primer, 2. second TRAP-assay amplification product, containing 4 telemeric repeats and therefore representing a 46-mer (calculated:

14341 Da/14674 Da for extendase elongated product) and 3. dimeric primer-ion and furthermore all their corresponding depurination signals. There is a gap observed between the signals of the second and fifth extension product. This signal gap corresponds to the reduced band intensities observed in some cases for the third and fourth extension product in autoradiographic analysis of TRAP-assays (N. W. Kim et al. (1994) *Science* 266: 2013).

The above-mentioned problems, caused by the dimeric primer and related signals, can be overcome using an ultrafiltration step employing a molecular weight cut-off membrane for primer removal prior to MALDI-TOF-MS analysis. This will permit an unambiguous assignment of the second amplification product.

EXAMPLE 14

A Method for Detecting Neuroblastoma-Specific Nested RT-amplified Products Via MALDI-TOF Mass Spectrometry Introduction Neuroblastoma is predominantly a tumor of early childhood with 66% of the cases presenting in children younger than 5 years of age. The most common symptoms are those due to tumor mass, bone pain, or those caused by excessive catecholamine secretion. In rare cases, neuroblastoma can be identified prenatally (R. W. Jennings et al, (1993) *J. Ped. Surgery* 28: 1168-1174). Approximately 70% of all patients with neuroblastoma have metastatic disease at diagnosis. The prognosis is dependent on age at diagnosis, clinical stage and other parameters.

For diagnostic purposes there is a high interest in reliable and sensitive methods of tumor cell detection, e.g., in control of autologous bone marrow transplants or on-going therapy.

Since catecholamine synthesis is a characteristic property of neuroblastoma cells and bone marrow cells lack this activity (H. Naito et al., (1991) *Eur. J. Cancer* 27: 762-765), neuroblastoma cells or metastasis in bone marrow can be identified by detection of human tyrosine 3-hydroxylase (E.C. 1.1 4.1 6.2, hTH) which catalyzes the first step in biosynthesis of catecholamines.

The expression of hTH can be detected via reverse transcription (RT) polymerase chain reaction (PCR) and the amplified product can be analyzed via MALDI-TOF mass spectrometry.

Materials and Methods

Cell- or Tissue-treatment

Cultures cells were pelleted (10 min. 8000 rpm) and washed twice with PBS (137 mM NaCl, 2.7 mM KCl, 4.3 mM $Na_2HPO_4.7H_2O$, 1.4 mM $KH_2PO_4$ in sterile PEPC water). The pellet was resuspended in 1 ml lysis/binding buffer (100 mM Tris-HCl, pH 8.0, 500 mM LiCl, 10 mM EDTA, 1% Li-dodecyl sulfate, 5 mM DTT) until the solution becomes viscose. Viscosity was reduced by DNA-shear step using a 1 ml syringe. The lysate may be stored in −75° C. or processed further directly. Solid tissues (e.g., patient samples) have to be homogenized before lysis.

Preparation of Magnetic Oligo-dT(25) Beads

100 μL beads per $1\times10^6$ cells were separated from the storage buffer and washed twice with 200 μL lysis/binding buffer.

Isolation of Poly $A^+$ RNA

The cell lysate was added to the prepared beads and incubated for 5 min. at ambient temperature. The beads were separated magnetically for 2-5 min. and washed twice with 0.5 ml LDS (10 mM Tris-HCl, pH 8.0, 0.15 M LiCl, 1 mM EDTA, 0.1% LiDS).

Solid-phase First-strand cDNA Synthesis

The poly $A^+$ RNA containing beads were resuspended in 20 μL of reverse transcription mix (50 mM Tris-HCl, pH 8.3, 8 mM $MgCl_2$, 30 mM KCl, 10 mM DTT, 1.7 mM dNTPs, 3 U AMV reverse transcriptase) and incubated for 1 hour at 45° C. (with a resuspension step all ten min.). The beads were separated from the reverse transcription mix, resuspended in 50 μL of elution buffer (2 mM EDTA pH 8.0) and heated to 95° C. for 1 min. fur elution of the RNA. The beads with the cDNA first-strand can be stored in TB (0.089 M Tris-base, 0.089 M boric acid, 0.2 mM EDTA pH 8.0), TE 10 mM Tris-HCl, 0.1 mM EDTA, pH 8.0) or 70% ethanol for further processing.

Nested Polymerase Chain Reaction

Beads containing cDNA first-strand were washed twice with 1×PCR buffer (20 mM Tris-HCl pH 8.75, 10 mM KCl, 10 mM $(NH_4)_2SO_4$, 2 mM $MgSO_4$, 0.1% Triton X-100, 0.1 mg bovine serum albumin) and resuspended in PCR mix (containing 100) pmol of each outer primer, 2.5 u Pfu (exo-) DNA polymerase, 200 μM of each dNTP and PCR buffer in a final volume of 50 μL). The mixture was incubated at 72° C. 1 min. and amplified by PCR for 30 cycles. for the nested reaction: 1 μL of the first PCR was added as template to a PCR mix d(as above but nested primers instead of outer primers) and subjected to the following temperature program: 94° C. 1 min., 65° C. 1 min. and 72° C. 1 min. for 20 cycles.

Purification of Nested Amplified Products

Primers and low-molecular reaction by-products are removed using 10,000 Da cut-off ultrafiltration-unit. Ultrafiltration was performed at 7,500 g for 25 minutes. For every PCR to be purified, 50 μL Streptavidin M-280 Dynabeads (10 mg/ml) were washed twice with 1×BW buffer (5 mM Tris-HCl, pH 7.5, 0.5 mM EDTA, 1 M NaCl), added to the ultrafiltration membrane and incubated under gentle shaking for 15 min. at ambient temperature. The supernatant was removed and the beads were washed twice with 1×BW buffer. 50 μL 25% ammonium hydroxide were added to the beads and incubated at ambient temperature for 10 min. The supernatant was saved, the procedure repeated, both supernatants were pooled and 300 μL ethanol (100%) were added. After 30 min. the DNA was pelleted at 13,000 rpm for 12 min., the pellet was air-dried and resuspended in 600 nl ultrapure water.

MALDI-TOF MS of Nested Amplified Products 300 nl sample was mixed with 500 nl of saturated matrix-solution (3-HPA: ammonium citrate=10:1 molar ratio in 50% aqueous acetonitrile), dried at ambient temperature and introduced into the mass spectrometer (Vision 2000, Finigan MAT). All spectra were collected in reflector mode using external calibration.

```
Outer primers:
hTH1: d(TGT CAG AGC TGG ACA AGT GT SEQ ID NO:47)

hTH2: d(GAT ATT GTC TTC CCG GTA GC SEQ ID NO:48)

Nested primers:
bio-hTH d(bio-CTC GGA CCA GGT GTA CCG CC SEQ ID

NO:49), mass: 6485 Da

hTH6: d(CCT GTA CTG GAA GGC GAT CTC SEQ ID NO:50),

mass:6422 21 Da

mass of biotinylated single strand amplified
```

-continued

```
product: 19253:6 Da

mass of nonbiotinylated single strand amplified

product: 18758.2 Da
```

Results

Figure 64:
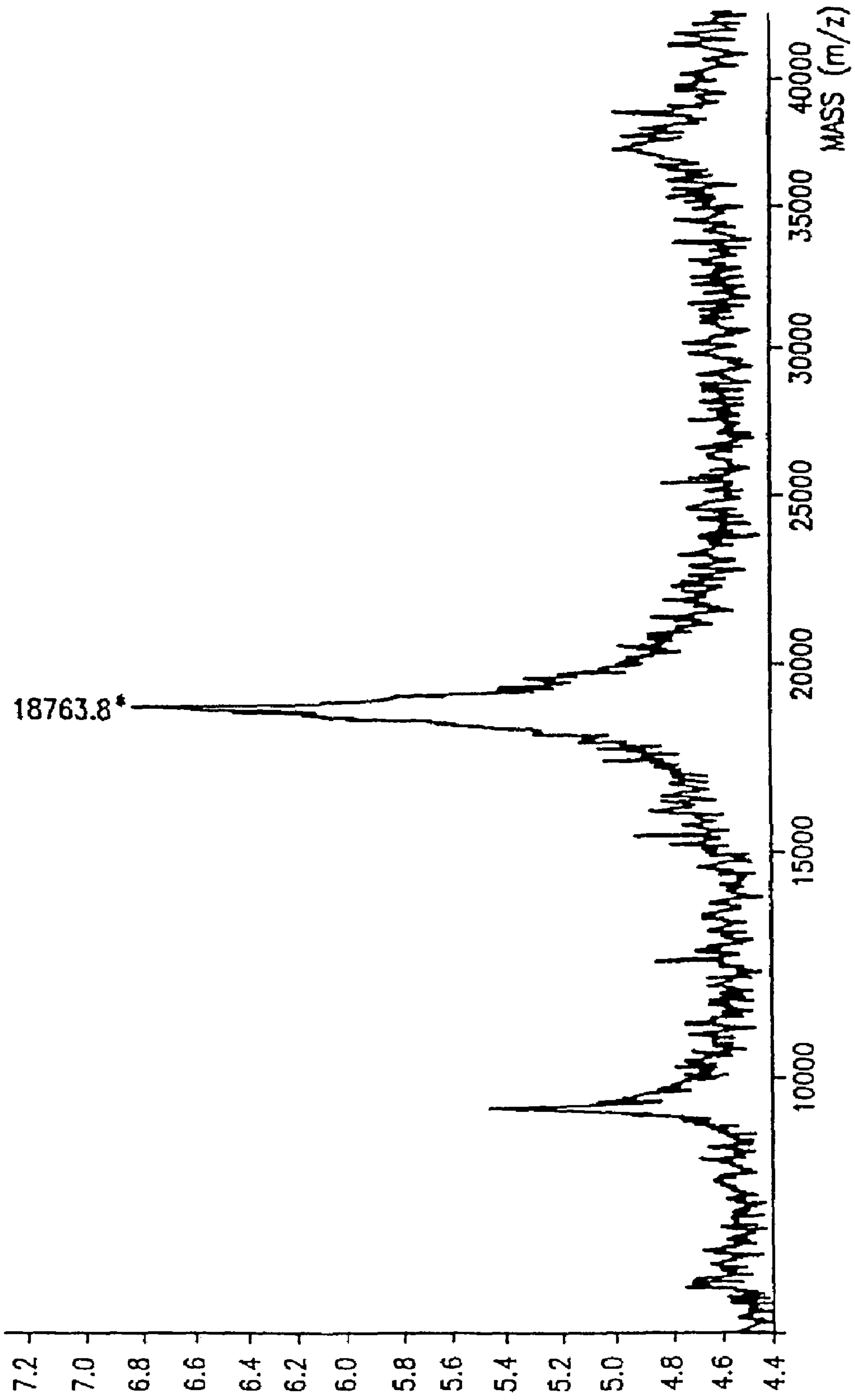
FIG. 64 displays a MALDI-TOF spectrum of the RT-amplified product of the human tyrosine hydroxylase mRNA indicating the presence of neuroblastoma cells (Example 14). The signal at 18,763.8 Da represents the non-biotinylated single-stranded 61 mer of the nested amplified product (calc. 18,758.2 Da).

A MALDI-TOF mass spectrum of a human tyrosine 3-hydroxylase (hTH) specific nested amplified product (61-mer) is depicted in FIG. 64. The signal at 18763 Da corresponds to non-biotinylated strand of the amplified product (calculated: 18758.2 Da, mass error: 0.02 Da). The signals below 10,000 and above 35,000 Da are due to multiply charged and dimeric amplified product-ions, respectively.

The product was obtained from a solid phase cDNA derived in a reverse transcription reaction from $1\times10^6$ cells of a neuroblastoma cell-line (L-A-N-1) as described above. The cDNA first-strand was subjected to a first PCR using outer primers (hTH1 and hTH2), an aliquot of this PCR was used as template in a second PCR using nested primers (biohTH and hTH6). The nested amplified product was purified and MALDI-TOF MS analyzed:

The spectrum in FIG. 64 demonstrates the possibility of neuroblastoma cell detection using nested RT-PCR and MALDI-TOF MS analysis.

EXAMPLE 15

Rapid Detection of the RET Proto-oncogene Codon 634 Mutation Using Mass Spectrometry Material and Methods Probe The identity of codon 634 in each of the three alleles was confirmed by Rsal enzymatic digestion, single strand conformational polymorphism or Sanger sequencing. Exon 11 of the RET gene was PCR amplified (40 cycles) from genomic DNA using Taq-Polymerase (Boehringer-Mannheim) with 8 pmol each of 5'-biotinylated forward (5'-biotin-CAT GAG GCA GAG CAT ACG CA-3' SEQ ID NO: 51) and unmodified reverse (5'-GAC AGC AGC ACC GAG ACG AT-3' SEQ ID NO: 52) primer per tube; amplified products were purified using the Qiagen (QIAquick" kit to remove unincorporated primers. 15 μl of amplified product were immobilized on 10 μL (10 mg/mL) Dynal streptavidin coated magnetic beads, denatured using the manufacturer's protocol, and the supernatant containing antisense strand discarded, the PROBE reaction was performed using thermoSequenase (TS) DNA Polymerase (Amersham) and Pharmacia dNTP/ddNTPs. 8 pmol of extension primer (5'-CGG CTG CGA TCA CCG TGC GG-3' SEQ ID NO: 53) was added to 13 μL $H_2O$, 2 μL TS-buffer, 2 μL 2 mM ddATP (or ddTTP), and 2 μL of 0.5 mM dGTP/dCTP/dTTP (or dGTP/DCTP/dATP), and the mixture heated for 30 sec@94° C., followed by 30 cycles of 10 sec@94° C. and 45 sec@50° C.; after a 5 min. incubation@95° C., the supernatant was decanted, and products were desalted by ethanol precipitation with the addition of 0.5 μL of 10 mg/mL glycogen. The resulting pellet was washed in 70% ethanol, air dried, and suspended in 1 μL $H_2O$. 300 nL of this was mixed with the MALDI matrix (0.7 M 3-hydroxypicolinic acid, 0.07 M ammonium citrate in 1:1 $H_2O$:$CH_3CN$) on a stainless steel sample probe and air dried. Mass, spectra were collected on a Thermo Bionalysis Vision 2000 MALDI-TOF operated in reflectron mode with 5 and 20 kV on the target and conversion dynode, respectively. Experimental masses ($m_r$(exp)) reported are those of the neutral molecules as measured using external calibration.

Direct Measurement of Diagnostic Products

PCR amplifications conditions for a 44 bp region containing codon 634 were the same as above but using Pfu polymerase; the forward primer contained a ribonucleotide at its 3'-terminus (forward, 5'-GAT CCA CTG TGC GAC GAG C (SEQ ID NO: 54) -ribo; reverse, 5'-GCG GCT GCG ATC ACC GTG C (SEQ ID NO: 55). After product immobilization and washing, 80 μL of 12.5% $NH_4OH$ was added and heated at 80° C. overnight to cleave the primer from 44-mer (sense strand) to give a 25-mer. Supernatant was pipetted off while still hot, dried resuspended in 50 μL $H_2O$, precipitated, resuspended, and measured by MALDI-TOF as above. MALDI-FTMS spectra of 25-mer synthetic analogs were collected as previously described (Li, Y. et al., (1996) *Anal. Chem.* 68: 2090-2096); briefly, 1-10 pmol DNA was mixed 1:1 with matrix on a direct insertion probe, admitted into the external ion source (positive ion mode), ionized upon irradiance with a 337 nm wavelength laser pulse, and transferred via rf-only quadruple rods into a 6.5 Tesla magnetic field where they were trapped collisionally. After a 15 second delay, ions were excited by a broadband chirp pulse and detected using 256K data points, resulting in time domain signals of 5 s duration. Reported (neutral) masses are those of the most abundant isotope peak after subtracting the mass of the charge carrying proton (1.01 Da).

Results

The first scheme presented utilizes the PROBE reaction shown schematically in FIG. 65. A 20-mer primer is designed to bind specifically to a region on the complementary template downstream of the mutation site; upon annealing to the template, which is labelled with biotin and immobilized to streptavidin coated magnetic beads, the PROBE primer is presented with a mixture of the three deoxynucleotide triphosphates (dNTPs), a di-dNTP (ddNTP), and a DNA polymerase (FIG. 65). The primer is extended by a series of bases specific to the identity of the variable base in codon 634; for any reaction mixture (e.g., ddA+dT+dC+dG), three possible extension products representing the three alleles are possible (FIG. 65).

For the negative control (FIG. 66), the PROBE reaction with ddATP+dNTPs (N=T, C, G) causes a $M_r$(exp) shift of the primer from 6135 to 6726 Da (Δm+591). The absence of a peak at 6432 rules out a C→A mutation (FIG. 65); the mass of the single observed peak is more consistent with extension by C-ddA ($M_r$(calc) 6721, +0.07% error) than by T-ddA ($M_r$(calc) 6736, −0.15% error) than of $A_3TC_2G$ expected for C→A mutant. Combining the ddA and ddT reaction data, it is clear that the negative control is as expected homozygous normal at codon 634.

Figures 65A, 65B:
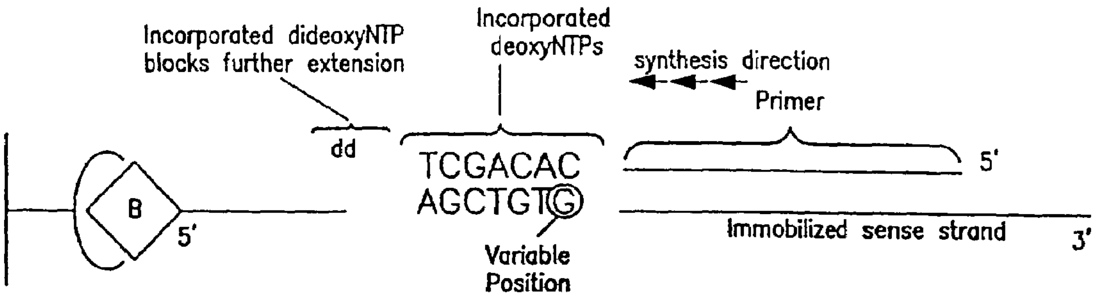
FIG. 65(*a*) shows a schematic representation of a PROBE reaction for the RET proto-oncogene with a mixture of dATP, dCTP, dGTP, and ddTTP (Example 15). B represents biotin, through which the sense template strand is bound through streptavidin to a solid support.
Figure 66A:
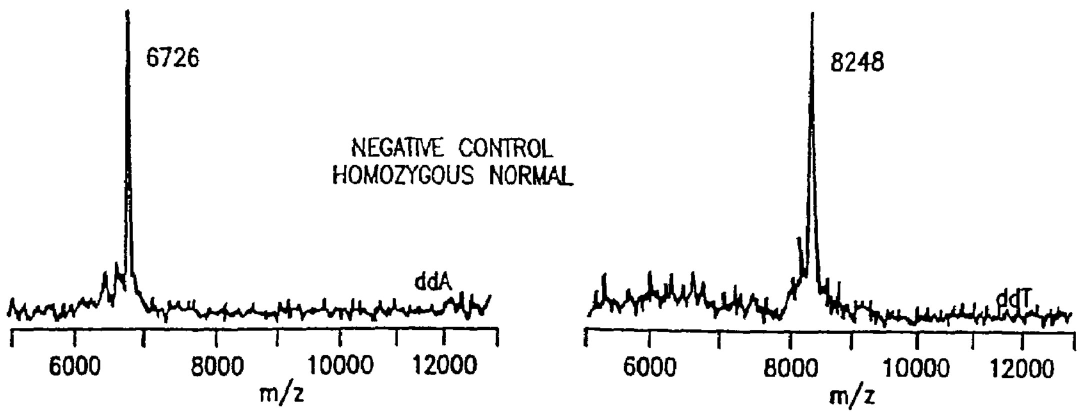
FIG. 66 shows the PROBE product mass spectra for (a) negative control, (b) Patient 1 being heterozygote (Wt/C→T) and (c) Patient 2 being heterozygote (Wt/C→A), reporting average $M_r$ values.
Figure 66B:
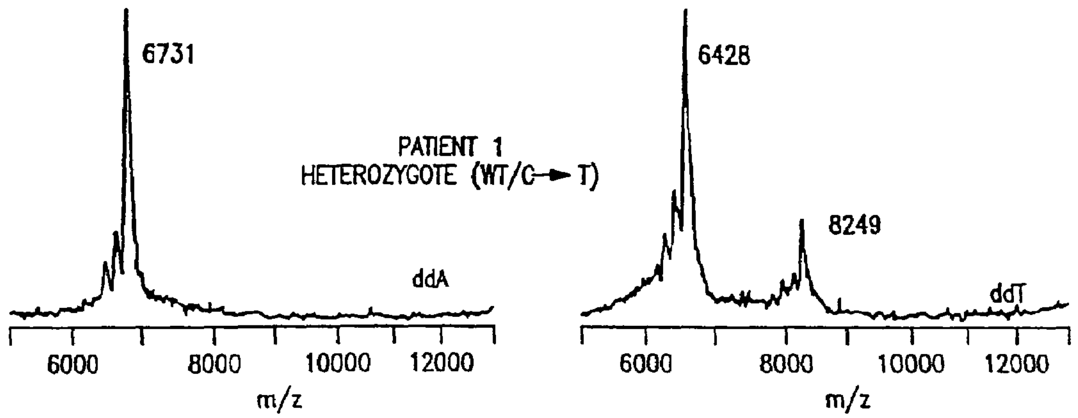
Figure 66C:
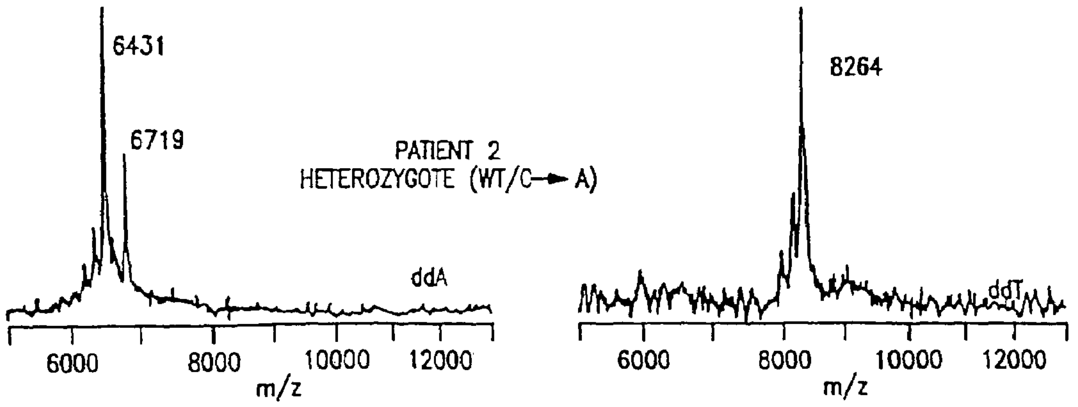
Figure 67A:
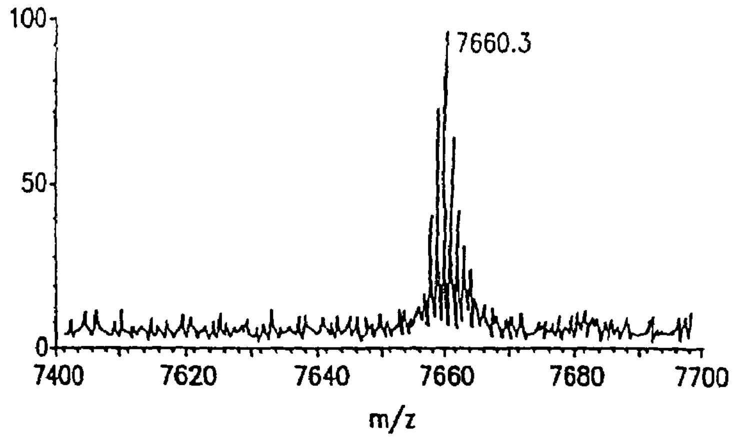
FIG. 67 shows the MALDI-FTMS spectra for synthetic analogs representing ribo-cleaved RET proto-oncogene amplified products from (a) wildtype, (b) G→A, and (c) G→T homozygotes, and (d) wildtype/G→A, (e) wildtype/G→T, and (f) G→A/G→T heterozygotes, reporting masses of most abundant isotope peaks.
Figure 67B:
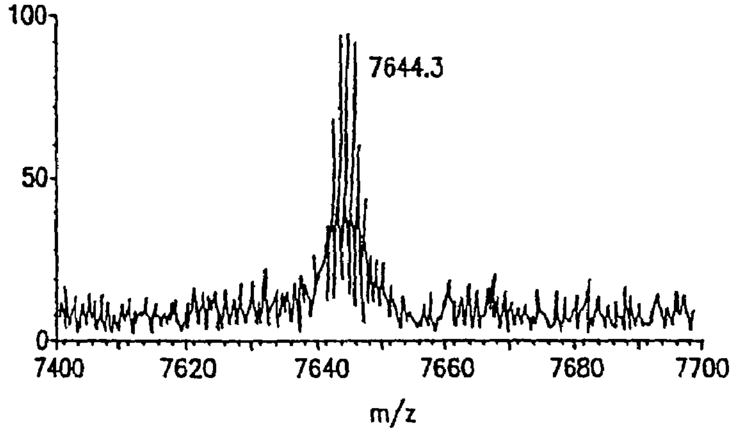
Figure 67C:
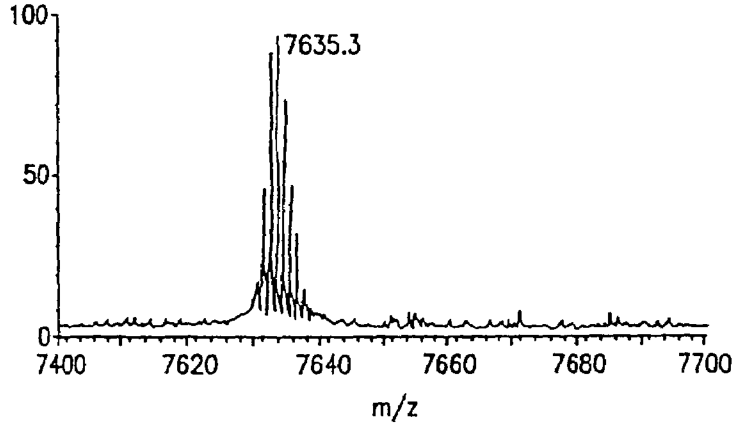
Figure 67D:
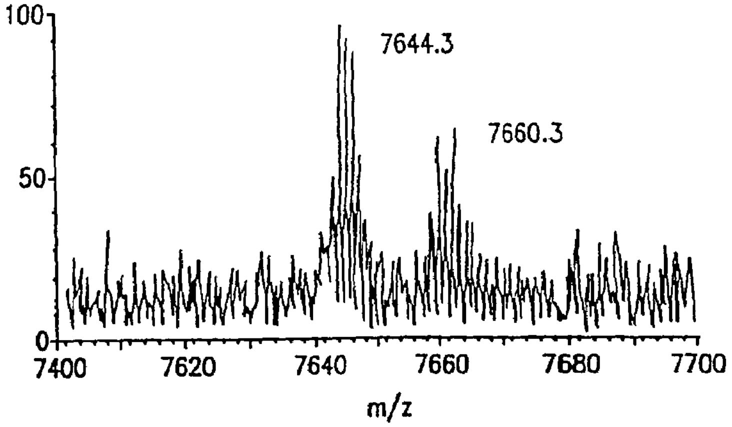
Figure 67E:
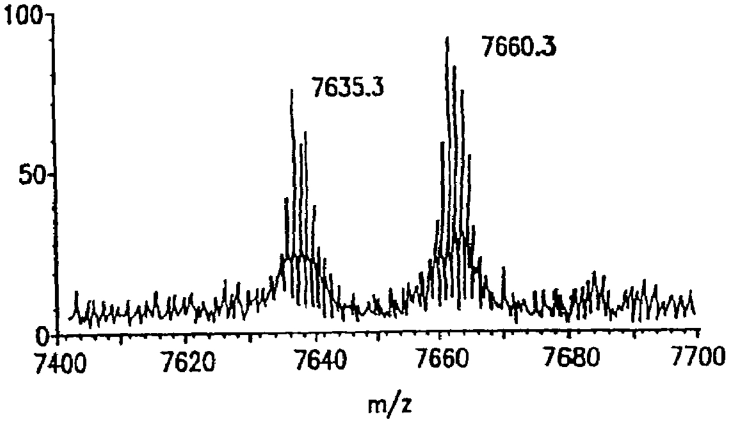
Figure 67F:
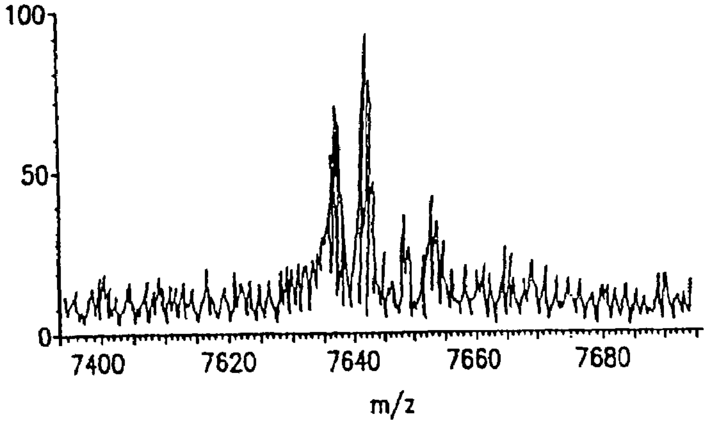

The ddA reaction for patient 1 also results in a single peak ($M_r$(exp)=6731) between expected values for wildtype and C→T mutation (FIG. 65*b*). The ddT reaction, however, results in two clearly resolved peaks consistent with a heterozygote wildtype ($M_r$(exp) 8249, +0.04% mass error)/ C→T mutant (Mr(exp) 6428 Da, +0.08% mass error). For patient 2, the pair of FIG. 66*c* ddA products represent a heterozygote C→A ($M_r$(exp) 6431, −0.06% mass error)/normal ($M_r$(exp) 6719, −0.03% mass error) allele. The ddT reaction confirms this, with a single peak measured at 8264 Da consistent with unresolved wildtype and C→A alleles. The value of duplicate experiments is seen by comparing FIGS. 66*a* and 66*b;* while for patient 1 the peak at 6726 from the ddA reaction represents only one species, similar peak from patient 1 is actually a pair of unresolved peaks differing in mass by 15 Da.

An alternate scheme for point mutation detection is differentiation of alleles by direct measurement of diagnostic product masses. A 44-mer containing the RET634 site was generated by the PCR, and the 19-mer sense primer removed by $NH_4OH$ cleavage at a ribonucleotide at its 3' terminus.

FIG. 67 shows a series of MALDI-FTMS spectra of synthetic analogs of short amplified products containing the RET634 mutant site. FIGS. 67*a-c* and 67*d-f* are homozygous and heterozygous genotypes, respectively. An internal calibration was done using the most abundant isotope peak for the wildtype allele; application of this (external) calibration to the five other spectra resulted in better than 20 ppm mass accuracy for each. Differentiation by mass alone of the alleles is straightforward, even for heterozygote mixtures whose components differ by 16.00 (FIG. 67*d*), 2501 (FIG. 67*e*), or 9.01 Da (FIG. 65*f*). The value of high performance MS is clear when recognition of small DNA mass shifts is the basis for diagnosis of the presence or absence of a mutation. The recent reintroduction of delayed extraction (DE) techniques has improved the performance of MALDI-TOF with shorts DNAs (Roskey, M. T. et al., (1996) *Anal. Chem.* 68: 941-946); a resolving power (RP) of $>10^3$ has been reported for a mixed-base 50-mer, and a pair of 31-mere with a C or a T ($\Delta$m 15 Da) at a variable position resolved nearly to baseline. Thus DE-TOF-MS has demonstrated the RP required for separation of the individual components of heterozygotes. Even with DE, however, the precision of DNA mass measurement with TOF is typically 0.1% (8 Da at 8 kDa) using external calibration, sufficiently high to result in incorrect diagnoses. Despite the possibility of space charge induced frequency shifts (Marshall, A. G. et al. (1991) *Anal. Chem.* 63:215A-229A), MALDI-FTMS mass errors are rarely as high as 0.005% (0.4 Da at 8 KDa), making internal calibration unnecessary.

The methods for DNA point mutation presented here are not only applicable to the analysis of single base mutations, but also to less demanding detection of single or multiple base insertions or deletions, and quantification of tandem two, three, or four base repeats. The PROBE reaction yields products amenable to analysis by relatively low performance ESI or MALDI instrumentation; direct measurement of short amplified product masses is an even more direct means of mutation detection, and will likely become more widespread with the increasing interest in high performance MS available with FTMS.

EXAMPLE 16

Immobilization of Nucleic Acids on Solid Supports Via an Acid-labile Covalent Bifunctional Trityl Linker Aminolinked DNA was prepared and purified according to standard methods. A portion (10 eq) was evaporated to dryness on a speedvac and suspended in anhydrous DMF/pyridine (9:1; 0.1 ml). To this was added the chlorotrityl chloride resin (1 eq, 1.05 μmol/mg loading) and the mixture was shaken for 24 hours. The loading was checked by taking a sample of the resin, detritylating this using 80% AcOH, and measuring the absorbance at 260 nm. Loading was ca. 150 pmol/mg resin.

In 80% acetic acid, the half-life of cleavage was found to be substantially less than 5 minutes—this compares with trityl ether-based approaches of half-lives of 105 and 39 minutes for para and meta substituted bifunctional dimethoxytrityl linkers respectively. Preliminary results have also indicated that the hydroxy picolinic acid matrix alone is sufficient to cleave the DNA from the chlorotrityl resin.

EXAMPLE 17

Immobilization of Nucleic Acids on Solid Supports Via Hydrophobic Trityl Linker The primer contained a 5'-dimethoxytrityl group attached using routine trityl-on DNA synthesis.

C18 beads from an oligo purification cartridge (0.2 mg) placed in a filter tip was washed with acetonitrile, then the solution of DNA (50 ng in 25 μl) was flushed through. This was then washed with 5% acetonitrile in ammonium citrate buffer (70 mM, 250 μl). To remove the DNA form the C18, the beads were washed with 40% acetonitrile in water (10 μl) and concentrated to ca 2 μl on the Speedvac. The sample was then submitted to MALDI.

The results showed that acetonitrile/water at levels of ca.>30% are enough to dissociate the hydrophobic interaction. Since the matrix used in MALDI contains 50% acetonitrile, the DNA can be released from the support and successfully detected using MALDI-TOF MS (with the trityl group removed during the MALDI process).

Figure 69:
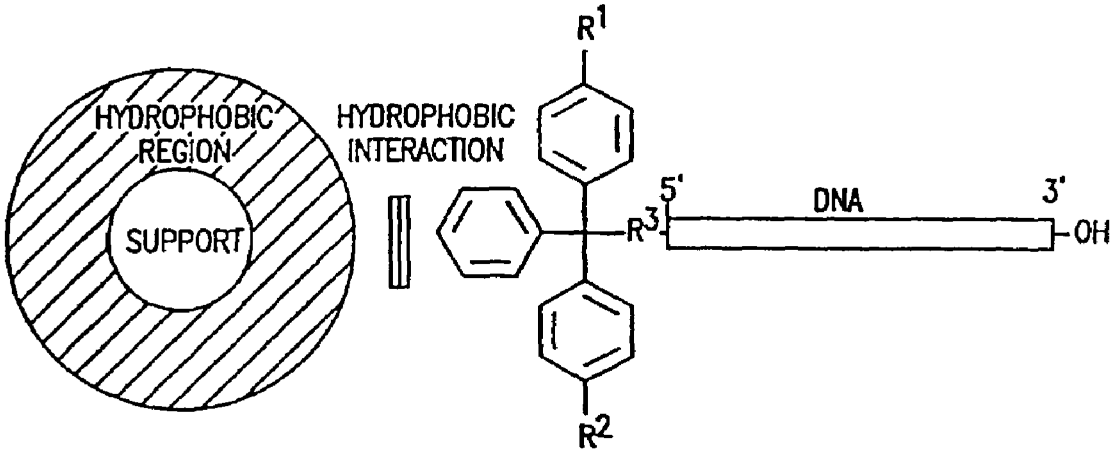
FIG. 69 is a schematic representation of nucleic acid immobilization via hydrophobic trityl linkers.

FIG. 69 is a schematic representation of nucleic acid immobilization via hydrophobic trityl linkers.

EXAMPLE 18

Immobilization of Nucleic Acids on Solid Supports Via Streptavidin-Iminobiotin Experimental Procedure 2-iminobiotin N-hydroxy-succinimid ester (Sigma) was conjugated to the oligonucleotides with a 3'- or 5-'amino linker following the conditions suggested by the manufacturer. The completion of the reaction was confirmed by MALDI-TOF MS analysis and the product was purified by reverse phase HPLC.

Figure 70:
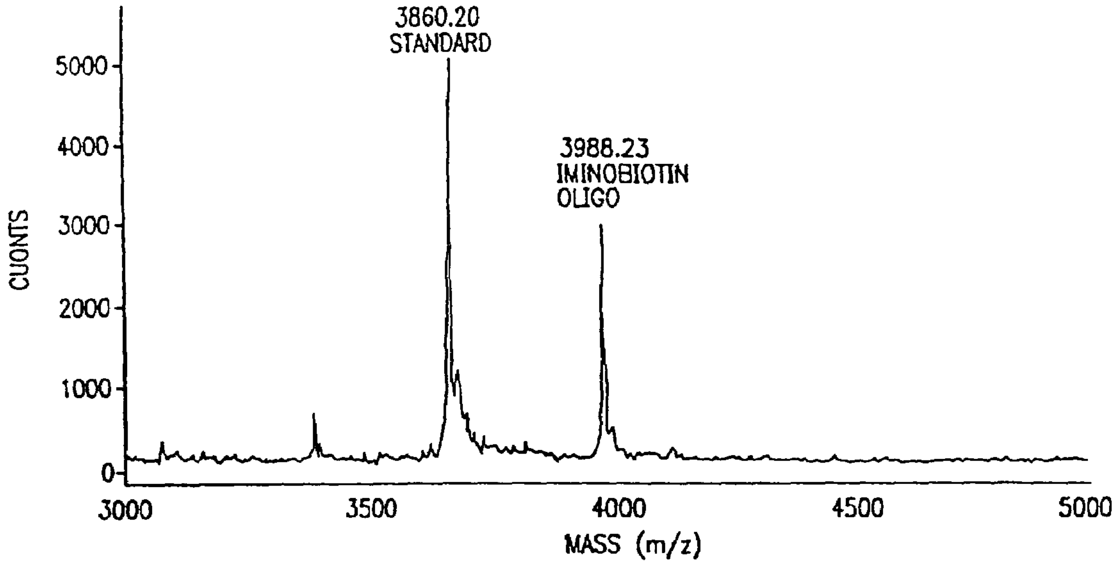
FIG. 70 shows a MALDI-TOF mass spectrum of a supernatant of the matrix treated Dynabeads containing bound oligo (5'-iminobiotin-TGCACCTGACTC, SEQ ID NO: 56). An internal standard (CTGTGGTCGTGC, SEQ ID NO: 57) was included in the matrix.
Figure 71:
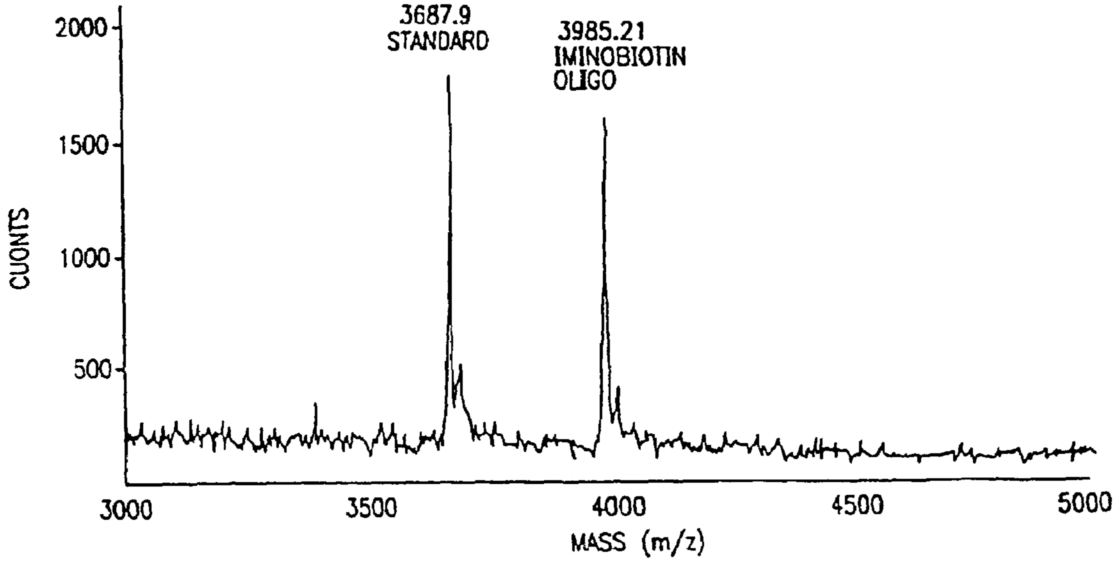
FIG. 71 shows a MALDI-TOF mass spectrum of a supernatant of the matrix treated Dynabeads containing bound oligo (5'-iminobiotin-TGCACCTGACTC, SEQ ID NO: 56). An internal standard (CTGTGGTCGTGC, SEQ ID NO: 57) was included in the matrix.

For each reaction, 0.1 mg of streptavidin-coated magnetic beads (Dynabeads M-280 Streptavidin from Dynal) were incubated with 80 pmol of the corresponding oligo in the presence of 1 M NaCl and 50 mM ammonium carbonate (pH 9.5) at room temperature for one hour. The beads bound with oligonucleotides were washed twice with 50 mM ammonium carbonate (pH 9.5). Then the beads were incubated in 2 μl of 3-HPA matrix at room temperature for 2 min. An aliquot of 0.5 μl of supernatant was applied to MALDI-TOF. For biotin displacement experiment, 1.6. mol of free biotin (80-fold excess to the bound oligo) in 1 μl of 50 mM ammonium citrate was added to the beads. After a 5 min. incubation at room temperature, 1 μl of 3-HPA matrix was added and 0.5 μl of supernatant was applied to MALDI-TOF MS. To maximize the recovery of the bound iminobiotin oligo, the beads from the above treatment were again incubated with a 2 μl of 3-HPA matrix and 0.5 μl of supernatant was applied to MALDI-TOF MS. The matrix alone and free biotin treatment quantitatively released iminobiotin oligo off the streptavidin beads as shown in FIGS. 70 and 71.

EXAMPLE 19

Mutation Analysis Using Loop Primer Oligo Base Extension

Materials and Methods

Genomic DNA. Genomic DNA was obtained from healthy individuals and patients suffering from sickle cell anemia.

The wildtype and mutated sequences have been evaluated conventionally by standard Sanger sequencing.

PCR-Amplification. PCR amplifications of a part of the β-globin was established and optimized to use the reaction product without a further purification step for capturing with streptavidin coated bead. The target amplification for LOOP-PROBE reactions were performed with the loop-cod5 d(GAG TCA GGT GCG CCA TGC CTC AAA CAG ACA CCA TGG CGC, SEQ ID NO: 58) as forward primer and β-11-bio d(TCT CTG TCT CCA CAT GCC CAG, SEQ ID NO: 59) as biotinylated reverse primer. The underlined nucleotide in the loop-cod5 primer is mutated to introduce an invariant CfoI restriction site into the amplicon and the nucleotides in italics are complementary to a part of the amplified product. The total PCR volume was 50 μl including 200 ng genomic DNA, 1 U Taq-polymerase (Boehringer-Mannheim, Cat #1596594), 1.5 mM $MgCl_2$, 0.2 mM dNTPs (Boehringer-Mannheim, Ca #1277049), and 10 pmol of each primer. A specific fragment of the β-globin gene was amplified using the following cycling condition: 5 min 94° C. followed by 40 cycles of: 30 sec@94° C., 30 sec@56° C., 30 sec@72° C., and a final extension of 2 min at 72° C.

Capturing and denaturation of biotinylated templates. 10 μl paramagnetic beads coated with streptavidin (10 mg/ml; Dynal, Dynabeads M-280 streptavidin Cat #112.06) and treated with 5× binding solution (5 M $NH_4Cl$, 0.3M $NH_4OH$) were added to 40 μl PCR volume (10 μl of the amplified product was saved for check electrophoresis). After incubation for 30 min at 37° C. the supernatant was discarded. The captured templates were denatured with 50 μl 1100 mM NaOH for 5 min at ambient temperature, then washed once with 50 μl 50 mM $NH_4OH$ and three times with 100 μl 10 mM Tris.Cl, pH 8.0. The single stranded DNA served as templates for PROBE reactions.

Primer oligo base extension (PROBE) reaction. The PROBE reactions were performed using Sequenase 2.0 (USB Cat #E70775Z including buffer) as enzyme and dNTPs and ddNTPs supplied by Boehringer-Mannheim (Cat #1277049 and 1008382). The ratio between dNTPs (dCTP, dGTP, dTTP) and ddATP was 1:1 and the total used concentration was 50 μM of each nucleotide. After addition of 5 μl 1-fold Sequenase-buffer the beads were incubated for 5 min at 65° C. and for 10 min at 37° C. During this time the partially self complementary primer annealed with the target site. The enzymatic reaction started after addition of 0.5 μl 100 mM dithiothreitol (DTT), 3.5 μl dNTP/ddNTP solution, and 0.5 μl Sequenase (0.8 U) and incubated at 37° C. for 10 min. Hereafter, the beads were washed once in 1-fold tE buffer (10 mM Tris, 1 mM EDTA, pH 8.0).

CfoI restriction digest. The restriction enzyme digest was performed in a total volume of 5 μl using 10 U CfoI in 1-fold buffer L purchased from Boehringer-Mannheim. The incubation time was 20 min at 37° C.

Conditioning of the Diagnostic Products for Mass Spectrometric Analysis

After the restriction digest, the supernatant was precipitated in 45 μl $H_2O$, 10 μl 3M $NH_4$-acetate (pH 6.5), 0.5 μl glycogen (10 mg/ml in water, Sigma, Cat #G1765), and 110 μl absolute ethanol for 1 hour at room temperature. After centrifugation at 13,000 g for 10 min the pellet was washed in 70% ethanol and resuspended in 2 μl 18 Mohm/cm $H_2O$. The beads were washed in 100 μl 0.7 M $NH_4$-citrate followed by 100 μl 0.05 M $NH_4$-citrate. The diagnostic products were obtained by heating the beads in 2 μl 50 mM $NH_4OH$ at 80° C. for 2 min.

Sample Preparation and Analysis on MALDI-TOF Mass Spectrometry.

Same preparation was performed by mixing 0.6 μl of matrix solution (0.7 M 3-hydroxypicolinic acid, 0.07 M dibasic ammonium citrate in 1:1 $H_2O$:$CH_3CN$) with 0.3 μl of either resuspended DNA/glycogen pellet or supernatant after heating the beads in 50 mM $NH_4OH$ on a sample target and allowed to air dry. The sample target was automatically introduced in to the source region of an unmodified Perspective Voyager MALDI-TOF operated in delayed extraction linear mode with 5 and 20 kV on the target and conversion dynode, respectively. Theoretical molecular mass ($M_r$(calc)) were calculated from atomic compositions; reported experimental ($M_r$(exp)) values are those of the singly-protonated form.

Results

The LOOP-PROBE has been applied to the detection of the most common mutation of codon 6 of the human β-globin gene leading to sickle cell anemia. The single steps of the method are schematically presented in FIG. 72. For the analysis of codon 6, a part of the β-globin gene was amplified by PCR using the biotinylated reverse primer β11bio and the primer loop-cod5 which is modified to introduce a CfoI recognition site (FIG. 72*a*). The amplified product is 192 bp in length. After PCR the amplification product was bound to streptavidin coated paramagnetic particles as described above. The antisense strand was isolated by denaturation of the double stranded amplified product (FIG. 72*b*). The intramolecule annealing of the complementary 3' end was accomplished by a short heat denaturation step and incubation at 37° C. The 3' end of the antisense strand is now partially double stranded (FIG. 72*c*). For analyzing the DNA downstream of the self annealed 3'-end of the antisense strand, the primer oligo base extension (PROBE) has been performed using ddATP, dCTP, dGTP, dTTP (FIG. 72*d*). This generates different products in length specific for the genotype of the analyzed individual. Before the determination of the length of these diagnostic products, the DNA was incubated with the CfoI restriction endonuclease that cuts 5' of the extended product. This step frees the stem loop from the template DNA whereas the extended product still keeps attached to the template. The extended products are then denatured by heating from the template stand and analyzed by MALDI-TOF mass spectrometry.

Figure 73A:
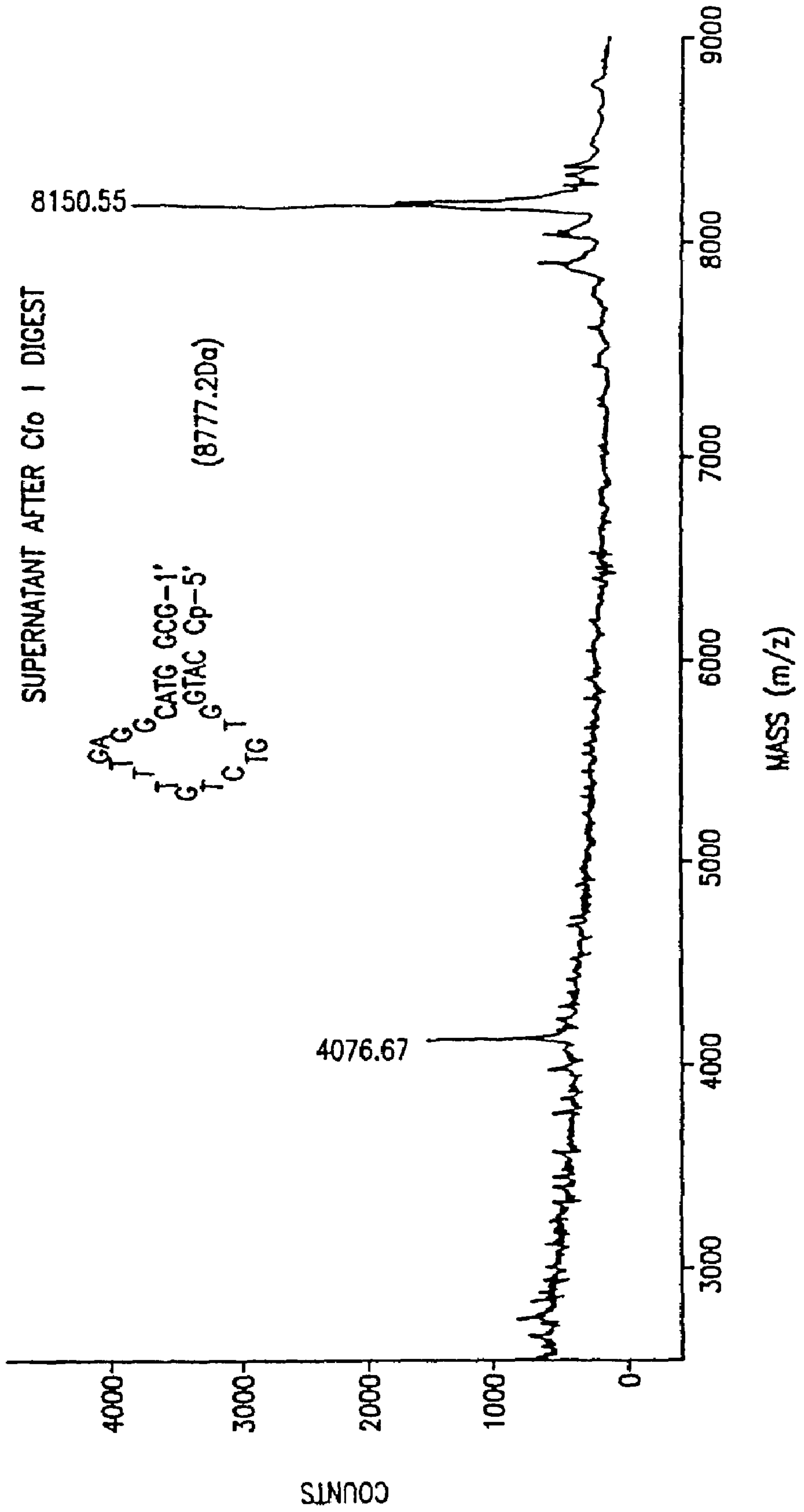
FIG. 73A shows a MALDI-TOF mass spectrum of a supernatant after CfoI digest of a stem loop (SEQ ID NO: 276).
Figure 73B:
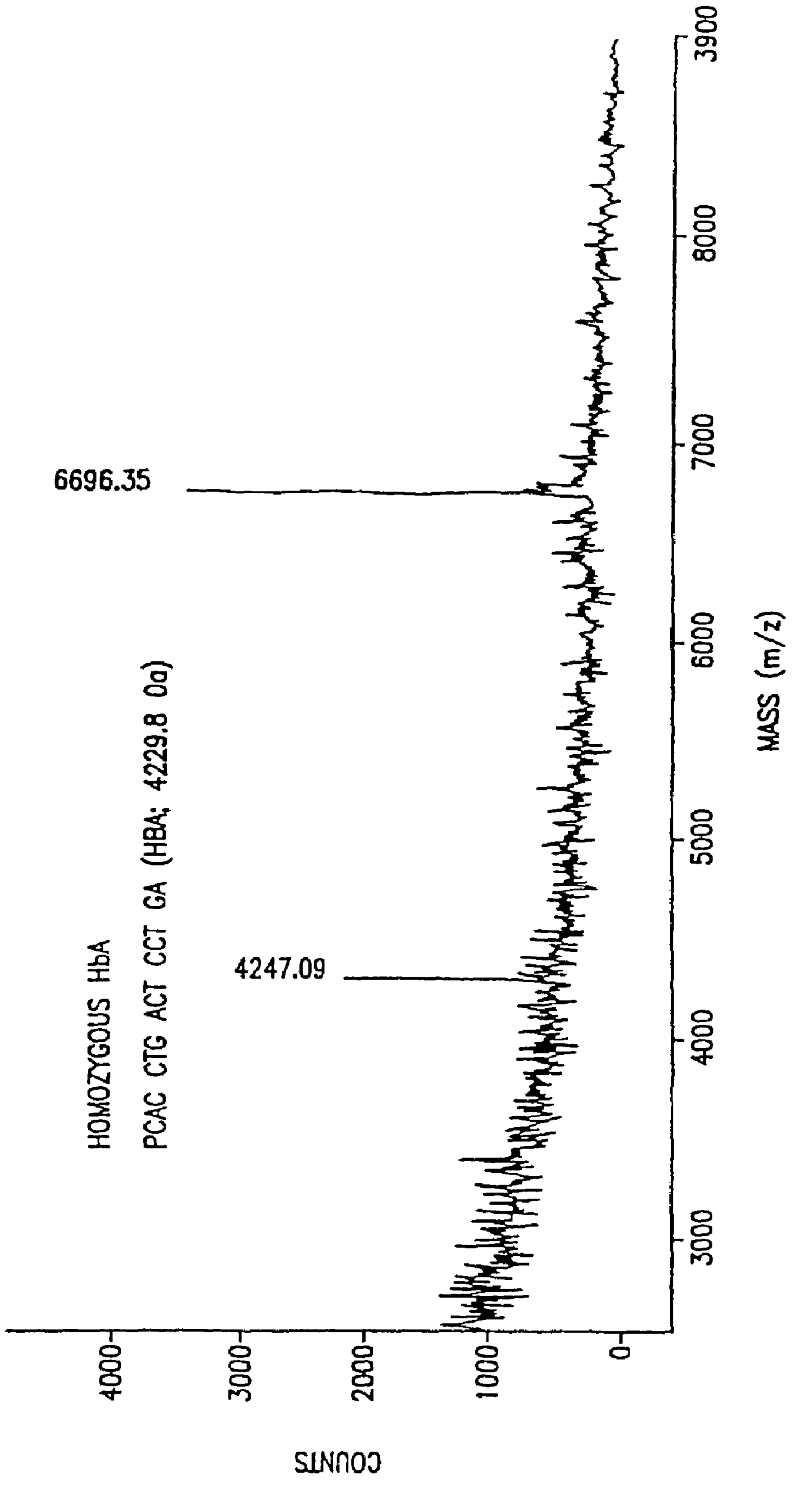
FIG. 73B-D show MALDI-TOF mass spectrum of different genotypes: HbA the wildtype genotype (74B (SEQ ID NO: 269)), HbC, a mutation of codon 6 of the β-globin gene which causes sickle cell disease (74C), and HbS, a different mutation of codon 6 of the β-globin gene which causes sickle cell disease (74D).
Figure 73C:
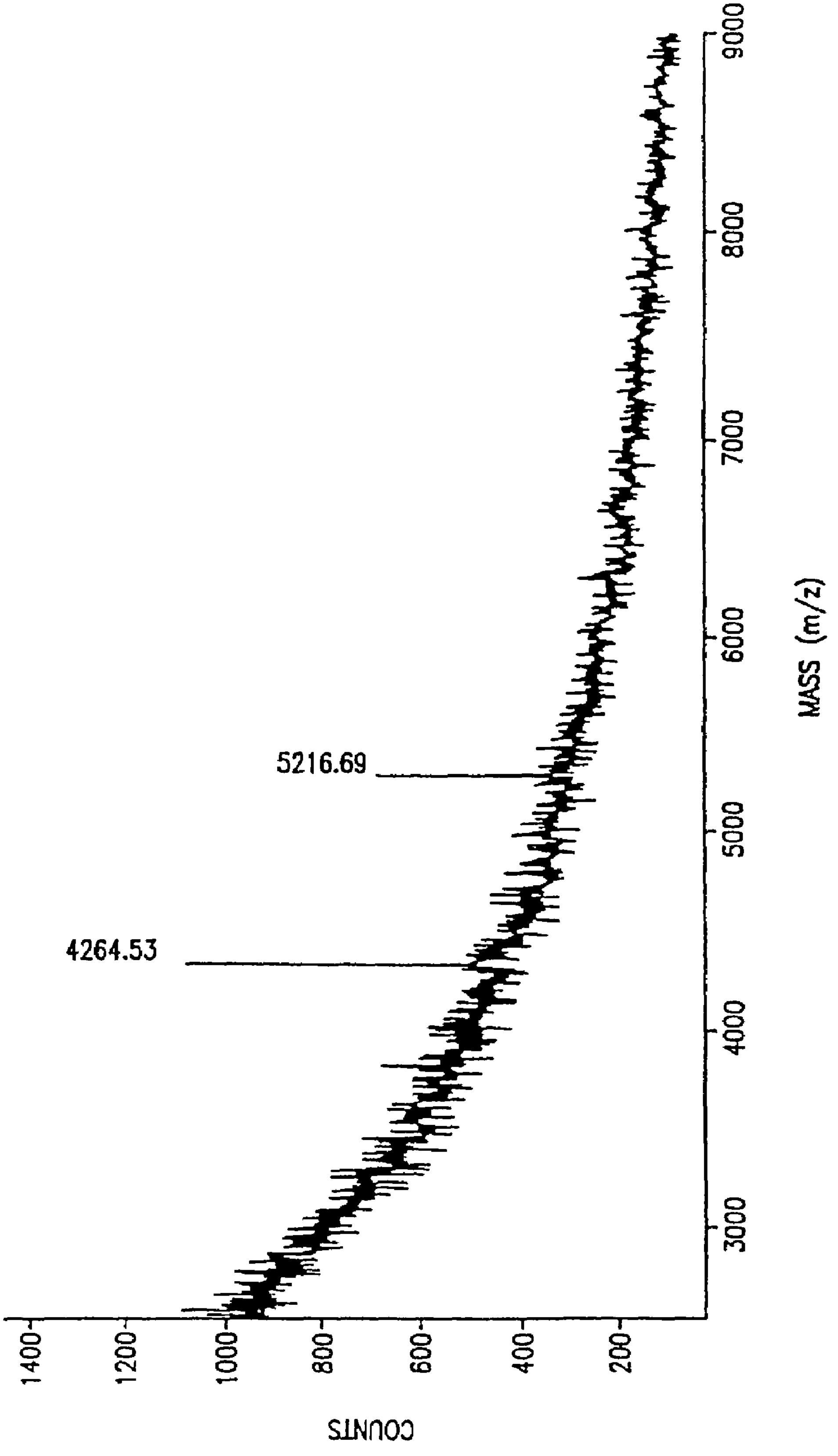
Figure 73D:
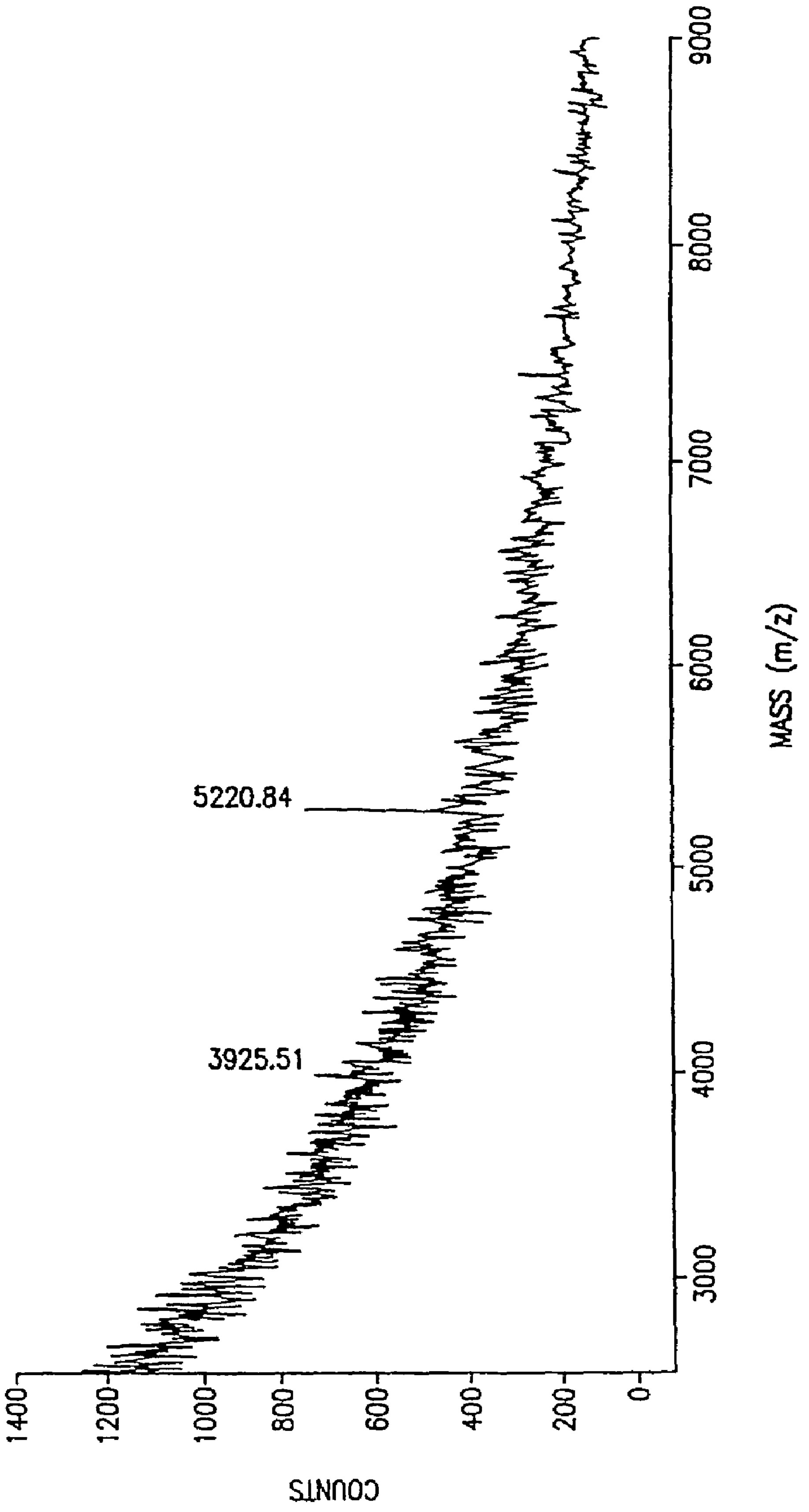
Figure 76:
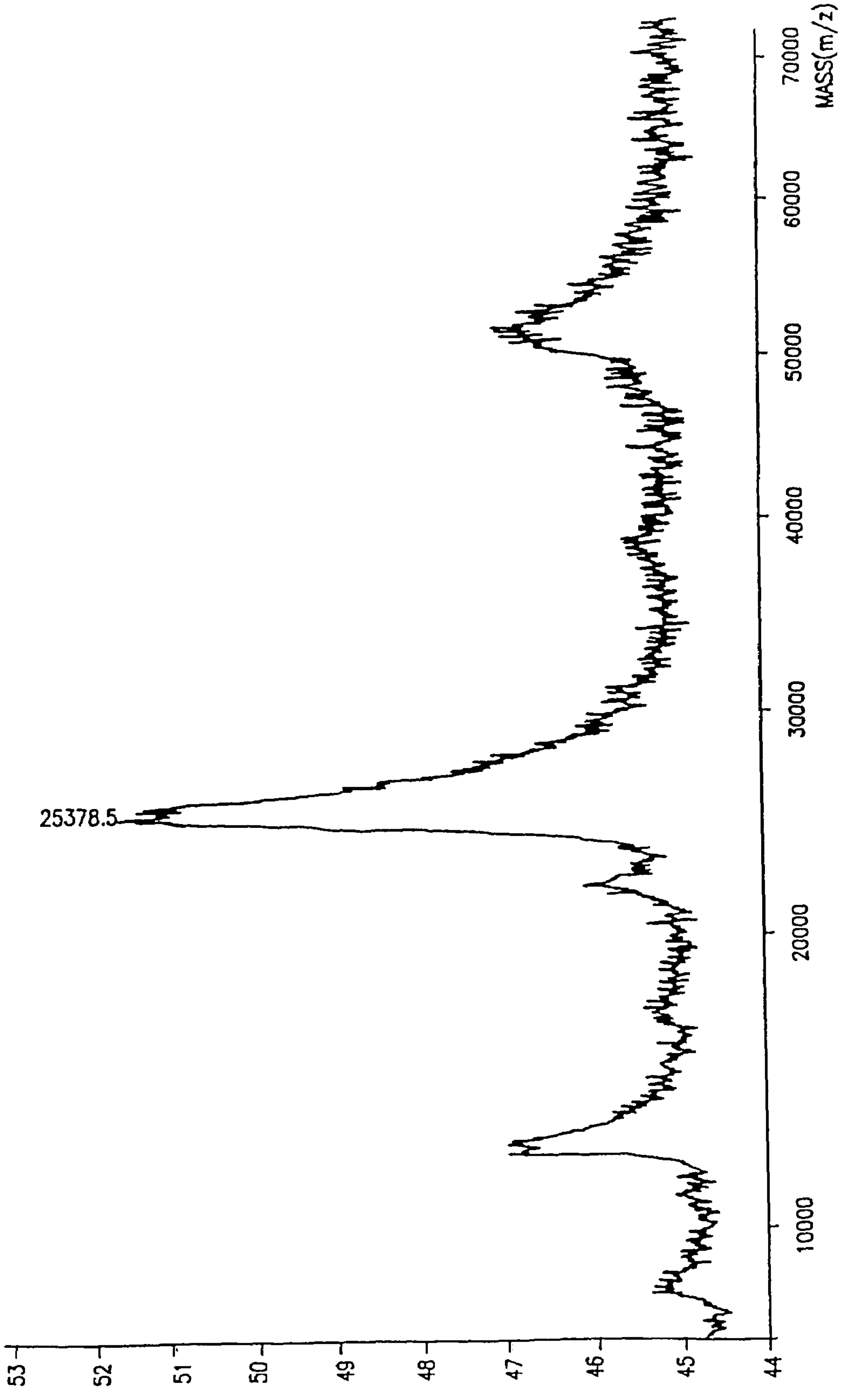
FIG. 76 is a MALDI-TOF mass spectrum of the CKR-5 amplification product, which was generated as described in the following Example 21.

Since the MALDI-TOF analyses were performed with a non-calibrated instrument, the mass deviation between observed and expected values was approximately 0.6% higher than theoretically calculated. Nevertheless, the results obtained were conclusive and reproducible within repeated experiments. In all analyzed supernatants after the restriction digest the stem loop could be detected. Independent of the genotype, the stem loop has had in all analyses molecular masses about 8150 Da (expected 8111 Da). An example is shown in FIG. 73*a*. The second peak in this figure with a mass of 4076 Da is a doubly charged ion of the stem loop. FIG. 73*b* to 73*d* show the analyses of different genotypes as indicated in the respective inserts. HbA is the wildtype genotype and HbC and HbS are two different mutations in codon 6 of the β-globin gene which cause sickle cell disease. In the wildtype situation a single peak with a molecular mass of 4247 Da and another with 6696 Da are detected (FIG. 73*b*). The latter corresponds to the biotinylated PCR primer (β-11-bio) unused in the PCR reaction which also has been removed in some experiments. The former corresponds to the diagnostic product for HbA. The analyses of the two individual DNA molecules with HbS trait as well as compound heterozygosity (HbS/HbC) for the sickle cell disorder lead also to unambiguous expected results (FIGS. 73*c* and 73*d*).

In conclusion, the LOOP-PROBE is a powerful means for detection of mutations especially predominant disease causing mutations or common polymorphisms. The technique eliminates one specific reagent for mutation detection and, therefore, simplifies the process and makes it more amenable to automation. The specific extended product that is analyzed is cleaved off from the primer and is therefore shorter compared to the conventional method. In addition, the annealing efficiency is higher compared to annealing of an added primer and should therefore generate more product. The process is compatible with multiplexing and various detection schemes (e.g., single base extension, oligo base extension and sequencing). For example, the extension of the loop-primer can be used for generation of short diagnostic sequencing ladders within highly polymorphic regions to perform, for example, HLA typing or resistance as well as species typing (e.g., *Mycobacterium tuberculosis*)).

EXAMPLE 20

T7-RNA Polymerase Dependent Amplification of CKR-5 and Detection by MALDI-MS

Materials and Methods

Genomic DNA. Human genomic DNA was obtained from healthy individuals.

PCR-Amplification and Purification. PCR amplification of a part of the CKR-5 gene was accomplished using ckrT7f as sense primer d(ACC TAG CGT TCA GTT CGA CTG AGA TAA TAC GAC TCA CTA TAG CAG CTC TCA TTT TCC ATA C (SEQ ID NO: 60). The underlined sequence corresponds to the sequence homologous to CKR-5, the bolded sequence corresponds to the T7-RNA polymerase promoter sequence and the italic sequence was chosen randomly. ckr5r was used as antisense primer d(AAC TAA GCC ATG TGC ACA ACA (SEQ ID NO: 61). Purification of the amplified product and removal of unincorporated nucleotides was carried out using the QIAquick purification kit (Qiagen, cat #28104). In the final PCR volume of 50 μl were 200 ng genomic DNA, 1 U Taq-polymerase (Boehringer-Mannheim, cat #1596594), 1.5 mM $MgCl_2$ 0.2 mM dNTPs (Boehringer-Mannheim, cat #1277049), and 10 pmol of each primer. The specific fragment of the CKR-5 gene was amplified using the following cycling conditions: 5 min@94° C. followed by 40 cycles of 45 sec@94° C., 45 sec 52° C., 5 sec@72° C., and a final extension of 5 min at 72° C.

T7-RNA Polymerase conditions. One third of the purified DNA (about 60 ng) was used in the T7-RNA polymerase reaction. (Boehringer-Mannheim, cat #881 767). The reaction was carried out for 2h at 37° C. according to the manufacturer's conditions using the included buffer. The final reaction volume was 20 μl 0.7 μl RNasin (33 U/μl) had been added. After the extension reaction, the enzyme was inactivated by incubation for 5 min at 65° C.

DNA Digestion and Conditioning of the Diagnostic Products for Mass Spec Analysis.

The template DNA was digested by adding RNase-free DNase I (Boehringer-Mannheimn, cat #776 758) to the inactivated T7 mixture and incubation for 20 min at room temperature. Precipitation was carried out by adding 1 μl glycogen (10 mg/ml, Sigma, cat #G1765), 1/10 volume 3M $NH_2$-acetate (pH 6.5), and 3 volume absolute ethanol and incubation for 1 hour at room temperature. After centrifugation at 13,000 g for 10 min, the pellet was washed in 70% ethanol and resuspended in 3 μl 18 Mohm/cm $H_2O$. 1 μl was analyzed on an agarose gel.

Sample Preparation and Analysis on MALDI-TOF Mass Spectrometry

Sample preparation was performed by mixing 0.6 μl of matrix solution (0.7 M 3-hydroxypicolinic acid, 0.07 M dibasic ammonium citrate in 1:1 $H_2O$:$CH_3CN$) with 0.3 μl of resuspended DNA/glycogen on a sample target and allowed to air dry. The sample target was introduced into the source region of an unmodified Finnigan VISION2000 MALDI-TOF operated in reflectron mode with 5 kV. The theoretical molecular mass was calculated form atomic composition; reported experimental values are those of singly-pronated form.

Results

The chemokine receptor CKR-5 has been identified as a major coreceptor in HIV-1 (see e.g., WO 96/39437 to Human Genome Sciences; Cohen, J. et al. *Science* 275: 1261). A mutant allele that is characterized by a 32 bp deletion is found in 16% of the HIV-1 seronegative population whereas the frequency of this allele is 35% lower in the HIV-1 seropositive population. It is assumed that individuals homozygous for this allele are resistant to HIV-1. The T7-RNA polymerase dependent amplification was applied to identify this specific region of the chemokine receptor CKR-5 (FIG. 74). Human genomic DNA was amplified using conventional PCR. The sense primer has been modified so that it contains a random sequence of 24 bases that facilitate polymerase binding and the T7-RNA polymerase promoter sequence (FIG. 75). The putative start of transcription is at the first base 5' of the promoter sequence. ckr5r was used as an antisense primer. PCR conditions are outlined above. The amplified product derived from wildtype alleles is 75 bp in length. Primer and nucleotides were separated from the amplification product using the Qiagen QIAquick purification kit. One third of the purified product was applied to in vitro transcription with T7-RNA polymerase. To circumvent interference of the template DNA, it was digested by adding RNase-free DNase I. RNA was precipitated and this step also leaves the degraded DNA in the supernatant. Part of the redissolved RNA was analyzed on an agarose gel and the rest of the sample was prepared for MALDI-TOF analysis. The expected calculated mass of the product is 24560 Da. A dominant peak, that corresponds to an approximate mass of 25378.5 Da can be observed. Since the peak is very broad, an accurate determination of molecular mass was not possible. The peak does not correspond to residual DNA template. First, the template DNA is digested, and second, the DNA strands would have a mass of 23036.0 and 23174 Da, respectively.

This example shows that T7 RNA polymerase can effectively amplify target DNA. The generated RNA can be detected by Mass spectrometry. In conjunction with modified (e.g., 3'-deoxy)ribonucleotides that are specifically incorporated by a RNA polymerase but not extended any further, this method can be applied to determine the sequence of a template DNA.

EXAMPLE 21

MALDI Mass Spectrometry of RNA Endonuclease Digests

Materials

Synthetic RNA (Sample A:5'-UCCGGUCUGAUGAGUCCGUGAGGAC-3' (SEQ ID NO: 62); sample B:5'-GUCACUACAGGUGAGCUCCA-3' (SEQ ID NO: 63); sample C:5'-CCAUGCGAGAGUAAGUAGUA-3' (SEQ ID NO: 64)) samples were obtained from DNA technology (Aahus, Denmark) and purified on a denaturing polyacrylamide gel (Shaler, T. A. et al. (1 996) *Anal. Chem.* 63: 5766-579). Rnases $T_1$ (Eurogentec), $U_2$ (Calbiochem), A (Boehringer-Mannheim) and PhyM (Pharmacia) were used without additional purification. Streptavidin-coated magnetic beads (Dynabeads M-280 Streptavidin, Dynal) were supplied as a suspension of 6-7×$10^8$ bead/ml (10 mg/ml) dissolved in phosphate-buffered saline (PBS) containing 0.1% BSA and 0.02% $NaN_3$. 3-Hydroxypicolinic acid (3-HPA) (Aldrich) was purified by a separate desalting step before use as described in more detail elsewhere (Little, D. P. et al. (1995) *Proc. Natl. Acad. Sci. U.S.A.* 92: 2318-2322).

Methods

In vitro transcription reaction. The 5'-biotinylated 49 nt in vitro transcript (SEQ ID NO: 65): AGGCCUGCGGCAA-GACGGAAAGACCAUGGUCCCUNAUCUGC-CGCAGGAUC was produced by transcription of the plasmid pUTMS2 (linearized with the restriction enzyme BamHI) with T7 RNA polymerase (Promega). For the transcription reaction 3 μg template DNA and 50u T7 RNA polymerase were used in a 50 μl volume of 1 u/μl RNA guard (Rnax inhibitor, Pharmacia), 0.5 mM NTP's 1.0 mM 5'-biotin-ApG dinucleotide, 40 mM Tris-HCl (pH 8.0), 6 mM $MgCl_2$ 2 mM spermidine and 10 mM DTT. Incubation was performed at 37° C. for 1 hour, then another aliquot of 50 units T7 RNA polymerase was added and incubation was continued for another hour. The mixture was adjusted to 2M $NH_4$.acetate and the RNA was precipitated by addition of one volume of ethanol and one volume of isopropanol. The precipitated RNA was collected by centrifugation at 20,000× g for 90 min at 4° C., the pellet was washed with 70% ethanol, dried and redissolved at 8 M urea. Further purification was achieved by electrophoresis through a denaturing polyacrylamide gel as described elsewhere (Shaler, T. A. et al. (1996) *Anal. Chem.* 68: 576-579). The ration of 5'-biotinylated to non-biotinylated transcripts was about 3:1.

Ribonuclease assay. For partial digestion with selected RNases different enzyme concentrations ad assay conditions were employed as summarized in table VII. The solvents for each enzyme were selected following the suppliers' instructions. The concentrations of the synthetic RNA samples and the in vitro transcript were adjusted to 5-10×$10^{-6}$ M.

The reaction was stopped at selected times by mixing 0.6 μl aliquots of the assay with 1.5 μl of 3 HPA-solution. The solvent was subsequently evaporated in a stream of cold air for the MALDI-MS analysis.

Limited alkaline hydrolysis was performed by mixing equal volumes (2.0 μl) of 25% ammonium hydroxide and RNA sample (5-10×$10^{-6}$ M) at 60° C. 1 μl aliquots were taken out at selected times and dried in a stream of cold air. For these samples it turned out to be important to first dry the digests in a stream of cold air, before 1.5 μl of the matrix solution and 0.7 μl of $NH_4$+ loaded cation exchanged polymer beads were added.

The reaction was stopped at selected times by mixing 0.6 μl aliquots of the assay with 1.5 μl of 3HPA-solution. The solvent was subsequently evaporated in a stream of cold air for the MALDI-MS analysis.

Limited alkaline hydrolysis was performed by mixing equal volumes (2.0 μl) of 25% ammonium hydroxide and RNA sample (5-10×$10^{-6}$ M) at 60° C. 1 μl aliquots were taken out at selected times and dried in a stream of cold air. For these samples it turned out to be important to first dry the digests in a stream of cold air, before 1.5 μl of the matrix solution and 0.7 μl of $NH_4$+ loaded cation exchange polymer beads were added.

The reaction was stopped at selected times by mixing 0.6 μl aliquots of the assay with 1.5 μl of 3HPA-solution. The solvent was subsequently evaporated in a stream of cold air for the MALDI-MS analysis.

Limited alkaline hydrolysis was performed by mixing equal volumes (2.0 μl) of 25% ammonium hydroxide and RNA sample (5-10×$10^{-6}$ M) at 60° C. 1 μl aliquots were taken out at selected times and dried in a stream of cold air. For these samples it turned out to be important to first dry the digest in a stream of cold air, before 1.5 μl of the matrix solution and 0.7 μl if a suspension of $NH_4^+$ loaded cation exchange polymer beads were added.

Separation of 5'-biotinylated fragments. Steptavidin-coated magnetic beads were utilized to separate 5'-biotinylated fragments of the in vitro transcript after partial RNase degradation. The biotin moiety in this sample was introduced during the transcription reaction initiated by the 5'-biotin-pApG-dinucleotide. Prior to use, the beads were washed twice with 2× binding & washing (b&w) buffer (20 mM Tris-HCl, 2 mM EDTA, 2 M NaCl pH 8.2) and resuspended at 10 mg/ml in 2×b&w buffer. Circa 25 pmol of the RNA in

TABLE VII

Overview and Assay Conditions of the RNAses

| Rnase | Source | Concentration [units Rnase/ μgRNA] | Conditions | Incubation Time (max. number of fragments) | References |
|---|---|---|---|---|---|
| $T_1$ | *Aspergillus oryzae* | 0.2 | 20 mM Tris-HCl, pH 5.7, 37° C. | 5 min. | Donis-Keller, H. et al., (1977) Nuc. Acids Res. 4: 2527-2537 |
| $U_2$ | *Ustilago Sphaerogena* | 0.01 | 20 mM DAC, pH 5.0, 37° C. | 15 min | Donis-Keller, H. et al., (1977) Nuc. Acids Res. 4: 2527-2537 |
| PhyM | *Physarum polycephalum* | 20 | 20 mM DAC, pH 5.0, 50° C. | 15 min | Donis-Keller, H. et al., (1980) Nucl. Acids Res. 8: 3133-3142 |
| A | bovine pancrease | 4 x $10^{-9}$ | 10 mM Tris-HCl, pH 7.5, 37° C. | 30 min | Breslow, R. and R. Xu. (1993) Proc. Natl. Acad. Sci. USA 90: 1201-1207 |
| $CL_3$ | chicken liver | 0.01 | 10 mM Tris-HCl, pH 6.5, 37° C. | 30 min | Boguski, et al., (1980) J. Biol. Chem. 255: 2160-2163 |
| cusativin | *cucumis sativus L.* | 0.05 ng | 10 mM Tris-HCl, pH 6.5, 37° C. | 30 min | Rojo, M. A. et al. (1994) Planta 194: 328-338 |

vitro transcript were digested by RNase U2 using the protocol described above. The digestion was stopped by adding 3 μl of 95% formamide containing 10 mM trans-1,2-diaminocyclohexane-N,N,$N^1$,$N^1$-tetraacetic acid (CDTA) at 90° C. for 5 min, followed by cooling on ice. Subsequently, capture of the biotinylated fragments was achieved by incubation of 6 μl of the digest with 6 μl of the bead suspension and 3 μl of b&w buffer at room temperature for 15 min. Given the binding capacity of the beads of 200 pmol of biotinylated oligonucleotide per mg of beads, as specified by the manufacturer, the almost 2-times excess of oligonucleotide was used to assure a full loading of the beads. The supernatant was removed, and the beads were washed twice with 6 μl of $H_2O$. The CDTA and 95% formamide at 90° C. for 5 min. After evaporation of the solvent and the formamide the ≦2.5 pmol of fragments were resuspended in 2 μl $H_2O$ and analyzed by MALDI-MS as described above.

Sample preparation for MALDI-MS. 3-Hydroxypicolinic acid (3-HPA) was dissolved in ultra pure water to a concentration of ca. 300 mM. Met al cations were exchanged against $NH_4^+$ as described in detail previously. (Little, D. P. et al. (1995) *Proc. Natl. Acad. Sci. U.S.A.* 92: 2318-2322). Aliquots of 0.6 μl of the analyte solution were mixed with 1.5 μl 3-HPA on a flat inert met al substrate. Remaining alkali cations, present in the sample solution as well as on the substrate surface, were removed by the addition of 0.7 μl of the solution of $NH_4^+$-loaded cation exchange polymer beads. During solvent evaporation, the beads accumulated in the center of the preparation, were not used for the analysis, and were easily removed with a pipette tip.

Instrument. A prototype of the Vision 2000 (ThermBioanalysis, Hemel, Hempstead, UK) reflectron time of flight mass spectrometer was used for the mass spectrometry. Ions were generated by irradiation with a frequency-tripled ND:YAG laser (355 nm, 5 ns; Spektrum GmbH, Berlin, Germany) and accelerated to 10 ke V. Delayed ion extraction was used for the acquisition of the spectra shown, as it was found to substantially enhance the signal to noise ratio and/or signal intensity. The equivalent flight path length of the system is 1.7 m, the base pressure is $10^{4-}$ Pa. Ions were detected with a discrete dynode secondary-electron multiplier (R2362, Hamamatsu Photonics), equipped with a conversion dynode for effective detection of high mass ions. The total impact energy of the ions on the conversion dynode was adjusted to values ranging from 16 to 25 keV, depending on the mass to be detected. The preamplified output signal of the SEM was digitized by a LeCroy 9450 transient recorder (LeCroy, Chestnut Ridge, N.Y., USA) with a sampling rate of up to 400 MHz. For storage and further evaluation, the data were transferred to a personal computer equipped with custom-made software (ULISSES). All spectra shown were taken in the positive ion mode. Between 20 and 30 single shot spectra were averaged for each of the spectra shown.

Results

Specificity of Rnases. Combining base-specific RNA cleavage with MALDI-MS requires reaction conditions optimized to retain the activity and specificity of the selected enzymes on the one hand and complying with the boundary conditions for MALDI on the other. Incompatibility mainly results because the alkaline-ion buffers, commonly used in the described reaction, such as Na-phosphate, Na-citrate or Na-acetate as well as EDTA interfere with the MALDI sample preparation; presumably they disturb the matrix crystallization and/or analyte incorporation. Tris-HCl or ammonium salt buffers, in contrast, are MALDI compatible (Shaler, T. A. et al. (1996) *Anal. Chem.* 68: 576-579). Moreover, alkaline salts in the sample lead to the formation of a heterogenous mixture of multiple salts of the analyte, a problem increasing with increasing number of phosphate groups. Such mixtures result in loss of mass resolution and accuracy as well as signal-to-noise ratio (Little, D. P. et al. (1995) *Proc. Natl. Acad. Sci. U.S.A.* 92: 2318-2322; Nordhoff, E., Cramer, R. Karas, M., Hillenkamp, F., Kirpekar, F., Kristiansen, K. and Roepstorff, P. (1993) *Nucleic Acids Res.,* 21, 3347-3357). Therefore, RNase digestions were carried out under somewhat modified conditions compared to the ones described in the literature. They are summarized above in table VII. For Rnase $T_1$, A, $CL_3$ ad Cusativin, Tris-HCl (pH 6-7.5) was used as buffer. 20 mM DAC provides the pH of 5, recommended for maximum activity of RNases $U_2$ and PhyM. The concentration of 10-20 mM of these compounds were found to not interfere significantly with the MALDI analysis. To examine the specificity of the selected ribonucleases under these conditions, three synthetic 20-25 mer RNA molecules with different nucleotide sequences were digested.

The MALDI-MS spectra of FIG. 77 shows five different cleavage patterns (A-E) of a 25 nt RNA obtained after partial digestion with RNases $T_1$, $U_2$, PhyM, A, and alkaline hydrolysis. These spectra were taken from aliquots which were removed from the assay after empirically determined incubation times, chosen to get an optimum coverage of the sequence. As the resulting samples were not fractionated prior to mass spectrometric analysis, they contain all fragments generated at that time by the respective RNases. In practice, uniformity of the cleavages, can be affected by a preferential attack on the specific phophodiester bonds (Donis-Keller, H., Maxam, A. M., and Gilbert, W. (1977) *Nucleic Acids Res.,* 4, 1957-1978; Donis-Keller, H. (1980) *Nucleic Acids Res.,* 8 3133-3142). The majority of the expected fragments are indeed observed in the spectra. It is also worth noting that for the reaction protocols as used, correct assignment of all fragment masses is only possible, if a 2', 3'-cyclic phosphate group is assumed. It is well known that such cyclic phosphates are intermediates in the cleavage reaction and get hydrolyzed in a second, independent and slower reaction step involving the enzyme (Richards, F. M., and Wycoff, H. W. in *The Enzymes* Vol. 4, 3rd Ed., (ed. Boyer, P. D.) 746-806 (1971, Academic Press, New York); Heinemann, U and W. Saenger (1985) *Pure Appl. Chem.* 57, 417-422; Ikehara, M. et al., (1987) *Pure Appl. Chem.* 59-965-968) Vreslow, R. and Xu, R. (1993) *Proc. Nal. Acad. Sci. USA,* 90, 1201-1207). In a few cases different fragments have equal mass of differ by as little as 1 Dalton., In these cases, mass peaks cannot unambiguously be assigned to one or the other fragments. Digestion of two additional different 20 nt RNA samples was, therefore, performed (Hahner, S., Kirpekar, F., Nordoff, E., Kristiansen, K., Roepstorff, P. and Hillenkamp, F. (1996) *Proceedings of the* 44*th ASMS Conference on Mass Spectrometry*, Portland, Oreg.) in order to sort out these ambiguities. For all samples tested, the selected ribonucleases appear to cleave exclusively at the specified nucleotides leading to fragments arising from single as well as multiple cleavages.

In FIG. 77, peaks, indicating fragments containing the original 5'-terminus, are marked by arrows. All non marked peaks can be assigned to internal sequences or those with retained 3'-terminus. For a complete sequence all possible fragments bearing exclusively either the 5'- or the 3'-terminus of the original RNA would suffice. In practice, the 5'-fragments are better suited for this purpose, because the spectra obtained after incubation of all three synthetic RNA samples contain the nearly complete set of originals of 5'-ions for all different RNases (Hahner, S., Kirpekar, F., Nordoff, E., Kristiansen, K., Roepstorff and Hillenkamp, F. (1996) *Proceed-*

*ings of the* 44*th ASMS Conference on Mass Spectrometry*, Portland, Oreg.). Internal fragments are somewhat less abundant and fragments containing the original 3'-terminus appear suppressed in the spectra. In agreement with observations reported in the literature (Gupta, R. C. and Randerath, K. (1977) *Nucleic Acids Res.,* 4, 1957-1978), cleavages close to the 3'-terminus were partially suppressed in partial digests of the RNA 25 mer by RNase $T_1$, and $U_2$ (even if they are internal or contain the original 5'-terminus). Fragments from such cleavages appear as weak and poorly resolved signals in the mass spectra.

For larger RNA molecules secondary structure is known to influence the uniformity of the enzymatic cleavages (Donis-Keller, H., Maxam, A. M. and Gilbert, A. (1977) *Nucleic Acids Res.* 8, 3133-3142). This can, in principle be, overcome by altered reaction conditions. In assay solutions containing 5-7 M urea, the activity of RNases such as $T_2$, $U_2$, A, $Cl_3$, and PhyM is known to be retained (Donis-Keller, H., Maxam, A. M. and Gilbert, W. (1977) *Nucleic Acids Res.,* 4, 2527-2537; Boguski, M. S., Hieter, P. A., and Levy, C. C. (1980) *J. Biol. Chem.,* 255, 2160-2163; Donis-Keller, H. (1980) *Nucleic Acids Res.,* 8, 3133-3142, while RNA is sufficiently denatured. UV-MALDI-analysis with 3-HPA as matrix is not possible under such high concentrations of urea in the sample. Up to a concentration of 2 M urea in the reaction buffer, MALDI analysis of the samples was still possible although significant changes in matrix crystallization were observed. Spectra of the RNA 20 mer (sample B), digested in the presence of 2 M urea still resembled those obtained under conditions listed in Table VII.

Figures 77A, 77B, 77C, 77D, 77E:
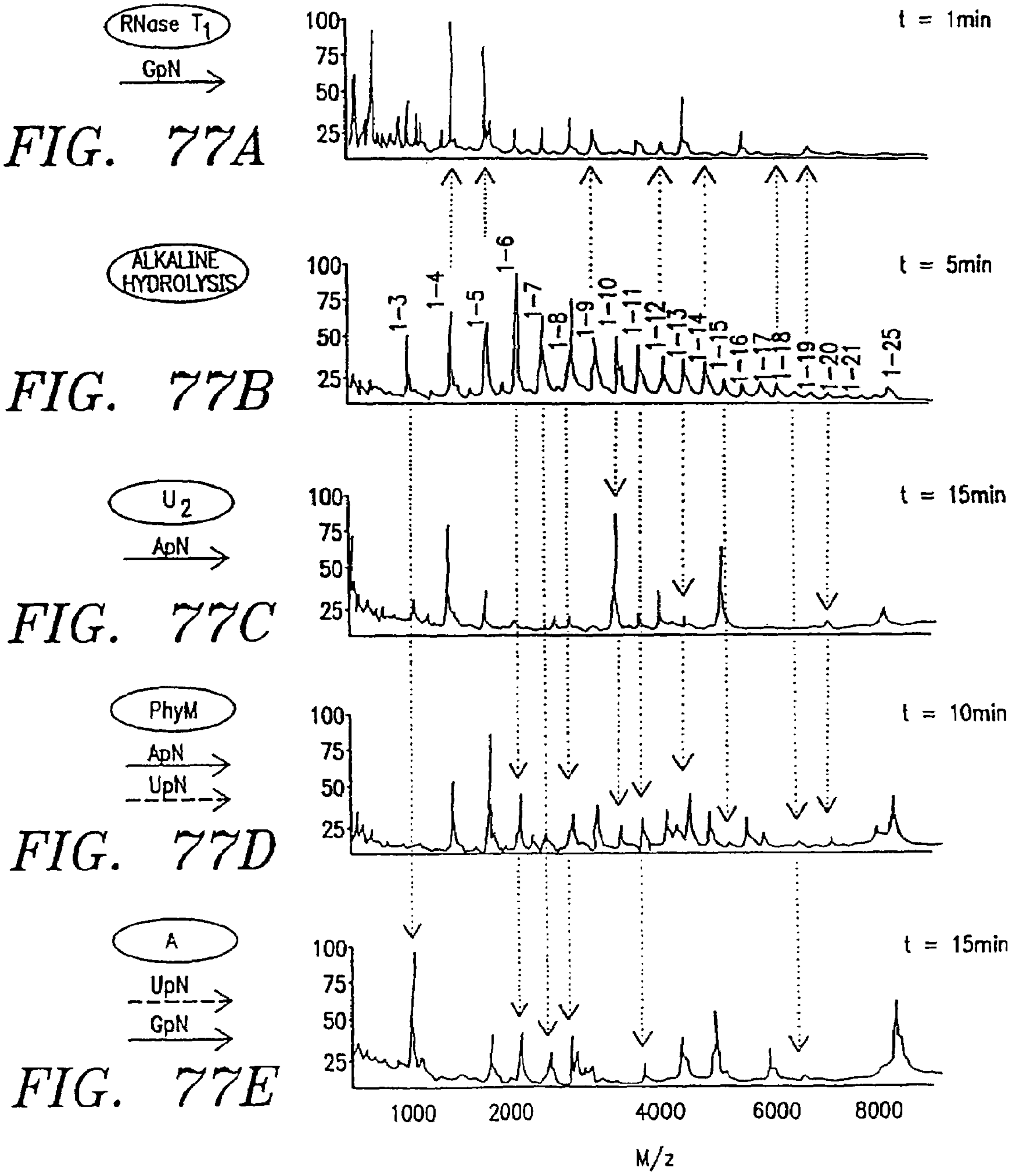
FIG. 77 is a positive ion UV-MALDI mass spectra of a synthetic RNA 25-mer (5'-UCCGGUCUGAUGAGUC-CGUGAGGAC-3' SEQ ID NO: 62) digested with selected RNAses. For each enzyme 0.6 μl aliquots of teh 4.5 μl assay containing a total of ca. 20 pmol of the RNA were fixed with 1.5 μl matrix (3-HPA) for analysis. Fragments with retained 5'-terminus are marked by different arrows, specific for the different RNAses, (Hahner et al., Proceedings of the 44$^{th}$ ASMS Conference on Mass Spectrometry and Allied Topics, p. 983 (1996)).
Figure 78:
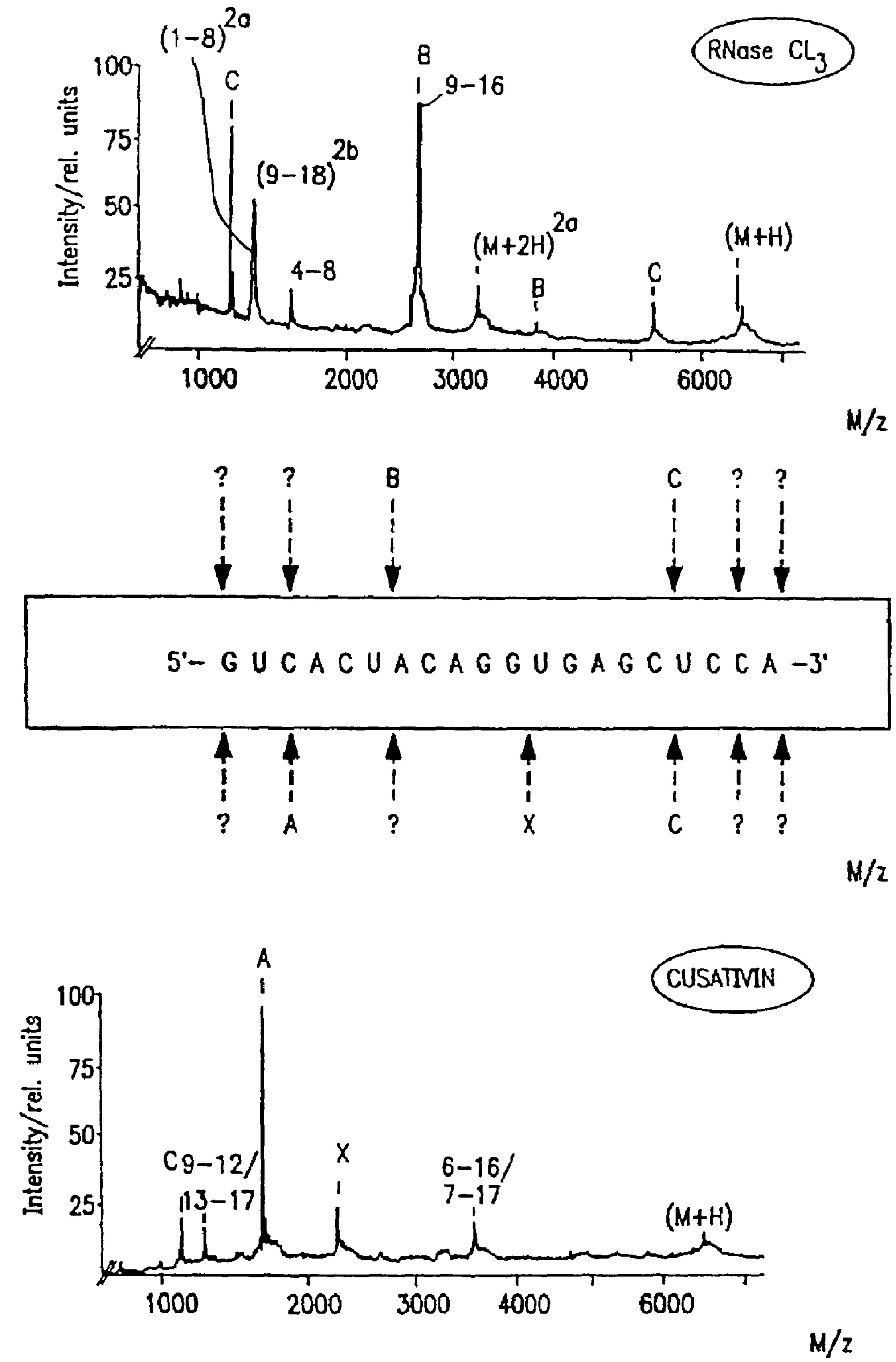
FIG. 78 is an investigation of the specificity of the RNAses $CL_3$ and Cusativin by positive ion UV-MALDI mass spectra of a synthetic RNA 20-mer. Expected and/or observed cleavage sites are indicated by arrows. A, B, C indicate correct cleavage sites and corresponding singly cleaved fragments. Missing cleavages are designated by a question mark (?), unspecific cleavages by an X.

Digestion by RNases which exclusively recognize one nucleobase is desirable to reduce the complexity of the fragment patterns and thereby facilitate the mapping of the respective nucleobase. RNases $CL_3$ and cursavitin are enzymes reported to cleave at cytidylic acid residues. Upon limited RNase $CL_3$ and cursativin digestion of the RNA-20 mer (sample B) under non-denaturing conditions, fragments corresponding to cleavages at cytidylic residues were indeed observed (FIG. 78). Similar to the data reported so far (Boguski, M. S., Hieter, P. A. and Levy, C. C. (1980) *J. Biol. Chem.,* 255, 2160-2163: Rojo, M. A., Arias, F. J., Iglesias, R., Ferreras, J. M., Munoz, R., Escarmis, C., Soriano, F., Llopez-Fando, Mendez, E., and Girbes, T. (1994) *Planta,* 194, 328-338). The degradation pattern in FIG. 78, however, reveals that not every cytidine residue is recognized, especially for neighboring C residues. RNase $CL_3$ is also reported to be susceptible to the influence of secondary structure (Boguski, M. S., Heiter, P. A., and Levy, C. C. (1980) *J Biol. Chem.,* 255, 2160-2163), but for RNA of the size employed in this study, such an influence should be negligible. Therefore, unrecognized cleavage sites in this case can be attributed to a lack of specificity of this enzyme. To confirm these data, a further RNase $CL_3$-digestion was performed with the RNA 20 mer (sample C). As a result of the sequence of this analyte, all three linkages containing cytidylic acid were readily hydrolyzed, but additional cleavages at uridylic acid residues were detected as well. Since altered reaction conditions such as increased temperature (90° C.), various enzyme to substrate ratios, and addition of 2 M urea did not result in a digestion of the expected specificity, application of this enzyme to sequencing was not pursued further. Introduction of a new cytidine-specific ribonuclease, cusativin, isolated form dry seeds of *Cucumis sativus L.* looked promising for RNA sequencing (Rojo, M. A., Arias, F. J., Iglesias, R., Ferreras, J. M., Munoz, R., Escarmis, C., Soriano, F., Llopez-Fando, J., Mendez, E. and Girbes, T. (1994) *Planta,* 194, 328-338). As shown in FIG. 78, not every cytidine residue was hydrolyzed and additional cleavages occurred at uridylic acid residues for the recommended concentration of the enzyme. RNases $CL_3$ and cusativin will, therefore not yield the desired sequence information for mapping of cytidine residues and their use was not further pursued. The distinction of pyrimidine residues can be achieved, however, by use of RNases with multiple specificities, such as *Physarum polycephalum* RNase (cleaves ApN, UpN) and pancreatic RNase A (cleaves UpN, CpN) (see FIG. 77). All 5'-terminus fragments, generated by the monospecific RNase $U_2$ and apparent in the spectrum of FIG. 77C were also evident in the spectrum of the RNase PhyM digest (FIG. 77D). Five of the six uridilic cleavage sites could, this way, be uniquely identified by this indirect method. In a next step, the knowledge of the uridine cleavage sites was used to identify sites of cleavage of cytidilic acid residues in the spectrum recorded after incubation with RNase A (FIG. 77E), again using exclusively ions containing the original 5'-terminus. Two of the four expected cleavage sites were identified this way. A few imitations are apparent from these spectra, if only the fragments containing the original 5'-terminus are used for the sequence determination. The first two nucleotides usually escape the analysis, because their signals get lost in the low mass matrix background. Because of this, the corresponding fragments are missing in the spectra of the U- and C-specific cleavages. Large fragments with cleavage sites close to the 3'-terminus are often difficult to identify, particularly in digests with RNases $T^1$, and $U_2$, because of their low yield (vide supra) and the often strong nearby signal of the non-digested transcript. Accordingly the cleavages in position 22 and 23 do not show up in the spectrum of the G-specific RNase T, (FIG. 77A) and the cleavage site 24 cannot be identified from the spectra of the $U_2$ and PhyM digests (FIGS. 77C and D). Also site 16 and 17 with two neighboring cytidilic acids cannot be identified in the RNase A spectrum of FIG. 77E. These observations demonstrate that a determination of exclusively the 5'-terminus fragments may not always suffice and the information contained in the internal fragments may be needed for a full sequence analysis.

Finally, limited alkaline hydrolysis provides a continuum of fragments (FIG. 77B), which can be used to complete the sequence data. Again, the spectrum is dominated by ions of fragments containing the 5'-terminus, although the hydrolysis should be equal for all phosphodiester bonds. As was true for the enzymatic digests, correct mass assignments requires one to assume that all fragments have a 2', 3'-cyclic phosphate. The distribution of peaks, therefore, resembles that obtained after a 3'-exonuclease digest (Pieles, U., Zurcher, W., Schar, M. and Moser, H. E., (1993) *Nucleic Acids Res.,* 21, 3191-3196; Nordhoff, E. et al. (1993) Book of Abstracts, $13^{th}$ Internat. Mass Spectrom. Conf., Budapest p. 218; Kirpekar, F., Nordhoff, E., Kristiansen, K., Roepstorff, P., Lezius, A. Hahner, S., Karas, M. and Hillenkamp. F. (1994) *Nucleic Acid Res.,* 22, 3866-3870). In principle, the alkaline hydrolysis alone could, therefore, be used for a complete sequencing. This is, however, only possible for quite small oligoribonucleotides, because larger fragment ions, differing in mass by only a few mass units will not be resolved in the spectra and the mass of larger ions cannot be determined with the necessary accuracy of better than 1 Da, even if peaks are partially or fully resolved. The interpretation of the spectra particularly from digests of unknown RNA samples is substantially simplified, if only the fragments containing the original 5'-terminus are separated out prior to the mass spectrometric analysis. A procedure for this approach is described in the following section.

Figure 79A:
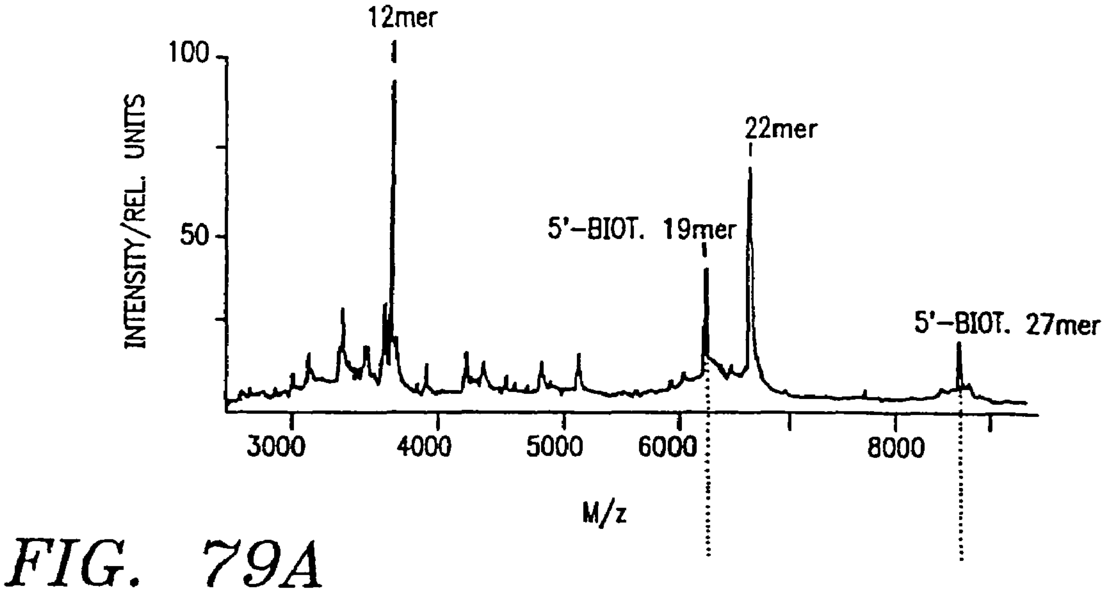
FIG. 79 shows the separation of a mixture of DNA molecules (12-mer, 5'-biot. 19-mer, 22-mer and 5'-biot. 27-mer) with streptavidin-coated magnetic beads. a) positive ion UV-MALDI mass spectrum of 0.6 μl of a mixture containing ca. 2-4 pmol of each species mixed with 1.5 μl matrix (3-HPA). b) same as a) but incubation of the mixture with magnetic beads and subsequent release of the captured fragments.
Figure 79B:
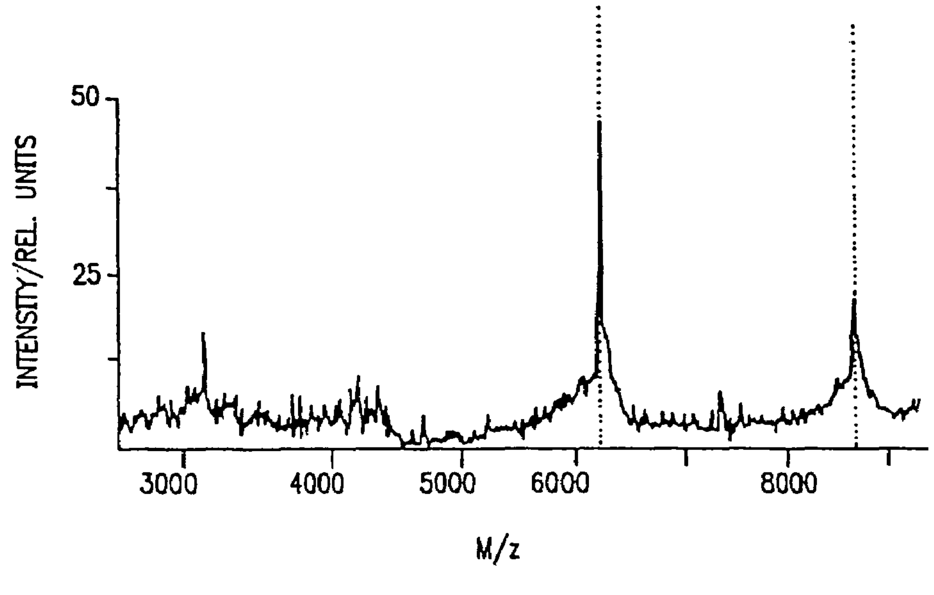
Figure 80A:
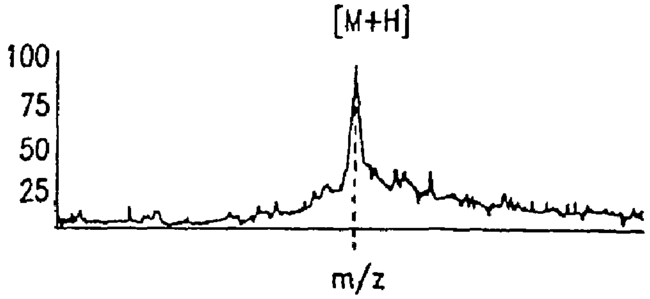
FIG. 80 Elution of immobilized 5' biotinylated 49 nt in vitro transcript from the streptavidin-coated magnetic beads. Positive UV-MALDI mass spectrum of the transcript prior to incubation with the magnetic beads (a). Spectra of the immobilized RNA transcript after elution with 95% formamide alone (b) and with various additives such as 10 mM EDTA (c), 10 mM CDTA (d) and 25% ammonium hydroxide (e); EDTA and CDTA were adjusted with 25% ammonium hydroxide to a pH of 8.
Figure 80B:
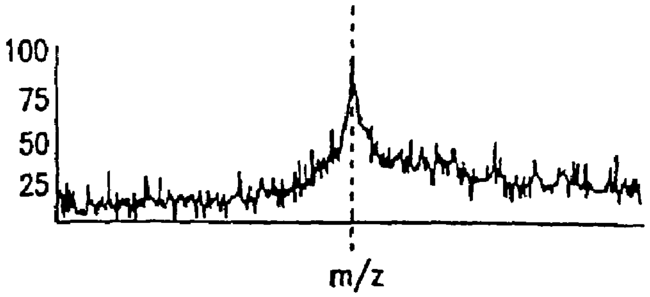
Figure 80C:
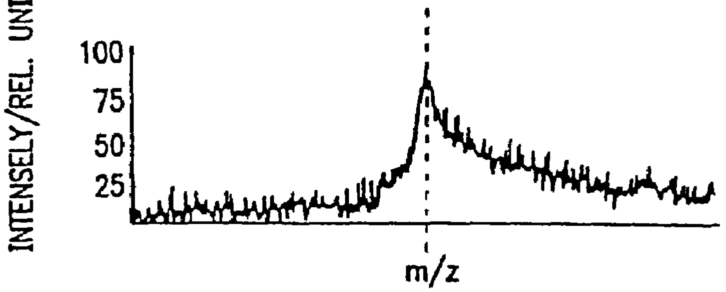
Figure 80D:
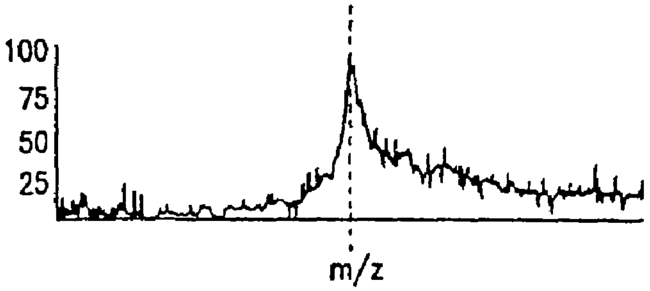
Figure 80E:
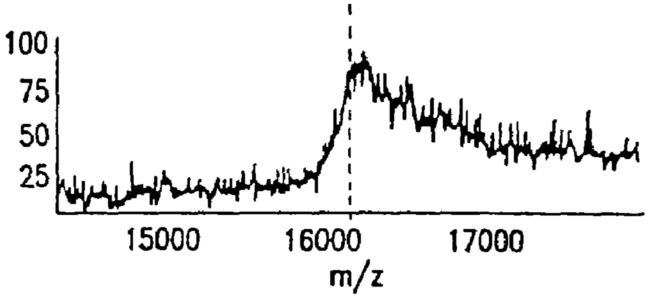

Separation of 5'-biotinylated fragments. Streptavidin-coated magnetic beads (Dynal) were tested for the extraction of fragments containing the original 5'-terminus from the digests. Major features to be checked for this solid-phase approach are the selective immobilization and efficient elution of biotinylated species. In preliminary experiments, a 5'-biotinylated DNA (19 nt) and streptavidin were incubated and MALDI analyzed after standard preparation. Despite the high affinity of the streptavidin-biotin interaction, the intact complex was not found in the MALDI spectra. Instead, signals of the monomeric subunit of streptavidin and the biotinylated DNA were detected. Whether the complex dissociates in the acidic matrix solution (pKA 3) or during the MALDI desorption process, is not known. Surprisingly, if the streptavidin is immobilized on a solid surface such as magnetic beads, the same results are not observed. A mixture of two 5'-biotinylated DNA samples (19 nt and 27 nt) and two unlabeled DNA sequences (12 nt and 22 nt) were incubated with the beads. The beads were extracted and carefully washed before incubation in the 3-HPA MALDI matrix. No analyte signals could be obtained from these samples. To test whether the biotinylated species had been bound to the beads altogether, elution form the extracted and washed beads was performed by heating at 90° C. in the presence of 95% formamide. This procedure is expected to denature the streptavidin, thereby breaking the streptavidin/biotin complex. FIG. 79B shows the expected signals of the two biotinylated species, proving that release of the bound molecules in the MALDI process is the problem rather than the binding of the beads; FIG. 79A shows a spectrum of the same sample after standard preparation, showing signals of all four analytes as a reference. Complete removal of the formamide after the elution and prior to the mass spectrometric analysis was found to be important, otherwise crystallization of the matrix is disturbed. Mass resolution and the signal-to-noise ration in spectrum 79B are comparable to those of the reference spectrum. These results testify to the specificity of the streptavidin-biotin interaction, since no or only minor signals of the non-biotinylated analyte were detected after incubation with the Dynal beads. Increased suppression of nonspecific binding was reported through an addition of the detergent Tween-20 to the binding buffer (Tong, X. and Smith, L. M. (1992) *Anal Chem.,* 64, 2672-2677). Although this effect could be confirmed in this study, peak broadening affected the quality of the spectra due to remaining amounts of the detergent. The necessity of an elution step as a prerequisite for detection of the captured biotinylated species can be attributed to a stabilizing effect of the complex by the immobilization of the streptavidin to the magnetic beads.

For practical application of this solid phase method to sequencing a maximum efficiency of binding and elution of biotinylated species is of prime importance. Among a variety of conditions investigated so far, addition of salts such as EDTA gave best results in the case of DNA sequencing by providing ionic strength to the buffer (Tong, X. and Smith, L. M. (1992) *Anal Chem.,* 64, 2672-2677). To examine such an effect on the solid-phase method, several salt additives were tested for the binding and elution of the 5'-biotinylated RNA in vitro transcript (49 nt). The results are shown in FIG. 80. Judging from the relative intensity, signal-to-noise ration, and resolution of the respective signals, a 95% formamide solution containing 10 mM CDTA (FIG. 80D) is most efficient for the binding/elution. Since CDTA acts as a chelating agent for divalent cation, formation of proper secondary an tertiary structure of the RNA is prevented. An improved sensitivity and spectral resolution has been demonstrated under such conditions for the analysis of RNA samples by electrospray mass spectrometry (Limbach, P. A., Crain, P. F. and McCloskey, J. A. (1995) *J Am. Soc. Mass. Spectrom.,* 6, 27-39). The improvement in the MALDI analysis is actually not very significant compared to the spectrum obtained for the solution containing formamide alone (FIG. 81*b*), but the reproducibility for spectra of good quality was substantially improved for the CDTA/formamide solution. Thus in addition to the improved binding/elution, this additive may also improve the incorporation of the analyte into the matrix crystals. Unfortunately, a striking signal broadening on the high mass side was observed in case of formamide solutions containing EDTA, CDTA or 25% ammonium hydroxide. Since this effect is most prominent in case of 25% ammonium hydroxide and this agent was also used for adjusting EDTA and CDTA to their optimum pH, a pronounced $NH_3$ adduct ion formation ca be assumed.

Figure 81A:
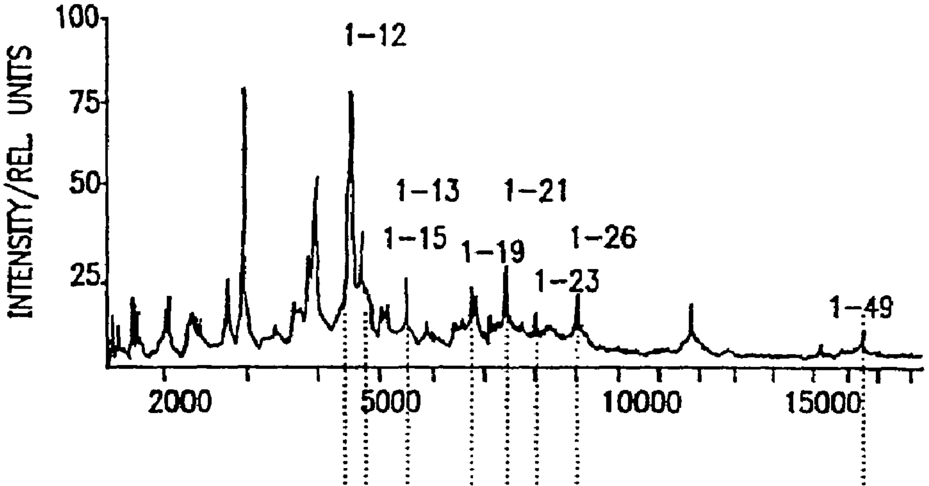
FIG. 81 Positive UV-MALDI mass spectra of the 5' biotinylated 49 nt in vitro transcript after RNAse $U_2$ digest for 15 minutes. a) Spectrum of the 25 ul assay containing ca. 100 pmol of the target RNA before separation; b) spectrum after isolation of the 5'-biotinylated fragments with magnetic beads. Captured fragments were released by a solution of 95% formamide containing 10 mM CDTA. 1 ul aliquots of the samples were mixed with 1.5 ul matrix (3-HPA) in both cases.
Figure 81B:
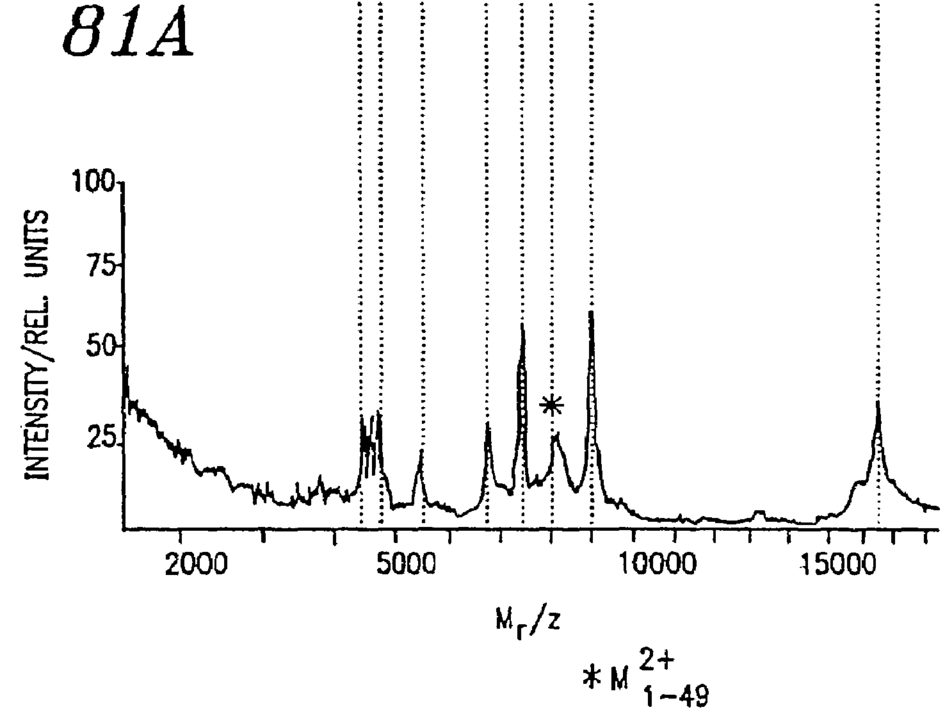

The applicability of streptavidin-coated magnetic beads separation to RNA sequencing was demonstrated for the Rnase $U_2$ digest of the 5'-biotinylated RNA in vitro transcript (49 nt) (FIG. 81). The entire fragment pattern obtained after incubation with Rnase $U_2$ is shown is spectrum 81A. Separation of the biotinylated fragments reduces the complexity of the spectrum (FIG. 81B) since only 5'-terminal fragments are captured by the beads. The signals in the spectrum are broadened and the increased number of signals in the low mass range indicate that even after stringent washing of the beads, some amounts of buffer and detergent used for the binding and elution remained. Further improvements of the method are, therefore, needed. Another possible strategy for application of the magnetic beads is the immobilization of the target RNA prior to RNase digestion by an elution of the remaining fragments for further analysis. Cleavage of the RNA was impeded in this case, as evidenced by a prolonged reaction time for the digest under otherwise identical reaction conditions.

EXAMPLE 22

Parallel DNA Sequencing Mutation Analysis and Microsatellite Analysis Using Primers with Tags and Mass Spectrometric Detection This EXAMPLE describes specific capturing of DNA products generated in DNA analysis. The capturing is mediated by a specific tag (5 to 8 nucleotides long) at the 5' end of the analysis product that binds to a complementary sequence. The capture sequence can be provided by a partially double stranded oligonucleotide bound to a solid support. Different DNA analysis (e.g., sequencing, mutation, diagnostic, microsatellite analysis) can be carried out in parallel, using, for example, a conventional tube or microtiter plate (MTP). The products are then specifically captured and sorted out via the complementary identification sequence on the tag oligonucleotide. The capture oligonucleotide can be bound onto a solid support (e.g., silicon chip) by a chemical or biological bond. Identification of the sample is provided by the predefined position of the capute oligonucleotide. Purification, conditioning and analysis by mass spectrometry are done on solid support. This method was applied for capturing specific primers that had a 6 base tag sequence.

Materials and Methods

Genomic DNA.

Genomic DNA was obtained from healthy individuals.

PCR Amplification

PCR amplifications of part of the β-globin gene were established using β2 d(CATTTGCTTCTGACACAACT SEQ ID NO: 66) as forward primer and β11 d(TCTCTGTCTCCA- CATGCCCAG SEQ ID NO: 67) as reverse primer. The total PCR volume was 50 μl including 200 ng genomic DNA, 1 U Taq-polymerase (Boehringer-Mannheim, Cat #159594), 1.5 mM $MgCl_2$, 0.2 mM dNTPs (Boehringer-Mannheim, Cat #1277049), and 10 pmol of each primer. A specific fragment of the β-globin gene was amplified using the following cycling conditions: 5 min@94° C. followed by 40 cycles of 30 sec@94° C., 45 sec@53° C., 30 sec@72° C., and a final extension of 2 min@72° C. Purification of the amplified product and removal of unincorporated nucleotides was carried out using the QIAquick purification kit (Qiagen, Cat 28104). One fifth of the purified product was used for the primer oligo base extension (PROBE) or sequencing reactions, respectively.

Primer Oligo Base Extension (PROBE) and Sequencing Reactions

Detection of putative mutations in the human β-globin gene at codon 5 and 6 and at codon 30 and in the IVS-1 donor site, respectively, was done in parallel (FIG. 82A). β-TAG1 (GTCGTCCCATGGTGCACCTGACTC SEQ ID NO: 68) served as primer to analyze codon 5 and 6 and β-TAG2 (CGCTGTGGTGAGGCCCTGGGCA SEQ ID NO: 69) for the analyses of codon 30 and the IVS-1 donor site. The primer oligo base extension (PROBE) reaction was done by cycling, using the following conditions: final reaction volume was 20 μl, β-TAG1 primer (5 pmol), β-TAG2 primer (5 pmol), dCTP, dGTP, dTTP, (final concentration each 25 μM), ddATP (final concentration 100 μM) dNTPs and ddNTPs purchased from Boeringer-Mannheim, Cat #1277049 and 1008382), 2 μl of 10× ThermoSequence buffer and 2.5 U ThermoSequenase (Amersham, CAT #E79000Y). The cycling program was as follows: 5 min@94° C., 30 sec@53° C., 30 sec@72° C. and a final extension step for 8 min@72° C. Sequencing was performed under the same conditions except that the reaction volume was 25 μl and the concentration of nucleotides was 250 μM for ddNTP.

Capturing Using TAG Sequence and Sample Preparation

The capture oligonucleotides cap-tagl d(GACGACGACTGCTACCTGACTCCA SEQ ID NO: 70) and cap-tag2 d(ACAGCGGACTGCTACCTGACTCCA SEQ ID NO: 71), respectively, were annealed to equimolar amounts of uni-as d(TGGAGTCAGGTAGCAGTC SEQ ID NO: 72) (FIG. 82A). Each oligonucleotide had a concentration of 10 pmol/μl in $ddH_2O$ and incubated for 2 min@80° C. and 5 min@37° C. This solution was stored at −20° C. and aliquots were taken. 10 pmol annealed capture oligonucleotides were bound to 10 μl paramagnetic beads coated with streptavidin (10 mg/ml; Dynal, Dynabeads M-280 streptavidin Cat #112.06) by incubation for 30 min@37° C. Beads were captured and the PROBE or sequencing reaction, respectively, was added to the capture oligonucleotides. To facilitate binding of β-TAG1 abd β-TAG2, respectively, the reaction was incubated for 5 min@25° C. and for 30 min@16° C. The beads were washed twice with ice cold 0.7 M $NH_4$ Citrate to wash away unspecific bound extension products and primers. The bound products were dissolved by adding 1 μl $DDH_2O$ and incubation for 2 min@65° C. and cooling on ice. 0.3 μl of the sample were mixed with 0.3 μl matrix solution (saturated 3-hydroxy-picolinic acid, 10% molar ratio ammonium-citrate in acetonitrile/water (50/50. v/v)) and allowed to air dry. The sample target was automatically introduced into the source region of an unmodified Perspective Voyager MALDI-TOF operated in delayed extraction linear mode with 5 and 20 kV on the target and conversion dynode, respectively. Theoretical average molecular mass ($M_r$(calc)) were calculated from atomic compositions; reported experimental $M_r$($M_r$(exp)) values are those of the singly-pronated form.

Results

Specific capturing of a mixture of extension products by a short complementary sequence has been applied to isolate sequencing and primer oligo base extension (PROBE) products. This method was used for the detection of putative mutations in the human β-globin gene at codon 5 and 6 and at codon 30 and IVS-1 donor site, respectively (FIG. 82A). Genomic DNA has been amplified using the primers β2 and β11. The amplification product was purified and the nucleotides separated. One fifth of the purified product was used for analyses by primer oligo base extension. To analyze both sites in a single reaction, primers, β-TAG1 and β-TAG2, were used respectively. β-TAG1 binds upstream of codons 5 and 6 and β-TAG2 upstream of codon 30 and the IVS-1 donor site. Extension of these primers was performed by cycling in the presence of ddATP and dCTP, dGTP and dTTP, leading to specific products, depending on the phenotype of the individual. The reactions were then mixed with the capture oligonucleotides. Capture oligonucleotides include the biotinylated capture primer cap-tag1 and cap-tag2, respectively. They have 6 bases at the 5' end, that are complementary to the 5' end of β-TAG1 and β-TAG2, respectively. Therefore, they specifically capture these primers and the extended products. By annealing a universal oligonucleotide (uni-as) to the capture oligonucleotide, the capture primer is transformed into a partially double stranded molecule where only the capture sequence stays single stranded (FIG. 82). This molecule is then bound to streptavidin coated paramagnetic particles, to which the PROBE or sequencing reaction, respectively is added. The mixture was washed to bind only the specifically annealed oligonucleotides. Captured oligonucleotides are dissolved and analyzed by mass spectrometry.

Figure 83:
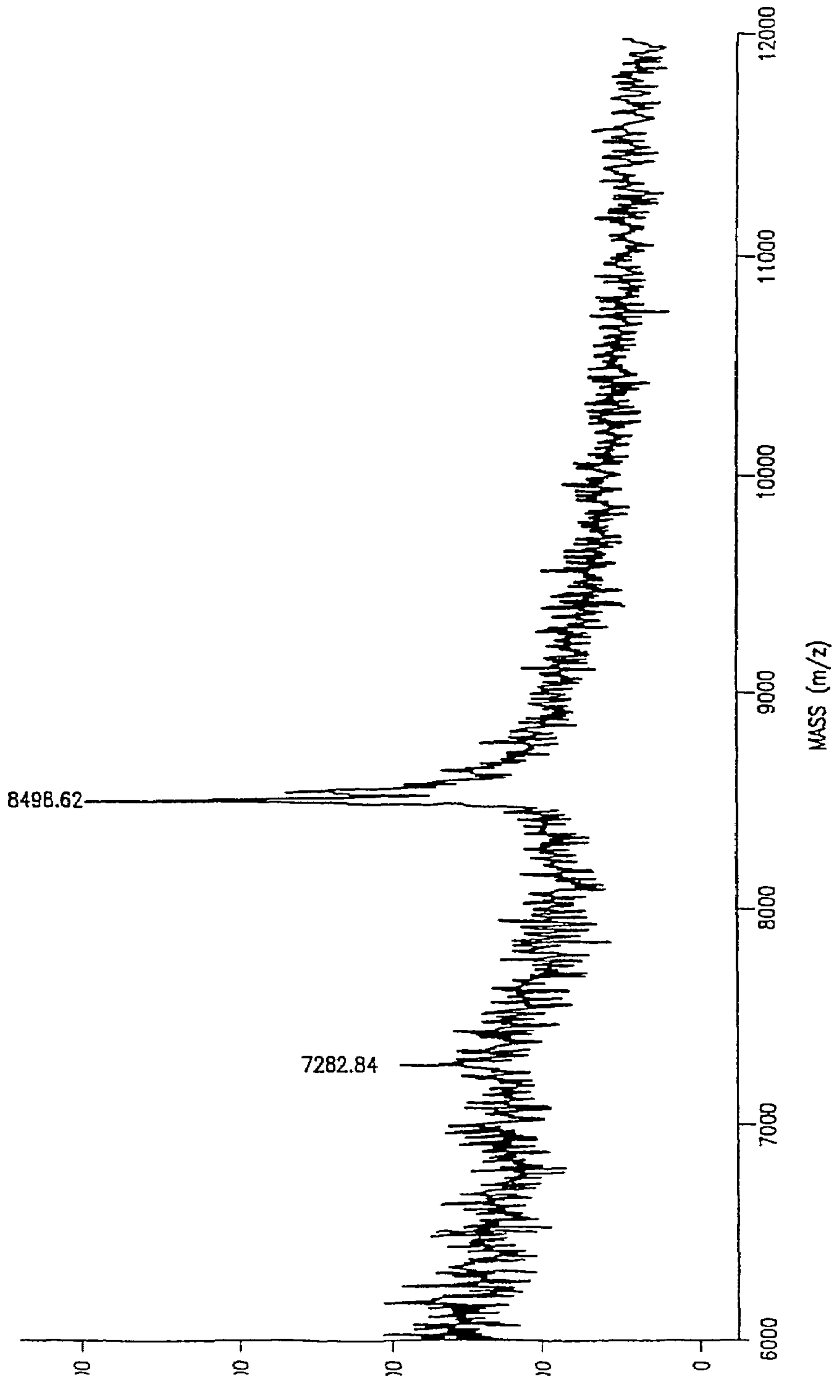
FIG. 83 shows a mass spectrum of the PROBE products of a DNA sample from one individual analyzed as described schematically in FIG. 82.

PROBE products of one individual (FIG. 83) show a small peak with a molecular mass of 7282.8 Da. This corresponds to the unextended β-TAG1 that has a calculated mass of 7287.8 Da. The peak at 8498.6 Da corresponds to a product, that has been extended by 4 bases. This corresponds to the wildtype situation. The calculated mass of this product is 8500.6 Da. There is no significant peak indicating a heterozygote situation. Furthermore only β-TAG1 and not β-TAG2 has been captured, indicating a high specificity of this method.

Figure 84:
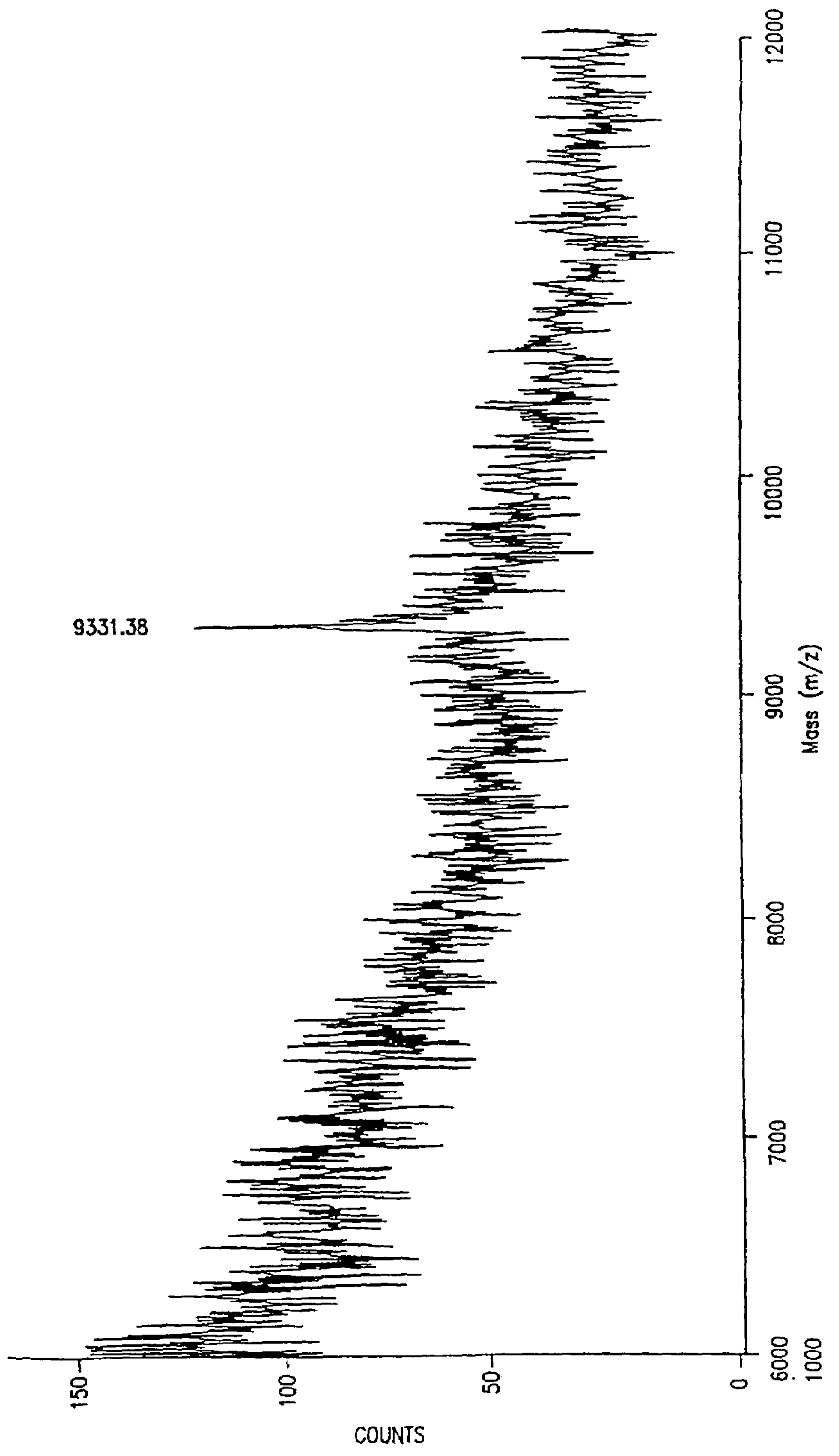
FIG. 84 shows a mass spectrum of the sequence bound to cap-tag-2.

Analyses of what was bound to cap-tag2 (FIG. 84) shows only one predominant peak with a molecular mass of 9331.5 Da. This corresponds to an extension of 8 nucleotides. It indicates a homozygous wildtype situation where the calculated mass of the expected product is 9355 Da. There is no significant amount of unextended primer and only β-TAG2 has been captured.

Figure 85:
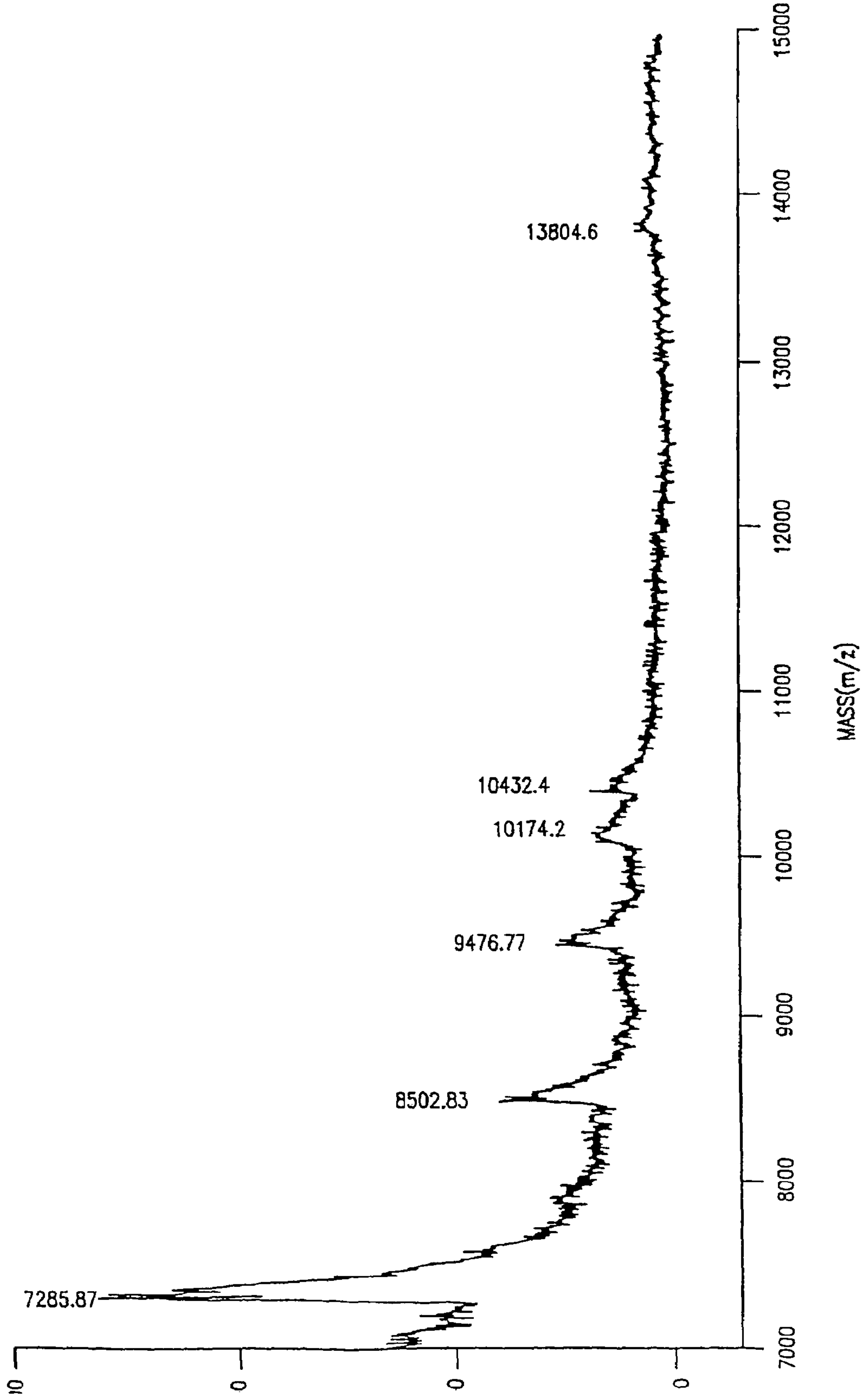
FIG. 85 shows a mass spectrum obtained by using the β-TAG1 and β-TAG 2 primers in one sequencing reaction using ddATP for termination and then sorting according to the method depicted in FIG. 82.
Figure 86:
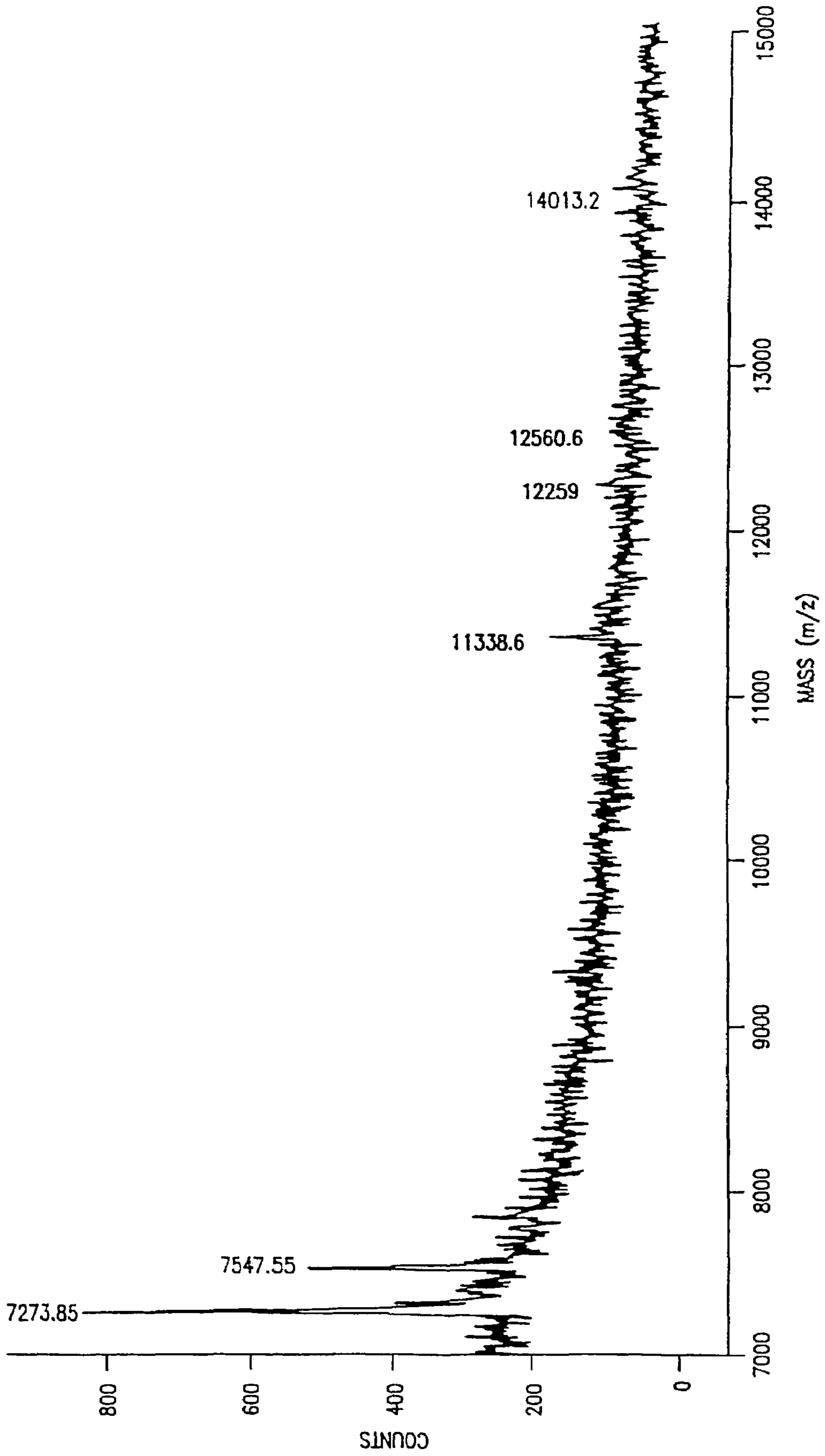
FIG. 86 shows a mass spectrum obtained by using the β-TAG1 and β-TAG2 primers in one sequencing reaction using ddCTP for termination and then sorting according to the method depicted in FIG. 82.

To prove that this approach is also suitable for capturing specific sequencing products, the same two primers β-TAG1 and β-TAG2, respectively, were used. The primers were mixed, used in one sequencing reaction and then sorted by applying the above explained method. Two different termination reactions using ddATP and ddCTP were performed with these primers (FIGS. 85 and 86, respectively). All observed peaks in the spectrograms correspond to the calculated masses in a wildtype situation.

As shown above, parallel analysis of different mutations (e.g., different PROBE primers) is now possible. Further, the described method is suitable for capturing specific sequencing products. Capturing can be used for separation of different sequencing primers out of one reaction tube/well, isolation of specific multiplex-amplified products, PROBE products, etc. Conventional methods, like cycle sequencing, and conventional volumes can be used. A universal chip design permits the use of many different applications. Further, this method can be automated for high throughput.

EXAMPLE 23

Deletion Detection by Mass-Spectrometry

Various formats can be employed for mass spectrometer detection of a deletion within a gene. For example, molecular mass of a double standard amplified product can be determined, or either or both of the strands of a double stranded product can be isolated and the mass measured as described in previous examples.

Alternatively, as described herein, a specific enzymatic reaction can be performed and the mass of the corresponding product can be determined by mass spectrometry. The deletion size can be up to several tenths of vases in length, still allowing the simultaneous detection of the wildtype and mutated allele. By simultaneous detection of the specific products, it is possible to identify in a single reaction whether the individual is homozygous or heterozygous for a specific allele or mutation.

Materials and Methods

Genomic DNA

Leukocyte genomic DNA was obtained from unrelated healthy individuals.

PCR Amplification

PCR amplification of the target DNA was established and optimized to use the reaction products without a further purification step for capturing with streptavidin coated beads. The primers for target amplification and for PROBE reactions were as follows:

CKRΔ-F:d(CAG CTC TCA TTT TCC ATA C SEQ ID NO: 73) and CKRΔ-R bio: d(AGC CCC AAG ATG ACT ATC SEQ ID NO: 74). CKR-5 was amplified by the following program: 2 min@94° C., 45 seconds@52° C., 5 seconds@72° C., and a final extension of 5 minutes at 72° C. The final volume was 50 μl including 200 ng genomic DNA 1 U Taq-polymerase (Boehringer-Mannheim, Cat #1596594), 1.5 Mm $MgCl_2$, 0.2 Mm DNTPS (Boehringer-Mannheim, Cat #1277049), 10 pmol of unmodified forward primers, and 8 pmol 5' biotinylated reverse primer.

Capturing and Denaturation of Biotinylated Templates

10 μl paramagnetic beads coated with streptavidin (10 mg/ml; Dynal, Dynabeads M-280 streptavidin Cat #112.06) in 5× binding solution (5 M $NH_4Cl$, 0.3 M $NH_4OH$) were added to 45 μl PCR reaction (5 μl of PCR reaction were saved for electrophoresis). After binding by incubation for 30 min. at 37° C. the supernatant was discarded. Captured templates were denatured with 50 μl of 100 Mm NaOH for 5 min. at ambient temperature, washed once with 50 μl 50 Mm $NH_4OH$ and three times with 100 μl 10 Mm Tris/Cl, Ph 8.0. The single stranded DNA served as templates for PROBE reactions.

Primer Oligo Base Extension (PROBE) Reaction

The PROBE reaction was performed using Sequence 2.0 (USB Cat #E70775Z including buffer). dATP/DGTP and ddTTP were supplied by Boehringer-Mannheim (Cat #1277049 and 1008382). d(CAG CTC TCA TTT TCC ATA C (SEQ ID NO: 73) was used as PROBE primer (FIG. 87). The following solutions were added tot he beads: 3.0 μl $H_2O$, 1.0 μl reaction buffer, 1.0 μl PROBE primer (10 pmol) and incubated at 65° C. for 5 minutes followed by 37° C. for 10 min. Then 0.5 μl DTT, 3.5 μl DNTPS/ddntp each 50 μM and 0.5 μl Sequenase (0.8 U) were added and incubated at 37° C. for 10 min.

T4 Treatment of DNA

To generate blunt ended DNA, amplification products were treated with T4 DNA polymerase (Boehringer-Mannheim Cat #1004786). The reactions were carried out according to the manufacturer's protocol for 20 min. at 11° C.

Direct Size Determination of Extended Products

To determine the size of the amplified product, MALDI-TOF was applied to one strand of the amplification product samples were bound to beads, as described above, conditioned and denatured, as described below.

DNA Conditioning

After the PROBE reaction the supernatant was discarded nd the beads were washed first in 50 μl 700 mM $NH_4$-citrate and second 50 μl 50 mM $NH_4$-citrate. The generated diagnostic products were removed for the template by heating the beads in 2 μl $H_2O$ at 80° C. for 2 min. The supernatant was used for MALDI-TOF analysis.

Sample Preparation and Analysis with MALDI-TOF Mass Spectrometry

Sample preparation was performed by mixing 0.6 μl of matrix solution (0.7 M 3-hydroxypicolinic acid, 0.07 M dibasic citrate in 1:1 $H_2O$:$CH_3CN$) with 0.3 μl of diagnostic PROBE products in water on a sample target and allowed to air dry. Up to 100 samples were spotted on a probe target disk for introduction into the source region of an unmodified Perspective Voyager MALDI-TOF instrument operated in linear mode with delayed extraction and 5 and 30 kV on the target and conversion dynode, respectively. Theoretical average molecular mass ($M_r$(calc)) of analytes were calculated from atomic compositions, reported experimental $M_r$($M_r$(exp)) values are those of the singly-pronated form, determined using internal calibration with unextended primers in the case of PROBE reactions.

Conventional Analyses

Conventional analyses were performed by native polyacrylamide gel electrophoresis according to standard protocols. The diagnostic products were denatured with formamide prior to loading onto the gels and stained with ethidium bromide or silver, respectively.

Results

Figure 88:
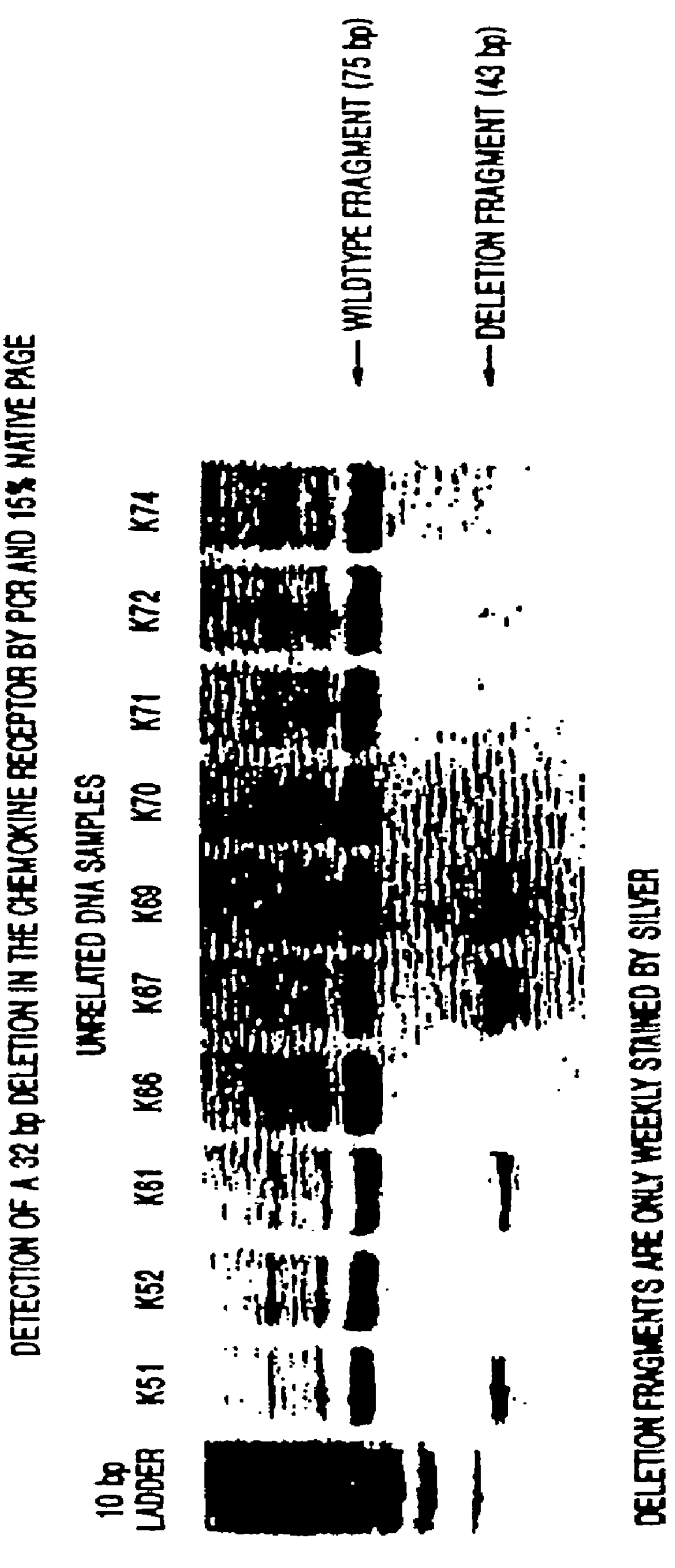
FIG. 88 shows the amplification products of different unrelated individuals as analyzed by native polyacrylamide gel electrophoreses (15%) and silver stain. The band corresponding to a wildtype CKR-5 runs at 75 bp and the band from the gene with the deletion at 43 bp. Bands bigger than 75 bp are due to unspecific amplification.
Figure 89A:
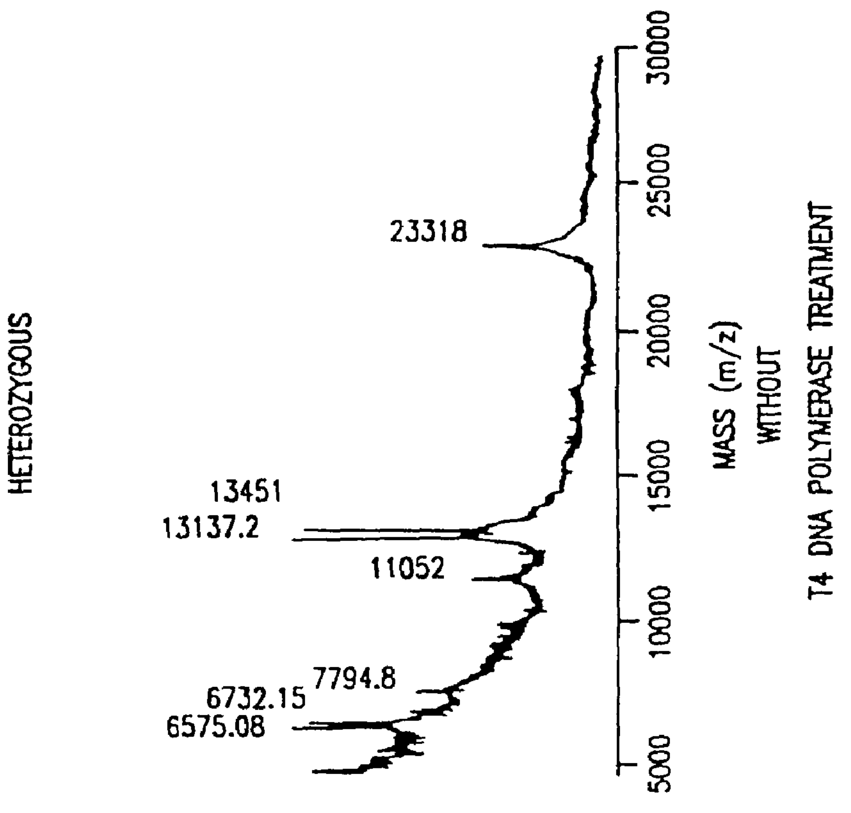
FIG. 89A shows a spectrograph of DNA derived from a heterozygous individual: the peak with a mass of 23319 Da corresponds to the wildtype CKR-5 and the peaks with masses of 13137 Da and 13451 Da to the deletion allele with and without an extra Adenosine, respectively.

The CKR-5 status of 10 randomly chosen DNA samples of healthy individuals were analyzed. Leukocyte DNA was amplified by PCR and an aliquot of the amplified product was analyzed by standard polyacrylamide gel electrophoresis and silver staining of the DNA (FIG. 88). Four samples showed two bands presumably indicating heterozygosity for CKR-5, whereas the other 6 samples showed one band, corresponding to a homozygous gene (FIG. 88). In the case where two bands were observed, they correspond to the expected size of 75 bp for the wildtype gene and 43 bp for the allele with the deletion (FIG. 87). Where one band was observed, the size was about 75 bp which indicated a homozygous wildtype CKR-5 allele. One DNA sample derived from a presumably heterozygous one from a homozygous individual were used for all further analysis. To determine the molecular mass of the amplified product, DNA was subjected to matrix assisted laser desorption/ionization coupled with time of flight analysis (MALDI-TOF). Double stranded DNA, bound to streptavidin coated paramagnetic particles, was denatured and the strand released into the supernatant was analyzed. FIG. 89A shows a spectrograph of a DNA sample, that was supposed to be heterozygous according to the result derived by polyacrylamide gel electrophoresis (FIG. 88). The calculated mass of the sense strand for a wildtype gene is 23036 Da and for the sense strand carrying the deletion allele 13143 (FIG. 87 and Table VI). Since many thermostable polymerases unspecifically add an adenosine to the 3' end of the product, those masses were also calculated. They are 23349 and 13456 Da. The masses of the observed peaks (FIG. 89A) are 23119 Da, which corresponds to the calculated mass of a wildtype DNA strand where an adenosine has been added (23349 Da). Since no peak with a mass of about 23036 Da was observed, the polymerase must have qualitatively added adenosine. Two peaks, which are close to each other, have a mass of 13451 and 13137 Da. This corresponds to the calculated masses of the allele, with the 32 bp deletion. The higher mass peak corresponds to the product, where adenosine has been added and the lower mass peak to the one without the unspecific adenosine. Both peaks have about the same height, indicating that to about half of the product adenosine has been added. The peak with a mass of 11682 Da is a doubly charged molecule of the DNA corresponding to 23319 Da (2×11682 Da=23364 Da). The peaks with masses of 6732 and 6575 Da are doubly charged molecules of the one with masses of 13451 and 13137 Da and the peak with 7794 Da corresponds to the triply charged molecule of 23319Da. Multiple charged molecules are routinely identified by calculation. Amplified DNA derived from a homozygous individual shows in the spectrograph (FIG. 89C) one peak with a mass 23349.6 and a much smaller peak with a mass of 23039.9 Da. The higher mass peak corresponds to DNA resulting from a wildtype allele with an added adenosine, that has a calculated mass of 23349 Da. The lower mass peak corresponds to the same product without adenosine. Three further peaks with a mass of 11686, 7804.6 and 5852.5 Da correspond to doubly, triply and quadruply charged molecules.

Figure 89B:
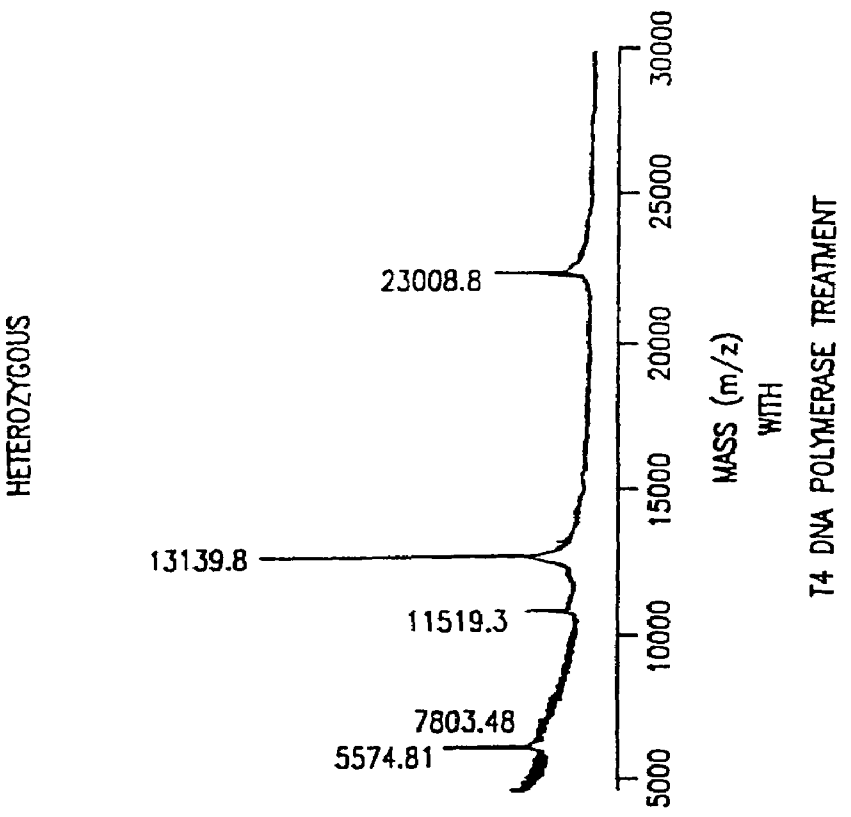
FIG. 89B shows a spectrograph of DNA obtained from the same individual as in FIG. 89A, but the DNA was treated with T4 DNA polymerase to remove the added Adenosine.
Figure 89C:
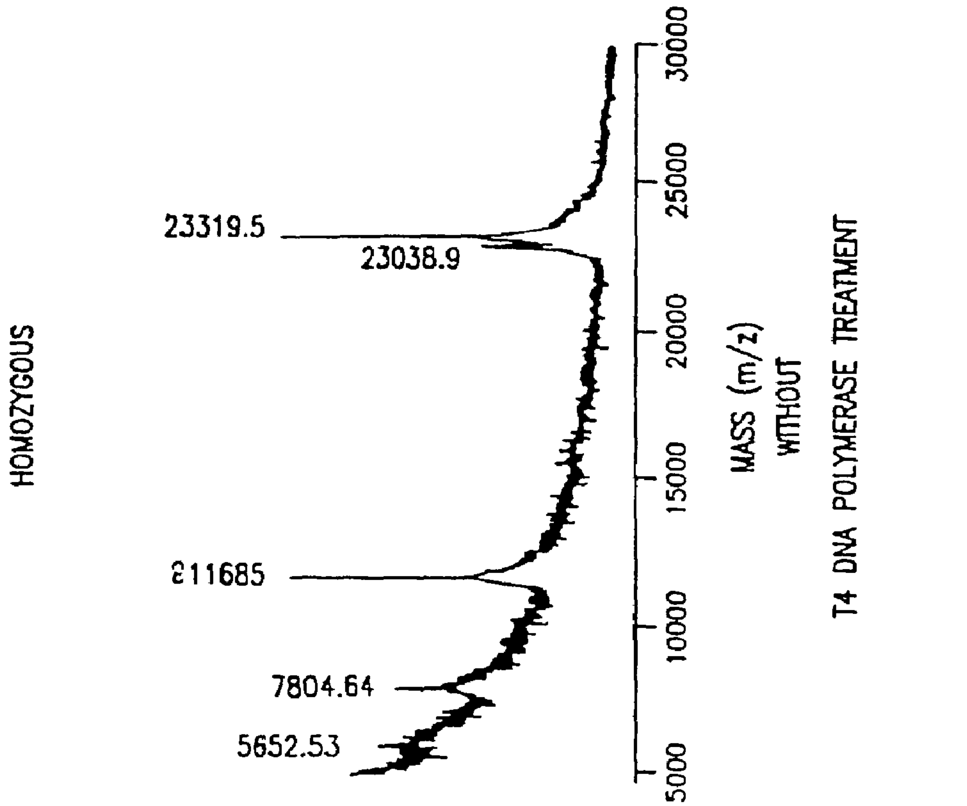
FIGS. 89C and 89D are spectrographs derived from homozygous individuals and in FIG. 89D, the Adenosine has been removed. All peaks with masses lower than 13000 Da are due to multiple charged molecules.
Figure 89D:
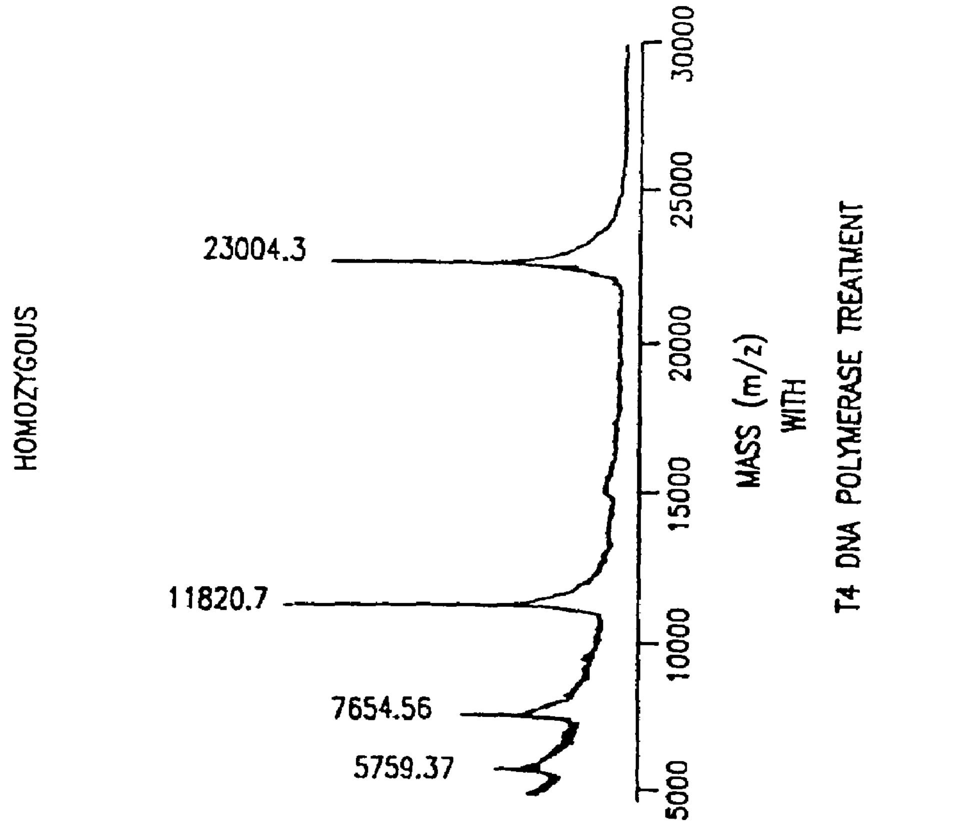

The unspecific added adenine can be removed from the amplified DNA by treatment of the DNA and T4 DNA polymerase. DNA derived from a heterozygous and a homozygous individual was analyzed after T4 DNA polymerase treatment. FIG. 89B shows the spectrograph derived from heterozygous DNA. The peak corresponding to the wildtype strand has a mass of 23008 Da indicating that the added adenine had been removed completely. The same is observed for the strand with a mass of 13140 Da.

Figure 90A:
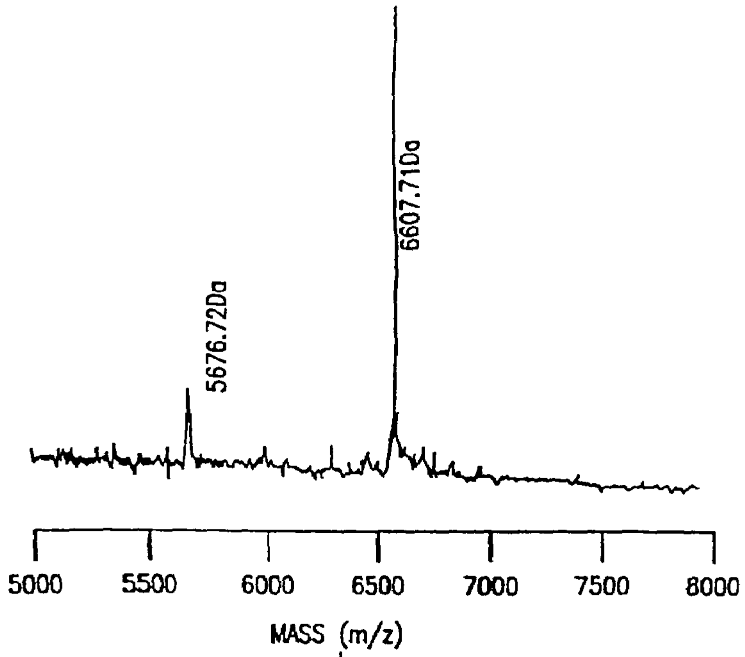
FIG. 90A shows the mass spectrum of the results of a PROBE reaction performed on DNA obtained from a heterozygous individual.
Figure 90B:
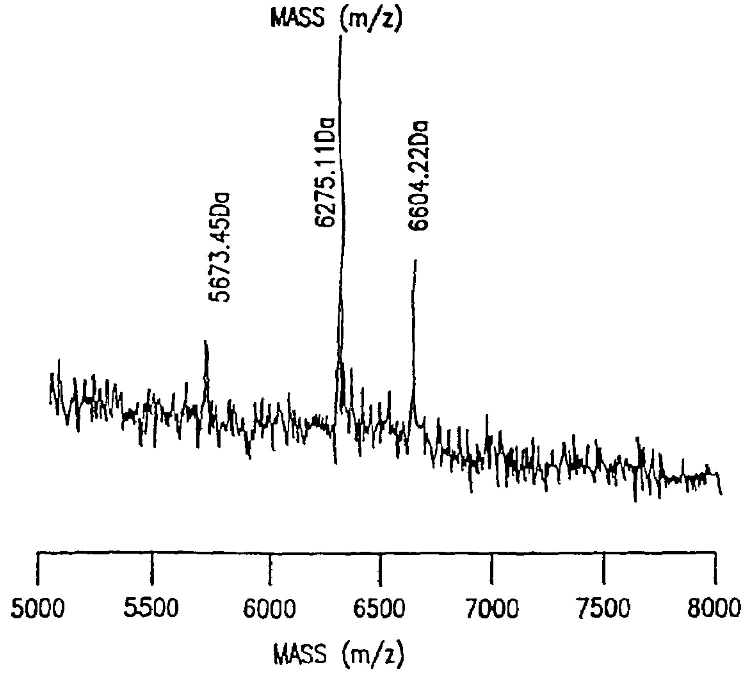
FIG. 90B shows a mass spectrum of the results of a PROBE reaction on a homozygous individual. The peaks with masses of 6604 Da and 6607 Da, respectively correspond to the wildtype allele, and the peak with a mass of 6275 Da to the deletion allele. The primer is detected with a mass of 5673 and 5676 Da, respectively.

The other three peaks are multiply charged molecules of the parent peaks. The mass spectrograph for the homozygous DNA shows one peak that has a mass of 23004 Da, corresponding to the wildtype DNA strand without an extra adenine added. All other peaks are derived from multiply charged molecules of this DNA. The amplified products can be analyzed by direct determination of their masses, as described above, or by measuring the masses of products, that are derived from the amplified product in a further reaction. In this "primer oligo base extension (PROBE)" reaction, a primer that can be internal, as it is in the nested PCR, or identical to one of the PCR primers, is extended for just a few bases before the termination nucleotide is incorporated. Depending on the extension length, the genotype can be specified. CKRΔ-F was used as a PROBE primer, and dATP/dGTP and ddTTP as nucleotides. The primer extension is AGT in case of a wildtype template and AT in case of the deletion (FIG. 87). The corresponding masses are 6604 Da for the wildtype and 6275 Da for the deletion, respectively. PROBE was applied to two standard DNAs. The spectrograph (FIG. 90A) shows peaks with masses of 6604 Da corresponding to the wildtype DNA and at 6275 Da corresponding to the CKR-5 deletion allele (Table VIII). The peak at a mass of 5673 Da corresponds to CKRA-F (calculated mass of 5674 Da). Further samples were analyzed in analogous way (FIG. 90B). It is unambiguously identified as homozygous DNA, since the peak with a mass of 6607 Da corresponds to the wildtype allele and the peak with a mass of 5677 Da to the unextended primer. No further peaks were observed.

The example demonstrates that deletion analysis can be performed by mass spectrometry. As shown herein, the deletion can be analyzed by direct detection of single stranded amplified products, or by analysis of specifically generated diagnostic products (PROBE). In addition, as shown in the following Example 26, double stranded DNA amplified products can be analyzed.

| | Size | |
|---|---|---|
| | Calculated Mass | Measured Mass |
| wildtype w/o A | 23036 | 23039/23009/23004 |
| wildtype with A | 23349 | 23319/23350 |
| deletion w/o A | 13143 | 13137/13139 |
| deletion with A | 13456 | 13451 |
| PROBE | | |
| wildtype | 6604 | 6604/6608 |
| deletion | 6275 | 6275 |

All masses are in Dalton.

EXAMPLE 24

Pentaplex tc-PROBE

Summary

The multiplexing of thermocycling primer oligo base extension (tc-PROBE) was performed using five polymorphic sites in three different apolipoprotein genes, which are thought to be involved in the pathogenesis of atherosclerosis. The apolipoprotein A IV gene (codons 347 and 360), the apolipoprotein E gene (codons 112 and 158), and the apolipoprotein B gene (codon 3500) were examined. All mass spectra were easy to interpret with respect to the five polymorphic sites.

Materials and Methods

PCR Amplification

Human leukocytic genomic DNA was used for PCR. Listed below are the primers used for the separated amplification of portions of the Apo A IV, Apo E and the Apo B genes:

| | | |
|---|---|---|
| Apo A IV: | A347F: | 5'-CGA GGA GCT CAA GGC CAG AAT-3' (SEQ ID NO:75) |
| | A360 R-2-bio: | *5'-CAG GGG CAG CTC AGC TCT C-3' (SEQ ID NO:76) |
| Apo E: | ApoE-F: | 5'-GGC ACG GCT GTC CAA GGA-3' (SEQ ID NO:77) |
| | ApoE-R bio: | *5'-AGG CCG CGC TCG GCG CCC TC-3' (SEQ ID NO:78) |
| Apo B: | ApoB-F2 bio: | *5'-CTT ACT TGA ATT CCA AGA GC-3' (SEQ ID NO:79) |
| | Apo B-R: | 5'-GGG CTG ACT TGC ATG GAC CGG A-3' (SEQ ID NO:80) |

*biotinylated

Taq polymerase and 10× buffer were purchased from Boehringer-Mannheim (Germany) and dNTPs for Pharmacia (Freiburg, Germany). The total PCR reaction volume was 50 μl including 10 pmol of each primer and 10% DMSO (dimethylsulfoxide, Sigma) (no DMSO for the PCR of the Apo B gene), with ~200 mg of genomic DNA used as template and a final dNTP concentration of 200 μM. Solutions were heated to 80° C. before the addition of 1 U Taq polymerase; PCR conditions were: 5 min at 95° C., followed by 2 cycles 30 sec 94° C., 30 sec 62° C., 30 sec 72° C., 2 cycles 30 sec 94° C. 30 sec 58° C., 30 sec 72° C., 35 cycles of 30 sec at 94° C., 30 sec at 56° C., 30 sec at 72° C., and a final extension time of 2 min at 72° C. To remove unincorporated primers and nucleotides, amplified products were purified using the "QIAquick" (Qiagen, Germany ) kit, with elution of the purified products in 50 μL of TE buffer (10 mM Tris-HCl, 1 mM EDTA, pH 8.0).

Binding of the Amplified Product on Beads

10 μl of each purified amplified product was bound to 5 μl DynaBeads (Dynal, M-280 Streptavidin) and denatured according to the protocol from Dynal. For the pentaplex tc-PROBE reaction the three different amplified product (bound on the beads) were pooled.

Tc-PROBE

For the PROBE reaction the following primers were used:

```
(Apo A) P347:
                                        (SEQ ID NO:81)
5'-AGC CAG GAC AAG-3'

(Apo A) P360:
                                        (SEQ ID NO:82)
5'-ACA GCA GGA ACA GCA-3'

(Apo E) P112:
                                        (SEQ ID NO:83)
5'-GCG GAC ATG GAG GAC GTG-3'

(Apo E) P158:
                                        (SEQ ID NO:84)
5'-GAT GCC GAT GAC CTG CAG AAG-3'

(Apo B) P3500:
                                        (SEQ ID NO:85)
5'-GTG CCC TGC AGC TTC ACT GAA GAC-3'
```

The tc-PROBE was carried out in a final volume of 25 μl containing 10 pmol of each primer listed above, 2.5 U Thermoquenase (Amersham), 2.5 μL Thermoquenase buffer, and 50 μM dTTP (final concentrations) and 200 μM of ddA/C/GTP, respectively. Tubes containing the mixture were placed in a thermocycler and subjected to the following cycling conditions: denaturation (94° C.) the supernatant was carefully removed from the beads and 'desalted' by ethanol precipitation to exchange nonvolatile cations such as Na+ and K+ with $NH_4$+, which evaporated during the ionization process; 5 μL 3 M ammonium acetate (pH 6.5) 0.5 μL glycogen (10 mg/mL, Sigma), 25 μL $H_2O$, and 110 μL absolute ethanol were added to 25 μL PROBE supernatant and incubated for 1 hour at 4° C. After a 10 min. centrifugation at 13,000× g, the pellet was washed in 70% ethanol and resuspended in 1 μL 18 Mohm/cm $H_2O$. A 0.35 μL aliquot of resuspended DNA was mixed with 0.35 μL matrix solution (0.7 M 3-hydroxypicolinic acid (3-HPA), 0.07 M ammonium citrate in 1:1 $H_2O$:$CH_3CN$) on a stainless steel sample target disk and allowed to air dry preceding spectrum acquisition using the Thermo Bioanalysis Version 2000 MALDI-TOF operated in reflectron mode with 5 and 20 kV on the target and conversion dynode, respectively, Theoretical average molecular masses ($M_1$(calc)) of the fragments were calculated from atomic compositions. External calibration generated from synthetic $(ATCG)_n$ oligonucleotide (3.6-18 kDa) was used. Positive ion spectra from 1-37500 Da were collected.

Results

Figure 91:
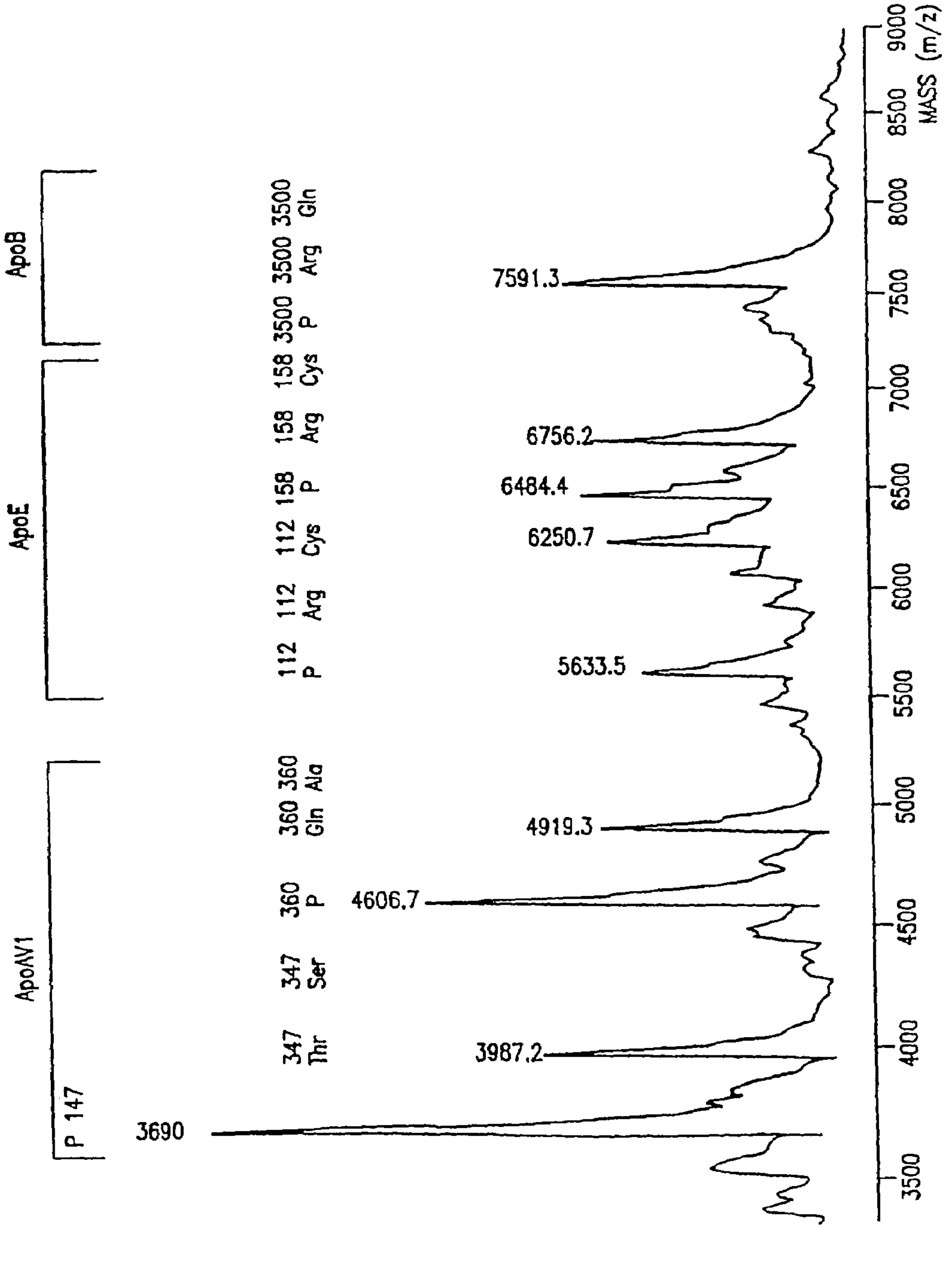
FIG. 91 shows a MALDI-TOF MS spectra of a thermocycling primer Oligo Base Extension (tc-PROBE) reaction as described in Example 24 using three different templates and 5 different PROBE primers simultaneously in one reaction.
Figure 92:
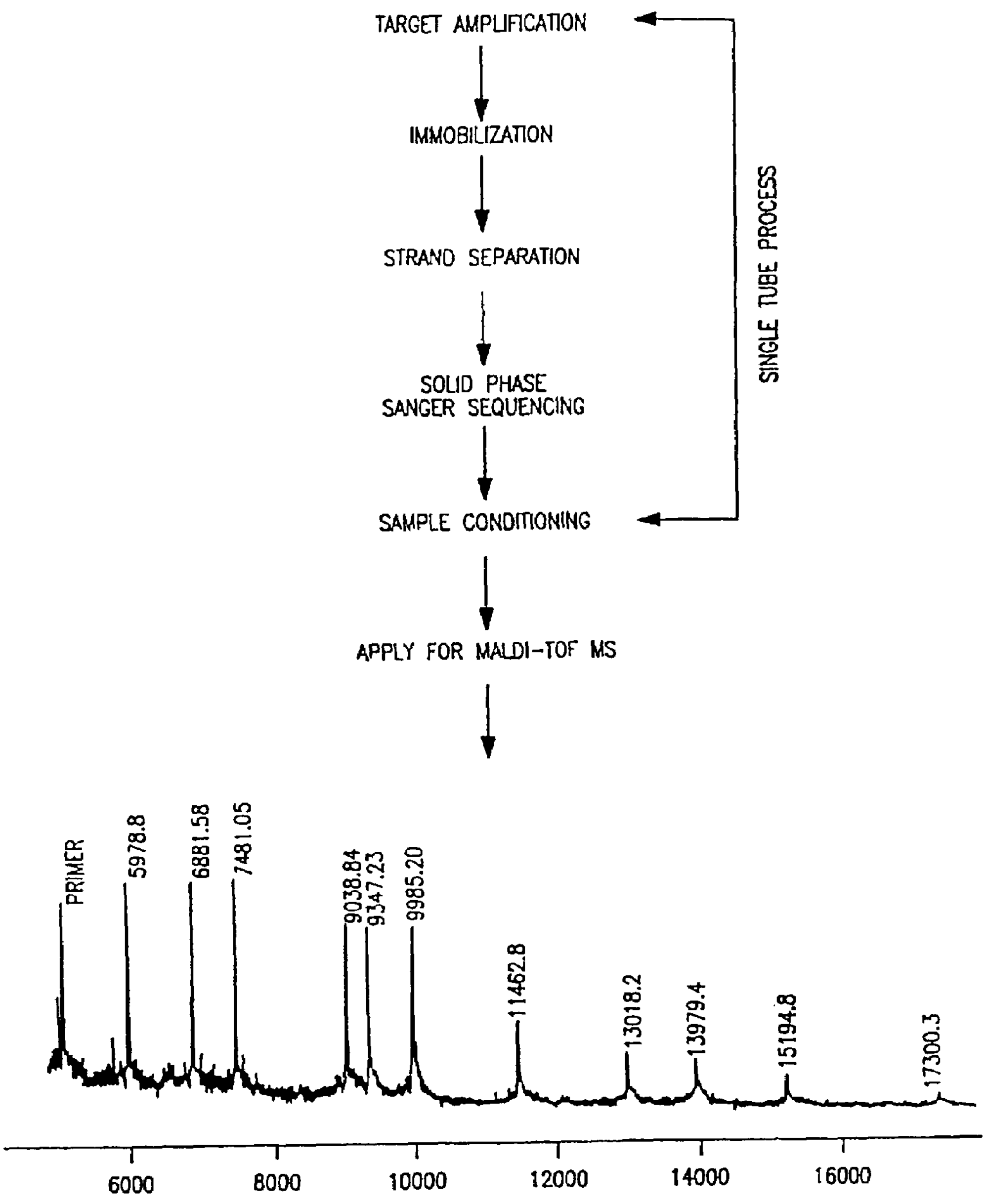
FIG. 92 schematically depicts a single tube process for amplifying and sequencing exons 5-8 of the p53 gene as described in Example 25. The mass spectrum is the A reaction of FIG. 93.
Figure 93:
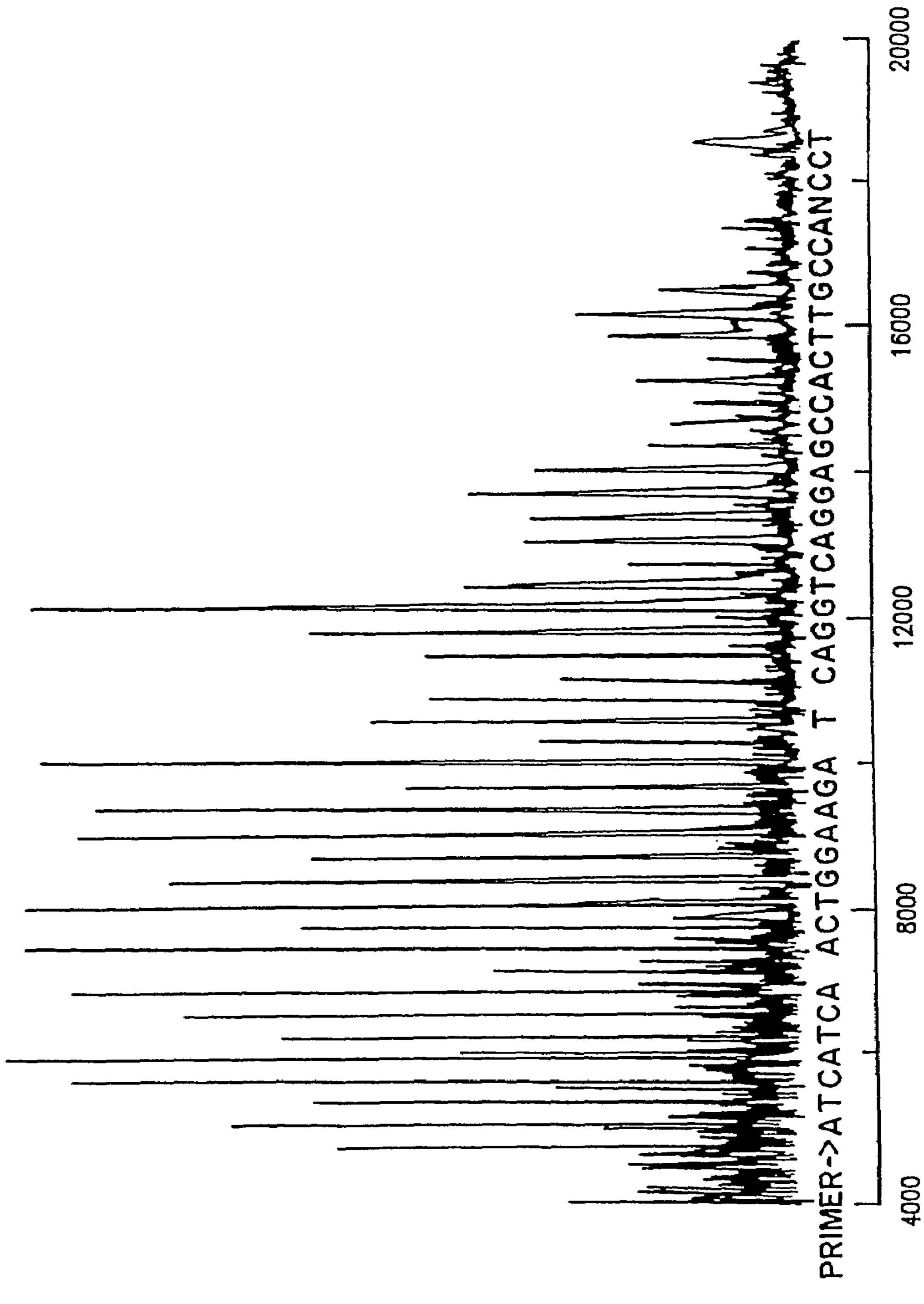
FIG. 93 shows a superposition plot of four separate reactions for sequencing a portion (SEQ ID NO: 318) of exon 7 of the p53 gene as described in Example 25.

Table VIII shows the calculated molecular masses of all possible extension products including the mass of the primer itself. FIG. 91 shows a respective MALDI-TOP MS spectra of a tc-PROBE using three different templates and 5 different PROBE primers simultaneously in one reaction. Comparison of the observed and calculated masses (see table VIII) allows a fast genetic profiling of various polymorphic sites in an individual DNA sample. The sample presented in FIG. 91 is homozygous for threonine and glutamine at position 347 and 360, respectively, in the apolipoprotein A IV gene, bears the epsilon 3 allele homozygous in the apolipoprotein E gene, and is also homozygous at the codon 3500 for arginine in the apolipoprotein B gene.

TABLE VIII

| | SEQ ID NO: | mass | allele |
|---|---|---|---|
| Apolipoprotein A IV | | | |
| 5'-AGCCAGGACAAG-3' (347) | 86 | 3688.40 | unextended primer |
| 5'-AGCCAGGACAAGTC-3' | 87 | 4265.80 | 347 Ser |
| 5'-AGCCAGGACAAGA-3' | 88 | 3985.60 | 347 Thr |
| 5'-ACAGCACCAACAGCA-3' (360) | 89 | 4604.00 | unextended primer |
| 5'-ACAGCAGGAACAGCATC-3' | 90 | 5181.40 | 360 His |
| 5'-ACAGCAGGAAGAGCAG-3' (112) | 91 | 4917.20 | 360 Gln |
| Apolipoprotein E | | | |
| 5'-GCGGACATGGAGGACGTG-3' (112) | 92 | 5629.60 | unextended primer |
| 5'-GCGGACATGGAGGACGTGGC-3' | 93 | 6247.00 | 112 Cys |
| 5'-GCGGACATGGAGGACGTGC-3' | 94 | 5902.80 | 112 Arg |
| 5'-GATGCCGATGACCTGCAGAAG-3' (158) | 95 | 6480.20 | unextended primer |
| 5'-GATGCCGATGACCTGCAGAAGC-3' | 96 | 6753.40 | 158 Arg |
| 5'-GATGCCGATGACCTGCAGAAGTG-3' | 97 | 7097.60 | 158 Cys |
| Apolipoprotein B-100 | | | |
| 5'-GTGCCCTGCAGCTTCACTGAAGAC-3' | 98 | 7313.80 | unextended |

TABLE VIII-continued

| | SEQ ID NO: | mass | allele |
|---|---|---|---|
| (3500) | | | primer |
| 5'-GTGCCCTGCAGCTTCACTGAAGACTG-3' | 99 | 7931.20 | 3500 Gln |
| 5'-GTGCCCTGCAGCTTCACTGAAGACC-3' | 100 | 7587.00 | 3500 Arg |

EXAMPLE 25

Sequencing Exons 5 to 8 of the p53 Gene by MALDI-TOF Mass Spectrometry

Materials & Methods

Thirty-five cycles of PCR reactions were performed in a 96 well microliter plate with each well containing a total volume of 50 μl including 200 ng genomic DNA, 1 unit Taq DNA polymerase, 1.5 mM Mg $C1_2$, 0.2 mM dNTPx, 10 pmol of the forward primer and 6 or 8 of the biotinylated reverse primer. The sequences of PCR primers prepared according to established chemistry (N. D. Sinha, J. Biernat, H. Kter, *Tetrahed. Lett.* 24: 5843-5846 (1983) are as follows:

```
exon 5:
d(biotin-TATCTGTTCACTTGTGCCC SEQ ID NO:101)
and

d(biotin-CAGAGGCCTGGGGACCCTG SEQ ID NO:102);

exon 6:
D(ACGACAGGGCTGGTTGCC SEQ ID NO:103)
and

d(biotin-ACTGACAACCACCCTTAAC SEQ ID NO:104);

exon 7:
d(CTGCTTGCCACAGGTCTC SEQ ID NO:105)
and

d(biotin-CACAGCAGGCCAGTGTGC SEQ ID NO:106;

exon 8:
d(GGACCTGATTTCCTTACTG SEQ ID NO:107)
and

d(biotin-TGAATCTGAGGCATAACTG SEQ ID NO:108).
```

To each well of the 96-well microliter plate containing unpurified amplified product, 0.1 mg of paramagnetic streptavidin beads (Dynal) in 10 μl of 5× binding solution (5 M $NH_4OH$) was added and incubated at 37° C. for 30 min.

Then beads were treated with 0.1 M NaOH at room temperature for 5 min followed by one wash with 50 mM $NH_4OH$ at room temperature for 5 min followed by one wash with 50 mM Tris-HCl.

Four dideoxy termination reactions were carried out in separate wells of the microliter plate. A total of 84 reactions (21 primers×4 reactions/primer) can be performed in a single microliter plate. To each well containing immobilized single-stranded template, a total volute of 10 μl reaction mixture was added including 1× reaction buffer, 10 pmol of sequencing primer, 250 mM of dNTPs, 25 mM of one of the ddNTPs, and 1~2 units of Thermosequenase (Amersham). Sequencing reactions were carried out on a thermal cycler using non-cycling conditions: 80° C., 1 min, 50° C., 1 min, 50° C. to 72° C., ramping 0.1°/sec, and 72° C., 5 min. The beads were then washed with 0.7 M ammonium citrate followed by 0.05 M ammonium citrate. Sequencing products were then removed from beads by heating the beads to 80° C. in 2 μl of 50 mM $NH_4OH$ for 2 min. The supernatant was used for MALDI-TOF MS analysis.

Matrix was prepared as described in Kter, et al (Kter, H. et al., *Nature Biotechnol.* 14: 1123-1128 (1996)). This saturated matrix solution was then diluted 1.52 times with pure water before use. 0.3 μl of the diluted matrix solution was then diluted 1.52 times with pure water before use. 0.3 μl of the diluted matrix solution was loaded onto the sample target and allowed to crystallize followed by addition of 0.3 μl of the aqueous analyte. A Perseptive Voyager DE mass spectrometer was used for the experiments, and the samples were typically analyzed in the manual mode. The target and middle plate were kept at +18.2 kV for 200 nanoseconds after each laser shot and then the garget voltage was raised to +20 kV. The ion guide wire in the flight tube was kept at −2V. Normally, 250 laser shots were accumulated foe each sample. ˆThe original spectrum was acquired under 500 MHz digitizing rate, and the final spectrum was smoothed by a 455 point average (Savitsky and Golay, (1964) Analytical Chemistry, 36:1627). Default calibration of the mass spectrometer was used to identify each peak and assign sequences. The theoretical mass values of two sequencing peaks were used to recalibrate each spectrum. (D. P. Little, T. J. Cornish, M. J. O'Donnel, A. Braun, R. J. Cotter, H. Kter, Anal. Chem., submitted).

Results

Alterations of the p53 gene are considered to be a critical step in the development of many human cancers (Greenblatt, et al., (1994) Cancer Res. 54, 4855-4878; C. C. Harris, (1996) J. Cancer, 73, 261-269; and D. Sidransky and M. Hollstein, (1996) Annu. Res. Med., 47, 285-301). Mutations may serve as molecular indicators of clonality or as early markers of relapse in a patient with a previously identified mutation in a primary tumor (Hainaut, et al., (1997) Nucleic Acid Res., 25, 151-157). The prognosis of the cancer may differ according to the nature of the p53 mutations present (H. S. Goh et al., (1995) Cancer Res, 55, 5217-5221). Since the discovery of the p53 gene, more than 6000 different mutations have been detected. Exons 5-8 were selected as sequencing targets where most of the mutations cluster (Hainaut et al. (1997) Nucleic Acids Res., 25, 151-7).

Figure 96A:
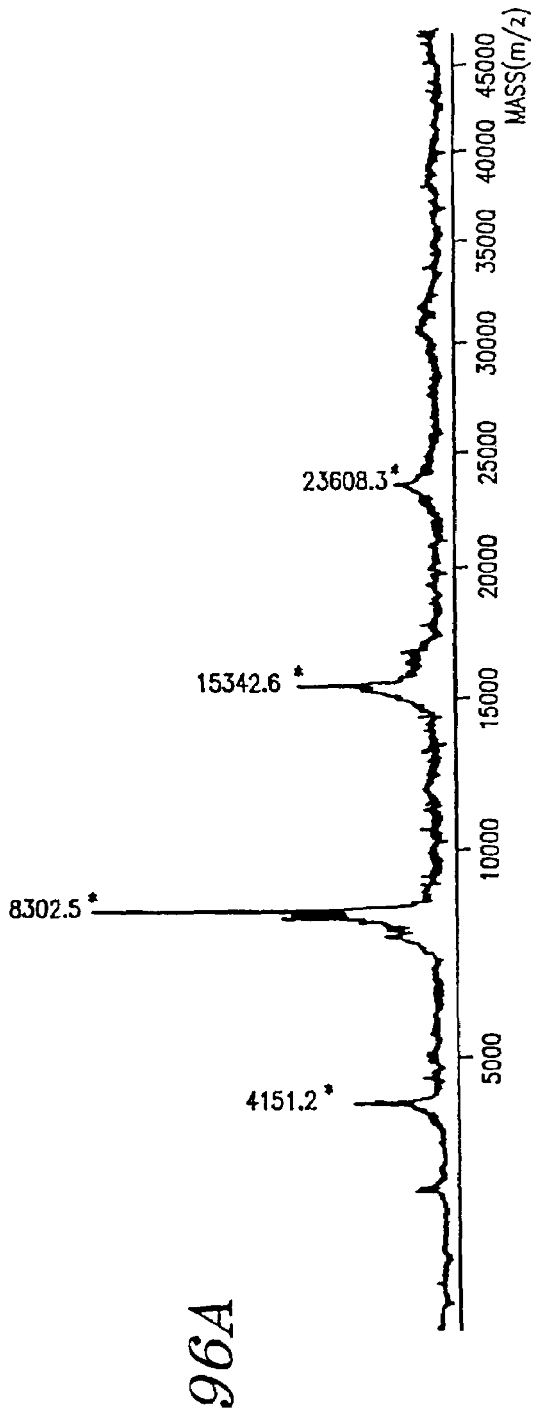
FIG. 96A shows a MALDI-TOF mass spectra of a synthetic 50-mer (15.34 kDa) mixed with 27-mer$_{nc}$ (non-complementary, 8.30 kDa).
Figure 96B:
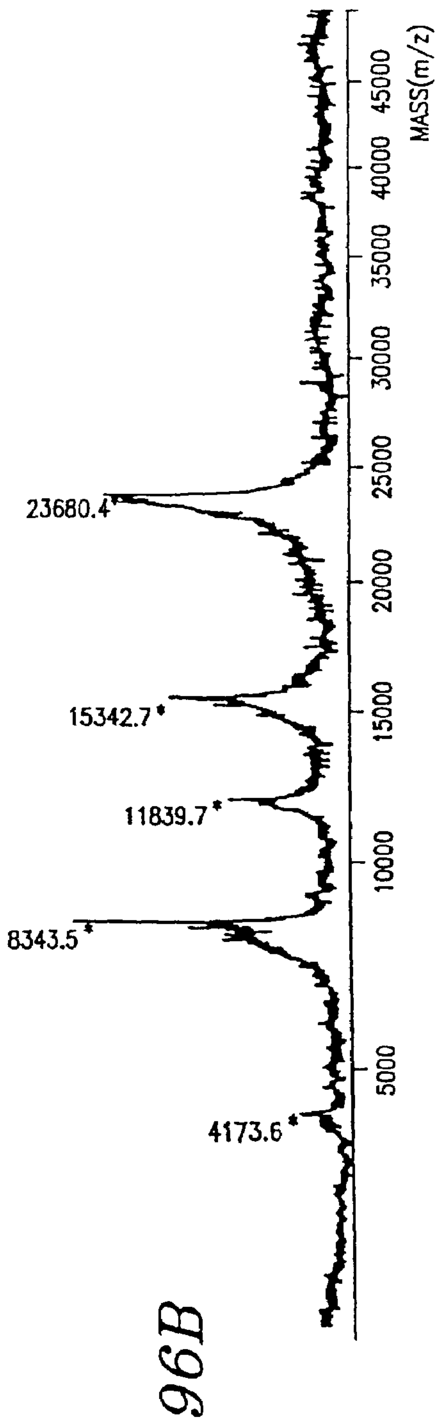
FIG. 96B shows a MALDI-TOF mass spectra of a synthetic 50-mer (15.34k Da) mixed with a 27-mer$_c$ (complementary, 8.34 kDa). The final concentration of each oligonucleotide was 10 μM. The signal at 23.68 kDa in FIG. 96B corresponds to WC-specific dsDNA.

FIG. 96 schematically depicts the single tube process for target amplification and sequencing, which was performed, as described in detail in the Materials and Methods. Each of exon 5-8 of the p53 gene was PCR amplified using flanking primers in the intron region; the down stream primer was biotinylated. Amplifications of different exons were optimized to use the same cycling profile, and the products were used without further purification. PCR reactions were performed in a 96 well microliter plate and the product generated in one well was used as the template for one sequencing reaction. Streptavidin-coated magnetic beads were added to the same microliter plate and amplified products were immobilized. The beads were then treated with NaOH to generate immobilized single-stranded DNA as sequencing template. The beads were washed extensively with Tris buffer since remaining base would reduce the activity of sequencing enzyme.

A total of 21 primers were selected to sequence exon 5-8 of the p53 gene by primer walking. The 3'-end nucleotide of all the primers is located at the site where no known mutation exists. Four termination reactions were performed separately which resulted in a total of 84 sequencing reactions on the same PCR microliter plate. Non-cycling conditions were adopted for sequencing since streptavidin coated beads do not tolerate the repeated application of high temperature. Sequencing reactions were designed so that mt terminated fragments were under 70 nucleotides, a size range easily accessible by MALDI-TOF MS and yet long enough to sequence through the next primer binding site. Thermequenase was the enzyme of choice since it could reproducible generate a high yield of sequencing products in the desired mass range. After the sequencing reactions, the beads were washed with ammonium ion buffers to replace all other cations. The sequencing ladders were then removed from the beads by heating in ammonium hydroxide solution or simply in water.

Figure 94:
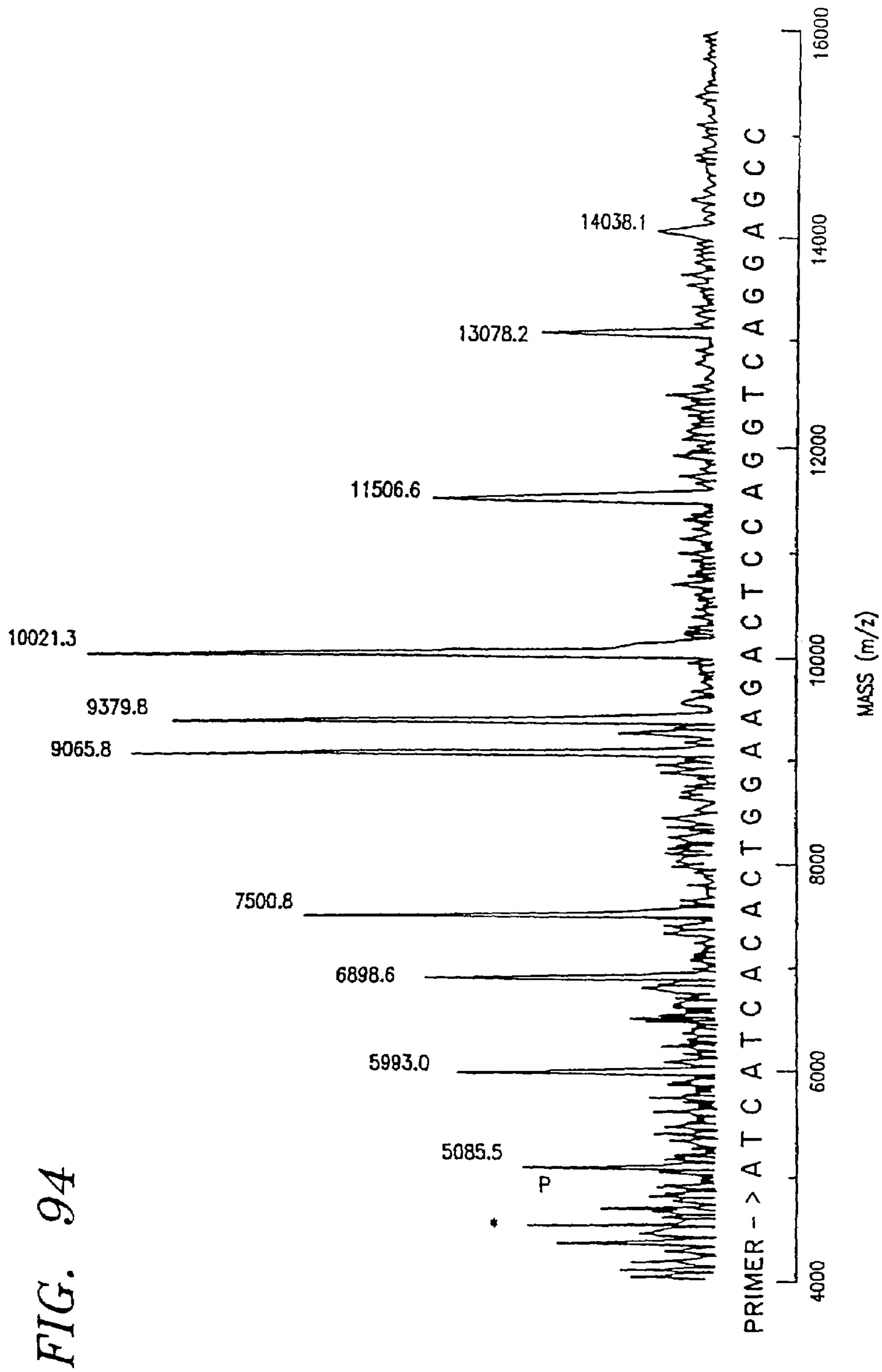
FIG. 94 shows the mass spectrum obtained from the A reaction for sequencing a portion (SEQ ID NO: 319) of exon 7 of the p53 gene as described in Example 25.
Figure 95A:
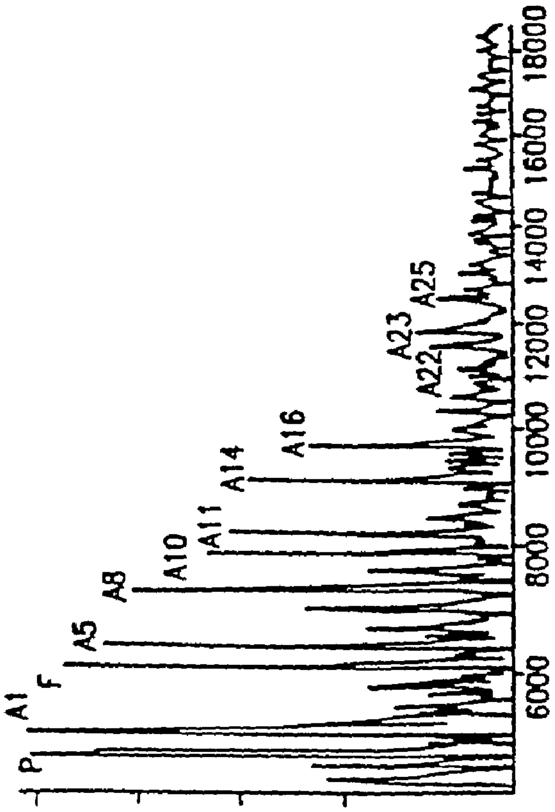
FIG. 95 shows the mass spectrum of a p53 sequencing ladder (set forth in SEQ ID NO: 320) for which 5 nL of each reaction were transferred to wells of a chip and measured by MALDI-TOF.
Figure 95B:
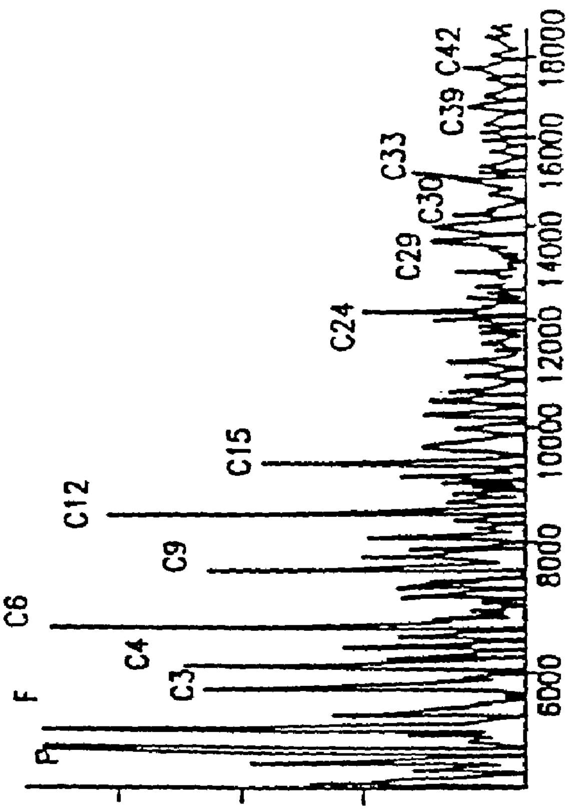
Figure 95C:
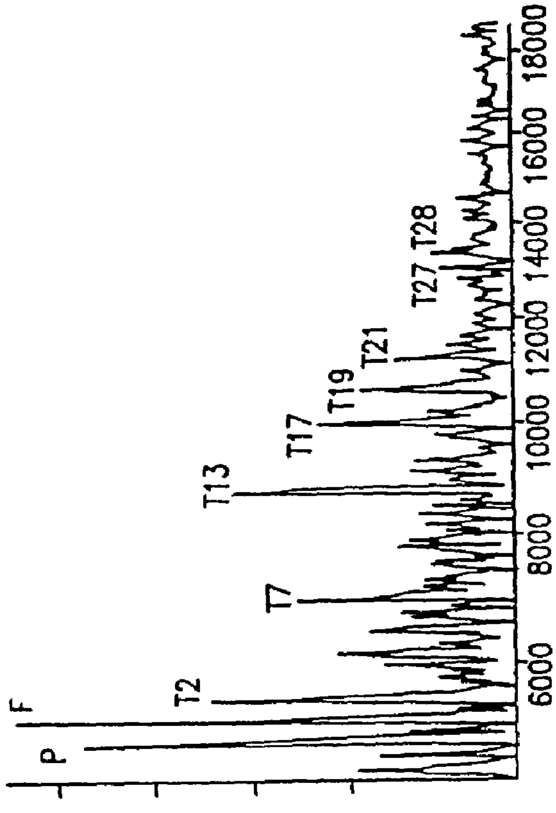
Figure 95D:
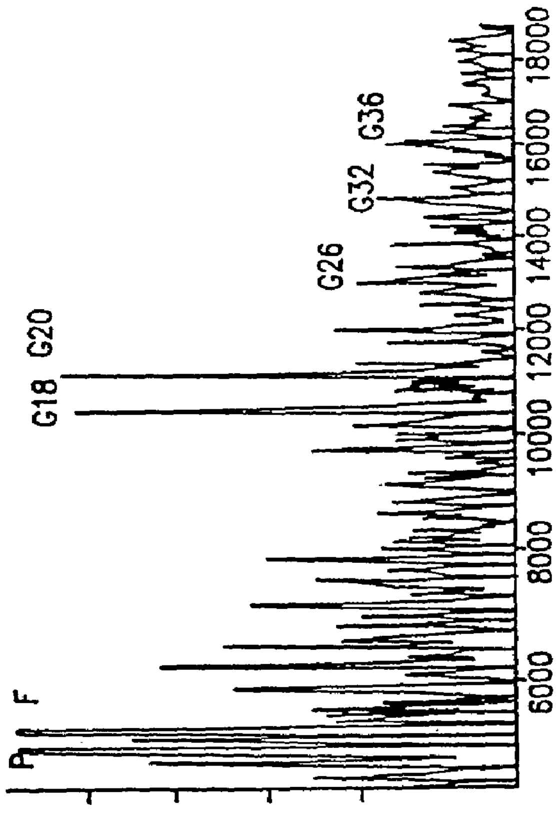

A sub-microliter aliquot of each of the 84 sequencing reactions was loaded onto one MS sample holder containing preloaded matrix. FIG. 94 gives an example of sequencing data generated from one primer; four spectra are superimposed.

All sequencing peaks were well resolved in the mass range needed to read through the next sequencing primer site. Sometimes doubly charged peaks were observed which could be easily identified by correlating the mass to that of the singly charged ion. False stops generated by early termination of the enzymatic extension can be observed close to the primer site. Since the mass resolution is high enough, it is easy to differentiate the false stop peaks from the real sequencing peaks by calculating the mass difference of the neighboring peaks and crs comparing the four spectra. Additionally, mt primers generated detectable data through the region of the downstream primer binding site thereby covering the false stop region.

Using optimized procedures of amplification, sequencing, and conditioning, exons 5-8 of the p53 gene were successfully sequenced. Correct wildtype sequence data were obtained from all exons with a mass resolution about 300 to 800 over the entire mass range. The overall mass accuracy is 0.05% or better. The average amount of each sequencing fragment loaded on the MS sample holder is estimated to be 50 fmol or less.

This example demonstrates the feasibility of sequencing exons of a human gene by MALDI-TOF MS. Compare to gel-based automated fluorescent DNA sequencing, the read lengths are shorter. Microchip technology can be incorporated to provide for parallel processing. Sequencing products generated in the microtiter plate can be directly transferred to a microchip which serves as a launching pad for MALDI-TOF MS analysis. Robot-driven serial and parallel nanoliter dispensing tools are being used to produce 100-1000 element DNA arrays on <1" square chips with flat or geometrically altered (e.g., with wells) surfaces for rapid mass spectrometric analysis.

FIG. 94 shows an MS spectrum obtained on a chip where the sample was transferred from a microtiter plate by a pintool. The estimated amount of each termination product loaded is 5 fmol or less which is in the range of amounts used in conventional Sanger sequencing with radiolabeled or fluorescent detection (0.5-1 fmol per fragment). The low volume MALDI sample deposition has the advantages of miniaturization (reduced reagent cts), enhanced reproducibility and automated signal acquisition.

EXAMPLE 26

Direct Detection of Synthetic and Biologically Generated Double-stranded DNA by MALDI-TOF MS Introduction Typically, matrix-associated laser desorption/ionization (Karas, et. al., (1989) *Int. J. Mass Spectrom, Ion Processes,* 92, 231) time-of-flight mass spectrometry (MALDI-TOF MS) of DNA molecules which are double stranded (ds) in solution yields molecular ions representative of the two single stranded components (Tang, et al. (1994) *Rapid Commun. Mass Spectrom.* 8: 183; Tang, et al. (1995) *Nucleic Acids Res.* 23: 3126; Benner, et al. (1995) *Rapid Commun. Mass Spectrom.* 9: 537; Liu, et al. (1995) *Anal. Chem.* 67: 3482; Siegert et al. (1996) *Anal. Biochem.* 243: 55; and Doktycz, et al. (1995) *Anal. Biochem.* 230: 205); this has been observed in several reports dealing with biologically generated DNA from a polymerase chain reaction (PCR) amplification (Tang, et al. (1994) *Rapid Commun. Mass Spectrom.* 8: 183; Liu, et al. (1995) *Anal. Chem.* 67: 3482; Siegert et al. (1996) *Anal. Biochem.* 243: 55; and Doktycz, et al. (1995) *Anal. Biochem.* 230: 205). It is not clear whether the double strand is destabilized because of the decreased pH in the matrix environment or because of absorbance by the duplex during desorption/ionization/acceleration of an energy sufficient to overcome the attractive van der Waals and "stacking" stabilization forces (Cantor and Shimmel, *Biophysical Chemistry Part I: The conformation of Biomolecules*, W. H. Freeman, New York, (1980), 176). When analyte is present at high concentrations formation of non-specific gas-phase DNA multimers is, as with proteins (Karas, et. al., (1989) *Int. J. Mass Spectrom, Ion Processes* 92:231), common; however, Lecchi and Pannell (Lecchi et al. (1995) *J. Am. Soc. Mass Spectrom.* 6: 972) have provided strong evidence for specific Watson Crick (WC) base pairing being maintained in the gas phase. They detected these specific dimers when using 6-aza-2-thiothymine as a matrix, but did not observe them with 3-hydroxypicolinic acid (3-HPA) or 2,4,6-hydroxyacetophenone matrix. As described below, by using a low acceleration voltage of the ions and preparing samples for MALDI analysis at reduced temperatures, routine detection of dsDNA is possible.

Materials and Methods

Synthetic DNA. Oligonucleotides were synthesized (Sinha, et al. (1984) *Nucleic Acids Res.,* 12, 4539) on a Perspective Expedite DNA synthesizer and reverse phase HPLC purified in-house. Sequences were: 50-mer (15337 Da): 5'-TTG CGT ACA CAC TGG CCG TCG TTT TAC AAC GTC GTG ACT GGG AAA ACC CT-3' (SEQ ID NO: 109); 27-mer$_c$ (complementary, 8343 Da): 5'-GTA AAA CGA CGG CCA GTG TGT ACG CAA-3' (SEQ ID NO: 110); 27-mer$_{nc}$ (non-complementary, 8293 Da): 5'-TAC TGG AAG GCG ATC TCA GCA ATC AGC-3' (SEQ ID NO: 111). 100 μM stock solutions were diluted to 20, 10, 5, and 2.5 μM using 18 Mohm/cm $H_2O$. 2 μL each of equimolar solutions of the 50-mer and either 27-mer$_c$ or 27-mer$_{nc}$ were mixed and allowed to anneal at room temperature for 10 minutes. 0.5 μL of these mixtures were mixed directly on a sample target with 1 μL matrix (0.7 M 3-HPA, 0.07 M ammonium citrate in 50% acetonitrile) and allowed to air dry.

Biological DNA. Enzymatic digestion of human genomic DNA from leukocytes was performed. PCR primers (forward, 5'-GGC ACG GCT GTC CAA GGA G-3' (SEQ ID NO: 112)); reverse, 5'-AGG CCG CGC TCG GCG CCC TC-3' (SEQ ID NO: 113) to amplify a portion of exon 4 of the apolipoprotein E gene were delineated from the published sequence (Das et al., (1985) *J. Biol. Chem.,* 260 6240). Taq polymerase and 10× buffer were purchased from Boehringer-Mannheim (Germany) and dNTPs from Pharmacia (Freiburg, Germany). The total reaction volume was 50 µl including 20 pmol of each primer and 10% DMSO (dimethylsulfoxide, Sigma) with approximately 200 ng of genomic DNA used as template. Solutions were heated to 80° C. before the addition of IU polymerase; PCR conditions were: 2 min at 94° C., followed by 40 cycles of 30 sec at 94° C., 45 sec at 63° C., 30 sec at 72° C., and a final extension time of 2 min at 72° C. While no quantitative data was collected to determine the final yield of amplified product, it is estimated that −2 pmol were available for the enzymatic digestion.

Cfol and Rsal and reaction buffer L were purchased from Boehringer-Mannheim. 20 µl of amplified products were diluted with 15 µl water and 4 µl buffer L; after addition of 10 units of restriction enzymes the samples were incubated for 60 min at 37° C. For precipitation of digest products 5 µl of 3 M ammonium acetate (pH 6.5), (5 µl glycogen (Braun, et al. (1997) *Clin. Chem.* 43: 1151) (10 mg/ml, Sigma), and 110 µl absolute ethanol were added to 50 µL of the analyte solutions and stored for 1 hour at room temperature. After at 10 min centrifugation at 13,000× g, the pellet was washed in 70% ethanol and resuspended in 1 µl 18 Mohm/cm $H_2O$.

Sample preparation and analysis by MALDI-TOF MS. 0.35 µl of resuspended DNA was mixed with 0.35-1.3 µL matrix solution (0.7 M 3-hydroxypicolinic acid (3-HPA), 0.07 M ammonium citrate in 1:1 $H_2O$:$CH_3CN$) (Wu, et al. (1993) *Rapid Commun. Mass Spectrom.* 7: 142) on a stainless steel sample target disk and allowed to air dry preceding spectrum acquisition using a Thermo Bioanalysis Vision 2000 MALDI-TOF instrument operated in pitive ion reflectron mode with 5 and 20 kV on the target and conversion dynode, respectively. Theoretical average molecular masses ($M_r$(calc)) of the fragments were calculated from atomic compositions; the mass of a proton (1.08 Da) was subtracted from raw data values in reporting experimental molecular masses ($M_r$(exp)) as neutral basis. External calibration generated from eight peaks (2000-18000 Da) was used for all spectra.

Results and Discussion

FIG. 96A is a MALDI-TOF mass spectrum of a mixture of the synthetic 50-mer with (non-complementary) 27-$mer_{nc}$ (each 10 µM, the highest final concentration used in this study); the laser power was adjusted to just above the threshold irradiation for ionization. The peaks at 8.30 and 15.34 kDa represent singly charged ions derived from the 27- and 50-mer single strands, respectively. Poorly resolved low intensity signals at −16.6 and −30.7 kDa represent homodimers of 27- and 50-mer, respectively; that at 23.6 kDa is consistent with a heterodimer containing one 27-mer and one 50-mer strand. Thus low intensity dimer ions representing all possible combinations from the two non-complementary oligonucleotides (27+27; 27+50; 50+50) were observed. Increasing the irradiance even to a point where depurination peaks dominated the spectrum resulted in slightly higher intensities of these dimer peaks. Note that the hybridization was performed at room temperature and with a very low salt concentration, conditions at which non-specific hybridization may occur.

FIG. 96 shows a MALDI-TOF spectrum of the same 50-mer mixed with (complementary) 27-$mer_c$; the final concentration of each oligonucleotide was again 10 µM. Using the same laser power as in FIG. 96A, intense signals were again observed at 88.34 and 15.34 Kda, consistent with single stranded 27- and 50-mer, respectively. Homodimer peaks (27+27; 50+50) were barely apparent in the noise; however, singly (23.68 Kda) and doubly (11.84 k Da) charged heterodimer (27+50) peaks were dominant. Although the 23.68 Kda dimer peak could be detected from all irradiated positions, its intensity relative to the monomer peaks varied slightly from spot-to-spot. Repeating the experiment with individual oligonucleotide concentrations of 5, 2.5, and 1.25 µM resulted in decreasing amounts of the 27-/50-mer Watson-Crick dimer peak relative to the 27- and 50-mer single stranded peaks. At the lowest concentrations, the observation of dimer was "crystal-dependent", that is, irradiation of some crystals produced significant 27-/50-mer dimer signal, while other crystals reproducibly yielded very little or none. This indicates that the incorporation of dsdna into the matrix crystals or the effectiveness of retaining this interaction through the ionization/desorption process is dependent upon the microscopic properties of the crystals, and/or that there exist steep concentration gradients of the duplex throughout the sample.

Thus the FIG. 96 spectra provide strong evidence that specific WC base paired dsdna can be observed using gentle laser conditions with high concentrations of oligonucleotides in this mass range, the first report of this using a 3-HPA matrix. The study was extended to a complex mixture of dsdna derived from an enzymatic digest (Rsal/Cfol) of a region of exon 4 of the apolipoprotein E gene (Das et. al., (1985) *J. Biol. Chem.,* 260 6240); expected fragment masses are given in Table IX.

TABLE IX

Cfol/Rsal Digestion Products from ApoE gene exon 4[a]

| bases[b] | | ssDNA | (Da) | dsdna |
|---|---|---|---|---|
| (+) | (−) | (+) | (−) | (Da) |
| 11 | 13 | 3428 | 4025 | 7453 |
| 16 | | 5004 | 4924 | 9928 |
| 18 | | 5412 | 5750 | 11162 |
| 17 | 19 | 5283 | 5880 | 11163 |
| 19 | | 5999 | 5781 | 11780 |
| 24 | 22 | 7510 | 6745 | 14225 |
| 31 | 29 | 9628 | 9185 | 18813 |
| 36 | 38 | 11279 | 11627 | 22906 |
| 48 | | 14845 | 14858 | 29703 |
| 55 | 53 | 17175 | 16240 | 33415 |

Figure 97A:
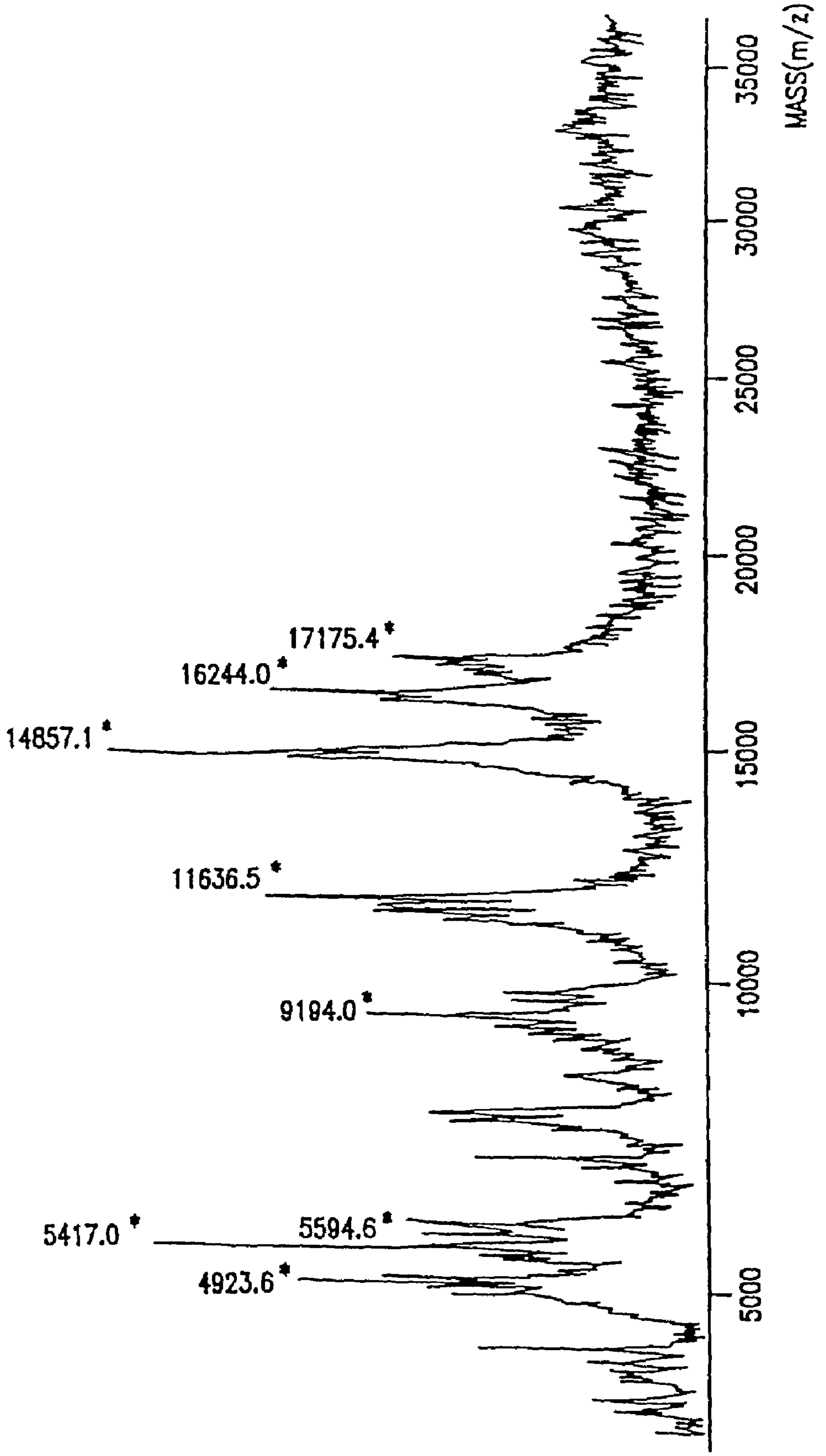
FIG. 97A shows a MALDI-TOF mass spectrum of CfoI/RsaI digest products of a region of exon 4 of the apolipoprotein E gene (ϵ3 genotype), using sample preparation as in FIG. 96.

[a]ε3 allele has no 17/19 or 19/19 pairs; ε4 allele contains no 36/38 pair.
[b](+) sense strand, (−) antisense strand After the digestion step, the samples were purified and concentrated by ethanol precipitation and resuspended in 1 µL $H_2O$ before mixing them at room temperature with matrix on the sample target. Nearly 20 peaks ranging in mass from 3.4-17.2 Kda were resolved in the products' MALDI spectrum (FIG. 97A), all consistent with denatured single stranded components of the double strand (Table IX). Many such analyses of similar biological products over a period of months also yielded spectra with negligible dsdna, consistent with previous reports (Tang, et al. (1994) *Rapid Commun. Mass Spectrom.* 8: 183; Liu, et al. (1995) *Anal. Chem.* 67: 3482; Siegert et al. (1996) *Anal. Biochem.* 243: 55; and Doktycz, et al. (1995) *Anal. Biochem.* 230: 205); contrarily, intact double strands were observed under similar conditions for the synthetic DNA (FIG. 96A). It is difficult to estimate the strand concentration available after the biological reactions, but presumably that it was far lower than that at which dimerization of synthetic samples occurred. Furthermore, maintaining specific hybrids within the two-component synthetic mixture may be kinetically favored relative to the far more complex mixture of 20 single-stranded DNA components from the digest.

The effect of reduced temperature on maintaining dsDNA was tested. An aliquot of the digested DNA solution, the matrix, pipette, pipette tips, and the stainless steel sample target were stored in a 4° C. "cold room" for 15 minutes; as with normal preparations matrix, and then analyte, were spotted on the target and allowed to co-crystallize while air drying. Crystallization for mixtures of 300 nL 3HPA (50% acetonitrile) with 300 nL analyte required ~1 minute at room temperature but ~15 minutes at the reduced temperature. Sample spots prepared in the cold room environment typically contained a high proportion of large transparent crystals.

Figure 97B:
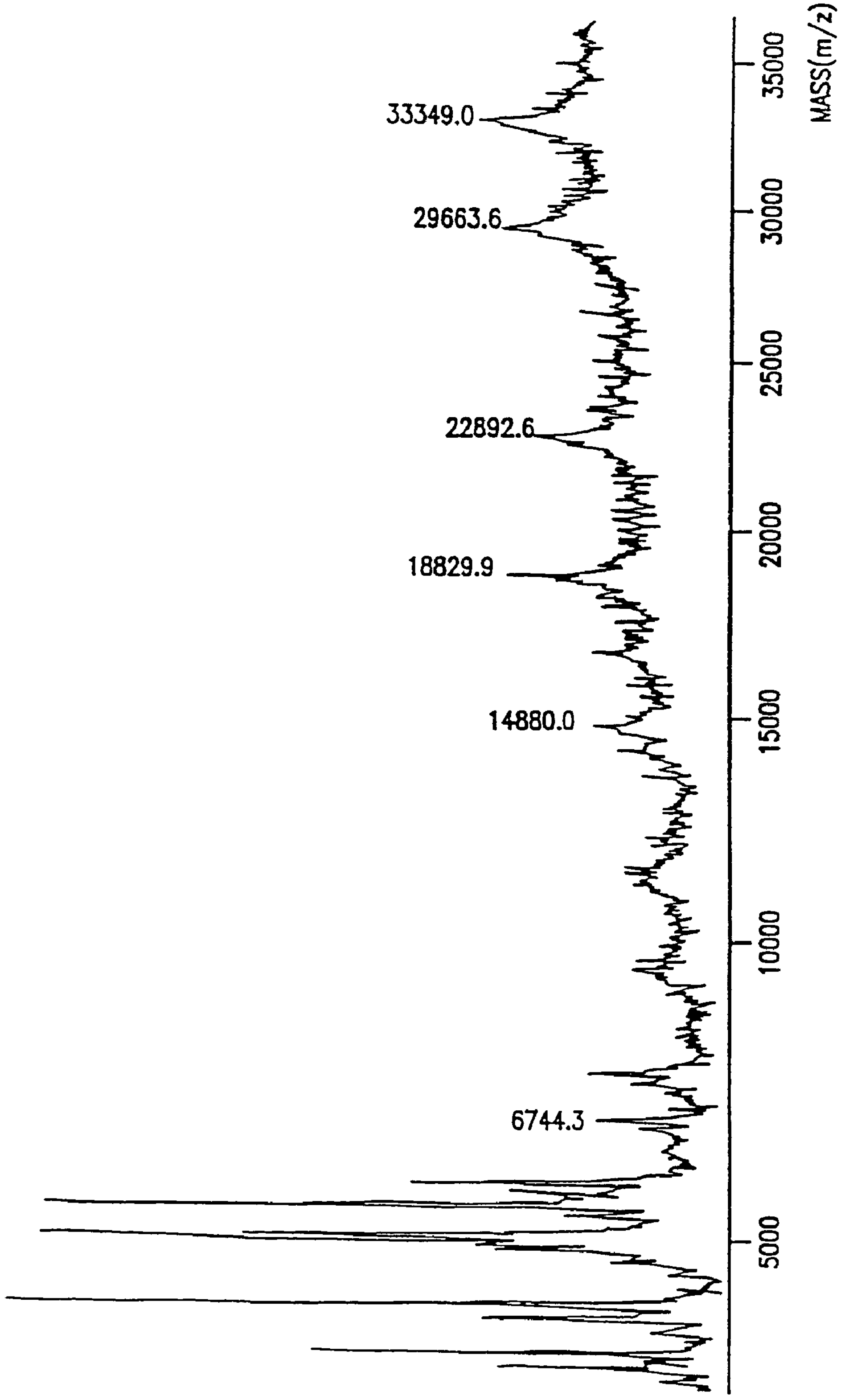
FIG. 97B is the same as FIG. 97A, except with samples prepared for MALDI-TOF analysis at 4° C.

MALDI-TOF analysis of an ApoE digest aliquot prepared at reduced temperature produced the FIG. 97B spectrum. While the low mass range appeared qualitatively similar to FIG. 97A, dramatic differences above 8 kDa were observed. Only signals consistent with single strands (Table IX) were observed in FIG. 97A, but the FIG. 97B cold room prepared samples did not yield signals for the same masses except below 8 kDa. Even more striking were the additional high mass peaks in FIG. 97B; clearly these represent dimer peaks containing lower mass components. As was done with the synthetic DNA, it was important to determine whether these represent non-specific heterodimers, specific WC heterodimers, or nonspecific homodimers. Consider first the 33.35 kDa fragment. Ignoring the unlikely possibility that the high mass fragment represents a trimer or higher multimer, as a dimer it must only contain the highest mass ssDNA components, i.e., the >16 kDa. Homodimerization of the 15.24 and 17.18 kDa fragments would result in 32.49 and 34.35 kDa peaks, respectively; corresponding mass errors for these incorrect assignments relative to the observed 33.35 kDa would be −2.6% and +3.0% respectively. A far better match is achieved if this peak originates from a heterodimer of the two highest mass single stranded fragments; their summed mass (16.24+17.18=33.42 kDa) differed by 0.2% from the observed dimer mass 33.35 kDa, an acceptable mass error for MALDI-TOF analysis of large DNA fragments using external calibration. Likewise, the 29.66kDa fragment was measured only 0.13% lower than the 29.70 Da expected for a heterodimer of 48-mers; the sum of no other possible homodimers or heterodimers were within a reasonable range of this mass. Similar arguments could be made for the 22.89 and 18.83 kDa fragments, representing 36-/38-mer and 31-/29-heterodimers, respectively; the signal at 14.86 kDa is consistent with singly charged single stranded and doubly charged double-stranded 48-mer. The agreement of the FIG. 97B masses above 15 kDa with the of dsDNA expected from this digest and the absence of homodimers and non-specific heterodimers at random masses indicated that the base pairings were indeed highly specific and provided further evidence that gas-phase WC interactions may be retained in MALDI-generated ions.

Figure 98:
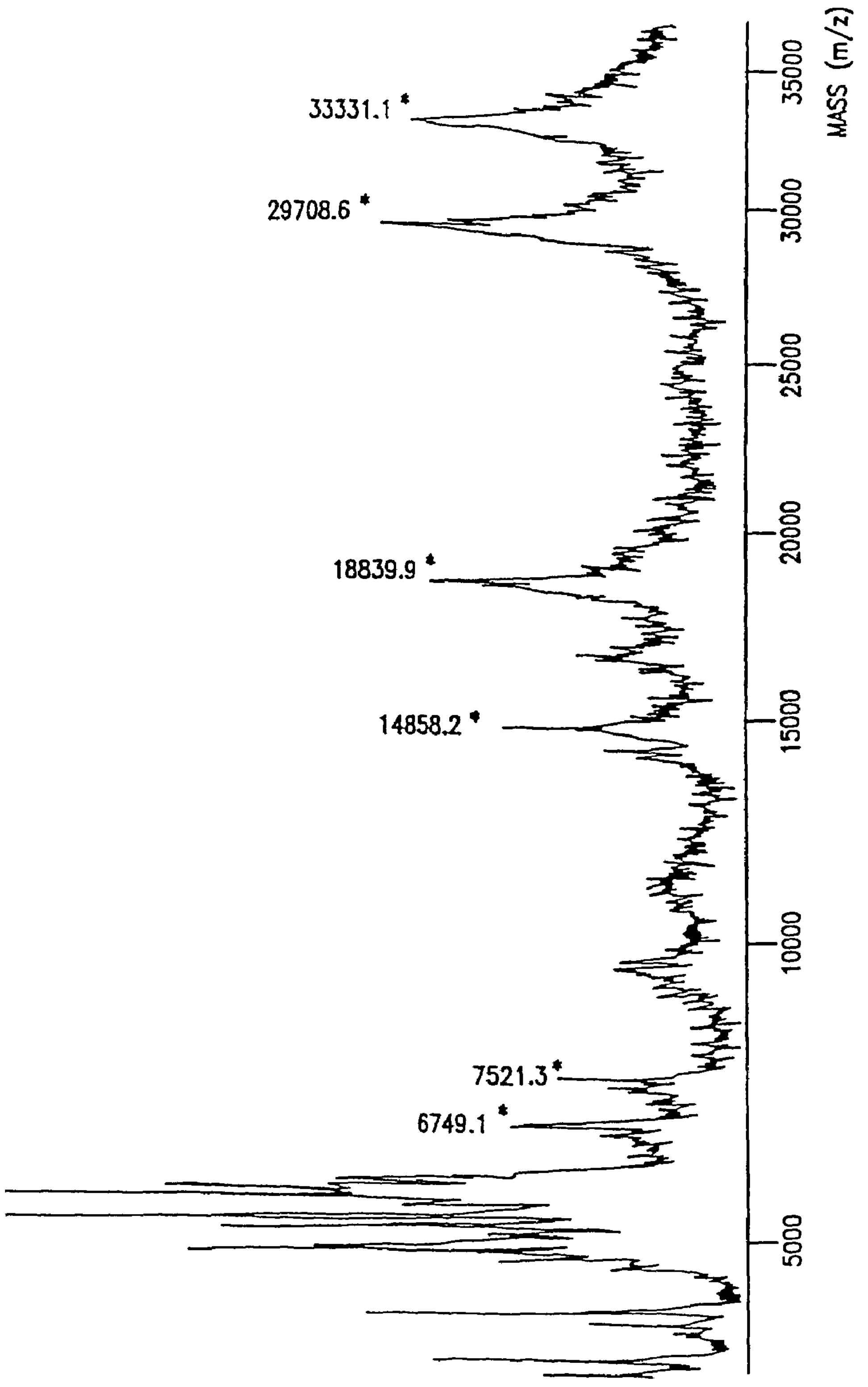
FIG. 98 shows a MALDI-TOF mass spectrum of CfoI/RsaI simultaneously double digest products of a 252 base pair region of exon 4 of the apolipoprotein E gene (e4 genotype), with samples prepared at 4° C.
Figure 99:
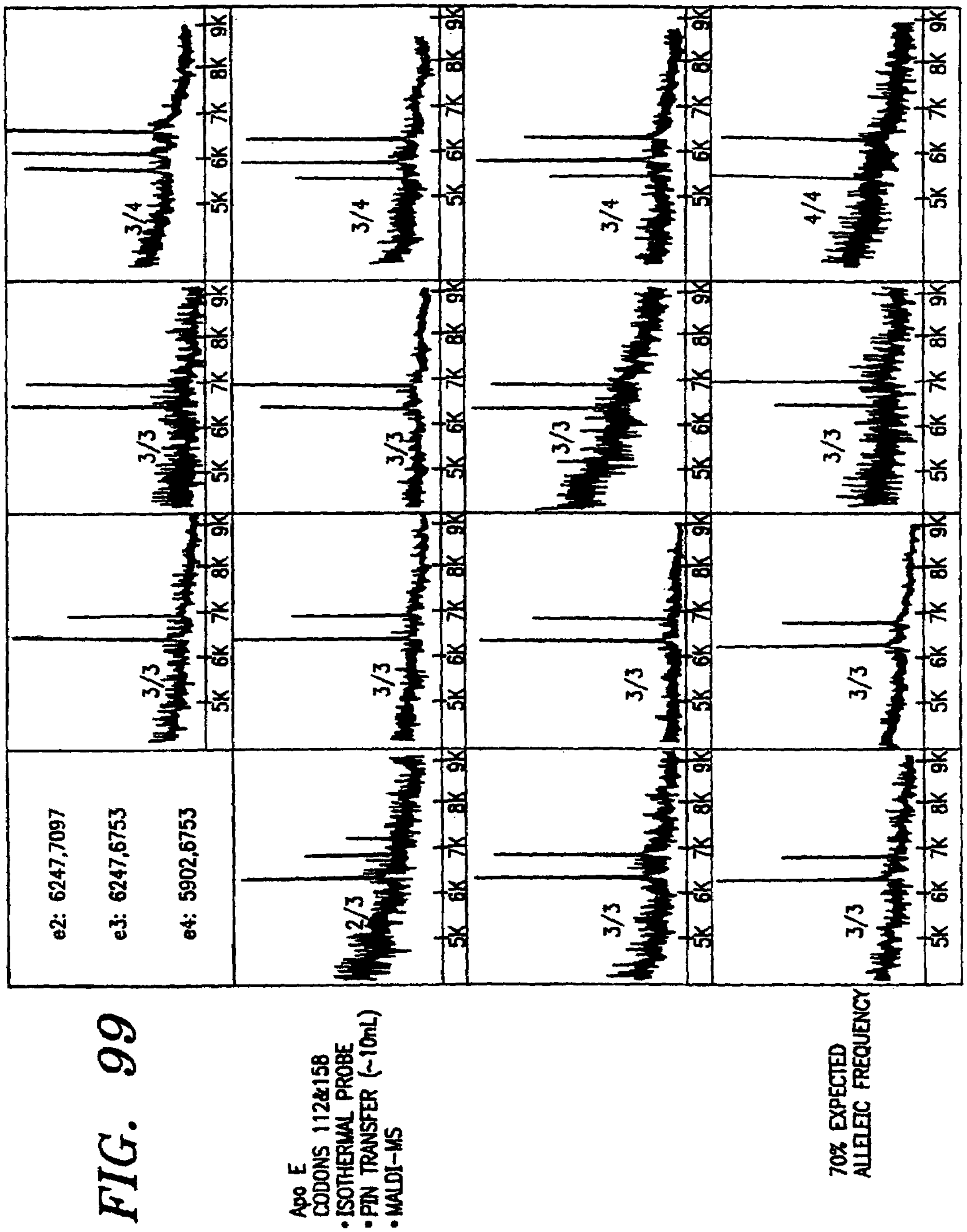
FIG. 99 shows the mass spectra obatined on a small population study of 15 patients with a 16 element array of diagnostic products transferred to a MALDI target using a pintool microdispenser.

FIG. 98 shows a MALDI-TOF spectrum of an ϵ4 allele, which, unlike the ϵ3, was expected to yield no 36-/38-mer pair upon Cfol/Rsal digestion. The ϵ3 and ϵ4 mass spectra were similar except that abundant 22.89 kDa fragment in FIG. 97B was not present in FIG. 98; with this information alone (Table IX) ϵ3 and ϵ4 alleles were easily distinguished, thereby demonstrating the genotyping by direct measurement of dsDNA by MALDI-TOF MS. Similarly dsDNA could be ionized, transferred to the gas phase, and detected by MALDI-TOF MS. The acceleration voltage typically employed on our instrument was only −5 kV corresponding to 1.5 kV/mm up to −2 mm from the sample target, with the electric field strength decreasing rapidly with distance from the sample target. Most previous work used at least 20 kV acceleration (Lecchi et al. (1995) *J. Am. Soc. Mass Spectrom.* 6: 972); in one exception a 27-mer dsDNA was detected using a frozen matrix solution and 100 V acceleration (Nelson, et al. (1990) *Rapid Commun. Mass Spectrom.* 4: 348). Without being bound by any theory MALDI-induced "denaturation" of dsDNA may be due to gas-phase collisional activation that disrupts the WC pairing when high acceleration fields are employed, analogous to the denaturation presumed to be a first step in the fragmentation used for sequencing the single stranded components of dsDNA using electrospray ionization (McLafferty et al. (1996) *Int. J. Mass Spectrom.*, Ion Processes). It appears that the high salt concentrations (typically >10 mM NaCl or KCl) required to stabilize WC paired dsDNA in solution are unsuitable for MALDI analysis (Nordhoff et al. (1993) *Nucleic Acids Res.* 21: 3347); reducing the concentration of such non-volatile cations is necessary to avoid cation-adducted MALDI signals, but destabilizes the double strands in solution. The low pH conditions of the matrix environment should also destabilize the duplex. As shown in FIGS. 97B and 98, storing and preparing even low concentrations of the biological samples at reduced temperature at least in part offset these denaturing effects, especially for longer strands where melting temperatures are higher due to a more extensive hydrogen bonding network. The conditions used here are recognized to be very non-stringent annealing conditions.

The low mass tails on high mass dsDNA peaks (e.g., FIG. 97B, 232 kDa) are consistent with depurination generated to a higher extent than the sum of depurination from each of the single strands combined. Although depurination in solution is an acid-catalyzed reaction, the weakly acidic conditions in the 3-HPA matrix do not induce significant depurination; molecular ion signals from a mixed-base 50-mer measured with De-MALDI-TOF had only minor contributions from depurination peaks (Juhaz, et al. (1996) *Anal. Chem.* 68: 941). Depurination from the single stranded components of the gas-phase dsDNA is observed even though these bases are expected to be hydrogen bonded to the complementary base of the accompanying strand, implying that covalent bonds are being broken before the strand is denatured.

EXAMPLE 27

Efficiency and Specificity Assay for Base-Specific Ribonucleases

Figure 100:
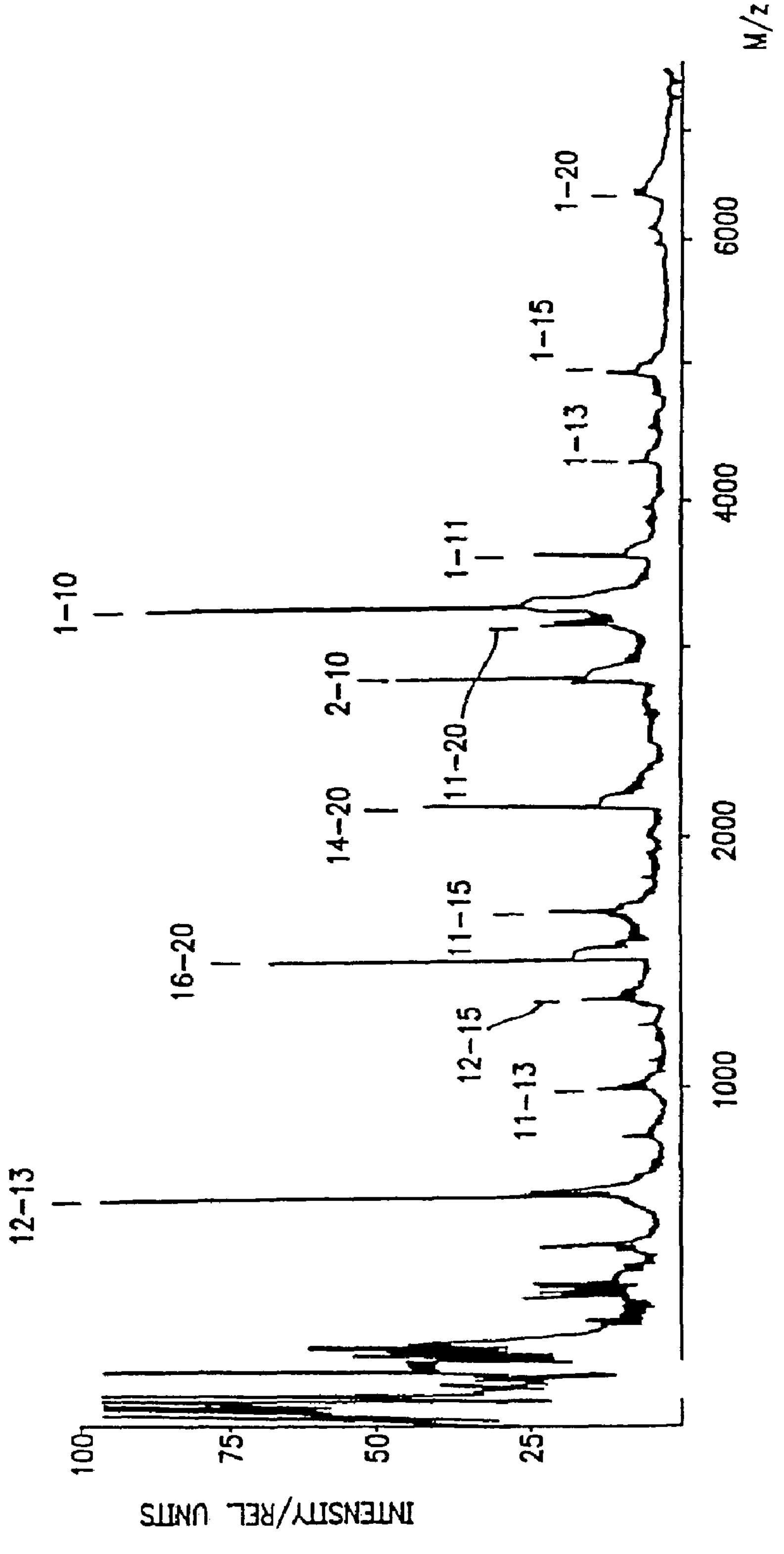
FIG. 100 is a MALDI mass spectrum of an aliquot sampled after a $T_1$ digest of a synthetic 20-mer RNA (SEQ ID NO: 63).

Aliquots sampled at regular time intervals during digestion of selected synthetic 20 to 25 mers were analyzed by mass spectrometry. Three of the RNAses were found to be efficient and specific. These include: the G-specific $T_1$, the A-specific $U_2$ and the A/U-specific PhyM. The ribonucleases presumed to be C-specific were found to be less reliable, e.g., did not cleave at every C or also cleaved at U in an unpredictable manner. The three promising RNAses all yielded cleavage at all of the predicted positions and a complete sequence coverage was obtained. In addition, the presence of cleavage products containing one or several uncleaved positions (short incubation times), allowed alignment of the cleavage products. An example of the MALDI-spectrum of an aliquot sampled after $T_1$ digest of a synthetic 20-mer (SEQ ID NO: 114) RNA is shown in FIG. 100.

EXAMPLE 28

Immobilization of Amplified DNA Targets to Silicon Wafers

Silicon Surface Preparation

Silicon wafers were washed with ethanol, flamed over bunsen burner, and immersed in an anhydrous solution of 25% (by volume) 3-aminopropyltriethoxysilane in toluene for 3 hours. The silane solution was then removed, and the wafers were washed three times with toluene and three times with dimethyl sulfoxide (DMSO). The wafers were then incubated in a 10 mM anhydrous solution of N-succinimidyl (4-iodoacetyl) aminobenzoate (SIAB) (Pierce Chemical, Rockford, Ill.) in anhydrous DMSO. Following the reaction, the SIAB solution was removed, and the wafers were washed three times with DMSO. In all cases, the iodoacetamido-functionalized wafers were used immediately to minimize hydrolysis of the labile iodoacetamido-functionality. Additionally, all further wafer manipulations were performed in the dark since the iodoacetamido-functionality is light sensitive.

Immobilization of Amplified Thiol-containing Nucleic Acids

The SIAB-conjugated silicon wafers were used to analyze specific free thiol-containing DNA fragments of a particular amplified DNA target sequence. A 23-mer oligodeoxynucleotide containing a 5'-disulfide linkage (purchased from Operon Technologies; SEQ ID NO: 117) that is complementary to the 3'-region of a 112 bp human genomic DNA template Genebank Acc. No.: Z52259; SEQ ID NO: 118) was used as a primer in conjunction with a commercially available 49-mer primer, which is complementary to a portion of the 5'-end of the genomic DNA (purchased from Operon Technologies; SEQ ID NO: 119), in PCR reactions to amplify a 135 bp DNA product containing a 5'-disulfide linkage attached to only one strand of the DNA duplex (SEQ ID NO: 120).

The PCR amplification reactions were performed using the Amplitaq GoldKit (Perkin Elmer Catalog No. N808-0249). Briefly, 200 ng 112 bp human genomic DNA template was incubated with 10 μM of 23-mer primer and 8 μM of commercially available 49-mer primer, 10 mM dNTPs, 1 unit of Amplitaq Gold DNA polymerase in the buffer provided by the manufacturer and PCR was performed in a thermocycler.

The 5'-disulfide bond of the resulting amplified product was fully reduced using 10 mM tris-(2-carboxyethyl) phosphine (TCEP) (Pierce Chemical, Rockford, Ill.) to generate a free 5'-thiol group. Disulfide reduction of the modified oligonucleotide was monitored by observing a shift in retention time on reverse-phase FPLC. It was determined that after five hours in the presence of 10 mM TCEP, the disulfide was fully reduced to a free thiol. Immediately following disulfide cleavage, the modified oligonucleotide was incubated with the iodacetamido-functionalized wafers and conjugated to the surface of the silicon wafer through the SIAB linker. To ensure complete thiol deprotonation, the coupling reaction was performed at pH 8.0. Using 10 mM TCEP to cleave the disulfide and the other reaction conditions described above, it was possible to reproducibly yield a surface density of 250 fmol per square mm of surface.

Hybridization and MALDI-TOF Mass Spectrometry

The silicon wafer conjugated with the 135 bp thiol-containing DNA was incubated with a complementary 12-mer oligonucleotide (SEQ ID NO: 121) and specifically hybridized DNA fragments were detected using MALDI-TOF MS analysis. The mass spectrum revealed a signal with an observed experimental mass-to-charge ratio of 3618.33; the theoretical mass-to-charge ratio of the 12-mer oligomer sequence is 3622.4 Da.

Thus, specific DNA target molecule that contain a 5'-disulfide linkage can be amplified. The molecules are immobilized at a high density on a SIAB-derivatized silicon wafer using the methods described herein and specific complementary oligonucleotides may be hybridized to these target molecules and detected using MALDI-TOF MS analysis.

EXAMPLE 29

Use of High Density Nucleic Acid Immobilization to Generate Nucleic Acid Arrays

Employing the high density attachment procedure described in EXAMPLE 28, an array of DNA oligomers amenable to MALDI-TOF mass spectrometry analysis was created on a silicon wafer having a plurality of locations, e.g., depressions or patches, on its surface. To generate the array, a free thiol-containing oligonucleotide primer was immobilized only at the selected locations of the wafer (e.g., see EXAMPLE 28). The each location of the array contained one of three different oligomers. To demonstrate that the different immobilized oligomers could be separately detected and distinguished, three distinct oligonucleotides of differing lengths that are complementary to one of the three oligomers were hybridized to the array on the wafer and analyzed by MALDI-TOF mass spectrometry.

Oligodeoxynucleotides

Three sets of complementary oligodeoxynucleotide pairs were synthesized in which one member of the complementary oligonucleotide pair contains a 3'- or 5'-disulfide linkage (purchased from Operon Technologies or Oligos, Etc.). For example, Oligomer 1 (d(CTGATGCGTCGGATCATCTTTTTT-SS); SEQ ID NO: 122) contains a 3'-disulfide linkage whereas Oligomer 2 (d(SS-CCTCTTGGGAACTGTGTAGTATT); a 5'-disulfide derivative of SEQ ID NO: 117) and Oligomer 3 (d(SS-GAATTCGAGCTCGGTACCCGG); a 5'-disulfide derivative of SEQ ID NO: 115) each contain a 5'-disulfide linkage.

The oligonucleotides complementary to Oligomers 1-3 were designed to be of different lengths that are easily resolvable from one another during MALDI-TOF MS analysis. For example, a 23-mer oligonucleotide (SEQ ID NO: 123) was synthesized complementary to a portion of Oligomer 1, a 12-mer oligonucleotide (SEQ ID NO: 121) was synthesized complementary to a portion of Oligomer 2 and a 21-mer (SEQ ID NO: 116) was synthesized complementary to a portion of Oligomer 3. In addition, a fourth 29-mer oligonucleotide (SEQ ID NO: 124) was synthesized that lacks complementarity to any of the three oligomers. This fourth oligonucleotide was used as a negative control.

Silicon Surface Chemistry and DNA Immobilization (a) 4×4 (16-Location) Array

A 2×2 $cm^2$ silicon wafer having 256 individual depressions or wells in the form of a 16×16 well array was purchased from a commercial supplier (Accelerator Technology Corp., College Station, Tex.). The wells were 800×800 $μm^2$, 120 μm deep, on a 1.125 pitch. The silicon wafer was reacted with 3-aminopropyltriethoxysilane to produce a uniform layer of primary amines on the surface and then exposed to the heterobifunctional crosslinker SIAB resulting in iodoacetamido functionalities on the surface (e.g., see EXAMPLE 28).

To prepare the oligomers for coupling to the various locations of the silicon array, the disulfide bond of each oligomer was fully reduced using 10 mM TCEP as depicted in EXAMPLE 28, and the DNA resuspended at a final concentration of 10 μM in a solution of 100 mM phosphate buffer, pH 8.0. Immediately following disulfide bond reduction, the free-thiol group of the oligomer was coupled to the iodoacetamido functionality at 16 locations on the wafer using the probe coupling conditions essentially as described above in EXAMPLE 28. To accomplish the separate coupling at 16 distinct locations of the wafer, the entire surface of the wafer was not flushed with an oligonucleotide solution but, instead, an ~30-nl aliquot of a predetermined modified oligomer was added in parallel to each of 16 locations (i.e., depressions) of the 256 wells on the wafer to create a 4×4 array of immobilized DNA using a robotic pintool.

The robotic pintool consists of 16 probes housed in a probe block and mounted on an X Y, Z robotic stage. The robotic stage was a gantry system which enables the placement of sample trays below the arms of the robot. The gantry unit itself is composed of X and Y arms which move 250 and 400 mm, respectively, guided by brushless linear servo motors with positional feedback provided by linear optical encoders. A lead screw driven Z axis (50 mm vertical travel) is mounted to the xy axis slide of the gantry unit and is controlled by an in-line rotary servo motor with positional feedback by a motor-mounted rotary optical encoder. The work area of the system is equipped with a slide-out tooling plate that holds five microtiter plates (most often, 2 plates of wash solution and 3 plates of sample for a maximum of 1152 different oligonucleotide solutions) and up to ten 20×20 mm wafers. The wafers are placed precisely in the plate against two banking pins and held secure by vacuum. The entire system is enclosed in plexi-glass housing for safety and mounted onto a steel support frame for thermal and vibrational damping. Motion control is accomplished by employing a commercial motion controller which was a 3-axis servo controller and is integrated to a computer; programming code for specific applications is written as needed.

To create the DNA array, a pintool with assemblies that have solid pin elements was dipped into 16 wells of a multiwell DNA source plate containing solutions of Oligomers 1-3 to wet the distal ends of the pins, the robotic assembly moves the pin assembly to the silicon wafer, and the sample spotted by surface contact. Thus, one of modified Oligomers 1-3 was covalently immobilized to each of 16 separate wells of the 256 wells on the silicon wafer thereby creating a 4×4 array of immobilized DNA.

In carrying out the hybridization reaction, the three complementary oligonucleotides and the negative control oligonucleotide were mixed at a final concentration of 10 μM for each oligonucleotide in 1 ml of TE buffer (10 mM Tris-HCl, pH 8.0, 1 mM EDTA) supplemented with 1 M NaCl, and the solution was heated at 65° C. for 10 min. Immediately thereafter, the entire surface of the silicon wafer was flushed with 800 μl of the heated oligonucleotide solution. The complementary oligonucleotides were annealed to the immobilized oligomers by incubating the silicon array at ambient temperature for 1 hr, followed by incubation at 4° C. for at least 10 min. Alternatively, the oligonucleotide solution can be added to the wafer which is then heated and allowed to cool for hybridization.

The hybridized array was then washed with a solution of 50 mM ammonium citrate buffer for cation exchange to remove sodium and potassium ions on the DNA backbone (Pieles et al., (1993) *Nucl. Acids Res.* 21: 3191-3196). A 6-nl aliquot of a matrix solution of 3-hydroxypicolinic acid (0.7 M 3-hydroxypicolinic acid-10% ammonium citrate in 50% acetonitrile; see Wu et al. *Rapid Commun. Mass Spectrom.* 7: 142-146 (1993)) was added in series to each location of the array using a robotic piezoelectric serial dispenser (i.e., a piezoelectric pipette system).

The piezoelectric pipette system is built on a system purchased from Microdrop GmbH, Norderstedt Germany and contains a piezoelectric element driver which sends a pulsed signal to a piezoelectric element bonded to and surrounding a glass capillary which holds the solution to be dispensed; a pressure transducer to load (by negative pressure) or empty (by positive pressure) the capillary; a robotic xyz stage and robot driver to maneuver the capillary for loading, unloading, dispensing, and cleaning, a stroboscope and driver pulsed at the frequency of the piezo element to enable viewing of 'suspended' droplet characteristics; separate stages for source and designation plates or sample targets (i.e. Si chip); a camera mounted to the robotic arm to view loading to designation plate; and a data station which controls the pressure unit, xyz robot, and piezoelectric driver.

The 3-HPA solution was allowed to dry at ambient temperature and thereafter a 6-nl aliquot of water was added to each location using the piezoelectric pipette to resuspend the dried matrix-DNA complex, such that upon drying at ambient temperature the matrix-DNA complex forms a uniform crystalline surface on the bottom surface of each location.

MALDI-TOF MS Analysis

The MALDI-TOF MS analysis was performed in series on each of the 16 locations of the hybridization array illustrated in FIG. 6 essentially as described in EXAMPLE 28. The resulting mass spectrum of oligonucleotides that specifically hybridized to each of the 16 locations of the DNA hybridization revealed a specific signal at each location representative of observed experimental mass-to-charge ratio corresponding to the specific complementary nucleotide sequence.

For example, in the locations that have only Oligomer 1 conjugated thereto, the mass spectrum revealed a predominate signal with an observed experimental mass-to-charge ratio of 7072.4 approximately equal to that of the 23-mer; the theoretical mass-to-charge ratio of the 23-mer is 7072.6 Da. Similarly, specific hybridization of the 12-mer oligonucleotide to the array, observed experimental mass-to-charge ratio of 3618.33 Da (theoretical 3622.4 Da), was detected only at those locations conjugated with Oligomer 2 whereas specific hybridization of MJM6 (observed experimental mass-to-charge ratio of 6415.4) was detected only at those locations of the array conjugated with Oligomer 3 (theoretical 6407.2 Da).

None of the locations of the array revealed a signal that corresponds to the negative control 29-mer oligonucleotide (theoretical mass-to-charge ratio of 8974.8) indicating that specific target DNA molecules can be hybridized to oligomers covalently immobilized to specific locations on the surface of the silicon array and a plurality of hybridization assays may be individually monitored using MALDI-TOF MS analysis.

(b) 8×8 (64-location) Array

A 2×2 $cm^2$ silicon wafer having 256 individual depressions or wells that form a 16×16 array of wells was purchased from a commercial supplier (Accelerator Technology Corp., College Station, Tex.). The wells were 800×800 $μm^2$, 120 μm deep, on a 1.125 pitch. The silicon wafer was reacted with 3-aminopropyltriethoxysilane to produce a uniform layer of primary amines on the surface and then exposed to the heterobifunctional crosslinker SIAB resulting in iodoacetamido functionalities on the surface as described above.

To make an array of 64 elements, a pintool was used following the procedures described above. The pintool was dipped into 16 wells of a 384 well DNA source plate containing solutions of Oligomers 1-3, moved to the silicon wafer, and the sample spotted by surface contact. Next, the tool was dipped in washing solution, then dipped into the same 16 wells of the source plate, and spotted onto the target 2.25 mm offset from the initial set of 16 spots; the entire cycle was repeated to make a 2×2 array from each pin to produce an 8×8 array of spots (2×2 elements/pin×16 pins=64 total elements spotted).

Oligomers 1-3 immobilized to the 64 locations were hybridized to complementary oligonucleotides and analyzed by MALDI-TOF MS analysis. As observed for the 16-location array, specific hybridization of the complementary oligonucleotide to each of the immobilized thiol-containing oligomers was observed in each of the locations of the DNA array.

EXAMPLE 30

Extension of Hybridized DNA Primers Bound to DNA Templates Immobilized on a Silicon Wafer The SIAB-derivatized silicon wafers can also be employed for primer extension reactions of the immobilized DNA template using the procedures essentially described in EXAMPLE 7.

A 27-mer oligonucleotide (SEQ ID NO: 125) containing a 3'-free thiol group was coupled to a SIAB-derivatized silicon wafer as described above, for example, in EXAMPLE 28. A 12-mer oligonucleotide primer (SEQ ID NO: 126) was hybridized to the immobilized oligonucleotide and the primer was extended using a commercially available kit (e.g., Sequenase or ThermoSequenase, U.S. Biochemical Corp). The addition of Sequenase DNA polymerase or ThermoSequenase DNA polymerase in the presence of three deoxyribonucleoside triphosphates (dNTPs; dATP, dGTP, dCTP) and dideoxyribonucleoside thymidine triphosphate (ddTTP) in buffer according to the instructions provided by the manufacturer resulted in a 3-base extension of the 12-mer primer while still bound to the silicon wafer. The wafer was then analyzed by MALDI-TOF mass spectrometry as described above. The mass spectrum results clearly distinguish the 15-mer (SEQ ID NO: 127) from the original unextended 12-mer thus indicating that specific extension can be performed on the surface of a silicon wafer and detected using MALDI-TOF MS analysis.

EXAMPLE 31

Effect of Linker Length on Polymerase Extension of Hybridized DNA Primers Bound to DNA Templates Immobilized on a Silicon Wafer The effect of the distance between the SIAB-conjugated silicon surface and the duplex DNA formed by hybridization of the target DNA to the immobilized oligomer template was investigated, as well as choice of enzyme.

Two SIAB-derivatized silicon wafers were conjugated to the 3'-end of two free thiol-containing oligonucleotides of identical DNA sequence except for a 3-base poly dT spacer sequence incorporated at the 3'-end:

```
                                SEQ ID NO:122
CTGATGCGTC GGATCATCTT TTTT

                                SEQ ID NO:125
CTGATGCGTC GGATCATCTT TTTTTTT.
```

These oligonucleotides were synthesized and each was separately immobilized to the surface of a silicon wafer through the SIAB cross-linker (e.g., see EXAMPLE 28). Each wafer was incubated with a 12-mer oligonucleotide:

```
                                SEQ ID NO:126
AAAAAAGATG AT

                                SEQ ID NO:128
GATGATCCGA CG

                                SEQ ID NO:129
GATCCGACGC AT,
```

which is complementary to portions of the nucleotide sequences common to both of the oligonucleotides, by denaturing at 75° C. and slow cooling the silicon wafer. The wafers were then analyzed by MALDI-TOF mass spectrometry as described above.

As described in EXAMPLE 30 above, a 3-base specific extension of the bound 12-mer oligonucleotide was observed using the oligomer primer where there is a 9-base spacer between the duplex and the surface (SEQ ID NO: 125). Similar results were observed when the DNA spacer lengths between the SIAB moiety and the DNA duplex were 0, 3, 6 and 12. In addition, the extension reaction may be performed using a variety of DNA polymerases, such as Sequenase and Thermo Sequenase (US Biochemical). Thus, the SIAB linker may be directly coupled to the DNA template or may include a linker sequence without effecting primer extension of the hybridized DNA.

EXAMPLE 32

Spectrochip Mutant Detection in ApoE Gene

This example describes the hybridization of an immobilized template, primer extension and mass spectrometry for detection of the wildtype and mutant Apolipoprotein E gene for diagnostic purposes. This example demonstrates that immobilized DNA molecules containing a specific sequence can be detected and distinguished using primer extension of unlabeled allele specific primers and analysis of the extension products using mass spectrometry.

A 50 base synthetic DNA template complementary to the coding sequence of allele 3 of the wildtype apolipoprotein E gene:

(SEQ ID NO:280)
5'-GCCTGGTACACTGCCAGGCGCTTCTGCAGGTCATCGGCATCGCGGAG GAG-3' or complement to the mutant apolipoprotein E gene carrying a G →A transition at codon 158:

(SEQ ID NO:281)
5'-GCCTGGTACACTGCCAGGCACTTCTGCAGGTCATCGGCATCGCGGAG GAG-3' containing a 3'-free thiol group was coupled to separate SIAB-derivatized silicon wafers as described in Example 28.

A 21-mer oligonucleotide primer: 5'-GAT GCC GAT GAC CTG CAG AAG-3' (SEQ ID NO: 282) was hybridized to each of the immobilized templates and the primer was extended using a commercially available kit (e.g., Sequenase or Thermosequenase, U.S. Biochemical Corp). The addition of Sequenase DNA polymerase or Thermosequenase DNA polymerase in the presence of three deoxyribonucleoside triphosphates (dNTPs; dATP, dGTP, dTTP) and dideoxyribonucleoside cytosine triphosphate (ddCTP) in buffer according to the instructions provided by the manufacturer resulted in a single base extension of the 21-mer primer bound to the immobilized template encoding the wildtype apolipoprotein E gene and a three base extension of the 21-mer primer bound to the immobilized template encoding the mutant form of apolipoprotein E gene.

The wafers were analyzed by mass spectrometry as described herein. The wildtype apolipoprotein E sequence results in a mass spectrum that distinguishes the primer with a single base extension (22-mer) with a mass to charge ratio of 6771.17 Da (the theoretical mass to charge ratio is 6753.5 Da) from the original 21-mer primer with a mass to charge ration of 6499.64 Da. The mutant apolipoprotein E sequence results in a mass spectrum that distinguishes the primer with a three base extension (24-mer) with a mass to charge ratio of 7386.9 (the theoretical mass charge is 7386.9) from the original 21-mer primer with a mass to charge ration of 6499.64 Da.

EXAMPLE 33

Detection of Double-Stranded Nucleic Acid Molecules Via Strand Displacement and Hybridization to an Immobilized Complementary Nucleic Acid This example describes immobilization of a 24-mer primer and the specific hybridization of one strand of a duplex DNA molecule, thereby permitting amplification of a selected target molecule in solution phase and permitting detection of the double stranded molecule. This method is useful for detecting single base changes, and, particularly for screening genomic libraries of double-stranded fragments.

A 24-mer DNA primer CTGATGCGTC GGATCATCTT TTTT SEQ ID NO: 122, containing a 3'-free thiol group was coupled to a SIAB-derivatized silicon wafer as described in Example 29.

An 18-mer synthetic oligonucleotide: 5'-CTGATGCGTCGGATCATC-3' (SEQ ID NO: 286) was premixed with a 12-mer 5'-GATGATCCGACG-3' (SEQ ID NO: 285) that has a sequence that is complementary to 12 base portion of the 18-mer oligonucleotide. The oligonucleotide mix was heated to 75° C. and cooled slowly to room temperature to facilitate the formation of a duplex molecule:

```
                    (SEQ ID NO:286)
5'-CTGATGCGTCGGATCATC-3'

                    (SEQ ID NO:287)
3'-GCAGCCTAGTAG-5'.
```

The specific hybridization of the 12-mer strand of the duplex molecule to the immobilized 24-mer primer was carried out by mixing 1 μM of the duplex molecule using the hybridization conditions described in Example 30.

The wafers were analyzed by mass spectrometry as described above. Specific hybridization was detected in a mass spectrum of the 12-mer with a mass to charge ratio of 3682.78 Da.

EXAMPLE 34

1-(2-Nitro-5-(3-O-4,4'-dimethoxytritylpropoxy)phenyl)-1-O-((2-cyanoethoxy)-diisopropylaminophosphino)ethane A. 2-Nitro-5-(3-hydroxypropoxy)benzaldehyde 3-Bromo-1-propanol (3.34 g, 24 mmol) was refluxed in 80 ml of anhydrous acetonitrile with 5-hydroxy-2-nitrobenzaldehyde (3.34 g, 20 mmol), $K_2CO_3$ (3.5 g), and KI (100 mg) overnight (15 h). The reaction mixture was cooled to room temperature and 150 ml of methylene chloride was added. The mixture was filtered and the solid residue was washed with methylene chloride. The combined organic solution was evaporated to dryness and redissolved in 100 ml methylene chloride. The resulted solution was washed with saturated NaCl solution and dried over sodium sulfate. 4.31 g (96%) of desired product was obtained after removal of the solvent in vacuo.

$R_f$=0.33 (dichloromethane/methanol, 95/5). UV (methanol) maximum: 313, 240 (shoulder), 215 nm; minimum: 266 nm. $^1$H NMR (DMSO-$d_6$) δ 10.28 (s, 1H), 8.17 (d, 1H), 7.35 (d, 1H), 7.22 (s, 1H), 4.22 (t, 2H), 3.54 (t, 2H), 1.90 (m, 2H). $^{13}$C NMR (DMSO-$d_6$) δ 189.9, 153.0, 141.6, 134.3, 127.3, 118.4, 114.0, 66.2, 56.9, 31.7.

B. 2-Nitro-5-(3-O-t-butyidimethylsilylpropoxy)benzaldehyde

2-Nitro-5-(3-hydroxypropoxy)benzaldehyde(1 g, 4.44 mmol) was dissolved in 50 ml anhydrous acetonitrile. To this solution, it was added 1 ml of triethylamine, 200 mg of imidazole, and 0.8 g (5.3 mmol) of tBDMSCl. The mixture was stirred at room temperature for 4 h. Methanol (1 ml) was added to stop the reaction. The solvent was removed in vacuo and the solid residue was redissolved in 100 ml methylene chloride. The resulted solution was washed with saturated sodium bicarbonate solution and then water. The organic phase was dried over sodium sulfate and the solvent was removed in vacuo. The crude mixture was subjected to a quick silica gel column with methylene chloride to yield 1.44 g (96%) of 2-nitro-5-(3-O-t-butyldimethylsilylpropoxy)benzaldehyde.

$R_f$=0.67 (hexane/ethyl acetate, 5/1). UV (methanol), maximum: 317, 243, 215 nm; minimum: 235, 267 nm. $^1$H NMR (DMSO-$d_6$) δ 10.28 (s, 1H), 8.14 (d, 1H), 7.32 (d, 1H), 7.20 (s, 1H), 4.20 (t, 2H), 3.75 (t, 2H), 1.90 (m, 2H), 0.85 (s, 9H), 0.02 (s, 6H). $^{13}$C NMR (DMSO-$d_6$) δ 189.6, 162.7, 141.5, 134.0, 127.1, 118.2, 113.8, 65.4, 58.5, 31.2, 25.5, −3.1, −5.7.

C. 1-(2-Nitro-5-(3-O-t-butyidimethylsilylpropoxy)phenyl)ethanol

High vacuum dried 2-nitro-5-(3-O-t-butyldimethylsilylpropoxy)benzaldehyde (1.02 g, 3 mmol) was dissolved 50 ml of anhydrous methylene chloride. 2 M Trimethylaluminium in toluene (3 ml) was added dropwise within 10 min and kept the reaction mixture at room temperature. It was stirred further for 10 min and the mixture was poured into 10 ml ice cooled water. The emulsion was separated from water phase and dried over 100 g of sodium sulfate to remove the remaining water. The solvent was removed in vacuo and the mixture was applied to a silica gel column with gradient methanol in methylene chloride. 0.94 g (86%) of desired product was isolated.

$R_f$=0.375 (hexane/ethyl acetate, 5/1). UV (methanol), maximum: 306, 233, 206 nm; minimum: 255, 220 nm. $^1$H NMR (DMSO-$d_6$) δ 8.00 (d, 1H), 7.36 (s, 1H), 7.00 (d, 1H), 5.49 (b, OH), 5.31 (q, 1H), 4.19 (m, 2H), 3.77 (t, 2H), 1.95 (m, 2H), 1.37 (d, 3H), 0.86 (s, 9H), 0.04 (s, 6H). $^{13}$C NMR (DMSO-$d_6$) δ 162.6, 146.2, 139.6, 126.9, 112.9, 112.5, 64.8, 63.9, 58.7, 31.5, 25.6, 24.9, −3.4, −5.8.

D. 1-(2-Nitro-5-(3-hydroxypropoxy)phenyl)ethanol 1-(2-Nitro-5-(3-O-t-butyldimethylsilylpropoxy)phenyl)ethanol (0.89 g, 2.5 mmol) was dissolved in 30 ml of THF and 0.5 mmol of $nBu_4NF$ was added under stirring. The mixture was stirred at room temperature for 5 h and the solvent was removed in vacuo. The remaining residue was applied to a silica gel column with gradient methanol in methylene chloride. 1-(2-Nitro-5-(3-hydroxypropoxy)phenyl)ethanol (0.6 g (99%) was obtained.

$R_f$=0.17 (dichloromethane/methanol, 95/5). UV (methanol), maximum: 304, 232, 210 nm; minimum: 255, 219 nm. $^1$H NMR (DMSO-$d_6$) δ 8.00 (d, 1H), 7.33 (s, 1H), 7.00 (d, 1H), 5.50 (d, OH), 5.28 (t, OH), 4.59 (t, 1H), 4.17 (t, 2H), 3.57

(m, 2H), 1.89 (m, 2H), 1.36 (d, 2H). $^{13}C$ NMR (DMOS-$d_6$) δ 162.8, 146.3, 139.7, 127.1, 113.1, 112.6, 65.5, 64.0, 57.0, 31.8, 25.0.

E. 1-(2-Nitro-5-(3-O-4,4'-dimethoxytritylpropoxy)phenyl)ethanol 1-(2-Nitro-5-(3-hydroxypropoxy)phenyl)ethanol (0.482 g, 2 mmol) was co-evaporated with anhydrous pyridine twice and dissolved in 20 ml anhydrous pyridine. The solution was cooled in ice-water bath and 750 mg (2.2 mmol) of DMTCI was added. The reaction mixture was stirred at room temperature overnight and 0.5 ml methanol was added to stop the reaction. The solvent was removed in vacuo and the residue was co-evaporated with toluene twice to remove trace of pyridine. The final residue was applied to a silica gel column with gradient methanol in methylene chloride containing drops of triethylamine to yield 0.96 g (89%) of the desired product 1-(2-nitro-5-(3-O-4,4'-dimethoxytrityl-propoxy)phenyl)ethanol.

$R_f$=0.50 (dichloromethane/methanol, 99/1). UV (methanol), maximum: 350 (shoulder), 305, 283, 276 (shoulder), 233, 208 nm; minimum: 290, 258, 220 nm. $^1H$ NMR (DMSO-$d_6$) δ 8.00 (d, 1H), 6.82-7.42 (ArH), 5.52 (d, OH), 5.32 (m, 1H), 4.23 (t, 2H), 3.71 (s, 6H), 3.17 (t, 2H), 2.00 (m, 2H), 1.37 (d, 3H). $^{13}C$ NMR (DMOS-$d_6$) δ 162.5, 157.9, 157.7, 146.1, 144.9, 140.1, 139.7, 135.7, 129.5, 128.8, 127.6, 127.5, 127.3, 126.9, 126.4, 113.0, 112.8, 112.6, 85.2, 65.3, 63.9, 59.0, 54.8, 28.9, 24.9.

F. 1-(2-Nitro-5-(3-O-4,4'-dimethoxytritylpropoxy)phenyl)-1-O-((2-cyanoethoxy)-diisopropylaminophosphino)ethane 1-(2-Nitro-5-(3-O-4,4'-dimethoxytritylpropoxy)phenyl)ethanol (400 mg, 0.74 mmol) was dried under high vacuum and was dissolved in 20 ml of anhydrous methylene chloride. To this solution, it was added 0.5 ml N,N-diisopropylethylamine and 0.3 ml (1.34 mmol) of 2-cyanoethyl-N,N-diisopropylchlorophosphoramidite. The reaction mixture was stirred at room temperature for 30 min and 0.5 ml of methanol was added to stop the reaction. The mixture was washed with saturated sodium bicarbonate solution and was dried over sodium sulfate. The solvent was removed in vacuo and a quick silica gel column with 1% methanol in methylene chloride containing drops of triethylamine yield 510 mg (93%) the desired phosphoramidite.

$R_f$=0.87 (dichloromethane/methanol, 99/1).

EXAMPLE 35

1-(4-(3-O-4,4'-Dimethoxytritylpropoxy)-3-methoxy-6-nitrophenyl)-1-O-((2-cyanoethoxy)-diisopropylaminophosphino)ethane A. 4-(3-Hydroxypropoxy)-3-methoxyacetophenone 3-Bromo-1-propanol (53 ml, 33 mmol) was refluxed in 100 ml of anhydrous acetonitrile with 4-hydroxy-3-methoxyacetophenone (5 g, 30 mmol), $K_2CO_3$ (5 g), and KI (300 mg) overnight (15 h). Methylenechloride (150 ml) was added to the reaction mixture after cooling to room temperature. The mixture was filtered and the solid residue was washed with methylene chloride. The combined organic solution was evaporated to dryness and redissolved in 100 ml methylene chloride. The resulted solution was washed with saturated NaCl solution and dried over sodium sulfate. 6.5 g (96.4%) of desired product was obtained after removal of the solvent in vacuo.

$R_f$=0.41 (dichloromethane/methanol, 95/5). UV (methanol), maximum: 304, 273, 227, 210 nm: minimum: 291, 244, 214 nm. $^1H$ NMR (DMSO-$d_6$) δ 7.64 (d, 1H), 7.46 (s, 1H), 7.04 (d, 1H), 4.58 (b, OH), 4.12 (t, 2H), 3.80 (s, 3H), 3.56 (t, 2H), 2.54 (s, 3H), 1.88 (m, 2H). $^{13}C$ NMR (DMSO-$d_6$) δ 196.3, 152.5, 148.6, 129.7, 123.1, 111.5, 110.3, 65.4, 57.2, 55.5, 31.9, 26.3.

B. 4-(3-Acetoxypropoxy)-3-methoxyacetophenone 4-(3-Hydroxypropoxy)-3-methoxyacetophenone (3.5 g, 15.6 mmol) was dried and dissolved in 80 ml anhydrous acetonitrile. This mixture, 6 ml of triethylamine and 6 ml of acetic anhydride were added. After 4 h, 6 ml methanol was added and the solvent was removed in vacuo. The residue was dissolved in 100 ml dichloromethane and the solution was washed with dilute sodium bicarbonate solution, then water. The organic phase was dried over sodium sulfate and the solvent was removed. The solid residue was applied to a silica gel column with methylene chloride to yield 4.1 g of 4-(3-acetoxypropoxy)-3-methoxyacetophenone (98.6%).

$R_f$=0.22 (dichloromethane/methanol, 99/1). UV (methanol), maximum: 303, 273, 227, 210 nm; minimum: 290, 243, 214 nm. $^1H$ NMR (DMSO-$d_6$) δ 7.62 (d, 1H), 7.45 (s, 1H), 7.08 (d, 1H), 4.12 (m, 4H, 3.82 (s, 3H), 2.54 (s, 3H), 2.04 (m, 2H), 2.00 (s, 3H). $^{13}C$ NMR (DMSO-$d_6$) δ 196.3, 170.4, 152.2, 148.6, 130.0, 123.0, 111.8, 110.4, 65.2, 60.8, 55.5, 27.9, 26.3, 20.7.

C. 4-(3-Acetoxypropoxy)-3-methoxy-6-nitroacetophenone 4-(3-Acetoxypropoxy)-3-methoxyacetophenone (3.99 g, 15 mmol) was added portionwise to 15 ml of 70% $HNO_3$ in water bath and keep the reaction temperature at the room temperature. The reaction mixture was stirred at room temperature for 30 min and 30 g of crushed ice was added. This mixture was extracted with 100 ml of dichloromethane and the organic phase was washed with saturated sodium bicarbonate solution. The solution was dried over sodium sulfate and the solvent was removed in vacuo. The crude mixture was applied to a silica gel column with gradient methanol in methylene chloride to yield 3.8 g (81.5%) of desired product 4-(3-acetoxypropoxy)-3-methoxy-6-nitroacetophenone and 0.38 g (8%) of ipso-substituted product 5-(3-acetoxypropoxy)-4-methoxy-1,2-dinitrobenzene.

Side ipso-substituted product 5-(3-acetoxypropoxy)-4-methoxy-1,2-dinitrobenzene:

$R_f$=0.47 (dichloromethane/methanol, 99/1). UV (methanol), maximum: 334, 330, 270, 240, 212 nm; minimum: 310, 282, 263, 223 nm. $^1H$ NMR ($CDCl_3$) δ 7.36 (s, 1H), 7.34 (s, 1H), 4.28 (t, 2H), 4.18 (t, 2H), 4.02 (s, 3H), 2.20 (m, 2H), 2.08 (s, 3H). $^{13}C$ NMR ($CDCl^3$) δ 170.9, 152.2, 151.1, 117.6, 111.2, 107.9, 107.1, 66.7, 60.6, 56.9, 28.2, 20.9.

Desired product 4-(3-acetoxypropoxy)-3-methoxy-6-nitroacetophenone:

$R_f$=0.29 (dichloromethane/methanol, 99/1). UV (methanol), maximum: 344, 300, 246, 213 nm; minimum: 320, 270, 227 nm. $^1H$ NMR ($CDCl_3$) δ 7.62 (s, 1H), 6.74 (s, 1H), 4.28 (t, 2H), 4.20 (t, 2H), 3.96 (s, 3H), 2.48 (s, 3H), 2.20 (m, 2H), 2.08 (s, 3H). $^{13}C$ NMR ($CDCl_3$) δ 200.0, 171.0, 154.3, 148.8, 138.3, 133.0, 108.8, 108.0, 66.1, 60.8, 56.6, 30.4, 28.2, 20.9.

D. 1-(4-(3-Hydroxypropoxy)-3-methoxy-6-nitrophenyl)ethanol 4-(3-Acetoxypropoxy)-3-methoxy-6-nitroacetophenone (3.73 g, 12 mmol) was added 150 ml ethanol and 6.5 g of $K_2CO_3$. The mixture was stirred at room temperature for 4 h and TLC with 5% methanol in dichloromethane indicated the completion of the reaction. To this same reaction mixture, it was added 3.5 g of $NaBH_4$ and the mixture was stirred at room temperature for 2 h. Acetone (10 ml) was added to react with the remaining $NaBH_4$. The solvent was removed in vacuo and the residue was uptaken into 50 g of silica gel. The silica gel mixture was applied on the top of a silica gel column with 5% methanol in methylene chloride to yield 3.15 g (97%) of desired product 1-(4-(3-hydroxypropoxy)-3-methoxy-6-nitrophenyl)ethanol.

Intermediate product 4-(3-hydroxypropoxy)-3-methoxy-6-nitroacetophenone after deprotection:

$R_f$=0.60 (dichloromethane/methanol, 95/5).

Final product 1-(4-(3-hydroxypropoxy)-3-methoxy-6-nitrophenyl)ethanol:

$R_f$=0.50 (dichloromethane/methanol, 95/5). UV (methanol), maximum: 344, 300, 243, 219 nm: minimum: 317, 264, 233 nm. $^1$H NMR (DMSO-$d_6$) δ 7.54 (s, 1H), 7.36 (s, 1H), 5.47 (d, OH), 5.27 (m, 1H), 4.55 (t, OH), 4.05 (t, 2H), 3.90 (s, 3H), 3.55 (q, 2H), 1.88 (m, 2H), 1.37 (d, 3H). $^{13}$C NMR (DMSO-$d_6$) δ 153.4, 146.4, 138.8, 137.9, 109.0, 108.1, 68.5, 65.9, 57.2, 56.0, 31.9, 29.6.

E. 1-(4-(3-O-4,4'-Dimethoxytritylpropoxy)-3-methoxy-6-nitrophenyl)ethanol 1-(4-(3-Hydroxypropoxy)-3-methoxy-6-nitrophenyl) ethanol (0.325 g, 1.2 mmol) was co-evaporated with anhydrous pyridine twice and dissolved in 15 ml anhydrous pyridine. The solution was cooled in ice-water bath and 450 mg (1.33 mmol) of DMTCI was added. The reaction mixture was stirred at room temperature overnight and 0.5 ml methanol was added to stop the reaction. The solvent was removed in vacuo and the residue was co-evaporated with toluene twice to remove trace of pyridine. The final residue was applied to a silica gel column with gradient methanol in methylene chloride containing drops of triethylamine to yield 605 mg (88%) of desired product 1-(4-(3-O-4,4'-dimethoxytritylpropoxy)-3-methoxy-6-nitrophenyl)ethanol.

$R_f$=0.50 (dichloromethane/methanol, 95/5). UV (methanol), maximum: 354, 302, 282, 274, 233, 209 nm; minimum: 322, 292, 263, 222 nm. $^1$H NMR (DMSO-$d_6$) δ 7.54 (s, 1H), 6.8-7.4 (ArH), 5.48 (d, OH), 5.27 (m, 1H), 4.16 (t, 2H), 3.85 (s, 3H), 3.72 (s, 6H), 3.15 (t, 2H), 1.98 (t, 2H), 1.37 (d, 3H). $^{13}$C NMR (DMSO-$d_6$) δ 157.8, 153.3, 146.1, 144.9, 138.7, 137.8, 135.7, 129.4, 128.7, 127.5, 127.4, 126.3, 112.9, 112.6, 108.9, 108.2, 85.1, 65.7, 63.7, 59.2, 55.8, 54.8, 29.0, 25.0.

F. 1-(4-(3-O-4,4'-Dimethoxytritylpropoxy)-3-methoxy-6-nitrophenyl)-1-O-((2-cyanoethoxy)-diisopropylaminophosphino)ethane 1-(4-(3-O-4,4'-Dimethoxytritylpropoxy)-3-methoxy-6-nitrophenyl)ethanol (200 mg, 3.5 mmol) was dried under high vacuum and was dissolved in 15 ml of anhydrous methylene chloride. To this solution, it was added 0.5 ml N,N-diisopropylethylamine and 0.2 ml (0.89 mmol) of 2-cyanoethyl-N,N-diisopropylchlorophosphoramidite. The reaction mixture was stirred at room temperature for 30 min and 0.5 ml of methanol was added to stop the reaction. The mixture was washed with saturated sodium bicarbonate solution and was dried over sodium sulfate. The solvent was removed in vacuo and a quick silica gel column with 1% methanol in methylene chloride containing drops of triethylamine yield 247 mg (91.3%) the desired phosphoramidite 1-(4-(3-O-4,4'-dimethoxytritylpropoxy)-3-methoxy-6-nitrophenyl)-1-O-((2-cyanoethoxy)-diisopropylaminophosphino)ethane.

$R_f$=0.87 (dichloromethane/methanol, 99/1).

EXAMPLE 36

Oligonucleotide Synthesis

The oligonucleotide conjugates containing photocleavable linker were prepared by solid phase nucleic acid synthesis (see: Sinha et al. *Tetrahedron Lett.* 1983, 24: 5843-5846; Sinha et al. *Nucleic Acids Res.* 1984, 12: 4539-4557; Beaucage et al. *Tetrahedron* 1993, 49: 6123-6194; and Matteucci et al. *J. Am. Chem. Soc.* 1981, 103: 3185-3191) under standard conditions. In addition a longer coupling time period was employed for the incorporation of photocleavable unit and the 5' terminal amino group. The coupling efficiency was detected by measuring the absorbance of released DMT cation and the results indicated a comparable coupling efficiency of phosphoramidite 1-(2-nitro-5-(3-O-4,4'-dimethoxytritylpropoxy)phenyl)-1-O-((2-cyanoethoxy)-diisopropylaminophosphino)ethane or 1-(4-(3-O-4,4'-dimethoxytritylpropoxy)-3-methoxy-6-nitrophenyl)-1-O-((2-cyanoethoxy)-diisopropylaminophosphino)ethane with those of common nucleoside phosphoramodites. Deprotection of the base protection and release of the conjugates from the solid support was carried out with concentrated ammonium at 55° C. overnight. Deprotection of the base protection of other conjugates was done by fast deprotection with AMA reagents. Purification of the MMT-on conjugates was done by HPLC (trityl-on) using 0.1 M triethylammonium acetate, pH 7.0 and a gradient of acetonitrile (5% to 25% in 20 minutes). The collected MMT or DMT protected conjugate was reduced in volume, detritylated with 80% aqueous acetic acid (40 min, 0° C.), desalted, stored at −20° C.

EXAMPLE 37

Photolysis Study

In a typical case, 2 nmol of oligonucleotide conjugate containing photocleavable linker in 200 μl distilled water was irradiated with a long wavelength UV lamp (Blak Ray XX-15 UV lamp, Ultraviolet products, San Gabriel, Calif.) at a distance of 10 cm (emission peak 365 nm, lamp intensity=1.1 mW/cm$^2$ at a distance of 31 cm). The resulting mixture was analyzed by HPLC (trityl-off) using 0.1 M triethylammonium acetate, pH 7.0 and a gradient of acetonitrile. Analysis showed that the conjugate was cleaved from the linker within minutes upon UV irradiation.

Equivalents

Those skilled in the art will recognize, or be able to ascertain using no more than routine experimentation, numerous equivalents to the specific procedures described herein. Such equivalents are considered to be within the scope of this invention and are covered by the following claims.

The invention claimed is:

1. A method for detecting the presence or absence of a target nucleic acid in a biological sample using RNA amplification, comprising:

a. amplifying a target nucleic acid, or portion thereof, using a primer comprising a sequence that is complementary to a polynucleotide sequence in the target nucleic acid, or a complement thereof, and a sequence that encodes an RNA polymerase promoter;

b. synthesizing RNA using an RNA polymerase that recognizes the promoter when the target nucleic acid is present; and c. detecting the presence or absence of the resulting RNA using mass spectrometry thereby detecting the presence or absence of the target nucleic acid in the biological sample.

2. A process of detecting the presence or absence of a target nucleic acid, comprising the steps of:

a. incubating in a reaction mixture i. an RNA polymerase ii. nucleoside triphosphates, and iii. a nucleic acid molecule comprising a sequence that is complementary to a polynucleotide sequence in the target nucleic acid, or a complement thereof, and a promoter for the RNA polymerase, thereby producing an RNA comprising the polynucleotide sequence of the target nucleic acid, or a complement thereof when the target nucleic acid is present; and b. detecting the presence or absence of the RNA by mass spectrometry, thereby detecting the presence or absence of the target nucleic acid.

3. The process of claim 2, wherein the target nucleic acid is DNA and the RNA polymerase is DNA dependent RNA polymerase.

4. The process of claim 3, further comprising, following step a) and prior to step b)

a. inactivating the RNA polymerase; and b. digesting the DNA using RNAse-free DNAse I.

5. The process of claim 2, further comprising:

a. hybridizing a detector oligonucleotide to the RNA, wherein the detector oligonucleotide is complementary to a portion of the polynucleotide sequence in the target nucleic acid, or complement thereof; and b. removing unhybridized detector oligonucleotide; wherein, in step b), the presence or absence of the RNA is detected by detecting the presence or absence of hybridized detector oligonucleotide.

6. A method for detecting the presence or absence of a target nucleic acid, comprising:

a. amplifying the target nucleic acid, or portion thereof, using a primer comprising a sequence that is complementary to at least a portion of the polynucleotide sequence of the target nucleic acid, or a complement thereof, and a sequence that encodes an RNA polymerase promoter, thereby producing an amplified nucleic acid molecule comprising the polynucleotide sequence of the target nucleic acid, or complement thereof, and the RNA polymerase promoter;

b. incubating the amplified nucleic acid molecule with nucleoside triphosphates and an RNA polymerase that recognizes the promoter, thereby producing an RNA corresponding to the target nucleic acid when target nucleic acid is present; and c. detecting the presence or absence of the RNA using mass spectrometry, thereby detecting the presence or absence of the target nucleic acid.

7. The process of claim 5, wherein the detector oligonucleotide is a peptide nucleic acid.

8. The process of any one of claims 1-6, wherein the RNA is immobilized to a solid support via a selectively cleavable linker.

9. The process of claim 1, wherein the primer is a peptide nucleic acid.

10. The process of claim 6, wherein the primer is a peptide nucleic acid.

* * * * *

SEQUENCE LISTING

<160> NUMBER OF SEQ ID NOS: 345

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
gcaagtgaat cctgagcgtg 20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gtgtgaaggg ttcatatgc 19

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
atctatattc atcataggaa acaccaca 28

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gtatctatat tcatcatagg aaacaccatt 30

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gctttggggc atggacattg acccgtataa 30

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 6

```
ctgactacta attccctgga tgctgggtct                                     30


<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

ttgcctgagt gcagtatggt                                                20


<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

agctctatat cgggaagcct                                                20


<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

ttgtgccacg cggttgggaa tgta                                           24


<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10

agcaacgact gtttgcccgc cagttg                                         26


<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11

tacattccca accgcgtggc acaac                                          25


<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
```

-continued aactggcggg caaacagtcg ttgct 25

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
gcaagtgaat cctgagcgtg 20

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
gtgtgaaggg cgtg 14

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ctatattcat cataggaaac acca 24

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gtcaccctcg acctgcag 18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
ttgtaaaacg acggccagt 19

<210> SEQ ID NO 18
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
cttccaccgc gatgttga 18

-continued

<210> SEQ ID NO 19
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
caggaaacag ctatgac 17

<210> SEQ ID NO 20
<211> LENGTH: 17
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
gtaaaacgac ggccagt 17

<210> SEQ ID NO 21
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
gtcaccctcg acctgcagc 19

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
gttgtaaaac gagggccagt 20

<210> SEQ ID NO 23
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
tctggcctgg tgcagggcct attgtagttg tgacgtaca 39

<210> SEQ ID NO 24
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
tgtacgtcac aact 14

-continued

<210> SEQ ID NO 25
<211> LENGTH: 78
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
aagatctgac cagggattcg gttagcgtga ctgctgctgc tgctgctgct gctggatgat 60
ccgacgcatc agatctgg 78

<210> SEQ ID NO 26
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
ctgatgcgtc ggatcatc 18

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
gatgatccga cgcatcacag ctc 23

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
tcggttccaa gagctgtgat gcgtcggatc atc 33

<210> SEQ ID NO 29
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
gatgatccga cgcatcacag ctc 23

<210> SEQ ID NO 30
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
gtgatgcgtc ggatcatc 18

-continued

```
<210> SEQ ID NO 31
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

tcggttccaa gagct                                                    15


<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

catttgcttc tgacacaact g                                             21


<210> SEQ ID NO 33
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

cttctctgtc tccacatgc                                                19


<210> SEQ ID NO 34
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

tgcacctgac tc                                                       12


<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

tgcttactta acccagtgtg                                               20


<210> SEQ ID NO 36
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36

cacactatgt aatactatgc                                               20
```

-continued

```
<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

gaaaatatct gacaaactca tc                                          22


<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

catggacacc aaattaagtt c                                           21


<210> SEQ ID NO 39
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

tgagactctg tctc                                                   14


<210> SEQ ID NO 40
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

ttccccaaat ccctg                                                  15


<210> SEQ ID NO 41
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

ggcacggctg tccaaggag                                              19


<210> SEQ ID NO 42
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

aggccgcgct cggcgccctc                                             20
```

-continued

<210> SEQ ID NO 43
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 43
gcggacatgg aggacgtg 18

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 44
gatgccgatg acctgcagaa g 21

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 45
cccttaccct tacccttacc ctaa 24

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 46
aatccgtgca gcagagtt 18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 47
tgtcagagct ggacaagtgt 20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 48
gatattgtct tcccggtagc 20

<210> SEQ ID NO 49

-continued

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
ctcggaccag gtgtaccgcc 20

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
cctgtactgg aaggcgatct c 21

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
catgaggcag agcatacgca 20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
gacagcagca ccgagacgat 20

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
cggctgcgat caccgtgcgg 20

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
gatccactgt gcgacgagc 19

<210> SEQ ID NO 55
<211> LENGTH: 19

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 55
gcggctgcga tcaccgtgc 19

<210> SEQ ID NO 56
<211> LENGTH: 12
<212> TYPE: DNA
<213> ORGANISM: Artificial Sequence
<220> FEATURE:
<223> OTHER INFORMATION: Description of Artificial Sequence: Synthetic
primer

<400> SEQUENCE: 56
tgcacctgac tc 12

<210> SEQ ID NO 57
<211> LENGTH: 12
<212> TYPE: DNA
<213> ORGANISM: Artificial Sequence
<220> FEATURE:
<223> OTHER INFORMATION: Description of Artificial Sequence: Synthetic
primer

<400> SEQUENCE: 57
ctgtggtcgt gc 12

<210> SEQ ID NO 58
<211> LENGTH: 39
<212> TYPE: DNA
<213> ORGANISM: Artificial Sequence
<220> FEATURE:
<223> OTHER INFORMATION: Description of Artificial Sequence: Synthetic
primer

<400> SEQUENCE: 58
gagtcaggtg cgccatgcct caaacagaca ccatggcgc 39

<210> SEQ ID NO 59
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 59
tctctgtctc cacatgccca g 21

<210> SEQ ID NO 60
<211> LENGTH: 61
<212> TYPE: DNA
<213> ORGANISM: Artificial Sequence
<220> FEATURE:
<223> OTHER INFORMATION: Description of Artificial Sequence: Synthetic
primer

<400> SEQUENCE: 60
acctagcgtt cagttcgact gagataatac gactcactat agcagctctc attttccata 60
c 61

<210> SEQ ID NO 61

-continued

<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 61
aactaagcca tgtgcacaac a 21

<210> SEQ ID NO 62
<211> LENGTH: 25
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 62
uccggucuga ugaguccgug aggac 25

<210> SEQ ID NO 63
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 63
gucacuacag gugagcucca 20

<210> SEQ ID NO 64
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 64
ccaugcgaga guaaguagua 20

<210> SEQ ID NO 65
<211> LENGTH: 50
<212> TYPE: RNA
<213> ORGANISM: Artificial Sequence
<220> FEATURE:
<223> OTHER INFORMATION: Description of Artificial Sequence: Synthetic oligonucleotide
<220> FEATURE:
<221> NAME/KEY: modified_base
<222> LOCATION: (35)
<223> OTHER INFORMATION: a, c, g, u, unknown or other

<400> SEQUENCE: 65
aggccugcgg caagacggaa agaccauggu cccunaucug ccgcaggauc 50

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 66
catttgcttc tgacacaact 20

-continued

<210> SEQ ID NO 67
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 67
tctctgtctc cacatgccca g 21

<210> SEQ ID NO 68
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 68
gtcgtcccat ggtgcacctg actc 24

<210> SEQ ID NO 69
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 69
cgctgtggtg aggccctggg ca 22

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 70
gacgacgact gctacctgac tcca 24

<210> SEQ ID NO 71
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 71
acagcggact gctacctgac tcca 24

<210> SEQ ID NO 72
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 72
tggagtcagg tagcagtc 18

-continued

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 73
cagctctcat tttccatac 19

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 74
agccccaaga tgactatc 18

<210> SEQ ID NO 75
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 75
cgaggagctc aaggccagaa t 21

<210> SEQ ID NO 76
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 76
caggggcagc tcagctctc 19

<210> SEQ ID NO 77
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 77
ggcacggctg tccaagga 18

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 78
aggccgcgct cggcgccctc 20

-continued

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 79
cttacttgaa ttccaagagc 20

<210> SEQ ID NO 80
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 80
gggctgactt gcatggaccg ga 22

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: Synthetic
primer

<400> SEQUENCE: 81
agccaggaca ag 12

<210> SEQ ID NO 82
<211> LENGTH: 15
<212> TYPE: DNA
<213> ORGANISM: Artificial Sequence
<220> FEATURE:
<223> OTHER INFORMATION: Description of Artificial Sequence: Synthetic
primer

<400> SEQUENCE: 82
acagcaggaa cagca 15

<210> SEQ ID NO 83
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 83
gcggacatgg aggacgtg 18

<210> SEQ ID NO 84
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 84
gatgccgatg acctgcagaa g 21

<210> SEQ ID NO 85

-continued

<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
gtgccctgca gcttcactga agac                                              24

<210> SEQ ID NO 86
<211> LENGTH: 12
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
agccaggaca ag                                                           12

<210> SEQ ID NO 87
<211> LENGTH: 14
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
agccaggaca agtc                                                         14

<210> SEQ ID NO 88
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
agccaggaca aga                                                          13

<210> SEQ ID NO 89
<211> LENGTH: 15
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
acagcaccaa cagca                                                        15

<210> SEQ ID NO 90
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
acagcaggaa cagcatc                                                      17

<210> SEQ ID NO 91
<211> LENGTH: 16

-continued

<212> TYPE: DNA
<213> ORGANISM: Artificial Sequence
<220> FEATURE:
<223> OTHER INFORMATION: Description of Artificial Sequence: Synthetic
primer

<400> SEQUENCE: 91
acagcaggaa cagcag 16

<210> SEQ ID NO 92
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 92
gcggacatgg aggacgtg 18

<210> SEQ ID NO 93
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 93
gcggacatgg aggacgtggc 20

<210> SEQ ID NO 94
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 94
gcggacatgg aggacgtgc 19

<210> SEQ ID NO 95
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 95
gatgccgatg acctgcagaa g 21

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 96
gatgccgatg acctgcagaa gc 22

<210> SEQ ID NO 97
<211> LENGTH: 23
<212> TYPE: DNA

-continued

<213> ORGANISM: Artificial Sequence
<220> FEATURE:
<223> OTHER INFORMATION: Description of Artificial Sequence: Synthetic
primer

<400> SEQUENCE: 97
gatgccgatg acctgcagaa gtg 23

<210> SEQ ID NO 98
<211> LENGTH: 24
<212> TYPE: DNA
<213> ORGANISM: Artificial Sequence
<220> FEATURE:
<223> OTHER INFORMATION: Description of Artificial Sequence: Synthetic
primer

<400> SEQUENCE: 98
gtgccctgca gcttcactga agac 24

<210> SEQ ID NO 99
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 99
gtgccctgca gcttcactga agactg 26

<210> SEQ ID NO 100
<211> LENGTH: 25
<212> TYPE: DNA
<213> ORGANISM: Artificial Sequence
<220> FEATURE:
<223> OTHER INFORMATION: Description of Artificial Sequence: Synthetic
primer

<400> SEQUENCE: 100
gtgccctgca gcttcactga agacc 25

<210> SEQ ID NO 101
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 101
tatctgttca cttgtgccc 19

<210> SEQ ID NO 102
<211> LENGTH: 19
<212> TYPE: DNA
<213> ORGANISM: Artificial Sequence
<220> FEATURE:
<223> OTHER INFORMATION: Description of Artificial Sequence: Synthetic
primer

<400> SEQUENCE: 102
cagaggcctg gggaccctg 19

<210> SEQ ID NO 103
<211> LENGTH: 18
<212> TYPE: DNA
<213> ORGANISM: Artificial Sequence -continued
<220> FEATURE:
<223> OTHER INFORMATION: Description of Artificial Sequence: Synthetic
      primer

<400> SEQUENCE: 103
acgacagggc tggttgcc 18

<210> SEQ ID NO 104
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
actgacaacc acccttaac 19

<210> SEQ ID NO 105
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ctgcttgcca caggtctc 18

<210> SEQ ID NO 106
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
cacagcaggc cagtgtgc 18

<210> SEQ ID NO 107
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
ggacctgatt tccttactg 19

<210> SEQ ID NO 108
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
tgaatctgag gcataactg 19

<210> SEQ ID NO 109
<211> LENGTH: 50
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 109
ttgcgtacac actggccgtc gttttacaac gtcgtgactg ggaaaaccct 50

<210> SEQ ID NO 110
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gtaaaacgac ggccagtgtg tacgcaa 27

<210> SEQ ID NO 111
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tactggaagg cgatctcagc aatcagc 27

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
ggcacggctg tccaaggag 19

<210> SEQ ID NO 113
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
aggccgcgct cggcgccctc 20

<210> SEQ ID NO 114
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 114
gucacuacag gugagcucca 20

<210> SEQ ID NO 115
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 115
gaattcgagc tcggtacccg g 21

<210> SEQ ID NO 116
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 116
ccgggtaccg agctcgaatt c 21

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 117
cctcttggga actgtgtagt att 23

<210> SEQ ID NO 118
<211> LENGTH: 112
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (86)..(88)
<223> OTHER INFORMATION: a, c, g, t, unknown or other

<400> SEQUENCE: 118
aggctgtctc tctccctctc tcatacacac acacacacac acacacacac acacacacac 60
acacacacac tcacactcac ccacannnaa atactacaca gttcccaaga gg 112

<210> SEQ ID NO 119
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 119
taatacgact cactataggg cgaaggctgt ctctctccct ctctcatac 49

<210> SEQ ID NO 120
<211> LENGTH: 135
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: modified_base
<222> LOCATION: (109)..(111)
<223> OTHER INFORMATION: a, c, g, t, unknown or other

<400> SEQUENCE: 120

-continued

```
taatacgact cactataggg cgaaggctgt ctctctccct ctctcataca cacacacaca     60

cacacacaca cacacacaca cacacacaca cactcacact cacccacann naaatactac    120

acagttccca agagg                                                     135


<210> SEQ ID NO 121
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 121

aatactacac ag                                                         12


<210> SEQ ID NO 122
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 122

ctgatgcgtc ggatcatctt tttt                                            24


<210> SEQ ID NO 123
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 123

gatgatccga cgcatcagaa tgt                                             23


<210> SEQ ID NO 124
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 124

gatctagctg ggccgagcta ggccgttga                                       29


<210> SEQ ID NO 125
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 125

ctgatgcgtc ggatcatctt ttttttt                                         27


<210> SEQ ID NO 126
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
```

-continued

<400> SEQUENCE: 126
gatgatccga cg 12

<210> SEQ ID NO 127
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 127
gatgatccga cgcat 15

<210> SEQ ID NO 128
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 128
aaaaaagatg at 12

<210> SEQ ID NO 129
<211> LENGTH: 12
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 129
gatccgacgc at 12

<210> SEQ ID NO 130
<211> LENGTH: 253
<212> TYPE: DNA
<213> ORGANISM: Homo sapiens

<400> SEQUENCE: 130
ggcacggctg tccaaggagc tgcaggcggc gcaggcccgg ctgggcgcgg acatggagga 60
cgtgtgcggc cgcctggtgc agtaccgcgg cgaggtgcag gccatgctcg gccagagcac 120
cgaggagctg cgggtgcgcc tcgcctccca cctgcgcaag ctgcgtaagc ggctcctccg 180
cgatgccgat gacctgcaga agtgcctggc agtgtaccag gccggggccc gcgagggcgc 240
cgagcgcggc ctc 253

<210> SEQ ID NO 131
<211> LENGTH: 58
<212> TYPE: DNA
<213> ORGANISM: Escherichia coli

<400> SEQUENCE: 131
gaattacatt cccaaccgcg tggcacaaca actggcgggc aaacagtcgt tgctgatt 58

<210> SEQ ID NO 132
<211> LENGTH: 57
<212> TYPE: DNA
<213> ORGANISM: Homo sapiens

<400> SEQUENCE: 132

-continued accattaaag aaaatatcat ctttggtgtt tcctatgatg aatatagaag cgtcatc 57

<210> SEQ ID NO 133
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 133
ctatattcat cataggaaac accaaagat 29

<210> SEQ ID NO 134
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 134
ctatattcat cataggaaac accaat 26

<210> SEQ ID NO 135
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 135
ctatattcat cataggaaac accaaagat 29

<210> SEQ ID NO 136
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 136
ctatattcat cataggaaac accaaagatg atattttc 38

<210> SEQ ID NO 137
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 137
ctatattcat cataggaaac accaatgata ttttc 35

<210> SEQ ID NO 138
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 138

-continued ctatattcat cataggaaac accaaagata ttttc 35

<210> SEQ ID NO 139
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 139
ctatattcat cataggaaac accaaagatg c 31

<210> SEQ ID NO 140
<211> LENGTH: 200
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 140
cttccaccgc gatgttgatg attatgtgtc tgaatttgat gggggcaggc ggcccccgtc 60
tgtttgtcgc gggtctggtg ttgatggtgg tttcctgcct tgtcaccctc gacctgcagc 120
ccaagcttgg gatccaccac catcaccatc actaataatg catgggctgc agccaattgg 180
cactggccgt cgttttacaa 200

<210> SEQ ID NO 141
<211> LENGTH: 99
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 141
gtcaccctcg acctgcagcc caagcttggg atccaccacc atcaccatca ctaataatgc 60
atgggctgca gccaattggc actggccgtc gttttacaa 99

<210> SEQ ID NO 142
<211> LENGTH: 15
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 142
tgtacgtcac aacta 15

<210> SEQ ID NO 143
<211> LENGTH: 16
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 143
tgtacgtcac aactac 16

<210> SEQ ID NO 144
<211> LENGTH: 17
<212> TYPE: DNA

-continued

<213> ORGANISM: Artificial Sequence
<220> FEATURE:
<223> OTHER INFORMATION: Description of Artificial Sequence: Synthetic
oligonucleotide

<400> SEQUENCE: 144
tgtacgtcac aactaca 17

<210> SEQ ID NO 145
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 145
tgtacgtcac aactacaa 18

<210> SEQ ID NO 146
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 146
tgtacgtcac aactacaat 19

<210> SEQ ID NO 147
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 147
tgtacgtcac aactacaata 20

<210> SEQ ID NO 148
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 148
tgtacgtcac aactacaata g 21

<210> SEQ ID NO 149
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 149
tgtacgtcac aactacaata gg 22

<210> SEQ ID NO 150
<211> LENGTH: 23
<212> TYPE: DNA
<213> ORGANISM: Artificial Sequence -continued
<220> FEATURE:
<223> OTHER INFORMATION: Description of Artificial Sequence: Synthetic
oligonucleotide

<400> SEQUENCE: 150
tgtacgtcac aactacaata ggc 23

<210> SEQ ID NO 151
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 151
tgtacgtcac aactacaata ggcc 24

<210> SEQ ID NO 152
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 152
tgtacgtcac aactacaata ggccc 25

<210> SEQ ID NO 153
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 153
tgtacgtcac aactacaata ggccct 26

<210> SEQ ID NO 154
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 154
tgtacgtcac aactacaata ggccctg 27

<210> SEQ ID NO 155
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 155
tgtacgtcac aactacaata ggccctgc 28

<210> SEQ ID NO 156
<211> LENGTH: 29
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 156
tgtacgtcac aactacaata ggccctgca 29

<210> SEQ ID NO 157
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
tgtacgtcac aactacaata ggccctgcac 30

<210> SEQ ID NO 158
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 158
tgtacgtcac aactacaata ggccctgcac c 31

<210> SEQ ID NO 159
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
tgtacgtcac aactacaata ggccctgcac ca 32

<210> SEQ ID NO 160
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
tgtacgtcac aactacaata ggccctgcac cag 33

<210> SEQ ID NO 161
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
tgtacgtcac aactacaata ggccctgcac cagg 34

<210> SEQ ID NO 162
<211> LENGTH: 35
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 162
tgtacgtcac aactacaata ggccctgcac caggc 35

<210> SEQ ID NO 163
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 163
tgtacgtcac aactacaata ggccctgcac caggcc 36

<210> SEQ ID NO 164
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 164
tgtacgtcac aactacaata ggccctgcac caggcca 37

<210> SEQ ID NO 165
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 165
tgtacgtcac aactacaata ggccctgcac caggccag 38

<210> SEQ ID NO 166
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 166
tgtacgtcac aactacaata ggccctgcac caggccaga 39

<210> SEQ ID NO 167
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 167
ctgatgcgtc ggatcatcc 19

<210> SEQ ID NO 168
<211> LENGTH: 20
<212> TYPE: DNA
<213> ORGANISM: Artificial Sequence
<220> FEATURE:
<223> OTHER INFORMATION: Description of Artificial Sequence: Synthetic
oligonucleotide -continued

<400> SEQUENCE: 168
ctgatgcgtc ggatcatcca 20

<210> SEQ ID NO 169
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 169
ctgatgcgtc ggatcatcca g 21

<210> SEQ ID NO 170
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 170
ctgatgcgtc ggatcatcca gc 22

<210> SEQ ID NO 171
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 171
ctgatgcgtc ggatcatcca gca 23

<210> SEQ ID NO 172
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 172
ctgatgcgtc ggatcatcca gcag 24

<210> SEQ ID NO 173
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 173
ctgatgcgtc ggatcatcca gcagc 25

<210> SEQ ID NO 174
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide -continued

<400> SEQUENCE: 174
ctgatgcgtc ggatcatcca gcagca 26

<210> SEQ ID NO 175
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 175
ctgatgcgtc ggatcatcca gcagcag 27

<210> SEQ ID NO 176
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 176
ctgatgcgtc ggatcatcca gcagcagc 28

<210> SEQ ID NO 177
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 177
ctgatgcgtc ggatcatcca gcagcagca 29

<210> SEQ ID NO 178
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 178
ctgatgcgtc ggatcatcca gcagcagcag 30

<210> SEQ ID NO 179
<211> LENGTH: 31
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 179
ctgatgcgtc ggatcatcca gcagcagcag c 31

<210> SEQ ID NO 180
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 180

-continued ctgatgcgtc ggatcatcca gcagcagcag ca 32

<210> SEQ ID NO 181
<211> LENGTH: 33
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 181
ctgatgcgtc ggatcatcca gcagcagcag cag 33

<210> SEQ ID NO 182
<211> LENGTH: 34
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 182
ctgatgcgtc ggatcatcca gcagcagcag cagc 34

<210> SEQ ID NO 183
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 183
ctgatgcgtc ggatcatcca gcagcagcag cagca 35

<210> SEQ ID NO 184
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 184
ctgatgcgtc ggatcatcca gcagcagcag cagcag 36

<210> SEQ ID NO 185
<211> LENGTH: 37
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 185
ctgatgcgtc ggatcatcca gcagcagcag cagcagc 37

<210> SEQ ID NO 186
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 186

-continued

```
ctgatgcgtc ggatcatcca gcagcagcag cagcagca                           38


<210> SEQ ID NO 187
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 187

ctgatgcgtc ggatcatcca gcagcagcag cagcagcag                          39


<210> SEQ ID NO 188
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 188

ctgatgcgtc ggatcatcca gcagcagcag cagcagcagc                         40


<210> SEQ ID NO 189
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 189

ctgatgcgtc ggatcatcca gcagcagcag cagcagcagc a                       41


<210> SEQ ID NO 190
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 190

ctgatgcgtc ggatcatcca gcagcagcag cagcagcagc ag                      42


<210> SEQ ID NO 191
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 191

ctgatgcgtc ggatcatcca gcagcagcag cagcagcagc agt                     43


<210> SEQ ID NO 192
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 192

ctgatgcgtc ggatcatcca gcagcagcag cagcagcagc agtc                    44
```

-continued

<210> SEQ ID NO 193
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 193
ctgatgcgtc ggatcatcca gcagcagcag cagcagcagc agtca 45

<210> SEQ ID NO 194
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 194
ctgatgcgtc ggatcatcca gcagcagcag cagcagcagc agtcac 46

<210> SEQ ID NO 195
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 195
ctgatgcgtc ggatcatcca gcagcagcag cagcagcagc agtcacg 47

<210> SEQ ID NO 196
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 196
ctgatgcgtc ggatcatcca gcagcagcag cagcagcagc agtcacgc 48

<210> SEQ ID NO 197
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 197
ctgatgcgtc ggatcatcca gcagcagcag cagcagcagc agtcacgct 49

<210> SEQ ID NO 198
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 198
ctgatgcgtc ggatcatcca gcagcagcag cagcagcagc agtcacgcta 50

-continued

<210> SEQ ID NO 199
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 199
ctgatgcgtc ggatcatcca gcagcagcag cagcagcagc agtcacgcta a 51

<210> SEQ ID NO 200
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 200
ctgatgcgtc ggatcatcca gcagcagcag cagcagcagc agtcacgcta ac 52

<210> SEQ ID NO 201
<211> LENGTH: 53
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 201
ctgatgcgtc ggatcatcca gcagcagcag cagcagcagc agtcacgcta acc 53

<210> SEQ ID NO 202
<211> LENGTH: 54
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 202
ctgatgcgtc ggatcatcca gcagcagcag cagcagcagc agtcacgcta accg 54

<210> SEQ ID NO 203
<211> LENGTH: 55
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 203
ctgatgcgtc ggatcatcca gcagcagcag cagcagcagc agtcacgcta accga 55

<210> SEQ ID NO 204
<211> LENGTH: 56
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 204
ctgatgcgtc ggatcatcca gcagcagcag cagcagcagc agtcacgcta accgaa 56

-continued

<210> SEQ ID NO 205
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 205
ctgatgcgtc ggatcatcca gcagcagcag cagcagcagc agtcacgcta accgaat 57

<210> SEQ ID NO 206
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 206
ctgatgcgtc ggatcatcca gcagcagcag cagcagcagc agtcacgcta accgaatc 58

<210> SEQ ID NO 207
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 207
ctgatgcgtc ggatcatcca gcagcagcag cagcagcagc agtcacgcta accgaatcc 59

<210> SEQ ID NO 208
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 208
ctgatgcgtc ggatcatcca gcagcagcag cagcagcagc agtcacgcta accgaatccc 60

<210> SEQ ID NO 209
<211> LENGTH: 61
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 209
ctgatgcgtc ggatcatcca gcagcagcag cagcagcagc agtcacgcta accgaatccc 60
t 61

<210> SEQ ID NO 210
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 210
ctgatgcgtc ggatcatcca gcagcagcag cagcagcagc agtcacgcta accgaatccc 60

-continued

```
tg                                                                  62


<210> SEQ ID NO 211
<211> LENGTH: 63
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 211

ctgatgcgtc ggatcatcca gcagcagcag cagcagcagc agtcacgcta accgaatccc     60

tgg                                                                 63


<210> SEQ ID NO 212
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 212

ctgatgcgtc ggatcatcca gcagcagcag cagcagcagc agtcacgcta accgaatccc     60

tggt                                                                64


<210> SEQ ID NO 213
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 213

ctgatgcgtc ggatcatcca gcagcagcag cagcagcagc agtcacgcta accgaatccc     60

tggtc                                                               65


<210> SEQ ID NO 214
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 214

ctgatgcgtc ggatcatcca gcagcagcag cagcagcagc agtcacgcta accgaatccc     60

tggtca                                                              66


<210> SEQ ID NO 215
<211> LENGTH: 67
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 215

ctgatgcgtc ggatcatcca gcagcagcag cagcagcagc agtcacgcta accgaatccc     60

tggtcag                                                             67


<210> SEQ ID NO 216
```

-continued

<211> LENGTH: 68
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 216
ctgatgcgtc ggatcatcca gcagcagcag cagcagcagc agtcacgcta accgaatccc 60
tggtcaga 68

<210> SEQ ID NO 217
<211> LENGTH: 69
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 217
ctgatgcgtc ggatcatcca gcagcagcag cagcagcagc agtcacgcta accgaatccc 60
tggtcagat 69

<210> SEQ ID NO 218
<211> LENGTH: 70
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 218
ctgatgcgtc ggatcatcca gcagcagcag cagcagcagc agtcacgcta accgaatccc 60
tggtcagatc 70

<210> SEQ ID NO 219
<211> LENGTH: 71
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 219
ctgatgcgtc ggatcatcca gcagcagcag cagcagcagc agtcacgcta accgaatccc 60
tggtcagatc t 71

<210> SEQ ID NO 220
<211> LENGTH: 72
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 220
ctgatgcgtc ggatcatcca gcagcagcag cagcagcagc agtcacgcta accgaatccc 60
tggtcagatc tt 72

<210> SEQ ID NO 221
<211> LENGTH: 13
<212> TYPE: DNA
<213> ORGANISM: Artificial Sequence
<220> FEATURE:

-continued

```
<223> OTHER INFORMATION: Description of Artificial Sequence: Synthetic
      oligonucleotide

<400> SEQUENCE: 221

tgcacctgac tcc                                                        13


<210> SEQ ID NO 222
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 222

tgcacctgac tcct                                                       14


<210> SEQ ID NO 223
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 223

tgcacctgac tcctg                                                      15


<210> SEQ ID NO 224
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 224

tgcacctgac tcctgt                                                     16


<210> SEQ ID NO 225
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 225

tgcacctgac tcctgtg                                                    17


<210> SEQ ID NO 226
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 226

tgcacctgac tcctgtgg                                                   18


<210> SEQ ID NO 227
<211> LENGTH: 19
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 227
tgcacctgac tcctgtgga 19

<210> SEQ ID NO 228
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 228
tgcacctgac tcctgtggag 20

<210> SEQ ID NO 229
<211> LENGTH: 21
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 229
tgcacctgac tcctgtggag a 21

<210> SEQ ID NO 230
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 230
tgcacctgac tcctgtggag aa 22

<210> SEQ ID NO 231
<211> LENGTH: 23
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 231
tgcacctgac tcctgtggag aag 23

<210> SEQ ID NO 232
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 232
tgcacctgac tcctgtggag aagt 24

<210> SEQ ID NO 233
<211> LENGTH: 25
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 233
tgcacctgac tcctgtggag aagtc 25

<210> SEQ ID NO 234
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 234
tgcacctgac tcctgtggag aagtct 26

<210> SEQ ID NO 235
<211> LENGTH: 27
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 235
tgcacctgac tcctgtggag aagtctg 27

<210> SEQ ID NO 236
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 236
tgcacctgac tcctgtggag aagtctgc 28

<210> SEQ ID NO 237
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 237
tgcacctgac tcctgtggag aagtctgcc 29

<210> SEQ ID NO 238
<211> LENGTH: 30
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 238
tgcacctgac tcctgtggag aagtctgccg 30

<210> SEQ ID NO 239
<211> LENGTH: 31
<212> TYPE: DNA
<213> ORGANISM: Artificial Sequence
<220> FEATURE:
<223> OTHER INFORMATION: Description of Artificial Sequence: Synthetic oligonucleotide -continued

<400> SEQUENCE: 239
tgcacctgac tcctgtggag aagtctgccg t 31

<210> SEQ ID NO 240
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 240
tgcacctgac tcctgtggag aagtctgccg tt 32

<210> SEQ ID NO 241
<211> LENGTH: 33
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 241
tgcacctgac tcctgtggag aagtctgccg tta 33

<210> SEQ ID NO 242
<211> LENGTH: 34
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 242
tgcacctgac tcctgtggag aagtctgccg ttac 34

<210> SEQ ID NO 243
<211> LENGTH: 35
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 243
tgcacctgac tcctgtggag aagtctgccg ttact 35

<210> SEQ ID NO 244
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 244
tgcacctgac tcctgtggag aagtctgccg ttactg 36

<210> SEQ ID NO 245
<211> LENGTH: 37
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 245

-continued tgcacctgac tcctgtggag aagtctgccg ttactgc 37

<210> SEQ ID NO 246
<211> LENGTH: 38
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 246
tgcacctgac tcctgtggag aagtctgccg ttactgcc 38

<210> SEQ ID NO 247
<211> LENGTH: 39
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 247
tgcacctgac tcctgtggag aagtctgccg ttactgccc 39

<210> SEQ ID NO 248
<211> LENGTH: 40
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 248
tgcacctgac tcctgtggag aagtctgccg ttactgccct 40

<210> SEQ ID NO 249
<211> LENGTH: 41
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 249
tgcacctgac tcctgtggag aagtctgccg ttactgccct g 41

<210> SEQ ID NO 250
<211> LENGTH: 42
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 250
tgcacctgac tcctgtggag aagtctgccg ttactgccct gt 42

<210> SEQ ID NO 251
<211> LENGTH: 43
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 251

-continued tgcacctgac tcctgtggag aagtctgccg ttactgccct gtg 43

<210> SEQ ID NO 252
<211> LENGTH: 44
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 252
tgcacctgac tcctgtggag aagtctgccg ttactgccct gtgg 44

<210> SEQ ID NO 253
<211> LENGTH: 45
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 253
tgcacctgac tcctgtggag aagtctgccg ttactgccct gtggg 45

<210> SEQ ID NO 254
<211> LENGTH: 46
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 254
tgcacctgac tcctgtggag aagtctgccg ttactgccct gtgggg 46

<210> SEQ ID NO 255
<211> LENGTH: 47
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 255
tgcacctgac tcctgtggag aagtctgccg ttactgccct gtggggc 47

<210> SEQ ID NO 256
<211> LENGTH: 48
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 256
tgcacctgac tcctgtggag aagtctgccg ttactgccct gtggggca 48

<210> SEQ ID NO 257
<211> LENGTH: 49
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 257
tgcacctgac tcctgtggag aagtctgccg ttactgccct gtggggcaa 49

<210> SEQ ID NO 258
<211> LENGTH: 50
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 258
tgcacctgac tcctgtggag aagtctgccg ttactgccct gtggggcaag 50

<210> SEQ ID NO 259
<211> LENGTH: 51
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 259
tgcacctgac tcctgtggag aagtctgccg ttactgccct gtggggcaag g 51

<210> SEQ ID NO 260
<211> LENGTH: 52
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 260
tgcacctgac tcctgtggag aagtctgccg ttactgccct gtggggcaag gt 52

<210> SEQ ID NO 261
<211> LENGTH: 209
<212> TYPE: DNA
<213> ORGANISM: Homo sapiens

<400> SEQUENCE: 261
catttgcttc tgacacaact gtgttcacta gcaacctcaa acagacacca tggtgcacct 60
gactcctgtg gagaagtctg ccgttactgc cctgtggggc aaggtgaacg tggatgaagt 120
tggtggtgag gccctgggca ggttggtatc aaggttacaa gacaggttta aggagaccaa 180
tagaaactgg gcatgtggag acagagaag 209

<210> SEQ ID NO 262
<211> LENGTH: 88
<212> TYPE: DNA
<213> ORGANISM: Homo sapiens

<400> SEQUENCE: 262
tgagactctg tctcaaaaat aaataaataa ataaataaat aaataaataa ataaataaat 60
aaataaataa gtaaaaaaga aagaatgc 88

<210> SEQ ID NO 263
<211> LENGTH: 53
<212> TYPE: DNA
<213> ORGANISM: Homo sapiens

<400> SEQUENCE: 263
gtgtgtgtgt gtgtgtgttt ttttttaaca gggatttggg gaattatttg aga 53

-continued

<210> SEQ ID NO 264
<211> LENGTH: 23
<212> TYPE: DNA
<213> ORGANISM: Artificial Sequence
<220> FEATURE:
<223> OTHER INFORMATION: Description of Artificial Sequence: Synthetic
allele

<400> SEQUENCE: 264
ttccccaaat ccctgttaaa aac 23

<210> SEQ ID NO 265
<211> LENGTH: 25
<212> TYPE: DNA
<213> ORGANISM: Artificial Sequence
<220> FEATURE:
<223> OTHER INFORMATION: Description of Artificial Sequence: Synthetic
allele

<400> SEQUENCE: 265
ttccccaaat ccctgttaaa aaaac 25

<210> SEQ ID NO 266
<211> LENGTH: 27
<212> TYPE: DNA
<213> ORGANISM: Artificial Sequence
<220> FEATURE:
<223> OTHER INFORMATION: Description of Artificial Sequence: Synthetic
allele

<400> SEQUENCE: 266
ttccccaaat ccctgttaaa aaaaaac 27

<210> SEQ ID NO 267
<211> LENGTH: 103
<212> TYPE: DNA
<213> ORGANISM: Artificial Sequence
<220> FEATURE:
<223> OTHER INFORMATION: Description of Artificial Sequence: Synthetic
cloning vector

<400> SEQUENCE: 267
gtaaaacgac cgccagtgcc aagcttgcat gcctgcaggt cgactctaga ggatccccgg 60
gtaccgagct cgaattcgta atcatggtca tagctgtttc ctg 103

<210> SEQ ID NO 268
<211> LENGTH: 190
<212> TYPE: DNA
<213> ORGANISM: Artificial Sequence
<220> FEATURE:
<221> NAME/KEY: Description of Artificial Sequence: Synthetic
modified beta-globin gene
<220> FEATURE:
<221> NAME/KEY: modified_base
<222> LOCATION: (57)..(169)
<223> OTHER INFORMATION: a, c, g, t, unknown or other

<400> SEQUENCE: 268
gagtcaggtg cgccatgcct caaacagaca ccatggtgca cctgactcct gaggagnnnn 60
nnnnnnnnnn nnnnnnnnnn nnnnnnnnnn nnnnnnnnnn nnnnnnnnnn nnnnnnnnnn 120
nnnnnnnnnn nnnnnnnnnn nnnnnnnnnn nnnnnnnnnn nnnnnnnnnc tgggcatgtg 180
gagacagaga 190

<210> SEQ ID NO 269
<211> LENGTH: 190

-continued

<212> TYPE: DNA
<213> ORGANISM: Artificial Sequence
<220> FEATURE:
<221> NAME/KEY: Description of Artificial Sequence: Synthetic
modified beta-globin gene
<220> FEATURE:
<221> NAME/KEY: modified_base
<222> LOCATION: (22)..(134)
<223> OTHER INFORMATION: a, c, g, t, unknown or other

<400> SEQUENCE: 269
tctctgtctc cacatgccca gnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnctcctc aggactcagg tgcacatggt gtctgtttga ggcatggcgc 180
acctgagctc 190

<210> SEQ ID NO 270
<211> LENGTH: 190
<212> TYPE: DNA
<213> ORGANISM: Artificial Sequence
<220> FEATURE:
<221> NAME/KEY: Description of Artificial Sequence: Synthetic
modified beta-globin gene
<220> FEATURE:
<221> NAME/KEY: modified_base
<222> LOCATION: (22)..(134)
<223> OTHER INFORMATION: a, c, g, t, unknown or other

<400> SEQUENCE: 270
tctctgtctc cacatgccca gnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnctcctc aggagtcagg tgcgccatgg tgtctgtttg aggcatggcg 180
cacgtgactc 190

<210> SEQ ID NO 271
<211> LENGTH: 194
<212> TYPE: DNA
<213> ORGANISM: Artificial Sequence
<220> FEATURE:
<221> NAME/KEY: Description of Artificial Sequence: Synthetic
modified beta-globin gene
<220> FEATURE:
<221> NAME/KEY: modified_base
<222> LOCATION: (22)..(134)
<223> OTHER INFORMATION: a, c, g, t, unknown or other

<400> SEQUENCE: 271
tctctgtctc cacatgccca gnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnctcctc aggagtcagg tgcgccatgg tgtctgtttg aggcatggcg 180
cacctgactc ctga 194

<210> SEQ ID NO 272
<211> LENGTH: 154
<212> TYPE: DNA
<213> ORGANISM: Artificial Sequence
<220> FEATURE:
<221> NAME/KEY: Description of Artificial Sequence: Synthetic
modified beta-globin gene
<220> FEATURE:
<221> NAME/KEY: modified_base
<222> LOCATION: (22)..(13)
<223> OTHER INFORMATION: a, c, g, t, unknown or other -continued

<400> SEQUENCE: 272
tctctgtctc cacatgccca gnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnctcctc aggagtcagg tgcg 154

<210> SEQ ID NO 273
<211> LENGTH: 13
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 273
cacctgactc cta 13

<210> SEQ ID NO 274
<211> LENGTH: 15
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 274
cacctgactc ctgga 15

<210> SEQ ID NO 275
<211> LENGTH: 14
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 275
cacctgactc ctga 14

<210> SEQ ID NO 276
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 276
ccatggtgtc tgtttgaggc atggcg 26

<210> SEQ ID NO 277
<211> LENGTH: 75
<212> TYPE: DNA
<213> ORGANISM: Homo sapiens

<400> SEQUENCE: 277
cagctctcat tttccataca gtcagtatca attctggaag aatttccaga cattaaagat 60
agtcatcttg gggct 75

<210> SEQ ID NO 278
<211> LENGTH: 61
<212> TYPE: DNA
<213> ORGANISM: Artificial Sequence
<220> FEATURE:
<223> OTHER INFORMATION: Description of Artificial Sequence: Synthetic -continued construct

<400> SEQUENCE: 278
acctagcgtt cagttcgact gagataatac gactcactat agcagctctc attttccata 60
c 61

<210> SEQ ID NO 279
<211> LENGTH: 20
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 279
gucacuacag gugagcucca 20

<210> SEQ ID NO 280
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 280
ctcagtccac gtggtaccct gctg 24

<210> SEQ ID NO 281
<211> LENGTH: 85
<212> TYPE: DNA
<213> ORGANISM: Homo sapiens

<400> SEQUENCE: 281
catttgcttc tgacacaact gtgttcacta gcaacctcaa acagacacca tggtgcacct 60
gactcctgag gagaagtctg ccgtt 85

<210> SEQ ID NO 282
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 282
acgggtcccg gagtggtgtc gc 22

<210> SEQ ID NO 283
<211> LENGTH: 76
<212> TYPE: DNA
<213> ORGANISM: Homo sapiens

<400> SEQUENCE: 283
actgccctgt ggggcaaggt gaacgtggat gaagttggtg gtgaggccct gggcaggttg 60
gtatcaaggt tacaag 76

<210> SEQ ID NO 284
<211> LENGTH: 76
<212> TYPE: DNA
<213> ORGANISM: Homo sapiens

<400> SEQUENCE: 284

-continued actgccctgt ggggcaaggt gaacgtggat gaagttggtg gtgaggccct gggcagattg 60
gtatcaaggt tacaag 76

<210> SEQ ID NO 285
<211> LENGTH: 76
<212> TYPE: DNA
<213> ORGANISM: Homo sapiens

<400> SEQUENCE: 285
actgccctgt ggggcaaggt gaacgtggat gaagttggtg gtgaggccct gggcaggttg 60
ctatcaaggt tacaag 76

<210> SEQ ID NO 286
<211> LENGTH: 76
<212> TYPE: DNA
<213> ORGANISM: Homo sapiens

<400> SEQUENCE: 286
actgccctgt ggggcaaggt gaacgtggat gaagttggtg gtgaggccct gggcaggttg 60
gcatcaaggt tacaag 76

<210> SEQ ID NO 287
<211> LENGTH: 48
<212> TYPE: DNA
<213> ORGANISM: Homo sapiens

<400> SEQUENCE: 287
acaggtttaa ggagaccaat agaaactggg catgtggaga cagagaag 48

<210> SEQ ID NO 288
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 288
gacgacgact gctacctgac tcca 24

<210> SEQ ID NO 289
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 289
acagcgcact gctacctgac tcca 24

<210> SEQ ID NO 290
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 290
tggagtcagg tagcagtc 18

<210> SEQ ID NO 291

-continued

<211> LENGTH: 60
<212> TYPE: DNA
<213> ORGANISM: Artificial Sequence
<220> FEATURE:
<223> OTHER INFORMATION: Description of Artificial Sequence: Synthetic
primer

<400> SEQUENCE: 291
cagctctcat tttccataca gtcagtatca attctggaag aatttccaga cattaaagat 60

<210> SEQ ID NO 292
<211> LENGTH: 65
<212> TYPE: DNA
<213> ORGANISM: Homo sapiens

<400> SEQUENCE: 292
agtcatcttg gggctgtcga gagtaaaagg tatgtcagtc atagttaaga ccttcttaaa 60
ggtct 65

<210> SEQ ID NO 293
<211> LENGTH: 25
<212> TYPE: DNA
<213> ORGANISM: Homo sapiens

<400> SEQUENCE: 293
gtaatttcta tcagtagaac cccga 25

<210> SEQ ID NO 294
<211> LENGTH: 60
<212> TYPE: DNA
<213> ORGANISM: Homo sapiens

<400> SEQUENCE: 294
cagctctcat tttccataca gtcagtatca attctggaag aatttccaga cattaaagat 60

<210> SEQ ID NO 295
<211> LENGTH: 15
<212> TYPE: DNA
<213> ORGANISM: Homo sapiens

<400> SEQUENCE: 295
agtcatcttg gggct 15

<210> SEQ ID NO 296
<211> LENGTH: 60
<212> TYPE: DNA
<213> ORGANISM: Homo sapiens

<400> SEQUENCE: 296
cagctctcat tttccataca gtcagtatca attctggaag aatttccaga cattaaagat 60

<210> SEQ ID NO 297
<211> LENGTH: 16
<212> TYPE: DNA
<213> ORGANISM: Homo sapiens

<400> SEQUENCE: 297
agtcatcttg gggcta 16

<210> SEQ ID NO 298
<211> LENGTH: 43
<212> TYPE: DNA
<213> ORGANISM: Homo sapiens -continued

<400> SEQUENCE: 298
cagctctcat tttccataca ttaaagatag tcatcttggg gct 43

<210> SEQ ID NO 299
<211> LENGTH: 44
<212> TYPE: DNA
<213> ORGANISM: Homo sapiens

<400> SEQUENCE: 299
cagctctcat tttccataca ttaaagatag tcatcttggg gcta 44

<210> SEQ ID NO 300
<211> LENGTH: 22
<212> TYPE: DNA
<213> ORGANISM: Homo sapiens

<400> SEQUENCE: 300
cagctctcat tttccataca gt 22

<210> SEQ ID NO 301
<211> LENGTH: 21
<212> TYPE: DNA
<213> ORGANISM: Homo sapiens

<400> SEQUENCE: 301
cagctctcat tttccataca t 21

<210> SEQ ID NO 302
<211> LENGTH: 50
<212> TYPE: DNA
<213> ORGANISM: Homo sapiens

<400> SEQUENCE: 302
gcctggtaca ctgccaggcg cttctgcagg tcatcggcat cgcggaggag 50

<210> SEQ ID NO 303
<211> LENGTH: 50
<212> TYPE: DNA
<213> ORGANISM: Homo sapiens

<400> SEQUENCE: 303
gcctggtaca ctgccaggca cttctgcagg tcatcggcat cgcggaggag 50

<210> SEQ ID NO 304
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 304
gatgccgatg acctgcagaa g 21

<210> SEQ ID NO 305
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 305
gatgccgatg acctgcagaa gc 22

-continued

<210> SEQ ID NO 306
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 306
gatgccgatg acctgcagaa gtgc 24

<210> SEQ ID NO 307
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 307
gatgatccga cg 12

<210> SEQ ID NO 308
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 308
ctgatgcgtc ggatcatc 18

<210> SEQ ID NO 309
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 309
gatgatccga cg 12

<210> SEQ ID NO 310
<211> LENGTH: 35
<212> TYPE: DNA
<213> ORGANISM: Homo sapiens

<400> SEQUENCE: 310
ggcgcggaca tggaggacgt gtgcggccgc ctggt 35

<210> SEQ ID NO 311
<211> LENGTH: 34
<212> TYPE: DNA
<213> ORGANISM: Homo sapiens

<400> SEQUENCE: 311
tccgcgatgc cgatgacctg cagaagcgcc tggc 34

<210> SEQ ID NO 312
<211> LENGTH: 27
<212> TYPE: DNA
<213> ORGANISM: Artificial Sequence
<220> FEATURE:

-continued

<223> OTHER INFORMATION: Description of Artificial Sequence: Synthetic
      oligonucleotide

<400> SEQUENCE: 312
cggctgcgat caccgtgcgg cacagct 27

<210> SEQ ID NO 313
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 313
cggctgcgat caccgtgcgg t 21

<210> SEQ ID NO 314
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 314
cggctgcgat caccgtgcgg aacagct 27

<210> SEQ ID NO 315
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 315
cggctgcgat caccgtgcgg ca 22

<210> SEQ ID NO 316
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 316
cggctgcgat caccgtgcgg ta 22

<210> SEQ ID NO 317
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 317
cggctgcgat caccgtgcgg a 21

<210> SEQ ID NO 318
<211> LENGTH: 42
<212> TYPE: DNA
<213> ORGANISM: Artificial Sequence
<220> FEATURE:
<223> OTHER INFORMATION: Description of Artificial Sequence: Synthetic -continued

```
      oligonucleotide
<220> FEATURE:
<221> NAME/KEY: modified_base
<222> LOCATION: (39)
<223> OTHER INFORMATION: a, c, g, t, unknown or other

<400> SEQUENCE: 318

atcatcaact ggaagatcag gtcaggagcc acttgccanc ct                          42


<210> SEQ ID NO 319
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 319

atcatcacac tggaagactc caggtcagga gcc                                    33


<210> SEQ ID NO 320
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 320

atccactaca actacatgtg taacagttcc wgcwwgddcd dc                          42


<210> SEQ ID NO 321
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 321

agcaacgact gtttgcccgc cagttgttgt gccacgcggt tgggaatgta                  50


<210> SEQ ID NO 322
<211> LENGTH: 58
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 322

aatcagcaac gactgtttgc ccgccagttg ttgtgccacg cggttgggaa tgtaattc         58


<210> SEQ ID NO 323
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 323

tacattccca accgcgtggc acaacaactg gcgggcaaac agtcgttgct                  50


<210> SEQ ID NO 324
<211> LENGTH: 110
<212> TYPE: DNA
```

-continued

<213> ORGANISM: Homo sapiens

<400> SEQUENCE: 324
aacgtgctgc cttccaccgc gatgttgatg attatgtgtc tgaatttgat gggggcaggc 60
ggcccccgtc tgtttgtcgc gggtctgctg ttgatggtgg tttcctgcct 110

<210> SEQ ID NO 325
<211> LENGTH: 110
<212> TYPE: DNA
<213> ORGANISM: Homo sapiens

<400> SEQUENCE: 325
aggcaggaaa ccaccatcaa cagcagaccc gcgacaaaga gacgggggcc ccctgccccc 60
atcaaattca gacacataat catcaacatc gcggtggaag gcagcacgtt 110

<210> SEQ ID NO 326
<211> LENGTH: 106
<212> TYPE: DNA
<213> ORGANISM: Homo sapiens

<400> SEQUENCE: 326
tgtcaccctc gacctggagc ccaagcttgg gatccaccac catcaccatc actaataatg 60
catgggctgc agccaattgg cactggcgtc gttttacaac gtcgtg 106

<210> SEQ ID NO 327
<211> LENGTH: 107
<212> TYPE: DNA
<213> ORGANISM: Homo sapiens

<400> SEQUENCE: 327
cacgacgttg taaaacgacg gccagtgcca attggctgca gcccatgcat tattagtgat 60
ggtgatggtg gtggatccca agcttgggct gcaggtcgag ggtgaca 107

<210> SEQ ID NO 328
<211> LENGTH: 110
<212> TYPE: DNA
<213> ORGANISM: Homo sapiens

<400> SEQUENCE: 328
acacaggaaa cagctatgac catgattacg aattcgagct cggtacccgg ggatcctcta 60
gagtcgacct gcaggcatgc aagcttggca ctggcggtcg ttttacaacg 110

<210> SEQ ID NO 329
<211> LENGTH: 110
<212> TYPE: DNA
<213> ORGANISM: Homo sapiens

<400> SEQUENCE: 329
cgttgtaaaa cgaccgccag tgccaagctt gcatgcctgg aggtcgactc tagaggatcc 60
ccgggtaccg agctcgaatt cgtaatcatg gtcatagctg tttcctgtgt 110

<210> SEQ ID NO 330
<211> LENGTH: 10
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 330

-continued

```
ttggaaccga                                                             10


<210> SEQ ID NO 331
<211> LENGTH: 65
<212> TYPE: DNA
<213> ORGANISM: Homo sapiens
<220> FEATURE:
<221> NAME/KEY: modified_base
<222> LOCATION: (25)
<223> OTHER INFORMATION: unknown nucleotide

<400> SEQUENCE: 331

atccacgttc accttgcccc acagngcagt aacggcagac ttctccacag gagtcaggtg      60

cacca                                                                  65


<210> SEQ ID NO 332
<211> LENGTH: 88
<212> TYPE: DNA
<213> ORGANISM: Homo sapiens

<400> SEQUENCE: 332

gcattctttc tttttactt atttatttat ttatttattt atttatttat ttatttattt      60

atttatttat ttttgagaca gagtctca                                         88


<210> SEQ ID NO 333
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 333

ttccccaaat ccctgtt                                                     17


<210> SEQ ID NO 334
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 334

cggctgcgat caccgtgcgg cacagct                                          27


<210> SEQ ID NO 335
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 335

cggctgcgat caccgtgcgg ca                                               22


<210> SEQ ID NO 336
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 336
```

-continued cggctgcgat caccgtgcgg t 21

<210> SEQ ID NO 337
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 337
cggctgcgat caccgtgcgg ta 22

<210> SEQ ID NO 338
<211> LENGTH: 27
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 338
cggctgcgat caccgtgcgg aacagct 27

<210> SEQ ID NO 339
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 339
cggctgcgat caccgtgcgg a 21

<210> SEQ ID NO 340
<211> LENGTH: 154
<212> TYPE: DNA
<213> ORGANISM: Artificial Sequence
<220> FEATURE:
<221> NAME/KEY: Description of Artificial Sequence: Synthetic
modified beta-globin gene
<220> FEATURE:
<221> NAME/KEY: modified_base
<222> LOCATION: (22)..(134)
<223> OTHER INFORMATION: a, c, g, t, unknown or other

<400> SEQUENCE: 340
tctctgtctc cacatgccca gnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnctcgtc aggagtcagg tgcg 154

<210> SEQ ID NO 341
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 341
ttttcccccc ccccccgggg ggggg 25

<210> SEQ ID NO 342
<211> LENGTH: 24

-continued

<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 342
atttccccgg gggggggggg gggg 24

<210> SEQ ID NO 343
<211> LENGTH: 190
<212> TYPE: DNA
<213> ORGANISM: Artificial Sequence
<220> FEATURE:
<221> NAME/KEY: Description of Artificial Sequence: Synthetic
      modified beta-globin gene
<220> FEATURE:
<221> NAME/KEY: modified_base
<222> LOCATION: (22)..(134)
<223> OTHER INFORMATION: a, c, g, t, unknown or other

<400> SEQUENCE: 343
tctctgtctc cacatgccca gnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnctcctc aggagtcagc tgcaccatgg tgtctgtttg aggcatggcg 180
cacgtgactc 190

<210> SEQ ID NO 344
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 344
aaaaattttt tttttttttt ttttt 25

<210> SEQ ID NO 345
<211> LENGTH: 190
<212> TYPE: DNA
<213> ORGANISM: Artificial Sequence
<220> FEATURE:
<221> NAME/KEY: Description of Artificial Sequence: Synthetic
      modified beta-globin gene
<220> FEATURE:
<221> NAME/KEY: modified_base
<222> LOCATION: (22)..(134)
<223> OTHER INFORMATION: a, c, g, t, unknown or other

<400> SEQUENCE: 345
tctctgtctc cacatgccca gnnnnnnnnn nnnnnnnnnn nnnnnnnnnn nnnnnnnnnn 60
nnnnnnnnnn nnnnnnnnnn nnnnnnnnnn nnnnnnnnnn nnnnnnnnnn nnnnnnnnnn 120
nnnnnnnnnn nnnnctcctc aggagtcagc tgcaccatgg tgtctgtttg aggcatggcg 180
gacctgactc 190